United States Patent
Jacobson et al.

(10) Patent No.: US 11,014,941 B2
(45) Date of Patent: May 25, 2021

(54) PYRROLOPYRIMIDINE DERIVATIVES USEFUL AS INHIBITORS OF INFLUENZA VIRUS REPLICATION

(71) Applicant: COCRYSTAL PHARMA, INC., Bothell, WA (US)

(72) Inventors: Irina C. Jacobson, Sammamish, WA (US); Michael David Feese, Seattle, WA (US); Sam S K Lee, Edmonds, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 0 days.

(21) Appl. No.: 16/603,951

(22) PCT Filed: Apr. 24, 2018

(86) PCT No.: PCT/US2018/028986
§ 371 (c)(1),
(2) Date: Oct. 9, 2019

(87) PCT Pub. No.: WO2018/200425
PCT Pub. Date: Nov. 1, 2018

(65) Prior Publication Data
US 2020/0123177 A1    Apr. 23, 2020

Related U.S. Application Data

(60) Provisional application No. 62/489,167, filed on Apr. 24, 2017.

(51) Int. Cl.
| | |
|---|---|
| *C07D 519/00* | (2006.01) |
| *A61K 31/519* | (2006.01) |
| *A61P 31/16* | (2006.01) |
| *A61K 9/00* | (2006.01) |
| *A61K 9/127* | (2006.01) |
| *A61K 9/14* | (2006.01) |
| *A61K 45/06* | (2006.01) |

(52) U.S. Cl.
CPC .......... *C07D 519/00* (2013.01); *A61K 9/0019* (2013.01); *A61K 9/0073* (2013.01); *A61K 9/127* (2013.01); *A61K 9/14* (2013.01); *A61P 31/16* (2018.01); *A61K 45/06* (2013.01)

(58) Field of Classification Search
CPC ...... C07D 519/00; A61K 31/519; A61P 31/16
USPC ........................................ 544/280; 514/265.1
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |

(Continued)

FOREIGN PATENT DOCUMENTS

| | | |
|---|---|---|
| EP | 69715 A1 | 1/1983 |
| GB | 2064336 A | 6/1981 |

(Continued)

OTHER PUBLICATIONS

Appleyard et al., A plaque assay for the study of influenza virus inhibitors, J. Antimicrob. Chemother., 1(4 Suppl):49-53 (Dec. 1975).s.

(Continued)

*Primary Examiner* — Paul V Ward
(74) *Attorney, Agent, or Firm* — Marshall, Gerstein & Borun LLP

(57) ABSTRACT

Methods of inhibiting the replication of influenza viruses in a biological sample or patient, of reducing the amount of influenza viruses in a biological sample or patient, and of treating influenza in a patient, comprises administering to said biological sample or patient a safe and effective amount of a compound represented by any of Formulas I-III, or a pharmaceutically acceptable salt thereof. A pharmaceutical composition comprises a safe and effective amount of such a compound or pharmaceutically acceptable salt thereof, and a pharmaceutically acceptable carrier, adjuvant or vehicle.

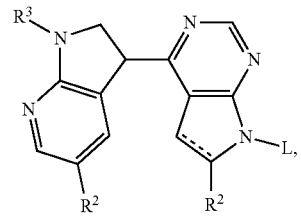

Formula I

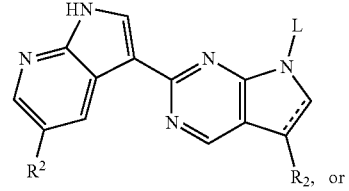

Formula II

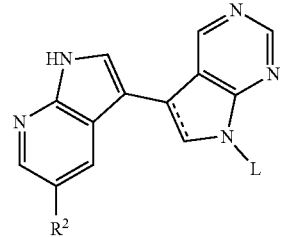

Formula III

20 Claims, No Drawings

(56) References Cited

U.S. PATENT DOCUMENTS

| | | | |
|---|---|---|---|
| 4,304,767 | A | 12/1981 | Heller et al. |
| 4,353,656 | A | 10/1982 | Sohl et al. |
| 4,501,729 | A | 2/1985 | Boucher et al. |
| 4,778,054 | A | 10/1988 | Newell et al. |
| 4,811,731 | A | 3/1989 | Newell et al. |
| 4,946,931 | A | 8/1990 | Heller et al. |
| 5,035,237 | A | 7/1991 | Newell et al. |
| 5,590,645 | A | 1/1997 | Davies et al. |
| 5,860,419 | A | 1/1999 | Davies et al. |
| 5,873,360 | A | 2/1999 | Davies et al. |
| 5,968,543 | A | 10/1999 | Heller et al. |
| 6,413,536 | B1 | 7/2002 | Gibson et al. |
| 6,596,296 | B1 | 7/2003 | Nelson et al. |
| 6,613,355 | B2 | 9/2003 | Ng et al. |
| 6,632,666 | B2 | 10/2003 | Baust et al. |
| 6,667,371 | B2 | 12/2003 | Ng et al. |
| 6,732,732 | B2 | 5/2004 | Edwards et al. |
| 6,749,835 | B1 | 6/2004 | Lipp et al. |
| 6,766,799 | B2 | 7/2004 | Edwards et al. |
| 6,848,197 | B2 | 2/2005 | Chen et al. |
| 6,956,021 | B1 | 10/2005 | Edwards et al. |
| 7,008,644 | B2 | 3/2006 | Batycky et al. |
| 7,032,593 | B2 | 4/2006 | Johnston et al. |
| 7,048,908 | B2 | 5/2006 | Basu et al. |
| 7,146,978 | B2 | 12/2006 | Edwards et al. |
| 7,182,961 | B2 | 2/2007 | Batycky et al. |
| 7,252,840 | B1 | 8/2007 | Batycky et al. |
| 7,279,182 | B2 | 10/2007 | Lipp et al. |
| 7,384,649 | B2 | 6/2008 | Batycky et al. |
| 7,678,364 | B2 | 3/2010 | Edwards et al. |
| 2019/0345101 | A1* | 11/2019 | Cameretti ................. C07C 7/04 |

FOREIGN PATENT DOCUMENTS

| | | |
|---|---|---|
| GB | 2129691 A | 5/1984 |
| GB | 2178965 A | 2/1987 |
| GB | 2242134 A | 9/1991 |
| WO | WO-03/015798 A1 | 2/2003 |
| WO | WO-2005/023335 A2 | 3/2005 |
| WO | WO-2005/095400 A1 | 10/2005 |
| WO | WO-2007/084557 A2 | 7/2007 |
| WO | WO-2010/148197 A1 | 12/2010 |
| WO | WO-2013/138236 A1 | 9/2013 |
| WO | WO-2015/073481 A1 | 5/2015 |
| WO | WO-2016/037953 A1 | 3/2016 |
| WO | WO-2016/045598 A1 | 3/2016 |
| WO | WO-2017/13364 A1 | 1/2017 |
| WO | WO-2017/097234 A1 | 6/2017 |
| WO | WO-2017/133667 A1 | 8/2017 |
| WO | WO-2017/198122 A1 | 11/2017 |

OTHER PUBLICATIONS

Berge et al., Pharmaceutical Salts, J. Pharm. Sci., 66(1):1-19 (Jan. 1977).

Chou et al., Quantitative analysis of dose-effect relationships: the combined effects of multiple drugs or enzyme inhibitors, Adv. Enzyme Regul., 22:27-55 (1984).

Furuta et al., T-705 (favipiravir) and related compounds: Novel broad-spectrum inhibitors of RNA viral infections, Antiviral Res., 82:95-102 (2009).

Holford et al., Understanding the dose-effect relationship: clinical application of pharmacokinetic-pharmacodynamic models, Clin. Pharmacokinet., 6(6):429-53 (Nov.-Dec. 1981).

International Application No. PCT/US2018/028986, International Search Report and Written Opinion, dated Jul. 13, 2018.

Muratore et al., Small molecule inhibitors of influenza A and B viruses that act by disrupting subunit interactions of the viral polymerase, Proc. Natl. Acad. Sci. USA, 109(16):6247-52 (Apr. 2012).

Shigeta et al., Synergistic anti-influenza virus A (H1N1) activities of PM-523 (polyoxometalate) and ribavirin in vitro and in vivo, Antimicrob. Agents Chemother., 41(7):1423-7 (Jul. 1997).

Willis et al., Therapeutic liposomal dry powder inhalation aerosols for targeted lung delivery, Lung, 190(3):251-62 (Jun. 2012).

\* cited by examiner

PYRROLOPYRIMIDINE DERIVATIVES USEFUL AS INHIBITORS OF INFLUENZA VIRUS REPLICATION

FIELD OF THE DISCLOSURE

This disclosure relates generally to inhibitors of influenza virus replication, and methods of treating or preventing an influenza infection by administering the inhibitors to a patient in need of treatment thereof.

BACKGROUND

Influenza spreads around the world in seasonal epidemics, resulting in the deaths of hundreds of thousands annually-millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogoto virus.

The Influenza virus A genus is responsible for seasonal flu and pandemic flu epidemics. It has one species, influenza A virus, and wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease.

The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus is responsible for season flu, and has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza viruses are very similar in structure. The influenza virus genome consists of eight single-stranded RNAs packed into rod-like structures of varying size, known as the ribonucleoprotein complex (RNP). Each RNP contains a unique viral RNA, multiple copies of the scaffolding nucleoprotein, and a heterotrimeric viral polymerase consisting of the PA, PB1, and PB2 subunits, which catalyzes the transcription and replication of the viral genome. Recent biochemical and structural studies of influenza polymerase complex provide insight into the mechanistic understanding of cap-snatching and RNA synthesis by influenza polymerase. Briefly, the PB2 cap-binding domain first sequesters the host pre-mRNAs by binding to their 5' cap. PA, the endonuclease subunit, then cleaves the captured pre-mRNA 10-13 nucleostides downstream of the cap. The PB2 subunit subsequently rotates about 700 to direct the capped primer into the PB1 polymerase active site. The PB1 subunit directly interacts with both PB2 and PA subunits. These subunits contain highly conserved domains among different influenza strains, and have attracted as an attractive anti-influenza drug target. In addition to the polymerase complex, the influenza genome encodes its own neuraminidase (NA), hemagglutinin (HA), nucleoprotein (NP), matrix proteins, M1 and M2, and non-structural proteins, NS1 and NS2. NA is the target for the antiviral drugs oseltamivir (Tamiflu) and zanamivir (Relenza). These drugs are sialic acid analogues which inhibit the enzymatic activity of NA, thus slowing down the release of progeny virus from infected cells.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with NA inhibitors being particularly effective, but viruses can develop resistance to the approved NA antiviral drugs. Also, emergence of a multidrug-resistant pandemic influenza A viruses has been well documented. Drug-resistant pandemic influenza A becomes a substantial public health threat. In addition to the drug resistant influenza A viruses, the NA inhibitors are approved for the treatment early influenza infection (within 48 hours of influenza symptom onset).

Thus, there is still a need for drugs for treating influenza infections, such as for drugs with expanded treatment window, and/or reduced sensitivity to viral titer.

SUMMARY

The present disclosure generally relates to methods of treating influenza, to methods of inhibiting the replication of influenza viruses, to methods of reducing the amount of influenza viruses, and to compounds and compositions that can be employed for such methods.

In one aspect, the present disclosure is directed to a method of inhibiting the replication of influenza viruses in a biological sample or in a patient. In one embodiment, the method comprises administering to said biological sample or patient a safe and effective amount of a compound disclosed herein.

Provided herein are compounds having a structure of any one of Formulas I-III:

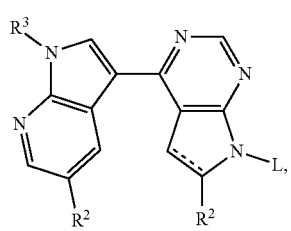

Formula I

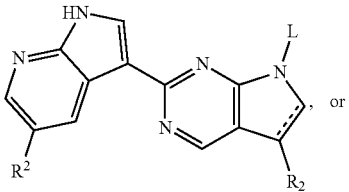

Formula II

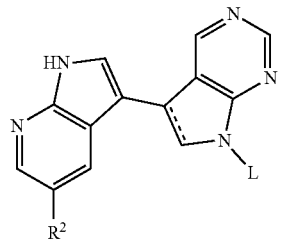

Formula III wherein
a dashed line represents either a single or a double bond,
L is:
i) H,
ii) —$C_{1-6}$ alkyl, —$C_{1-6}$ alkyl-OCONR$_2$, —$C_{1-6}$ alkyl-CONR$_2$, $C_{1-6}$ alkyl-CO$_2$R, $C_{1-6}$ alkyl-COR, $C_{1-6}$ alkyl-NRC(O)NR$_2$, $C_{1-6}$ alkyl-NRC(O)OR, $C_{1-6}$ alkyl-NRC(O)R, and $C_{1-6}$ alkyl-NR$_2$, wherein the $C_{2-6}$ alkyl can optionally include a double bond;
iii) $C_{5-6}$ cycloalkyl-OCONR$_2$, $C_{5-6}$ cycloalkyl-CONR$_2$, $C_{5-6}$ cycloalkyl-CO$_2$R, $C_{5-6}$ cycloalkyl-COR, $C_{5-6}$ cycloalkyl-NRC(O)NR$_2$, $C_{5-6}$ cycloalkyl-NRC(O)OR, $C_{5-6}$ cycloalkyl-NRC(O)R, and $C_{5-6}$ cycloalkyl-NR$_2$, where the cycloalkyl ring can be substituted with from one to three $C_{1-6}$ alkyl groups, and where the $C_{5-6}$ cycloalkyl ring can optionally include a double bond, an oxygen, or an NR group;
iv) —$C_{1-6}$ alkyl—$C_{5-6}$ cycloalkyl, —$C_{1-6}$ alkyl—$C_{5-6}$ cycloalkyl-OCONR$_2$, —$C_{1-6}$ alkyl—$C_{5-6}$ cycloalkyl-CONR$_2$, —$C_{1-6}$ alkyl—$C_{5-6}$ cycloalkyl-CO$_2$R, —$C_{1-6}$ alkyl—$C_{5-6}$ cycloalkyl-COR, —$C_{1-6}$ alkyl—$C_{5-6}$ cycloalkyl-NRC(O)NR$_2$, —$C_{1-6}$ alkyl—$C_{5-6}$ cycloalkyl-NRC(O)OR, —$C_{1-6}$ alkyl—$C_{5-6}$ cycloalkyl-NRC(O)R, and —$C_{1-6}$ alkyl—$C_{5-6}$ cycloalkyl-NR$_2$, where the cycloalkyl ring can be substituted with from one to three $C_{1-6}$ alkyl groups, and where the $C_{5-6}$ cycloalkyl ring can optionally include a double bond, an oxygen, or a nitrogen;
v) 2.2.2 bicyclooctyl-OCONR$_2$, 2.2.2 bicyclooctyl-CONR$_2$, 2.2.2 bicyclooctyl-CO$_2$R, 2.2.2 bicyclooctyl-COR, 2.2.2 bicyclooctyl-NRC(O)NR$_2$, 2.2.2 bicyclooctyl-NRC(O)OR, 2.2.2 bicyclooctyl-NRC(O)R, and 2.2.2 bicyclooctyl-NR$_2$, wherein the 2.2.2 bicyclooctyl ring can optionally include a double bond;
R is H, $C_{1-6}$alkyl, $C_{1-6}$alkyl-CO$_2$R$^1$, —CO$_2$R$^1$, CON(R$^1$)$_2$, or $C_{1-6}$ alkyl-CON(R')$_2$, and R$^1$ is H or $C_{1-6}$ alkyl;
each R$^2$ is independently H, halo, —CN, $C_{1-6}$ alkyl, $C_{1-6}$ haloalkyl, $C_{2-6}$ alkenyl, $C_{2-6}$ alkynyl, CO$_2$R, CONR$_2$, phenyl, pyridinyl, thiophenyl, furanyl, or imidazolyl, wherein the phenyl, pyridinyl, thiophenyl, furanyl, or imidazolyl is optionally substituted with one or more (e.g., 1 or 2) substituents selected from the group consisting of hydroxy, $C_{1-6}$ alkoxy, $C_{2-8}$ alkoxyalkyl, alkoxycarbonyl, $C_{1-8}$ alkyl, arylalkoxycarbonyl, $C_{2-6}$ alkenyl, $C_{2-6}$ alkynyl, carboxy, halogen, haloalkyl (e.g., CF$_3$), N$_3$, ON, N(R')$_2$, SR', OCOR', N(COR')R', N(COR')COR', SCOR', S(O)$_2$NR'$_2$, S(O)$_2$R', and each R$^1$ is independently H or $C_{1-6}$ alkyl;

R³ is H, or —SO₂-phenyl, wherein the phenyl is optionally substituted with one or more (e.g., one or two) substituents selected from the group consisting of hydroxy, $C_{1-6}$ alkoxy, $C_{2-8}$ alkoxyalkyl, alkoxycarbonyl, $C_{1-8}$ alkyl, arylalkoxycarbonyl, $C_{2-6}$ alkenyl, $C_{2-6}$ alkynyl, carboxy, halogen, haloalkyl (e.g., $CF_3$), $N_3$, CN, N(R')₂, SR', OCOR', N(COR')R¹, N(COR')COR', SCOR', S(O)₂NR'₂, S(O)₂R', and each R' is independently H or $C_{1-6}$ alkyl;

wherein a $C_{1-6}$ alkyl, $C_{2-6}$ alkenyl, or $C_{2-6}$ alkynyl moiety, wherever it occurs, can optionally be substituted with from one to three substituents which are not further substituted and which are independently selected from the group consisting of —CN, thio, aryl—$C_{1-6}$ alkyl, pyridinyl, ethoxymethyl-pyridinyl, indolinyl, $C_{1-6}$ alkyl, $C_{1-6}$ alkyl—$C_{3-6}$cycloalkyl, $C_{3-6}$cycloalkyl, —$C_{1-6}$ thioalkyl, $C_{1-6}$ haloalkyl, —$C_{1-6}$ hydroxyalkyl, —$C_{1-6}$ alkoxy, —$C_{1-6}$ alkoxy—$C_{1-6}$ alkoxy, —$C_{1-6}$ alkoxy—$C_{1-6}$ alkoxy—$C_{1-6}$ alkoxy, $CO_2H$, $CO_2C_{1-6}$alkyl, $CO_2NH_2$, $CO_2NHC_{1-6}$alkyl, and —$CO_2N(C_{1-6}alkyl)_2$; and wherein if two alkyl groups reside on an amide moiety, they can optionally together form a 5-7 membered ring with the nitrogen of the amide moiety;

or a pharmaceutically acceptable salt thereof.

In another embodiment, the method comprises administering to a biological sample or patient a safe and effective amount of a compound represented by Formulas I-III.

In another embodiment, the present disclosure is directed to a method of reducing the amount of influenza viruses in a biological sample or in a patient. The method comprises administering to said biological sample or patient a safe and effective amount of a compound represented by any of Formulas I-III, each independently as described above.

In yet another embodiment, the present disclosure is directed to a method of treating or preventing influenza in a patient, comprising administering to said patient a safe and effective amount of a compound represented by Formulas I-III, each and independently as described above.

In yet another embodiment, the present disclosure is directed to a pharmaceutical composition comprising a compound represented by any of Formulas I-III, or a pharmaceutically acceptable salt thereof, and a pharmaceutically acceptable carrier, adjuvant or vehicle, wherein the values of the variables in the Formulae are each and independently as described above for the compounds of the disclosure.

The present disclosure also provides use of a compound described herein for inhibiting the replication of influenza viruses in a biological sample or patient, for reducing the amount of influenza viruses in a biological sample or patient, or for treating influenza in a patient.

Also provided herein is use of a compound described herein for the manufacture of a medicament for treating influenza in a patient, for reducing the amount of influenza viruses in a biological sample or in a patient, or for inhibiting the replication of influenza viruses in a biological sample or patient.

DETAILED DESCRIPTION

Provided herein are compounds, and their for use in treating or preventing an influenza infection. Also provided are uses of the compounds described herein, or pharmaceutically acceptable salts thereof, or pharmaceutically acceptable compositions comprising such a compound or a pharmaceutically acceptable salt thereof, for inhibiting the replication of influenza viruses in a biological sample or in a patient, for reducing the amount of influenza viruses (reducing viral titer) in a biological sample or in a patient, and for treating influenza in a patient.

The present disclosure will be better understood with reference to the following definitions.

Definitions and General Terminology

For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the disclosure may optionally be substituted with one or more substituents, such as illustrated generally below, or as exemplified by particular classes, subclasses, and species of the disclosure. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted $C_1$—$C_3$alkyl or phenyl; X may be either optionally substituted $C_1$—$C_3$ alkyl or optionally substituted phenyl. Likewise, if the term "optionally substituted" follows a list, said term also refers to all of the substitutable groups in the prior list unless otherwise indicated. For example: if X is $C_1$—$C_3$alkyl or phenyl wherein X is optionally and independently substituted by $J^X$, then both $C_1$—$C_3$alkyl and phenyl may be optionally substituted by $J^X$. As is apparent to one having ordinary skill in the art, groups such as H, halogen, $NO_2$, CN, $NH_2$, OH, or $OCF_3$ would not be substitutable groups.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this disclosure are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is $C_1$—$C_6$ alkyl or $C_1$—$C_4$ alkyl. In some embodiments, the "alkenyl" is $C_2$—$C_6$ alkenyl or $C_2$—$C_4$ alkenyl. In some embodiments, the "alkynyl" is $C_2$—$C_6$ alkynyl or $C_2$—$C_4$ alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopentenyl, cyclopropyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", "aryloxyalkyl", or "heteroaryl" refers to both carbocyclic or heterocyclic aromatic ring systems.

"Carbocyclic aromatic ring" or "carbocyclic aryl ring" groups have only carbon ring atoms (typically six to fourteen or six to ten) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6.5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, and tri-cyclic ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can optionally include a double bond in the bridged bicyclic ring system. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "bridge" refers to a bond or an atom or an unbranched chain of atoms connecting two different parts of a molecule. The two atoms that are connected through the bridge (usually but not always, two tertiary carbon atoms) are denoted as "bridgeheads".

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

As used herein an optionally substituted aralkyl can be substituted on both the alkyl and the aryl portion. Unless otherwise indicated as used herein optionally substituted aralkyl is optionally substituted on the aryl portion.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above, for example, in the definitions of compound structures discussed throughout. Some suitable substitutents include those listed as suitable for the unsaturated carbon of a carbocyclic aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from hydrogen or an optionally substituted $C_{1-6}$ aliphatic. Optional substituents on the aliphatic group of R* are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo ($C_{1-4}$ aliphatic), wherein each of the foregoing $C_{1-4}$aliphatic groups of R* is unsubstituted.

In some embodiments, optional substituents on the nitrogen of a non-aromatic heterocyclic ring include include —$R^+$, —N($R^+$)$_2$, —C(O)$R^+$, —CO$_2R^+$, —C(O)C(O)$R^+$, —C(O)CH$_2$C(O)$R^+$, —SO$_2R^+$, —SO$_2$N($R^+$)$_2$, —C(=S)N($R^+$)$_2$, —C(=NH)—N($R^+$)$_2$, or —$NR^+$SO$_2R^+$; wherein $R^+$is hydrogen, an optionally substituted $C_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of $R^+$, on the same substituent or different substituents, taken together with the atom(s) to which each $R^+$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of $R^+$ are selected from NH$_2$, NH($C_{1-4}$ aliphatic), N($C_{1-4}$ aliphatic)$_2$, halogen, $C_{1-4}$ aliphatic, OH, O($C_{1-4}$ aliphatic), NO$_2$, CN, CO$_2$H, CO$_2$($C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted.

In some embodiments, a carbocyclic aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of a carbocyclic aryl or heteroaryl group are selected from those listed above. Other suitable substituents include: halogen; —R°; —OR°; —SR°; 1,2-methylenedioxy; 1,2-ethylenedioxy; phenyl (Ph) optionally substituted with R°; —O(Ph) optionally substituted with R°; —(CH₂)₁₋₂(Ph), optionally substituted with R°; —CH=CH(Ph), optionally substituted with R°; —NO₂; —CN; —N(R°)₂; —NR°C(O)R°; —NR°C(S)R°)₂; —NR°C(O)N(R°)₂; —NR°C(S)N(R°)₂; —NR°CO₂R; —NR°NR°C(O)R°; —NR°NR°C(O)N(R°)₂; —NR°NR°CO₂R; —C(O)C(O)R°; —C(O)CH₂C(O)R°; —CO₂R; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R; —S(O)₃R; —SO₂N(R°)₂; —S(O)R°; —NR°SO₂N(R°)₂; —NR°SO₂R; —N(OR°)R°; —C(=NH)—N(R°)₂; or —(CH₂)₀₋₂NHC(O)R; wherein each independent occurrence of R° is selected from hydrogen, optionally substituted C₁₋₆ aliphatic, an unsubstituted 5-6 membered heteroaryl or heterocyclic ring, phenyl, —O(Ph), or —CH₂(Ph), or, two independent occurrences of R°, on the same substituent or different substituents, taken together with the atom(s) to which each R° group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO₂(C₁₋₄aliphatic), O(haloC₁₋₄ aliphatic), or haloC₁₋₄aliphatic, CHO, N(CO)(C₁₋₄ aliphatic), C(O)N(C₁₋₄ aliphatic), wherein each of the foregoing C₁₋₄aliphatic groups of R° is unsubstituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

The term "unsaturated", as used herein, means that a moiety has one or more units of unsaturation (e.g., double and/or triple bonds).

As detailed above, in some embodiments, two independent occurrences of R° (or R⁺, or any other variable similarly defined herein), may be taken together with the atom(s) to which each variable is bound to form a 5-8-membered heterocyclyl, carbocyclic aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

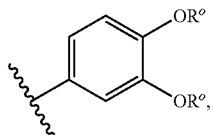

these two occurrences of R° are taken together with the oxygen atoms to which they are bound to form a fused 6-membered oxygen containing ring:

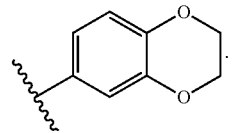

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

As used herein, an "amino" group refers to —NRˣRʸ wherein each of Rˣ and Rʸ is independently —H, C₁—C₆ aliphatic, a C₃₋₇ non-aromatic carbocycle, a 5-6 membered carbocyclic aryl or heteroaryl, or a 4-7 membered non-aromatic heterocycle, each of which independently being defined herein and being optionally substituted. Suitable substituents for the carbocycle, carbocyclic aryl, heteroaryl, and heterocyl are each independently include halogen, cyano, hydroxy, oxo, —NH₂, —NH(C₁—C₆ alkyl), —N(C₁—C₆ alkyl)₂, C₁—C₆ alkyl, —O(C₁—C₆ alkyl), —C(O)OH, —C(O)O(C₁—C₆ alkyl), —OC(O)(C₁—C₆ alkyl), —NHC(O)(C₁—C₆ alkyl), —NHC(O)O(C₁—C₆ alkyl), —C(O)NH(C₁—C₆ alkyl), and —C(O)N(C₁—C₆ alkyl)₂, wherein each of said alkyl groups is optionally and independently substituted with one or more substituents selected from the group consisting of halogen, cyano, hydroxy, oxo, —NH₂, —NH(C₁—C₄ alkyl), and —N(C₁—C₄ alkyl)₂, —OCO(C₁—C₄ alkyl), —CO(C₁—C₄ alkyl), —CO₂H, —CO₂(C₁—C₄ alkyl), and C₁—C₄ alkoxy. Suitable substituents for the C₁—C₆ aliphatic (including C₁—C₆ alkyl) include halogen, cyano, hydroxy, oxo, —NH₂, —NH (C₁—C₆ alkyl), —N(C₁—C₆ alkyl)₂, —O(C₁—C₆ alkyl), —C(O)OH, —C(O)O(C₁—C₆ alkyl), —OC(O)(C₁—C₆ alkyl), —NHC(O)(C₁—C₆ alkyl), —NHC(O)O(C₁—C₆ alkyl), —C(O)NH(C₁—C₆ alkyl), —C(O)N(C₁—C₆ alkyl)₂, phenyl, a 5-6 membered heteroaryl, a 5-6 membered non-aromatic heterocycle, and a C₃—C₇ carbocycle, wherein each of said alkyl groups is optionally and independently substituted with one or more substituents selected from the group consisting of halogen, cyano, hydroxy, oxo, —NH₂, —NH(C₁—C₄ alkyl), —N(C₁—C₄ alkyl)₂, —OCO (C₁—C₄ alkyl), —CO(C₁—C₄ alkyl), —CO₂H, —CO₂ (C₁—C₄ alkyl), and C₁—C₄ alkoxy, and wherein each of said phenyl, heteroaryl, heterocycle and carbocycle is optionally and independently substituted with one or more substituents described above for the carbocycle, carbocyclic aryl, heteroaryl, and heterocycle represented by Rˣ and Rʸ. In some embodiments, each of Rˣ and Rʸ is independently —H, an optionally substituted C₁₋₆ aliphatic group, or an optionally substituted C₃₋₈ non-aromatic carbocycle. In some embodiments, each of Rˣ and Rʸ is independently —H or an optionally substituted $C_{1-6}$ aliphatic group. In some embodiments, each of $R^X$ and $R^Y$ is independently —H or $C_{1-6}$ alkyl optionally substituted with one or more substituents selected from the group consisting of halogen, cyano, hydroxy, oxo, —NH$_2$, —NH($C_1$—$C_4$ alkyl), —N($C_1$—$C_4$ alkyl)$_2$, —OCO($C_1$—$C_4$ alkyl), —CO($C_1$—$C_4$ alkyl), —CO$_2$H, —CO$_2$($C_1$—$C_4$ alkyl), and $C_1$—$C_4$ alkoxy. Examples of amino groups include —NH$_2$, aliphatic amino, alkylamino, dialkylamino, or arylamino.

As used herein, an "aliphatic amino" group refers to —NR$^X$R$^Y$ wherein R$^X$ is a $C_{1-6}$ aliphatic group optionally substituted as described above; and R$^Y$ is —H or a $C_{1-6}$ aliphatic group optionally substituted as described above. As used herein, an "alkylamino" group refers to —NHR$^X$ wherein R$^X$ is a $C_{1-6}$ alkyl group optionally substituted as described above. As used herein, a "dialkylamino" group refers to —NR$^X$R$^Y$ wherein each of R$^X$ and R$^Y$ is independently a $C_{1-6}$ alkyl group optionally substituted as described above. As used herein, an "arylamino" group refers to —NR$^X$R$^Y$ wherein R$^X$ is 5-6 membered, carbocyclic aryl or heteroaryl, and R$^Y$ is —H or 5-6 membered, carbocyclic aryl or heteroaryl, wherein each of said carbocyclic aryl and heteroaryl groups is independently and optionally substituted as described above. When the term "amino" is not the terminal group (e.g., alkylcarbonylamino), it is represented by —NR$^X$—. R$^X$ has the same meaning as defined above. In one embodiment, the amino group is —NH$_2$ or an aliphatic amino. In another embodiment, the amino group is —NH$_2$, alkylamino or dialkylamino. In yet another embodiment, the amino group is —NH$_2$ or an arylamino. In yet another embodiment, the amino group is —NH$_2$, —NH($C_1$—$C_6$ alkyl) or —N($C_1$—$C_6$ alkyl)$_2$, wherein each of the alkyl groups is optionally and independently substituted with one or more substituents selected from the group consisting of halogen, cyano, hydroxy, oxo, —NH$_2$, —NH($C_1$—$C_4$ alkyl), —N($C_1$—$C_4$ alkyl)$_2$, —OCO($C_1$—$C_4$ alkyl), —CO($C_1$—$C_4$ alkyl), —CO$_2$H, —CO$_2$($C_1$—$C_4$ alkyl), and $C_1$—$C_4$ alkoxy.

As used herein, an "amido" encompasses both "aminocarbonyl" and "carbonylamino". These terms when used alone or in connection with another group refer to an amido group such as N(R$^X$R$^Y$)—C(O)— or R$^Y$C(O)—N(R$^X$)— when used terminally and —C(O)—N(R$^X$)— or —N(R$^X$)—C(O)— when used internally, wherein R$^X$ and R$^Y$ are defined above. Examples of amido groups include alkylamido (such as alkylcarbonylamino or alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido. In some embodiments, the amido group is —NHC(O)($C_1$—$C_6$ alkyl), —N($C_1$—$C_6$ alkyl)C(O)($C_1$—$C_6$ alkyl), —C(O)NH$_2$, —C(O)NH($C_1$—$C_6$ alkyl), or —C(O)NH($C_1$—$C_6$ alkyl)$_2$, wherein each of said alkyl is optionally and independently substituted with one or more substituents selected from the group consisting of halogen, cyano, hydroxy, oxo, —NH$_2$, —NH($C_1$—$C_6$ alkyl), —N($C_1$—$C_6$ alkyl)$_2$, —OCO($C_1$—$C_4$ alkyl), —CO($C_1$—$C_4$ alkyl), —CO$_2$H, —CO$_2$($C_1$—$C_4$ alkyl), and $C_1$—$C_4$ alkoxy. In some embodiments, the amido group is —NHC(O)($C_1$—$C_6$ alkyl), —N($C_1$—$C_6$ alkyl)C(O)($C_1$—$C_6$ alkyl), —C(O)NH$_2$, —C(O)NH($C_1$—$C_6$ alkyl), or —C(O)NH($C_1$—$C_6$ alkyl)$_2$, wherein each of the alkyl groups is optionally and independently substituted with one or more substituents selected from the group consisting of halogen, cyano, hydroxy, oxo, —NH$_2$, —NH($C_1$—$C_6$ alkyl), —N($C_1$—$C_6$ alkyl)$_2$, —OCO($C_1$—$C_4$ alkyl), —CO($C_1$—$C_4$ alkyl), —CO$_2$H, —CO$_2$($C_1$—$C_4$ alkyl), and $C_1$—$C_4$ alkoxy.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ are each independently as defined above.

As used herein, an "acyl" group refers to a formyl group or R$^X$—C(O)— (such as —alkyl —C(O)—, also referred to as "alkylcarbonyl") where R$^X$ and "alkyl" have been defined previously. Acetyl and pivaloyl are examples of acyl groups.

As used herein, a "carboxy" group refers to —COOH, —COOR$^X$, —OC(O)H, —OC(O)R$^X$ when used as a terminal group; or —OC(O)— or —C(O)O— when used as an internal group, wherein R$^X$ is as defined above.

The term "hydroxyl" or "hydroxy" or "alcohol moiety" refers to —OH.

As used herein, an "alkoxycarbonyl," which is encompassed by the term carboxy, used alone or in connection with another group refers to a group such as (alkyl-O)—C(O)—.

As used herein, a "carbonyl" refers to —C(O)—.

As used herein, an "oxo" refers to =O.

As used herein, the term "alkoxy", or "alkylthio", as used herein, refers to an alkyl group, as previously defined, attached to the molecule through an oxygen ("alkoxy" e.g., —O-alkyl) or sulfur ("alkylthio" e.g., —S-alkyl) atom.

As used herein, the terms "halogen", "halo", and "hal" mean F, Cl, Br, or I.

As used herein, the term "cyano" or "nitrile" refer to —CN or —C≡N.

The terms "alkoxyalkyl", "alkoxyalkenyl", "alkoxyaliphatic", and "alkoxyalkoxy" mean alkyl, alkenyl, aliphatic or alkoxy, as the case may be, substituted with one or more alkoxy groups.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF$_3$ and —CF$_2$CF$_3$.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. In some embodiments, the cyanoalkyl is (NC)—alkyl —.

The terms "aminoalkyl", "aminoalkenyl", "aminoaliphatic", and "aminoalkoxy" mean alkyl, alkenyl, aliphatic or alkoxy, as the case may be, substituted with one or more amino groups, wherein the amino group is as defined above. In some embodiments, the aminoaliphatic is a $C_1$—$C_6$ aliphatic group substituted with one or more —NH$_2$ groups. In some embodiments, the aminoalkyl refers to the structure (R$^X$R$^Y$)N—alkyl —, wherein each of R$^X$ and R$^Y$ independently is as defined above. In some specific embodiments, the aminoalkyl is $C_1$—$C_6$ alkyl substituted with one or more —NH$_2$ groups. In some specific embodiments, the aminoalkenyl is $C_1$—$C_6$ alkenyl substituted with one or more —NH$_2$ groups. In some embodiments, the aminoalkoxy is —O($C_1$—$C_6$ alkyl) wherein the alkyl group is substituted with one or more —NH$_2$ groups.

The terms "hydroxyalkyl", "hydroxyaliphatic", and "hydroxyalkoxy" mean alkyl, aliphatic or alkoxy, as the case may be, substituted with one or more —OH groups.

The terms "alkoxyalkyl", "alkoxyaliphatic", and "alkoxyalkoxy" mean alkyl, aliphatic or alkoxy, as the case may be, substituted with one or more alkoxy groups. For example, an "alkoxyalkyl" refers to an alkyl group such as (alkyl-O)—alkyl —, wherein alkyl is as defined above.

The term "carboxyalkyl" means alkyl substituted with one or more carboxy groups, wherein alkyl and carboxy are as defined above.

In some embodiments, each of the amino groups referred to in the descriptions for the variables of Formulas I-III above is independently —NH$_2$, —NH(C$_1$—C$_6$ alkyl), —NH(C$_3$—C$_6$ carbocycle), —N(C$_1$—C$_6$ alkyl)$_2$, or —N(C$_1$—C$_6$ alkyl)(C$_3$—C$_6$ carbocycle), wherein said alkyl and carbocycle groups are each optionally and independently substituted with one or more substituents independently selected from the group consisting of halogen, cyano, hydroxy, oxo, —NH$_2$, —NH(C$_1$—C$_4$ alkyl), —N(C$_1$—C$_4$ alkyl)$_2$, —OCO(C$_1$—C$_4$ alkyl), —CO(C$_1$—C$_4$ alkyl), —CO$_2$H, —CO$_2$(C$_1$—C$_4$ alkyl), and C$_1$—C$_4$ alkoxy; each of the carboxy groups referred to in the descriptions for the variables of Formulas I-III can independently be —C(O)O(C$_1$—C$_6$ alkyl), —OC(O)(C$_1$—C$_6$ alkyl), —C(O)O(C$_3$—C$_6$ carbocycle), —OC(O)(C$_3$—C$_6$ carbocycle), or —CO$_2$H, wherein said alkyl and carbocycle groups are each optionally and independently substituted with one or more substituents independently selected from the group consisting of halogen, cyano, hydroxy, oxo, —NH$_2$, —NH(C$_1$—C$_4$ alkyl), —N(C$_1$—C$_4$ alkyl)$_2$, —OCO(C$_1$—C$_4$ alkyl), —CO(C$_1$—C$_4$ alkyl), —CO$_2$H, —CO$_2$(C$_1$—C$_4$ alkyl), and C$_1$—C$_4$ alkoxy.

Each of the amido groups referred to in the descriptions for the variables of Formulas I-III above is independently —NHC(O)(C$_1$—C$_6$ alkyl), —N(C$_1$—C$_6$ alkyl)C(O)(C$_1$—C$_6$ alkyl), —C(O)NH(C$_1$—C$_6$ alkyl), —C(O)N(C$_1$—C$_6$ alkyl)$_2$, —NHC(O)(C$_3$—C$_6$ carbocycle), —N(C$_1$—C$_6$ alkyl)C(O)(C$_3$—C$_6$ carbocycle), —C(O)NH(C$_3$—C$_6$ carbocycle), —C(O)N(C$_1$—C$_6$ alkyl)(C$_3$—C$_6$ carbocycle), or —C(O)NH$_2$, wherein said alkyl and carbocycle groups are each optionally and independently substituted with one or more substituents independently selected from the group consisting of halogen, cyano, hydroxy, oxo, —NH$_2$, —NH(C$_1$—C$_4$ alkyl), —N(C$_1$—C$_4$ alkyl)$_2$, —OCO(C$_1$—C$_4$ alkyl), —CO(C$_1$—C$_4$ alkyl), —CO$_2$H, —CO$_2$(C$_1$—C$_4$ alkyl), and C$_1$—C$_4$ alkoxy.

Each of the aminoalkyl groups referred to in the descriptions for the variables of Formulas I, II, or III above is independently a C$_1$—C$_6$ alkyl group substituted with one or more amino groups independently selected from the group consisting of —NH$_2$, —NH(C$_1$—C$_4$ alkyl), and —N(C$_1$—C$_4$ alkyl)$_2$.

Each of the aminoalkoxy groups referred to in the descriptions for the variables of Formulas I, II, or III above is independently is a —O(C$_1$—C$_6$ alkyl) group wherein the alkyl group is substituted with one or more one or more amino groups independently selected from the group consisting of —NH$_2$, —NH(C$_1$—C$_4$ alkyl), and —N(C$_1$—C$_4$ alkyl)$_2$.

In some embodiments, each of the amino groups referred to in the descriptions for the variables of Formulas I-III above is independently —NH$_2$, —NH(C$_1$—C$_6$ alkyl), or —N(C$_1$—C$_6$ alkyl)$_2$, wherein said alkyl groups are each optionally and independently substituted with one or more substituents independently selected from the group consisting of halogen, cyano, hydroxy, oxo, —NH$_2$, —NH(C$_1$—C$_4$ alkyl), —N(C$_1$—C$_4$ alkyl)$_2$, —OCO(C$_1$—C$_4$ alkyl), —CO(C$_1$—C$_4$ alkyl), —CO$_2$H, —CO$_2$(C$_1$—C$_4$ alkyl), and C$_1$—C$_4$ alkoxy.

Each of the carboxy groups referred to in the descriptions for the variables of Formulas I-III above is independently —C(O)O(C$_1$—C$_6$ alkyl), —OC(O)(C$_1$—C$_6$ alkyl), or —CO$_2$H, wherein said alkyl groups are each optionally and independently substituted with one or more substituents independently selected from the group consisting of halogen, cyano, hydroxy, oxo, —NH$_2$, —NH(C$_1$—C$_4$ alkyl), —N(C$_1$—C$_4$ alkyl)$_2$, —OCO(C$_1$—C$_4$ alkyl), —CO(C$_1$—C$_4$ alkyl), —CO$_2$H, —CO$_2$(C$_1$—C$_4$ alkyl), and C$_1$—C$_4$ alkoxy.

Each of the amido groups referred to in the descriptions for the variables of Formulas I-III above is independently —NHC(O)(C$_1$—C$_6$ alkyl), —N(C$_1$—C$_6$ alkyl)C(O)(C$_1$—C$_6$ alkyl), —C(O)NH(C$_1$—C$_6$ alkyl), —C(O)N(C$_1$—C$_6$ alkyl)$_2$, or —C(O)NH$_2$, wherein said alkyl groups are each optionally and independently substituted with one or more substituents independently selected from the group consisting of halogen, cyano, hydroxy, oxo, —NH$_2$, —NH(C$_1$—C$_4$ alkyl), —N(C$_1$—C$_4$ alkyl)$_2$, —OCO(C$_1$—C$_4$ alkyl), —CO(C$_1$—C$_4$ alkyl), —CO$_2$H, —CO$_2$(C$_1$—C$_4$ alkyl), and C$_1$—C$_4$ alkoxy.

Each of the aminoalkyl groups referred to in the descriptions for the variables of Formulas I-III above is independently a C$_1$—C$_6$ alkyl group substituted with one or more amino groups independently selected from the group consisting of —NH$_2$, —NH(C$_1$—C$_4$ alkyl), and —N(C$_1$—C$_4$ alkyl)$_2$; and each of the aminoalkoxy groups referred to in the descriptions for the variables of Formulas I-III above is independently is a —O(C$_1$—C$_6$ alkyl) group wherein the alkyl group is substituted with one or more one or more amino groups independently selected from the group consisting of —NH$_2$, —NH(C$_1$—C$_4$ alkyl), and —N(C$_1$—C$_4$ alkyl)$_2$.

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999.

As used herein, the term "displaceable moiety" or "leaving group" refers to a group that is associated with an aliphatic or aromatic group as defined herein and is subject to being displaced by nucleophilic attack by a nucleophile.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this disclosure, unless only one of the isomers is specifically indicated. Therefore, single stereochemical isomers as well as enantiomeric, diastereomeric, cis/trans, conformational, and rotational mixtures of the present compounds are within the scope of the disclosure.

Unless otherwise indicated, all tautomeric forms of the compounds of the disclosure are within the scope of the disclosure.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this disclosure. For example, compounds of Formulae I-III that have —D at the position corresponding to $R^2$ are also within the scope of this disclosure. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds of the disclosure are defined herein by their chemical structures and/or chemical names. Where a compound is referred to by both a chemical structure and a chemical name, and the chemical structure and chemical name conflict, the chemical structure is determinative of the compound's identity.

I. Compounds

Provided herein are compounds of Formulas I-III, or pharmaceutically acceptable salts thereof:

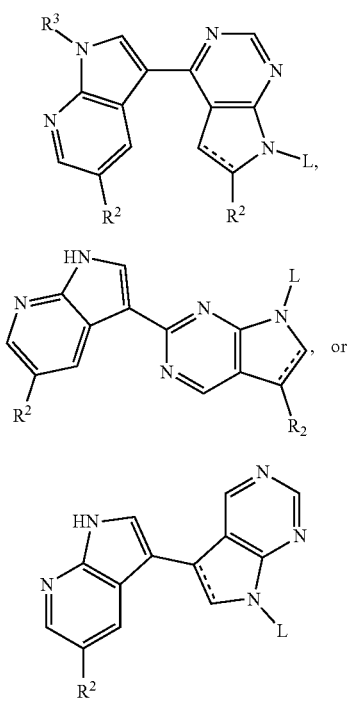

where the dashed line represents either a single or a double bond, and where L is:

i) H, ii) —$C_{1-6}$ alkyl, —$C_{1-6}$ alkyl-$CO_2NR_2$, $C_{1-6}$ alkyl-$CO_2R$, $C_{1-6}$ alkyl-NRC(O)$NR_2$, $C_{1-6}$ alkyl-NRC(O)OR, $C_{1-6}$ alkyl-NRC(O)R, and $C_{1-6}$ alkyl-$NR_2$, wherein the $C_{1-6}$ alkyl can optionally include a double bond, iii) $C_{5-6}$ cycloalkyl-$CO_2NR_2$, $C_{5-6}$ cycloalkyl-$CO_2R$, $C_{5-6}$ cycloalkyl-NRC(O)$NR_2$, $C_{5-6}$ cycloalkyl-NRC(O)OR, $C_{5-6}$ cycloalkyl-NRC(O)R, and $C_{5-6}$ cycloalkyl-$NR_2$, where the cycloalkyl ring can be substituted with from one to three $C_{1-6}$ alkyl groups, and where the $C_{5-6}$ cycloalkyl ring can optionally include a double bond, iv) —$C_{1-6}$ alkyl—$C_{5-6}$ cycloalkyl-$CO_2NR_2$, —$C_{1-6}$ alkyl—$C_{5-6}$ cycloalkyl-$CO_2R$, —$C_{1-6}$ alkyl—$C_{5-6}$ cycloalkyl-NRC(O)$NR_2$, —$C_{1-6}$ alkyl—$C_{5-6}$ cycloalkyl-NRC(O)OR, —$C_{1-6}$ alkyl—$C_{5-6}$ cycloalkyl-NRC(O)R, and —$C_{1-6}$ alkyl—$C_{5-6}$ cycloalkyl-$NR_2$, where the cycloalkyl ring can be substituted with from one to three $C_{1-6}$ alkyl groups, and where the $C_{5-6}$ cycloalkyl ring can optionally include a double bond, an oxygen, or an NR group, v) 2.2.2 bicyclooctyl-$CO_2NR_2$, 2.2.2 bicyclooctyl-$CO_2R$, 2.2.2 bicyclooctyl-NRC(O)$NR_2$, 2.2.2 bicyclooctyl-NRC(O)OR, 2.2.2 bicyclooctyl-NRC(O)R, and 2.2.2 bicyclooctyl-$NR_2$, wherein the 2.2.2 bicyclooctyl ring can optionally include a double bond, where the ring nitrogen with an open valence is linked to a moiety selected from the group consisting of H, —C(O)R, —C(O)$NR_2$, alkyl-$CO_2R$ and alkenyl-$CO_2R$, wherein R=H, alkyl, alkyl-$CO_2H$, alkyl-$CO_2$alkyl, alkyl-$CONR^{12}$, $R^1$ is H or $C_{1-6}$ alkyl, $R^2$ is H, halo, —CN, $C_{1-6}$ alkyl, $C_{1-6}$ haloalkyl, $C_{2-8}$ alkynyl, $CO_2R$, $CO_2NR_2$, phenyl, pyridinyl, thiophenyl, furanyl, imidazolyl, (where the phenyl, pyridinyl, thiophenyl, furanyl, or imidazolyl can be optionally substituted with one or more substituents selected from the group consisting of hydroxy, $C_{1-6}$ alkoxy, $C_{2-8}$ alkoxyalkyl, alkoxycarbonyl, $C_{1-8}$ alkyl, arylalkoxycarbonyl, $C_{2-6}$ alkenyl, $C_{2-6}$ alkynyl, carboxy, halogen (F, Cl, Br, I), haloalkyl, $CF_3$, $N_3$, ON, N(R')$_2$, SR', OCOR', N(COR')R', N(COR')COR', SCOR', S(O)$_2$NR'$_2$, S(O)$_2$R'. Each R' is independently H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, arylalkyl, or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl;

$R^3$ is H, or —SO$_2$-phenyl (where the phenyl can be optionally substituted with one or more substituents selected from the group consisting of hydroxy, $C_{1-6}$ alkoxy, $C_{2-8}$ alkoxyalkyl, alkoxycarbonyl, $C_{1-8}$ alkyl, arylalkoxycarbonyl, $C_{2-6}$ alkenyl, $C_{2-6}$ alkynyl, carboxy, halogen (F, Cl, Br, I), haloalkyl, $CF_3$, $N_3$, CN, N(R')$_2$, SR', OCOR', N(COR')R$^1$, N(COR')COR', SCOR', S(O)$_2$NR'$_2$, S(O)$_2$R'. Each R' is independently H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, arylalkyl, or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl, wherein a $C_{1-6}$ alkyl, $C_{2-6}$ alkenyl, or $C_{2-6}$ alkynyl moiety (including those present on an ester or an amide moiety) can optionally be substituted with from one to three —CN, thio, aryl—$C_{1-6}$ alkyl, $C_{1-6}$ alkyl, —$C_{1-6}$ thioalkyl, $C_{1-6}$ haloalkyl, —$C_{1-6}$ hydroxyalkyl, —$C_{1-6}$ alkoxy, —$C_{1-6}$ alkoxy—$C_{1-6}$ alkoxy, —$C_{1-6}$ alkoxy—$C_{1-6}$ alkoxy—$C_{1-6}$ alkoxy, —$C_{1-6}$ thioalkyl, $CO_2R^1$, and —$CO_2NR^{12}$ moieties, and the two R groups on an amide moiety can optionally link to form a 5-7 membered azacyclic ring.

In various cases, the compound disclosed herein has a structure of any one of:

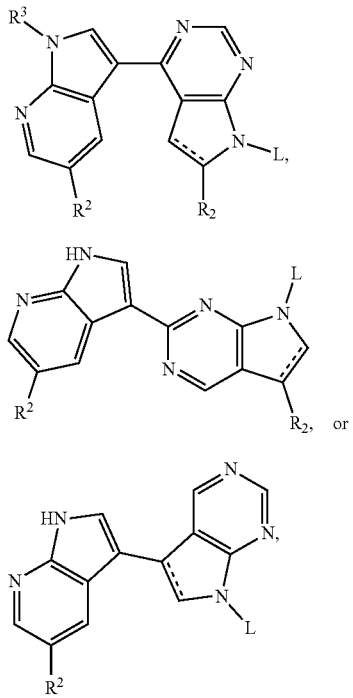

wherein
a dashed line represents either a single or a double bond,
L is:
i) H,
ii) —C$_{1-6}$ alkyl, —C$_{1-6}$ alkyl-OCONR$_2$, —C$_{1-6}$ alkyl-CONR$_2$, C$_{1-6}$ alkyl-CO$_2$R, C$_{1-6}$ alkyl-COR, C$_{1-6}$ alkyl-NRC(O)NR$_2$, C$_{1-6}$ alkyl-NRC(O)OR, C$_{1-6}$ alkyl-NRC(O)R, and C$_{1-6}$ alkyl-NR$_2$, wherein the C$_{2-6}$ alkyl can optionally include a double bond;
iii) C$_{5-6}$ cycloalkyl-OCONR$_2$, C$_{5-6}$ cycloalkyl-CONR$_2$, C$_{5-6}$ cycloalkyl-CO$_2$R, C$_{5-6}$ cycloalkyl-COR, C$_{5-6}$ cycloalkyl-NRC(O)NR$_2$, C$_{5-6}$ cycloalkyl-NRC(O)OR, C$_{5-6}$ cycloalkyl-NRC(O)R, and C$_{5-6}$ cycloalkyl-NR$_2$, where the cycloalkyl ring can be substituted with from one to three C$_{1-6}$ alkyl groups, and where the C$_{5-6}$ cycloalkyl ring can optionally include a double bond, an oxygen, or an NR group;
iv) —C$_{1-6}$ alkyl—C$_{5-6}$ cycloalkyl, —C$_{1-6}$ alkyl—C$_{5-6}$ cycloalkyl-OCONR$_2$, —C$_{1-6}$ alkyl—C$_{5-6}$ cycloalkyl-CONR$_2$, —C$_{1-6}$ alkyl—C$_{5-6}$ cycloalkyl-CO$_2$R, —C$_{1-6}$ alkyl—C$_{5-6}$ cycloalkyl-COR, —C$_{1-6}$ alkyl—C$_{5-6}$ cycloalkyl-NRC(O)NR$_2$, —C$_{1-6}$ alkyl—C$_{5-6}$ cycloalkyl-NRC(O)OR, —C$_{1-6}$ alkyl—C$_{5-6}$ cycloalkyl-NRC(O)R, and —C$_{1-6}$ alkyl—C$_{5-6}$ cycloalkyl-NR$_2$, where the cycloalkyl ring can be substituted with from one to three C$_{1-6}$ alkyl groups, and where the C$_{5-6}$ cycloalkyl ring can optionally include a double bond, an oxygen, or nitrogen;
v) 2.2.2 bicyclooctyl-OCONR$_2$, 2.2.2 bicyclooctyl-CONR$_2$, 2.2.2 bicyclooctyl-CO$_2$R, 2.2.2 bicyclooctyl-COR, 2.2.2 bicyclooctyl-NRC(O)NR$_2$, 2.2.2 bicyclooctyl-NRC(O)OR, 2.2.2 bicyclooctyl-NRC(O)R, and 2.2.2 bicyclooctyl-NR$_2$, wherein the 2.2.2 bicyclooctyl ring can optionally include a double bond;
R is H, C$_{1-6}$alkyl, C$_{1-6}$alkyl-CO$_2$R$^1$, —CO$_2$R$^1$, CON(R$^1$)$_2$, or C$_{1-6}$ alkyl-CON(R$^1$)$_2$, and R$^1$ is H or C$_{1-6}$ alkyl;
each R$^2$ is independently H, halo, —CN, C$_{1-6}$ alkyl, C$_{1-6}$ haloalkyl, C$_{2-6}$ alkenyl, C$_{2-6}$ alkynyl, CO$_2$R, CONR$_2$, phenyl, pyridinyl, thiophenyl, furanyl, or imidazolyl, wherein the phenyl, pyridinyl, thiophenyl, furanyl, or imidazolyl is optionally substituted with one or more (e.g., 1 or 2) substituents selected from the group consisting of hydroxy, C$_{1-6}$ alkoxy, C$_{2-8}$ alkoxyalkyl, alkoxycarbonyl, C$_{1-8}$ alkyl, arylalkoxycarbonyl, C$_{2-6}$ alkenyl, C$_{2-6}$ alkynyl, carboxy, halogen, haloalkyl (e.g., CF$_3$), N$_3$, CN, N(R')$_2$, SR', OCOR', N(COR')R', N(COR')COR', SCOR', S(O)$_2$NR'$_2$, S(O)$_2$R', and each R' is independently H or C$_{1-6}$ alkyl;
R$^3$ is H, or —SO$_2$-phenyl, wherein the phenyl is optionally substituted with one or more (e.g., one or two) substituents selected from the group consisting of hydroxy, C$_{1-6}$ alkoxy, C$_{2-8}$ alkoxyalkyl, alkoxycarbonyl, C$_{1-8}$ alkyl, arylalkoxycarbonyl, C$_{2-6}$ alkenyl, C$_{2-6}$ alkynyl, carboxy, halogen, haloalkyl (e.g., CF$_3$), N$_3$, CN, N(R')$_2$, SR', OCOR', N(COR')R', N(COR')COR', SCOR', S(O)$_2$NR'$_2$, S(O)$_2$R$^1$, and each R$^1$ is independently H or C$_{1-6}$ alkyl;
wherein a C$_{1-6}$ alkyl, C$_{2-6}$ alkenyl, or C$_{2-6}$ alkynyl moiety, wherever it occurs, can optionally be substituted with from one to three substituents which are not further substituted and which are independently selected from the group consisting of —CN, thio, aryl—C$_{1-6}$ alkyl, pyridinyl, ethoxymethyl-pyridinyl, indolinyl, C$_{1-6}$ alkyl, C$_{1-6}$ alkyl—C$_{36}$cycloalkyl, C$_{3-6}$cycloalkyl, —C$_{1-6}$ thioalkyl, C$_{1-6}$ haloalkyl, —C$_{1-6}$ hydroxyalkyl, —C$_{1-6}$ alkoxy, —C$_{1-6}$ alkoxy—C$_{1-6}$ alkoxy, —C$_{1-6}$ alkoxy—C$_{1-6}$ alkoxy—C$_{1-6}$ alkoxy, CO$_2$H, CO$_2$C$_{1-6}$alkyl, CO$_2$NH$_2$, CO$_2$NHC$_{1-6}$alkyl, and —CO$_2$N(C$_{1-6}$alkyl)$_2$; and
wherein if two alkyl groups reside on an amide moiety, they can optionally together form a 5-7 membered ring with the nitrogen of the amide moiety;
or a pharmaceutically acceptable salt thereof.

In some cases, Formula I has a structure of IA:

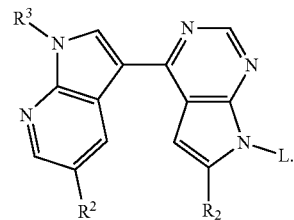

In some cases, Formula II has a structure of IIA:

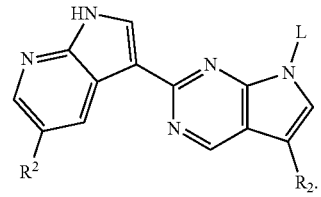

In some cases, Formula III has a structure of IIA:

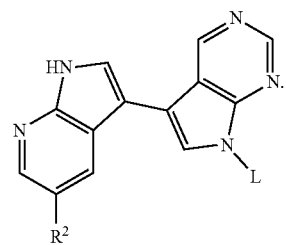

In various embodiments, L is $C_{1-6}$alkylCONR$_2$. In some cases, L is CH$_2$CONHMe, CH$_2$CONMe$_2$, CH$_2$CH$_2$CONHMe, CH$_2$CH$_2$CONMe$_2$, CH$_2$CH(Me)CONHMe, CH$_2$CH(Me)CONMe$_2$, C(Me)(Et)CONHCH$_2$CF$_3$, CH$_2$CONHCH$_2$CO$_2$H, CH$_2$CH$_2$CONHCH$_2$CO$_2$H, CH$_2$CONHCH(Me)CO$_2$H, CH$_2$CH$_2$CONHCH(Me)CO$_2$H, CH$_2$CONHCH(CH$_2$OH)CO$_2$H, CH$_2$CH$_2$CONHCH(CH$_2$OH)CO$_2$H, CH$_2$CONHCH(CH$_2$Ph)CO$_2$H, CH$_2$CH$_2$CONHCH(CH$_2$Ph)CO$_2$H, CH$_2$CONHCH(CO$_2$H)CH$_2$CO$_2$H, CH$_2$CH$_2$CONHCH(CO$_2$H)CH$_2$CO$_2$H, CH$_2$CONHCH(CO$_2$H)CH$_2$CONH$_2$, CH$_2$CH$_2$CONHCH(CO$_2$H)CH$_2$CONH$_2$, CH$_2$CONHCH(CO$_2$Me)CH$_2$CO$_2$H, CH$_2$CH$_2$CONHCH(CO$_2$Me)CH$_2$CO$_2$H, CH$_2$CONHCH(CO$_2$Me)CH$_2$CONH$_2$, CH$_2$CH$_2$CONHCH(CO$_2$Me)CH$_2$CONH$_2$, CH$_2$CONHCH$_2$CO$_2$Me, CH$_2$CH$_2$CONHCH$_2$CO$_2$Me, CH$_2$CONHCH(Me)CO$_2$Me, CH$_2$CH$_2$CONHCH(Me)CO$_2$Me, CH$_2$CONHCH(CH$_2$OH)CO$_2$Me, CH$_2$CH$_2$CONHCH(CH$_2$OH)CO$_2$Me, CH$_2$CONHCH(CH$_2$Ph)CO$_2$Me, CH$_2$CONHCH(CO$_2$Me)CH$_2$CO$_2$Me, CH$_2$CONHCH(CO$_2$H)CH$_2$CO$_2$Me,

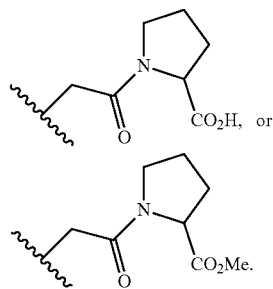

In some cases, L is $C_{1-6}$alkyl-CO$_2$R. For example, L can be CH$_2$CO$_2$H, CH$_2$CH$_2$CO$_2$H, CH═CHCO$_2$H, CH$_2$CH═CHCO$_2$H, CH(CMe$_3$)CO$_2$H, CH$_2$CH(CMe$_3$)CO$_2$H, CH$_2$CH(Me)CO$_2$H, CH(Me)CO$_2$H, CH(Me)CH$_2$CO$_2$H, CH$_2$CO$_2$Me, CH$_2$CH$_2$CO$_2$Me, CH═CHCO$_2$Me, CH$_2$CH═CHCO$_2$Me, CH(CMe$_3$)CO$_2$Me, CH$_2$CH(CMe$_3$)CO$_2$Me, CH$_2$CH(Me)CO$_2$Me, CH(Me)CO$_2$Me, CH(Me)CH$_2$CO$_2$Me, CH$_2$CO$_2$Et, CH$_2$CH$_2$CO$_2$Et, CH═CHCO$_2$Et, CH$_2$CH═CHCO$_2$Et, CH(CMe$_3$)CO$_2$Et, CH$_2$CH(CMe$_3$)CO$_2$Et, CH$_2$CH(Me)CO$_2$Et, CH(Me)CO$_2$Et, CH(Me)CH$_2$CO$_2$Et, CH$_2$CO$_2$CMe$_3$, CH$_2$CH$_2$CO$_2$CMe$_3$, CH═CHCO$_2$CMe$_3$, CH$_2$CH═CHCO$_2$CMe$_3$, CH(CMe$_3$)CO$_2$CMe$_3$, CH$_2$CH(CMe$_3$)CO$_2$CMe$_3$, CH$_2$CH(Me)CO$_2$CMe$_3$, CH(Me)CO$_2$CMe$_3$, or CH(Me)CH$_2$CO$_2$CMe$_3$.

In some cases, L is $C_{1-6}$alkyl-NRC(O)R, $C_{1-6}$alkyl-NRC(O)OR, or $C_{1-6}$alkyl-NRC(O)NR. For example, L can be CH$_2$CH$_2$NHCOMe, CH$_2$CH$_2$NHCO$_2$CMe$_3$, CH$_2$CH$_2$NHCONHMe, CH$_2$CH$_2$NHCO$_2$Me, or CH$_2$CH$_2$NHCONMe$_2$.

In some cases, L is X-A, where X is is a bond, CH$_2$, or CH$_2$CH$_2$; and A is

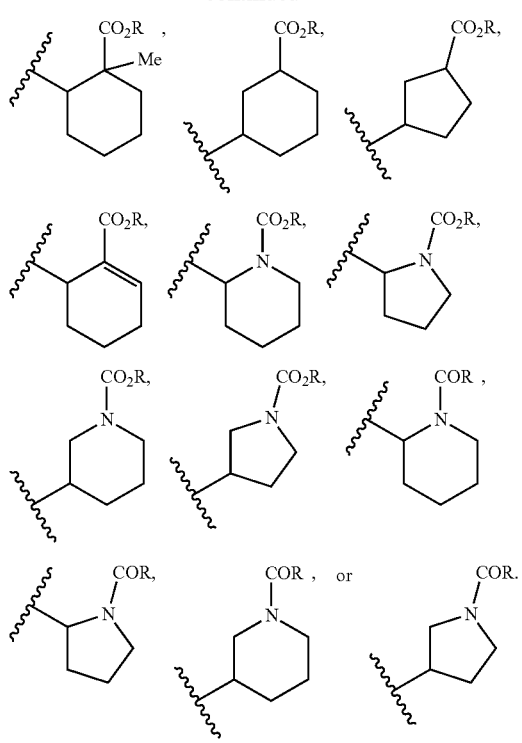

In some embodiments here, R is H, Me, Et, or CMe$_3$.

In some cases, L is $C_{5-6}$cycloalkyl-CONR$_2$, $C_{5-6}$cycloalkyl-NRCONR$_2$, $C_{5-6}$cycloalkyl-NRCOR, $C_{5-6}$cycloalkyl-COR, or $C_{5-6}$cycloalkyl-NR$_2$. For example, L can be X-A; X is a bond, CH$_2$, or CH$_2$CH$_2$; and A is

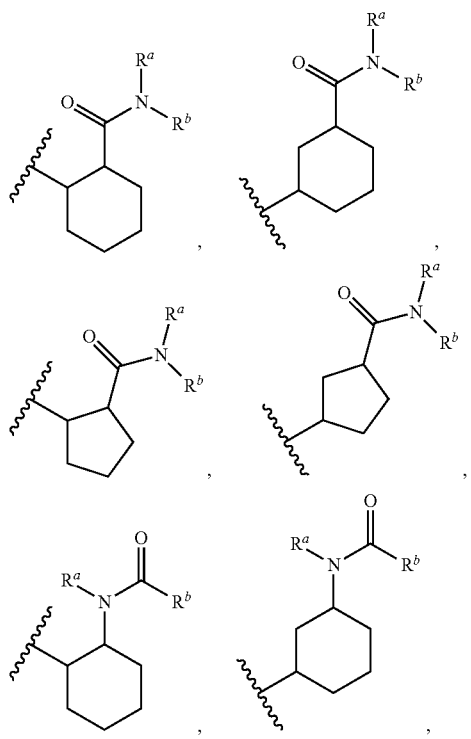

-continued
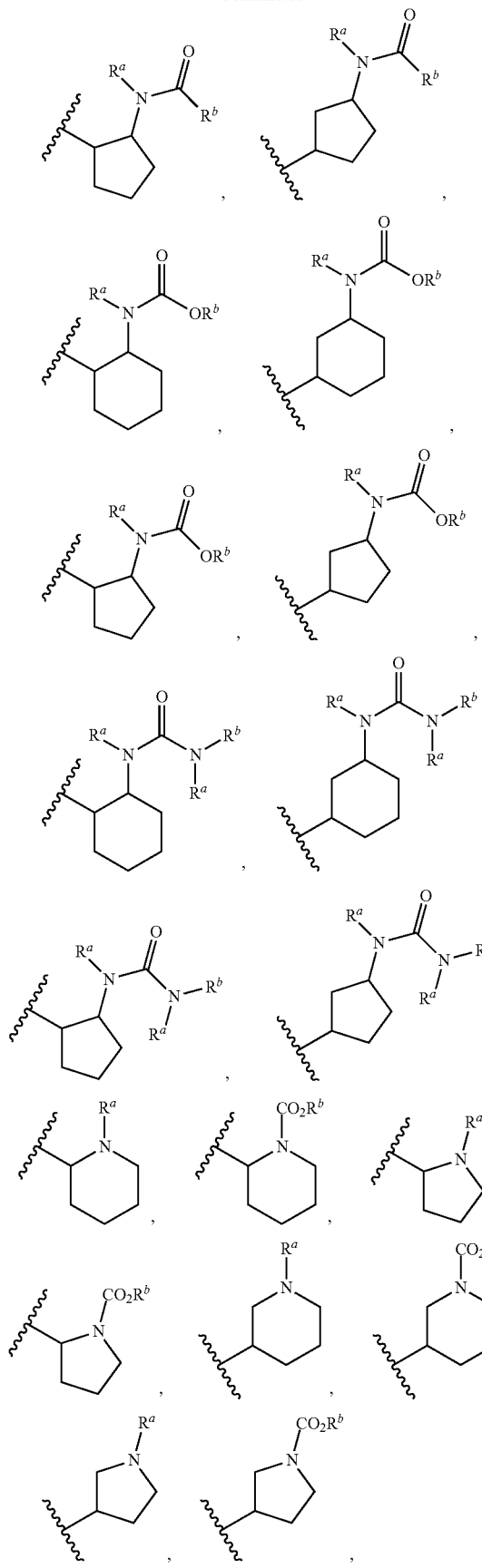
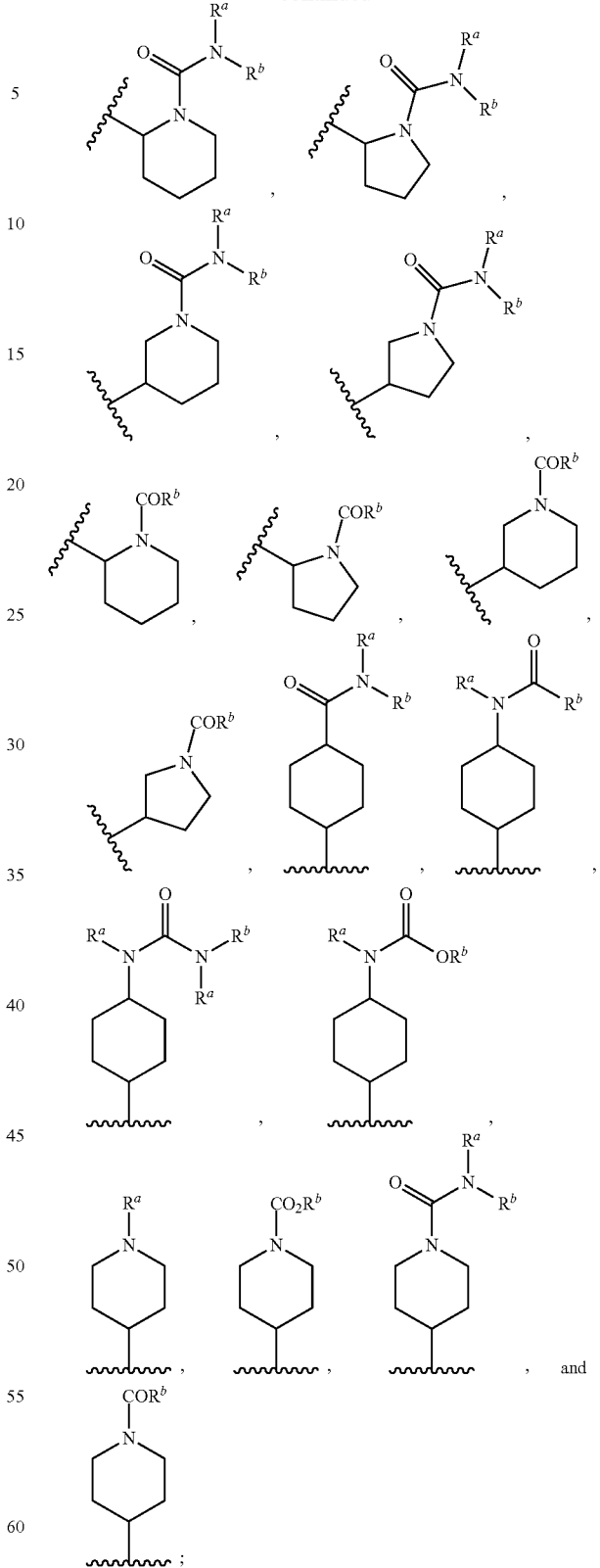
$R^a$ is independently H or Me; and each $R^b$ is independently H, Me, $CMe_3$, $(CH_2CH_2O)_3Et$, $CH_2O(CH_2CH_2O)_2Et$, $CH_2CH_2OCH_2CH_2O(CH_2)_3Me$, $(CH_2)_5O(CH_2)_4Me$, $(CH_2)_4O(CH_2)_4Me$, $CH_2CH_2O(CH_2)_5OEt$, CH₂CH₂OCH₂CH₂O(CH₂)₄Me, (CH₂)₅OCH₂CH₂OEt, (CH₂)₄OCH₂CH₂OEt, CH₂OCH₂CH₂O(CH₂)₄Me, pyrindinyl, or

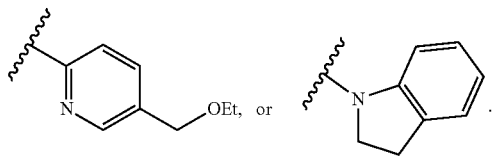

In some cases, L is

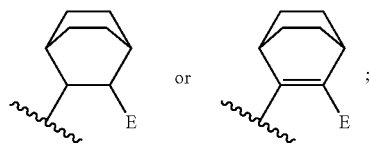

E is CO₂Rᵃ, CONRᵃRᵇ, NRᵃRᵇ, NRᵃCONRᵃRᵇ, NRᵃCORᵃ; or NRᵃCO₂Rᵃ; each Rᵃ is independently H, Me, Et, or CMe₃; and each Rᵇ is independently H, Me, Et, CH₂CONHMe, CH₂CONMe₂, or CH₂CONH₂. In some cases, L is

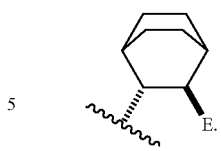

In some aspects, for any of Formulas I-III, each $R^2$ and $R^3$ are independently, H, F or Cl. In various cases, at least one $R^2$ is F. In some cases, at least one $R^2$ is Cl. In some cases, one $R^2$ is F and the other $R^2$ is F or Cl. In some cases, at least one $R^2$ is H. In some cases, each $R^2$ is H. In some cases, at least one $R^2$ is phenyl, pyridinyl, hydroxyphenyl, $CF_3$, —C≡C—CH₂cyclopropyl, —C≡C— cyclopropyl, furanyl, thienyl, methyl, imidazolyl, $CH(CH_3)_2$, —(CH₂)₂pyridinyl, —C≡C—(CH₂)₂SCH₃, ON, —(CH₂)₄SCH₃, —(CH₂)₄CN, CO₂H, CONHCH₃, —C≡C—(CH₂)₂CN, CON(CH₃)₂, CO₂CH₂CH₃, —CH=CH₂, fluoropyridinyl, chloropyridinyl, or cyanopyridinyl. In some cases, $R^3$ is H.

It is understood that selections of values of each variable are those that result in the formation of stable or chemically feasible compounds.

Specific compounds contemplated include compounds in the following Tables. Compounds showing particular stereocenters indicate at least a relative stereoisomerism. Compounds having a chiral center without indication of a particular stereoisomerism indicates a mixture of sterocenters at that chiral center.

The compound can be a compound as listed in Table A, or a pharmaceutically acceptable salt thereof.

TABLE A

| A1 | 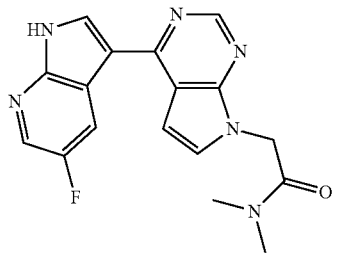 [SMILES: CN(C)C(=O)Cn1ccc2c(-c3c[nH]c4ncc(F)cc34)ncnc21] |
|---|---|
| A2 | 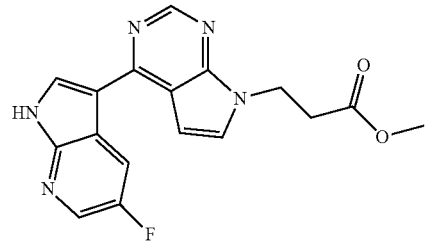 [SMILES: COC(=O)CCn1ccc2c(-c3c[nH]c4ncc(F)cc34)ncnc21] |
| A3 | 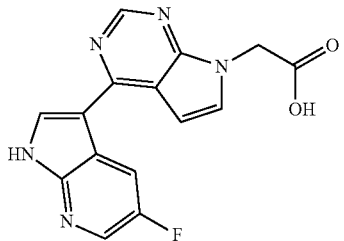 [SMILES: O=C(O)Cn1ccc2c(-c3c[nH]c4ncc(F)cc34)ncnc21] |

TABLE A-continued
A4 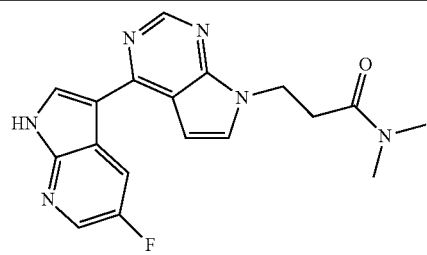
A5 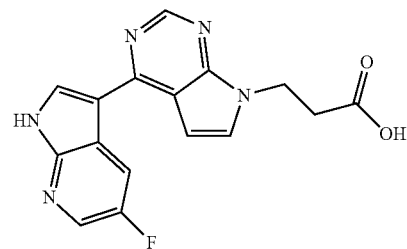 [SMILES: O=C(O)CCn1ccc2c(-c3c[nH]c4ncc(F)cc34)ncnc21]
A6 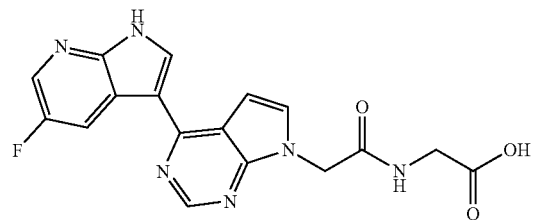 [SMILES: O=C(O)CNC(=O)Cn1ccc2c(-c3c[nH]c4ncc(F)cc34)ncnc21]
A7 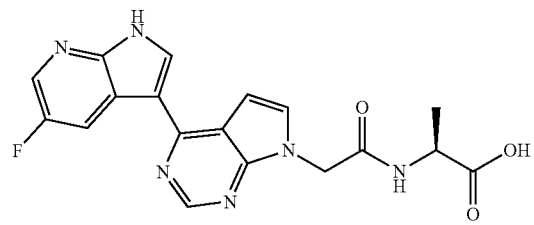 [SMILES: C[C@H](NC(=O)Cn1ccc2c(-c3c[nH]c4ncc(F)cc34)ncnc21)C(=O)O]
A8 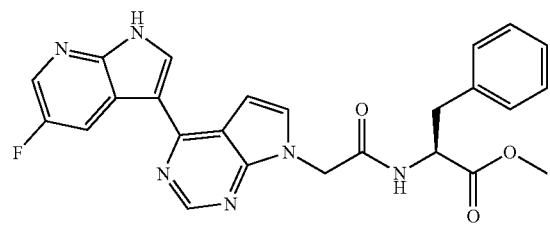 [SMILES: COC(=O)[C@H](Cc1ccccc1)NC(=O)Cn1ccc2c(-c3c[nH]c4ncc(F)cc34)ncnc21]
A9 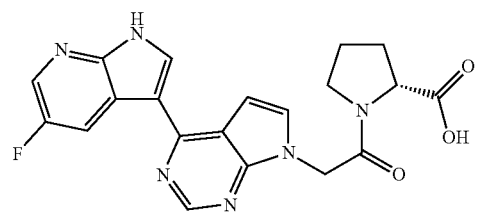 [SMILES: O=C(O)[C@H]1CCCN1C(=O)Cn1ccc2c(-c3c[nH]c4ncc(F)cc34)ncnc21]
A10 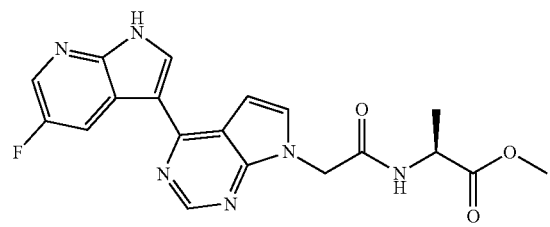 [SMILES: COC(=O)[C@H](C)NC(=O)Cn1ccc2c(-c3c[nH]c4ncc(F)cc34)ncnc21]

TABLE A-continued
A11 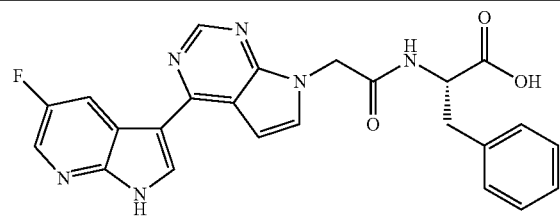
A12 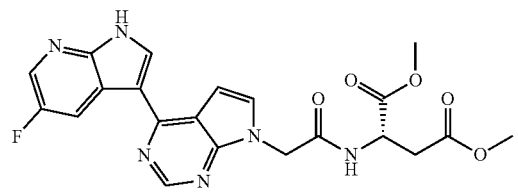 [SMILES: COC(=O)C[C@H](NC(=O)Cn1ccc2c(-c3c[nH]c4ncc(F)cc34)ncnc21)C(=O)OC]
A13 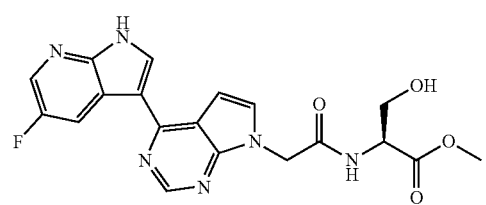 [SMILES: COC(=O)[C@H](CO)NC(=O)Cn1ccc2c(-c3c[nH]c4ncc(F)cc34)ncnc21]
A14 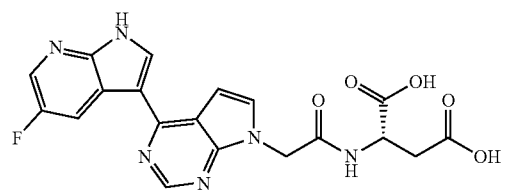 [SMILES: O=C(O)C[C@H](NC(=O)Cn1ccc2c(-c3c[nH]c4ncc(F)cc34)ncnc21)C(=O)O]
A15 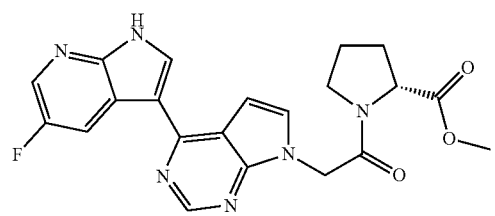 [SMILES: COC(=O)[C@H]1CCCN1C(=O)Cn1ccc2c(-c3c[nH]c4ncc(F)cc34)ncnc21]
A16 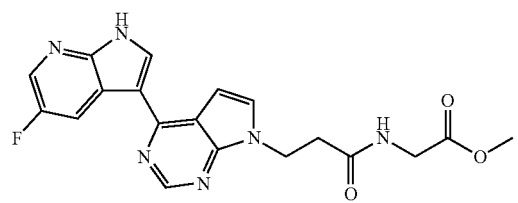 [SMILES: COC(=O)CNC(=O)CCn1ccc2c(-c3c[nH]c4ncc(F)cc34)ncnc21]
A17 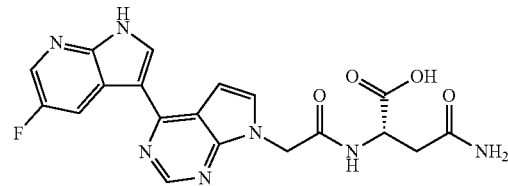 [SMILES: NC(=O)C[C@H](NC(=O)Cn1ccc2c(-c3c[nH]c4ncc(F)cc34)ncnc21)C(=O)O]
A18 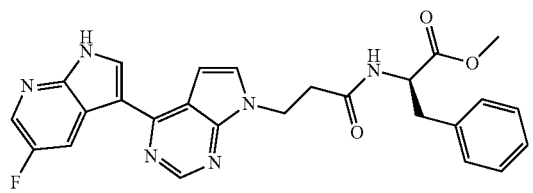 [SMILES: COC(=O)[C@@H](Cc1ccccc1)NC(=O)CCn1ccc2c(-c3c[nH]c4ncc(F)cc34)ncnc21]

TABLE A-continued
A19 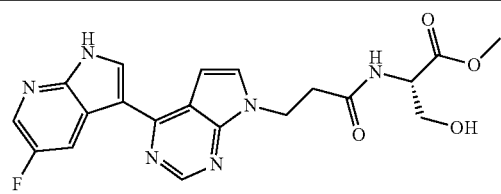
A20 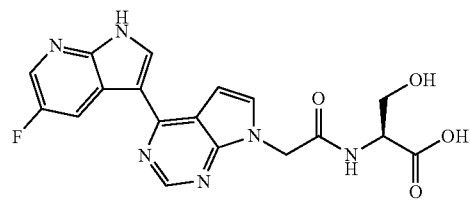 [SMILES: O=C(Cn1ccc2c(-c3c[nH]c4ncc(F)cc34)ncnc21)N[C@@H](CO)C(=O)O]
B1 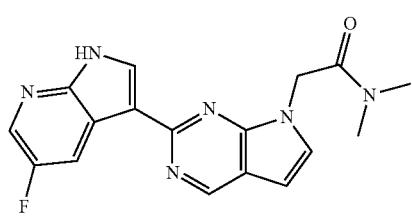 [SMILES: CN(C)C(=O)Cn1ccc2cnc(-c3c[nH]c4ncc(F)cc34)nc21]
B2 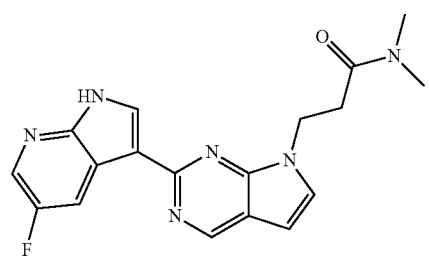 [SMILES: CN(C)C(=O)CCn1ccc2cnc(-c3c[nH]c4ncc(F)cc34)nc21]
B3 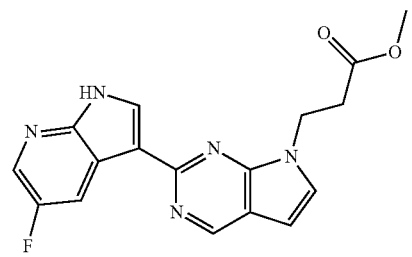 [SMILES: COC(=O)CCn1ccc2cnc(-c3c[nH]c4ncc(F)cc34)nc21]
B4 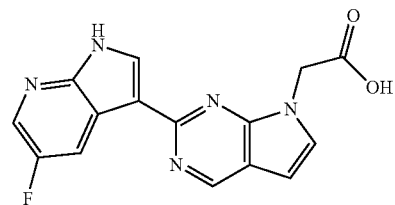 [SMILES: O=C(O)Cn1ccc2cnc(-c3c[nH]c4ncc(F)cc34)nc21]
B5 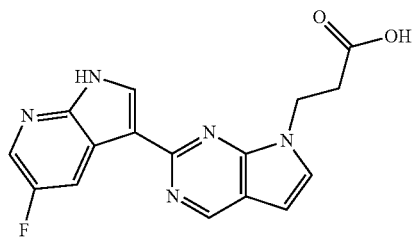 [SMILES: O=C(O)CCn1ccc2cnc(-c3c[nH]c4ncc(F)cc34)nc21]

TABLE A-continued
B6 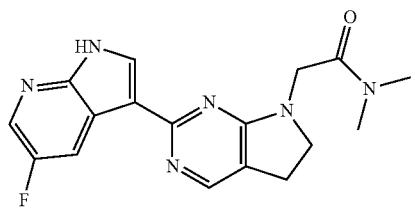
B7 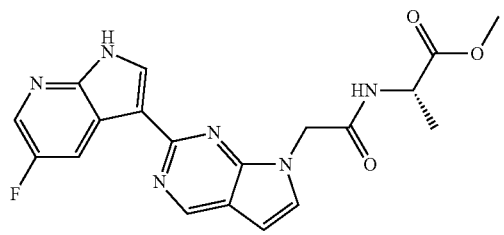 [SMILES: COC(=O)[C@H](C)NC(=O)Cn1ccc2cnc(-c3c[nH]c4ncc(F)cc34)nc21]
B8 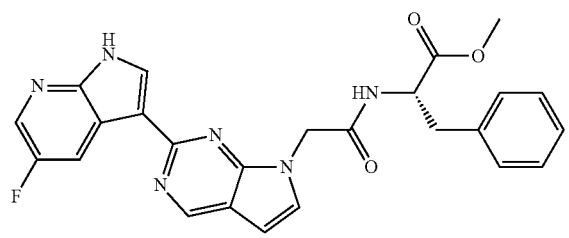 [SMILES: COC(=O)[C@H](Cc1ccccc1)NC(=O)Cn1ccc2cnc(-c3c[nH]c4ncc(F)cc34)nc21]
B9 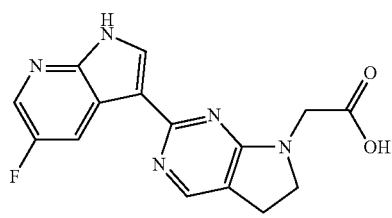 [SMILES: O=C(O)CN1CCc2cnc(-c3c[nH]c4ncc(F)cc34)nc21]
B10 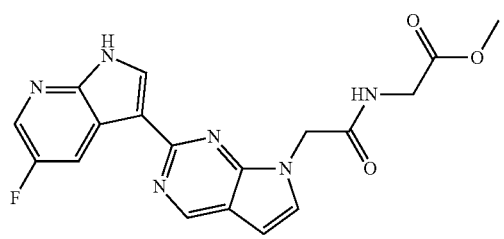 [SMILES: COC(=O)CNC(=O)Cn1ccc2cnc(-c3c[nH]c4ncc(F)cc34)nc21]
B11 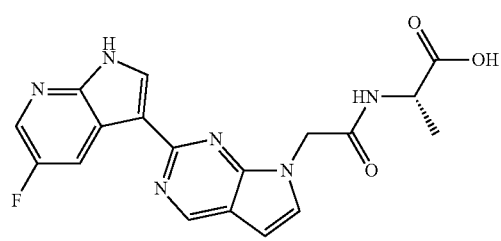
B12 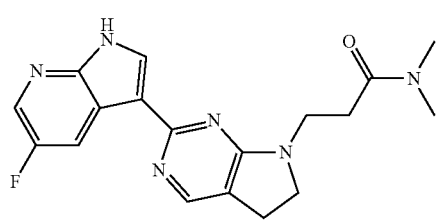 [SMILES: CN(C)C(=O)CCN1CCc2cnc(-c3c[nH]c4ncc(F)cc34)nc21]

TABLE A-continued
B13 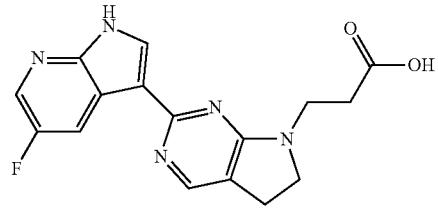 [SMILES: O=C(O)CCN1CCc2cnc(-c3c[nH]c4ncc(F)cc34)nc21]
B14 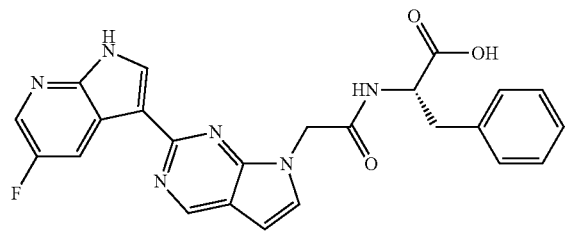 [SMILES: O=C(Cn1ccc2cnc(-c3c[nH]c4ncc(F)cc34)nc21)N[C@@H](Cc1ccccc1)C(=O)O]
B15 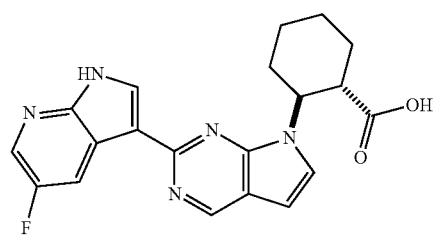
B16 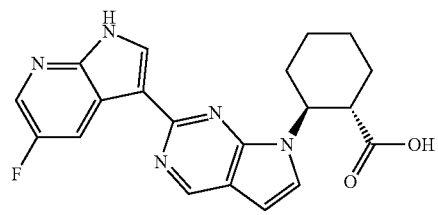 [SMILES: O=C(O)[C@H]1CCCC[C@@H]1n1ccc2cnc(-c3c[nH]c4ncc(F)cc34)nc21]
B17 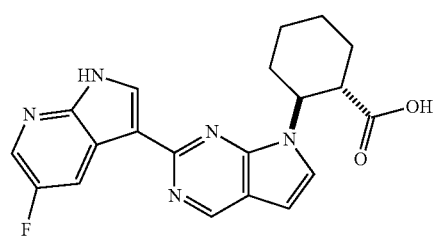
B18 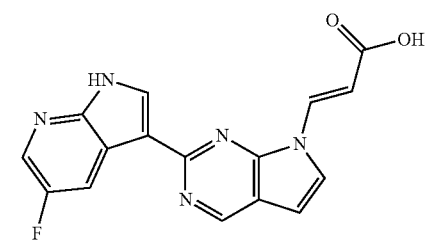 [SMILES: O=C(O)/C=C/n1ccc2cnc(-c3c[nH]c4ncc(F)cc34)nc21]
B19 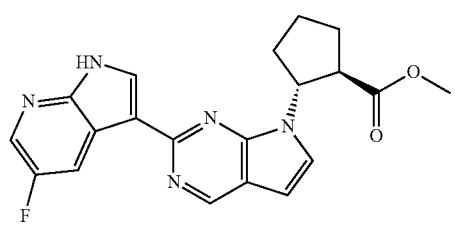 [SMILES: COC(=O)[C@@H]1CCC[C@H]1n1ccc2cnc(-c3c[nH]c4ncc(F)cc34)nc21]

TABLE A-continued
B20 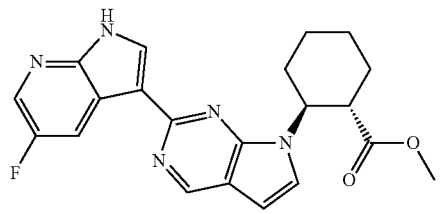 [SMILES: COC(=O)[C@H]1CCCC[C@@H]1n1ccc2cnc(-c3c[nH]c4ncc(F)cc34)nc21]
B21 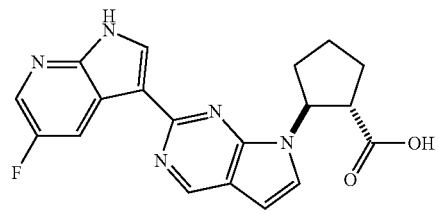
B22 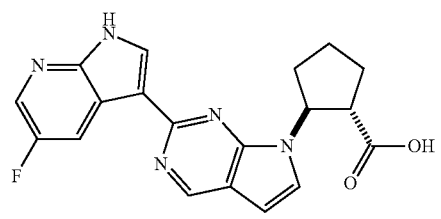
B23 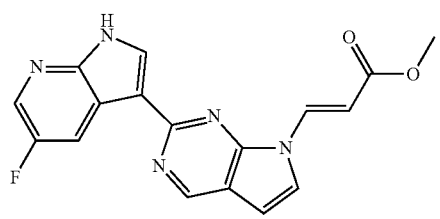 [SMILES: COC(=O)/C=C/n1ccc2cnc(-c3c[nH]c4ncc(F)cc34)nc21]
B24 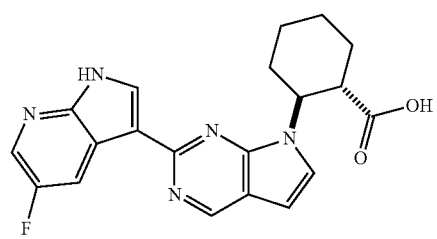
B25 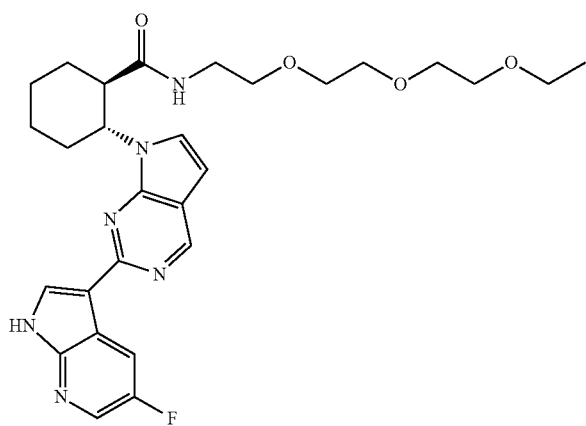 [SMILES: CCOCCOCCOCCNC(=O)[C@@H]1CCCC[C@H]1n1ccc2cnc(-c3c[nH]c4ncc(F)cc34)nc21]

TABLE A-continued
B26
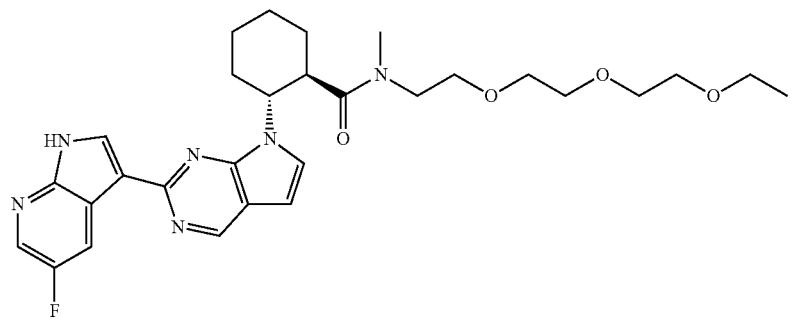 [SMILES: CCOCCOCCOCCN(C)C(=O)[C@@H]1CCCC[C@H]1n1ccc2cnc(-c3c[nH]c4ncc(F)cc34)nc21]
B27
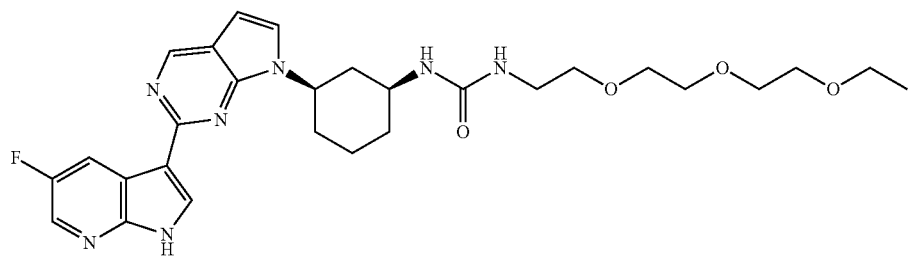 [SMILES: CCOCCOCCOCCNC(=O)N[C@H]1CCC[C@@H](n2ccc3cnc(-c4c[nH]c5ncc(F)cc45)nc32)C1]
B28
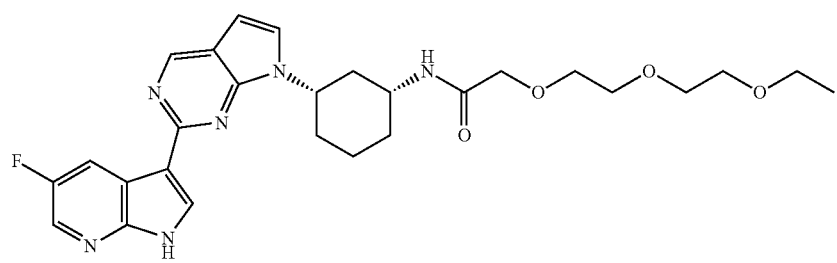 [SMILES: CCOCCOCCOCC(=O)N[C@@H]1CCC[C@H](n2ccc3cnc(-c4c[nH]c5ncc(F)cc45)nc32)C1]
B29
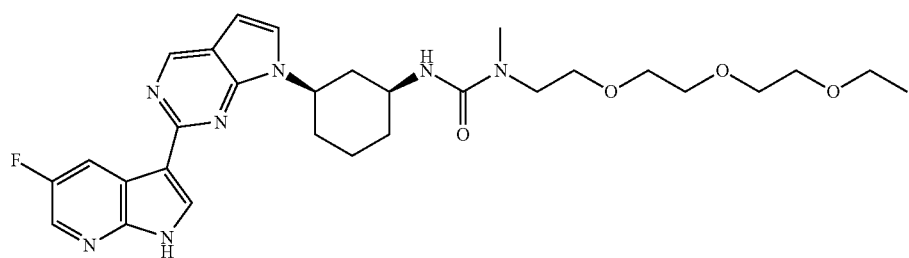 [SMILES: CCOCCOCCOCCN(C)C(=O)N[C@H]1CCC[C@@H](n2ccc3cnc(-c4c[nH]c5ncc(F)cc45)nc32)C1]
B30
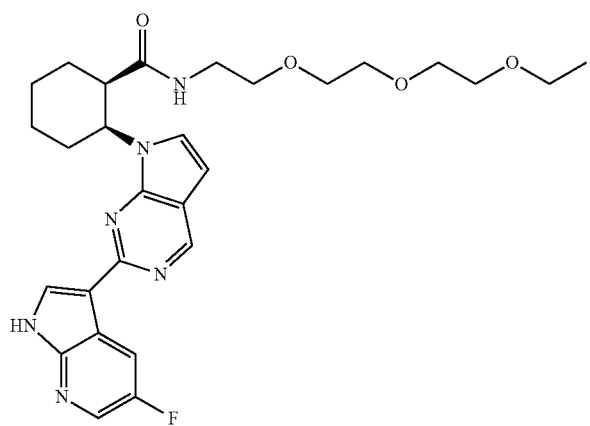 [SMILES: CCOCCOCCOCCNC(=O)[C@@H]1CCCC[C@@H]1n1ccc2cnc(-c3c[nH]c4ncc(F)cc34)nc21]

TABLE A-continued
B31
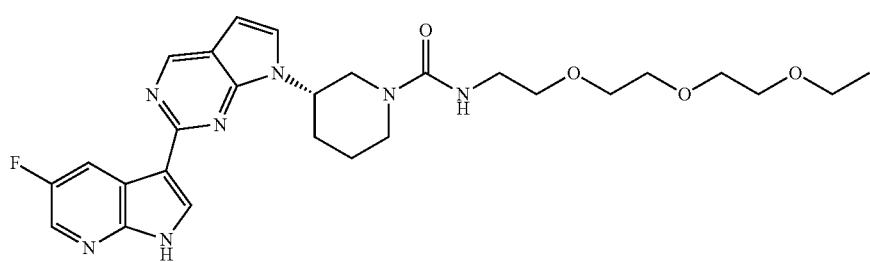 [SMILES: CCOCCOCCOCCNC(=O)N1CCC[C@H](n2ccc3cnc(-c4c[nH]c5ncc(F)cc45)nc32)C1]
B32
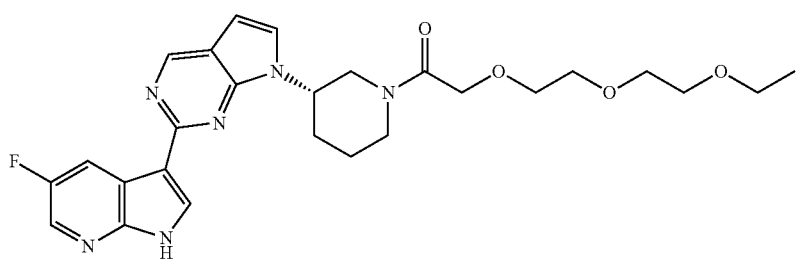 [SMILES: CCOCCOCCOCC(=O)N1CCC[C@H](n2ccc3cnc(-c4c[nH]c5ncc(F)cc45)nc32)C1]
B33
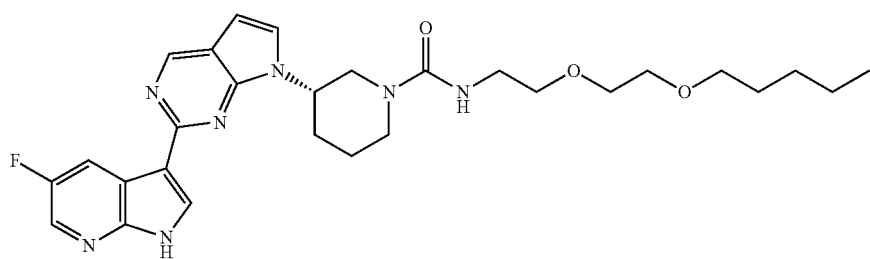 [SMILES: CCCCCOCCOCCNC(=O)N1CCC[C@H](n2ccc3cnc(-c4c[nH]c5ncc(F)cc45)nc32)C1]
B34
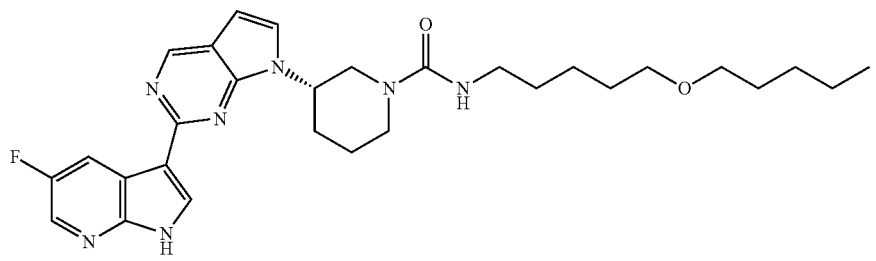 [SMILES: CCCCCOCCCCCNC(=O)N1CCC[C@H](n2ccc3cnc(-c4c[nH]c5ncc(F)cc45)nc32)C1]
B35
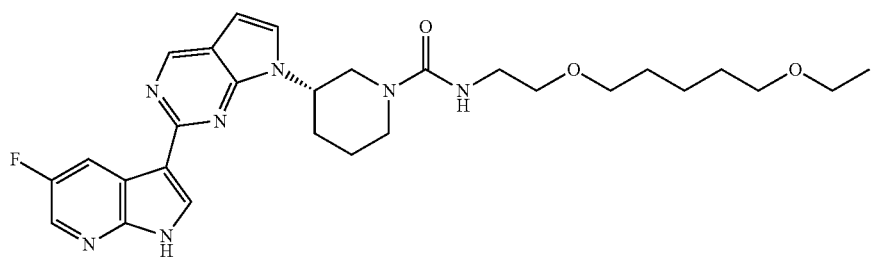 [SMILES: CCOCCCCCOCCNC(=O)N1CCC[C@H](n2ccc3cnc(-c4c[nH]c5ncc(F)cc45)nc32)C1]
B36
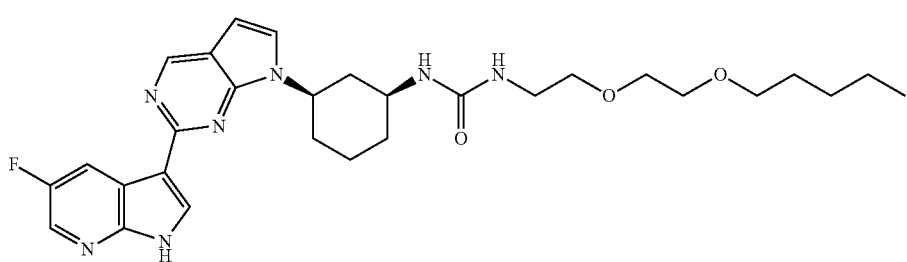 [SMILES: CCCCCOCCOCCNC(=O)N[C@H]1CCC[C@@H](n2ccc3cnc(-c4c[nH]c5ncc(F)cc45)nc32)C1]

TABLE A-continued
B37 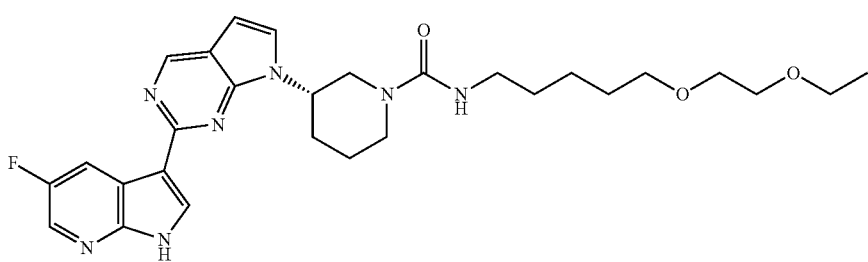 [SMILES: CCOCCOCCCCCNC(=O)N1CCC[C@H](n2ccc3cnc(-c4c[nH]c5ncc(F)cc45)nc32)C1]
B38 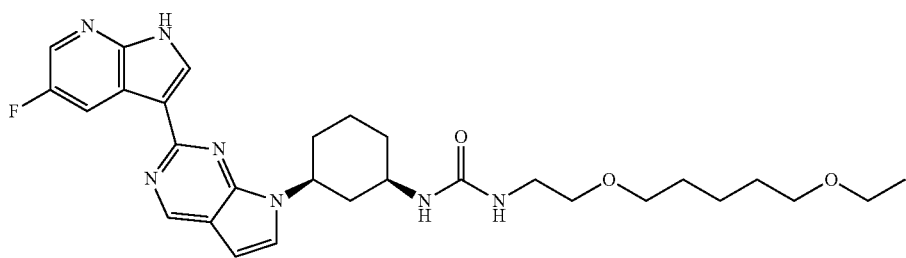 [SMILES: CCOCCCCCOCCNC(=O)N[C@@H]1CCC[C@H](n2ccc3cnc(-c4c[nH]c5ncc(F)cc45)nc32)C1]
B39 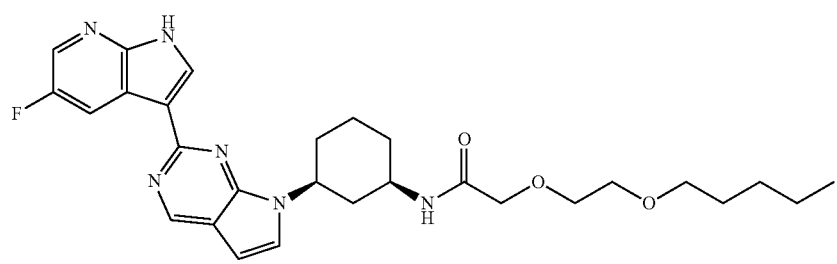 [SMILES: CCCCCOCCOCC(=O)N[C@@H]1CCC[C@H](n2ccc3cnc(-c4c[nH]c5ncc(F)cc45)nc32)C1]
B40 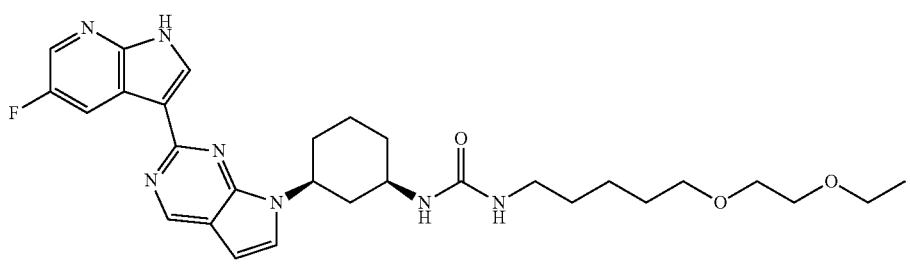 [SMILES: CCOCCOCCCCCNC(=O)N[C@@H]1CCC[C@H](n2ccc3cnc(-c4c[nH]c5ncc(F)cc45)nc32)C1]
B41 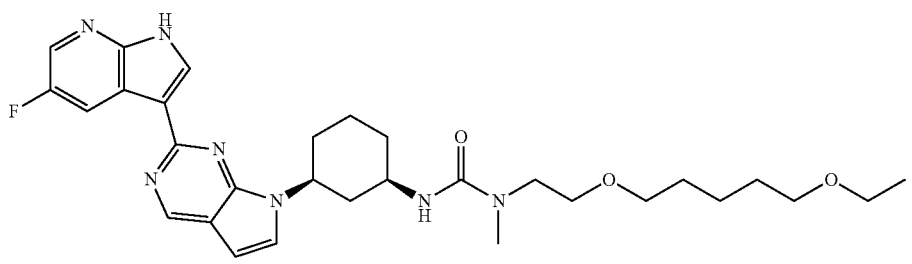 [SMILES: CCOCCCCCOCCN(C)C(=O)N[C@@H]1CCC[C@H](n2ccc3cnc(-c4c[nH]c5ncc(F)cc45)nc32)C1]
B42 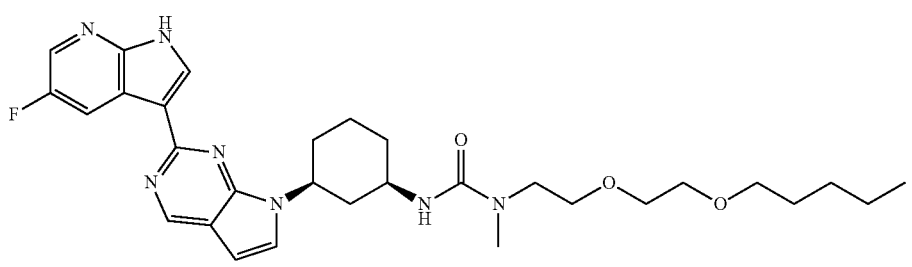 [SMILES: CCCCCOCCOCCN(C)C(=O)N[C@@H]1CCC[C@H](n2ccc3cnc(-c4c[nH]c5ncc(F)cc45)nc32)C1]

TABLE A-continued
B43
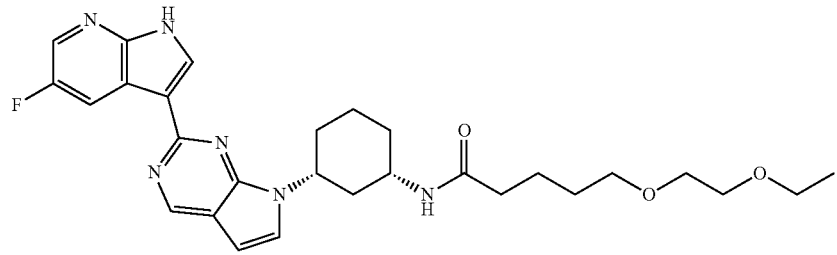 [SMILES: CCOCCOCCCCC(=O)N[C@H]1CCC[C@@H](n2ccc3cnc(-c4c[nH]c5ncc(F)cc45)nc32)C1]
B44
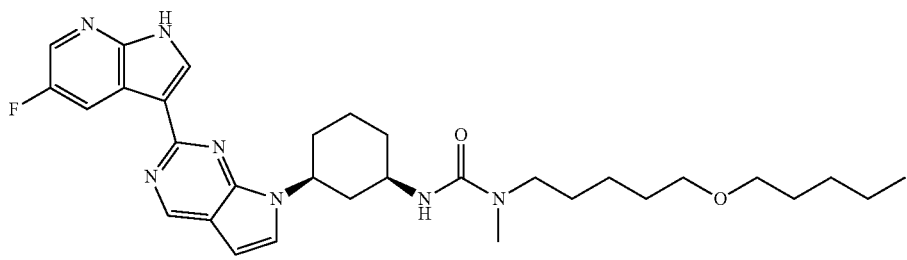 [SMILES: CCCCCOCCCCCN(C)C(=O)N[C@@H]1CCC[C@H](n2ccc3cnc(-c4c[nH]c5ncc(F)cc45)nc32)C1]
B45
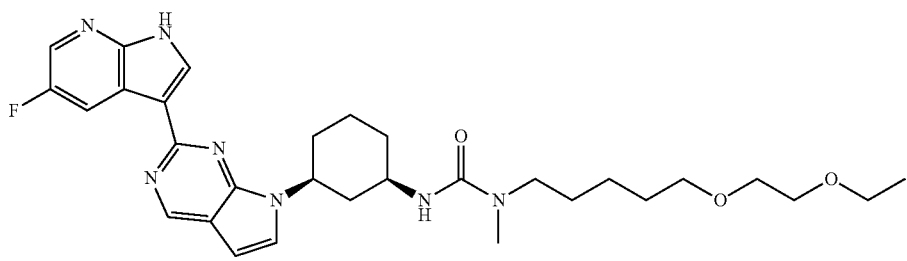 [SMILES: CCOCCOCCCCCN(C)C(=O)N[C@@H]1CCC[C@H](n2ccc3cnc(-c4c[nH]c5ncc(F)cc45)nc32)C1]
B46
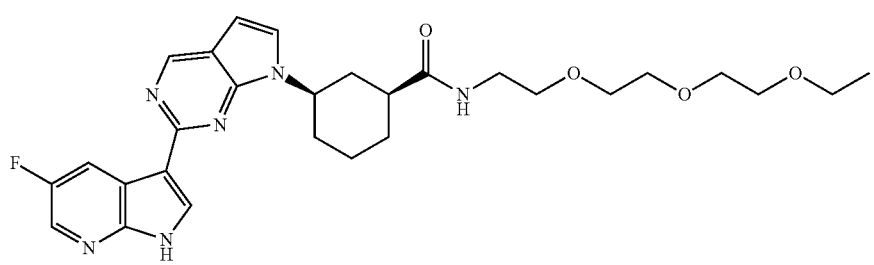 [SMILES: CCOCCOCCOCCNC(=O)[C@H]1CCC[C@@H](n2ccc3cnc(-c4c[nH]c5ncc(F)cc45)nc32)C1]
B47
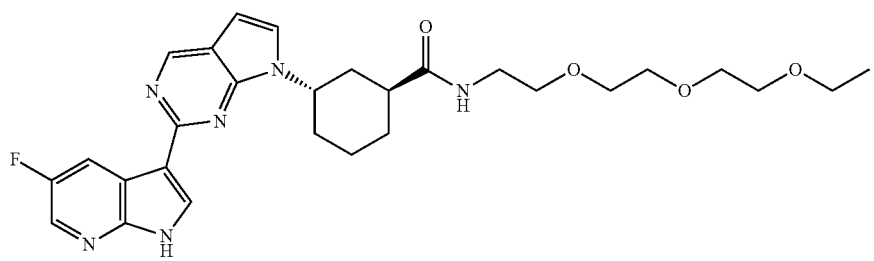 [SMILES: CCOCCOCCOCCNC(=O)[C@H]1CCC[C@H](n2ccc3cnc(-c4c[nH]c5ncc(F)cc45)nc32)C1]
B48
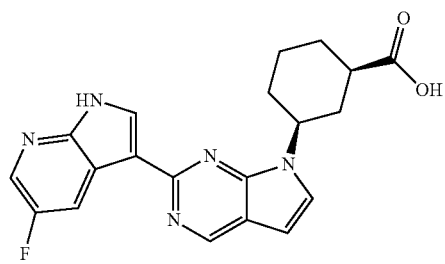 [SMILES: O=C(O)[C@@H]1CCC[C@H](n2ccc3cnc(-c4c[nH]c5ncc(F)cc45)nc32)C1]

TABLE A-continued
B49
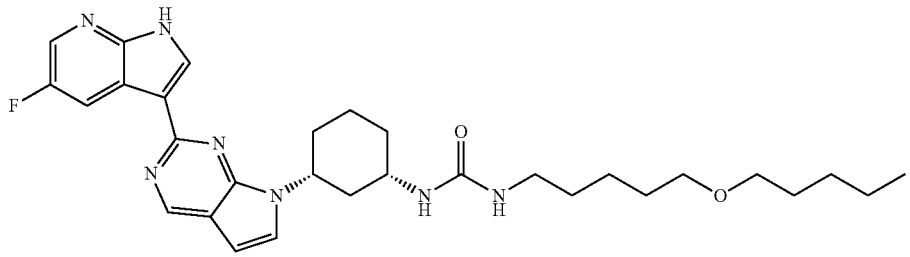 [SMILES: CCCCCOCCCCCNC(=O)N[C@H]1CCC[C@@H](n2ccc3cnc(-c4c[nH]c5ncc(F)cc45)nc32)C1]
B50
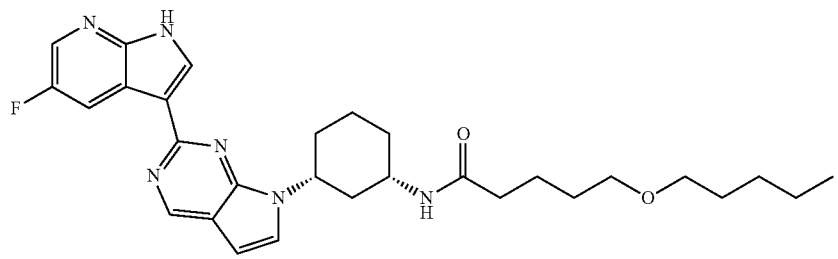 [SMILES: CCCCCOCCCCC(=O)N[C@H]1CCC[C@@H](n2ccc3cnc(-c4c[nH]c5ncc(F)cc45)nc32)C1]
B51
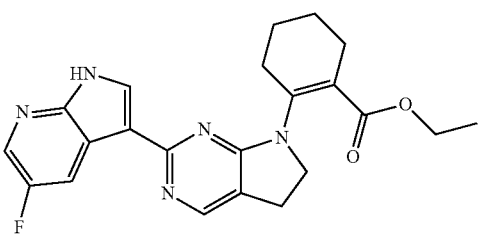 [SMILES: CCOC(=O)C1=C(N2CCc3cnc(-c4c[nH]c5ncc(F)cc45)nc32)CCCC1]
B100
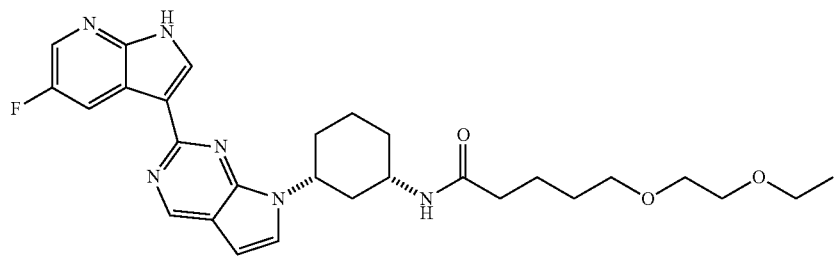
B52
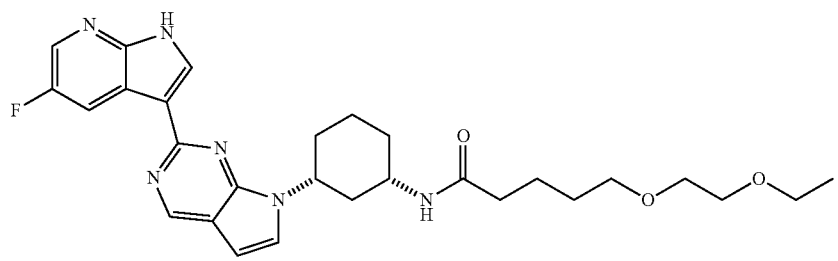
B53
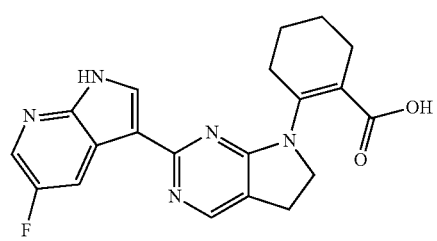 [SMILES: O=C(O)C1=C(N2CCc3cnc(-c4c[nH]c5ncc(F)cc45)nc32)CCCC1]

TABLE A-continued
B54 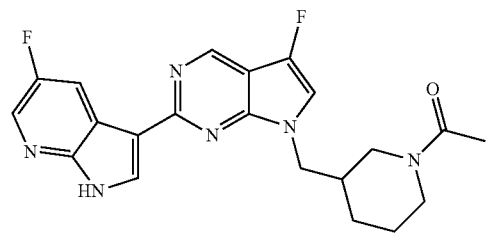 [SMILES: CC(=O)N1CCCC(Cn2cc(F)c3cnc(-c4c[nH]c5ncc(F)cc45)nc32)C1]
B55 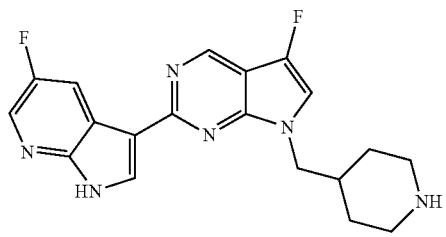 [SMILES: Fc1cnc2[nH]cc(-c3ncc4c(F)cn(CC5CCNCC5)c4n3)c2c1]
B56 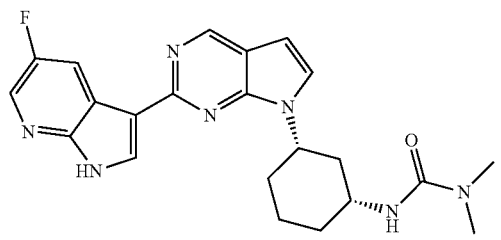 [SMILES: CN(C)C(=O)N[C@@H]1CCC[C@H](n2ccc3cnc(-c4c[nH]c5ncc(F)cc45)nc32)C1]
B57 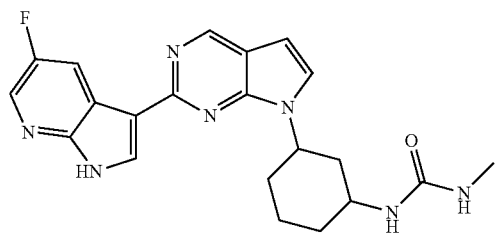 [SMILES: CNC(=O)NC1CCCC(n2ccc3cnc(-c4c[nH]c5ncc(F)cc45)nc32)C1]
B58 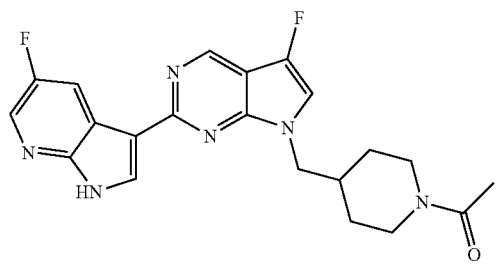 [SMILES: CC(=O)N1CCC(Cn2cc(F)c3cnc(-c4c[nH]c5ncc(F)cc45)nc32)CC1]
B59 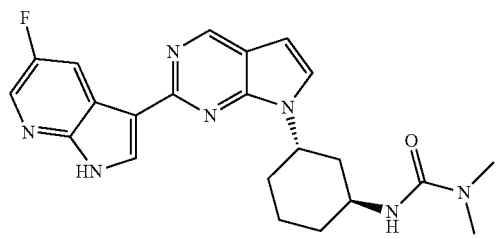 [SMILES: CN(C)C(=O)N[C@H]1CCC[C@H](n2ccc3cnc(-c4c[nH]c5ncc(F)cc45)nc32)C1]

TABLE A-continued
B60 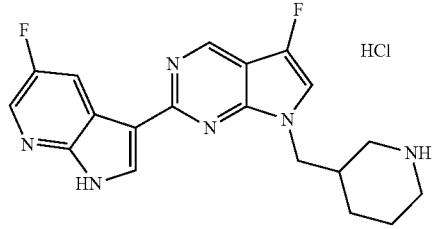 [SMILES: Fc1cnc2[nH]cc(-c3ncc4c(F)cn(CC5CCCNC5)c4n3)c2c1 ; Cl]
B61 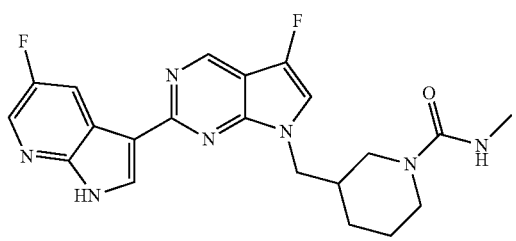 [SMILES: CNC(=O)N1CCCC(Cn2cc(F)c3cnc(-c4c[nH]c5ncc(F)cc45)nc32)C1]
B62 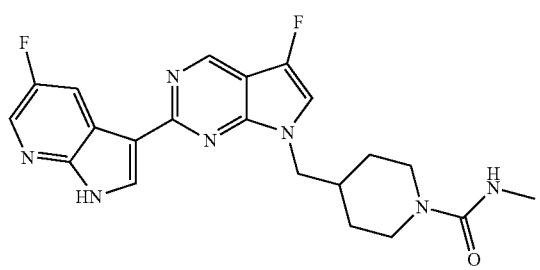 [SMILES: CNC(=O)N1CCC(Cn2cc(F)c3cnc(-c4c[nH]c5ncc(F)cc45)nc32)CC1]
B63 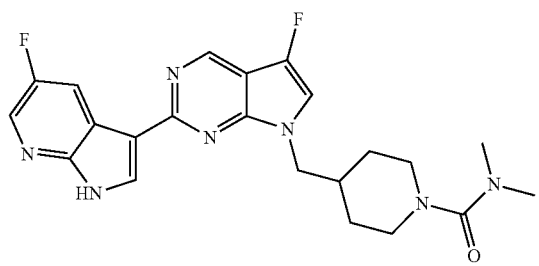 [SMILES: CN(C)C(=O)N1CCC(Cn2cc(F)c3cnc(-c4c[nH]c5ncc(F)cc45)nc32)CC1]
B64 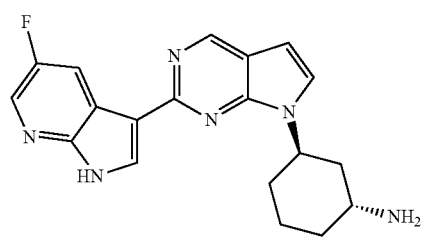 [SMILES: N[C@@H]1CCC[C@@H](n2ccc3cnc(-c4c[nH]c5ncc(F)cc45)nc32)C1]
B65 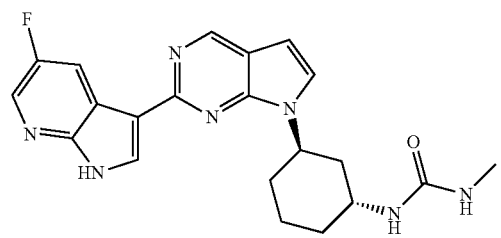 [SMILES: CNC(=O)N[C@@H]1CCC[C@@H](n2ccc3cnc(-c4c[nH]c5ncc(F)cc45)nc32)C1]

TABLE A-continued
B66 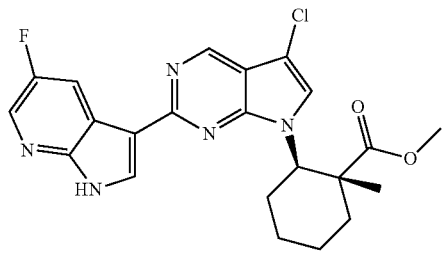 [SMILES: COC(=O)[C@]1(C)CCCC[C@H]1n1cc(Cl)c2cnc(-c3c[nH]c4ncc(F)cc34)nc21]
B67 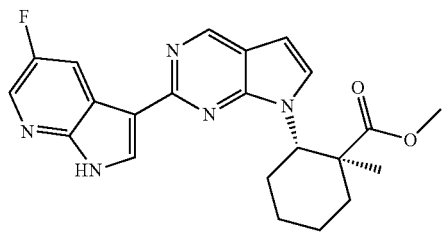 [SMILES: COC(=O)[C@@]1(C)CCCC[C@@H]1n1ccc2cnc(-c3c[nH]c4ncc(F)cc34)nc21]
B68 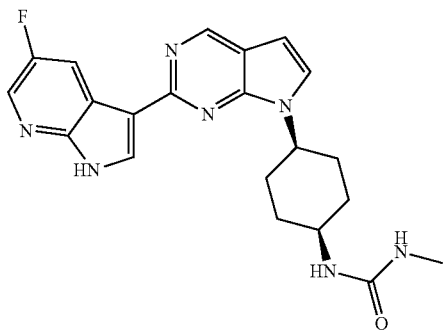 [SMILES: CNC(=O)N[C@H]1CC[C@@H](n2ccc3cnc(-c4c[nH]c5ncc(F)cc45)nc32)CC1]
B69 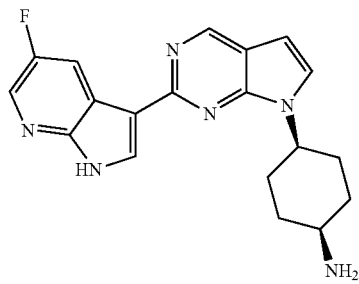 [SMILES: N[C@H]1CC[C@@H](n2ccc3cnc(-c4c[nH]c5ncc(F)cc45)nc32)CC1]
B70 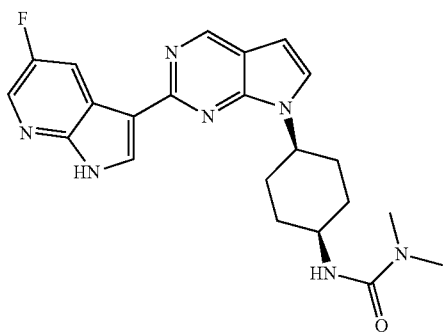 [SMILES: CN(C)C(=O)N[C@H]1CC[C@@H](n2ccc3cnc(-c4c[nH]c5ncc(F)cc45)nc32)CC1]

TABLE A-continued
B71 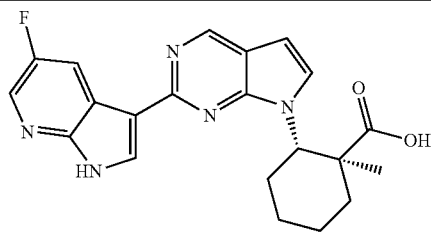
B72 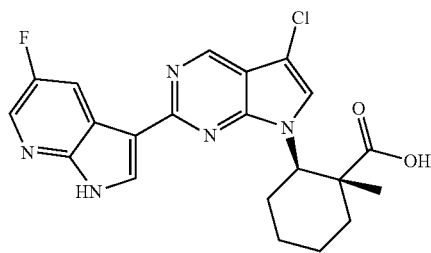
B73 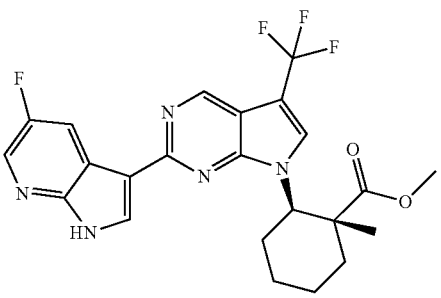 [SMILES: COC(=O)[C@]1(C)CCCC[C@H]1n1cc(C(F)(F)F)c2cnc(-c3c[nH]c4ncc(F)cc34)nc21]
B74 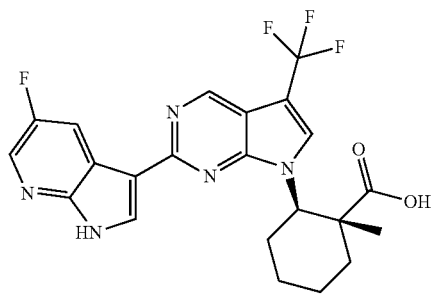 [SMILES: C[C@@]1(C(=O)O)CCCC[C@H]1n1cc(C(F)(F)F)c2cnc(-c3c[nH]c4ncc(F)cc34)nc21]
B75 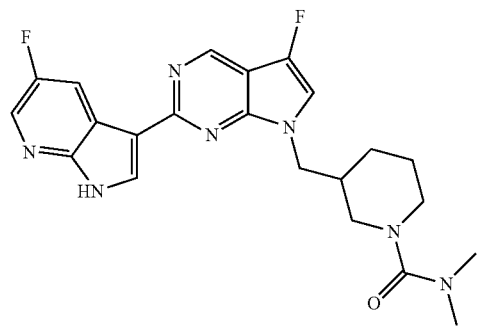 [SMILES: CN(C)C(=O)N1CCCC(Cn2cc(F)c3cnc(-c4c[nH]c5ncc(F)cc45)nc32)C1]

TABLE A-continued
B76
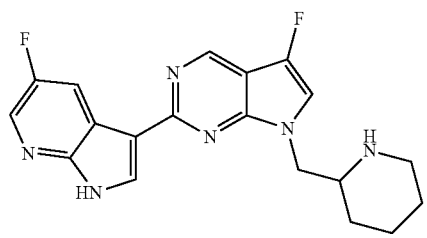 [SMILES: Fc1cnc2[nH]cc(-c3ncc4c(F)cn(CC5CCCCN5)c4n3)c2c1]
B77
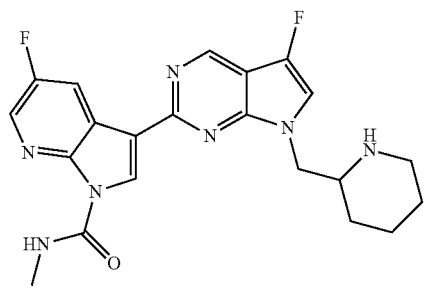 [SMILES: CNC(=O)n1cc(-c2ncc3c(F)cn(CC4CCCCN4)c3n2)c2cc(F)cnc21]
B78
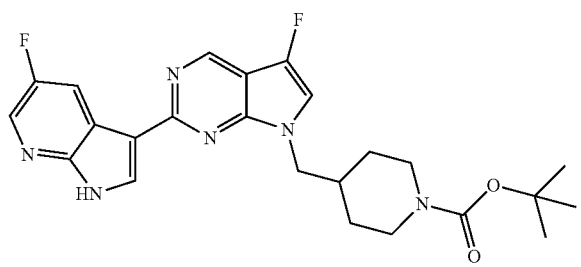 [SMILES: CC(C)(C)OC(=O)N1CCC(Cn2cc(F)c3cnc(-c4c[nH]c5ncc(F)cc45)nc32)CC1]
B79
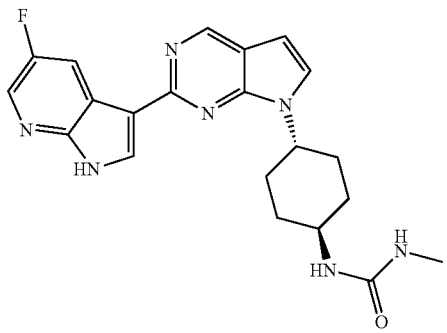 [SMILES: CNC(=O)N[C@H]1CC[C@H](n2ccc3cnc(-c4c[nH]c5ncc(F)cc45)nc32)CC1]
B80
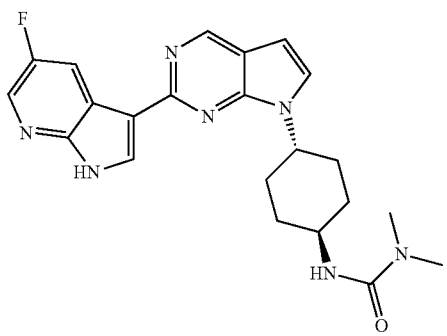 [SMILES: CN(C)C(=O)N[C@H]1CC[C@H](n2ccc3cnc(-c4c[nH]c5ncc(F)cc45)nc32)CC1]

TABLE A-continued
B81 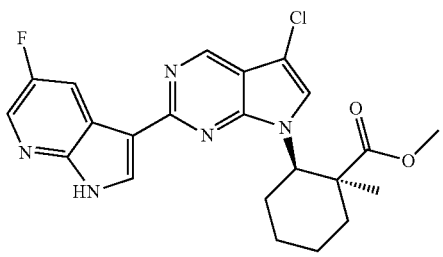 [SMILES: COC(=O)[C@@]1(C)CCCC[C@H]1n1cc(Cl)c2cnc(-c3c[nH]c4ncc(F)cc34)nc21]
B82 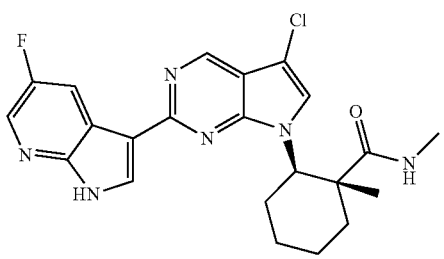 [SMILES: CNC(=O)[C@]1(C)CCCC[C@H]1n1cc(Cl)c2cnc(-c3c[nH]c4ncc(F)cc34)nc21]
B83 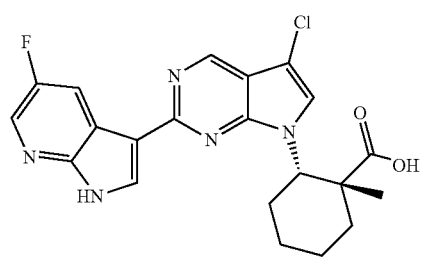 [SMILES: C[C@@]1(C(=O)O)CCCC[C@@H]1n1cc(Cl)c2cnc(-c3c[nH]c4ncc(F)cc34)nc21]
B84 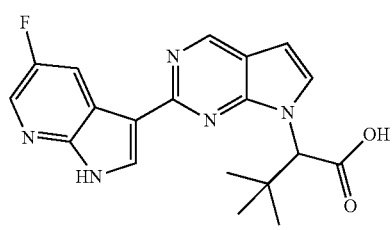 [SMILES: CC(C)(C)C(C(=O)O)n1ccc2cnc(-c3c[nH]c4ncc(F)cc34)nc21]
B85 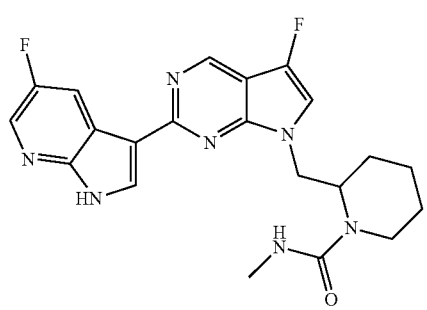 [SMILES: CNC(=O)N1CCCCC1Cn1cc(F)c2cnc(-c3c[nH]c4ncc(F)cc34)nc21]
B86 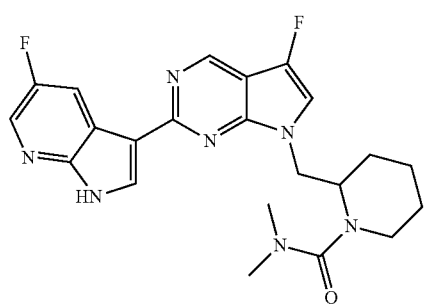 [SMILES: CN(C)C(=O)N1CCCCC1Cn1cc(F)c2cnc(-c3c[nH]c4ncc(F)cc34)nc21]

TABLE A-continued
B87 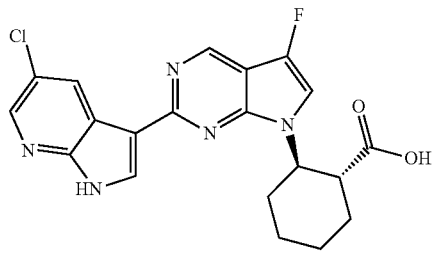 [SMILES: O=C(O)[C@@H]1CCCC[C@H]1n1cc(F)c2cnc(-c3c[nH]c4ncc(Cl)cc34)nc21]
B88 
B89 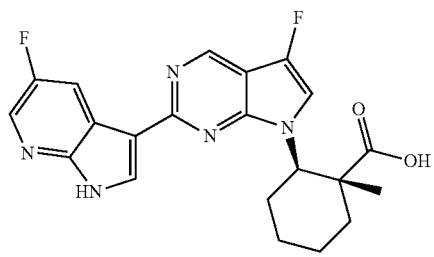 [SMILES: C[C@@]1(C(=O)O)CCCC[C@H]1n1cc(F)c2cnc(-c3c[nH]c4ncc(F)cc34)nc21]
B90 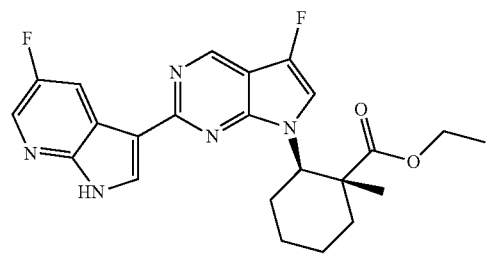
B91 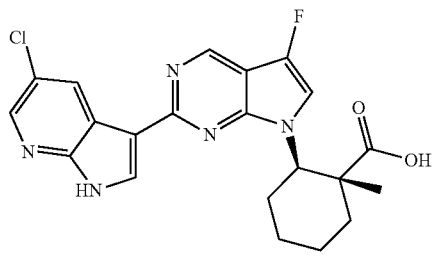 [SMILES: C[C@@]1(C(=O)O)CCCC[C@H]1n1cc(F)c2cnc(-c3c[nH]c4ncc(Cl)cc34)nc21]
B92 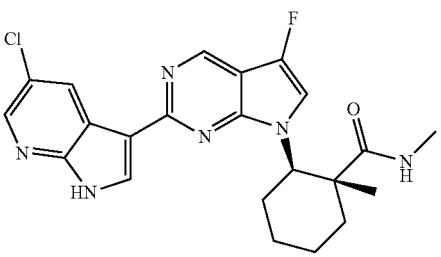 [SMILES: CNC(=O)[C@]1(C)CCCC[C@H]1n1cc(F)c2cnc(-c3c[nH]c4ncc(Cl)cc34)nc21]

TABLE A-continued
B93 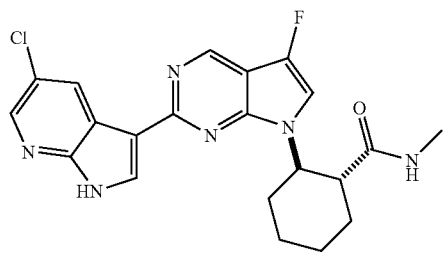
B94 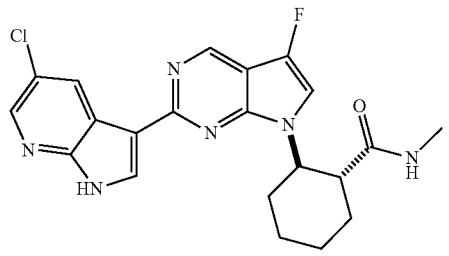
B95 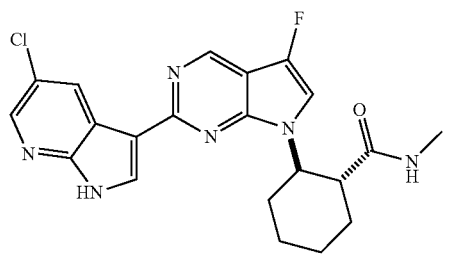
B96 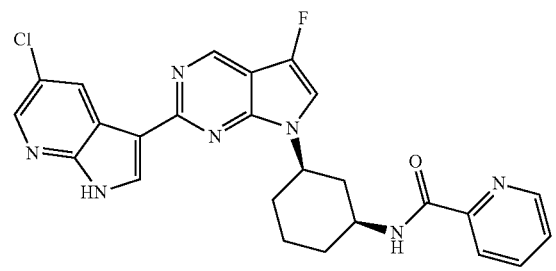 [SMILES: O=C(N[C@H]1CCC[C@@H](n2cc(F)c3cnc(-c4c[nH]c5ncc(Cl)cc45)nc32)C1)c1ccccn1]
B97 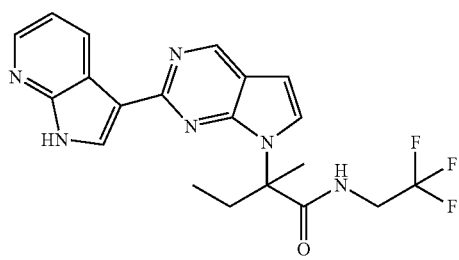 [SMILES: CCC(C)(C(=O)NCC(F)(F)F)n1ccc2cnc(-c3c[nH]c4ncccc34)nc21]
B98 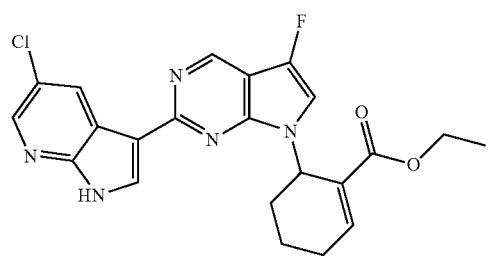 [SMILES: CCOC(=O)C1=CCCCC1n1cc(F)c2cnc(-c3c[nH]c4ncc(Cl)cc34)nc21]

TABLE A-continued
B99
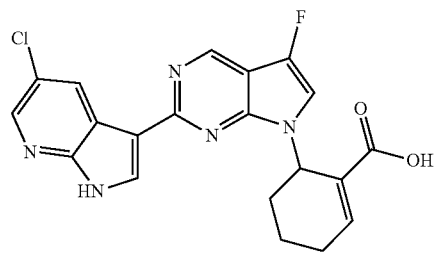 [SMILES: O=C(O)C1=CCCCC1n1cc(F)c2cnc(-c3c[nH]c4ncc(Cl)cc34)nc21]
B101
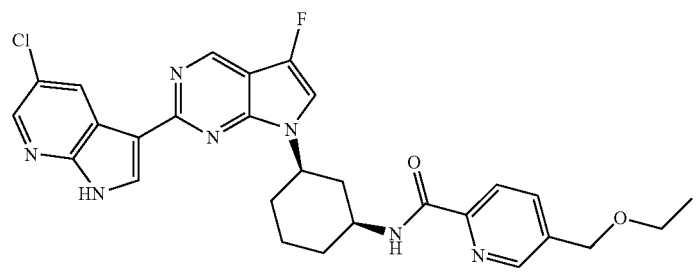 [SMILES: CCOCc1ccc(C(=O)N[C@H]2CCC[C@@H](n3cc(F)c4cnc(-c5c[nH]c6ncc(Cl)cc56)nc43)C2)nc1]
B102
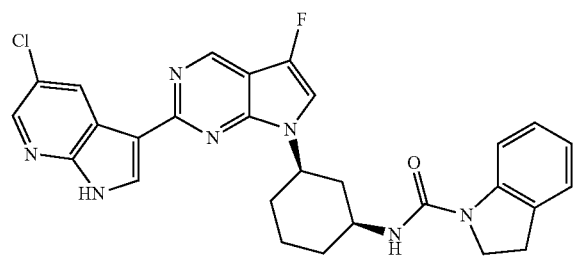 [SMILES: O=C(N[C@H]1CCC[C@@H](n2cc(F)c3cnc(-c4c[nH]c5ncc(Cl)cc45)nc32)C1)N1CCc2ccccc21]
B103
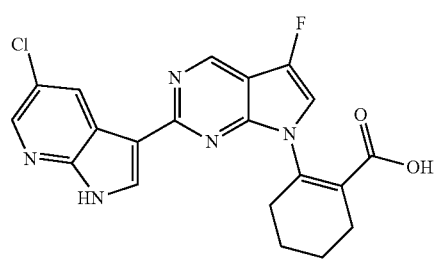 [SMILES: O=C(O)C1=C(n2cc(F)c3cnc(-c4c[nH]c5ncc(Cl)cc45)nc32)CCCC1]
B109
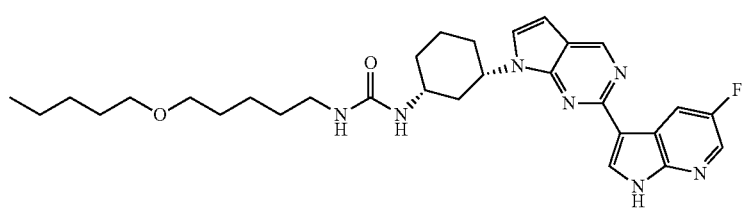 [SMILES: CCCCCOCCCCCNC(=O)N[C@@H]1CCC[C@H](n2ccc3cnc(-c4c[nH]c5ncc(F)cc45)nc32)C1]
B120
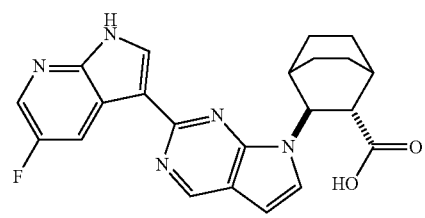

TABLE A-continued
B121 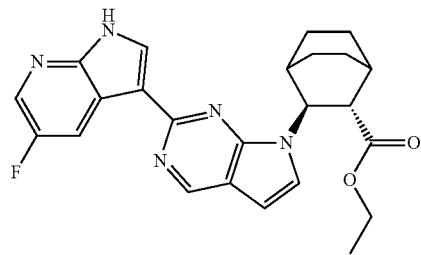 [SMILES: CCOC(=O)[C@H]1C2CCC(CC2)[C@@H]1n1ccc2cnc(-c3c[nH]c4ncc(F)cc34)nc21]
B122 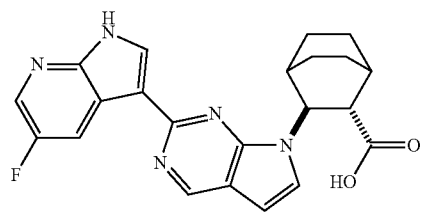
B123 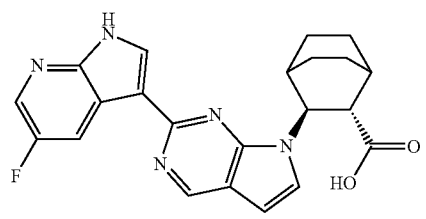
B124 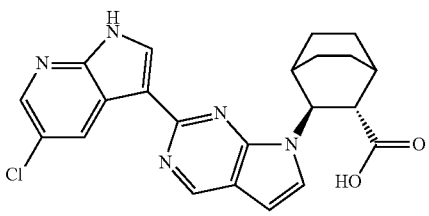 [SMILES: O=C(O)[C@H]1C2CCC(CC2)[C@@H]1n1ccc2cnc(-c3c[nH]c4ncc(Cl)cc34)nc21]
B125 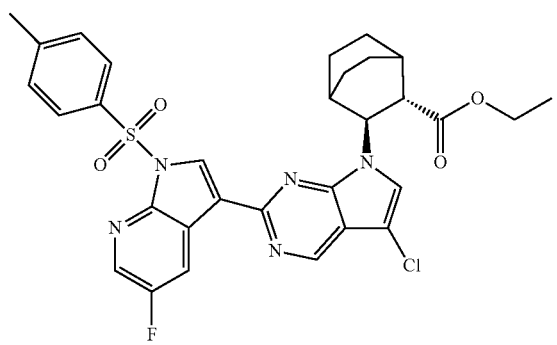 [SMILES: CCOC(=O)[C@H]1C2CCC(CC2)[C@@H]1n1cc(Cl)c2cnc(-c3cn(S(=O)(=O)c4ccc(C)cc4)c4ncc(F)cc34)nc21]
B126 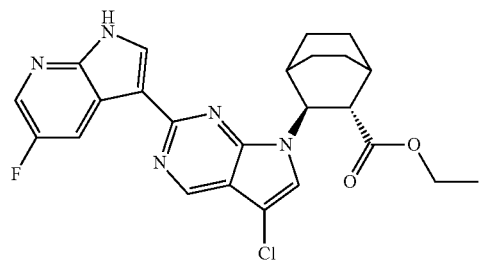

TABLE A-continued
B127 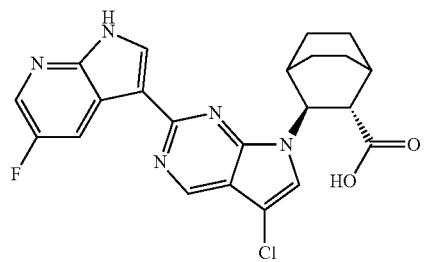
B128 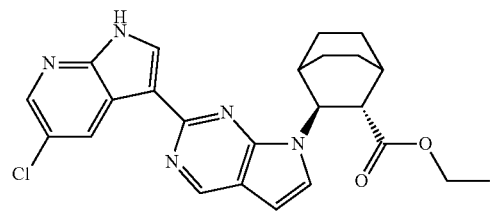 [SMILES: CCOC(=O)[C@H]1C2CCC(CC2)[C@@H]1n1ccc2cnc(-c3c[nH]c4ncc(Cl)cc34)nc21]
B129 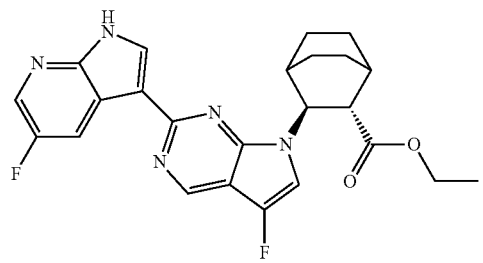 [SMILES: CCOC(=O)[C@H]1C2CCC(CC2)[C@@H]1n1cc(F)c2cnc(-c3c[nH]c4ncc(F)cc34)nc21]
B130 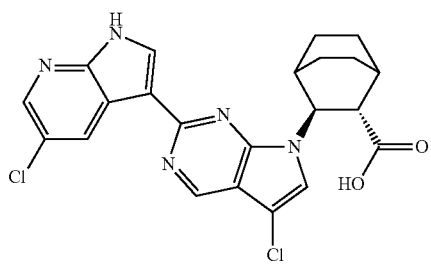 [SMILES: O=C(O)[C@H]1C2CCC(CC2)[C@@H]1n1cc(Cl)c2cnc(-c3c[nH]c4ncc(Cl)cc34)nc21]
B131 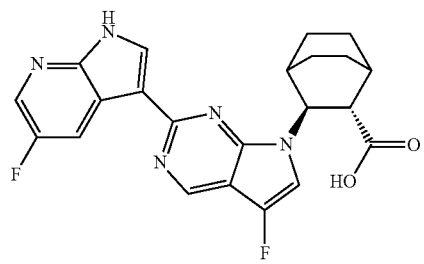
B132 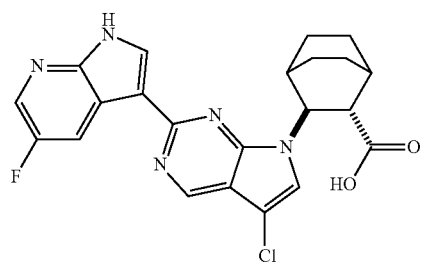

TABLE A-continued
| | |
|---|---|
| B133 | 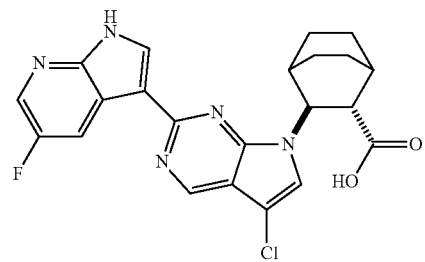 |
| B134 | 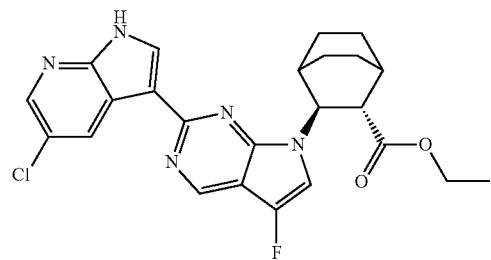 [SMILES: CCOC(=O)[C@H]1C2CCC(CC2)[C@@H]1n1cc(F)c2cnc(-c3c[nH]c4ncc(Cl)cc34)nc21] |
| B135 | 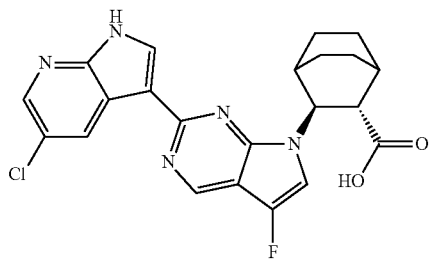 [SMILES: O=C(O)[C@H]1C2CCC(CC2)[C@@H]1n1cc(F)c2cnc(-c3c[nH]c4ncc(Cl)cc34)nc21] |
| B136 | 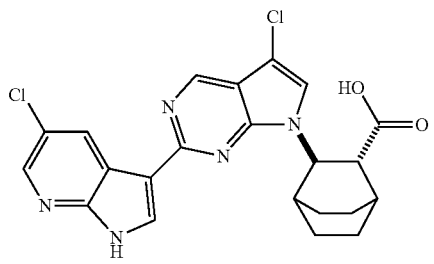 |
| B137 | 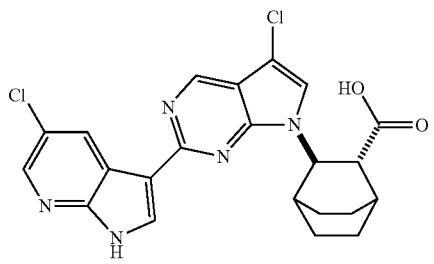 |
| B138 | 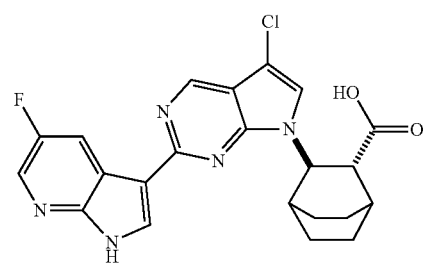 |

TABLE A-continued
B139
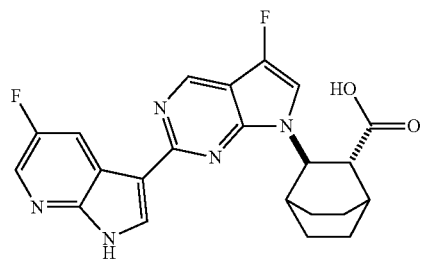
B140
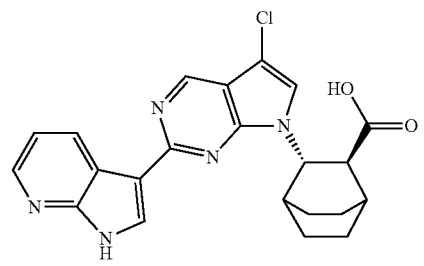 [SMILES: O=C(O)[C@H]1C2CCC(CC2)[C@@H]1n1cc(Cl)c2cnc(-c3c[nH]c4ncccc34)nc21]
B141
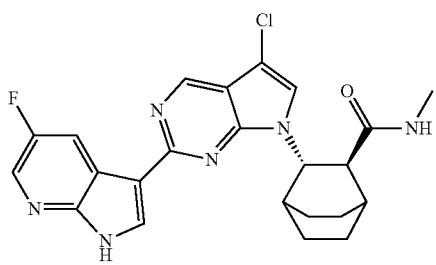 [SMILES: CNC(=O)[C@H]1C2CCC(CC2)[C@@H]1n1cc(Cl)c2cnc(-c3c[nH]c4ncc(F)cc34)nc21]
B142
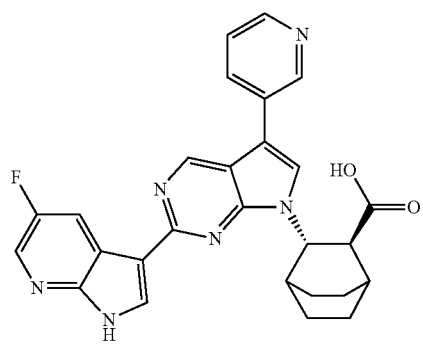 [SMILES: O=C(O)[C@H]1C2CCC(CC2)[C@@H]1n1cc(-c2cccnc2)c2cnc(-c3c[nH]c4ncc(F)cc34)nc21]
B143
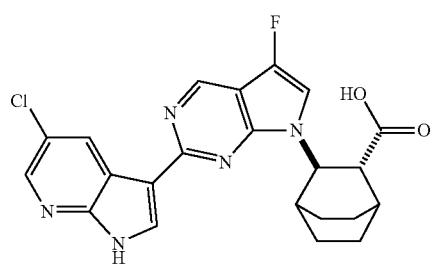

TABLE A-continued
B144
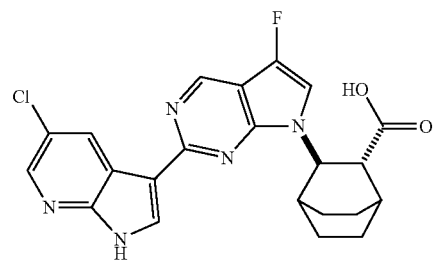
B145
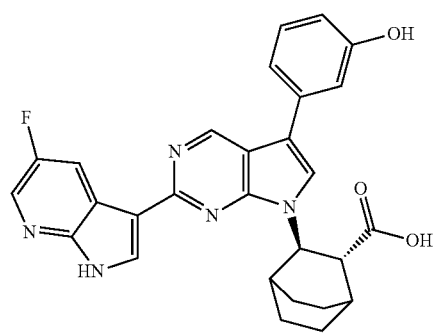 [SMILES: O=C(O)[C@@H]1C2CCC(CC2)[C@H]1n1cc(-c2cccc(O)c2)c2cnc(-c3c[nH]c4ncc(F)cc34)nc21]
B146
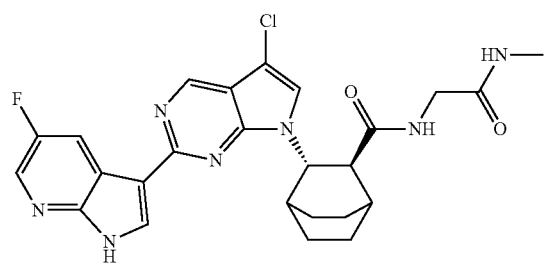 [SMILES: CNC(=O)CNC(=O)[C@H]1C2CCC(CC2)[C@@H]1n1cc(Cl)c2cnc(-c3c[nH]c4ncc(F)cc34)nc21]
B147
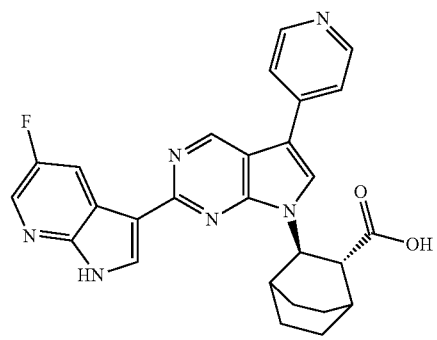 [SMILES: O=C(O)[C@@H]1C2CCC(CC2)[C@H]1n1cc(-c2ccncc2)c2cnc(-c3c[nH]c4ncc(F)cc34)nc21]
B148
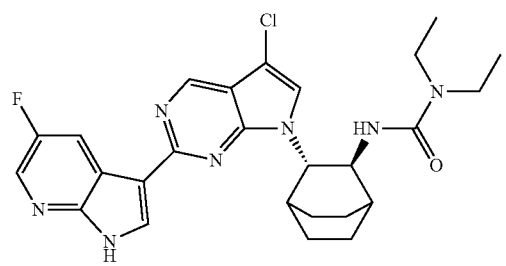 [SMILES: CCN(CC)C(=O)N[C@H]1C2CCC(CC2)[C@@H]1n1cc(Cl)c2cnc(-c3c[nH]c4ncc(F)cc34)nc21]

TABLE A-continued
B149
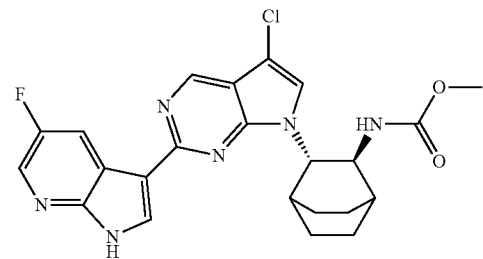 [SMILES: COC(=O)N[C@H]1C2CCC(CC2)[C@@H]1n1cc(Cl)c2cnc(-c3c[nH]c4ncc(F)cc34)nc21]
B150
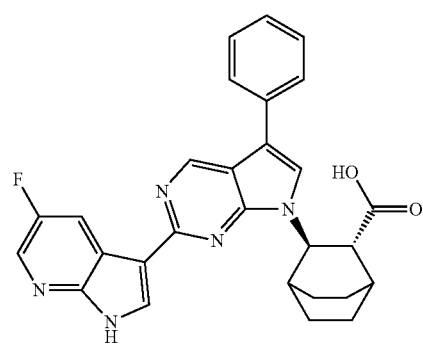 [SMILES: O=C(O)[C@@H]1C2CCC(CC2)[C@H]1n1cc(-c2ccccc2)c2cnc(-c3c[nH]c4ncc(F)cc34)nc21]
B151
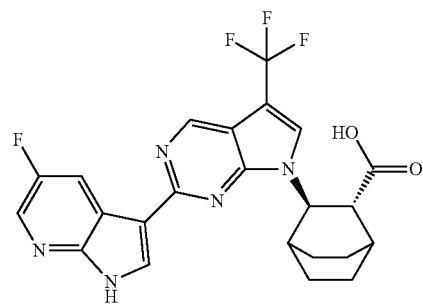 [SMILES: O=C(O)[C@@H]1C2CCC(CC2)[C@H]1n1cc(C(F)(F)F)c2cnc(-c3c[nH]c4ncc(F)cc34)nc21]
B152
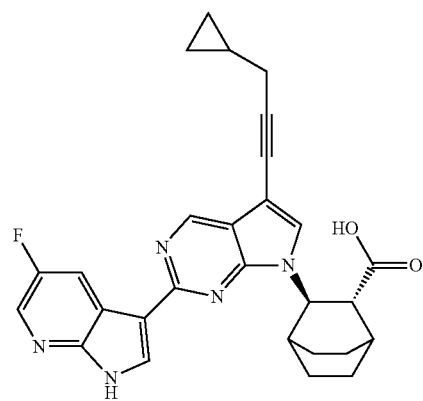 [SMILES: O=C(O)[C@@H]1C2CCC(CC2)[C@H]1n1cc(C#CCC2CC2)c2cnc(-c3c[nH]c4ncc(F)cc34)nc21]

TABLE A-continued
B153
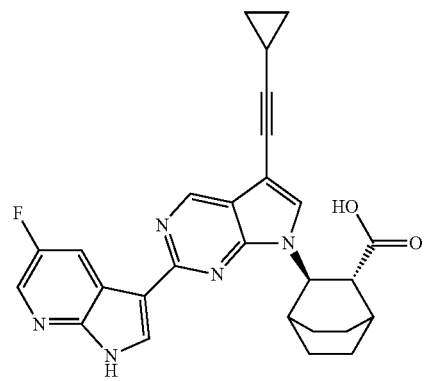 [SMILES: O=C(O)[C@@H]1C2CCC(CC2)[C@H]1n1cc(C#CC2CC2)c2cnc(-c3c[nH]c4ncc(F)cc34)nc21]
B154
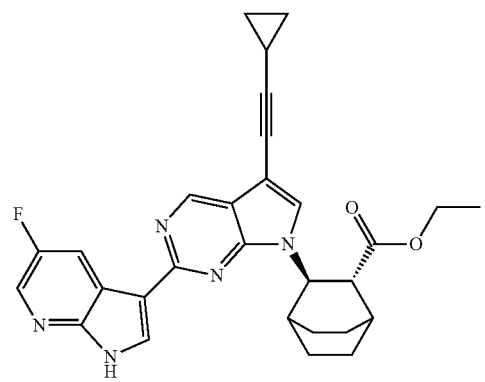 [SMILES: CCOC(=O)[C@@H]1C2CCC(CC2)[C@H]1n1cc(C#CC2CC2)c2cnc(-c3c[nH]c4ncc(F)cc34)nc21]
B160
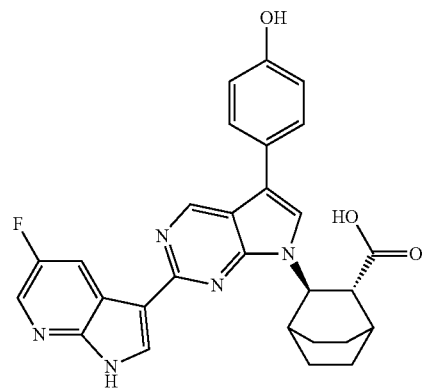 [SMILES: O=C(O)[C@@H]1C2CCC(CC2)[C@H]1n1cc(-c2ccc(O)cc2)c2cnc(-c3c[nH]c4ncc(F)cc34)nc21]
B161
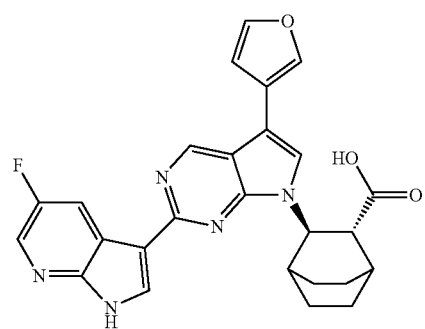

TABLE A-continued
B162
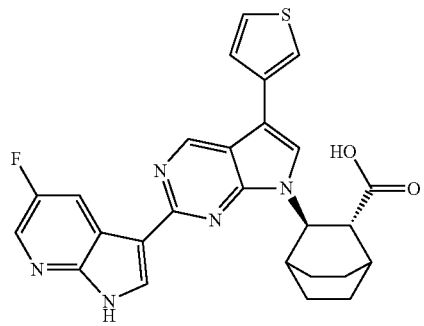 [SMILES: O=C(O)[C@@H]1C2CCC(CC2)[C@H]1n1cc(-c2ccoc2)c2cnc(-c3c[nH]c4ncc(F)cc34)nc21]
B163
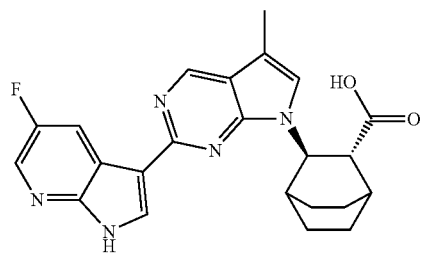 [SMILES: Cc1cn([C@@H]2C3CCC(CC3)[C@H]2C(=O)O)c2nc(-c3c[nH]c4ncc(F)cc34)ncc12]
B164
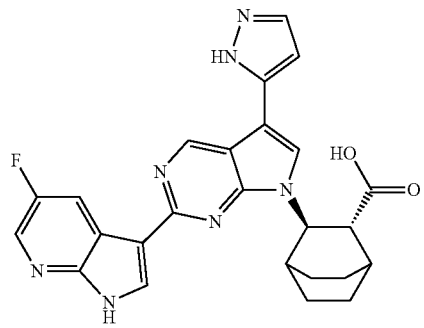 [SMILES: O=C(O)[C@@H]1C2CCC(CC2)[C@H]1n1cc(-c2ccn[nH]2)c2cnc(-c3c[nH]c4ncc(F)cc34)nc21]
B165
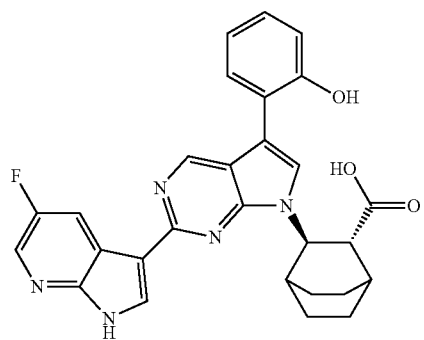 [SMILES: O=C(O)[C@@H]1C2CCC(CC2)[C@H]1n1cc(-c2ccccc2O)c2cnc(-c3c[nH]c4ncc(F)cc34)nc21]
B166
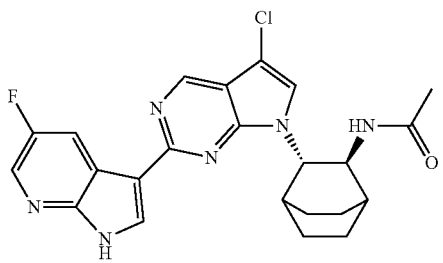 [SMILES: CC(=O)N[C@H]1C2CCC(CC2)[C@@H]1n1cc(Cl)c2cnc(-c3c[nH]c4ncc(F)cc34)nc21]

TABLE A-continued
B167
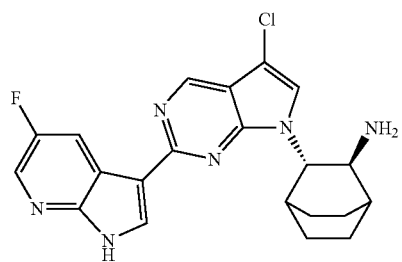 [SMILES: N[C@H]1C2CCC(CC2)[C@@H]1n1cc(Cl)c2cnc(-c3c[nH]c4ncc(F)cc34)nc21]
B168
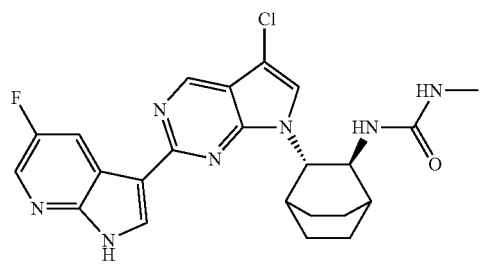 [SMILES: CNC(=O)N[C@H]1C2CCC(CC2)[C@@H]1n1cc(Cl)c2cnc(-c3c[nH]c4ncc(F)cc34)nc21]
B169
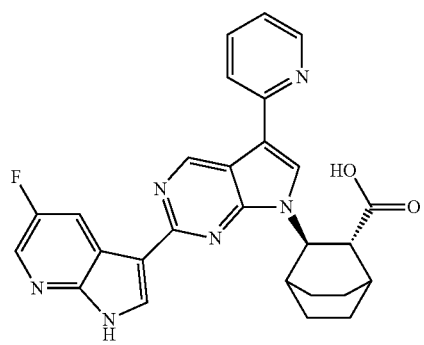 [SMILES: O=C(O)[C@@H]1C2CCC(CC2)[C@H]1n1cc(-c2ccccn2)c2cnc(-c3c[nH]c4ncc(F)cc34)nc21]
B170
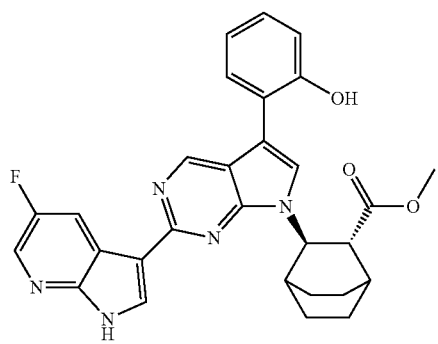 [SMILES: COC(=O)[C@@H]1C2CCC(CC2)[C@H]1n1cc(-c2ccccc2O)c2cnc(-c3c[nH]c4ncc(F)cc34)nc21]
B171
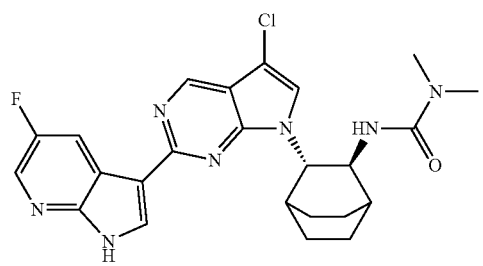 [SMILES: CN(C)C(=O)N[C@H]1C2CCC(CC2)[C@@H]1n1cc(Cl)c2cnc(-c3c[nH]c4ncc(F)cc34)nc21]

TABLE A-continued
B172
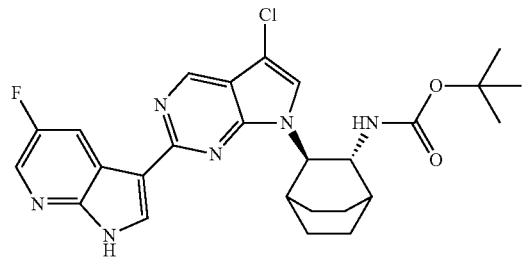 [SMILES: CC(C)(C)OC(=O)N[C@@H]1C2CCC(CC2)[C@H]1n1cc(Cl)c2cnc(-c3c[nH]c4ncc(F)cc34)nc21]
B173
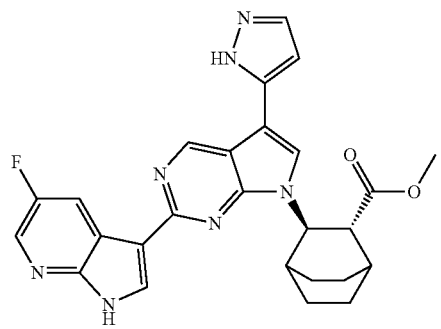 [SMILES: COC(=O)[C@@H]1C2CCC(CC2)[C@H]1n1cc(-c2ccn[nH]2)c2cnc(-c3c[nH]c4ncc(F)cc34)nc21]
B174
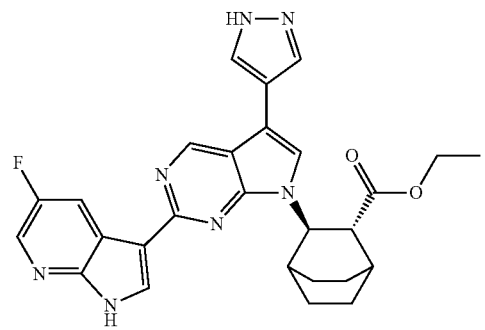 [SMILES: CCOC(=O)[C@@H]1C2CCC(CC2)[C@H]1n1cc(-c2cn[nH]c2)c2cnc(-c3c[nH]c4ncc(F)cc34)nc21]
B175
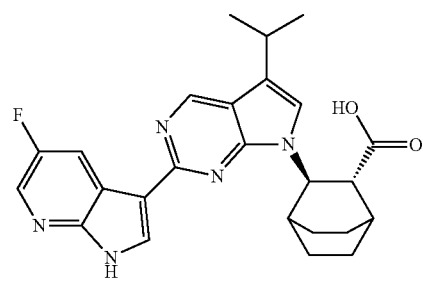 [SMILES: CC(C)c1cn([C@@H]2C3CCC(CC3)[C@H]2C(=O)O)c2nc(-c3c[nH]c4ncc(F)cc34)ncc12]
B176
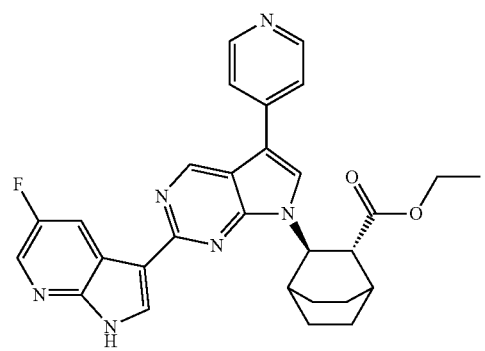 [SMILES: CCOC(=O)[C@@H]1C2CCC(CC2)[C@H]1n1cc(-c2ccncc2)c2cnc(-c3c[nH]c4ncc(F)cc34)nc21]

TABLE A-continued
B177
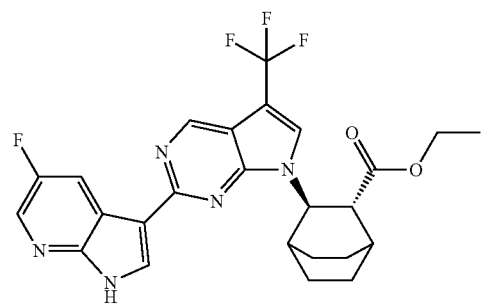 [SMILES: CCOC(=O)[C@@H]1C2CCC(CC2)[C@H]1n1cc(C(F)(F)F)c2cnc(-c3c[nH]c4ncc(F)cc34)nc21]
B178
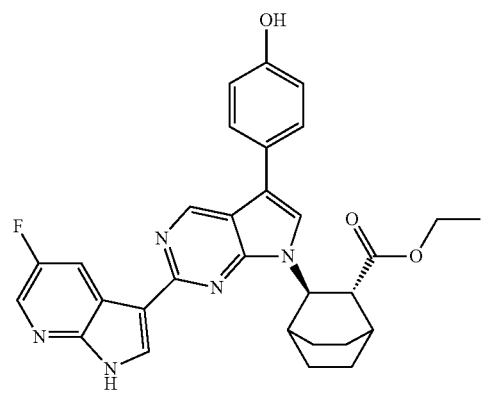 [SMILES: CCOC(=O)[C@@H]1C2CCC(CC2)[C@H]1n1cc(-c2ccc(O)cc2)c2cnc(-c3c[nH]c4ncc(F)cc34)nc21]
B179
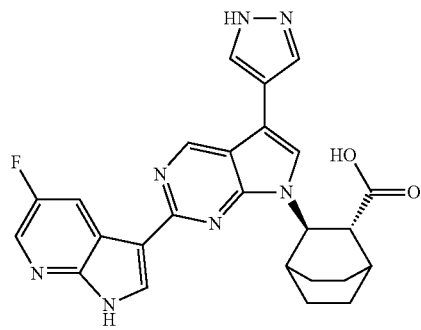 [SMILES: O=C(O)[C@@H]1C2CCC(CC2)[C@H]1n1cc(-c2cn[nH]c2)c2cnc(-c3c[nH]c4ncc(F)cc34)nc21]
B180
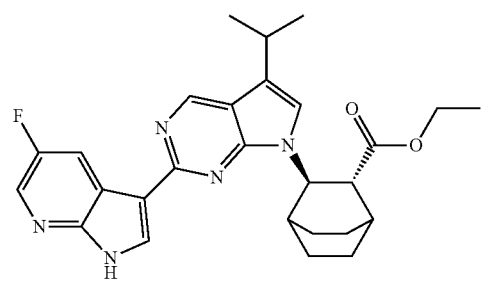 [SMILES: CCOC(=O)[C@@H]1C2CCC(CC2)[C@H]1n1cc(C(C)C)c2cnc(-c3c[nH]c4ncc(F)cc34)nc21]
B181
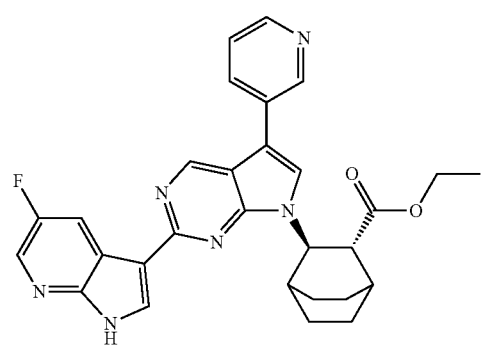 [SMILES: CCOC(=O)[C@@H]1C2CCC(CC2)[C@H]1n1cc(-c2cccnc2)c2cnc(-c3c[nH]c4ncc(F)cc34)nc21]

TABLE A-continued
B182
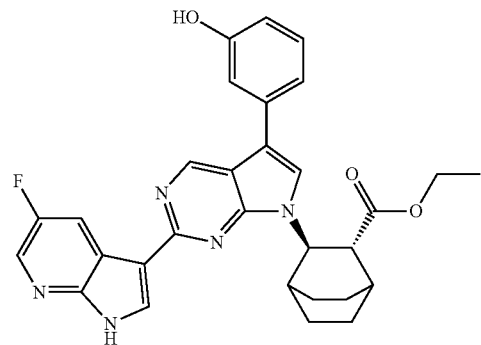 [SMILES: CCOC(=O)[C@@H]1C2CCC(CC2)[C@H]1n1cc(-c2cccc(O)c2)c2cnc(-c3c[nH]c4ncc(F)cc34)nc21]
B183
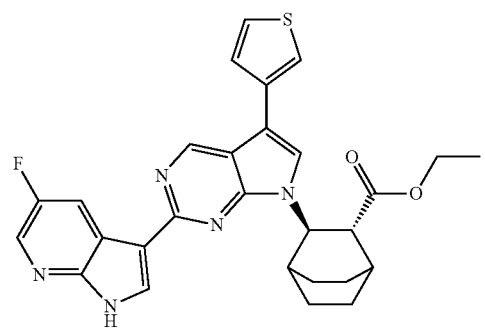 [SMILES: CCOC(=O)[C@@H]1C2CCC(CC2)[C@H]1n1cc(-c2ccsc2)c2cnc(-c3c[nH]c4ncc(F)cc34)nc21]
B184
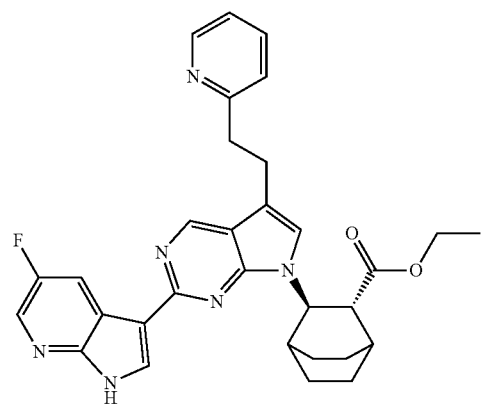 [SMILES: CCOC(=O)[C@@H]1C2CCC(CC2)[C@H]1n1cc(CCc2ccccn2)c2cnc(-c3c[nH]c4ncc(F)cc34)nc21]
B185
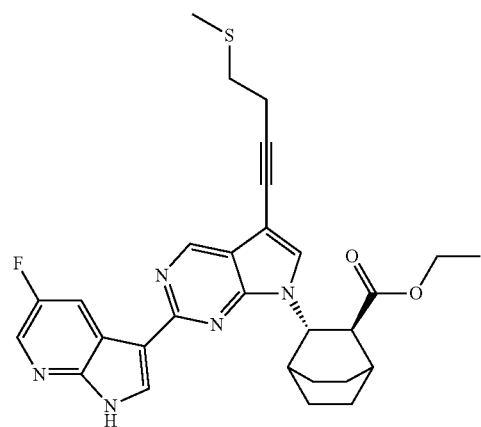 [SMILES: CCOC(=O)[C@H]1C2CCC(CC2)[C@@H]1n1cc(C#CCCSC)c2cnc(-c3c[nH]c4ncc(F)cc34)nc21]

TABLE A-continued
B186
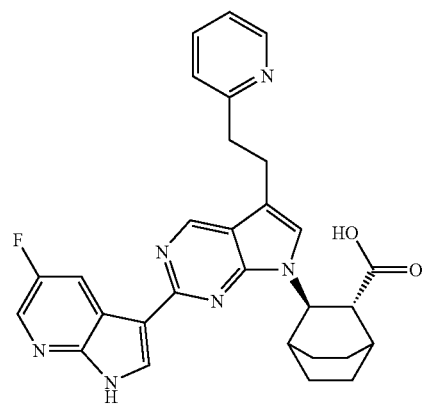 [SMILES: O=C(O)[C@@H]1C2CCC(CC2)[C@H]1n1cc(CCc2ccccn2)c2cnc(-c3c[nH]c4ncc(F)cc34)nc21]
B187
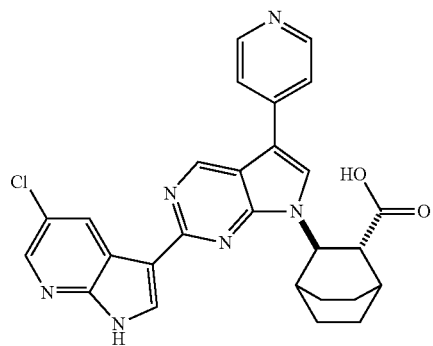
B188
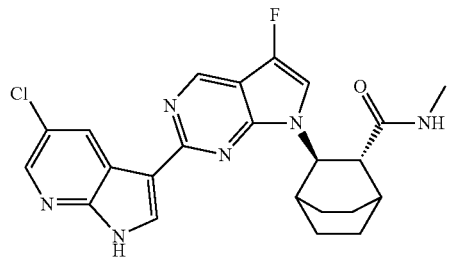
B189
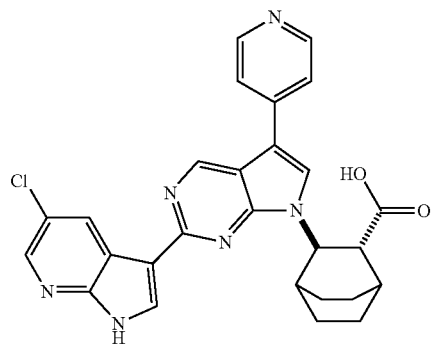

TABLE A-continued
B190 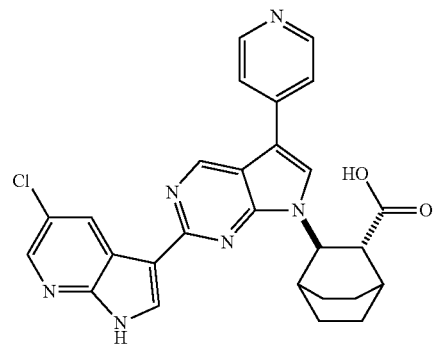
B191 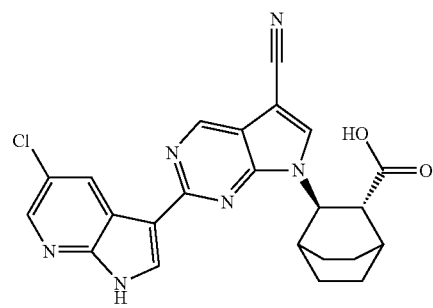 [SMILES: N#Cc1cn([C@@H]2C3CCC(CC3)[C@H]2C(=O)O)c2nc(-c3c[nH]c4ncc(Cl)cc34)ncc12]
B192 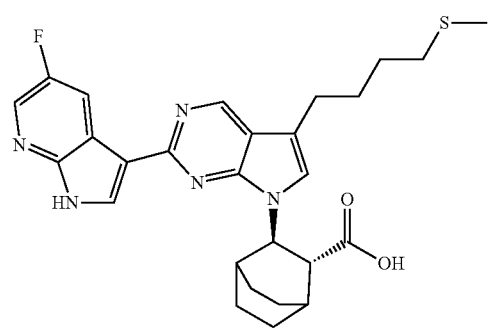 [SMILES: CSCCCCc1cn([C@@H]2C3CCC(CC3)[C@H]2C(=O)O)c2nc(-c3c[nH]c4ncc(F)cc34)ncc12]
B193 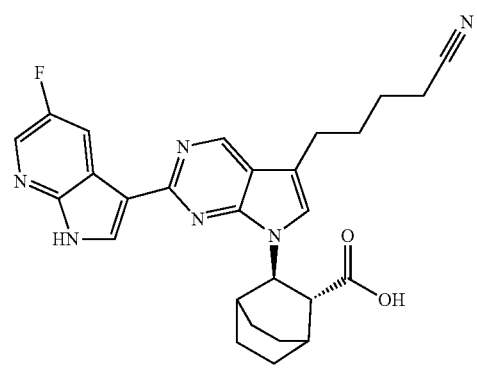 [SMILES: N#CCCCCc1cn([C@@H]2C3CCC(CC3)[C@H]2C(=O)O)c2nc(-c3c[nH]c4ncc(F)cc34)ncc12]
B194 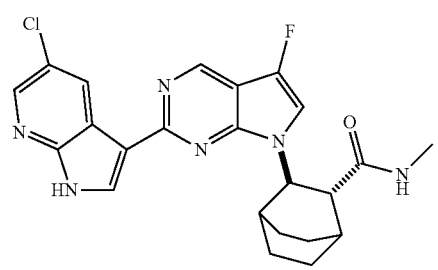

TABLE A-continued
B195 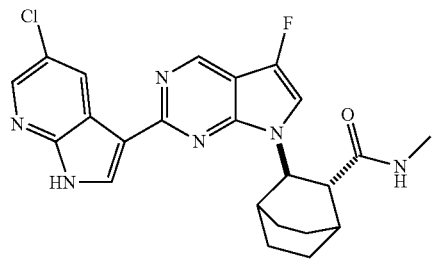
B196 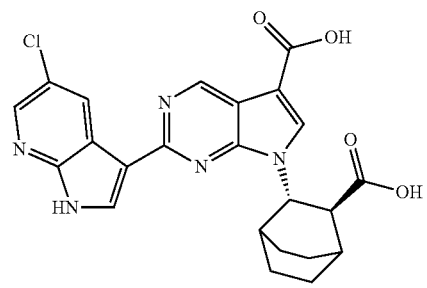 [SMILES: O=C(O)c1cn([C@H]2C3CCC(CC3)[C@@H]2C(=O)O)c2nc(-c3c[nH]c4ncc(Cl)cc34)ncc12]
B197 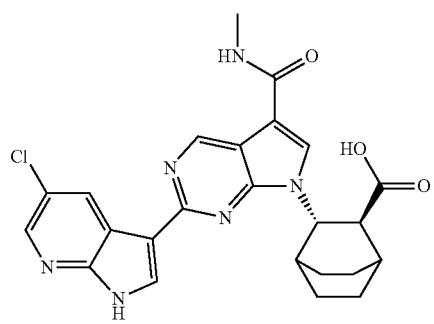 [SMILES: CNC(=O)c1cn([C@H]2C3CCC(CC3)[C@@H]2C(=O)O)c2nc(-c3c[nH]c4ncc(Cl)cc34)ncc12]
B198 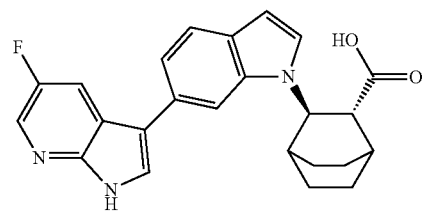 [SMILES: O=C(O)[C@@H]1C2CCC(CC2)[C@H]1n1ccc2ccc(-c3c[nH]c4ncc(F)cc34)cc21]
B199 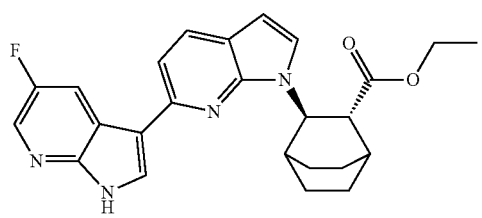 [SMILES: CCOC(=O)[C@@H]1C2CCC(CC2)[C@H]1n1ccc2ccc(-c3c[nH]c4ncc(F)cc34)nc21]
B200 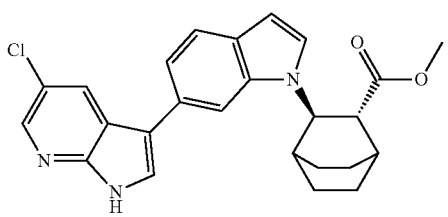 [SMILES: COC(=O)[C@@H]1C2CCC(CC2)[C@H]1n1ccc2ccc(-c3c[nH]c4ncc(Cl)cc34)cc21]

TABLE A-continued
B201
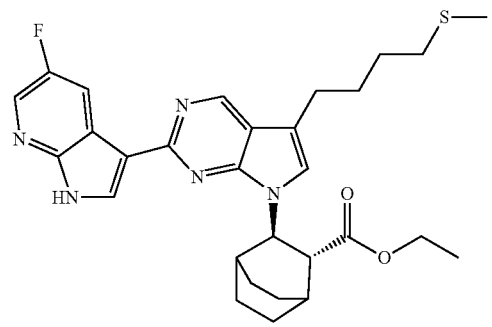 [SMILES: CCOC(=O)[C@@H]1C2CCC(CC2)[C@H]1n1cc(CCCCSC)c2cnc(-c3c[nH]c4ncc(F)cc34)nc21]
B202
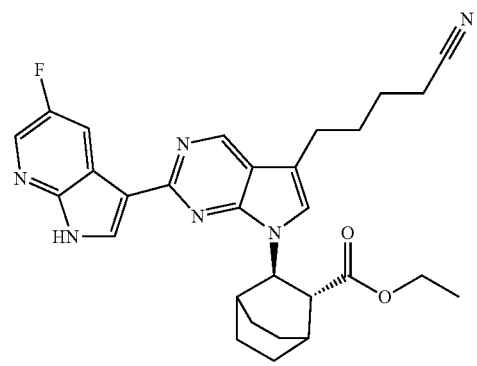 [SMILES: CCOC(=O)[C@@H]1C2CCC(CC2)[C@H]1n1cc(CCCCC#N)c2cnc(-c3c[nH]c4ncc(F)cc34)nc21]
B203
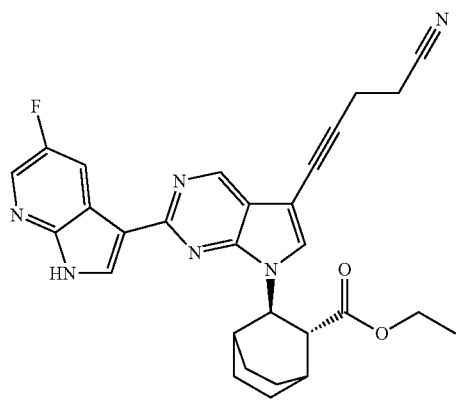 [SMILES: CCOC(=O)[C@@H]1C2CCC(CC2)[C@H]1n1cc(C#CCCC#N)c2cnc(-c3c[nH]c4ncc(F)cc34)nc21]
B204
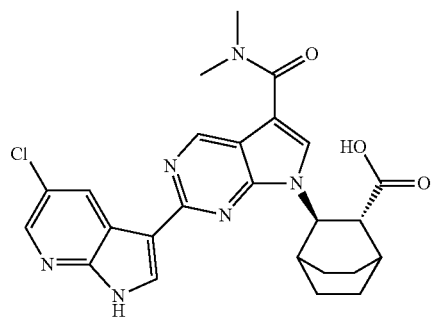 [SMILES: CN(C)C(=O)c1cn([C@@H]2C3CCC(CC3)[C@H]2C(=O)O)c2nc(-c3c[nH]c4ncc(Cl)cc34)ncc12]
B205
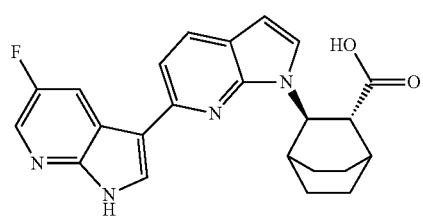 [SMILES: O=C(O)[C@@H]1C2CCC(CC2)[C@H]1n1ccc2ccc(-c3c[nH]c4ncc(F)cc34)nc21]

TABLE A-continued
B206 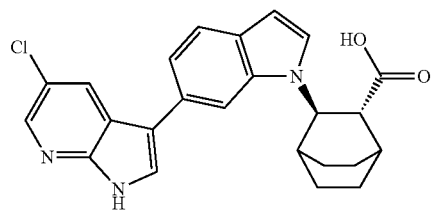 [SMILES: O=C(O)[C@@H]1C2CCC(CC2)[C@H]1n1ccc2ccc(-c3c[nH]c4ncc(Cl)cc34)cc21]
B207 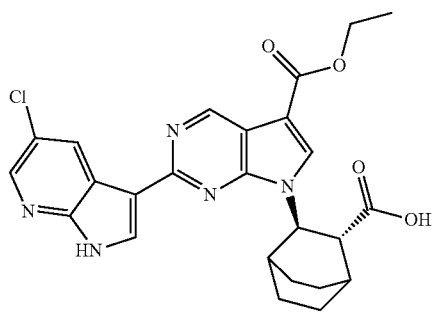 [SMILES: CCOC(=O)c1cn([C@@H]2C3CCC(CC3)[C@H]2C(=O)O)c2nc(-c3c[nH]c4ncc(Cl)cc34)ncc12]
B208 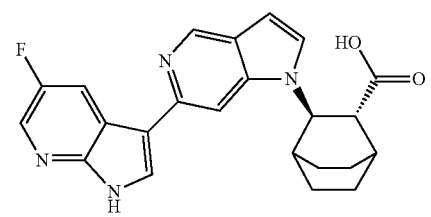 [SMILES: O=C(O)[C@@H]1C2CCC(CC2)[C@H]1n1ccc2cnc(-c3c[nH]c4ncc(F)cc34)cc21]
B209 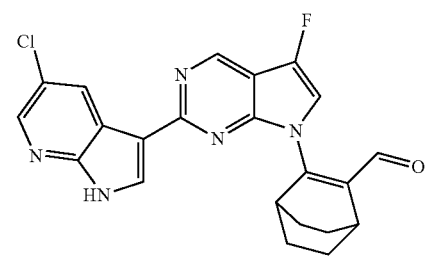 [SMILES: O=CC1=C(n2cc(F)c3cnc(-c4c[nH]c5ncc(Cl)cc45)nc32)C2CCC1CC2]
B210 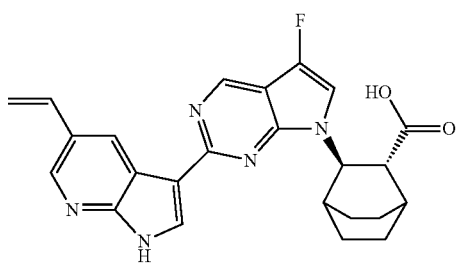 [SMILES: C=Cc1cnc2[nH]cc(-c3ncc4c(F)cn([C@@H]5C6CCC(CC6)[C@H]5C(=O)O)c4n3)c2c1]
B211 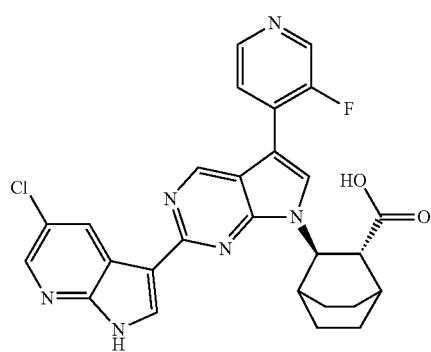

TABLE A-continued
B212
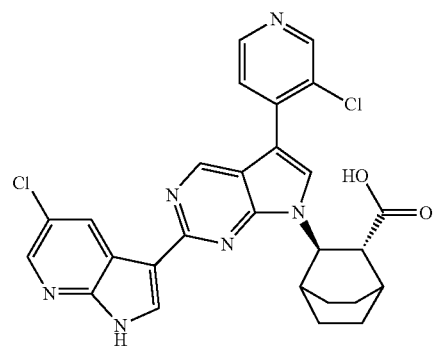 [SMILES: O=C(O)[C@@H]1C2CCC(CC2)[C@H]1n1cc(-c2ccncc2F)c2cnc(-c3c[nH]c4ncc(Cl)cc34)nc21]
B213
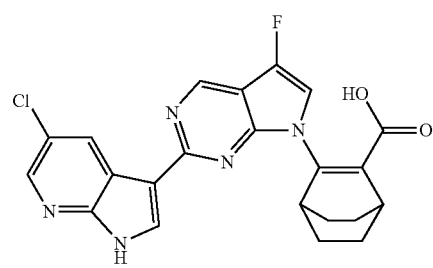 [SMILES: O=C(O)C1=C(n2cc(F)c3cnc(-c4c[nH]c5ncc(Cl)cc45)nc32)C2CCC1CC2]
B214
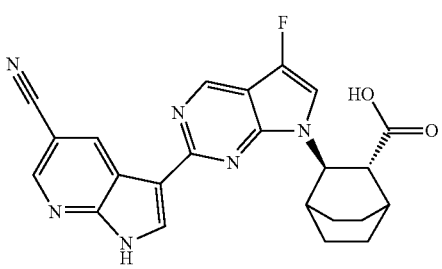 [SMILES: N#Cc1cnc2[nH]cc(-c3ncc4c(F)cn([C@@H]5C6CCC(CC6)[C@H]5C(=O)O)c4n3)c2c1]
B215
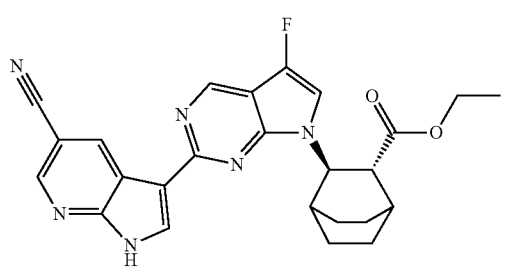
B216
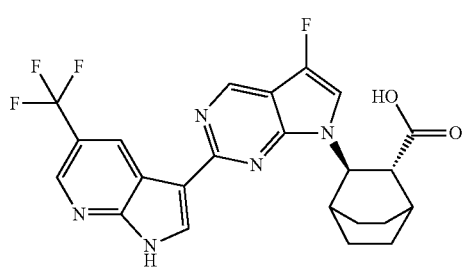 [SMILES: O=C(O)[C@@H]1C2CCC(CC2)[C@H]1n1cc(F)c2cnc(-c3c[nH]c4ncc(C(F)(F)F)cc34)nc21]

TABLE A-continued
B217
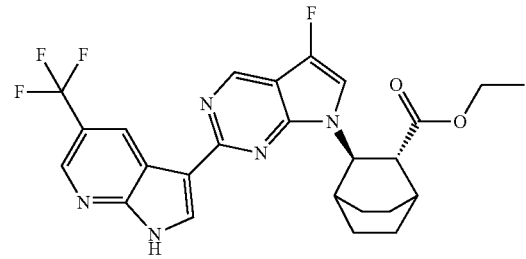 [SMILES: CCOC(=O)[C@@H]1C2CCC(CC2)[C@H]1n1cc(F)c2cnc(-c3c[nH]c4ncc(C(F)(F)F)cc34)nc21]
B218
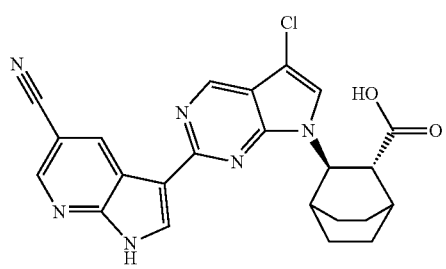
B219
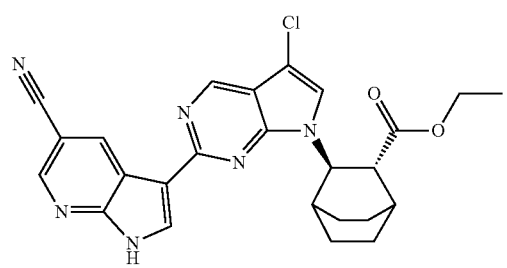
B220
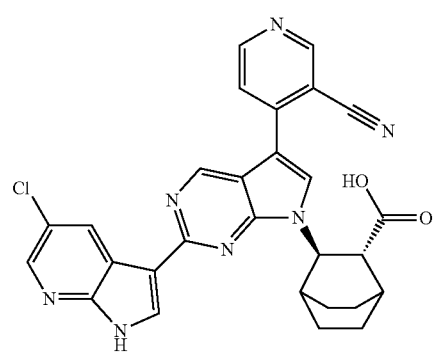 [SMILES: N#Cc1cnccc1-c1cn([C@@H]2C3CCC(CC3)[C@H]2C(=O)O)c2nc(-c3c[nH]c4ncc(Cl)cc34)ncc12]
B221
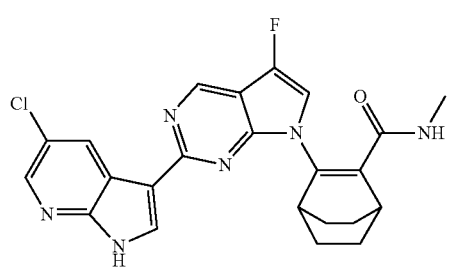 [SMILES: CNC(=O)C1=C(n2cc(F)c3cnc(-c4c[nH]c5ncc(Cl)cc45)nc32)C2CCC1CC2]

TABLE A-continued
B222 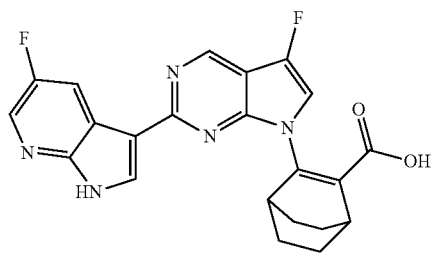 [SMILES: O=C(O)C1=C(n2cc(F)c3cnc(-c4c[nH]c5ncc(F)cc45)nc32)C2CCC1CC2]
C1 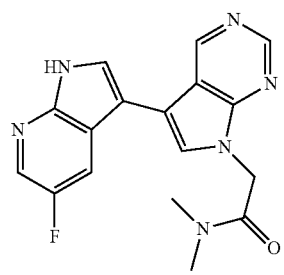 [SMILES: CN(C)C(=O)Cn1cc(-c2c[nH]c3ncc(F)cc23)c2cncnc21]
C2 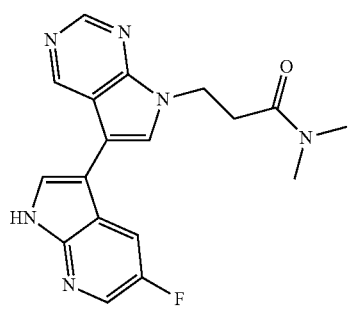 [SMILES: CN(C)C(=O)CCn1cc(-c2c[nH]c3ncc(F)cc23)c2cncnc21]
C3 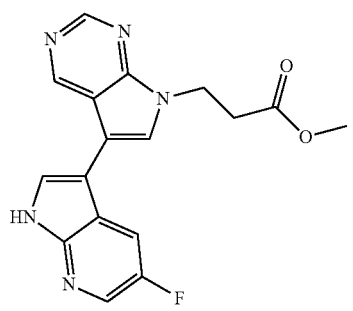 [SMILES: COC(=O)CCn1cc(-c2c[nH]c3ncc(F)cc23)c2cncnc21]
C4 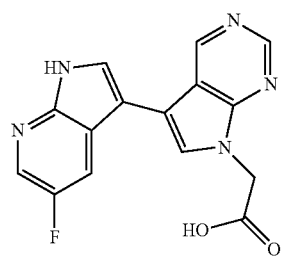 [SMILES: O=C(O)Cn1cc(-c2c[nH]c3ncc(F)cc23)c2cncnc21]

TABLE A-continued
| | |
|---|---|
| C5 | 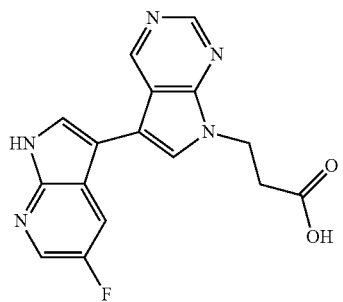 [SMILES: O=C(O)CCn1cc(-c2c[nH]c3ncc(F)cc23)c2cncnc21] |
| C6 | 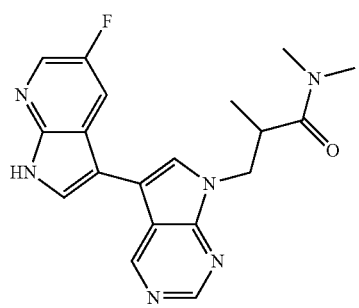 [SMILES: CC(Cn1cc(-c2c[nH]c3ncc(F)cc23)c2cncnc21)C(=O)N(C)C] |
| C7 | 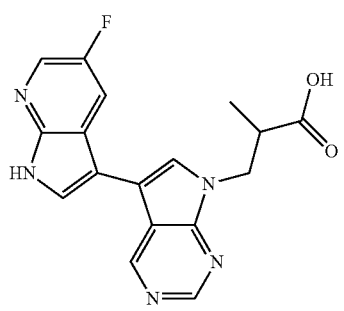 [SMILES: CC(Cn1cc(-c2c[nH]c3ncc(F)cc23)c2cncnc21)C(=O)O] |
| C8 | 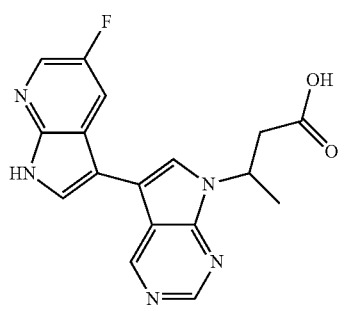 |
| C9 | 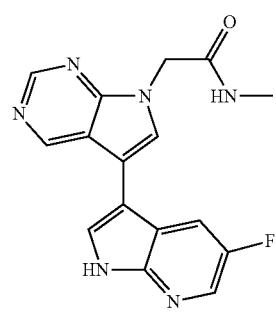 [SMILES: CNC(=O)Cn1cc(-c2c[nH]c3ncc(F)cc23)c2cncnc21] |

TABLE A-continued
C10 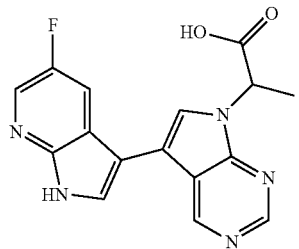 [SMILES: CC(C(=O)O)n1cc(-c2c[nH]c3ncc(F)cc23)c2cncnc21]
C11 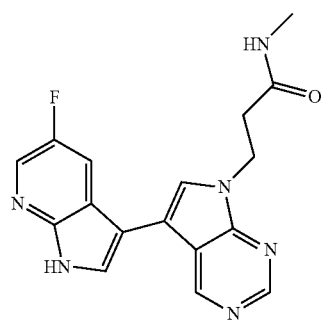 [SMILES: CNC(=O)CCn1cc(-c2c[nH]c3ncc(F)cc23)c2cncnc21]
C12 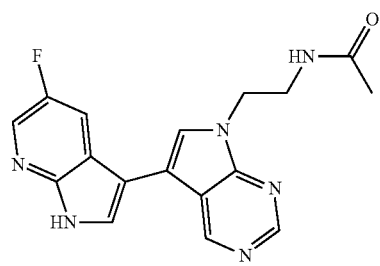 [SMILES: CC(=O)NCCn1cc(-c2c[nH]c3ncc(F)cc23)c2cncnc21]
C13 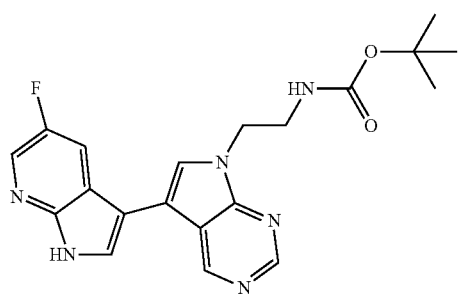 [SMILES: CC(C)(C)OC(=O)NCCn1cc(-c2c[nH]c3ncc(F)cc23)c2cncnc21]
C14 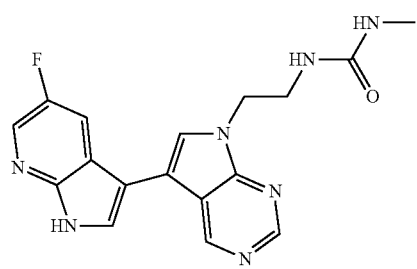 [SMILES: CNC(=O)NCCn1cc(-c2c[nH]c3ncc(F)cc23)c2cncnc21]

TABLE A-continued
C15 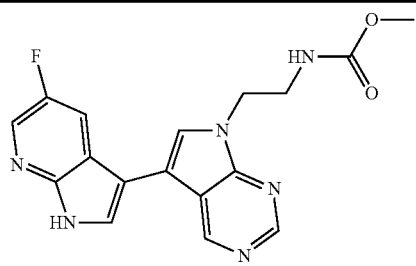
C16 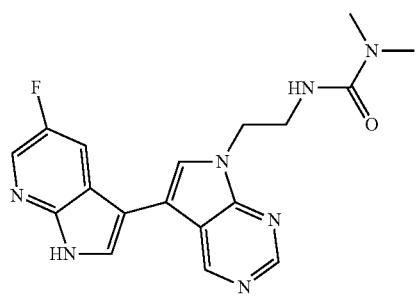 [SMILES: CN(C)C(=O)NCCn1cc(-c2c[nH]c3ncc(F)cc23)c2cncnc21]
C17 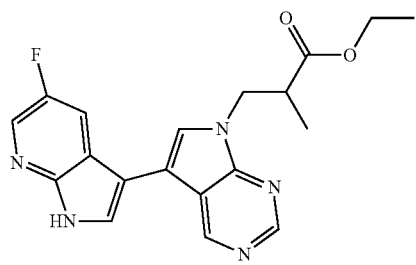 [SMILES: CCOC(=O)C(C)Cn1cc(-c2c[nH]c3ncc(F)cc23)c2cncnc21]
C18 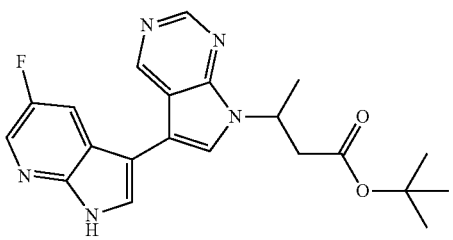 [SMILES: CC(CC(=O)OC(C)(C)C)n1cc(-c2c[nH]c3ncc(F)cc23)c2cncnc21]
Specific compounds of Formula I include compounds as listed in Table B, or a pharmaceutically acceptable salt thereof:
TABLE B
A1 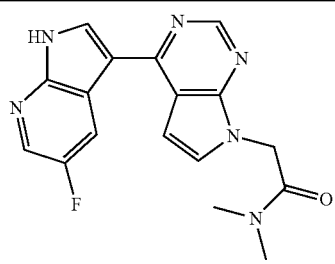

TABLE B-continued
A2 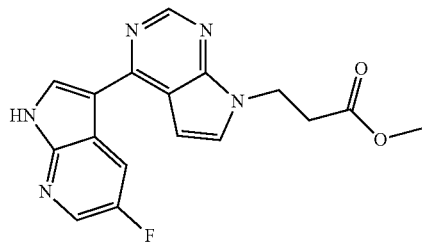 [SMILES: COC(=O)CCn1ccc2c(-c3c[nH]c4ncc(F)cc34)ncnc21]
A3 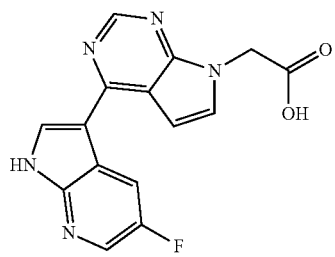 [SMILES: O=C(O)Cn1ccc2c(-c3c[nH]c4ncc(F)cc34)ncnc21]
A4 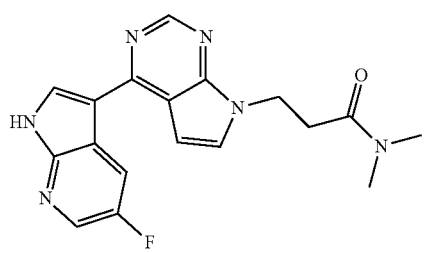 [SMILES: CN(C)C(=O)CCn1ccc2c(-c3c[nH]c4ncc(F)cc34)ncnc21]
A5 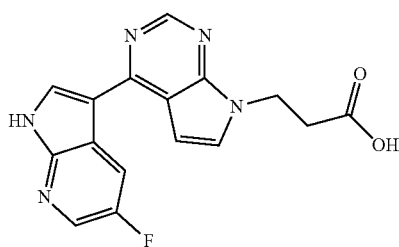 [SMILES: O=C(O)CCn1ccc2c(-c3c[nH]c4ncc(F)cc34)ncnc21]
A6 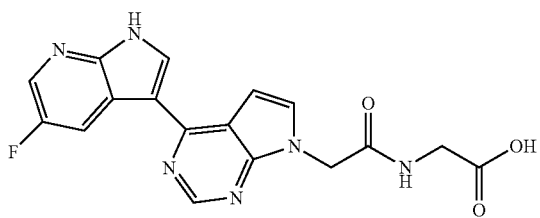 [SMILES: O=C(O)CNC(=O)Cn1ccc2c(-c3c[nH]c4ncc(F)cc34)ncnc21]
A7 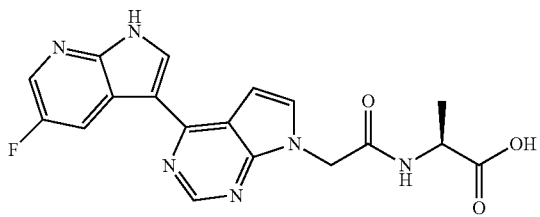 [SMILES: C[C@H](NC(=O)Cn1ccc2c(-c3c[nH]c4ncc(F)cc34)ncnc21)C(=O)O]

TABLE B-continued
A8 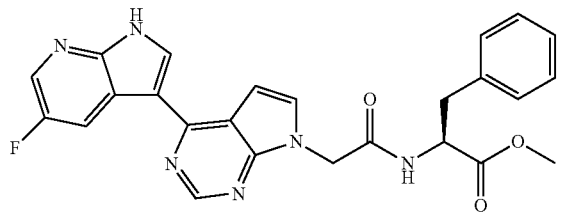 [SMILES: COC(=O)[C@H](Cc1ccccc1)NC(=O)Cn1ccc2c(-c3c[nH]c4ncc(F)cc34)ncnc21]
A9 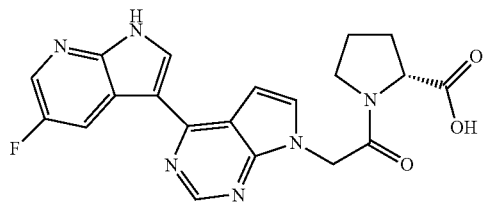 [SMILES: O=C(O)[C@H]1CCCN1C(=O)Cn1ccc2c(-c3c[nH]c4ncc(F)cc34)ncnc21]
A10 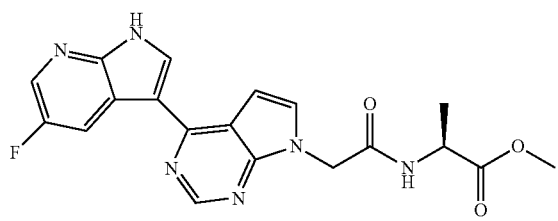 [SMILES: COC(=O)[C@H](C)NC(=O)Cn1ccc2c(-c3c[nH]c4ncc(F)cc34)ncnc21]
A11 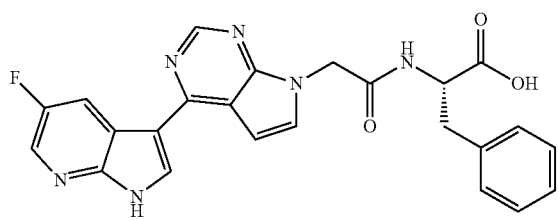 [SMILES: O=C(Cn1ccc2c(-c3c[nH]c4ncc(F)cc34)ncnc21)N[C@@H](Cc1ccccc1)C(=O)O]
A12 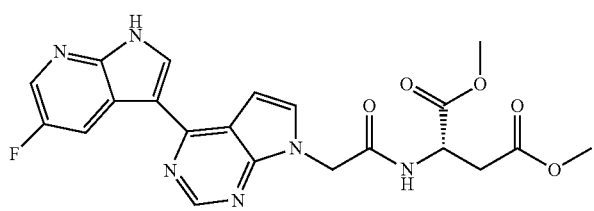 [SMILES: COC(=O)C[C@H](NC(=O)Cn1ccc2c(-c3c[nH]c4ncc(F)cc34)ncnc21)C(=O)OC]
A13 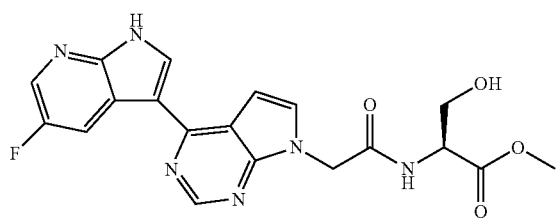 [SMILES: COC(=O)[C@H](CO)NC(=O)Cn1ccc2c(-c3c[nH]c4ncc(F)cc34)ncnc21]
A14 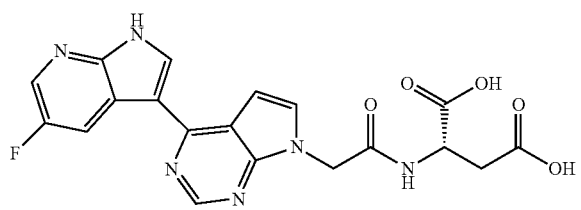 [SMILES: O=C(O)C[C@H](NC(=O)Cn1ccc2c(-c3c[nH]c4ncc(F)cc34)ncnc21)C(=O)O]

TABLE B-continued
A15 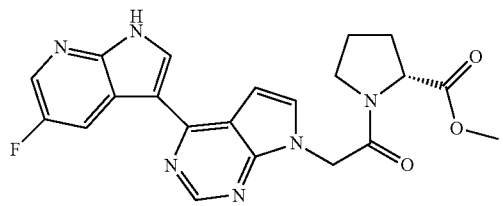 [SMILES: COC(=O)[C@H]1CCCN1C(=O)Cn1ccc2c(-c3c[nH]c4ncc(F)cc34)ncnc21]
A16 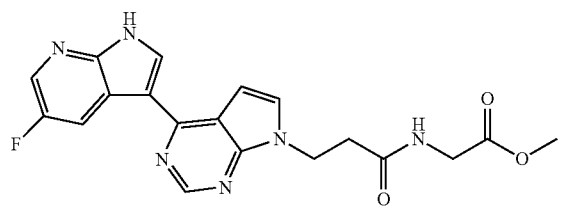 [SMILES: COC(=O)CNC(=O)CCn1ccc2c(-c3c[nH]c4ncc(F)cc34)ncnc21]
A17 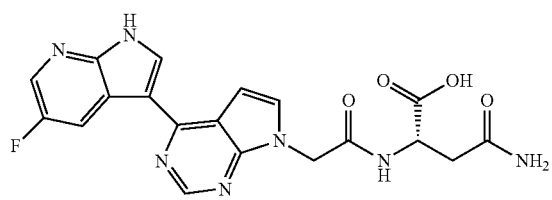 [SMILES: NC(=O)C[C@H](NC(=O)Cn1ccc2c(-c3c[nH]c4ncc(F)cc34)ncnc21)C(=O)O]
A18 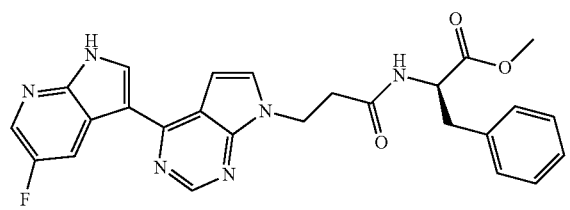 [SMILES: COC(=O)[C@@H](Cc1ccccc1)NC(=O)CCn1ccc2c(-c3c[nH]c4ncc(F)cc34)ncnc21]
A19 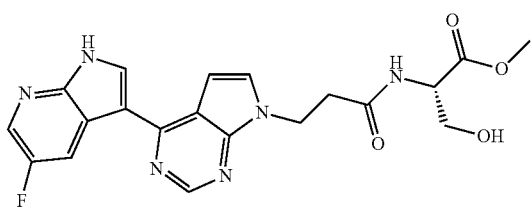 [SMILES: COC(=O)[C@H](CO)NC(=O)CCn1ccc2c(-c3c[nH]c4ncc(F)cc34)ncnc21]
A20 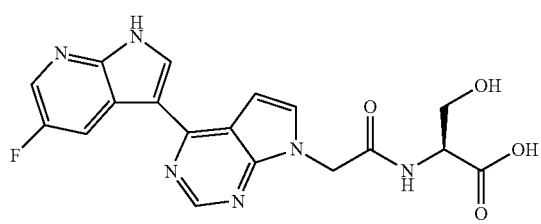 [SMILES: O=C(Cn1ccc2c(-c3c[nH]c4ncc(F)cc34)ncnc21)N[C@@H](CO)C(=O)O]

Specific compounds of Formula II include a compound as listed in Table C, or a pharmaceutically acceptable salt thereof.
TABLE C
B1
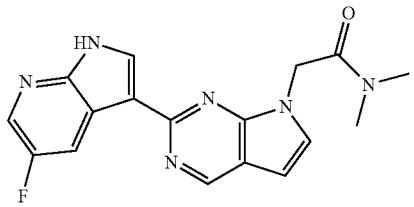 [SMILES: CN(C)C(=O)Cn1ccc2cnc(-c3c[nH]c4ncc(F)cc34)nc21]
B2
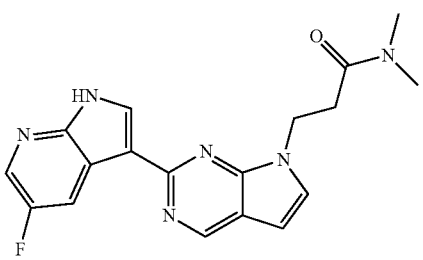 [SMILES: CN(C)C(=O)CCn1ccc2cnc(-c3c[nH]c4ncc(F)cc34)nc21]
B3
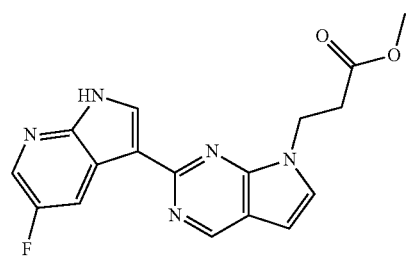 [SMILES: COC(=O)CCn1ccc2cnc(-c3c[nH]c4ncc(F)cc34)nc21]
B4
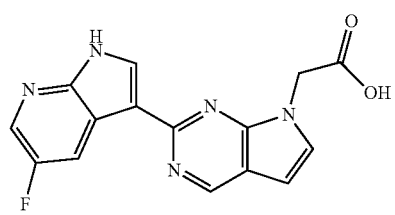 [SMILES: O=C(O)Cn1ccc2cnc(-c3c[nH]c4ncc(F)cc34)nc21]
B5
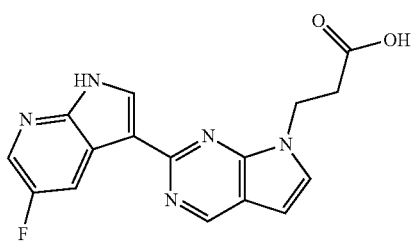 [SMILES: O=C(O)CCn1ccc2cnc(-c3c[nH]c4ncc(F)cc34)nc21]
B6
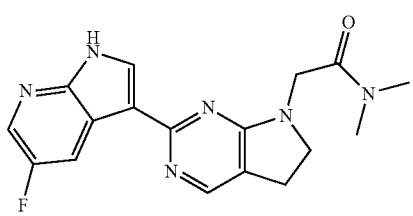 [SMILES: CN(C)C(=O)CN1CCc2cnc(-c3c[nH]c4ncc(F)cc34)nc21]

TABLE C-continued
| B7 | 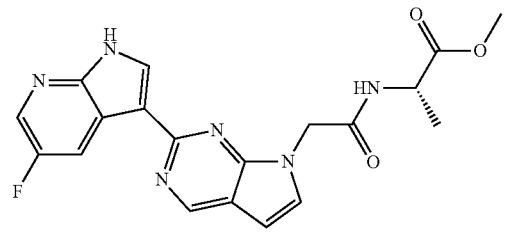 [SMILES: COC(=O)[C@H](C)NC(=O)Cn1ccc2cnc(-c3c[nH]c4ncc(F)cc34)nc21] |
| --- | --- |
| B8 | 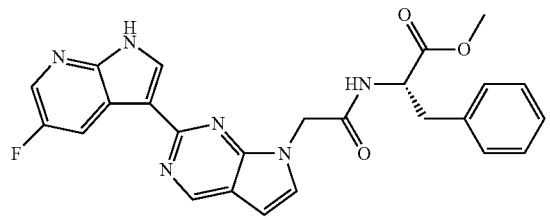 [SMILES: COC(=O)[C@H](Cc1ccccc1)NC(=O)Cn1ccc2cnc(-c3c[nH]c4ncc(F)cc34)nc21] |
| B9 | 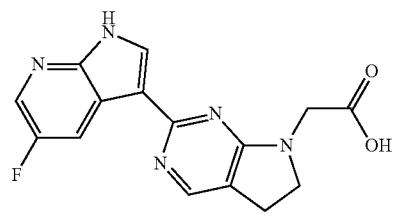 [SMILES: O=C(O)CN1CCc2cnc(-c3c[nH]c4ncc(F)cc34)nc21] |
| B10 | 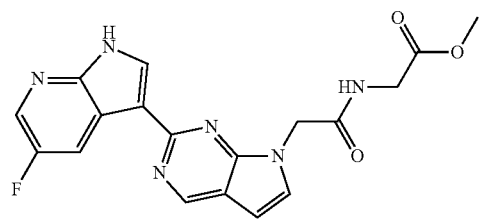 [SMILES: COC(=O)CNC(=O)Cn1ccc2cnc(-c3c[nH]c4ncc(F)cc34)nc21] |
| B11 | 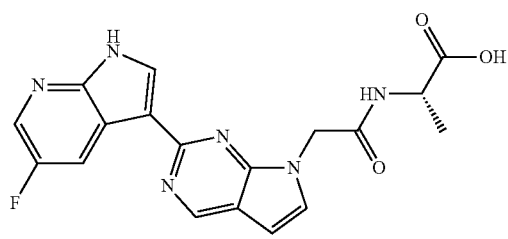 [SMILES: C[C@H](NC(=O)Cn1ccc2cnc(-c3c[nH]c4ncc(F)cc34)nc21)C(=O)O] |
| B12 | 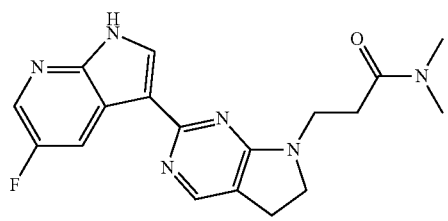 [SMILES: CN(C)C(=O)CCN1CCc2cnc(-c3c[nH]c4ncc(F)cc34)nc21] |
| B13 | 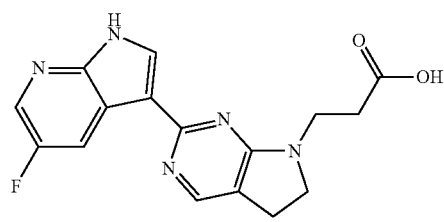 [SMILES: O=C(O)CCN1CCc2cnc(-c3c[nH]c4ncc(F)cc34)nc21] |

TABLE C-continued
B14 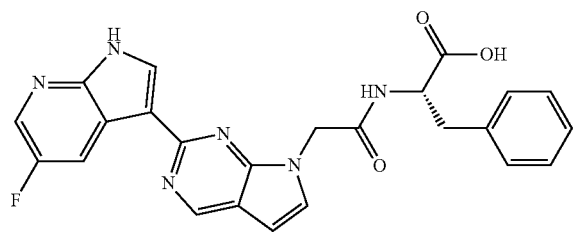 [SMILES: O=C(Cn1ccc2cnc(-c3c[nH]c4ncc(F)cc34)nc21)N[C@@H](Cc1ccccc1)C(=O)O]
B15 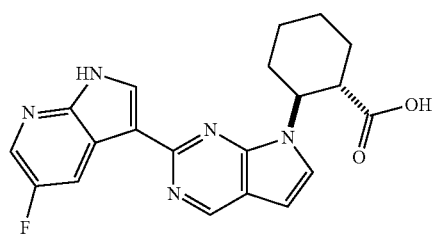
B16 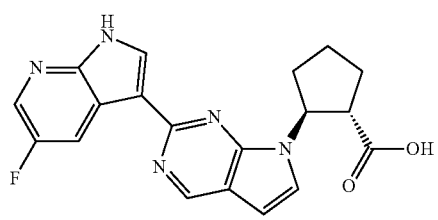
B17 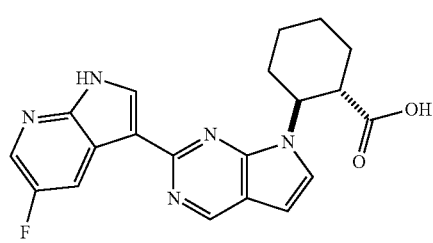
B18 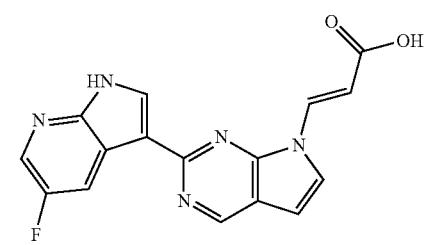 [SMILES: O=C(O)/C=C/n1ccc2cnc(-c3c[nH]c4ncc(F)cc34)nc21]
B19 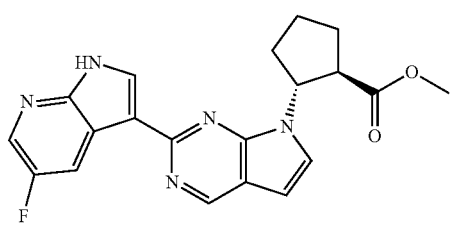 [SMILES: COC(=O)[C@@H]1CCC[C@H]1n1ccc2cnc(-c3c[nH]c4ncc(F)cc34)nc21]
B20 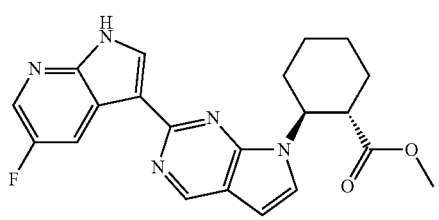 [SMILES: COC(=O)[C@H]1CCCC[C@@H]1n1ccc2cnc(-c3c[nH]c4ncc(F)cc34)nc21]

TABLE C-continued
B21
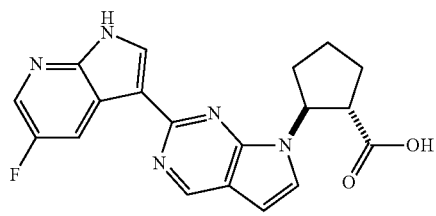
B22
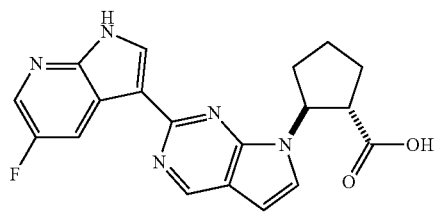
B23
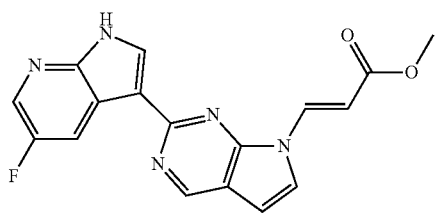 [SMILES: COC(=O)/C=C/n1ccc2cnc(-c3c[nH]c4ncc(F)cc34)nc21]
B24
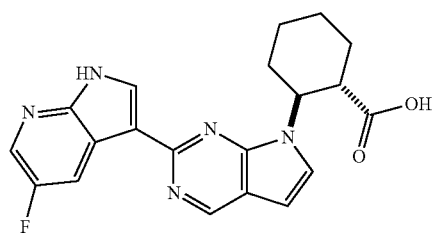
B25
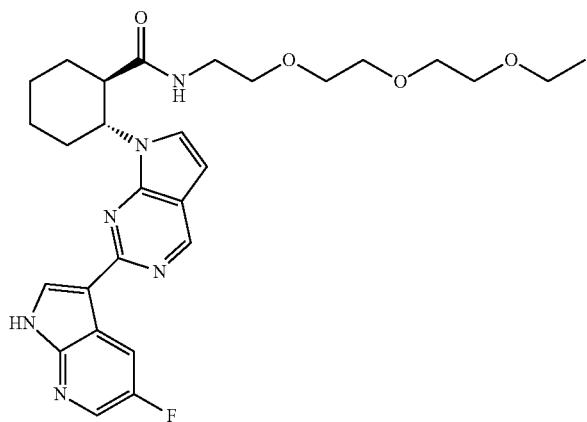 [SMILES: CCOCCOCCOCCNC(=O)[C@@H]1CCCC[C@H]1n1ccc2cnc(-c3c[nH]c4ncc(F)cc34)nc21]
B26
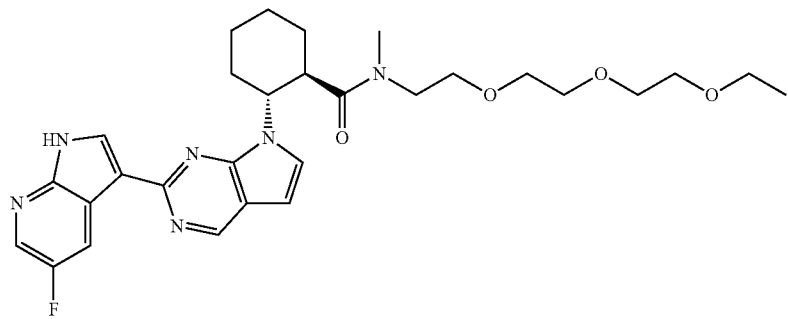 [SMILES: CCOCCOCCOCCN(C)C(=O)[C@@H]1CCCC[C@H]1n1ccc2cnc(-c3c[nH]c4ncc(F)cc34)nc21]

TABLE C-continued
B27
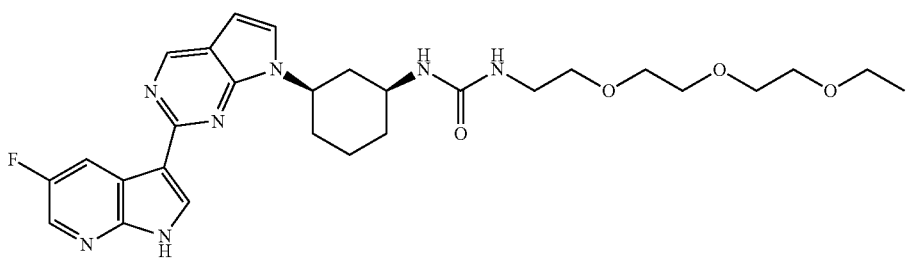 [SMILES: CCOCCOCCOCCNC(=O)N[C@H]1CCC[C@@H](n2ccc3cnc(-c4c[nH]c5ncc(F)cc45)nc32)C1]
B28
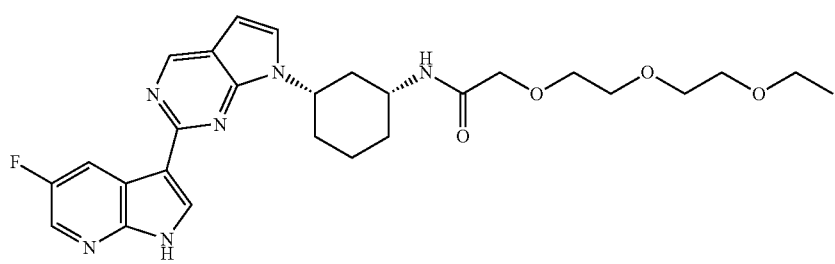 [SMILES: CCOCCOCCOCC(=O)N[C@@H]1CCC[C@H](n2ccc3cnc(-c4c[nH]c5ncc(F)cc45)nc32)C1]
B29
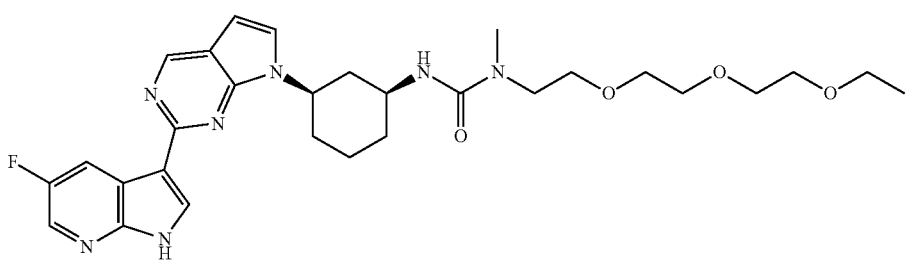 [SMILES: CCOCCOCCOCCN(C)C(=O)N[C@H]1CCC[C@@H](n2ccc3cnc(-c4c[nH]c5ncc(F)cc45)nc32)C1]
B30
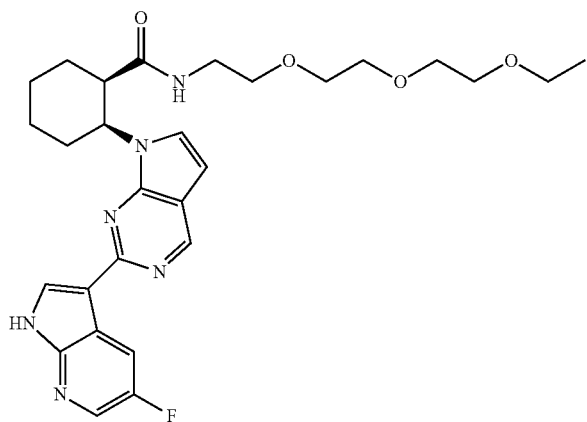 [SMILES: CCOCCOCCOCCNC(=O)[C@@H]1CCCC[C@@H]1n1ccc2cnc(-c3c[nH]c4ncc(F)cc34)nc21]
B31
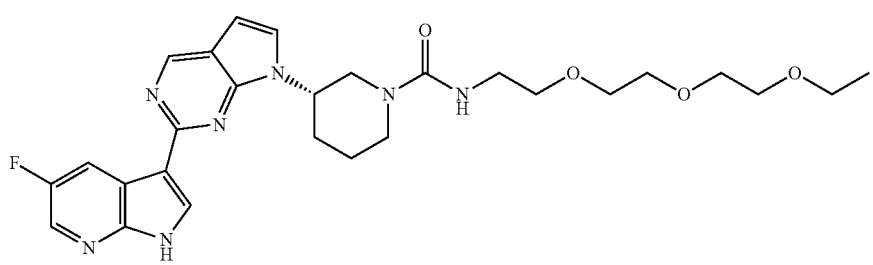 [SMILES: CCOCCOCCOCCNC(=O)N1CCC[C@H](n2ccc3cnc(-c4c[nH]c5ncc(F)cc45)nc32)C1]

TABLE C-continued
B32
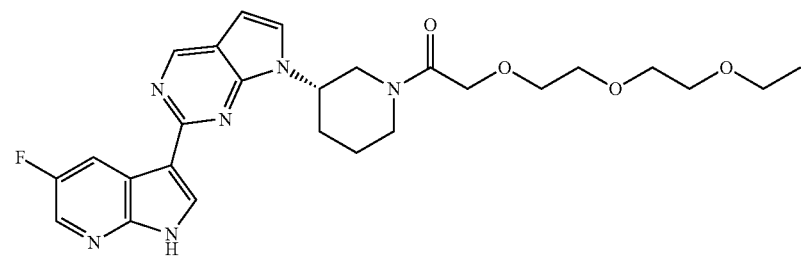 [SMILES: CCOCCOCCOCC(=O)N1CCC[C@H](n2ccc3cnc(-c4c[nH]c5ncc(F)cc45)nc32)C1]
B33
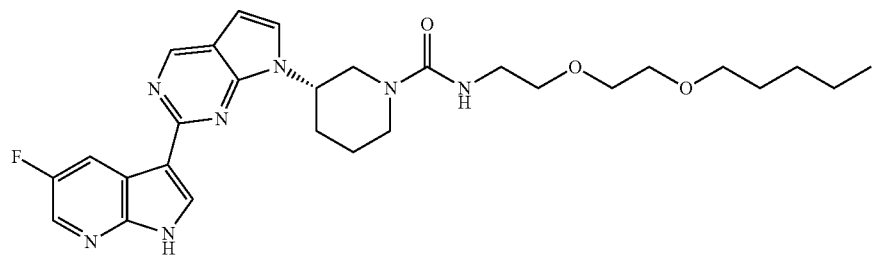 [SMILES: CCCCCOCCOCCNC(=O)N1CCC[C@H](n2ccc3cnc(-c4c[nH]c5ncc(F)cc45)nc32)C1]
B34
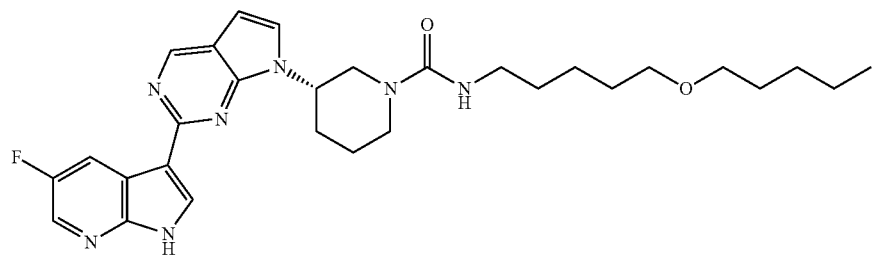 [SMILES: CCCCCOCCCCCNC(=O)N1CCC[C@H](n2ccc3cnc(-c4c[nH]c5ncc(F)cc45)nc32)C1]
B35
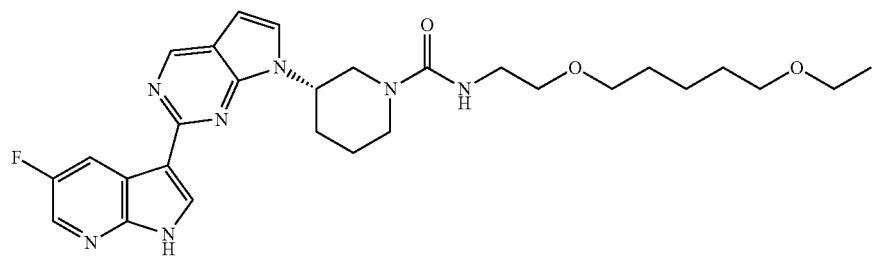 [SMILES: CCOCCCCCOCCNC(=O)N1CCC[C@H](n2ccc3cnc(-c4c[nH]c5ncc(F)cc45)nc32)C1]
B36
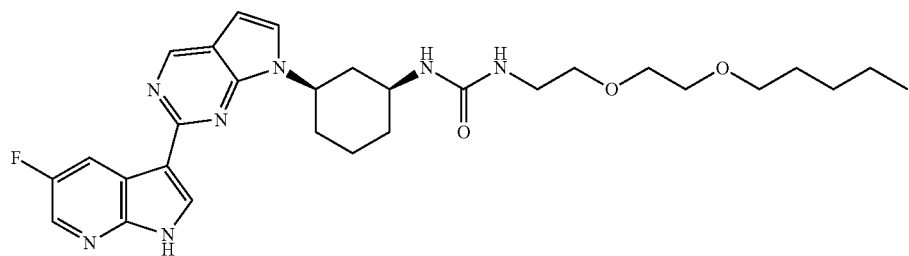 [SMILES: CCCCCOCCOCCNC(=O)N[C@H]1CCC[C@@H](n2ccc3cnc(-c4c[nH]c5ncc(F)cc45)nc32)C1]
B37
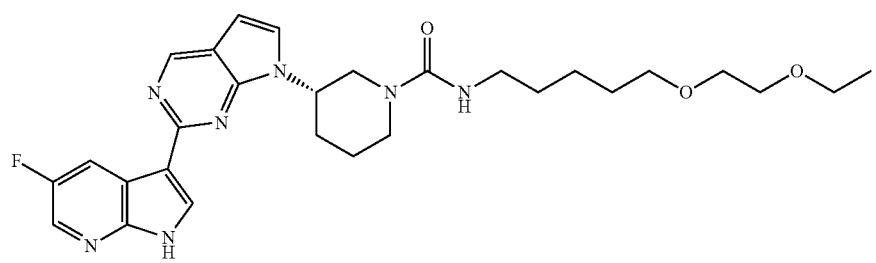 [SMILES: CCOCCOCCCCCNC(=O)N1CCC[C@H](n2ccc3cnc(-c4c[nH]c5ncc(F)cc45)nc32)C1]

TABLE C-continued
B38 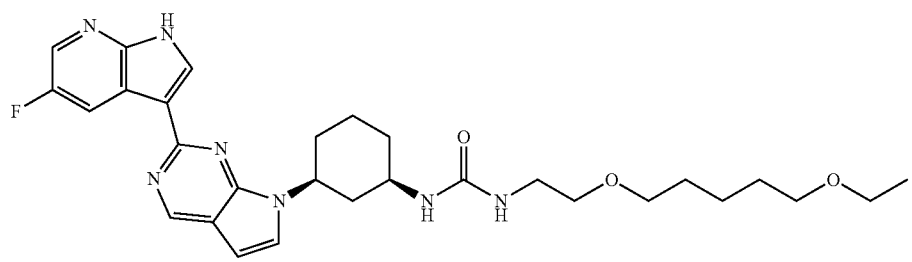 [SMILES: CCOCCCCCOCCNC(=O)N[C@@H]1CCC[C@H](n2ccc3cnc(-c4c[nH]c5ncc(F)cc45)nc32)C1]
B39 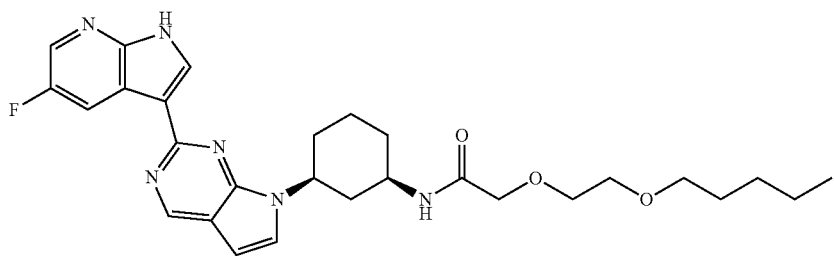 [SMILES: CCCCCOCCOCC(=O)N[C@@H]1CCC[C@H](n2ccc3cnc(-c4c[nH]c5ncc(F)cc45)nc32)C1]
B40 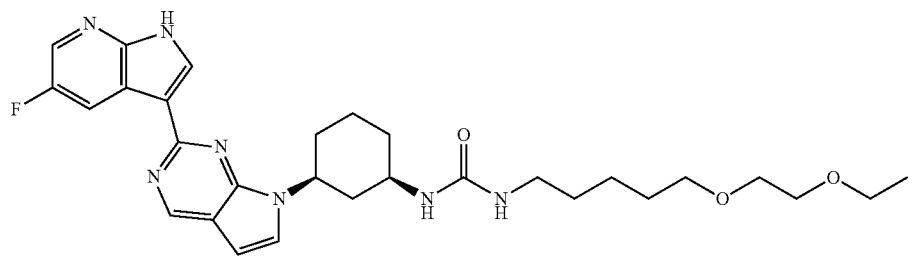 [SMILES: CCOCCOCCCCCNC(=O)N[C@@H]1CCC[C@H](n2ccc3cnc(-c4c[nH]c5ncc(F)cc45)nc32)C1]
B41 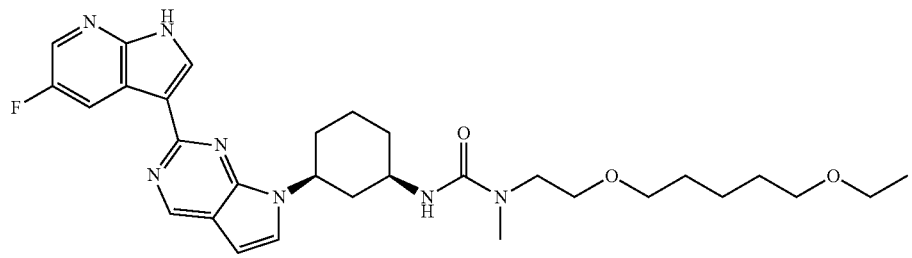 [SMILES: CCOCCCCCOCCN(C)C(=O)N[C@@H]1CCC[C@H](n2ccc3cnc(-c4c[nH]c5ncc(F)cc45)nc32)C1]
B42 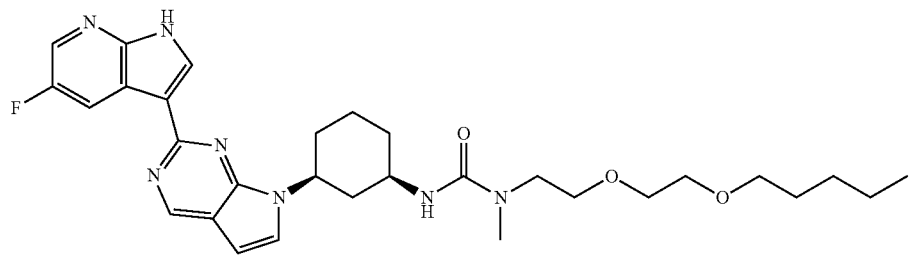 [SMILES: CCCCCOCCOCCN(C)C(=O)N[C@@H]1CCC[C@H](n2ccc3cnc(-c4c[nH]c5ncc(F)cc45)nc32)C1]
B43 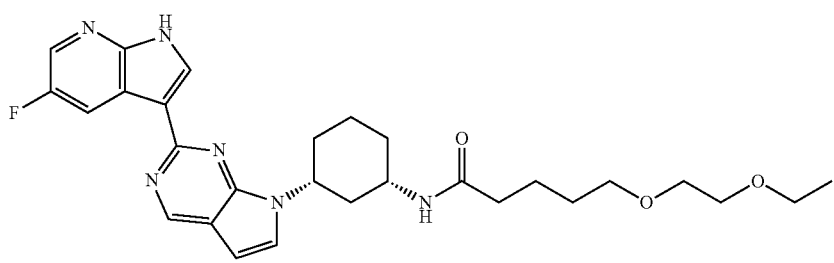 [SMILES: CCOCCOCCCCC(=O)N[C@H]1CCC[C@@H](n2ccc3cnc(-c4c[nH]c5ncc(F)cc45)nc32)C1]

TABLE C-continued
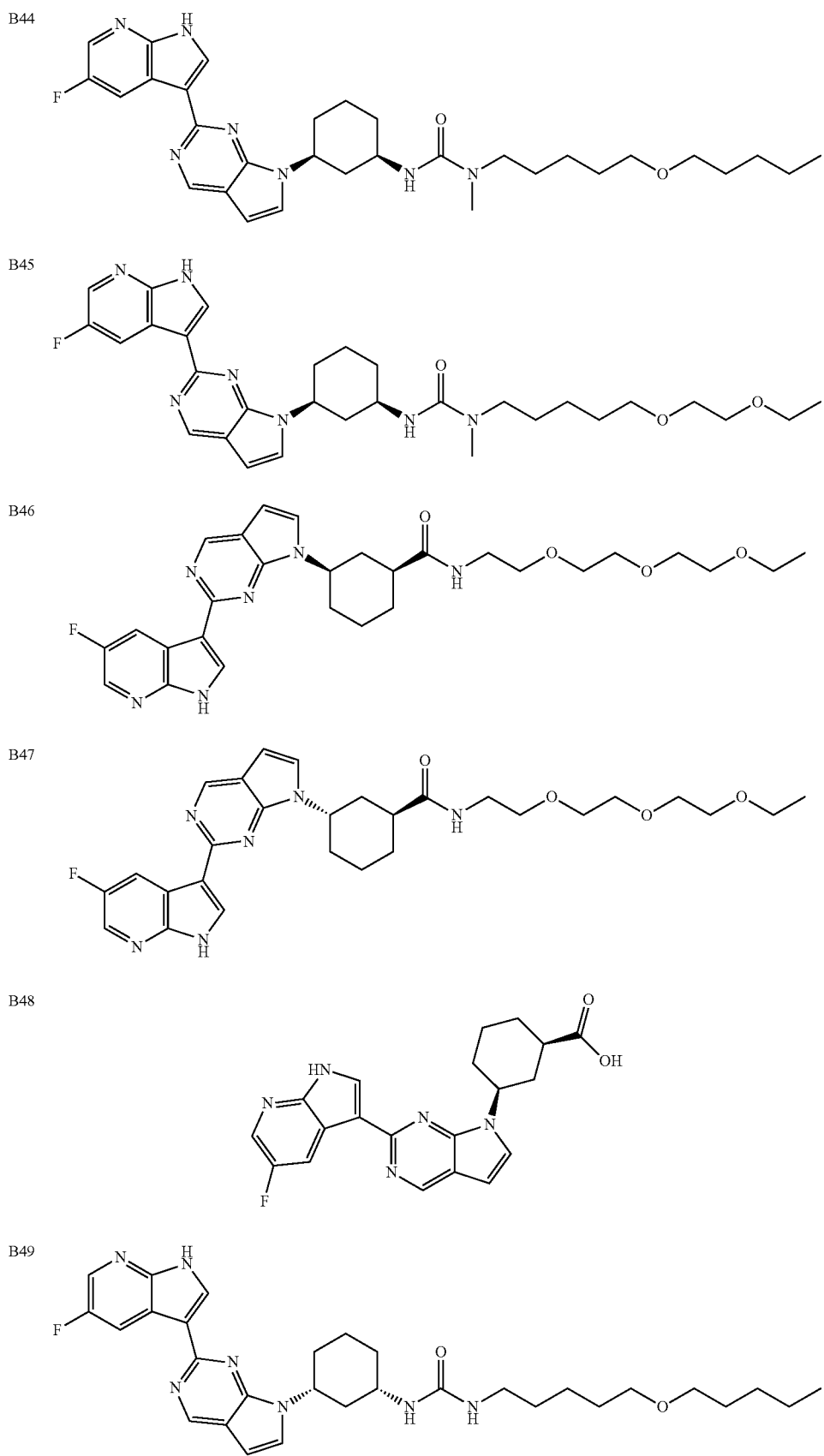

TABLE C-continued
B50
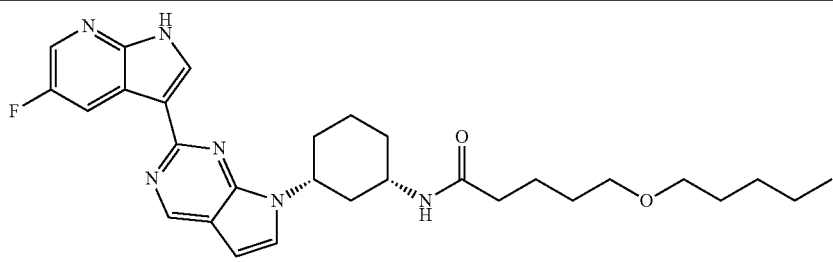
B51
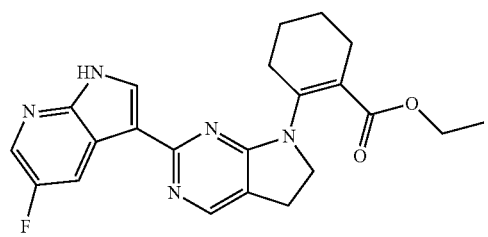 [SMILES: CCOC(=O)C1=C(N2CCc3cnc(-c4c[nH]c5ncc(F)cc45)nc32)CCCC1]
B100
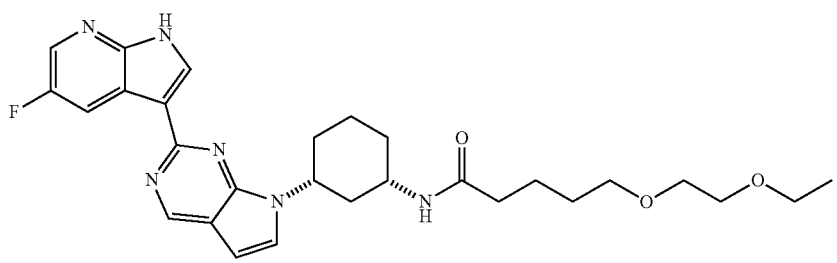
B52
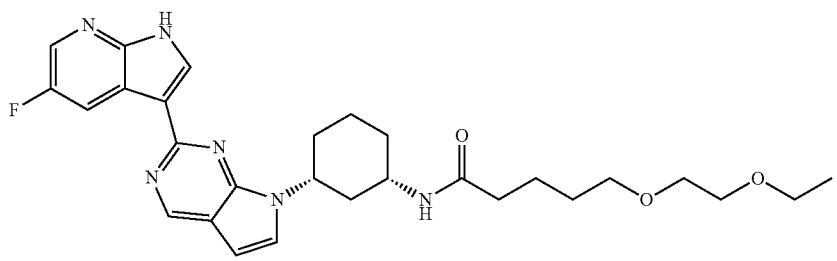 [SMILES: CCOCCOCCCCC(=O)N[C@H]1CCC[C@@H](n2ccc3cnc(-c4c[nH]c5ncc(F)cc45)nc32)C1]
B53
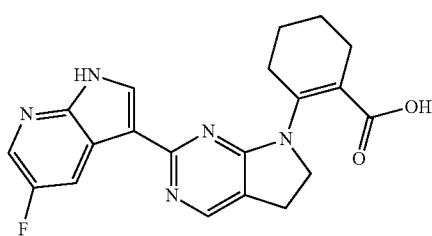 [SMILES: O=C(O)C1=C(N2CCc3cnc(-c4c[nH]c5ncc(F)cc45)nc32)CCCC1]
B54
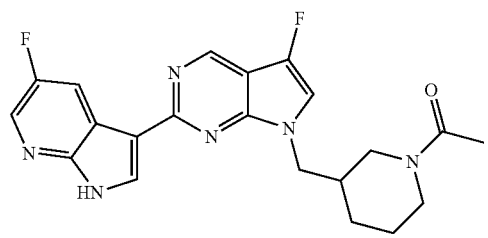 [SMILES: CC(=O)N1CCCC(Cn2cc(F)c3cnc(-c4c[nH]c5ncc(F)cc45)nc32)C1]

TABLE C-continued
B55
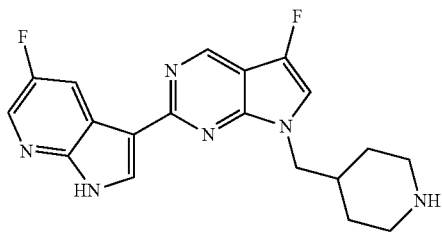 [SMILES: Fc1cnc2[nH]cc(-c3ncc4c(F)cn(CC5CCNCC5)c4n3)c2c1]
B56
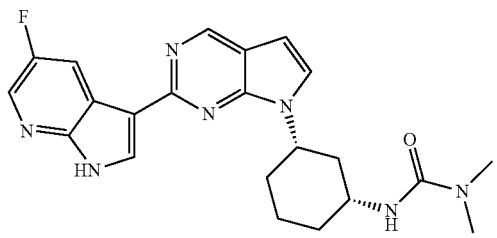 [SMILES: CN(C)C(=O)N[C@@H]1CCC[C@H](n2ccc3cnc(-c4c[nH]c5ncc(F)cc45)nc32)C1]
B57
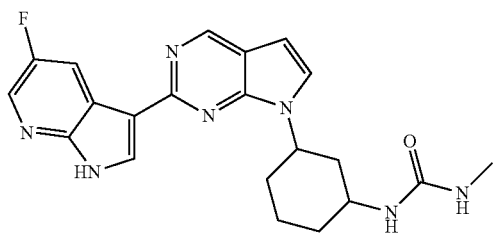 [SMILES: CNC(=O)NC1CCCC(n2ccc3cnc(-c4c[nH]c5ncc(F)cc45)nc32)C1]
B58
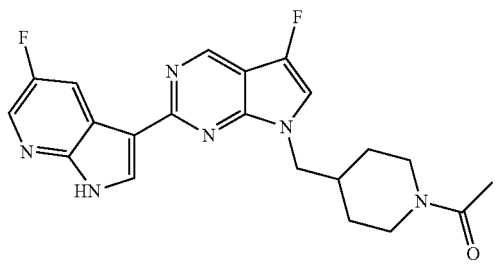 [SMILES: CC(=O)N1CCC(Cn2cc(F)c3cnc(-c4c[nH]c5ncc(F)cc45)nc32)CC1]
B59
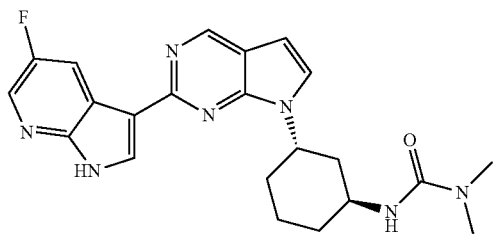 [SMILES: CN(C)C(=O)N[C@H]1CCC[C@H](n2ccc3cnc(-c4c[nH]c5ncc(F)cc45)nc32)C1]
B60
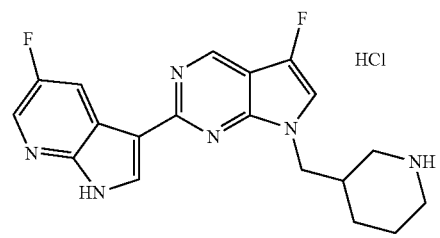 [SMILES: Fc1cnc2[nH]cc(-c3ncc4c(F)cn(CC5CCCNC5)c4n3)c2c1 ; Cl]

TABLE C-continued
B61 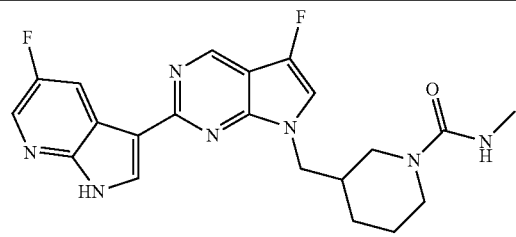
B62 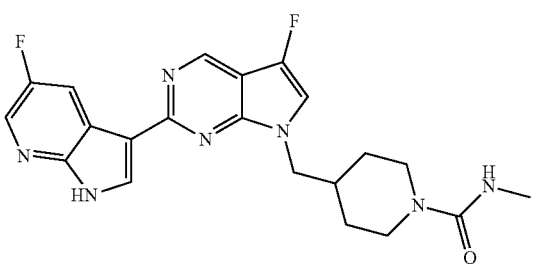 [SMILES: CNC(=O)N1CCC(Cn2cc(F)c3cnc(-c4c[nH]c5ncc(F)cc45)nc32)CC1]
B63 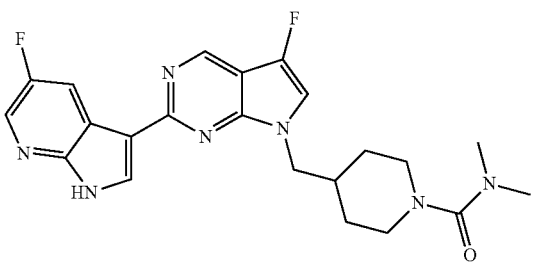 [SMILES: CN(C)C(=O)N1CCC(Cn2cc(F)c3cnc(-c4c[nH]c5ncc(F)cc45)nc32)CC1]
B64 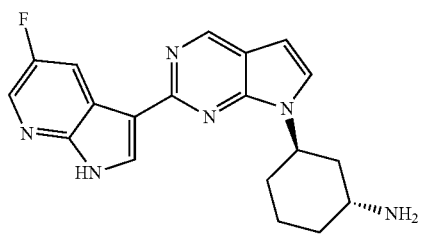 [SMILES: N[C@@H]1CCC[C@@H](n2ccc3cnc(-c4c[nH]c5ncc(F)cc45)nc32)C1]
B65 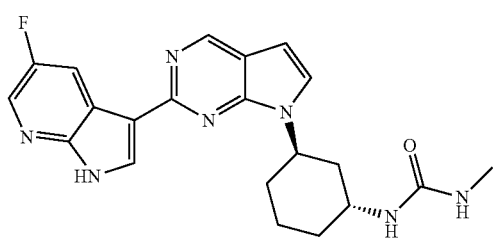 [SMILES: CNC(=O)N[C@@H]1CCC[C@@H](n2ccc3cnc(-c4c[nH]c5ncc(F)cc45)nc32)C1]
B66 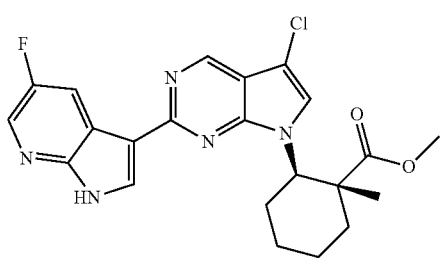

TABLE C-continued
B67
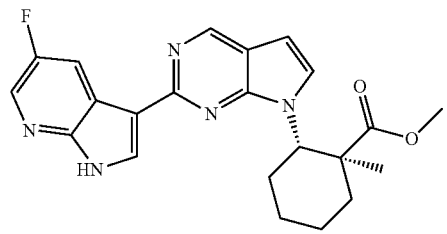 [SMILES: COC(=O)[C@@]1(C)CCCC[C@@H]1n1ccc2cnc(-c3c[nH]c4ncc(F)cc34)nc21]
B68
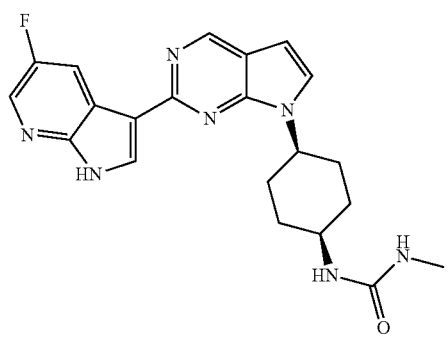 [SMILES: CNC(=O)N[C@H]1CC[C@@H](n2ccc3cnc(-c4c[nH]c5ncc(F)cc45)nc32)CC1]
B69
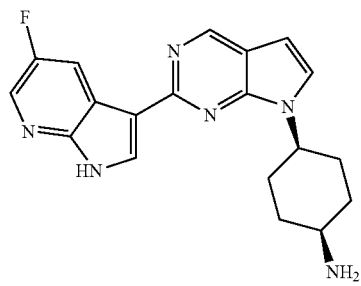 [SMILES: N[C@H]1CC[C@@H](n2ccc3cnc(-c4c[nH]c5ncc(F)cc45)nc32)CC1]
B70
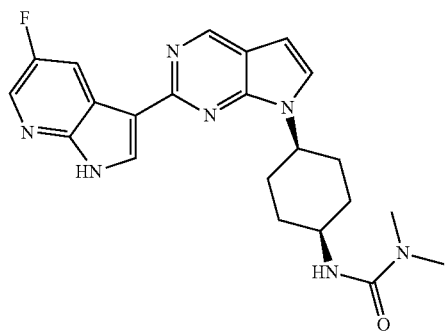 [SMILES: CN(C)C(=O)N[C@H]1CC[C@@H](n2ccc3cnc(-c4c[nH]c5ncc(F)cc45)nc32)CC1]
B71
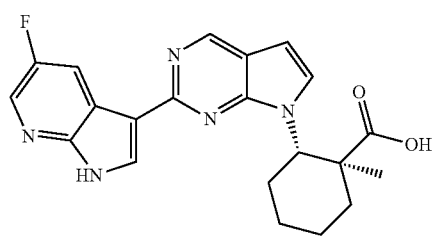 [SMILES: C[C@]1(C(=O)O)CCCC[C@@H]1n1ccc2cnc(-c3c[nH]c4ncc(F)cc34)nc21]

TABLE C-continued
B72 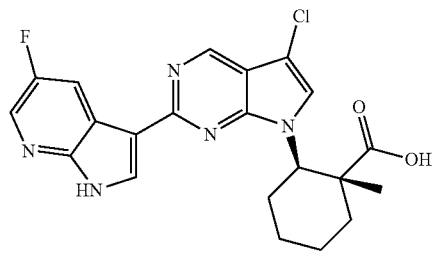 [SMILES: C[C@@]1(C(=O)O)CCCC[C@H]1n1cc(Cl)c2cnc(-c3c[nH]c4ncc(F)cc34)nc21]
B73 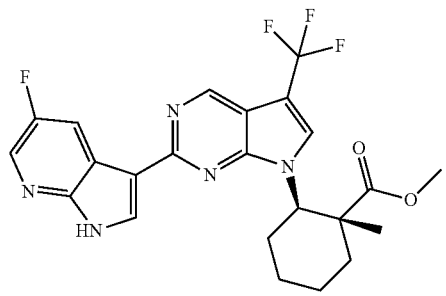 [SMILES: COC(=O)[C@]1(C)CCCC[C@H]1n1cc(C(F)(F)F)c2cnc(-c3c[nH]c4ncc(F)cc34)nc21]
B74 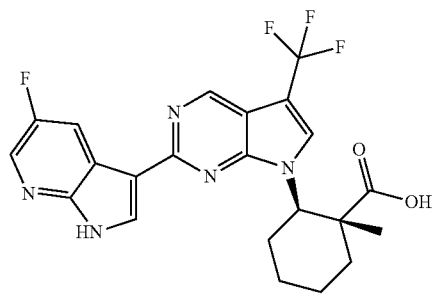 [SMILES: C[C@@]1(C(=O)O)CCCC[C@H]1n1cc(C(F)(F)F)c2cnc(-c3c[nH]c4ncc(F)cc34)nc21]
B75 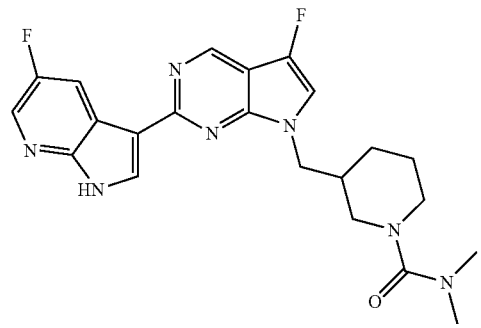 [SMILES: CN(C)C(=O)N1CCCC(Cn2cc(F)c3cnc(-c4c[nH]c5ncc(F)cc45)nc32)C1]
B76 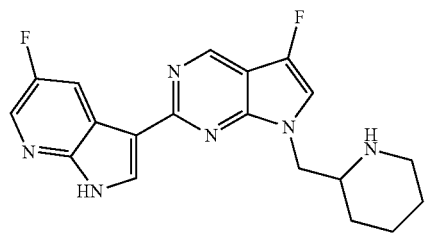 [SMILES: Fc1cnc2[nH]cc(-c3ncc4c(F)cn(CC5CCCCN5)c4n3)c2c1]

TABLE C-continued
B77 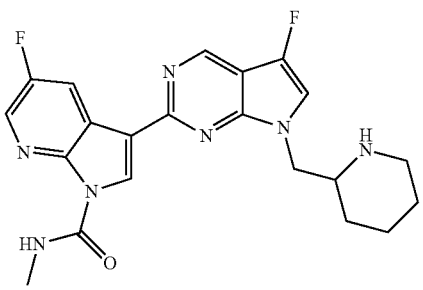 [SMILES: CNC(=O)n1cc(-c2ncc3c(F)cn(CC4CCCCN4)c3n2)c2cc(F)cnc21]
B78 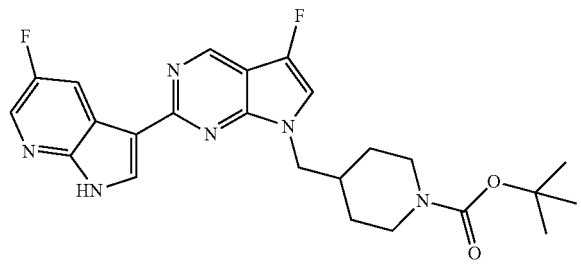 [SMILES: CC(C)(C)OC(=O)N1CCC(Cn2cc(F)c3cnc(-c4c[nH]c5ncc(F)cc45)nc32)CC1]
B79 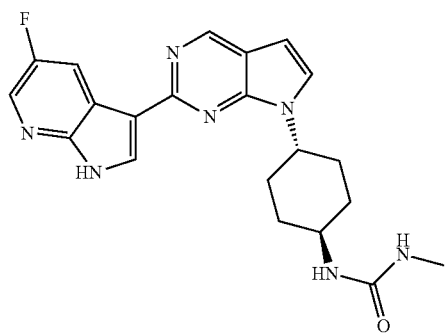 [SMILES: CNC(=O)N[C@H]1CC[C@H](n2ccc3cnc(-c4c[nH]c5ncc(F)cc45)nc32)CC1]
B80 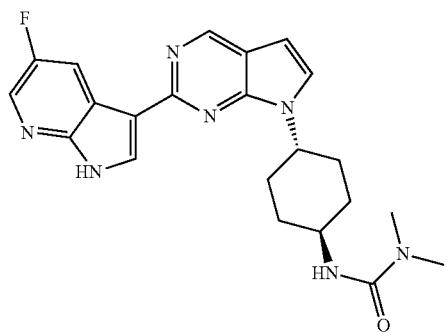 [SMILES: CN(C)C(=O)N[C@H]1CC[C@H](n2ccc3cnc(-c4c[nH]c5ncc(F)cc45)nc32)CC1]
B81 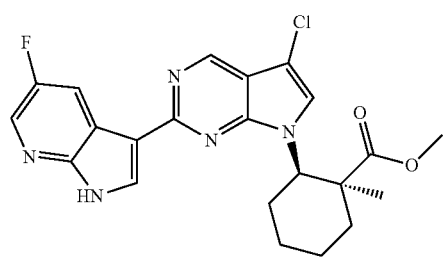 [SMILES: COC(=O)[C@@]1(C)CCCC[C@H]1n1cc(Cl)c2cnc(-c3c[nH]c4ncc(F)cc34)nc21]

TABLE C-continued
B82 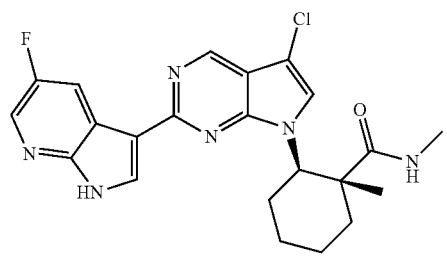
B83 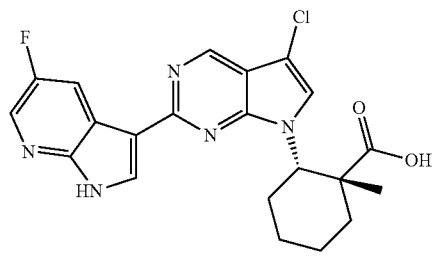 [SMILES: C[C@@]1(C(=O)O)CCCC[C@@H]1n1cc(Cl)c2cnc(-c3c[nH]c4ncc(F)cc34)nc21]
B84 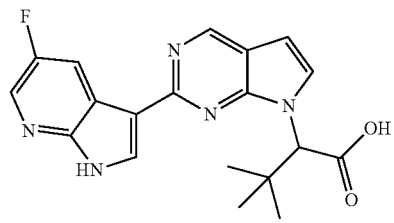 [SMILES: CC(C)(C)C(C(=O)O)n1ccc2cnc(-c3c[nH]c4ncc(F)cc34)nc21]
B85 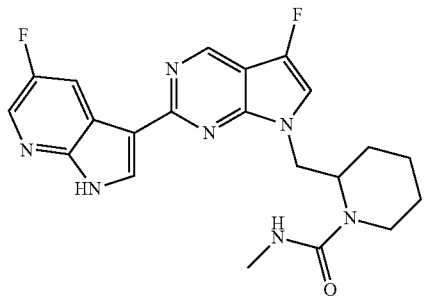 [SMILES: CNC(=O)N1CCCCC1Cn1cc(F)c2cnc(-c3c[nH]c4ncc(F)cc34)nc21]
B86 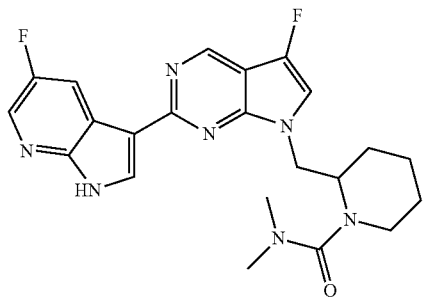 [SMILES: CN(C)C(=O)N1CCCCC1Cn1cc(F)c2cnc(-c3c[nH]c4ncc(F)cc34)nc21]
B87 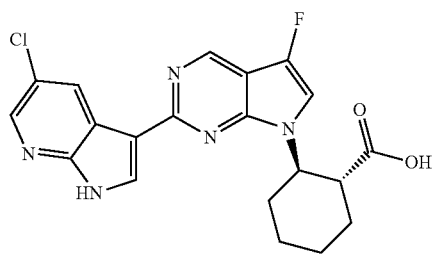 [SMILES: O=C(O)[C@@H]1CCCC[C@H]1n1cc(F)c2cnc(-c3c[nH]c4ncc(Cl)cc34)nc21]

TABLE C-continued
B88 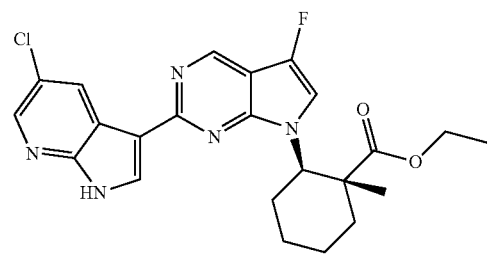
B89 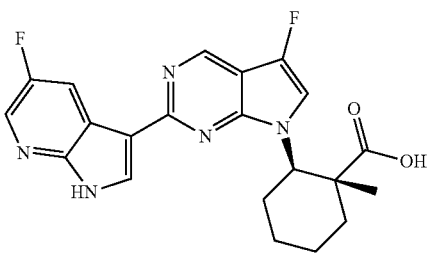
B90 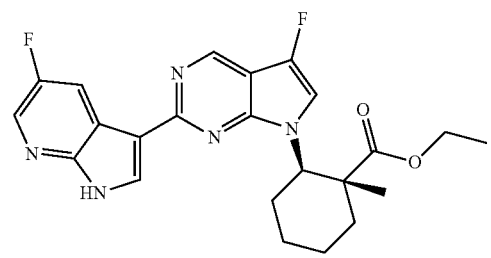 [SMILES: CCOC(=O)[C@]1(C)CCCC[C@H]1n1cc(F)c2cnc(-c3c[nH]c4ncc(F)cc34)nc21]
B91 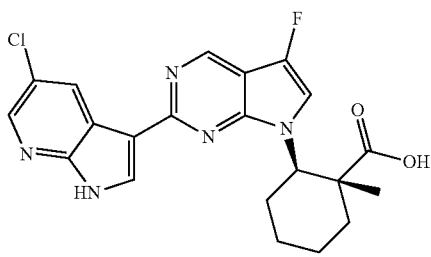
B92 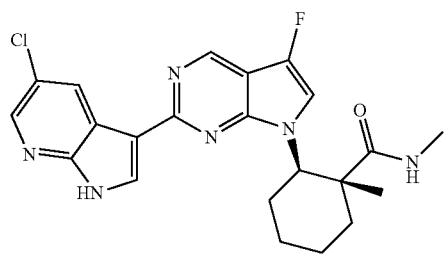 [SMILES: CNC(=O)[C@]1(C)CCCC[C@H]1n1cc(F)c2cnc(-c3c[nH]c4ncc(Cl)cc34)nc21]
B93 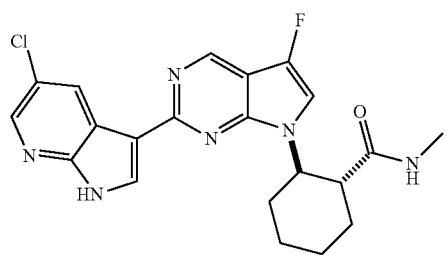

TABLE C-continued
B94
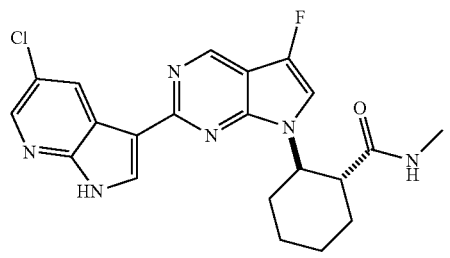
B95
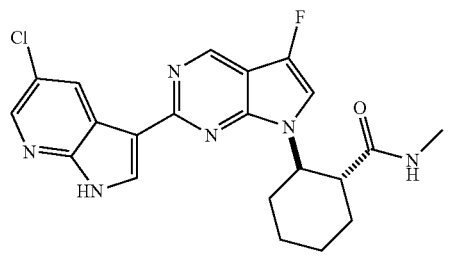
B96
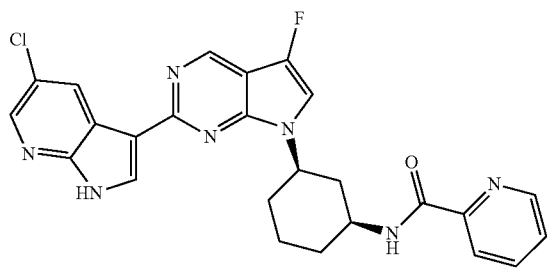 [SMILES: O=C(N[C@H]1CCC[C@@H](n2cc(F)c3cnc(-c4c[nH]c5ncc(Cl)cc45)nc32)C1)c1ccccn1]
B97
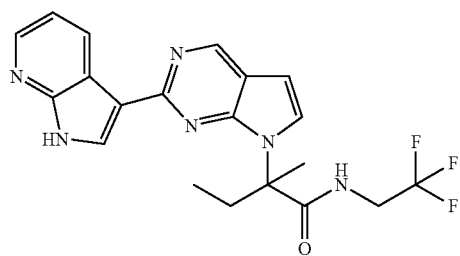 [SMILES: CCC(C)(C(=O)NCC(F)(F)F)n1ccc2cnc(-c3c[nH]c4ncccc34)nc21]
B98
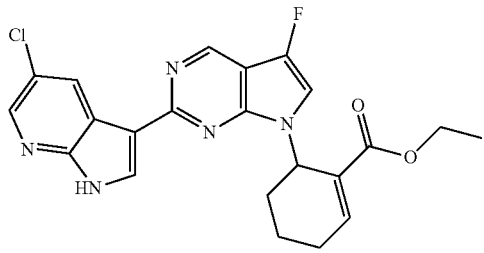 [SMILES: CCOC(=O)C1=CCCCC1n1cc(F)c2cnc(-c3c[nH]c4ncc(Cl)cc34)nc21]
B99
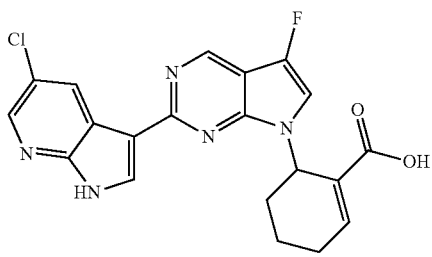 [SMILES: O=C(O)C1=CCCCC1n1cc(F)c2cnc(-c3c[nH]c4ncc(Cl)cc34)nc21]

TABLE C-continued
B101
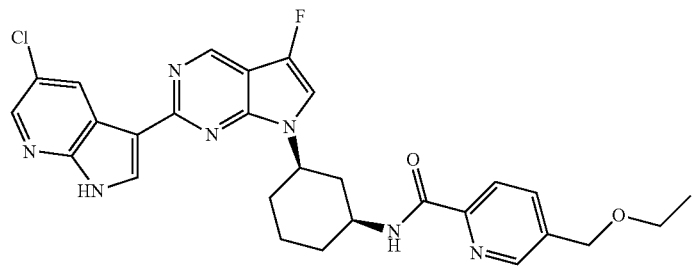 [SMILES: CCOCc1ccc(C(=O)N[C@H]2CCC[C@@H](n3cc(F)c4cnc(-c5c[nH]c6ncc(Cl)cc56)nc43)C2)nc1]
B102
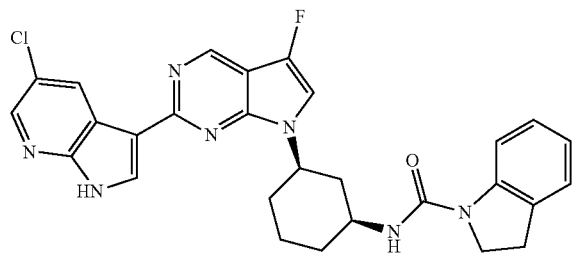 [SMILES: O=C(N[C@H]1CCC[C@@H](n2cc(F)c3cnc(-c4c[nH]c5ncc(Cl)cc45)nc32)C1)N1CCc2ccccc21]
B103
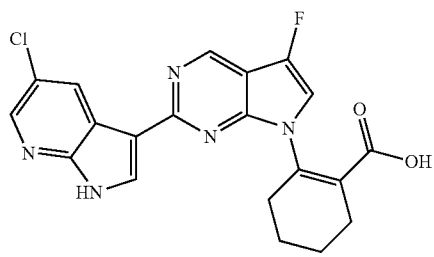 [SMILES: O=C(O)C1=C(n2cc(F)c3cnc(-c4c[nH]c5ncc(Cl)cc45)nc32)CCCC1]
B109
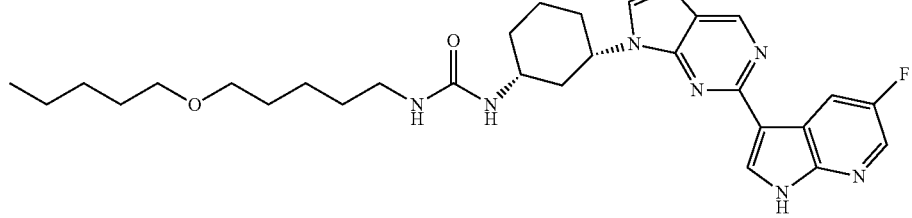
B120
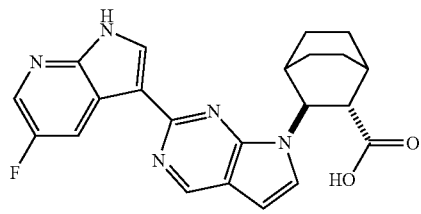
B121
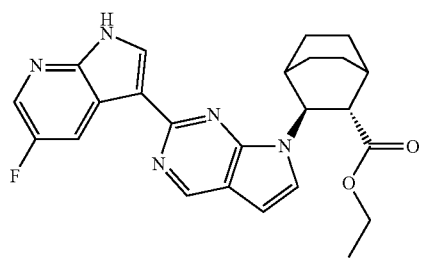

TABLE C-continued
B122 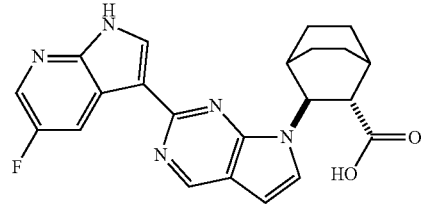
B123 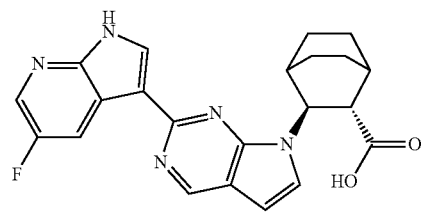
B124 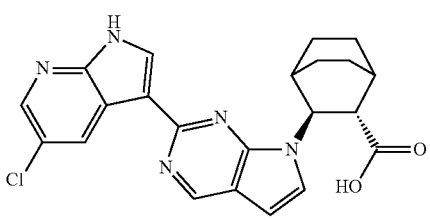 [SMILES: O=C(O)[C@H]1C2CCC(CC2)[C@@H]1n1ccc2cnc(-c3c[nH]c4ncc(Cl)cc34)nc21]
B125 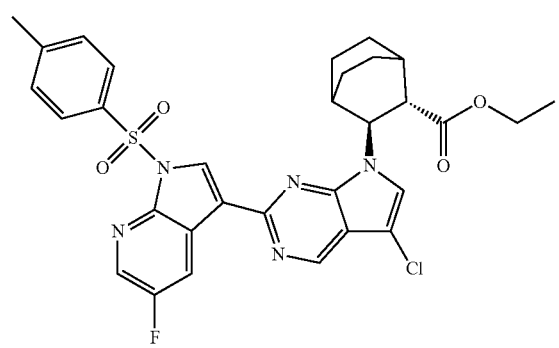 [SMILES: CCOC(=O)[C@H]1C2CCC(CC2)[C@@H]1n1cc(Cl)c2cnc(-c3cn(S(=O)(=O)c4ccc(C)cc4)c4ncc(F)cc34)nc21]
B126 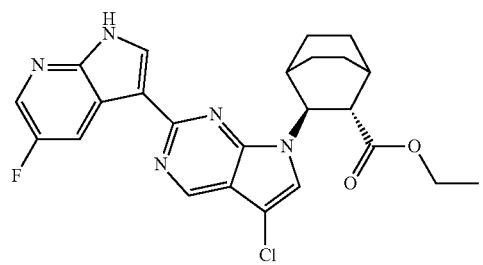
B127 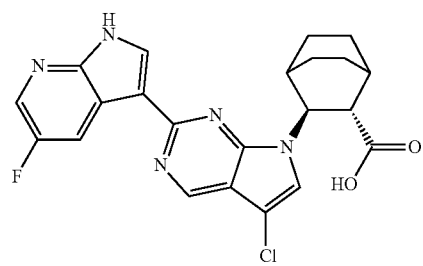 [SMILES: O=C(O)[C@H]1C2CCC(CC2)[C@@H]1n1cc(Cl)c2cnc(-c3c[nH]c4ncc(F)cc34)nc21]

TABLE C-continued
B128 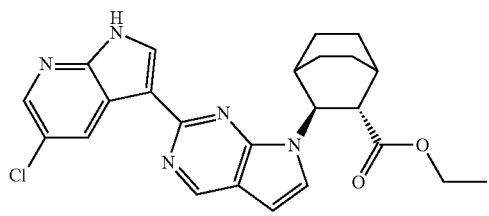 [SMILES: CCOC(=O)[C@H]1C2CCC(CC2)[C@@H]1n1ccc2cnc(-c3c[nH]c4ncc(Cl)cc34)nc21]
B129 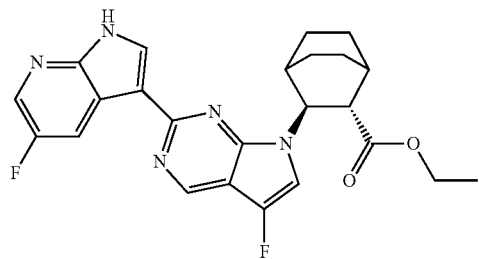
B130 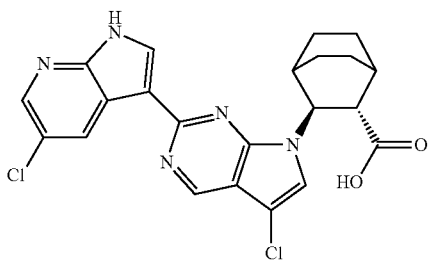 [SMILES: O=C(O)[C@H]1C2CCC(CC2)[C@@H]1n1cc(Cl)c2cnc(-c3c[nH]c4ncc(Cl)cc34)nc21]
B131 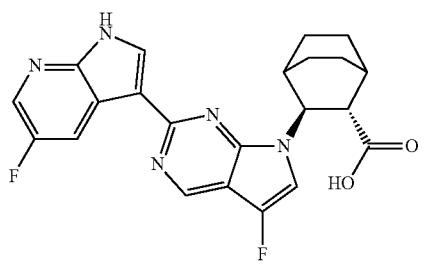 [SMILES: O=C(O)[C@H]1C2CCC(CC2)[C@@H]1n1cc(F)c2cnc(-c3c[nH]c4ncc(F)cc34)nc21]
B132 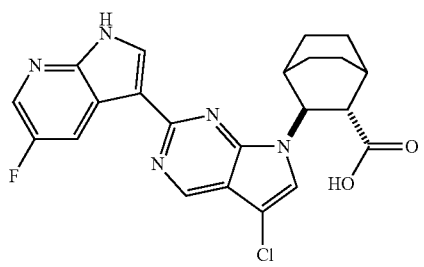
B133 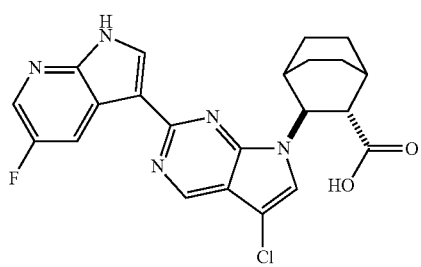

TABLE C-continued
B134
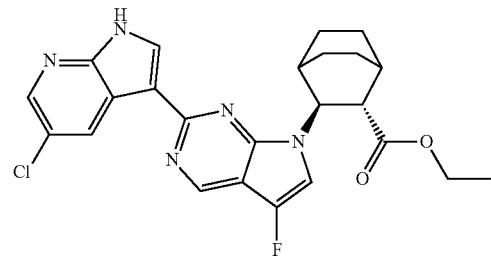 [SMILES: CCOC(=O)[C@H]1C2CCC(CC2)[C@@H]1n1cc(F)c2cnc(-c3c[nH]c4ncc(Cl)cc34)nc21]
B135
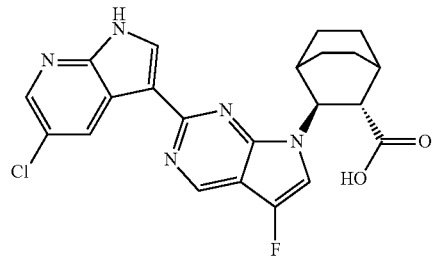 [SMILES: O=C(O)[C@H]1C2CCC(CC2)[C@@H]1n1cc(F)c2cnc(-c3c[nH]c4ncc(Cl)cc34)nc21]
B136
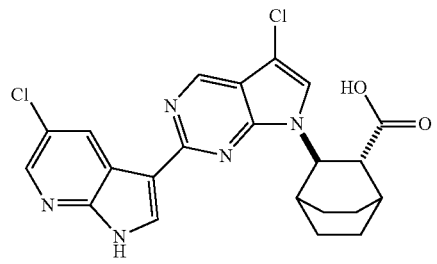
B137
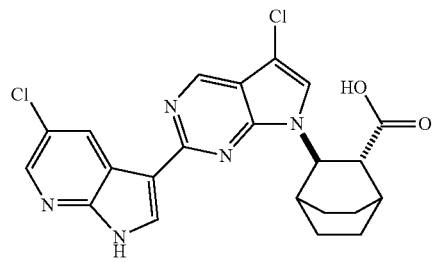
B138
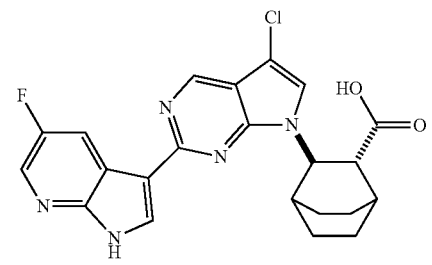
B139
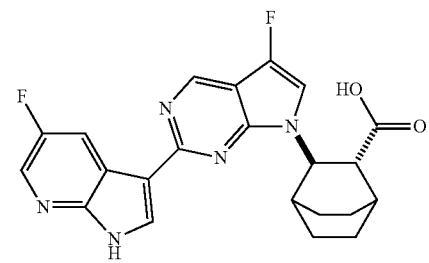

TABLE C-continued
B140
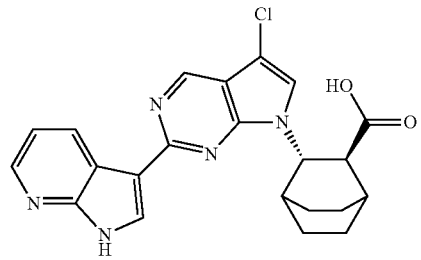 [SMILES: O=C(O)[C@H]1C2CCC(CC2)[C@@H]1n1cc(Cl)c2cnc(-c3c[nH]c4ncccc34)nc21]
B141
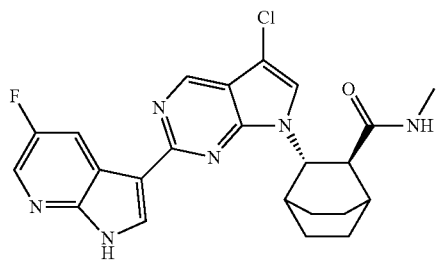 [SMILES: CNC(=O)[C@H]1C2CCC(CC2)[C@@H]1n1cc(Cl)c2cnc(-c3c[nH]c4ncc(F)cc34)nc21]
B142
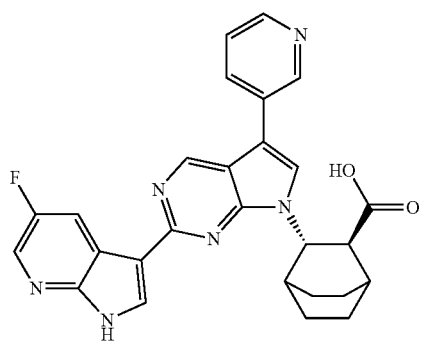 [SMILES: O=C(O)[C@H]1C2CCC(CC2)[C@@H]1n1cc(-c2cccnc2)c2cnc(-c3c[nH]c4ncc(F)cc34)nc21]
B143
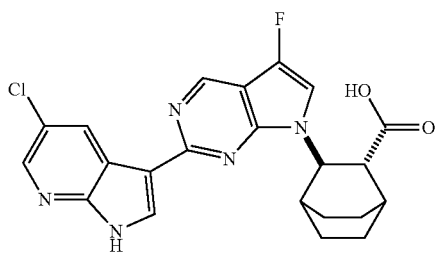
B144
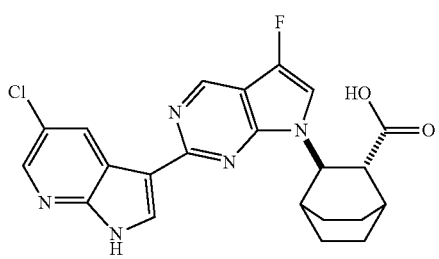

TABLE C-continued
B145
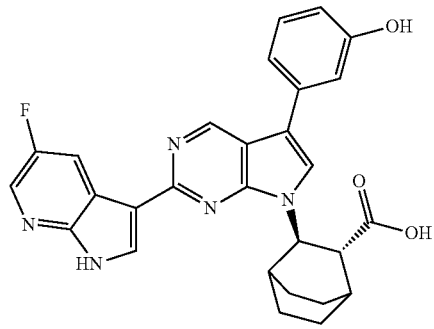 [SMILES: O=C(O)[C@@H]1C2CCC(CC2)[C@H]1n1cc(-c2cccc(O)c2)c2cnc(-c3c[nH]c4ncc(F)cc34)nc21]
B146
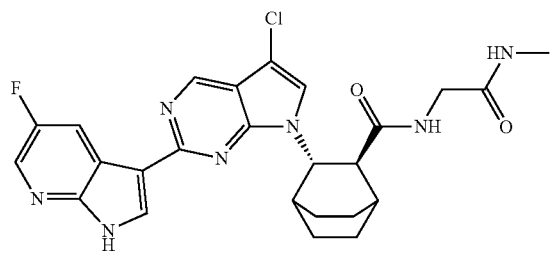 [SMILES: CNC(=O)CNC(=O)[C@H]1C2CCC(CC2)[C@@H]1n1cc(Cl)c2cnc(-c3c[nH]c4ncc(F)cc34)nc21]
B147
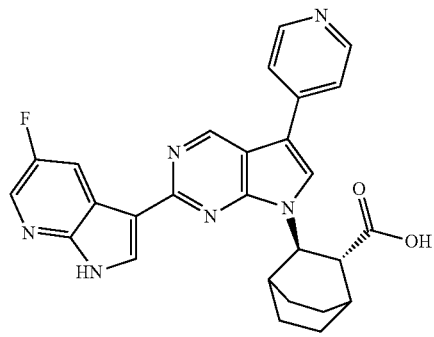 [SMILES: O=C(O)[C@@H]1C2CCC(CC2)[C@H]1n1cc(-c2ccncc2)c2cnc(-c3c[nH]c4ncc(F)cc34)nc21]
B148
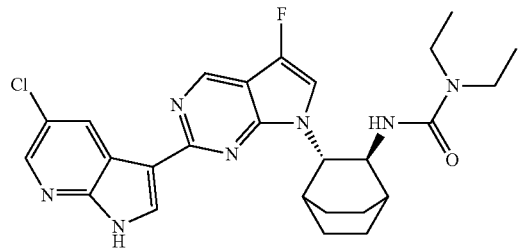 [SMILES: CCN(CC)C(=O)N[C@H]1C2CCC(CC2)[C@@H]1n1cc(F)c2cnc(-c3c[nH]c4ncc(Cl)cc34)nc21]
B149
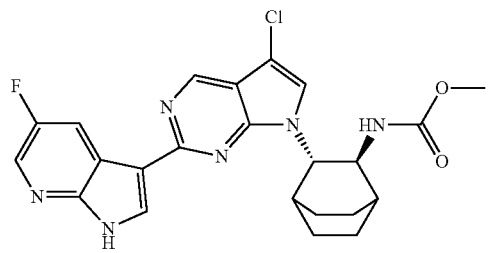 [SMILES: COC(=O)N[C@H]1C2CCC(CC2)[C@@H]1n1cc(Cl)c2cnc(-c3c[nH]c4ncc(F)cc34)nc21]

TABLE C-continued
B150
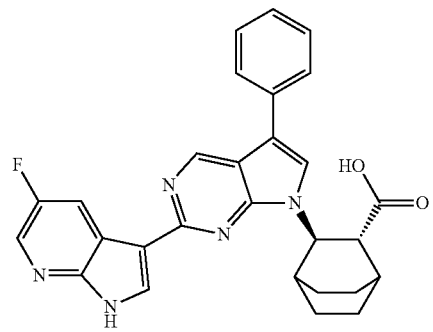 [SMILES: O=C(O)[C@@H]1C2CCC(CC2)[C@H]1n1cc(-c2ccccc2)c2cnc(-c3c[nH]c4ncc(F)cc34)nc21]
B151
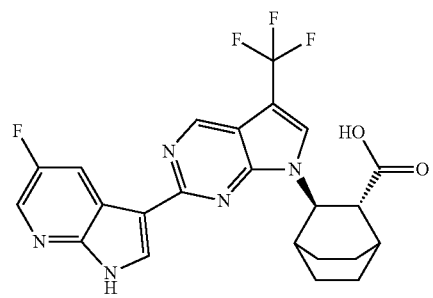 [SMILES: O=C(O)[C@@H]1C2CCC(CC2)[C@H]1n1cc(C(F)(F)F)c2cnc(-c3c[nH]c4ncc(F)cc34)nc21]
B152
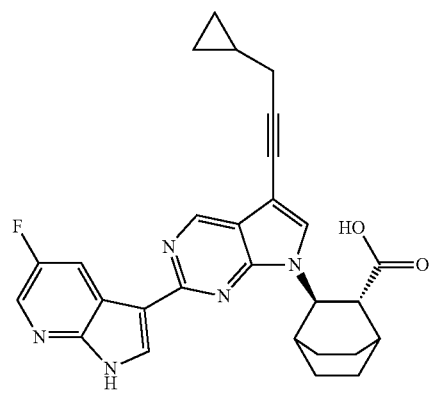 [SMILES: O=C(O)[C@@H]1C2CCC(CC2)[C@H]1n1cc(C#CCC2CC2)c2cnc(-c3c[nH]c4ncc(F)cc34)nc21]
B153
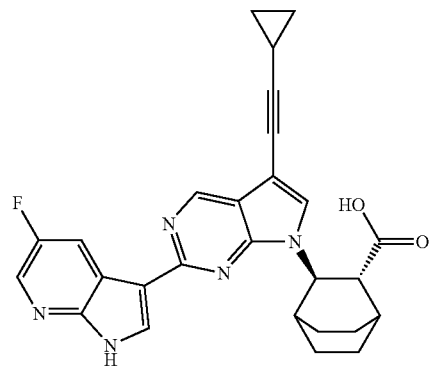 [SMILES: O=C(O)[C@@H]1C2CCC(CC2)[C@H]1n1cc(C#CC2CC2)c2cnc(-c3c[nH]c4ncc(F)cc34)nc21]

TABLE C-continued
B154
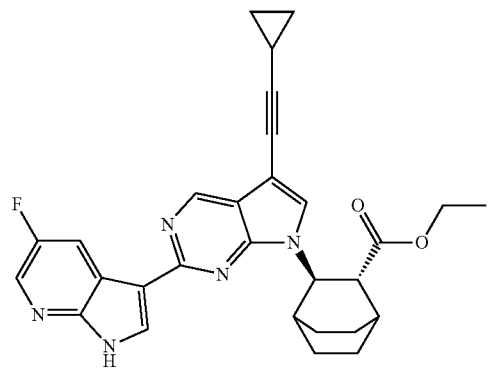 [SMILES: CCOC(=O)[C@@H]1C2CCC(CC2)[C@H]1n1cc(C#CC2CC2)c2cnc(-c3c[nH]c4ncc(F)cc34)nc21]
B160
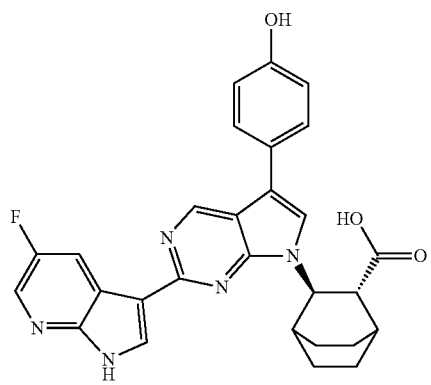 [SMILES: O=C(O)[C@@H]1C2CCC(CC2)[C@H]1n1cc(-c2ccc(O)cc2)c2cnc(-c3c[nH]c4ncc(F)cc34)nc21]
B161
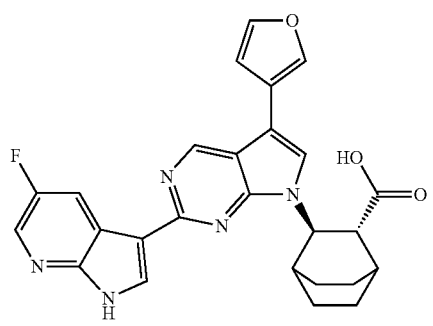 [SMILES: O=C(O)[C@@H]1C2CCC(CC2)[C@H]1n1cc(-c2ccoc2)c2cnc(-c3c[nH]c4ncc(F)cc34)nc21]
B162
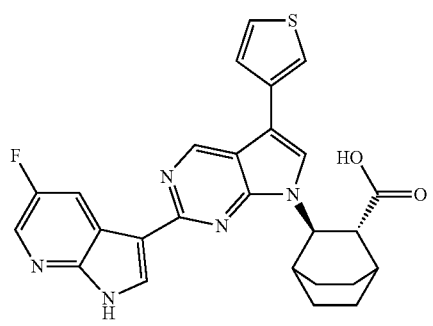 [SMILES: O=C(O)[C@@H]1C2CCC(CC2)[C@H]1n1cc(-c2ccsc2)c2cnc(-c3c[nH]c4ncc(F)cc34)nc21]
B163
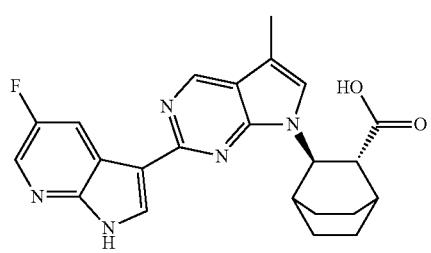 [SMILES: Cc1cn([C@@H]2C3CCC(CC3)[C@H]2C(=O)O)c2nc(-c3c[nH]c4ncc(F)cc34)ncc12]

TABLE C-continued
B164
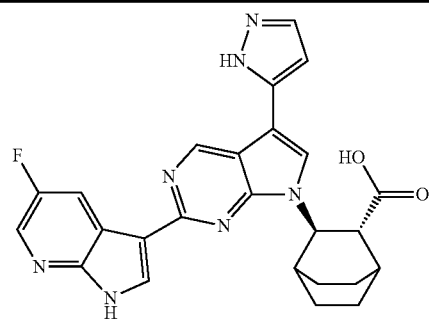
B165
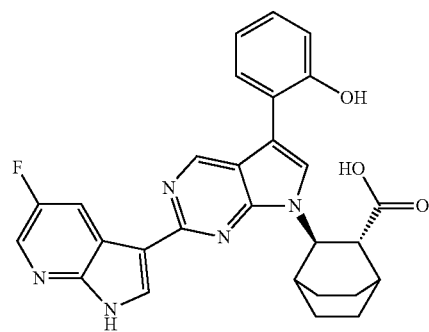 [SMILES: O=C(O)[C@@H]1C2CCC(CC2)[C@H]1n1cc(-c2ccccc2O)c2cnc(-c3c[nH]c4ncc(F)cc34)nc21]
B166
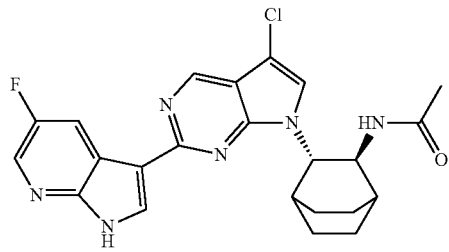 [SMILES: CC(=O)N[C@H]1C2CCC(CC2)[C@@H]1n1cc(Cl)c2cnc(-c3c[nH]c4ncc(F)cc34)nc21]
B167
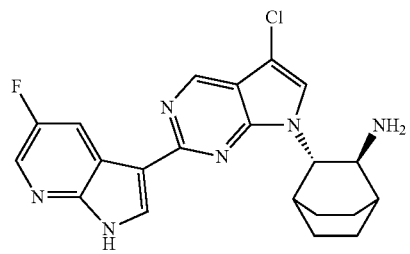 [SMILES: N[C@H]1C2CCC(CC2)[C@@H]1n1cc(Cl)c2cnc(-c3c[nH]c4ncc(F)cc34)nc21]
B168
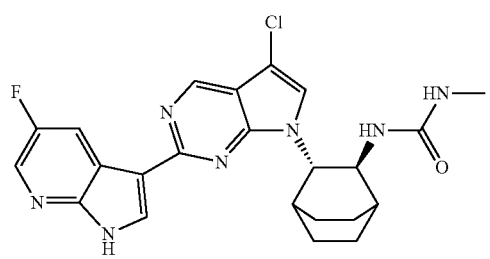 [SMILES: CNC(=O)N[C@H]1C2CCC(CC2)[C@@H]1n1cc(Cl)c2cnc(-c3c[nH]c4ncc(F)cc34)nc21]

TABLE C-continued
B169
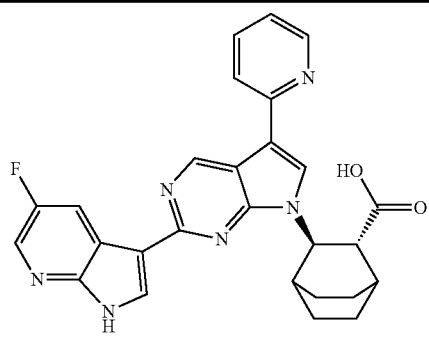
B170
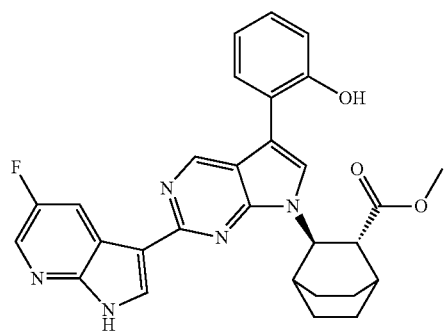 [SMILES: COC(=O)[C@@H]1C2CCC(CC2)[C@H]1n1cc(-c2ccccc2O)c2cnc(-c3c[nH]c4ncc(F)cc34)nc21]
B171
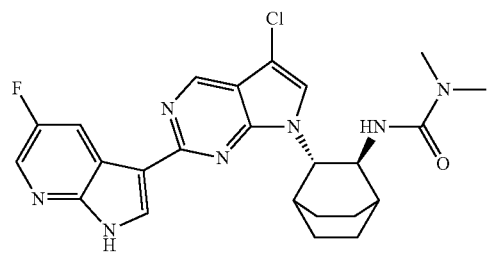 [SMILES: CN(C)C(=O)N[C@H]1C2CCC(CC2)[C@@H]1n1cc(Cl)c2cnc(-c3c[nH]c4ncc(F)cc34)nc21]
B172
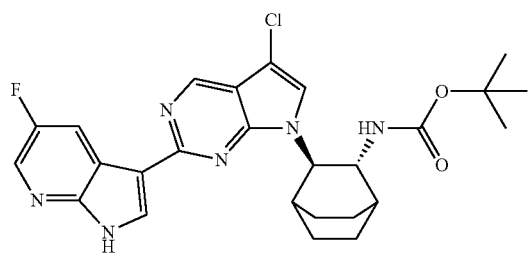 [SMILES: CC(C)(C)OC(=O)N[C@@H]1C2CCC(CC2)[C@H]1n1cc(Cl)c2cnc(-c3c[nH]c4ncc(F)cc34)nc21]
B173
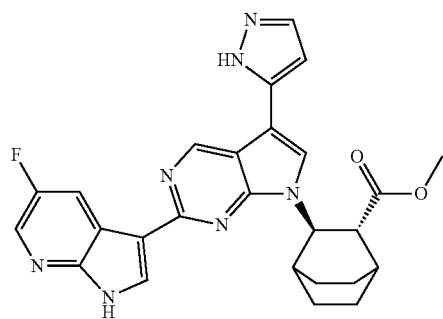 [SMILES: COC(=O)[C@@H]1C2CCC(CC2)[C@H]1n1cc(-c2ccn[nH]2)c2cnc(-c3c[nH]c4ncc(F)cc34)nc21]

TABLE C-continued
B174
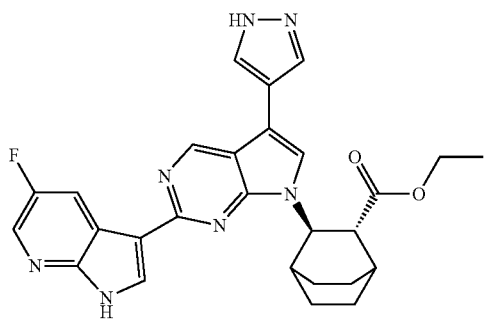 [SMILES: CCOC(=O)[C@@H]1C2CCC(CC2)[C@H]1n1cc(-c2cn[nH]c2)c2cnc(-c3c[nH]c4ncc(F)cc34)nc21]
B175
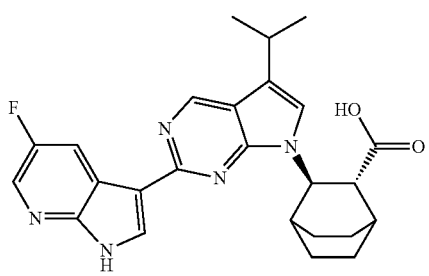 [SMILES: CC(C)c1cn([C@@H]2C3CCC(CC3)[C@H]2C(=O)O)c2nc(-c3c[nH]c4ncc(F)cc34)ncc12]
B176
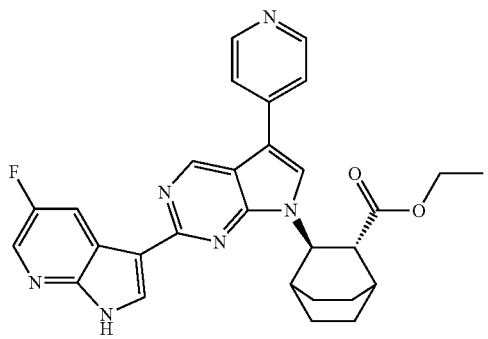 [SMILES: CCOC(=O)[C@@H]1C2CCC(CC2)[C@H]1n1cc(-c2ccncc2)c2cnc(-c3c[nH]c4ncc(F)cc34)nc21]
B177
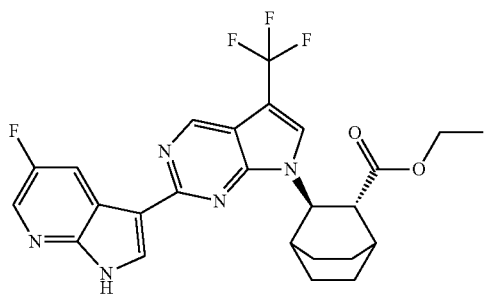 [SMILES: CCOC(=O)[C@@H]1C2CCC(CC2)[C@H]1n1cc(C(F)(F)F)c2cnc(-c3c[nH]c4ncc(F)cc34)nc21]
B178
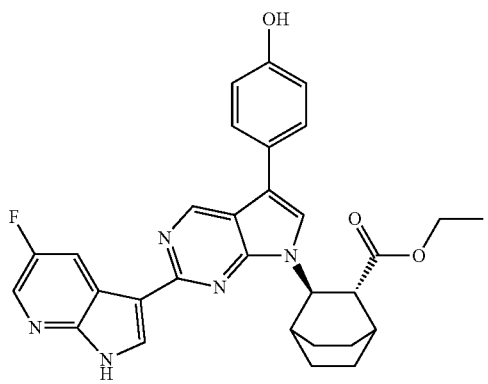 [SMILES: CCOC(=O)[C@@H]1C2CCC(CC2)[C@H]1n1cc(-c2ccc(O)cc2)c2cnc(-c3c[nH]c4ncc(F)cc34)nc21]

TABLE C-continued
B179 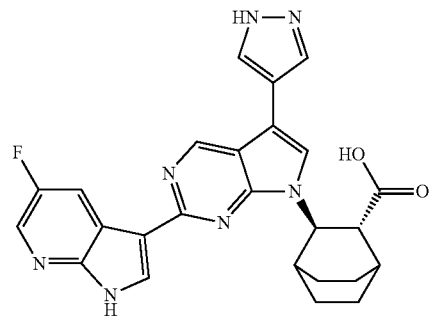 [SMILES: O=C(O)[C@@H]1C2CCC(CC2)[C@H]1n1cc(-c2cn[nH]c2)c2cnc(-c3c[nH]c4ncc(F)cc34)nc21]
B180 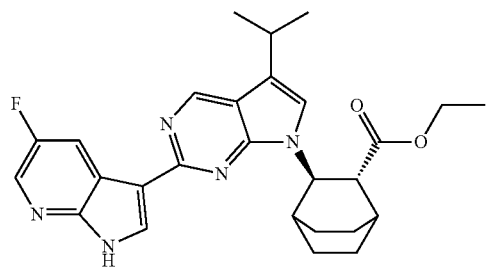 [SMILES: CCOC(=O)[C@@H]1C2CCC(CC2)[C@H]1n1cc(C(C)C)c2cnc(-c3c[nH]c4ncc(F)cc34)nc21]
B181 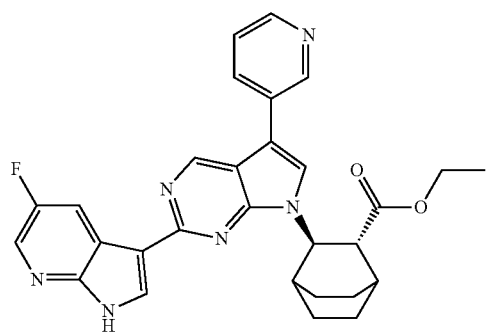 [SMILES: CCOC(=O)[C@@H]1C2CCC(CC2)[C@H]1n1cc(-c2cccnc2)c2cnc(-c3c[nH]c4ncc(F)cc34)nc21]
B182 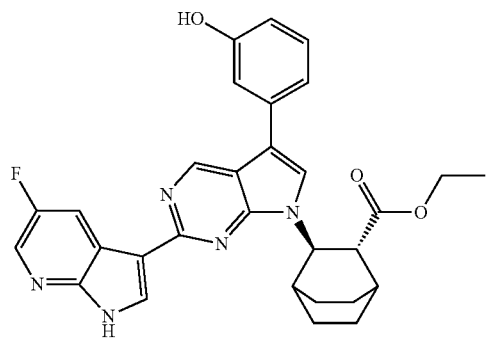 [SMILES: CCOC(=O)[C@@H]1C2CCC(CC2)[C@H]1n1cc(-c2cccc(O)c2)c2cnc(-c3c[nH]c4ncc(F)cc34)nc21]
B183 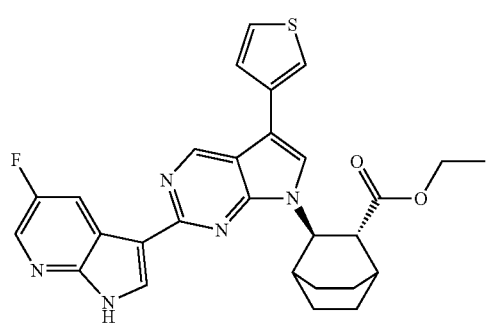 [SMILES: CCOC(=O)[C@@H]1C2CCC(CC2)[C@H]1n1cc(-c2ccsc2)c2cnc(-c3c[nH]c4ncc(F)cc34)nc21]

TABLE C-continued
B184
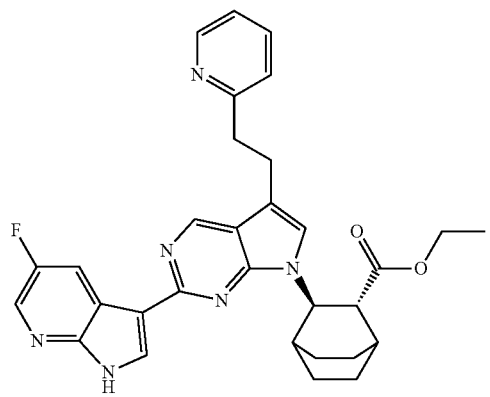 [SMILES: CCOC(=O)[C@@H]1C2CCC(CC2)[C@H]1n1cc(CCc2ccccn2)c2cnc(-c3c[nH]c4ncc(F)cc34)nc21]
B185
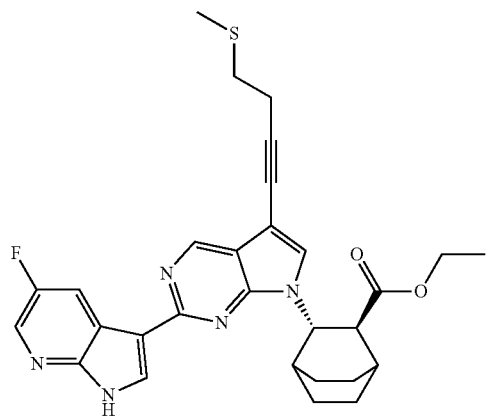 [SMILES: CCOC(=O)[C@H]1C2CCC(CC2)[C@@H]1n1cc(C#CCCSC)c2cnc(-c3c[nH]c4ncc(F)cc34)nc21]
B186
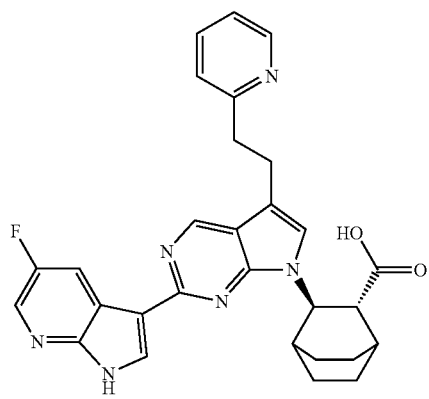 [SMILES: O=C(O)[C@@H]1C2CCC(CC2)[C@H]1n1cc(CCc2ccccn2)c2cnc(-c3c[nH]c4ncc(F)cc34)nc21]
B187
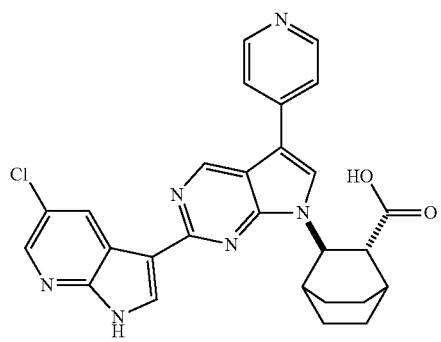

TABLE C-continued
B188
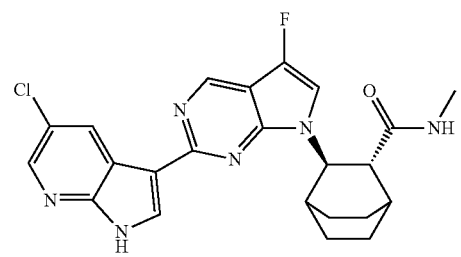 [SMILES: CNC(=O)[C@@H]1C2CCC(CC2)[C@H]1n1cc(F)c2cnc(-c3c[nH]c4ncc(Cl)cc34)nc21]
B189
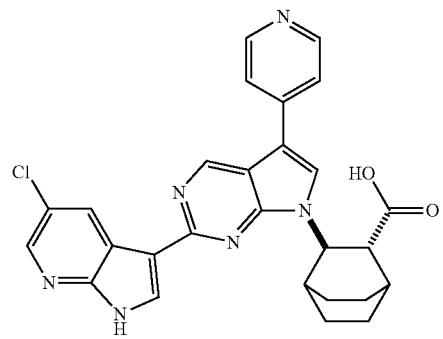
B190
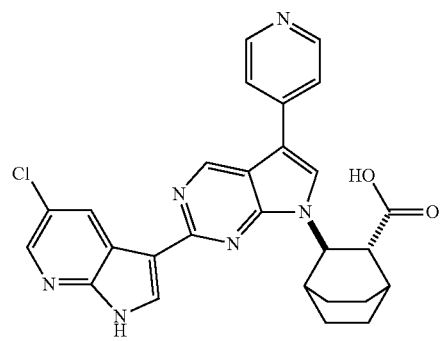
B191
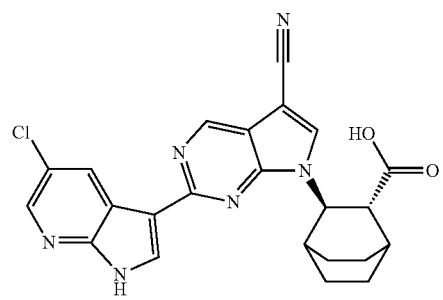 [SMILES: N#Cc1cn([C@@H]2C3CCC(CC3)[C@H]2C(=O)O)c2nc(-c3c[nH]c4ncc(Cl)cc34)ncc12]
B192
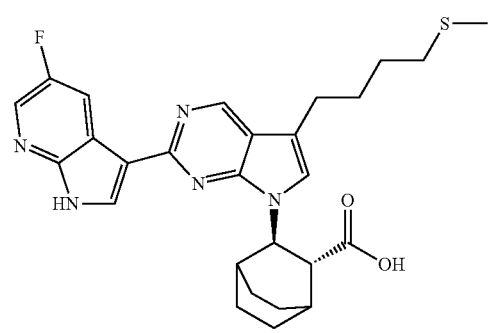 [SMILES: CSCCCCc1cn([C@@H]2C3CCC(CC3)[C@H]2C(=O)O)c2nc(-c3c[nH]c4ncc(F)cc34)ncc12]

TABLE C-continued
B193
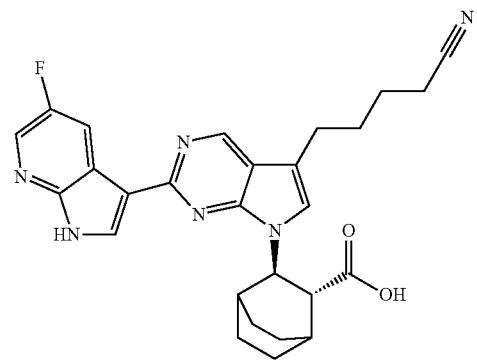 [SMILES: N#CCCCCc1cn([C@@H]2C3CCC(CC3)[C@H]2C(=O)O)c2nc(-c3c[nH]c4ncc(F)cc34)ncc12]
B194
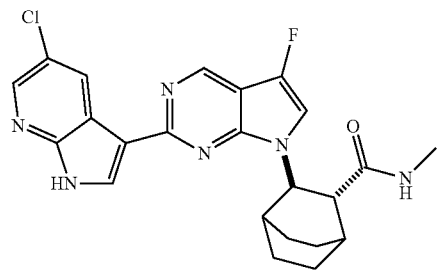
B195
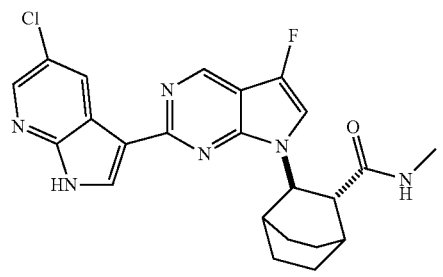
B196
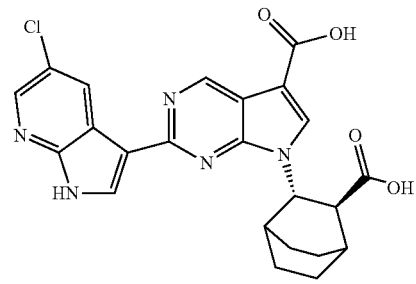 [SMILES: O=C(O)c1cn([C@H]2C3CCC(CC3)[C@@H]2C(=O)O)c2nc(-c3c[nH]c4ncc(Cl)cc34)ncc12]
B197
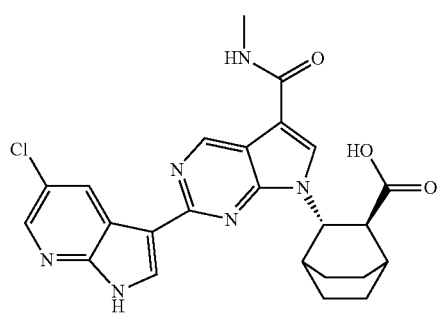 [SMILES: CNC(=O)c1cn([C@H]2C3CCC(CC3)[C@@H]2C(=O)O)c2nc(-c3c[nH]c4ncc(Cl)cc34)ncc12]

TABLE C-continued
B198
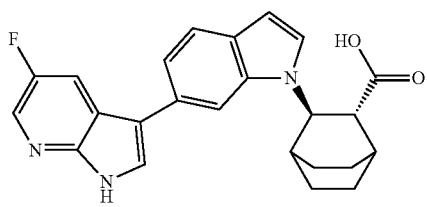 [SMILES: O=C(O)[C@@H]1C2CCC(CC2)[C@H]1n1ccc2ccc(-c3c[nH]c4ncc(F)cc34)cc21]
B199
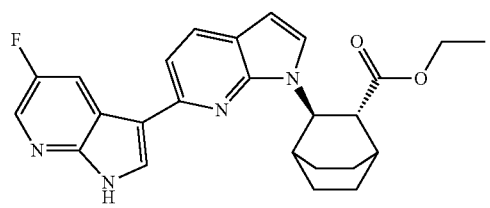 [SMILES: CCOC(=O)[C@@H]1C2CCC(CC2)[C@H]1n1ccc2ccc(-c3c[nH]c4ncc(F)cc34)nc21]
B200
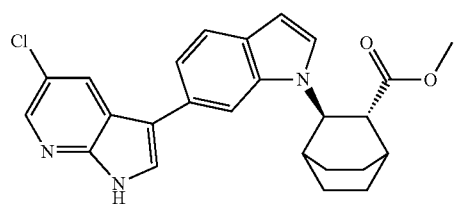 [SMILES: COC(=O)[C@@H]1C2CCC(CC2)[C@H]1n1ccc2ccc(-c3c[nH]c4ncc(Cl)cc34)cc21]
B201
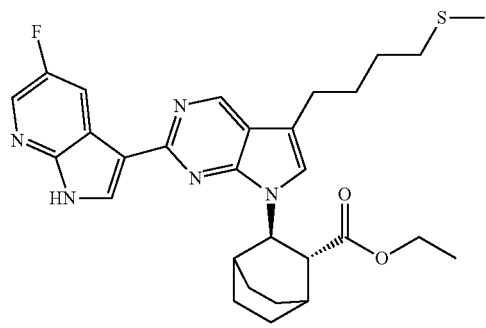 [SMILES: CCOC(=O)[C@@H]1C2CCC(CC2)[C@H]1n1cc(CCCCSC)c2cnc(-c3c[nH]c4ncc(F)cc34)nc21]
B202
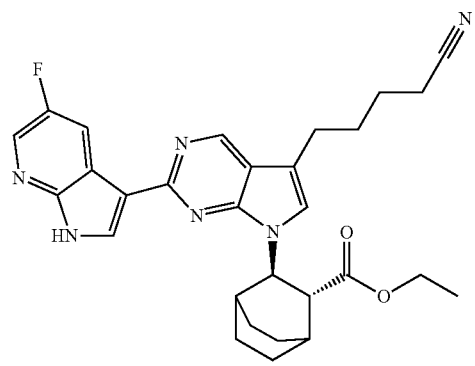 [SMILES: CCOC(=O)[C@@H]1C2CCC(CC2)[C@H]1n1cc(CCCCC#N)c2cnc(-c3c[nH]c4ncc(F)cc34)nc21]

TABLE C-continued
B203
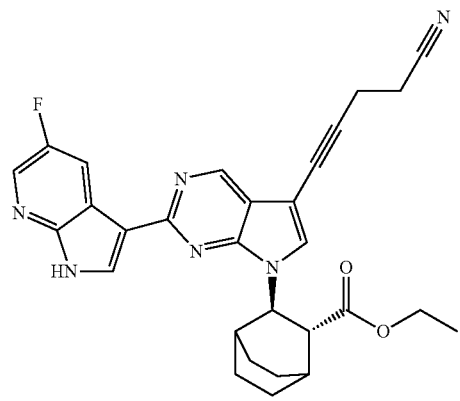 [SMILES: CCOC(=O)[C@@H]1C2CCC(CC2)[C@H]1n1cc(C#CCCC#N)c2cnc(-c3c[nH]c4ncc(F)cc34)nc21]
B204
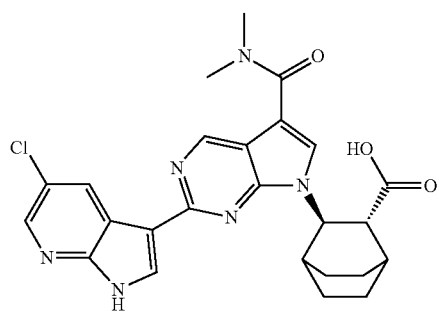 [SMILES: CN(C)C(=O)c1cn([C@@H]2C3CCC(CC3)[C@H]2C(=O)O)c2nc(-c3c[nH]c4ncc(Cl)cc34)ncc12]
B205
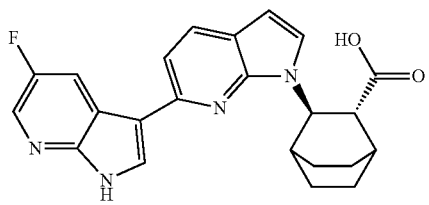 [SMILES: O=C(O)[C@@H]1C2CCC(CC2)[C@H]1n1ccc2ccc(-c3c[nH]c4ncc(F)cc34)nc21]
B206
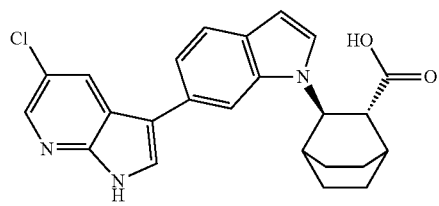 [SMILES: O=C(O)[C@@H]1C2CCC(CC2)[C@H]1n1ccc2ccc(-c3c[nH]c4ncc(Cl)cc34)cc21]
B207
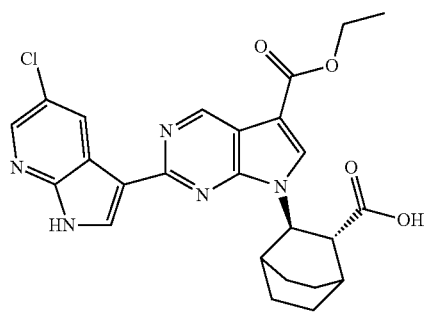 [SMILES: CCOC(=O)c1cn([C@@H]2C3CCC(CC3)[C@H]2C(=O)O)c2nc(-c3c[nH]c4ncc(Cl)cc34)ncc12]

TABLE C-continued
B208
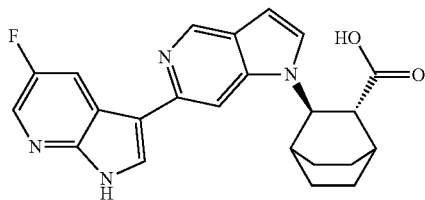 [SMILES: O=C(O)[C@@H]1C2CCC(CC2)[C@H]1n1ccc2cnc(-c3c[nH]c4ncc(F)cc34)cc21]
B209
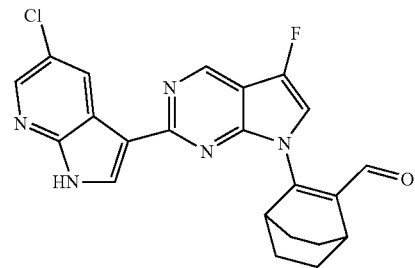 [SMILES: O=CC1=C(n2cc(F)c3cnc(-c4c[nH]c5ncc(Cl)cc45)nc32)C2CCC1CC2]
B210
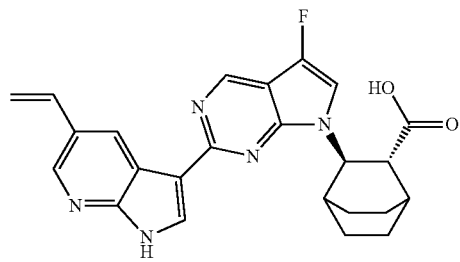 [SMILES: C=Cc1cnc2[nH]cc(-c3ncc4c(F)cn([C@@H]5C6CCC(CC6)[C@H]5C(=O)O)c4n3)c2c1]
B211
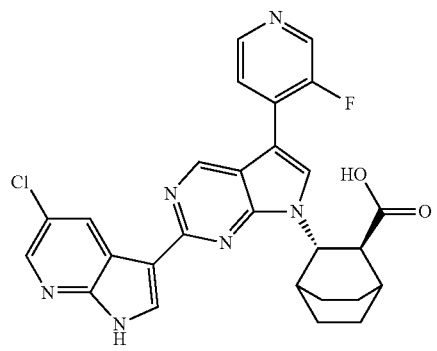 [SMILES: O=C(O)[C@H]1C2CCC(CC2)[C@@H]1n1cc(-c2ccncc2F)c2cnc(-c3c[nH]c4ncc(Cl)cc34)nc21]
B212
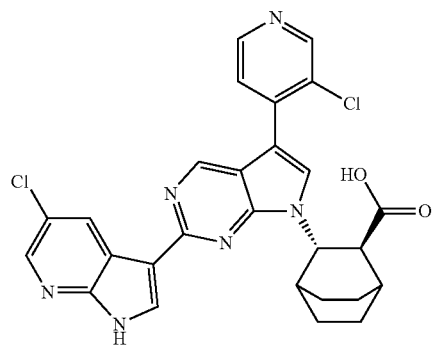 [SMILES: O=C(O)[C@H]1C2CCC(CC2)[C@@H]1n1cc(-c2ccncc2Cl)c2cnc(-c3c[nH]c4ncc(Cl)cc34)nc21]

TABLE C-continued
B213
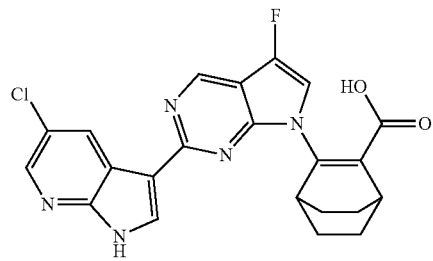 [SMILES: O=C(O)C1=C(n2cc(F)c3cnc(-c4c[nH]c5ncc(Cl)cc45)nc32)C2CCC1CC2]
B214
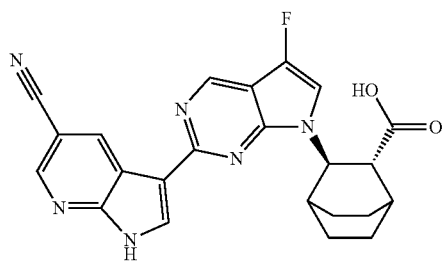
B215
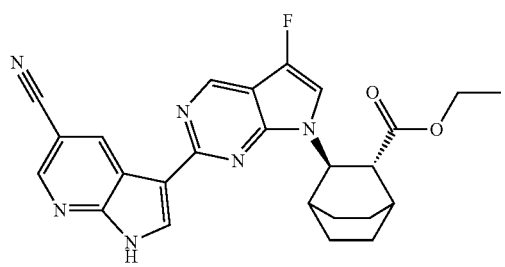
B216
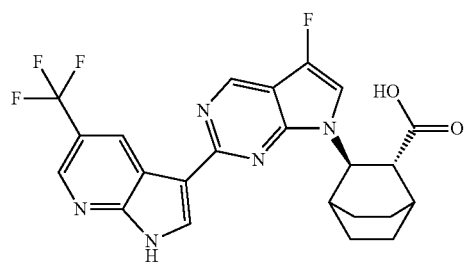 [SMILES: O=C(O)[C@@H]1C2CCC(CC2)[C@H]1n1cc(F)c2cnc(-c3c[nH]c4ncc(C(F)(F)F)cc34)nc21]
B217
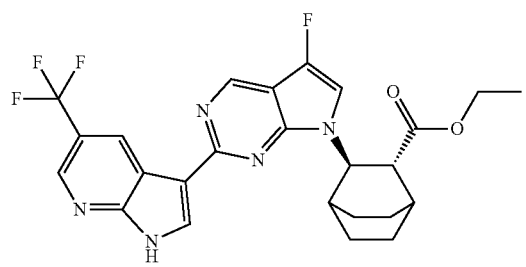 [SMILES: CCOC(=O)[C@@H]1C2CCC(CC2)[C@H]1n1cc(F)c2cnc(-c3c[nH]c4ncc(C(F)(F)F)cc34)nc21]
B218
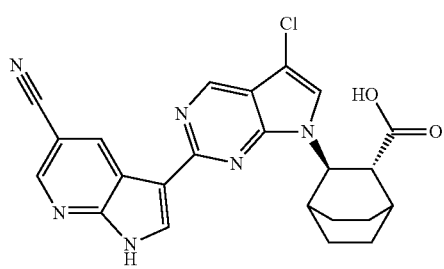 [SMILES: N#Cc1cnc2[nH]cc(-c3ncc4c(Cl)cn([C@@H]5C6CCC(CC6)[C@H]5C(=O)O)c4n3)c2c1]

TABLE C-continued
B219
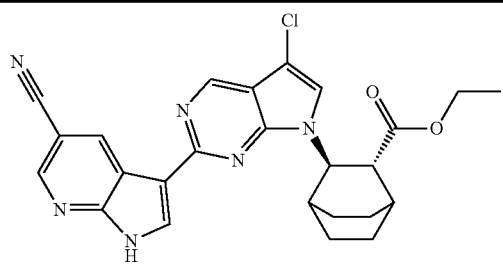
B220
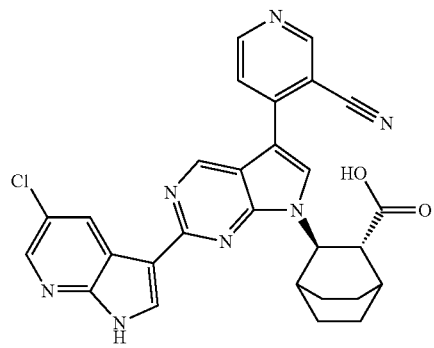 [SMILES: N#Cc1cnccc1-c1cn([C@@H]2C3CCC(CC3)[C@H]2C(=O)O)c2nc(-c3c[nH]c4ncc(Cl)cc34)ncc12]
B221
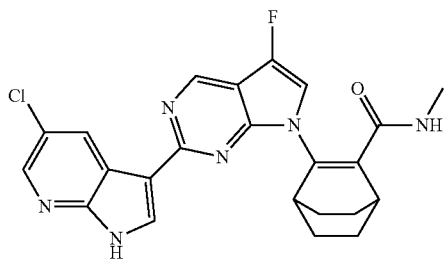 [SMILES: CNC(=O)C1=C(n2cc(F)c3cnc(-c4c[nH]c5ncc(Cl)cc45)nc32)C2CCC1CC2]
B222
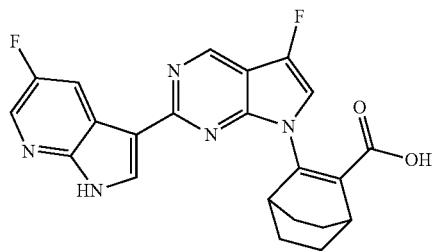 [SMILES: O=C(O)C1=C(n2cc(F)c3cnc(-c4c[nH]c5ncc(F)cc45)nc32)C2CCC1CC2]
Specific compounds of Formula III include a compound as listed in Table D or a pharmaceutically acceptable salt thereof:
TABLE D
C1
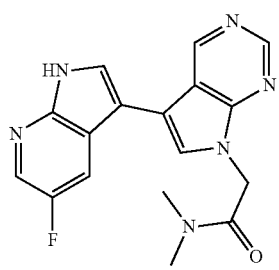 [SMILES: CN(C)C(=O)Cn1cc(-c2c[nH]c3ncc(F)cc23)c2cncnc21]
TABLE D-continued
C2
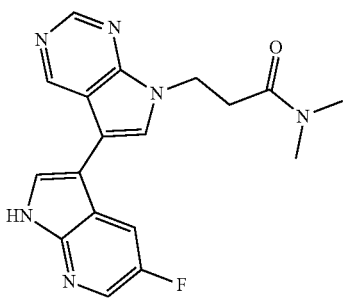 [SMILES: CN(C)C(=O)CCn1cc(-c2c[nH]c3ncc(F)cc23)c2cncnc21]

TABLE D-continued
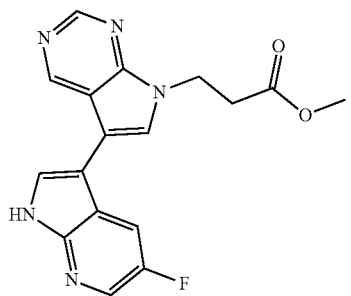 [SMILES: COC(=O)CCn1cc(-c2c[nH]c3ncc(F)cc23)c2cncnc21]
C3
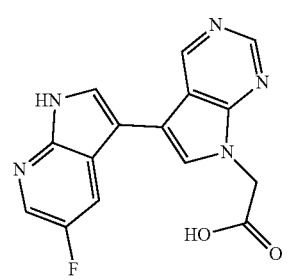 [SMILES: O=C(O)Cn1cc(-c2c[nH]c3ncc(F)cc23)c2cncnc21]
C4
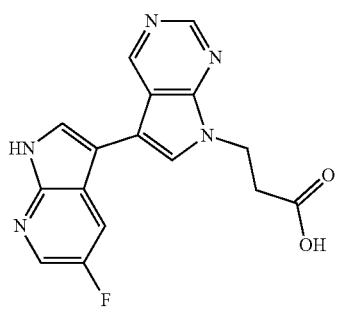 [SMILES: O=C(O)CCn1cc(-c2c[nH]c3ncc(F)cc23)c2cncnc21]
C5
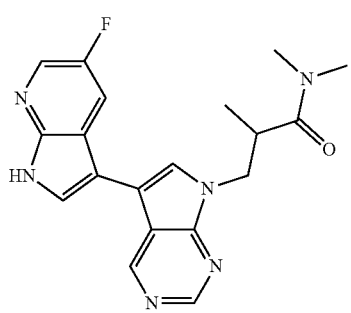 [SMILES: CC(Cn1cc(-c2c[nH]c3ncc(F)cc23)c2cncnc21)C(=O)N(C)C]
C6
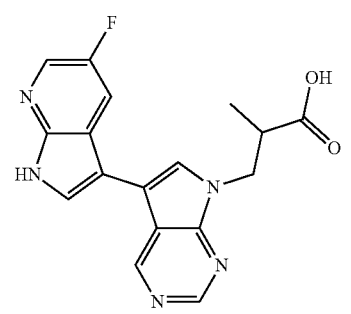 [SMILES: CC(Cn1cc(-c2c[nH]c3ncc(F)cc23)c2cncnc21)C(=O)O]
C7
TABLE D-continued
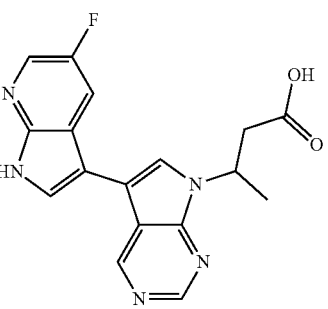
C8
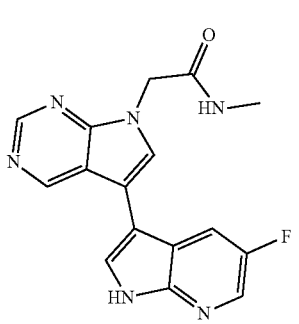 [SMILES: CNC(=O)Cn1cc(-c2c[nH]c3ncc(F)cc23)c2cncnc21]
C9
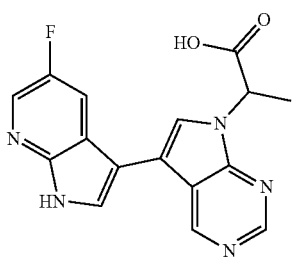 [SMILES: CC(C(=O)O)n1cc(-c2c[nH]c3ncc(F)cc23)c2cncnc21]
C10
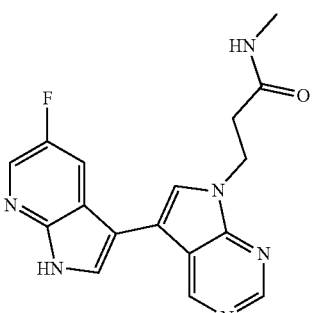
C11
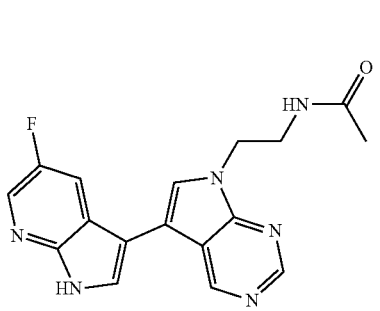 [SMILES: CC(=O)NCCn1cc(-c2c[nH]c3ncc(F)cc23)c2cncnc21]
C12

TABLE D-continued

| | |
|---|---|
| C13 | 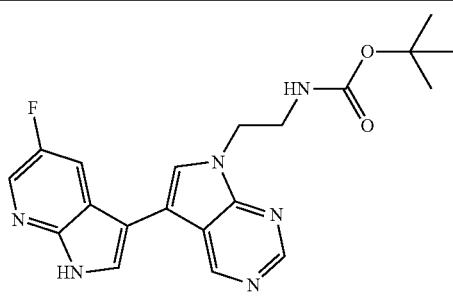 |
| C14 | 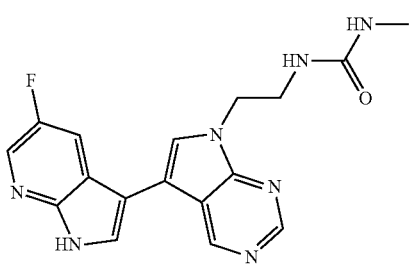 |
| C15 | 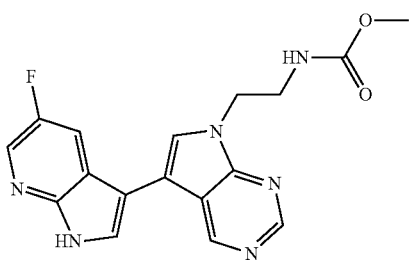 [SMILES: COC(=O)NCCn1cc(-c2c[nH]c3ncc(F)cc23)c2cncnc21] |
| C16 | 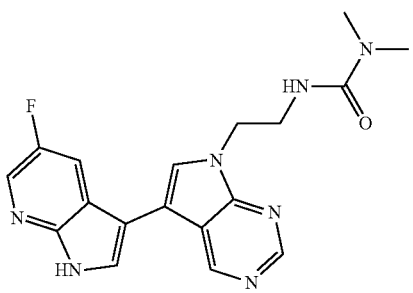 [SMILES: CN(C)C(=O)NCCn1cc(-c2c[nH]c3ncc(F)cc23)c2cncnc21] |
| C17 | 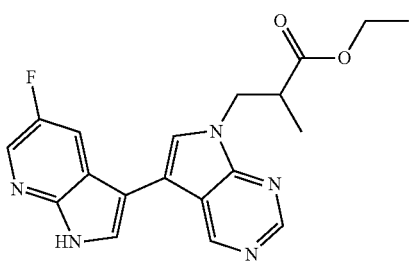 [SMILES: CCOC(=O)C(C)Cn1cc(-c2c[nH]c3ncc(F)cc23)c2cncnc21] |
| C18 | 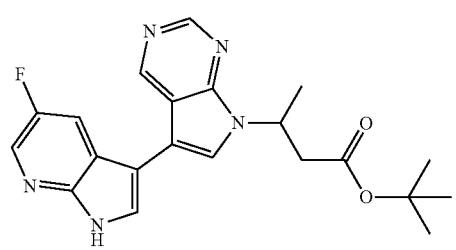 [SMILES: CC(CC(=O)OC(C)(C)C)n1cc(-c2c[nH]c3ncc(F)cc23)c2cncnc21] |

In some cases, the compound is selected from B25, B26, B27, B28, B29, B30, B50, B31, B32, B33, B34, B35, B36, B100, B52, B37, B38, B39, B40, B41, B42, B43, B44, B45, B46, B47, and B49, or a pharmaceutically acceptable salt thereof.

In some cases, the compound is selected from B1, B2, B3, B4, B5, B6, B7, B8, B9, B10, B11, B12, B13, B14, B15, B16, B17, B18, B19, B20, B21, B22, B23, B24, B48, B51, B54, B55, B56, B57, B58, B59, B60, B61, B62, B63, B64, B65, B66, B67, B68, B69, B70, B71, B72, B73, B74, B75, B76, B77, B78, B79, B80, B81, B82, B83, B84, B85, B86, B87, B88, B89, B90, B91, B92, B93, B94, B95, B96, B97, B98, B99, B101, B102, and B103, or a pharmaceutically acceptable salt thereof.

In some cases, the compound is selected from B120, B121, B122, B123, B124, B125, B126, B127, B128, B129, B130, B131, B132, B133, B134, B135, B136, B137, B138, B139, B140, B141, B142, B143, B144, B145, B146, B147, B148, B149, B150, B151, B152, B153, B154, B160, B161, B162, B163, B164, B165, B166, B167, B168, B169, B170, B171, B172, B173, B174, B175, B176, B177, B178, B179, B180, B181, B182, B183, B184, B185, B186, B187, B188, B190, B191, B192, B193, B194, B195, B196, B197, B198, B199, B200, B201, B202, B203, B204, B205, B206, B207, B208, B209, B210, B211, B212, B213, B214, B215, B216, B217, B218, B219, B220, B221, and B222, or a pharmaceutically acceptable salt thereof.

In some cases, the compound is selected from B120, B121, B122, B123, B124, B126, B127, B128, B129, B213, B130, B131, B132, B133, B134, B135, B136, B137, B138, B139, B221, B140, B141, B143, B144, B146, B148, B149, B222, B166, B167, B168, B171, B172, B188, B194, B195, B198, B199, B200, B205, B206, B207, and B208, or a pharmaceutically acceptable salt thereof.

In some cases, the compound is selected from B120, B122, B123, B124, B127, B130, B131, B132, B133, B135, B136, B137, B138, B139, B140, B143, B144, B213, B221, and B222, or a pharmaceutically acceptable salt thereof.

In some cases, the compounds disclosed herein are stereoisomers. "Stereoisomers" refer to compounds that differ in the chirality of one or more stereocenters. Stereoisomers include enantiomers and diastereomers. The compounds disclosed herein can exist as a single stereoisomer, or as a mixture of stereoisomers. Stereochemistry of the compounds shown in the Tables above are relative stereochemistry, not absolute, unless discussed otherwise. As indicated herein, a single stereoisomer, diastereomer, or enantiomer refers to a compound that is at least more than 50% of the indicated stereoisomer, diastereomer, or enantiomer, and more preferably at least 90% of the indicated stereoisomer, diastereomer, or enantiomer.

For example, B15 is a mixture of stereoisomers of the indicated structure, while B17 is one enantiomer and B24 the other enantiomer of the indicated structure. B21 and B22 are each different stereoisomers of the indicated structure. B95 is a mixture of stereoisomers of the indicated structure, while B93 is one stereoisomer and B94 the other stereoisomer of the indicated structure. B52 and B100 are each different stereoisomers of the indicated structure. B120 is a mixture of stereoisomers of the indicated structure, while B122 is one stereoisomers and B123 the other stereoisomers of the indicated structure. B132 and B133 are each different stereoisomers of the indicated structure. B136 and B137 are each different stereoisomers of the indicated structure. B138 and B139 are each different stereoisomers of the indicated structure. B143 and B144 are each different stereoisomers of the indicated structure. B187 is a mixture of stereoisomers of the indicated structure, while B189 is one stereoisomer and B190 the other stereoisomers of the indicated structure. B194 and B195 are each different stereoisomers of the indicated structure.

The compounds disclosed herein can be useful as inhibitors of influenza virus replication in biological samples or in a patient. These compounds can also be useful in reducing the amount of influenza viruses (viral titer) in a biological sample or in a patient. They can also be useful for therapeutic and prophylactic treatment of infections caused by the influenza viruses in a biological sample or in a patient.

Pharmaceutically Acceptable Salts, Solvates, Clathrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the disclosure or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that a compound disclosed herein can be present as a mixture/combination of different pharmaceutically acceptable salts. Also contemplated are mixtures/combinations of compounds in free form and pharmaceutically acceptable salts.

In addition to the compounds described herein, pharmaceutically acceptable solvates (e.g., hydrates) and clathrates of these compounds may also be employed in compositions to treat or prevent the herein identified disorders.

As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitorily active metabolite or residue thereof. Particularly favored derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this disclosure include, but are not limited to, analogs or derivatives of compounds of the disclosure that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —NO$_2$, —ONO, or —ONO$_2$ moieties. Prodrugs can typically be prepared using well-known methods, such as those described by Burger's Medicinal Chemistry And Drug Discovery (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

Pharmaceutically acceptable prodrugs of the compounds described herein include, without limitation, esters, amino acid esters, phosphate esters, metal salts and sulfonate esters.

II. Methods of Treatment

Provided herein are uses of a compound described herein (e.g., compounds of Formulas I-III described above, or a pharmaceutically acceptable salt thereof). The compounds described herein or pharmaceutically acceptable salts thereof can be used to reduce viral titre in a biological sample (e.g. an infected cell culture) or in humans (e.g. lung viral titre in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenzavirus A, Influenzavirus B, Influenzavirus C, Isavirus and Thogotovirus. Influenzavirus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Influenzavirus B genus has one species, influenza B virus. Influenza B almost exclusively infects humans and is less common than influenza A. Influenzavirus C genus has one species, Influenzavirus C virus, which infects humans and pigs and can cause severe illness and local epidemics. However, Influenzavirus C is less common than the other types and usually seems to cause mild disease in children.

In some embodiments, the compounds used herein are for treatment of influenza or influenza viruses which are associated with Influenzavirus A or B. In some embodiments, influenza or influenza viruses are associated with Influenzavirus A. In some specific embodiments, Influenzavirus A is H1N1, H2N2, H3N2 or H5N1.

In some embodiments, the compounds disclosed herein can be used in the treatment of influenza, wherein the compound binds to free virus, binds to pre-mRNA bound PB2, or binds to trimeric polymerase complex. In some cases, the compound can target all three (free virus, pre-mRNA bound PB2, and trimeric polymerase complex).

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the disclosure depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed in the disclosure depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titre)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, ..., $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the disclosure). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease.

The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc). It also includes the use among populations who require protection from the influenza but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc).

According to the United States Center for Disease Control (US CDC), an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc) over the normal background rate or when any subject in the population being analyzed tests positive for influenza. One case of confirmed influenza by any testing method is considered an outbreak.

A "cluster" is defined as a group of three or more cases of AFR1 occurring within a 48 to 72 hour period, in a group of people who are in close proximity to each other (e.g. in the same area of an assisted living facility, in the same household, etc).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In some embodiments, the methods of the disclosure are a preventative or "prophylactic" measure to a patient, specifically a human, having a predisposition to complications resulting from infection by an influenza virus. The term "prophylactic" as used herein as for example in prophylactic use, "prophylacticly", etc, is the prophylactic use in situations in which an "index case" or an "outbreak" has been confirmed, in order to prevent the spread of infection in the rest of the community or population group.

In embodiments, the methods of the disclosure are applied as a "prophylactic" measure to members of a community or population group, specifically humans, in order to prevent the spread of infection.

As used herein, an "effective amount" refers to an amount sufficient to elicit the desired biological response. In the present disclosure the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, a safe and effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts.

The skilled artisan can readily determine and prescribe the effective amount of the compounds described herein required to treat, to prevent, inhibit (fully or partially) or arrest the progress of the disease.

Dosages of the compounds for uses described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), tree times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Influenza is a serious viral infectious disease responsible for seasonal and pandemic flu. Because influenza is highly contagious, those who come into contact with infected individuals are at increased risk of catching influenza. For this reason, many patients undergo yearly vaccinations to prevent and/or control influenza infection. In addition to, or in place of, a vaccine, patients can use the compounds described herein to not only treat an active infection, but also to prevent an infection from occurring.

Various types of administration methods can be employed in the disclosure, and are described in detail below under the section entitled "Administration Methods."

Combination Therapy

The compounds described herein can be used in conjunction with other anti-influenza compounds, and in conjunction with vaccination. Combination therapy can be particularly advantageous where a patient might be exposed to more than one form of the influenza virus.

A safe and effective amount can be achieved in the method or pharmaceutical composition of the disclosure employing a compound of any one of Formulas I-III, or a pharmaceutically acceptable salt or solvate (e.g., hydrate) thereof alone or in combination with an additional suitable therapeutic agent, for example, an antiviral agent or a vaccine. When "combination therapy" is employed, a safe and effective amount can be achieved using a first amount of a compound of any one of Formulas I-III, or a pharmaceutically acceptable salt or solvate (e.g., hydrate) thereof, and a second amount of an additional suitable therapeutic agent (e.g. an antiviral agent or vaccine).

In embodiments, the compound of any one of Formulas I-III, or a pharmaceutically acceptable salt or solvate (e.g., hydrate) thereof, and the additional therapeutic agent, are each administered in a safe and effective amount (i.e., each in an amount which would be therapeutically effective if administered alone). In other embodiments, the compound of any one of Formulas I-III, or a pharmaceutically acceptable salt or solvate (e.g., hydrate) thereof, and the additional therapeutic agent, are each administered in an amount which alone does not provide a therapeutic effect (a sub-therapeutic dose). In yet other embodiments, the compound of any one of Formulas I-III, or a pharmaceutically acceptable salt or solvate (e.g., hydrate) thereof can be administered in a safe and effective amount, while the additional therapeutic agent is administered in a sub-therapeutic dose. In still other embodiments, the compound of any one of Formulas I-III, a pharmaceutically acceptable salt or solvate (e.g., hydrate) thereof can be administered in a sub-therapeutic dose, while the additional therapeutic agent, for example, a suitable antiviral therapeutic agent is administered in a safe and effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In embodiments, the present disclosure is directed to methods of combination therapy for inhibiting Flu viruses replication in biological samples or patients, or for treating or preventing Influenza virus infections in patients using the compounds or pharmaceutical compositions described herein, e.g., a compound of any one of Formulas I-III, or a pharmaceutically acceptable salt or solvate (e.g., hydrate) thereof. Accordingly, pharmaceutical compositions also include those comprising a compound as disclosed herein (e.g., an inhibitor of Flu virus replication) in combination with an anti-viral compound exhibiting anti-Influenza virus activity.

Methods of use of the compounds and compositions disclosed herein also include combination of chemotherapy with a compound or composition of any one of Formulas I-III, or a pharmaceutically acceptable salt or solvate (e.g., hydrate) thereof or with a combination of a compound or composition of this disclosure with another anti-viral agent and vaccination with a Flu vaccine.

When co-administration involves the separate administration of the first amount of a compound of any one of Formulas I-III, or a pharmaceutically acceptable salt or solvate (e.g., hydrate) thereof and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of any one of Formulas I-III, or a pharmaceutically acceptable salt or solvate (e.g., hydrate) thereof and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the disclosure) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of any one of Formulas I-III, or a pharmaceutically acceptable salt or solvate (e.g., hydrate) thereof and a second amount of an additional therapeutic agent can result in an enhanced or synergistic therapeutic effect, wherein the combined effect is greater than the additive effect that would result from separate administration of the first amount of the compound of any one of Formulas I-III, or a pharmaceutically acceptable salt or solvate (e.g., hydrate) thereof and the second amount of the additional therapeutic agent.

As used herein, the term "synergistic" refers to a combination of a compound disclosed herein and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using compounds as disclosed herein, e.g., any one of Formulas I-III, or a pharmaceutically acceptable salt or solvate (e.g., hydrate) thereof, is in combination with a Flu vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Anti-Influenza Vaccines

The compounds described herein can be prophylactically administered in conjunction with anti-influenza vaccines. These vaccines can be administered, for example, via subcutaneous or intranasal administration. Vaccination via subcutaneous injection typically induces an IgG antibody having a neutralizing activity in the serum, and is highly effective for preventing progression of the condition into a more severe one such as pneumonia and the like. However, in the upper airway mucosa, which is the infection site, IgA is the main prophylactic component. Since IgA is not induced by subcutaneous administration, it can also be advantageous to administer vaccines via an intranasal route.

Antiviral Inhibitors

A variety of other compounds can be used, in combination with the compounds described herein, to treat or prevent an influenza infection. Approved compounds include neuraminidase (NA) inhibitors, ion channel (M2) inhibitors, polymerase (PB1) inhibitors, and other influenza antivirals.

There are three FDA-approved influenza antiviral drugs for use against influenza viruses, including Relenza (zanamivir), Tamiflu (oseltamivir phosphate), and Rapivab (peramivir). Older drugs, Symmetrel (amantadine) and Flumadine (rimantadine), are approved for treating and preventing influenza A.

Neuraminidase (NA) inhibitors are a class of drugs which block the neuraminidase enzyme. They are commonly used as antiviral drugs because they block the function of viral neuraminidases of the influenza virus, by preventing its reproduction by budding from the host cell.

Representative neuraminidase inhibitors include Oseltamivir (Tamiflu), Zanamivir (Relenza), Laninamivir (Inavir), and Peramivir.

M2 inhibitors can also be used. The Matrix-2 (M2) protein is a proton-selective ion channel protein, integral in the viral envelope of the influenza A virus. Two different sites for drug interaction have been proposed. One is a lipid-facing pocket between 2 adjacent transmembrane helices (around Asp-44), at which the drug binds and inhibits proton conductance allosterically. The other is inside the pore (around Ser-31), at which the drug directly blocks proton passage.

The anti-influenza virus drug, amantadine, is a specific blocker of the M2H+ channel. In the presence of amantadine, viral uncoating is incomplete, and the RNP core fails to promote infection. Aminoadamantanes, including amantadine and rimantadine have been widely abandoned due to virus resistance, but combination therapy can lessen the development of drug resistance, as virus which becomes resistant to one active agent can still be treated by the other agent(s) in the combination therapy.

Inhibitors of influenza RNA-dependent RNA polymerase (RdRp) include favipiravir and compounds described in PCT WO 2013/138236. Additional compounds, disclosed in Muratore et al., "Small molecule inhibitors of influenza A and B viruses that act by disrupting subunit interactions of the viral polymerase," PNAS, vol. 109 no. 16, 6247-6252 (April 2012), include the following:

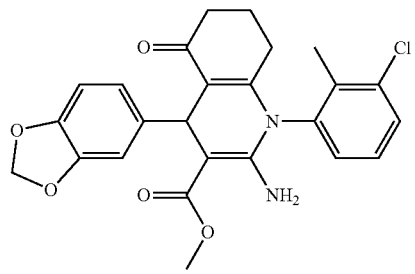

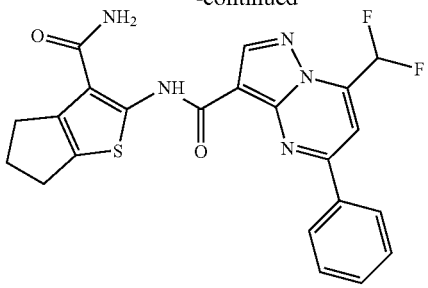

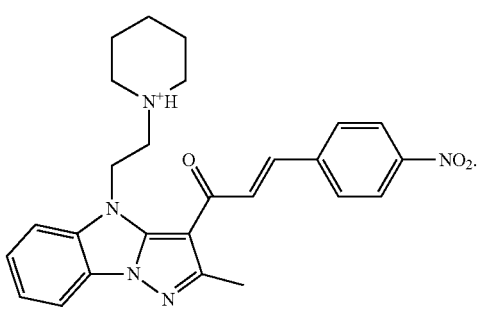

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See also Ruruta et al., Antiviral Research, 82: 95-102 (2009), "T-705 (flavipiravir) and related compounds: Novel broad-spectrum inhibitors of RNA viral infections.") In some embodiments, the compounds described herein can be co-administered with a traditional influenza vaccine.

III. Compound Preparation

Also provided herein are methods of preparing a compound as disclosed herein. In embodiments, the methods are directed to prepare compounds represented by Formulas I-III, or pharmaceutically acceptable salts thereof.

Also provided are methods of preparing a compound as disclosed herein. The compounds described herein, and pharmaceutical salts thereof, all include a common core that includes an azaindole ring coupled with a diazaindole ring.

Those compounds of Formula II where L is a 2.2.2 bicyclooctyl or bicyclooctenyl ring can be prepared as follows:

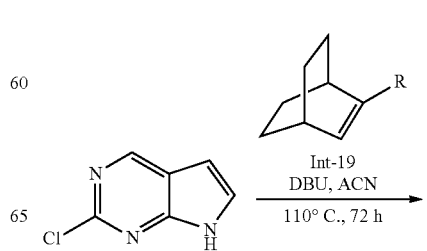

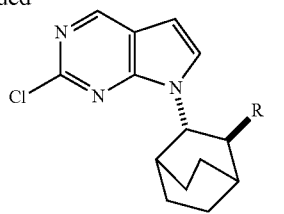

If fluorination is desired, the following step can be performed:

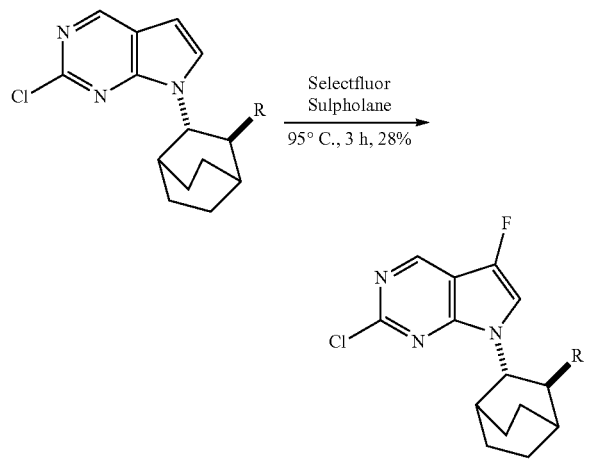

The following coupling step is shown where flourination was performed, but can be performed whether or not the flourine has been added.

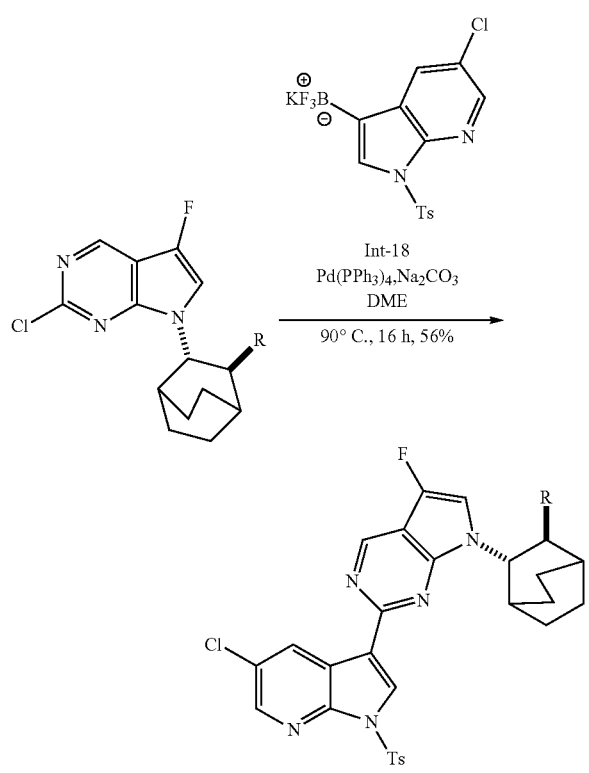

Workup with HCl in dioxane/acetonitrile provides the desired compound.

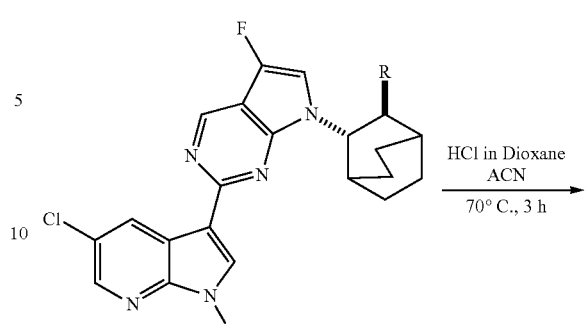

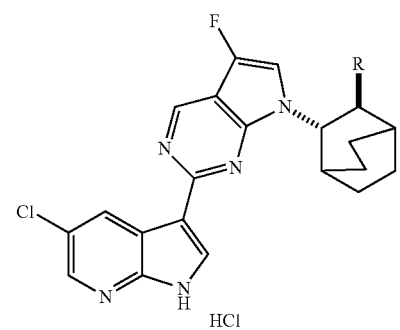

In place of the ring fluorine, or the ring chlorine, shown in the above reaction schemes, other halogens can be provided using known halogenation conditions.

In this reaction scheme, X can be —$CO_2NR_2$, —$CO_2R$, —$NRC(O)NR_2$, —NRC(O)OR, —NRC(O)R, or —$NR_2$. The chemistry works substantially the same whether the ring is a 2.2.2 bicyclooctyl or 2.2.2 bicyclooctenyl ring.

If compounds of Formula I or Formula III are desired, then rather than using the compound:

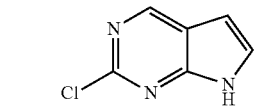

in the first step, one would use the compound:

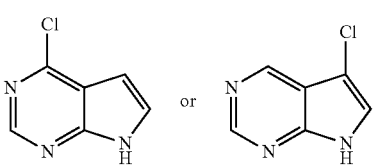 [SMILES: Clc1ncnc2[nH]ccc12 ; Clc1c[nH]c2ncncc12]

to make the compounds of Formulas I and III, respectively.

For those compounds where L is H, it can be desirable to protect the amine group not involved with the coupling chemistry before the two rings are connected, then deprotect the ring after the coupling chemistry. A representative reaction scheme is shown below, where "Pr" indicates a protecting group:

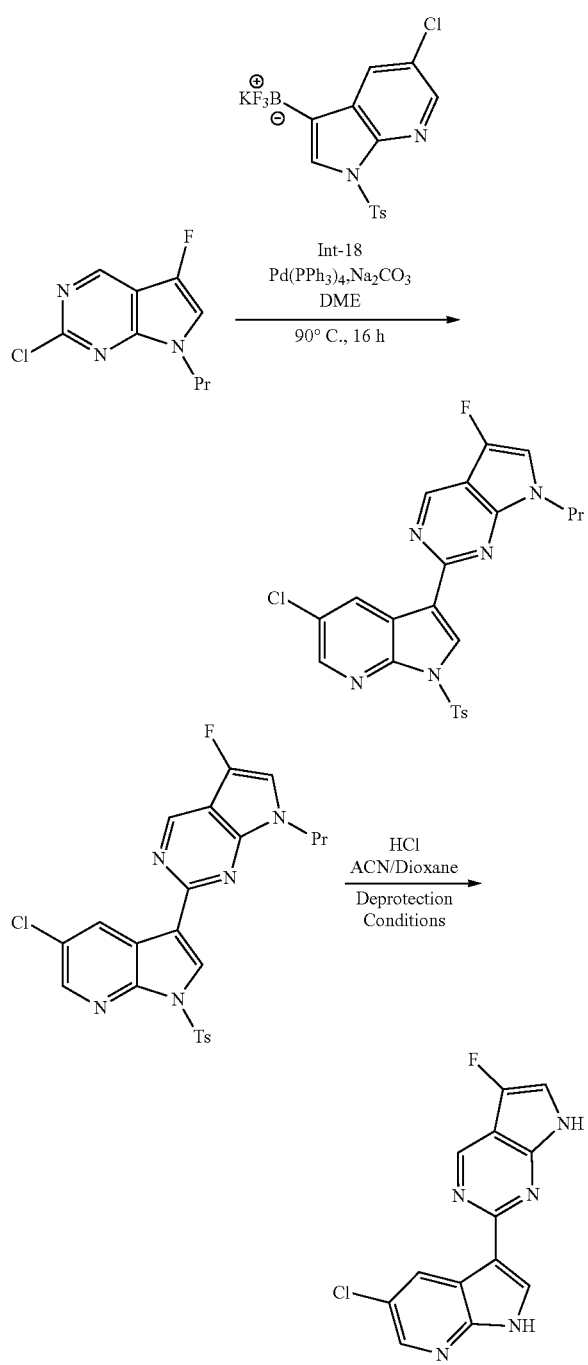

As with the earlier-described chemistry, the above reaction scheme shows the synthesis of compounds of Formula II, where L is H. Should compounds of Formula I or III (where L is H) be desired, one would use the compound:

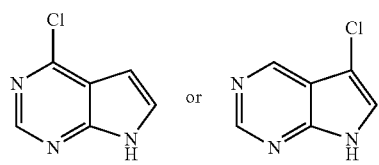 [SMILES: Clc1ncnc2[nH]ccc12 ; Clc1c[nH]c2ncncc12]

to make the compounds of Formulas I and III, respectively.

To synthesize compounds of Formula II, where L is (ii), (iii), or (iv) as discussed above, rather than starting the coupling reaction with a compound of the formula:

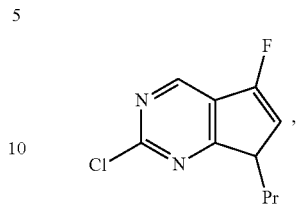

one would start with an appropriate moiety from groups ii), iii) or iv) in place of protecting group Pr.

As with the earlier-described coupling chemistry, this approach relates to the synthesis of compounds of Formula II, where L is one of groups ii), iii) or iv). Should compounds of Formula I or III be desired, one would use compounds similar to:

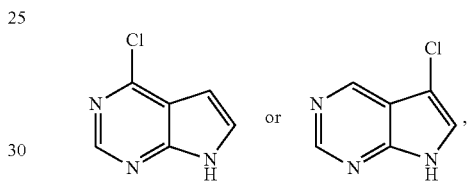

where the amine group is functionalized with one of groups ii), iii) or iv), to make the compounds of Formulas I and III, respectively.

The L moieties can be attached to the diazaindole ring, for example, by performing a nucleophilic substitution reaction using the amine on the diazaindole ring as the nucleophile, and a compound with a suitable leaving group. Should ester moieties on the compound with the leaving group react more quickly with the amine on the diazaindole ring than the carbon with the leaving group, then the ester moieties can be suitably protected, then converted to esters after the coupling chemistry is complete.

After the coupling chemistry is complete, should it be desired to do so, the ring nitrogen with an open valence (protected as a tosylate, or Ts, moiety in Intermediate 19 shown in the first scheme) can participate in a similar nucleophilic substitution reaction, with a suitable compound with a leaving group, to form a moiety selected from the group consisting of —C(O)R, —C(O)NR$_2$, alkyl-CO$_2$R and alkenyl-CO$_2$R.

Scaffolds

In addition to the synthetic methods described above, the synthesis of the compounds described herein can be simplified using one or more scaffolds. For example, a scaffold of one of the following formulas can be reacted with a suitably functionalized diazaindole ring to form the core structure including the azaindole and diazaindole rings linked to each other.

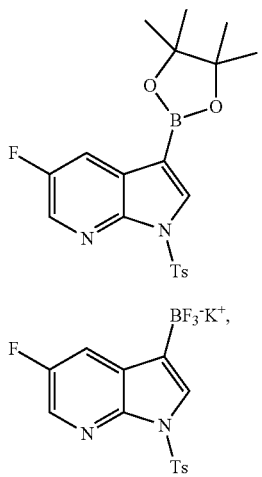

where Ts is toluene sulfonate, also known as "tosyl" or "tosylate."

The variables in these formulae are either the same as the definitions provided in the section defining the compounds described herein, or, where the functional groups defined by the variables would be labile under the reaction conditions described herein, can be either protected forms of the functional groups, or synthons for such groups. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference.

Any suitable reaction condition known in the art, for example, in PCT WO 2005/095400 and PCT WO 2007/084557 for the coupling of a dioxaboraolan with a chlorodiazaindole can be employed. For example, the reaction between these precursors can be performed in the presence of Pd(PPh$_3$)$_4$. Specific exemplary conditions are described in the working examples in the Examples section of the instant application.

In some embodiments of the chemistry described herein, the leaving group is a tosylate group, and the tosylate group is "de-tosylated" to generate the compounds of Formulas I, II or III after the coupling chemistry is completed. Any suitable condition for deprotecting a Ts group known in the art can be employed in the disclosure. Specific exemplary conditions are described in working examples. De-tosylation can generate the compounds of Formulas I, II or III where L is —H. If desired, this position can be alkylated by any suitable method known in the art to form the compounds of Formula I, II, or III where L is, for example, the moieties in ii), iii), iv), or v). Specific exemplary synthetic methods are described in more detail below in the working examples.

Chiral Separations

The compounds described herein can have asymmetric centers and occur as racemates, racemic mixtures, individual diastereomers or enantiomers, with all isomeric forms being included in the present disclosure. Compounds of the present disclosure having a chiral center can exist in and be isolated in optically active and racemic forms. Some compounds can exhibit polymorphism. The present disclosure encompasses racemic, optically-active, polymorphic, or stereoisomeric forms, or mixtures thereof, of a compound of the disclosure, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatoqraphy: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Pharmaceutical Compositions

The compounds described herein can be formulated into pharmaceutical compositions that further comprise a pharmaceutically acceptable carrier, diluent, adjuvant or vehicle. In embodiments, the present disclosure relates to a pharmaceutical composition comprising a compound described above or salt thereof, and a pharmaceutically acceptable carrier, diluent, adjuvant or vehicle. In embodiments, the pharmaceutical composition comprises a safe and effective amount of a compound as disclosed herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient. The term "prophylactically effective amount" refers to an amount effective in preventing and/or substantially lessening the chances or the size of influenza virus infection outbreak.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Formulations for Pulmonary Delivery

In some embodiments, the pharmaceutical compositions disclosed herein are adapted to be administered to the lower respiratory tract (e.g., the lungs) directly through the airways by inhalation. Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360, and 5,590,645 (all illustrating the "Diskus" device), or GB2i78965, GB2129691, GB2169265, U.S. Pat. Nos. 4,778,054, 4,811,731 and 5,035,237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurized packs, such as a metered dose inhaler (MDI), with the use of a suitable liquefied propellant, including hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof. Aerosol compositions suitable for inhalation can be presented either as suspensions or as solutions.

Medicaments for administration by inhalation typically have a controlled particle size. The optimum particle size for inhalation into the bronchial system is usually about 1 to about 10 µm, and in some embodiments, from about 2 to about 5 µm. Particles having a size above about 20 µm are generally too large when inhaled to reach the small airways. To achieve these particle sizes the particles of the active ingredient may be subjected to a size reducing process such as micronization. The desired size fraction may be separated out by air classification or sieving. Preferably, the particles will be crystalline.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical compositions disclosed herein can be formulated with supplementary active ingredients.

In some embodiments, the pharmaceutical composition disclosed herein is administered from a dry powder inhaler. In other embodiments, the pharmaceutical composition disclosed herein is administered by an aerosol dispensing device, optionally in conjunction with an inhalation chamber such as the "Volumatic" ® inhalation chamber.

The carrier can be a solvent or dispersion medium containing, for example, water, ethanol, polyol (for example, glycerol, propylene glycol and liquid polyethylene glycol, and the like), suitable mixtures thereof, and/or vegetable oils. The proper fluidity can be maintained, for example, by the use of a coating such as, for example, lecithin, by the maintenance of the required particle size in the case of dispersion and by the use of surfactants. Preventing the action of microorganisms in the compositions disclosed herein is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a pharmaceutical composition can be within a matrix which controls the release of the composition. In some embodiments, the matrix can comprise lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and combinations thereof and other polymers such as those disclosed, for example, in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. In these embodiments, the matrix sustainedly releases the drug.

Pharmaceutically acceptable carriers and/or diluents may also include any solvents, dispersion media, coatings, antibacterials and/or antifungals, isotonic and absorption delaying agents and the like. The use of such media and agents for pharmaceutically active substances is well known in the art. Except insofar as any conventional medium or agent is incompatible with the active ingredient, use thereof in the pharmaceutical compositions is contemplated.

The pharmaceutical compositions can be formulated for administration in accordance with conventional techniques. See, e.g., Remington, The Science and Practice of Pharmacy (20th Ed. 2000). For example, the intranasal pharmaceutical compositions of the present disclosure can be formulated as an aerosol (this term includes both liquid and dry powder aerosols). Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles (e.g., lyophilized, freeze dried, etc.) can likewise be produced with any solid particulate medicament aerosol generator, by techniques known in the pharmaceutical art. As another example, the pharmaceutical compositions can be formulated as an on-demand dissolvable form, which provides a lyophilized portion of the pharmaceutical composition and a dissolving solution portion of the pharmaceutical composition.

In some embodiments, the pharmaceutical composition is in the form of an aqueous suspension, which can be prepared from solutions or suspensions. With respect to solutions or suspensions, dosage forms can be comprised of micelles of lipophilic substances, liposomes (phospholipid vesicles/membranes) and/or a fatty acid (e.g., palmitic acid). In particular embodiments, the pharmaceutical composition is a solution or suspension that is capable of dissolving in the fluid secreted by mucous membranes of the epithelium of the tissue to which it is administered, applied and/or delivered, which can advantageously enhance absorption.

The pharmaceutical composition can be an aqueous solution, a nonaqueous solution or a combination of an aqueous and nonaqueous solution. Suitable aqueous solutions include, but are not limited to, aqueous gels, aqueous suspensions, aqueous microsphere suspensions, aqueous microsphere dispersions, aqueous liposomal dispersions, aqueous micelles of liposomes, aqueous microemulsions, and any combination of the foregoing, or any other aqueous solution that can dissolve in the fluid secreted by the mucosal membranes of the nasal cavity. Exemplary nonaqueous solutions include, but are not limited to, nonaqueous gels, nonaqueous suspensions, nonaqueous microsphere suspensions, nonaqueous microsphere dispersions, nonaqueous liposomal dispersions, nonaqueous emulsions, nonaqueous microemulsions, and any combination of the foregoing, or any other nonaqueous solution that can dissolve or mix in the fluid secreted by mucosal membranes.

Examples of powder formulations include, without limitation, simple powder mixtures, micronized powders, freeze dried powder, lyophilized powder, powder microspheres, coated powder microspheres, liposomal dispersions, and any combination of the foregoing. Powder microspheres can be formed from various polysaccharides and celluloses, which include without limitation starch, methylcellulose, xanthan gum, carboxymethylcellulose, hydroxypropyl cellulose, carbomer, alginate polyvinyl alcohol, acacia, chitosans, and any combination thereof.

In particular embodiments, the composition is one that is at least partially, or even substantially (e.g., at least 80%, 90%, 95% or more) soluble in the fluids that are secreted by mucosa so as to facilitate absorption. Alternatively or additionally, the composition can be formulated with a carrier and/or other substances that foster dissolution of the agent within secretions, including without limitation fatty acids (e.g., palmitic acid), gangliosides (e.g., GM-1), phospholipids (e.g., phosphatidylserine), and emulsifiers (e.g., polysorbate 80).

Those skilled in the art will appreciate that for intranasal administration or delivery, because the volume of the pharmaceutical composition administered is generally small, nasal secretions may alter the pH of the administered dose since the range of pH in the nasal cavity can be as wide as 5 to 8. Such alterations can affect the concentration of un-ionized drug available for absorption. Accordingly, in representative embodiments, the pharmaceutical composition further comprises a buffer to maintain or regulate pH in situ. Typical buffers include, but are not limited to, ascorbate, acetate, citrate, prolamine, carbonate, and phosphate buffers.

In embodiments, the pH of the pharmaceutical composition is selected so that the internal environment of the mucosal tissue after administration is on the acidic to neutral side, which (1) can provide the active compound in an un-ionized form for absorption, (2) prevents growth of pathogenic bacteria, which is more likely to occur in an alkaline environment, and (3) reduces the likelihood of irritation of the mucosa.

For liquid and powder sprays or aerosols, the pharmaceutical composition can be formulated to have any suitable and desired particle or droplet size. In illustrative embodiments, the majority and/or the mean size of the particles or droplets range from equal to or greater than about 1, 2.5, 5, 10, 15 or 20 microns and/or equal to or less than about 25, 30, 40, 45, 50, 60, 75, 100, 125, 150, 175, 200, 225, 250, 275, 300, 325, 350, 375, 400, or 425 microns (including all combinations of the foregoing). Representative examples of suitable ranges for the majority and/or mean particle or droplet size include, without limitation, from about 5 to 100 microns, from about 10 to 60 microns, from about 175 to 325 microns, and from about 220 to 300 microns which facilitate the deposition of a safe and effective amount of the active compound, for example, in the nasal cavity (e.g., in the upper third of the nasal cavity, the superior meatus, the olfactory region and/or the sinus region to target the olfactory neural pathway). In general, particles or droplets smaller than about 5 microns will be deposited in the trachea or even the lung, whereas particles or droplets that are about 50 microns or larger generally do not reach the nasal cavity and are deposited in the anterior nose.

International patent publication WO 2005/023335 (Kurve Technology, Inc.) describes particles and droplets having a diameter size suitable for the practice of representative embodiments of pharmaceutical compositions disclosed herein. In particular embodiments, the particles or droplets have a mean diameter of about 5 to 30 microns, about 10 to 20 microns, about 10 to 17 microns, about 10 to 15 microns, about 12 to 17 microns, about 10 to 15 microns or about 10 to 12 microns. The particles can "substantially" have a mean diameter or size as described herein, i.e., at least about 50%, 60%, 70%, 80%, 90% or 95 or more of the particles are of the indicated diameter or size range.

The pharmaceutical composition can be delivered as a nebulized or atomized liquid having a droplet size as described above.

According to particular embodiments of this disclosure that comprise methods of intranasal delivery, it can be desirable to prolong the residence time of the pharmaceutical composition in the nasal cavity (e.g., in the upper third of the nasal cavity, the superior meatus, the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl), which are agents that enhance residence time in the nasal cavity. As a further approach, increasing the viscosity of the formulation can also provide a means of prolonging contact of the agent with the nasal epithelium. The pharmaceutical composition can be formulated as a nasal emulsion, ointment or gel, which offers advantages for local application because of their viscosity.

Moist and highly vascularized membranes can facilitate rapid absorption; consequently, the pharmaceutical composition can optionally comprise a humectant, particularly in the case of a gel-based composition so as to assure adequate intranasal moisture content. Examples of suitable humectants include but are not limited to glycerin or glycerol, mineral oil, vegetable oil, membrane conditioners, soothing agents, and/or sugar alcohols (e.g., xylitol, sorbitol; and/or mannitol). The concentration of the humectant in the pharmaceutical composition will vary depending upon the agent selected and the formulation.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In representative embodiments, the preservative is present in an amount of about 2% by weight or less.

The pharmaceutical compositions described herein can optionally contain an odorant, e.g., as described in EP 0 504 263 B1, to provide a sensation of odor, to aid in inhalation of the composition so as to promote delivery to the olfactory region and/or to trigger transport by the olfactory neurons.

As another option, the composition can comprise a flavoring agent, e.g., to enhance the taste and/or acceptability of the composition to the subject.

Porous Particles for Pulmonary Administration

In some embodiments, the particles are porous, so that they have an appropriate density to avoid deposition in the back of the throat when administered via an inhaler. The combination of relatively large particle size and relatively low density avoids phagocytosis in the lungs, provides appropriately targeted delivery, avoids systemic delivery of the components, and provides a high concentration of the components in the lung.

Representative methods for preparing such particles, and for delivering such particles, are described, for example, in U.S. Pat. No. 7,384,649, entitled, "Particulate compositions for pulmonary delivery," U.S. Pat. No. 7,182,961, entitled "Particulate compositions for pulmonary delivery," U.S. Pat. No. 7,146,978, entitled, "Inhalation device and method," U.S. Pat. No. 7,048,908, entitled "Particles for inhalation having sustained release properties," U.S. Pat. No. 6,956,021, entitled "Stable spray-dried protein formulations," U.S. Pat. No. 6,766,799, entitled "Inhalation device," and U.S. Pat. No. 6,732,732, entitled "Inhalation device and method."

Additional patents disclosing such particles include U.S. Pat. No. 7,279,182, entitled "Formulation for spray-drying large porous particles," U.S. Pat. No. 7,252,840, entitled "Use of simple amino acids to form porous particles," U.S. Pat. No. 7,032,593, entitled "Inhalation device and method," U.S. Pat. No. 7,008,644, entitled "Method and apparatus for producing dry particles," U.S. Pat. No. 6,848,197, entitled "Control of process humidity to produce large, porous particles," and U.S. Pat. No. 6,749,835, entitled "Formulation for spray-drying large porous particles."

U.S. Pat. No. 7,678,364, entitled "Particles for inhalation having sustained release properties," discloses methods for delivering particles to the pulmonary system comprising: administering to the respiratory tract of a patient in need of treatment, prophylaxis or diagnosis a safe and effective amount of a dry powder comprising: a) a multivalent metal cation which is complexed with a therapeutic, prophylactic or diagnostic agent; b) a pharmaceutically acceptable carrier; and c) a multivalent metal cation-containing component wherein the dry powder is spray-dried and has a total amount of multivalent metal cation which is about 10% w/w or more of the total weight of the agent, a tap density of about 0.4 g/cm$^3$ or less, a median geometric diameter of from about 5 micrometers to about 30 micrometers and an aerodynamic diameter of from about 1 to about 5 microns.

The amount of the compounds described herein, or salts thereof, present in the particles can range from about 0.1 weight % to about 95 weight %, though in some cases, can even be as high as 100%. For example, from about 1 to about 50%, such as from about 5 to about 30%. Particles in which the compound is distributed throughout a particle can be preferred.

In some embodiments, the particles include a surfactant other than the phospholipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles disclosed herein include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85); Tween® 80 and tyloxapol.

The surfactant can be present in the particles in an amount ranging from about 0 to about 5 weight %. Preferably, it can be present in the particles in an amount ranging from about 0.1 to about 1.0 weight %.

Particles that have a tap density less than about 0.4 g/cm$^3$, median diameters of at least about 5 μm, and an aerodynamic diameter of from about 1 μm to about 5 μm, or from about 1 μm to about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

Liposomal Delivery

The compositions described herein are advantageously delivered to the lungs, so as to provide the compounds at the site of an actual or potential influenza infection. This can be accomplished by pulmonary delivery via metered-dose inhalers or other pulmonary delivery devices, and also by lodging particles in the capillary beds surrounding the alveoli in the lungs.

Nanocarriers, such as liposomes, including small unilamellar vesicles, show several advantages over other conventional approaches for delivering drugs to the lungs, including prolonged drug release and cell-specific targeted drug delivery. Nano-sized drug carriers can also be advantageous for delivering poorly water soluble drugs, and certain of the compounds described herein are poorly water-soluble. Additional advantages include their ability to provide controlled release, protection from metabolism and degradation, decreased drug toxicity and targeting capabilities.

The liposomes (preferably unilamellar vesicles) have a size less than 200 nm as measured by dynamic light scattering, and preferably characterized by being comprised of chemically pure synthetic phospholipids, most preferably having aliphatic side chains of a length of at least 16 carbons, and containing one or more of the compounds described herein, or a pharmaceutically acceptable salt thereof, sufficient to preferentially deliver (i.e., target) a quantity of the compounds thereof to the capillary beds surrounding the alveoli. Vesicle diameter can be measured, for example, by dynamic light scattering using a helium-neon 100 mW NEC gas laser and a Malvern K7027 correlator, ideally with at least two or three measurements made for each for each size determination.

The expression "chemically pure phospholipids" is meant to define phospholipids which are essentially free of deleterious detergent moieties and impurities which cause aggregation of small unilamellar vesicles (SUVs) formed therefrom, and which are more than 97% pure. Preferably, the liposomes have a diameter predominantly of from about 50 to about 160 nm, are essentially neutral in charge, and incorporate phospholipids having a side chain length of from 16 to 18 carbon atoms. More preferably, the liposomes are prepared from distearoyl phosphatidylcholine (DSPC) and include cholesterol (most preferably in an amount of from 10 to 50% of total lipid) as a vesicle stabilizer.

It can also be advantageous that the liposomes have a melting point above body temperature (i.e., above 37° C.). For this reason, it can be advantageous to use pure phospholipids, preferably ones that are saturated, and have a carbon chain length of at least 16 carbons, preferably between 16 and 18 carbons. Distearoylphosphatidyl choline (DSPC) is a preferred phospholipid.

Cholesterol helps to stabilize the liposomes, and is preferably added in a sufficient amount to provide liposome stability. Most preferably, the liposomes further comprise a pegylated phospholipid, such as DSPEPEG. The method involves introducing into a patient's bloodstream an amount of liposomes, of a size of less than 200 nm (preferably unilamellar vesicles) and preferably characterized by being comprised of chemically pure synthetic phospholipids, most preferably having aliphatic side chains of a length of at least 16 carbons, and containing the compounds described herein, or a pharmaceutically acceptable salt or prodrug thereof, sufficient to preferentially deliver (i.e., target) a quantity of the compounds to the capillary beds in the lungs, surrounding the alveoli.

The compounds described herein can be combined with other anti-influenza agents, as also described herein. Such additional agents can also be present in the liposomes, can be present in different liposomes, or can be co-administered via a different route.

The liposomes include one or more of the compounds described herein, or a pharmaceutically acceptable salt thereof, and can optionally include other anti-influenza agents. The liposomes can be prepared by dissolving the phospholipid and cholesterol in an appropriate organic solvent, such as chloroform, and evaporating the solvent to form a lipid film. If an ionophore is employed to load the compounds described herein into the liposomes, the ionophore may be added to the lipid solution before evaporation. The dried lipid film is then rehydrated in an appropriate aqueous phase, such as phosphate-buffered saline or other physiologically appropriate solution. Water-soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as extrusion, sonication, or processing through a homogenizer according to the method described in U.S. Pat. No. 4,753,788; to produce vesicles within the specified size.

The liposomes can then be processed to remove undesirable compounds from the suspending solution, for example, un-encapsulated drug, which may be accomplished through processes such as gel chromatography or ultrafiltration.

The use of liposomes in dry powder aerosols for targeted lung delivery is described, for example, in Willis et al., *Lung*, June 2012, 190(3):251-262. One advantage is that the phospholipids used to prepare the liposomes are similar to endogenous lung surfactant.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, to the pulmonary system, such as by using an inhaler, such as a metered dose inhaler (MDI), or the like, depending on the severity of the infection being treated. In some embodiments, the compound or composition disclosed herein is administered orally, via inhalation, or intravenously.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. In some cases, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added.

For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

The present disclosure will be better understood with reference to the following non-limiting examples.

EXAMPLES

Example 1: Sidechain Preparation

Some of the compounds described herein include a relatively long sidechain moiety. The synthesis of precursors for some of these sidechains is shown below.

Sidechain-1

2-(2-(2-ethoxy ethoxy) ethoxy) acetic acid (Sidechain-1)

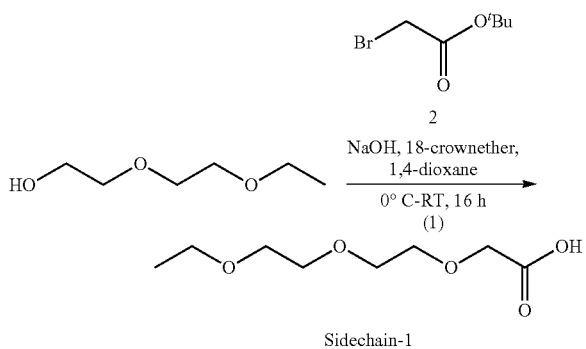

To a stirred solution of 2-(2-ethoxyethoxy) ethan-1-ol 1 (2.68 g, 20 mmol) in 1, 4-dioxan (60 mL) was added NaOH (1.2 g, 30 mmol) at 0° C. The mixture was stirred at room temperature for 15 minutes. Then cooled to 0° C., tert-butyl 2-bromoacetate 2 (7.8 g, 40 mmol) and 18-crownether (250 mg) were added to the reaction mixture and stirred at room temperature for 16 h. After consumption of starting material, the mixture was diluted with ice cold water (200 mL), extracted with diethyl ether (2×100 mL). The separated aqueous layer was acidified (pH~2) with concentrated HCl (30 mL) and extracted with dichloromethane (2×250 mL). The organic layer was washed with water (2×100 mL), and with brine solution (50 mL), dried over sodium sulfate and concentrated under reduced pressure to afford pure 2-(2-(2-ethoxy ethoxy) ethoxy) acetic acid Sidechain-1 (1.5 g, 7.8 mmol, 39% yield) as a brown liquid. TLC system: 10% Methanol in dichloromethane: $R_f$: 0.10

Sidechain-2

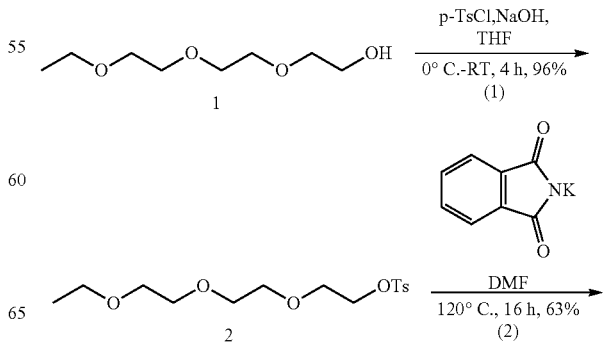

229

-continued

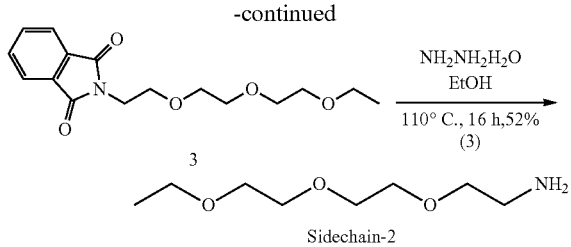

2-(2-(2-ethoxyethoxy) ethoxy) ethyl 4-methylbenzenesulfonate (2)

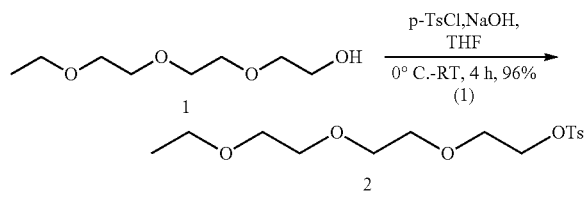

To a stirred solution of 2-(2-(2-ethoxyethoxy)ethoxy)ethan-1-ol 1 (5.0 g, 28.05 mmol) in THF (20 mL) were added a solution of NaOH (2.28 g, 57.22 mmol) in water (10 mL) at 0° C. followed by a solution of p-toluene sulfonyl chloride (6.84 g, 35.90 mmol) in THF (10 mL) at 0° C. Then the mixture was allowed to RT and stirred for 4 h. After consumption of starting material, the mixture was quenched with water (100 mL) and extracted with ether (2×100 mL) washed with ice cold water (2×25 mL), brine solution (25 mL), dried over sodium sulphate and concentrated to afford 2-(2-(2-ethoxyethoxy)ethoxy)ethyl 4-methylbenzenesulfonate 2 (9.02 g, 27.16 mmol, 96% yield) as colorless oil. TLC system: 40% ethyl acetate in hexanes; $R_f$: 0.3 LCMS: m/z=332.83 (M+H)$^+$ 2-(2-(2-(2-ethoxyethoxy) ethoxy) ethyl) isoindoline-1, 3-dione (3)

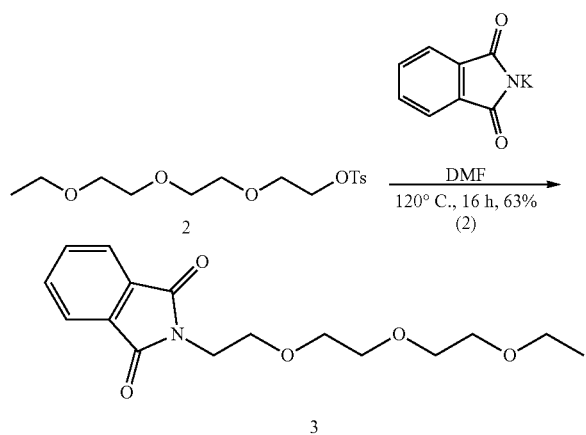

To a stirred solution of 2-(2-(2-ethoxyethoxy) ethoxy) ethyl 4-methylbenzenesulfonate 2 (6 g, 18.07 mmol) in DMF (15 mL) was added potassium phthalimide (4.418 g,

230

23.85 mmol) at room temperature then stirred at 110° C. for 16 h. After completion of reaction as indicated by TLC, reaction mixture was cooled to RT, added ether (50 mL) and stirred at RT for 15 minutes, filtered, washed with ether. The filtrate was washed with 1M NaOH solution (50 mL), water (50 mL), brine solution (50 mL), dried over Na$_2$SO$_4$ and concentrated under reduced pressure to obtained 2-(2-(2-(2-ethoxyethoxy)ethoxy)ethyl)isoindoline-1,3-dione 3 (3.5 g, 11.40 mmol, 63%) as yellow oily liquid. TLC system: 40% ethyl acetate in hexanes; $R_f$: 0.50; LCMS: m/z=308.11 (M+H)$^+$ 2-(2-(2-ethoxyethoxy) ethoxy) ethan-1-amine (Sidechain-2)

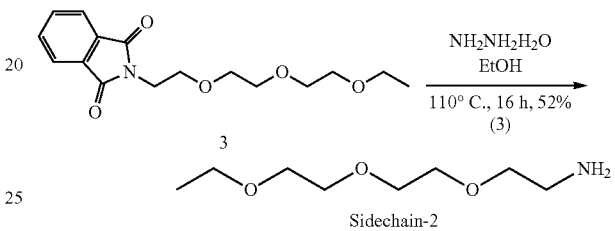

To a stirred solution of 2-(2-(2-(2-ethoxy ethoxy) ethoxy) ethyl) isoindoline-1, 3-dione 3 (500 mg, 1.62 mmol) in ethanol (5 mL) was added hydrazine hydrate (5 mL) and stirred at 110° C. for 16 h. After completion of the reaction as indicated by TLC, reaction mixture was cooled to room temperature and extracted with toluene (2×50 mL) and washed with brine solution (25 mL), dried over Na$_2$SO$_4$ and concentrated under reduced pressure to obtained 2-(2-(2-ethoxyethoxy)ethoxy)ethan-1-amine (Sidechain 2) (150 mg, 0.84 mmol, 52%) as yellow oily liquid. TLC system: 10% Methanol in dichloromethane, $R_f$: 0.10

Sidechain-3

2-(2-(2-ethoxyethoxy) ethoxy)-N-methylethan-1-amine (Sidechain-3)

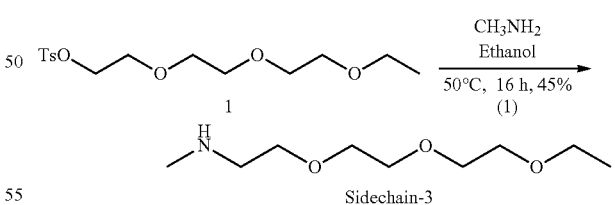

In a sealed tube 2-(2-(2-ethoxyethoxy) ethoxy) ethyl 4-methylbenzenesulfonate 1 (Synthesis of Cpd-1 was reported in Sidechain-2) (500 mg, 1.50 mmol) and 33% methyl amine in ethanol solution (3 mL) was heated at 50° C. for 16 h. After completion of reaction as indicated by TLC, evaporated the organic solvents, the crude was dissolved in water (25 mL) and extracted with dichloromethane (2×50 mL). The combined organic layer was washed with brine solution (25 mL), dried over Na$_2$SO$_4$ and to afford 2-(2-(2-ethoxyethoxy) ethoxy)-N-methylethan-1- amine Sidechain-3 (210 mg, 1.09 mmol, 73%) as yellow oily liquid. TLC system: 10% Methanol in dichloromethane; R$_f$: 0.20

Sidechain-4

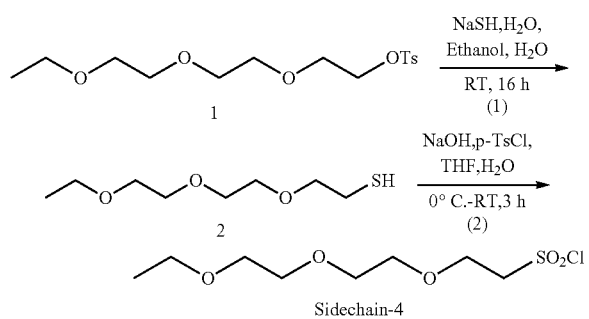

2-(2-(2-ethoxyethoxy) ethoxy) ethane-1-thiol (2)

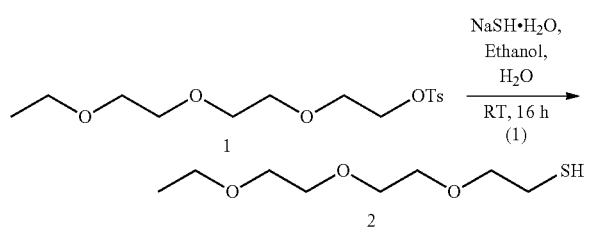

To a stirred solution of 2-(2-(2-ethoxyethoxy) ethoxy) ethyl 4-methylbenzenesulfonate 1 (Synthesis of Cpd-1 was reported in Sidechain-2) (2.2 g, 6.626 mmol) in ethanol (10 mL), THF (1 mL) was added Sodium Hydrogensulfide Hydrate (3.7 g, 66.26 mmol) and stirred at room temperature for 16 h. After completion of reaction as indicated by TLC, evaporated organic solvents, the crude was diluted with water (100 ml) and extracted into ethyl acetate (2×100 mL). Organic layer was washed with brine solution (100 mL), dried over Na$_2$SO$_4$ and concentrated to obtained 2-(2-(2-ethoxyethoxy) ethoxy) ethane-1-thiol 2 (1.1 g, 5.67 mmol, 85%) as a pale brown liquid. TLC system: 50% ethyl acetate in hexanes; R$_f$: 0.20

2-(2-(2-ethoxyethoxy) ethoxy) ethane-1-sulfonyl chloride (Sidechain-4)

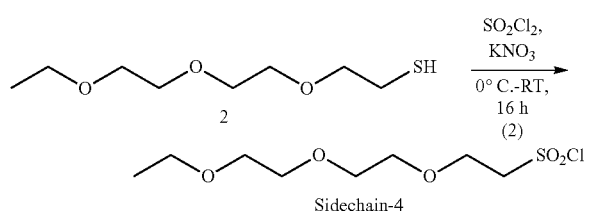

To a stirred solution of 2-(2-(2-ethoxyethoxy)ethoxy) ethane-1-thiol 2 (1.4 g, 7.21 mmol) and potassium nitrate (2.41 g, 18.04 mmol) was added sulfuryl chloride (1.5 ml) at 0° C. and stirred at room temperature for 16 h. After completion of reaction as indicated by TLC, added water (200 mL) and extracted with DCM (2×200 mL), organic layer was washed with brine solution (100 mL), dried over Na$_2$SO$_4$ and concentrated to afford 2-(2-(2-ethoxyethoxy) ethoxy)ethane-1-sulfonyl chloride Sidechain-4 (1.4 g, 5.38 mmol, 74%) as a brown liquid. TLC system: 50% ethyl acetate in hexanes; R$_f$: 0.40

Sidechain-5

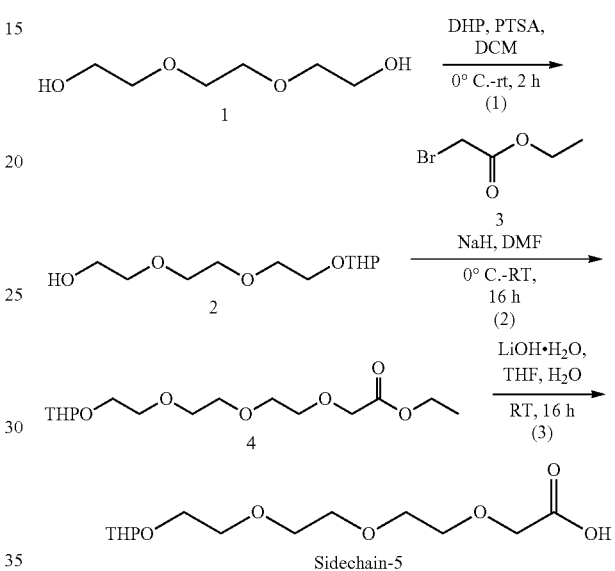

2-(2-(2-(tetrahydro-2H-pyran-2-yloxy) ethoxy) ethoxy) ethanol (2)

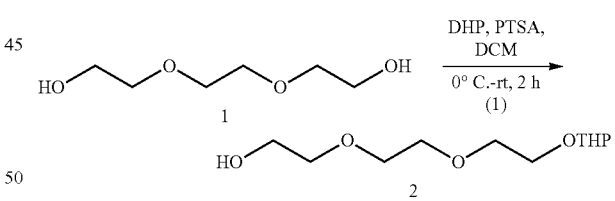

To a stirred solution of 2,2'-(ethane-1,2-diylbis(oxy))di-ethanol 1 (50 g, 333.3 mmol) in dichloromethane (1.5 L) was added dihydropyran (20 g, 233.3 mmol) and p-toluene sulfonic acid (6.3 g, 33.33 mmol) at 0° C., and stirred at room temperature for 4 h. The reaction mixture diluted with water (1000 mL) and extracted with dichloromethane (3×800 mL), the combined organic layers were was washed with brine (2×200 mL) and dried over sodium sulphate and concentrated. The residue was purified by flash column chromatography (100-200 silica) using 3% methanol in dichloromethane to afford 2-(2-(2-(tetrahydro-2H-pyran-2-yloxy) ethoxy) ethoxy) ethanol 2 (3 g, 12.82 mmol, 10% yield) as a colorless oily liquid. TLC system: 15% Acetone in dichloromethane; R$_f$: 0.35

Ethyl 2-(2-(2-(2-(tetrahydro-2H-pyran-2-yloxy) ethoxy) ethoxy) ethoxy) acetate (4)

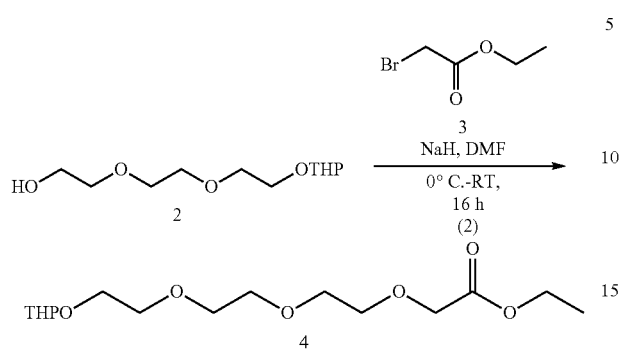

To a stirred solution of 2-(2-(2-(tetrahydro-2H-pyran-2-yloxy)ethoxy)ethoxy)ethanol 2 (2.7 g, 11.54 mmol) in N,N-dimethyl formamide (5 mL) was added NaH (554 mg, 23.08 mmol) at 0° C. and stirred at room temperature for 30 min. Then a solution of ethyl 2-bromoacetate 3 (2.3 g, 13.84 mmol) in N, N-dimethyl formamide (5 mL) was added to the above reaction mixture at 0° C. and stirred at room temperature for 16 h under nitrogen atmosphere. The reaction mixture was quenched with ice-cold water and extracted with ethyl acetate (3×100 mL). Combined organic layers were was washed with brine (2×100 mL) and dried over $Na_2SO_4$, evaporated under reduced pressure. Crude residue was purified by combi-flash chromatography using 40% ethyl acetate in hexanes to afford ethyl 2-(2-(2-(2-(tetrahydro-2H-pyran-2-yloxy) ethoxy) ethoxy) ethoxy) acetate 4 (550 mg, 1.7187 mmol, 15% yield) as a pale yellow oily liquid. TLC system: 70% ethyl acetate in hexanes; $R_f$: 0.50

2-(2-(2-(2-(tetrahydro-2H-pyran-2-yloxy) ethoxy) ethoxy) ethoxy) acetic acid (Sidechain-5)

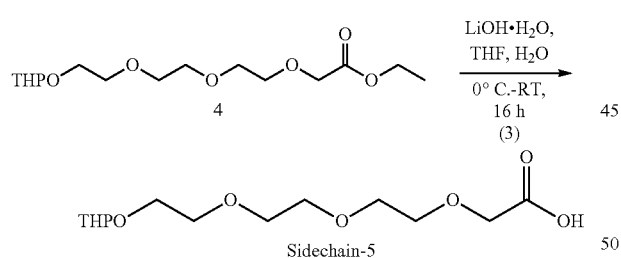

To a stirred solution of ethyl 2-(2-(2-(2-(tetrahydro-2H-pyran-2-yloxy) ethoxy) ethoxy) ethoxy) acetate 3 (550 mg, 1.7187 mmol) in a mixture of $THF:H_2O$ (3:1) (12 mL) was added lithium hydroxide monohydrate (288 mg, 6.875 mmol) at 0° C. and stirred at room temperature for 16 h. The reaction mixture was concentrated to remove organic volatiles, to the crude added water (50 mL) and extracted with ethyl acetate (2×20 mL). Aqueous layer was acidified with saturated citric acid solution and extracted with 10% methanol in dichloromethane (2×50 mL). The combined organic layers were washed with brine solution (15 mL), dried over sodium sulphate and concentrated to afford 2-(2-(2-(2-(tetrahydro-2H-pyran-2-yloxy) ethoxy) ethoxy) ethoxy) acetic acid (340 mg, 1.1643 mmol, 68%) as a pale yellow gummy liquid. TLC system: 10% Methanol in dichloromethane; $R_f$: 0.10

Sidechain-6

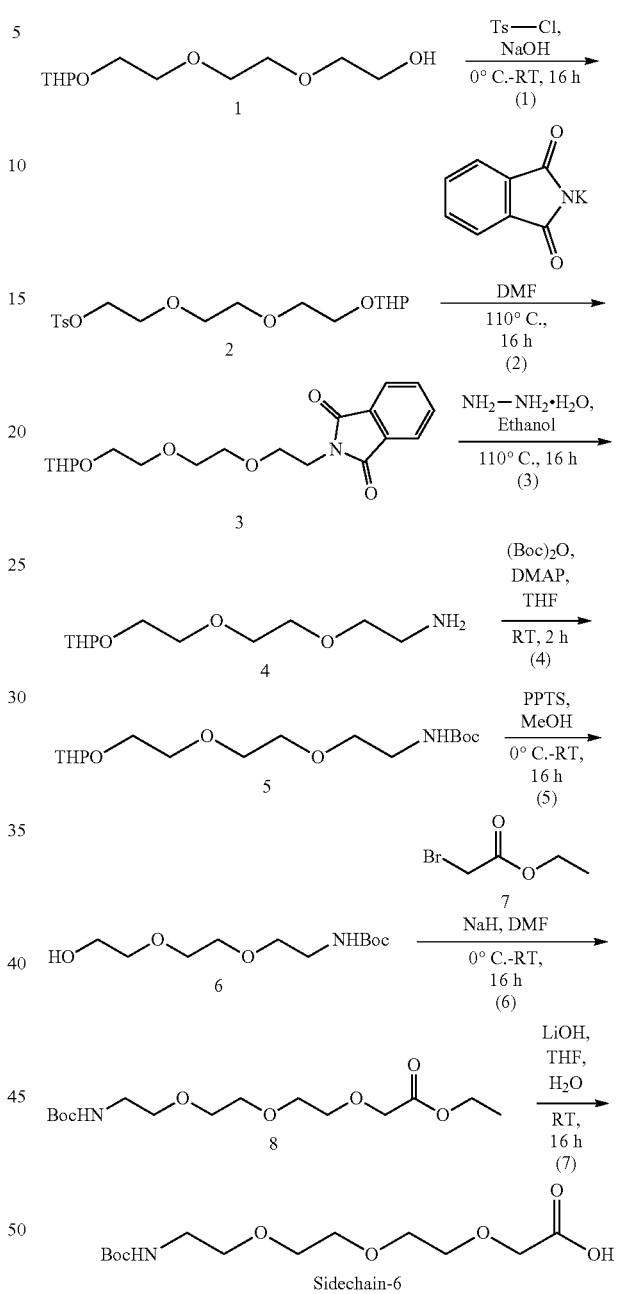

2-(2-(2-((tetrahydro-2H-pyran-2-yl)oxy)ethoxy) ethoxy) ethyl 4-methylbenzenesulfonate (2)

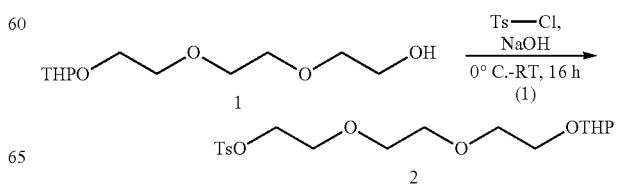

To a stirred solution of 2-(2-(2-((tetrahydro-2H-pyran-2-yl)oxy)ethoxy)ethoxy)ethan-1-ol 1 (9.5 g, 40.598 mmol, (Synthesis of Cpd-1 was reported in Sidechain-5)) in THF (100 mL) was added NaOH (3.25 g, 81.196 mmol) and p-toluene sulfonyl chloride (9.3 g, 48.718 mmol) at 0° C. then stirred at room temperature for 16 h. After consumption of starting material, the mixture was diluted with ethyl acetate (50 mL) and washed with ice cold water (2×20 mL), brine solution (20 mL), dried over sodium sulphate and concentrated under reduced pressure to afford 2-(2-(2-((tetrahydro-2H-pyran-2-yl) oxy) ethoxy) ethoxy) ethyl 4-methylbenzenesulfonate 2 (14 g, 36.08 mmol, crude) as a colorless oily liquid. TLC system: 70% ethyl acetate in pet ether: $R_f$: 0.50; LCMS: m/z=305.04 (M-THP)+

2-(2-(2-(2-((tetrahydro-2H-pyran-2-yl) oxy) ethoxy) ethoxy) ethyl) isoindoline-1, 3-dione (3)

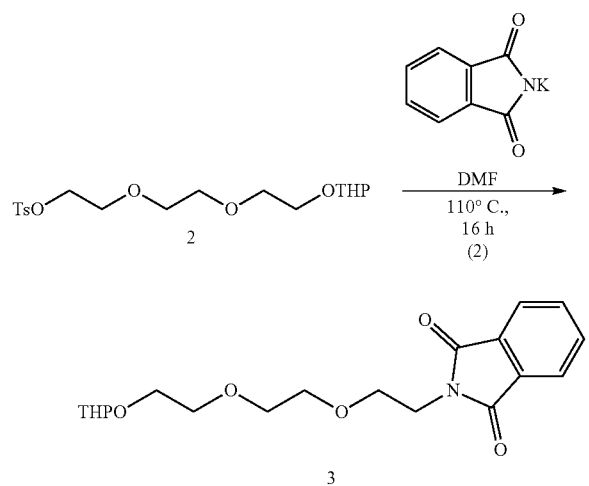

To a stirred solution of 2-(2-(2-((tetrahydro-2H-pyran-2-yl)oxy)ethoxy)ethoxy)ethyl 4-methylbenzenesulfonate 2 (14 g, 36.08 mmol) in DMF (35 mL) was added potassium phthalimide (8.8 g, 47.62 mmol) at room temperature then stirred at 110° C. for 16 h. After completion of reaction as indicated by TLC, reaction mixture was concentrated, residue was suspended in diethyl ether and stirred for 15 minutes and filtered, the filtrate was washed with 1M NaOH solution (2×100 mL), water (100 mL) and brine solution (100 mL), dried over sodium sulphate and concentrated under reduced pressure to afford 2-(2-(2-(2-((tetrahydro-2H-pyran-2-yl)oxy)ethoxy)ethoxy)ethyl)isoindoline-1,3-dione 3 (9 g, 24.79 mmol, 69% yield) as a yellow oily liquid. TLC system: 40% ethyl acetate in pet ether: $R_f$: 0.50; LCMS: m/z=364 (M+H)+

2-(2-(2-((tetrahydro-2H-pyran-2-yl) oxy) ethoxy) ethoxy) ethan-1-amine (4)

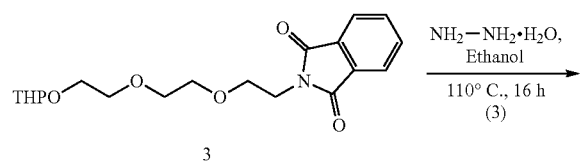

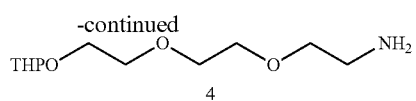

To a stirred solution of 2-(2-(2-(2-((tetrahydro-2H-pyran-2-yl) oxy) ethoxy) ethoxy) ethyl) isoindoline-1, 3-dione 3 (9 g, 24.79 mmol) in ethanol was added hydrazine hydrate (18 mL) and stirred at 110° C. for 16 h. After completion of reaction as indicated by TLC, evaporated organic solvents, to the crude added water (100 mL) and extracted with toluene (3×200 mL). Organic layer was washed brine solution (100 mL), dried over Na₂SO₄ and concentrated to afford 2-(2-(2-((tetrahydro-2H-pyran-2-yl) oxy) ethoxy) ethoxy) ethan-1-amine 4 (3.4 g, 14.59 mmol, 59%) as a colorless liquid. TLC system: 15% acetone in dichloromethane—$R_f$: 0.10; LCMS: m/z=234 (M+H)+

Tert-butyl (2-(2-(2-((tetrahydro-2H-pyran-2-yl) oxy) ethoxy) ethoxy) ethyl) carbamate (5)

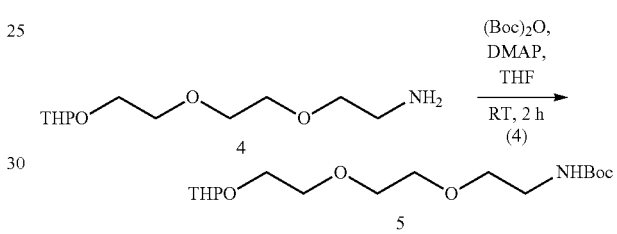

To a stirred solution of 2-(2-(2-((tetrahydro-2H-pyran-2-yl) oxy) ethoxy) ethoxy) ethan-1-amine 4 (3.2 g, 13.7 mmol) in THF (30 mL) was added (Boc)₂O (3.15 mL, 13.73 mmol) and 0.1 eq. of DMAP (167 mg, 1.37 mmol) then stirred at room temperature for 2 h. After completion of reaction as indicated by TLC, to the reaction mixture was added water (100 ml) and extracted with ethyl acetate (2×100 mL). The combined organic layer was washed with brine solution (100 mL), dried over Na₂SO₄ and concentrated. Crude compound was purified by 100-200 silica gel column chromatography by eluting with 25% ethyl acetate in pet ether to afford tert-butyl (2-(2-(2-((tetrahydro-2H-pyran-2-yl)oxy)ethoxy)ethoxy)ethyl)carbamate 5 (2.8 g, 8.408 mmol, 61%) as a colorless liquid. TLC system: 40% ethyl acetate in pet ether; $R_f$: 0.50

Tert-butyl (2-(2-(2-hydroxyethoxy) ethoxy) ethyl) carbamate (6)


To a stirred solution of tert-butyl (2-(2-(2-((tetrahydro-2H-pyran-2-yl)oxy)ethoxy)ethoxy)ethyl)carbamate 5 (2.8 g, 8.408 mmol) in methanol (30 mL) was added pyridinium p-toluenesulphonate (1.4 g, 5.885 mmol) at 0° C. and stirred at room temperature for 16 h. Organic solvents were distilled-off, to the crude added water (100 mL) and extracted with ethyl acetate (3×150 mL). The combined organic layers washed with brine solution (100 mL), dried over sodium sulphate and concentrated under reduced pressure. Crude compound was purified through flash column chromatography (100-200 silica) using 50% ethyl acetate in pet ether to afford tert-butyl (2-(2-(2-hydroxyethoxy) ethoxy) ethyl) carbamate 6 (1.8 g, 7.229 mmol, 86% yield) as a colorless gummy liquid. TLC system: 40% ethyl acetate in pet ether—$R_f$: 0.10

Ethyl 2, 2-dimethyl-4-oxo-3, 8, 11, 14-tetraoxa-5-azahexadecan-16-oate (8)

To a stirred solution of tert-butyl (2-(2-(2-hydroxyethoxy) ethoxy)ethyl)carbamate 6 (125 mg, 0.502 mmol) in N,N-dimethyl formamide (2 mL) was treated with NaH (30 mg, 1.255 mmol) at 0° C. and stirred at room temperature for 30 minutes. Ethyl 2-bromoacetate 7 (125 mg, 0.7530 mmol) in N, N-dimethyl formamide (1 mL) was added to above reaction mixture at 0° C. and stirred the mixture at room temperature for 16 h under argon atmosphere. The reaction mixture was quenched with ice water (50 mL) and extracted with ethyl acetate (3×20 mL). Combined organic layers were washed with brine solution (20 mL), dried over $Na_2SO_4$ and evaporated under reduced pressure. Crude residue was purified by combi-flash chromatography by using 70% ethyl acetate in pet-ether to afford ethyl 2, 2-dimethyl-4-oxo-3, 8, 11, 14-tetraoxa-5-azahexadecan-16-oate 8 (35 mg, 0.144 mmol, 20% yield) as a colorless liquid. TLC system: 70% ethyl acetate in pet-ether—$R_f$: 0.20; Direct mass: m/z=236.1 (M-Boc)⁺

2, 2-dimethyl-4-oxo-3, 8, 11, 14-tetraoxa-5-aza-hexadecan-16-oic acid (Sidechain-6)

To a stirred solution of ethyl 2,2-dimethyl-4-oxo-3,8,11, 14-tetraoxa-5-azahexadecan-16-oate 8 (300 mg, 0.895 mmol) in a mixture of THF:$H_2O$ (4:1) (20 mL) was added lithium hydroxide (112 mg, 2.685 mmol) at room temperature for 16 h. Reaction mixture was concentrated to remove organic volatiles, to the residue added water (50 mL) and extracted with ethyl acetate (2×50 mL). The combined organic layers were washed with brine solution (20 mL), dried over sodium sulphate and concentrated under reduced pressure to afford crude compound of 2,2-dimethyl-4-oxo-3,8,11,14-tetraoxa-5-azahexadecan-16-oic acid Sidechain-6 (280 mg, 0.9120 mmol, crude) as a colorless liquid. TLC system: 70% ethyl acetate in pet-ether—$R_f$: 0.10; Direct mass: m/z=208.07 (M-Boc)

Sidechain-7

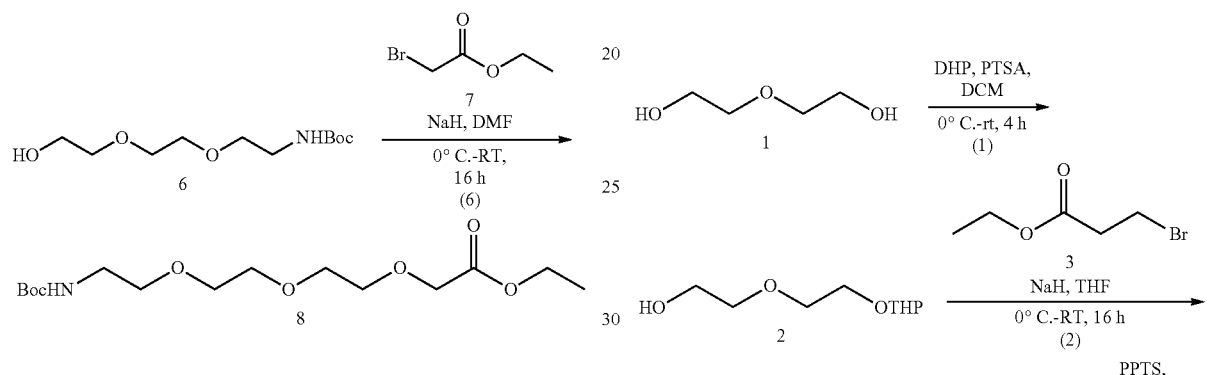

2-(2-(tetrahydro-2H-pyran-2-yloxy) ethoxy) ethanol (2)

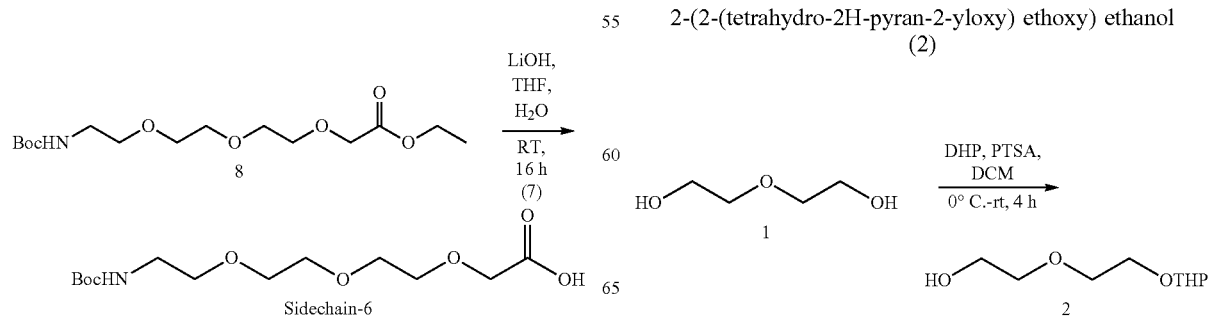

To a stirred solution of 2, 2'-oxydiethanol 1 (25 g, 235.58 mmol) in dichloromethane (750 mL) was added dihydropyran (13.8 g, 164.85 mmol) and pyridinium p-toluenesulphonate (4.48 g, 23.55 mmol) at 0° C., and the mixture was stirred at room temperature for 4 h. The reaction mixture diluted with water (600 mL) extracted into dichloromethane (3×250 mL), the combined organic layers were washed with brine (2×100 mL) and dried over sodium sulphate and concentrated. The residue was purified by column chromatography (100-200 silica) using 2% methanol/dichloromethane to afford 2-(2-(tetrahydro-2H-pyran-2-yloxy) ethoxy) ethanol 2 (7.8 g, 41.0 mmol, 17% yield) as light yellow oily liquid. TLC system: 10% Methanol in dichloromethane—R$_f$: 0.3

Ethyl 3-(2-(2-(tetrahydro-2H-pyran-2-yloxy) ethoxy) ethoxy) propionate (4)

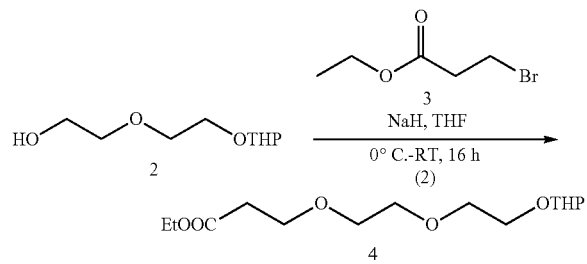

To a stirred suspension of NaH (1.74 g, 43.42 mmol) in THF (70 mL) was added a solution of 2-(2-(tetrahydro-2H-pyran-2-yloxy)ethoxy)ethanol 2 (5.5 g, 28.947 mmol) in THF (20 mL) at 0° C. and stirred at room temperature for 30 min. Ethyl 3-bromopropanoate 3 (7.85 g, 43.42 mmol) in THF (10 mL) was added to above reaction mixture at 0° C. and stirred at room temperature for 16 h under nitrogen atmosphere. The reaction mixture was quenched with ice water (200 mL) and extracted with ethyl acetate (3×100 mL). Combined organic layers were washed with brine (2×100 mL) and dried over Na$_2$SO$_4$, evaporated under reduced pressure. Crude residue was purified by column chromatography (100-200 silica) using 20% Ethyl acetate/pet-ether to ethyl 3-(2-(2-(tetrahydro-2H-pyran-2-yloxy) ethoxy) ethoxy) propanoate 4 (3.4 g, 11.72 mmol, 40% yield) as yellowish oily liquid. TLC system: 40% Ethyl acetate in pet-ether—R$_f$: 0.50

Ethyl 3-(2-(2-hydroxyethoxy) ethoxy) propanoate (5)

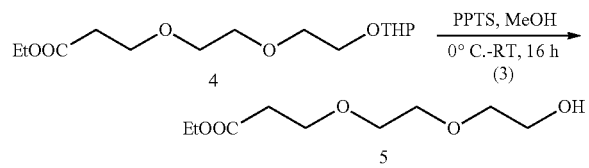

To a stirred solution of ethyl 3-(2-(2-(tetrahydro-2H-pyran-2-yloxy)ethoxy)ethoxy)propanoate 4 (4.3 g, 14.827 mmol) in methanol (40 mL) was added pyridinium p-toluenesulphonate (1.86 g, 7.413 mmol) at 0° C. and stirred at room temperature for 16 h. The solvents were distilled-off under reduced pressure to get residue, residue was diluted with water (50 ml) and extracted with ethyl acetate (3×50 mL). The combined organic layers were washed with brine (50 mL), dried over sodium sulphate and concentrated. The crude residue was purified by column chromatography (100-200 silica) using 70% ethyl acetate in pet ether to afford ethyl 3-(2-(2-hydroxyethoxy) ethoxy) propanoate 5 (2.6 g, 12.62 mmol, 86% yield) as a yellowish gummy liquid. TLC system: 70% ethyl acetate in pet ether—R$_f$: 0.20

Ethyl 3-(2-(2-(2-tert-butoxy-2-oxoethoxy) ethoxy) ethoxy) propionate (6)

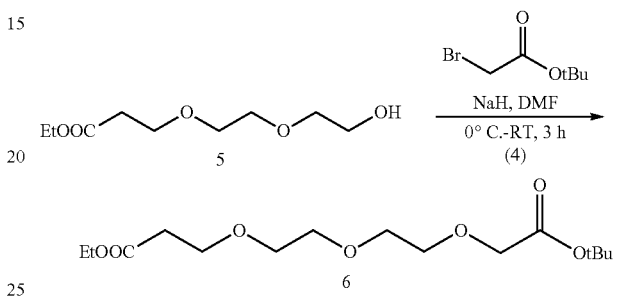

A stirred solution of ethyl 3-(2-(2-hydroxyethoxy)ethoxy) propanoate 5 (2.0 g, 9.708 mmol) in N,N-dimethyl formamide (20 mL) was treated with NaH (0.35 g, 14.65 mmol) at 0° C. and stirred at room temperature for 30 minutes. Tert-butyl 2-bromoacetate (2.27 g, 11.65 mmol) in N, N-dimethyl formamide (10 mL) was added to above reaction mixture at 0° C. and stirred at room temperature for 3 h under nitrogen atmosphere. The reaction mixture was quenched with ice water (50 ml) and extracted with ethyl acetate (3×50 mL). Combined organic layers were washed with brine (2×50 mL) and dried over Na$_2$SO$_4$, evaporated under reduced pressure. Crude residue was purified by column chromatography (100-200 silica) using 20% ethyl acetate in pet-ether to afford ethyl 3-(2-(2-(2-tert-butoxy-2-oxoethoxy) ethoxy) ethoxy) propanoate 6 (600 mg, 1.875 mmol, 19% yield) as yellowish oily liquid. TLC system: 70% ethyl acetate in pet ether—R$_f$: 0.6

12-oxo-3, 6, 9, 13-tetraoxapentadecan-1-oic acid (Sidechain-7)

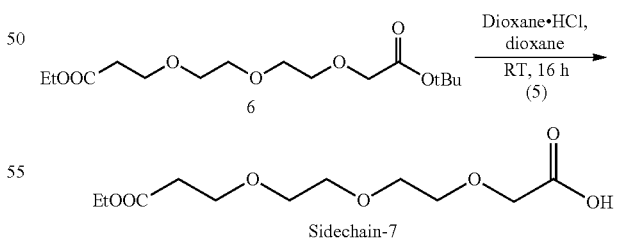

To a stirred solution of ethyl 3-(2-(2-(2-tert-butoxy-2-oxoethoxy) ethoxy) ethoxy) propanoate 6 (600 mg, 1.875 mmol) in dioxane (5 mL) was added 4N of HCl in dioxane (1 mL), then stirred at room temperature for 16 h. After completion of reaction as indicated by TLC, evaporated organic solvents, the crude was diluted with water (50 ml) and extracted into ethyl acetate (2×30 mL). Organic layer was washed with brine solution (30 mL), dried over Na$_2$SO$_4$ and concentrated. Crude compound was purified by trituration with diethyl ether (30 mL) to obtain 12-oxo-3, 6, 9, 13-tetraoxapentadecan-1-oic acid (Sidechain-7) (400 mg, 1.51 mmol, 81%) as a yellowish oily liquid. TLC system: 10% Methanol in dichloromethane—R$_f$: 0.20

2, 2-dimethyl-4-oxo-3, 6, 9, 12-tetraoxapentadecan-15-oic acid (Sidechain-8)

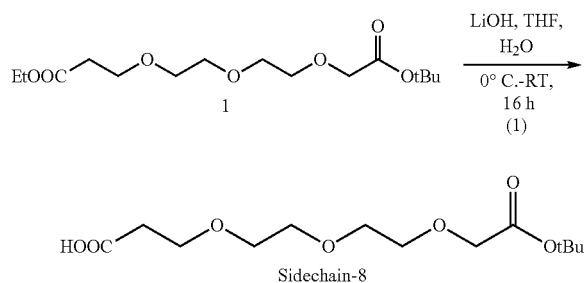 [SMILES: CCOC(=O)CCOCCOCCOCC(=O)OC(C)(C)C ; CC(C)(C)OC(=O)COCCOCCOCCC(=O)O]

To a stirred solution of ethyl 3-(2-(2-(2-(tert-butoxy)-2-oxoethoxy)ethoxy)ethoxy)propionate (200 mg, 0.625 mmol, synthesis of Compd-1 reported in Sidechain-7) in a mixture of THF:H$_2$O (4:1) (10 mL) was added lithium hydroxide (26 mg, 0.625 mmol) at 0° C. then stirred at room temperature for 4 h. The reaction mixture was concentrated to remove organic volatiles, added water (50 mL) and extracted with ethyl acetate (2×30 mL). The combined organic layers were washed with brine solution (20 mL), dried over sodium sulphate and concentrated under reduced pressure. Crude residue was purified by column chromatography by eluting with 20% ethyl acetate in pet ether to afford 2, 2-dimethyl-4-oxo-3, 6, 9, 12-tetraoxapentadecan-15-oic acid Sidechain-8 (70 mg, 0.239 mmol, 38%) as a colorless oily liquid. TLC system: 40% ethyl acetate in pet ether—R$_f$: 0.40

Sidechain-9

2-(2-(2-(2-((tetrahydro-2H-pyran-2-yl) oxy) ethoxy) ethoxy) ethoxy) ethan-1-ol (2)

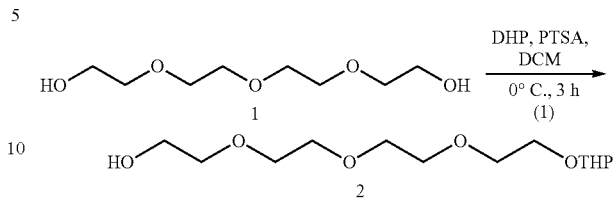

To a stirred solution of 2,2'-((oxybis(ethane-2,1-diyl))bis (oxy))bis(ethan-1-ol) 1 (10 g, 51.546 mmol) in dichloromethane (100 mL) was added dihydropyran (2.8 mL, 30.6 mmol) and p-toluene sulphonic acid (979 mg, 5.154 mmol) at 0° C., and stirred at room temperature for 4 h. The reaction mixture diluted with water (100 mL) extracted with dichloromethane (3×200 mL), the combined organic layers were washed with brine (2×75 mL) and dried over sodium sulphate and concentrated. The residue was purified by flash column chromatography (100-200 silica) using 2% methanol/dichloromethane to afford 2-(2-(2-(2-((tetrahydro-2H-pyran-2-yl) oxy) ethoxy) ethoxy) ethoxy) ethan-1-ol 2 (2.2 g, 7.913 mmol, 15.4% yield) as yellow thick liquid. TLC system: 10% Methanol in dichloromethane—R$_f$: 0.20

2-(2-(2-(2-((tetrahydro-2H-pyran-2-yl) oxy) ethoxy) ethoxy) ethoxy) ethyl 4-methylbenzenesulfonate (3)

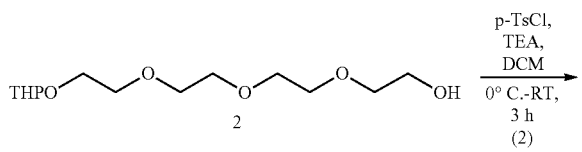

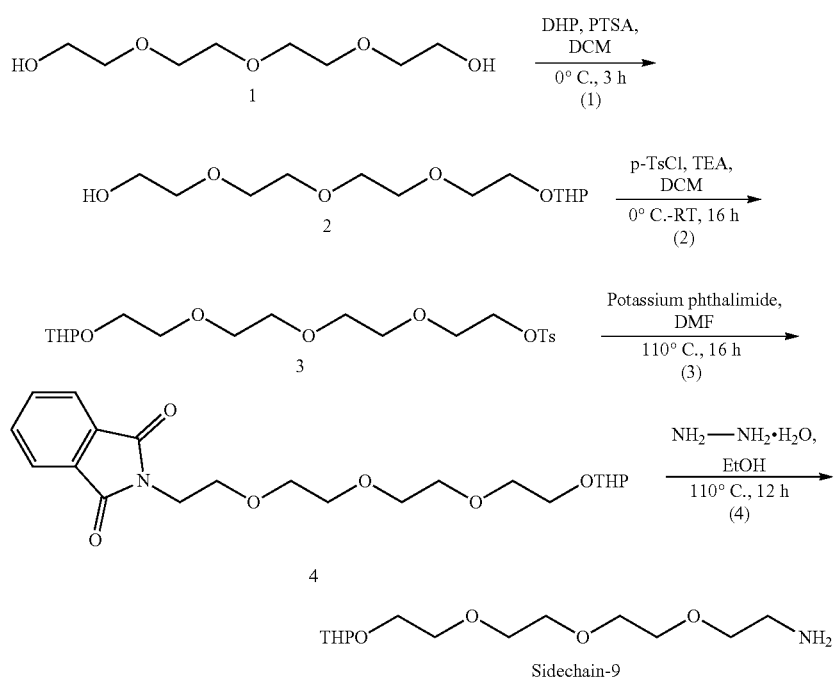

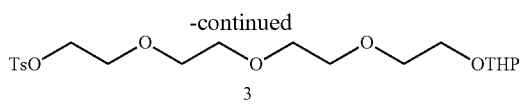

3

To a stirred solution of 2-(2-(2-(2-((tetrahydro-2H-pyran-2-yl) oxy) ethoxy) ethoxy) ethoxy) ethan-1-ol 2 (1 g, 4.27 mmol) in DCM (20 mL) was added Et₃N (0.8 ml, 5.55 mmol) and p-toluene sulfonyl chloride (1.05 g, 5.55 mmol) at 0° C., the reaction mixture and stirred at room temperature for 3 h. After consumption of starting material, the mixture was diluted with ethyl acetate (50 mL) and washed with ice cold water (2×20 mL), NaHCO₃ solution (2×20 mL), brine solution (20 mL), dried over sodium sulfate and concentrated. Crude compound was purified by combi-flash chromatography and eluted with 50% ethyl acetate in hexanes to afford 2-(2-(2-(2-((tetrahydro-2H-pyran-2-yl) oxy) ethoxy) ethoxy) ethoxy) ethyl 4-methylbenzenesulfonate 3 (1 g, 2.31 mmol, 54% yield) as pale brown liquid. TLC system: 100% ethyl acetate—R$_f$: 0.50; LCMS: m/z=455.39 (M+Na)⁺

2-(2-(2-(2-(2-((tetrahydro-2H-pyran-2-yl) oxy) ethoxy) ethoxy) ethoxy) ethyl) isoindoline-1, 3-dione (4)

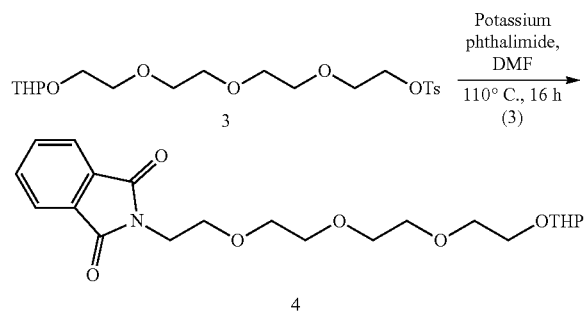

To a stirred solution of 2-(2-(2-(2-((tetrahydro-2H-pyran-2-yl) oxy) ethoxy) ethoxy) ethoxy) ethyl 4-methylbenzenesulfonate 3 (500 Mg, 1.15 mmol) in DMF (10 mL) was added potassium phthalimide (282 mg, 1.52 mmol) at room temperature then stirred at 110° C. for 16 h. After completion of reaction as indicated by TLC, to the reaction mixture added ice water (2×200 mL) and extracted with ethyl acetate (2×100 mL). Organic layer was washed with brine solution (100 mL), dried over Na₂SO₄ and concentrated to obtain 2-(2-(2-(2-(2-((tetrahydro-2H-pyran-2-yl) oxy) ethoxy) ethoxy) ethoxy) ethyl) isoindoline-1, 3-dione 4 (400 mg, 9.828 mmol, 84%) as a pale brown liquid. TLC system: 50% ethyl acetate in hexanes—R$_f$: 0.20; LCMS: m/z=429.97 (M+Na)⁺

2-(2-(2-(2-((tetrahydro-2H-pyran-2-yl) oxy) ethoxy) ethoxy) ethoxy) ethan-1-amine (Sidechain-9)

To a stirred solution of 2-(2-(2-(2-(2-((tetrahydro-2H-pyran-2-yl) oxy) ethoxy) ethoxy) ethoxy) ethyl) isoindoline-1,3-dione 4 (400 g, 0.98 mmol) in ethanol (3 mL) was added hydrazine hydrate (3 ml) and stirred at 110° C. for 12 h. After completion of reaction as indicated by TLC, to the reaction mixture added toluene (10 ml), two layers are formed and separated two layers. Toluene layer was washed with brine solution (10 mL), dried over Na₂SO₄ and concentrated to obtained 2-(2-(2-(2-((tetrahydro-2H-pyran-2-yl) oxy) ethoxy) ethoxy) ethoxy) ethan-1-amine Sidechain-9 (150 mg, 0.541 mmol, 55%) as a brown liquid. TLC system: 10% methanol in dichloromethane—R$_f$: 0.20

Sidechain-10

N-methyl-2-(2-(2-(2-((tetrahydro-2H-pyran-2-yl) oxy) ethoxy) ethoxy) ethoxy) ethan-1-amine (Sidechain-10)

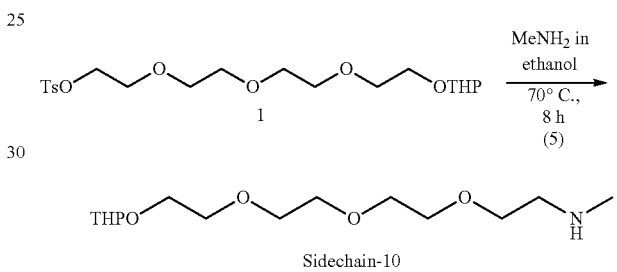

To a stirred solution of 2-(2-(2-(2-((tetrahydro-2H-pyran-2-yl) oxy) ethoxy) ethoxy) ethoxy) ethyl 4-methylbenzenesulfonate 1 (500 mg, 1.15 mmol, synthesis of compound-1 is reported in Sidechain-9) in a sealed tube was added 33% of MeNH₂ in ethanol (5 mL) at room temperature then stirred at 60° C. for 12 h. After completion of reaction as indicated by TLC, evaporated organic solvents, sodium bicarbonate solution (20 mL) was added to the residue and extracted with 10% methanol in dichloromethane (3×20 mL). The combined organic layer was washed with brine solution (100 mL), dried over anhydrous Na₂SO₄ and concentrated to afford N-methyl-2-(2-(2-(2-((tetrahydro-2H-pyran-2-yl) oxy) ethoxy) ethoxy) ethoxy) ethan-1-amine Sidechain-10 (150 mg, 0.515 mmol, 44%) as a brown liquid. TLC system: 10% methanol in dichloromethane—R$_f$: 0.20

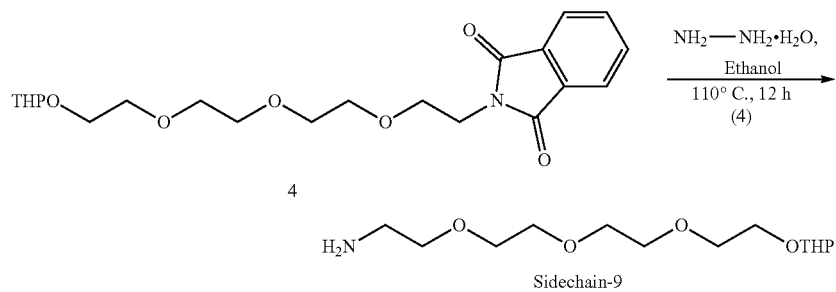

Sidechain-11

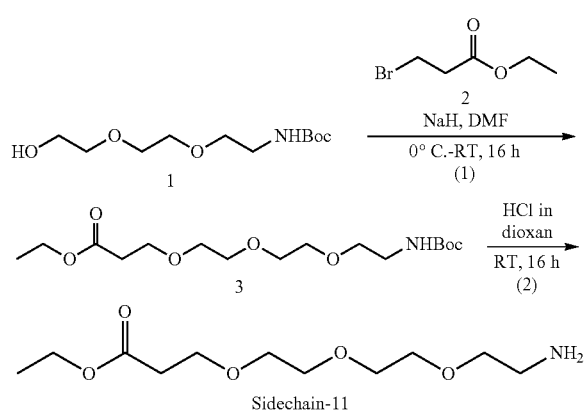

Ethyl 2, 2-dimethyl-4-oxo-3, 8, 11, 14-tetraoxa-5-azaheptadecan-17-oate (3)

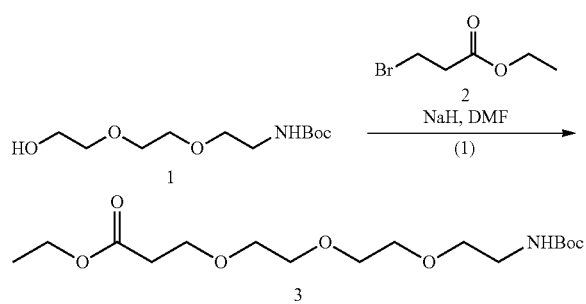

To a stirred solution of tert-butyl (2-(2-(2-hydroxyethoxy) ethoxy)ethyl)carbamate 1 (1 g, 4.01 mmol) in N,N-dimethyl formamide (15 mL) was treated with NaH (240 mg, 10.04 mmol) at 0° C. to RT for 30 min. ethyl 3-bromopropanoate 2 (1.1 g, 6.02 mmol) in N, N-dimethyl formamide (5 mL) was added to above reaction mixture at 0° C. and stirred at room temperature for 16 h under argon atmosphere. The reaction mixture was quenched with ice water and extracted with ethyl acetate (3×50 mL). Combined organic layers were washed with brine (50 mL) and dried over $Na_2SO_4$, evaporated under reduced pressure. Crude residue was purified by column chromatography by eluting with 70% ethyl acetate in pet ether to afford ethyl 2,2-dimethyl-4-oxo-3,8,11,14-tetraoxa-5-azaheptadecan-17-oate 3 (310 mg, 0.925 mmol, 24% yield) as a colorless liquid. TLC system: 70% ethyl acetate in pet-ether—$R_f$: 0.50; Direct Mass: m/z=372.15 $(M+Na)^+$.

Ethyl 3-(2-(2-(2-aminoethoxy) ethoxy) ethoxy) propionate (Sidechain-11)

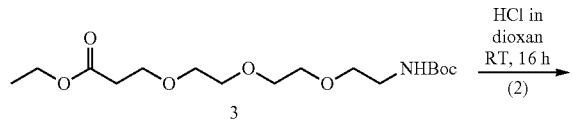

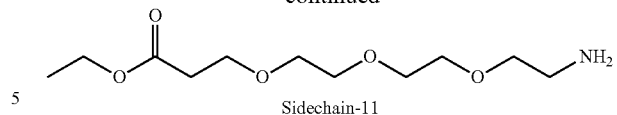

To a stirred solution of ethyl 2, 2-dimethyl-4-oxo-3, 8, 11, 14-tetraoxa-5-azaheptadecan-17-oate 3 (310 mg, 0.888 mmol) in dioxane (1 mL) was added HCl in dioxane (4M, 3 mL) at room temperature and stirred for 16 h under argon atmosphere. Organic solvents distilled off and co-distilled with dichloromethane to afford ethyl 3-(2-(2-(2-aminoethoxy) ethoxy) ethoxy) propionate Sidechain 11 (260 mg, 1.044 mmol, crude) as a colorless liquid. TLC system: 20% Methanol in dichloromethane—$R_f$: 0.10; Direct mass: m/z=250.12 $(M+H)^+$ Sidechain-12

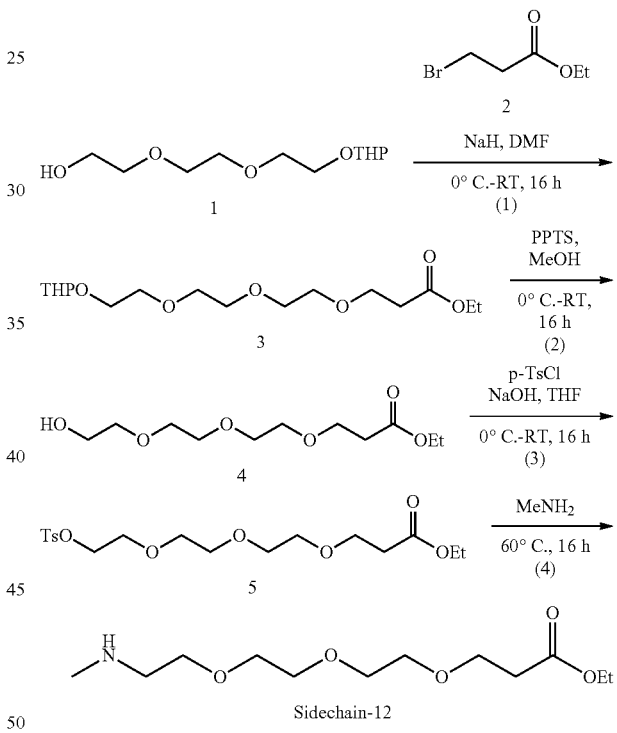

Ethyl 3-(2-(2-(2-(tetrahydro-2H-pyran-2-yloxy) ethoxy) ethoxy) ethoxy) propionate (3)

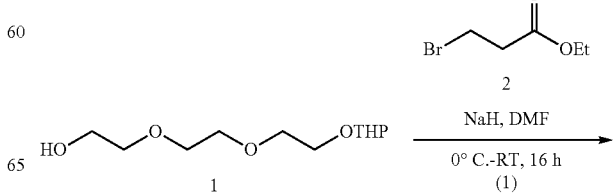

-continued

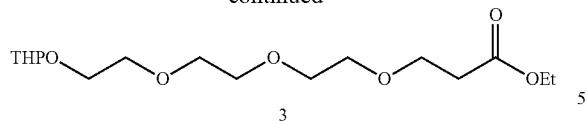

To a stirred solution of 2-(2-(2-(tetrahydro-2H-pyran-2-yloxy) ethoxy) ethoxy)ethanol 1 (Synthesis of Cpd-1 was reported in Sidechain-5) (5 g, 21.367 mmol) in N,N-dimethyl formamide (30 mL) was treated with NaH (1.3 g, 53.417 mmol) at 0° C. and stirred at room temperature for 30 minutes. Ethyl 3-bromopropanoate 2 (5.8 g, 32.05 mmol) in N, N-dimethyl formamide (20 mL) was added to above reaction mixture at 0° C. and stirred at room temperature for 16 h under nitrogen atmosphere. The reaction mixture was quenched with ice water and extracted with ethyl acetate (3×100 mL). Combined organic layers were washed with brine (2×100 mL) and dried over $Na_2SO_4$, evaporated under reduced pressure. Crude residue was purified by Combi-flash chromatography using 30% ethyl acetate in hexanes to afford ethyl 3-(2-(2-(2-(tetrahydro-2H-pyran-2-yloxy) ethoxy) ethoxy) propionate 3 (1 g, 2.994 mmol, 14% yield) as a pale yellow oily liquid. TLC system: 70% ethyl acetate in hexanes—$R_f$: 0.60

Ethyl 3-(2-(2-(2-hydroxyethoxy) ethoxy) ethoxy) propionate (4)

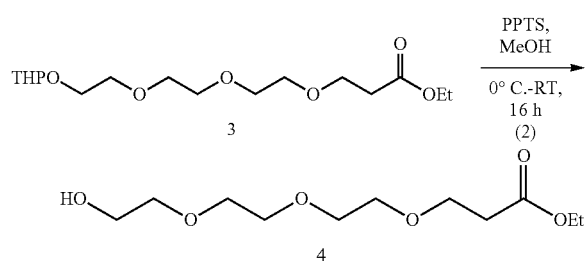

To a stirred solution of ethyl 3-(2-(2-(2-(tetrahydro-2H-pyran-2-yloxy) ethoxy) ethoxy) ethoxy) propionate 3 (1 g, 2.994 mmol) in methanol (10 mL) was added pyridinium p-toluenesulphonate (376 mg, 1.497 mmol) at 0° C. and stirred at room temperature for 16 h. The volatiles were removed under reduced pressure, added water (50 mL) and extracted with ethyl acetate (2×30 mL). The combined organic layers were washed with brine solution (30 mL), dried over sodium sulphate and concentrated to afford ethyl 3-(2-(2-(2-hydroxyethoxy) ethoxy) ethoxy) propionate 4 (580 mg, 2.32 mmol, 77% yield) as a pale yellow oily liquid. TLC system: 5% Methanol in dichloromethane—$R_f$: 0.20

Ethyl 3-(2-(2-(2-(tosyloxy) ethoxy) ethoxy) ethoxy) propionate (5)

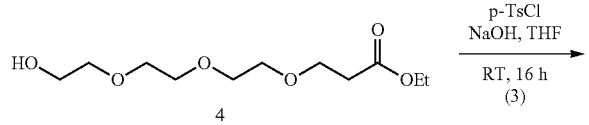

-continued

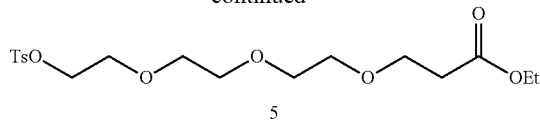

To a stirred solution of ethyl 3-(2-(2-(2-hydroxyethoxy) ethoxy) ethoxy) propionate 4 (580 mg, 2.32 mmol) in THF (5 mL) was added NaOH (186 mg, 4.64 mmol) at 0° C. and stirred at room temperature for 15 min. Then cooled to 0° C., p-toluene sulfonyl chloride (530 mg, 2.784 mmol) was added to the reaction mixture and stirred at room temperature for 16 h. After consumption of starting material by the TLC, reaction mixture was diluted with ethyl acetate (50 mL) and washed with ice cold water (2×40 mL), brine solution (20 mL), dried over sodium sulfate and concentrated to afford ethyl 3-(2-(2-(2-(tosyloxy) ethyl) ethyl) ethoxy) propionate 5 (750 mg, 1.856 mmol, 80% yield) as a pale yellow oily liquid. TLC system: 70% ethyl acetate in hexanes—$R_f$: 0.70

Ethyl 5,8,11-trioxa-2-azatetradecan-14-oate (Sidechain-12)

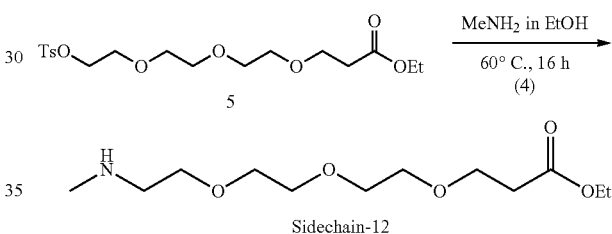

Ethyl 3-(2-(2-(2-(tosyloxy)ethoxy)ethoxy)ethoxy)propionate 5 (750 mg, 1.856 mmol) was placed in a sealed tube, dissolved in ethanol (5 mL) and 33% of $MeNH_2$ in ethanol (0.9 mL, 9.282 mmol) was added at room temperature then stirred at 60° C. for 16 h. After completion of the reaction as indicated by TLC, the volatiles were removed under reduced pressure, added water (50 mL) and acidified with 1N HCl up to pH=2. Aqueous layer was extracted with ethyl acetate (50 mL), brine solution (30 mL), dried over $Na_2SO_4$ and concentrated to afford Sidechain-12 (200 mg, 0.7604 mmol, 41%) as a reddish brown gummy liquid. TLC system: 10% Methanol in dichloromethane—$R_f$: 0.10

Sidechain-13

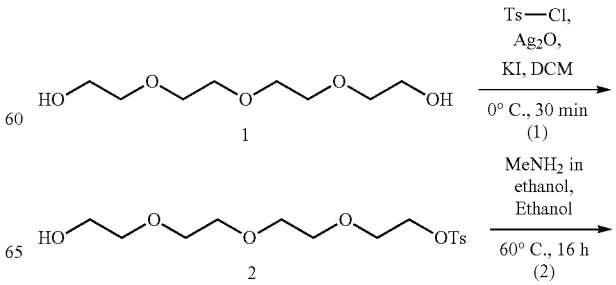

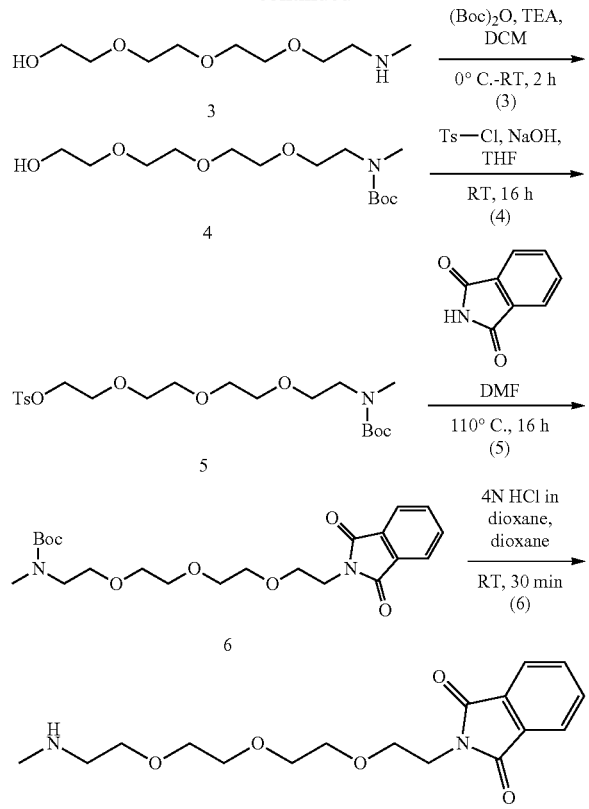

Sidechain-13

2-(2-(2-(2-hydroxyethoxy) ethoxy) ethoxy) ethyl 4-methylbenzenesulfonate (2)

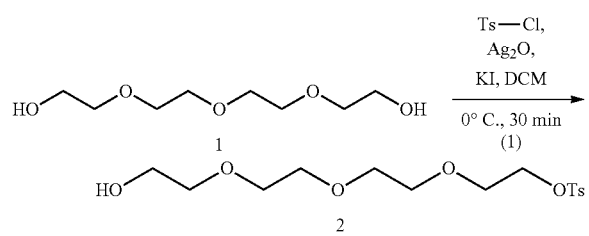

To a stirred solution of 2,2'-((oxybis(ethane-2,1-diyl))bis(oxy))bis(ethan-1-ol) 1 (2 g, 10.30 mmol) in dichloromethane (30 mL) was added silver oxide (3.5 g, 15.46 mmol), p-toluene sulphonyl chloride (2.3 g, 12.37 mmol), potassium iodide (342 mg, 2.06 mmol) at 0° C. The mixture was stirred at 0° C. for 30 min. After consumption of starting material, the mixture was filtered through celite pad and the pad was washed several times with DCM. The filtrate was washed with water, brine solution (50 mL), dried over sodium sulfate and concentrated. Crude compound was purified by column chromatography and eluted with 3% methanol in dichloromethane to afford 2-(2-(2-(2-hydroxyethoxy) ethoxy) ethoxy) ethyl 4-methylbenzenesulfonate 2 (2.6 g, 7.471 mmol, 72% yield) as a colorless oily liquid. TLC system: 10% Methanol in dichloromethane—$R_f$: 0.50; LCMS: m/z=371.19 (M+Na)$^+$ 5, 8, 11-trioxa-2-azatridecan-13-ol (3)

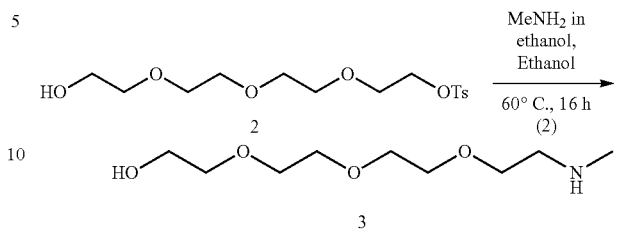

In a sealed tube, to a stirred solution of 2-(2-(2-(2-hydroxyethoxy) ethoxy) ethoxy) ethyl 4-methylbenzenesulfonate 2 (600 mg, 1.724 mmol) in ethanol (5 mL) was added 33% of MeNH$_2$ in ethanol (0.8 mL) (267 mg, 8.62 mmol) at room temperature then stirred at 60° C. for 16 h. After completion of reaction as indicated by TLC, organic solvents were evaporated, (10 mL) to afford 5,8,11-trioxa-2-azatridecan-13-ol 3 (650 mg, 3.14 mmol, crude) as a colorless gummy liquid. TLC system: 10% Methanol in dichloromethane—$R_f$: 0.20; Direct mass: m/z=208.15 (M+H)$^+$ Tert-butyl (2-(2-(2-(2-hydroxyethoxy) ethoxy) ethoxy) ethyl) (methyl) carbamate (4)

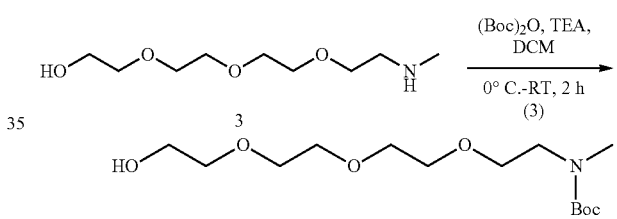

To a stirred solution of 5,8,11-trioxa-2-azatridecan-13-ol 3 (2.9 g, 14.09 mmol) in DCM (30 mL) was added triethylamine (3.8 mL, 28.01 mmol) and di-tert-butyl dicarbonate (3.2 mL, 14.09 mmol) at 0° C. then stirred at room temperature for 2 h. After consumption of starting material, the mixture was diluted with ethyl acetate (150 mL) and washed with ice cold water (2×20 mL), brine solution (20 mL), dried over sodium sulphate and concentrated under reduced pressure. Crude compound was purified by 100-200 silica gel column chromatography by eluting with 5% methanol in dichloromethane to afford tert-butyl (2-(2-(2-(2-hydroxyethoxy) ethoxy) ethoxy) ethyl) (methyl) carbamate 4 (1.8 g, 5.863 mmol, 42% yield) as pale brown liquid. TLC system: 100% ethyl acetate—$R_f$: 0.50; LCMS: m/z=330.04 (M+Na)$^+$ 2, 2, 5-trimethyl-4-oxo-3, 8, 11, 14-tetraoxa-5-azahexadecan-16-yl 4-methylbenzenesulfonate (5)

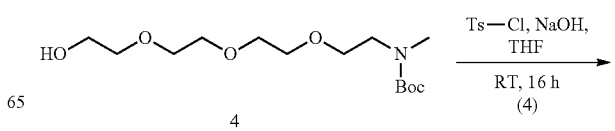

251

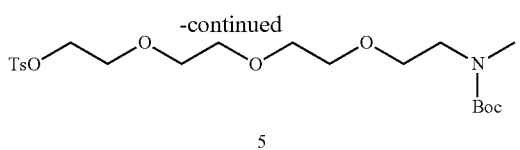

To a stirred solution of tert-butyl (2-(2-(2-(2-hydroxyethoxy)ethoxy)ethoxy)ethyl)(methyl)carbamate 4 (1.85 g, 6.026 mmol) in THF (20 mL) was added sodium hydroxide (485 mg, 12.052 mmol) and p-toluene sulphonyl chloride (1.63 g, 7.231 mmol) at 0° C. then stirred at room temperature for 16 h. After completion of reaction as indicated by TLC, the mixture was diluted with ethyl acetate (150 mL) and washed with ice cold water (2×20 mL), brine solution (20 mL), dried over sodium sulfate and concentrated under reduced pressure. Crude compound was purified by 100-200 silica gel column chromatography by eluting with 40% ethyl acetate in pet ether to afford 2,2,5-trimethyl-4-oxo-3, 8, 11, 14-tetraoxa-5-azahexadecan-16-yl 4-methylbenzenesulfonate 5 (2.5 g, 5.423 mmol, 90% yield) as a colorless gummy liquid. TLC system: 70% ethyl acetate in pet ether—$R_f$: 0.50; LCMS: m/z=484.4 (M+Na)$^+$ Tert-butyl (2-(2-(2-(2-(1, 3-dioxoisoindolin-2-yl)ethoxy)ethoxy)ethoxy)ethyl)(methyl) carbamate (6)

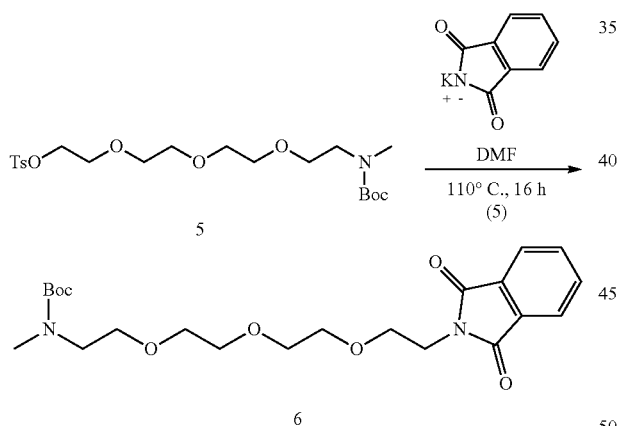

To a stirred solution of 2,2,5-trimethyl-4-oxo-3,8,11,14-tetraoxa-5-azahexadecan-16-yl 4-methylbenzenesulfonate 5 (2.5 g, 5.423 mmol) in DMF (10 mL) was added potassium phthalimide (1.3 g, 7.049 mmol) at room temperature then stirred at 110° C. for 16 h. Reaction mixture was cooled to room temperature then added diethyl ether (100 ml) and stirred for 15 minutes, filtered. The filtrate was washed with 1M NaOH solution (50 mL), water (100 mL), brine solution (100 mL), dried over Na$_2$SO$_4$ and concentrated under reduced pressure to afford tert-butyl (2-(2-(2-(2-(1, 3-dioxoisoindolin-2-yl)ethoxy)ethoxy)ethoxy)ethyl)(methyl) carbamate 6 (1.65 g, 3.784 mmol, crude) as a pale brown gummy liquid. TLC system: 70% ethyl acetate in pet ether—$R_f$: 0.50; LCMS: m/z=459.45 (M+Na)$^+$

252

2-(5, 8, 11-trioxa-2-azatridecan-13-yl) isoindoline-1,3-dione (Sidechain-13)

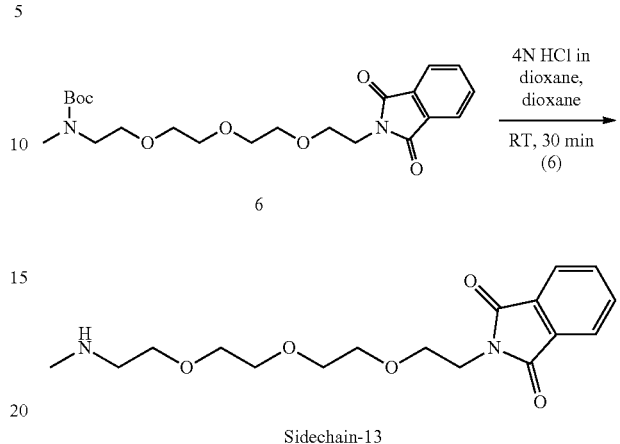

To a stirred solution of tert-butyl (2-(2-(2-(2-(1, 3-dioxoisoindolin-2-yl)ethoxy)ethoxy)ethoxy)ethyl)(methyl)carbamate 6 (1.55 g, 3.555 mmol) in dioxane (5 mL) was added 4N of HCl in dioxane (5 mL), then stirred at room temperature for 30 minutes. The reaction mixture was concentrated, water (50 ml) was added to the crude, basified with sodium bicarbonate solution (100 mL) and extracted with ethyl acetate (2×50 mL). Combined organic layers were washed with brine solution (50 mL), dried over Na$_2$SO$_4$ and concentrated under reduced pressure to afford 2-(5,8,11-trioxa-2-azatridecan-13-yl)isoindoline-1,3-dione Sidechain-13 (700 mg, 2.083 mmol, crude) as a yellowish oily liquid. TLC system: 70% ethyl acetate in pet ether—$R_f$: 0.10; LCMS: m/z=337.41 (M+H)$^+$ Sidechain-14

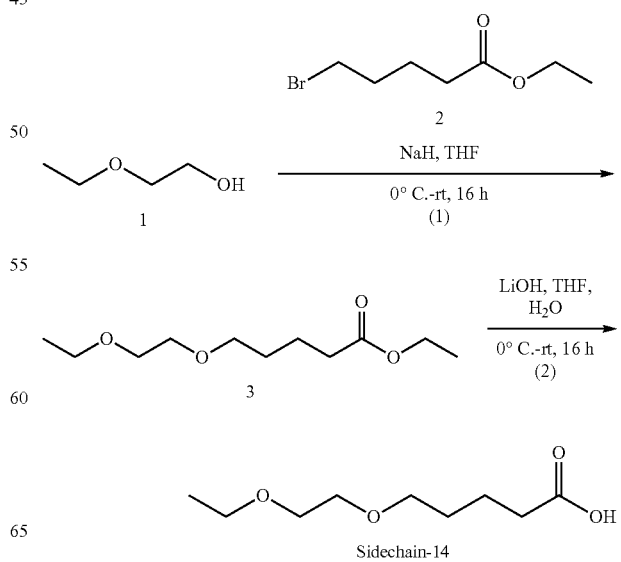

253
Ethyl 5-(2-ethoxyethoxy) pentanoate (3)

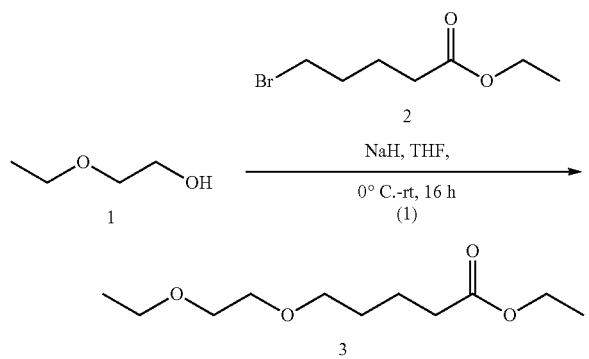

To a stirred solution of 2-ethoxyethanol 1 (500 mg, 5.555 mmol) in tetrahydrofuran (10 mL) was added NaH (267 mg, 11.11 mmol) at 0° C. and stirred at room temperature for 30 minutes. Ethyl 5-bromopentanoate 2 (1.74 g, 8.333 mmol) in tetrahydrofuran (5 mL) was added to above reaction mixture at 0° C. and stirred at room temperature for 16 h under nitrogen atmosphere. The reaction mixture was quenched with ice cold water (50 mL) and extracted with ethyl acetate (3×30 mL). Combined organic layers were washed with brine (50 mL), dried over $Na_2SO_4$ and evaporated under reduced pressure. Crude residue was purified by 100-200 silica gel chromatography using 6% ethyl acetate in hexanes to afford ethyl 5-(2-ethoxyethoxy) pentanoate 3 (220 mg, 1.009 mmol, 18% yield) as a colorless oily liquid. TLC system: 50% ethyl acetate in hexanes—$R_f$: 0.45

5-(2-ethoxyethoxy) pentanoic acid (Sidechain-14)

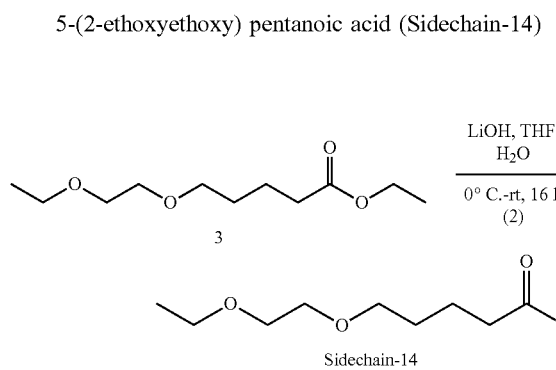

To a stirred solution of ethyl 5-(2-ethoxyethoxy)pentanoate 3 (220 mg, 1.009 mmol) in a mixture of THF:$H_2O$ (3:1) (4 mL) was added lithium hydroxide monohydrate (127 mg, 3.027 mmol) at room temperature and stirred for 16 h. The reaction mixture was concentrated to remove organic volatiles, water (50 mL) was added to the crude and extracted with ethyl acetate (2×20 mL). Aqueous solution was acidified with saturated citric acid solution and extracted with 10% methanol in dichloromethane (2×30 mL). The combined organic layers were washed with brine solution (15 mL), dried over sodium sulphate and concentrated to afford 5-(2-ethoxyethoxy) pentanoic acid Sidechain-14 (110 mg, 0.5789 mmol, 57%) as a colorless oily liquid. TLC system: 70% ethyl acetate in hexanes—$R_f$: 0.10

254
Sidechain-15

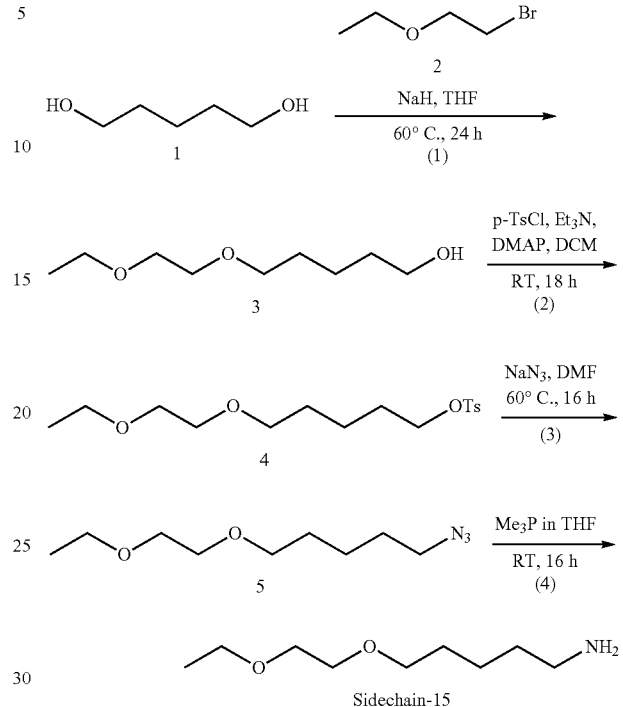

5-(2-ethoxyethoxy) pentan-1ol (3)

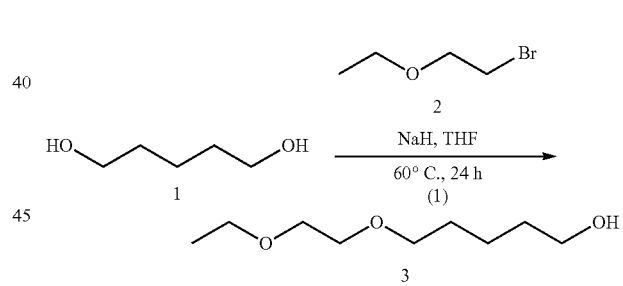

To a stirred solution of pentane 1,5-diol 1 (11 g, 105.76 mmol) in N,N-dimethyl formamide (30 mL) was treated with 60% of NaH (4.5 g, 116.34 mmol) at 0° C. and stirred at room temperature for 30 min. 1-bromo-2-ethoxyethane 2 (12 mL, 105.76 mmol) in N, N-dimethyl formamide (20 mL) was added to the above reaction mixture at 0° C. and stirred at room temperature and stirred for 16 h under argon atmosphere. The reaction mixture was quenched with ice water (200 mL) and extracted with ethyl acetate (3×250 mL). Combined organic layers were washed with brine (2×100 mL) and dried over $Na_2SO_4$, evaporated under reduced pressure. Crude residue was purified by column chromatography (100-200 silica gel) using 30% ethyl acetate in hexanes to afford 5-(2-ethoxyethoxy) pentan-1ol 3 (5.1 g, 28.97 mmol, 27% yield) as an oily liquid. TLC system: 70% ethyl acetate in hexanes—$R_f$: 0.50; LCMS: m/z=199.12 $(M+Na)^+$ 5-(2-ethoxyethoxy) pentyl 4-methylbenzenesulfonate (4)

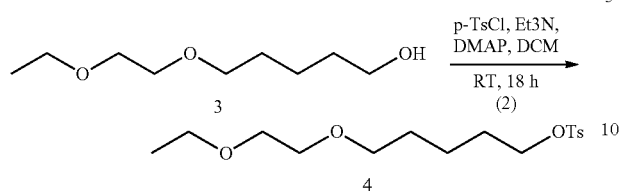

To a stirred solution of 5-(2-ethoxyethoxy) pentan-1ol 3 (4.6 g, 26.136 mmol) in DCM (45 mL) was added triethylamine (11 mL, 78.40 mmol) at 0° C. The mixture was stirred at 0° C. for 10 min. Then cooled to 0° C., added p-toluene sulfonyl chloride (5.95 g, 31.36 mmol) and DMAP (31 mg, 0.261 mmol) was added to the reaction mixture and stirred at room temperature for 16 h. After consumption of starting material, the mixture was diluted with dichloromethane (100 mL) and washed with ice cold water (2×50 mL), brine solution (50 mL), dried over sodium sulfate and concentrated under reduced pressure. Crude compound was purified by combi-flash chromatography and eluted with 35% ethyl acetate in pet ether to afford 5-(2-ethoxyethoxy) pentyl 4-methylbenzenesulfonate 4 (3.9 g, 11.81 mmol, 45% yield) as a yellow oily liquid. TLC system: 50% ethyl acetate in hexanes—$R_f$: 0.60; LCMS: m/z=353.20 $(M+Na)^+$+

1-azido-5-(2-ethoxyethoxy) pentane (5)

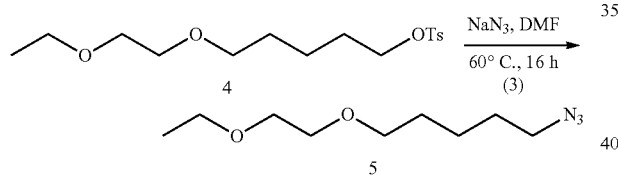

To a stirred solution of 5-(2-ethoxyethoxy) pentyl 4-methylbenzenesulfonate 4 (1.4 g, 4.242 mmol) in DMF (15 mL) was added NaN₃ (441 mg, 6.787 mmol) at room temperature then stirred at 60° C. for 16 h. After completion of reaction as indicated by TLC, organic solvents were evaporated, water (200 ml) was added to the crude and extracted with diethyl ether (2×50 mL). The combined organic layer was washed with brine solution (50 mL), dried over Na₂SO₄ and concentrated. Crude compound was purified by column chromatography (silica gel 100-200) by eluting with 30% ethyl acetate in pet ether to afford 1-azido-5-(2-ethoxyethoxy) pentane 5 (750 mg, 3.731 mmol, 88%) as a liquid. TLC system: 30% ethyl acetate in hexanes—$R_f$: 0.40

5-(2-ethoxyethoxy) pentan-1-amine (Sidechain-15)

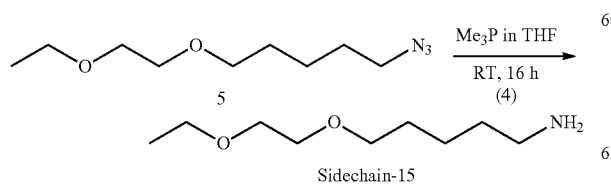

To a stirred solution of 1-azido-5-(2-ethoxyethoxy) pentane 5 (840 mg, 4.179 mmol) in THF:H₂O (4:1) (10 mL) was added 1M of P(Me)₃ in THF (8.3 mL, 8.358 mmol) at 0° C. then stirred at room temperature for 16 h. After completion of reaction as indicated by TLC, organic solvents were evaporated to complete dryness, and 5-(2-ethoxyethoxy) pentan-1-amine Sidechain-15 (1.1 g, crude) was obtained as a liquid. TLC system: 10% Methanol in dichloromethane—$R_f$: 0.10; LCMS: m/z=176.18 $(M+H)^+$ 5-(2-ethoxyethoxy)-N-methyl pentan-1-amine (Sidechain-16)

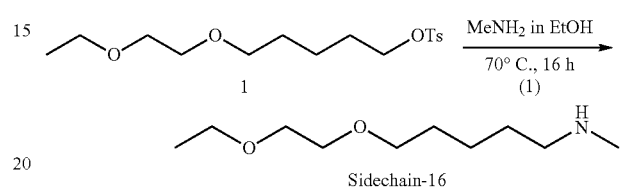

A solution of 5-(2-ethoxyethoxy) pentyl 4-methylbenzenesulfonate 1 (Synthesis of Cpd-1 was reported in Sidechain-15) (3 g, 9.090 mmol) in 1M solution of methylamine in ethanol (70 mL) was stirred at 70° C. for 16 h. After completion of reaction as indicated by TLC, the reaction mixture was evaporated and diluted with ethyl acetate (150 mL). Organic layer was basified with tri ethylamine added water and extract with ethyl acetate (2×100 ml). The combined organic layer was washed with brine solution (50 mL), dried over Na₂SO₄ and concentrated to obtain 5-(2-ethoxyethoxy)-N-methylpentan-1-amine Sidechain-16 (1.6 g, 8.465 mmol, crude) as a brown colored oily liquid. TLC system: 10% Methanol in dichloromethane/triethylamine—$R_f$: 0.20; Direct mass: m/z=190 $(M+H)^+$ Sidechain-17

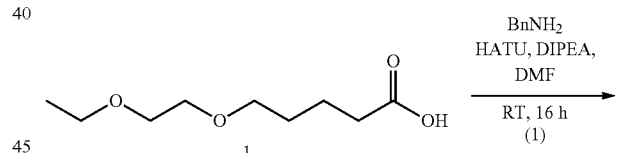

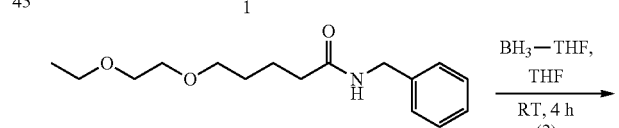

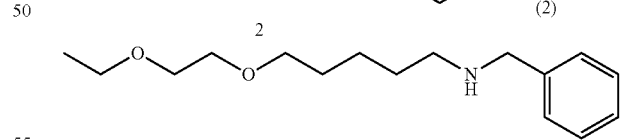

Sidechain-17

N-benzyl-5-(2-ethoxyethoxy) pentanamide (2)

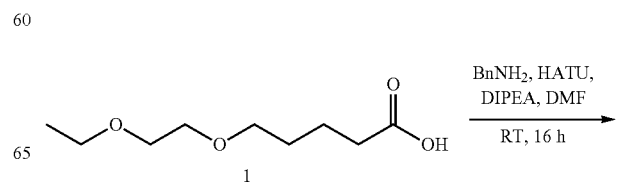

-continued

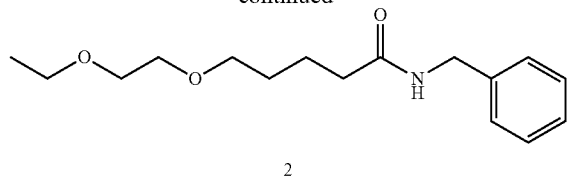

To a stirred solution of 5-(2-ethoxyethoxy) pentanoic acid 1 (Synthesis of Cpd-1 was reported in Sidechain-14) (500 mg, 2.64 mmol) in DMF (5 mL) were added di isopropyl ethyl amine (1.4 mL, 7.9 mmol), HATU (2 g, 5.28 mmol) at room temperature and stirred for 10 minutes, then benzyl amine (420 mg, 3.96 mmol) was added and stirred at room temperature for 16 h. After completion of reaction as indicated by TLC, to the reaction mixture ice-cold water was added (50 ml) and extracted with ethyl acetate (2×100 mL). The combined organic layer was washed with brine solution (50 mL), dried (Na$_2$SO$_4$) and concentrated. Crude compound was purified by combi-flash chromatography and eluted with 25% ethyl acetate in pet ether to afford N-benzyl-5-(2-ethoxyethoxy) pentanamide 2 (400 mg, 1.43 mmol, 54% yield) as a pale yellow liquid. TLC system: 50% ethyl acetate in hexanes—R$_f$: 0.40; LCMS: m/z=280.39 (M+H)$^+$ N-benzyl-5-(2-ethoxyethoxy) pentan-1-amine
(Sidechain 17)

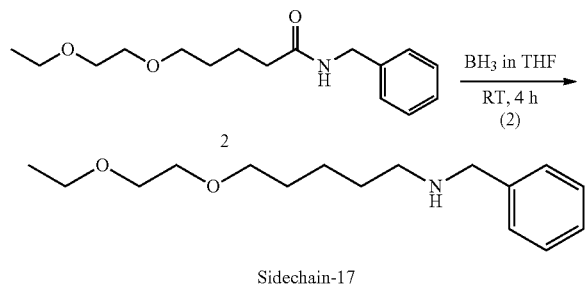

To a stirred solution of N-benzyl-5-(2-ethoxyethoxy) pentanamide 2 (400 mg, 1.43 mmol) in THF (5 mL) was added 1M solution of borane in THF (5.7 ml, 5.73 mmol) at 0° C. and the mixture was stirred at room temperature for 4 h. After completion of reaction as indicated by TLC, excess borane was carefully quenched with 1 ml methanol, ice water (50 ml) and extracted with ethyl acetate (2×50 mL). Combined organic layers were washed with brine (50 mL) and dried over Na$_2$SO$_4$ evaporated under reduced pressure to afford N-benzyl-5-(2-ethoxyethoxy) pentan-1-amine Sidechain 17 (300 mg, 1.13 mmol, 79% yield) as light yellow liquid. TLC system: 50% ethyl acetate in hexanes—R$_f$: 0.50; LCMS: m/z=288.14 (M+Na)$^+$ Sidechain-18

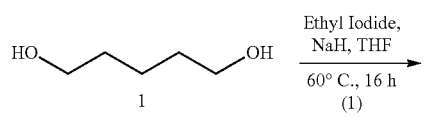

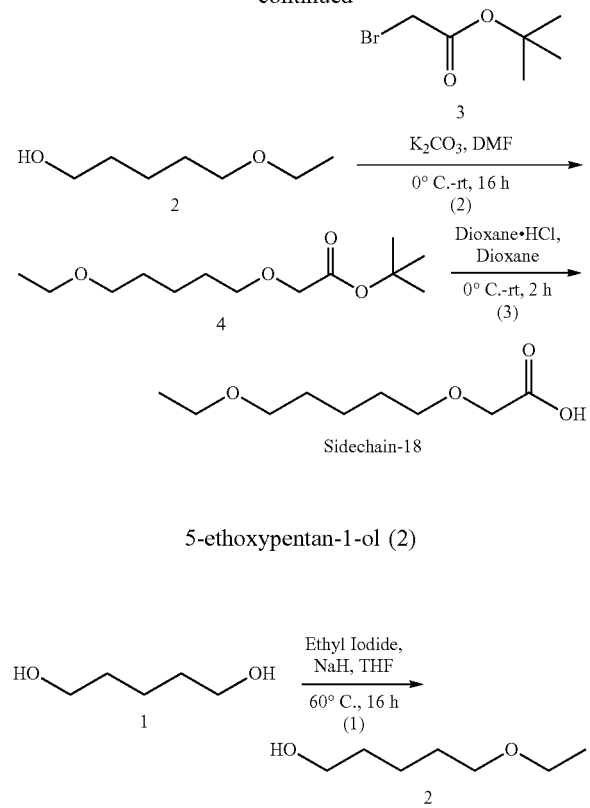

5-ethoxypentan-1-ol (2)

To a stirred solution of pentane-1, 5-diol 1 (500 mg, 4.807 mmol) in tetrahydrofuran (10 mL) was added NaH (115 mg, 4.807 mmol) at 0° C. and stirred at room temperature for 1 h. Ethyl iodide (740 mg, 4.807 mmol) in tetrahydrofuran (5 mL) was added to the above reaction mixture at 0° C. and stirred at 60° C. for 16 h under nitrogen atmosphere. The reaction mixture was quenched with ice water and extracted with ethyl acetate (2×50 mL). Combined organic layers were washed with brine (20 mL), dried over Na$_2$SO$_4$ and evaporated under reduced pressure. Crude residue was purified by 100-200 silica gel chromatography using 35% ethyl acetate in hexanes to afford 5-ethoxypentan-1-ol 2 (310 mg, 2.348 mmol, 49% yield) as a reddish brown oily liquid. TLC system: 70% ethyl acetate in hexanes—R$_f$: 0.50 tert-butyl 2-(5-ethoxypentyloxy) acetate (4)

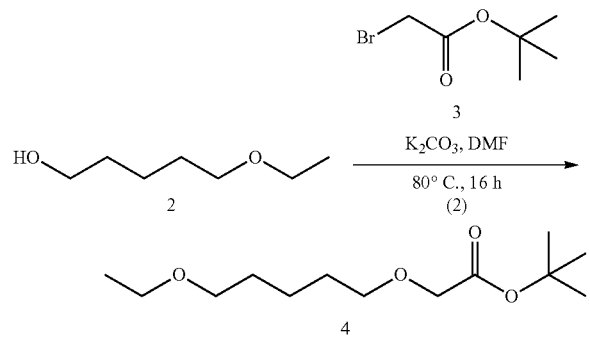

To a stirred solution of 5-ethoxypentan-1-ol 2 (500 mg, 3.7878 mmol) in N,N-dimethyl formamide (5 mL) was added potassium carbonate (1.6 g, 11.363 mmol) and tert-butyl 2-bromoacetate 3 (1.85 g, 9.4697 mmol), then stirred at 80° C. for 16 h under nitrogen atmosphere. The reaction mixture was quenched with ice water and extracted with ethyl acetate (2×50 mL). Combined organic layers were washed with brine solution (20 mL), dried over $Na_2SO_4$ and evaporated under reduced pressure. Crude residue was purified by 100-200 silica gel chromatography using 8% ethyl acetate in hexanes to afford tert-butyl 2-(5-ethoxypentyloxy) acetate 4 (600 mg, 2.439 mmol, 64% yield) as a colorless oily liquid. TLC system: 30% ethyl acetate in hexanes—$R_f$: 0.50

2-(5-ethoxypentyloxy) acetic acid (Sidechain-18)

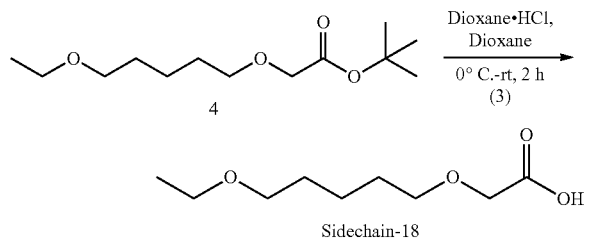

To a stirred solution of tert-butyl 2-(5-ethoxypentyloxy) acetate 4 (2 g, 8.13 mmol) in dioxane (10 mL) was added 4N of HCl in dioxane (15 mL) then stirred at room temperature for 2 h. the reaction mixture was concentrated, water (100 ml) was added to the crude and extracted with ethyl acetate (2×50 mL). The aqueous layer was acidified with 1N HCl solution up to pH=2 and then extracted with ethyl acetate (2×50 mL). The combined organic layer was washed with brine solution (100 mL), dried over $Na_2SO_4$ and concentrated to afford 2-(5-ethoxypentyloxy) acetic acid Sidechain-18 (1.3 g, 6.842 mmol, 83%) as a colorless gummy liquid. TLC system: 100% ethyl acetate—$R_f$: 0.10

Sidechain-19

5-ethoxypentan-1-ol (2)

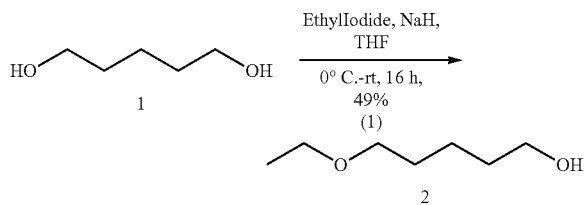

To a stirred suspension of NaH (3.8 g, 96.15 mmol) was added a solution of pentane-1, 5-diol 1 (10 g, 96.15 mmol) in THF (100 mL) at 0° C. and stirred at room temperature for 1 h. Ethyl iodide (3.7 ml, 96.15 mmol) in THF (50 mL) was added to above reaction mixture at 0° C. and stirred at room temperature for 16 h under argon atmosphere. The reaction mixture was quenched with ice-cold water (200 mL) and extracted with ethyl acetate (3×200 mL). Combined organic layers were washed with brine (100 mL), dried over $Na_2SO_4$ and evaporated under reduced pressure. Crude residue was purified by column chromatography by eluting with 40% ethyl acetate in pet ether to afford 5-ethoxypentan-1-ol 2 (6.5 g, 49.24 mmol, 49% yield) as an oily liquid. TLC system: 70% ethyl acetate in pet ether—$R_f$: 0.50; DIRECT MASS: m/z=133.36 $(M+H)^+$ ((2-bromoethoxy) methanetrityl) tribenzene (4)

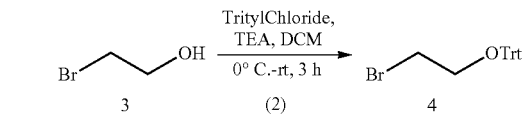

To a stirred solution of 2-bromoethan-1-ol 3 (7 g, 56 mmol) in DCM (175 mL) was added triethylamine (15.5 mL, 112 mmol) and trityl chloride at 0° C. and stirred at

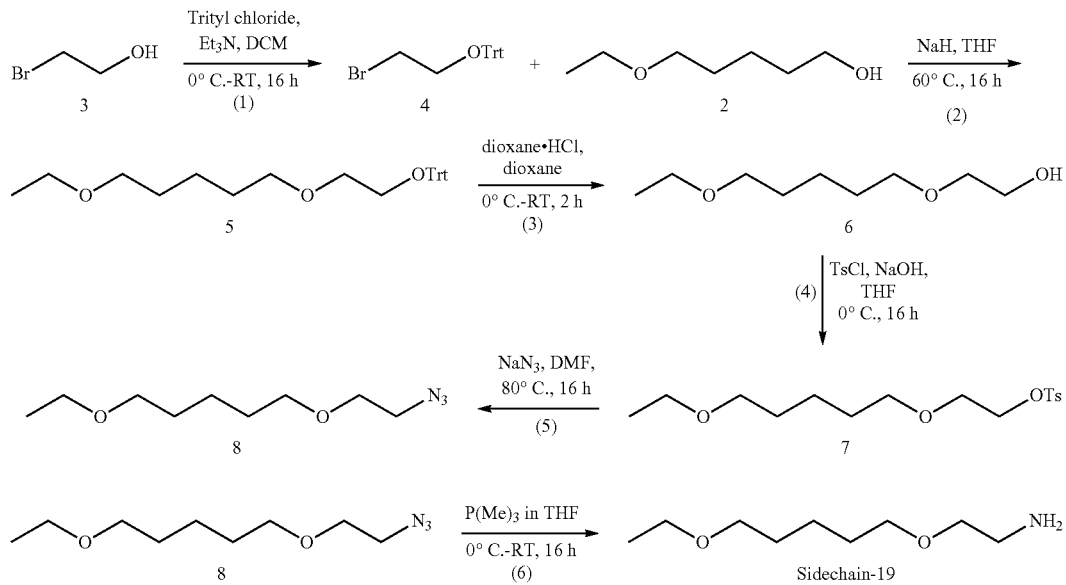

room temperature 3 h. After completion of the reaction as indicated by TLC, the reaction mixture was diluted with water (300 ml) and extracted with dichloromethane (2×200 mL). Combined organic layers were washed with brine solution (100 mL), dried over $Na_2SO_4$ and concentrated under reduced pressure. Crude compound was purified through 100-200 silica gel column chromatography by eluting 5% ethyl acetate in pet ether to afford ((2-bromoethoxy) methanetrityl) tribenzene 4 (4.5 g, 12.295 mmol, 22% yield) as an off-white solid. TLC system: 10% ethyl acetate in pet ether—$R_f$: 0.60; LCMS: m/z=367.24 (M+H)$^+$ ((2-((5-ethoxypentyl) oxy) ethoxy) methane trityl) tribenzene (5)

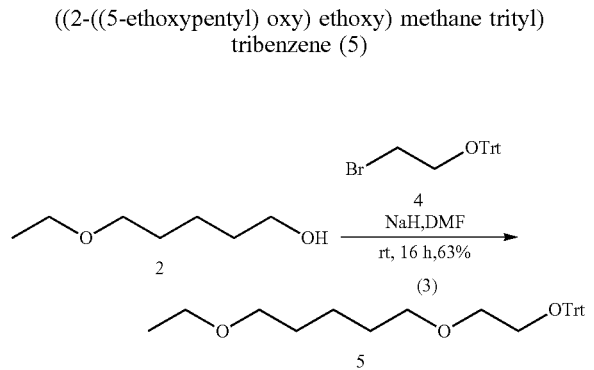

To a stirred suspension of NaH (568 mg, 23.67 mmol), was added a solution of 5-ethoxypentan-1-ol 2 (1.25 g, 9.469 mmol) in DMF (20 mL) at 0° C. and stirred at room temperature for 30 minutes. Then ((2-bromoethoxy) methanetrityl) tribenzene 4 (4.5 g, 12.31 mmol) in DMF (5 mL) was added to the above reaction mixture at 0° C. and stirred at room temperature for 16 h under argon atmosphere. The reaction mixture was quenched with ice-cold water (200 mL) and extracted with ethyl acetate (3×100 mL). Combined organic layers were washed with brine (100 mL), dried over $Na_2SO_4$ and evaporated under reduced pressure. Crude residue was purified by 100-200 silica gel column chromatography by eluting with 5% ethyl acetate in pet ether to afford ((2-((5-ethoxypentyl)oxy)ethoxy)methanetrityl)tribenzene 5 (2.5 g, 5.980 mmol, 63% yield) as a colorless oily liquid. TLC system: 5% ethyl acetate in pet ether—$R_f$: 0.40; LCMS: m/z=441.46 (M+Na)$^+$ 2-((5-ethoxypentyl) oxy) ethan-1-ol (6)

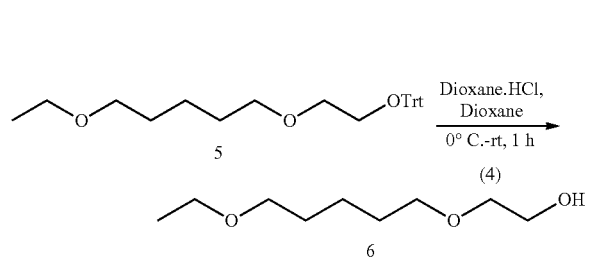

To a stirred solution of ((2-((5-ethoxypentyl)oxy)ethoxy) methanetrityl)tribenzene 5 (12 g, 28.70 mmol) in dioxane (60 mL) was added HCl in dioxane (4N, 24 mL) at 0° C. then stirred at room temperature for 1 h. After completion of the reaction as indicated by TLC, the reaction mixture was concentrated, water (50 ml) was added to the residue, basified with sodium bicarbonate solution (100 mL) and extracted with ethyl acetate (2×200 mL). Combined organic layers were washed with brine solution (100 mL), dried over $Na_2SO_4$ and concentrated under reduced pressure. Crude compound was purified through 100-200 silica gel column chromatography by eluting with 70% ethyl acetate in pet ether to afford 2-((5-ethoxypentyl)oxy)ethan-1-ol 6 (4.4 g, 25.0 mmol, 88% yield) as a colorless oily liquid. TLC system: 50% ethyl acetate in pet ether—$R_f$: 0.30; Direct mass: m/z=177.22 (M+H)$^+$ 2-((5-ethoxypentyl) oxy) ethyl 4-methylbenzenesulfonate (7)

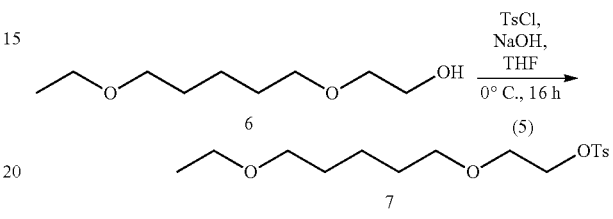

To a stirred solution of 2-((5-ethoxypentyl)oxy)ethan-1-ol 6 (3 g, 17.04 mmol) in THF (5 mL) was added NaOH (1.3 g, 34.09 mmol) and p-toluene sulfonyl chloride (3.8 g, 20.45 mmol) at 0° C. to the reaction mixture and stirred at room temperature for 16 h. After consumption of starting material, to the reaction mixture was quenched with water (200 mL) and extracted with ethyl acetate (2×100 mL). The combined organic layers were washed with brine solution (50 mL), dried over sodium sulphate and concentrated. Crude compound was purified through 100-200 silica gel column chromatography by eluting with 20% ethyl acetate in pet ether to afford 2-((5-ethoxypentyl)oxy)ethyl 4-methylbenzenesulfonate 7 (5.2 g, 15.75 mmol, 92% yield) as liquid. TLC system: 20% ethyl acetate in pet ether—$R_f$: 0.50; LCMS: m/z=331.04 (M+H)$^+$ 1-(2-azidoethoxy)-5-ethoxypentane (8)

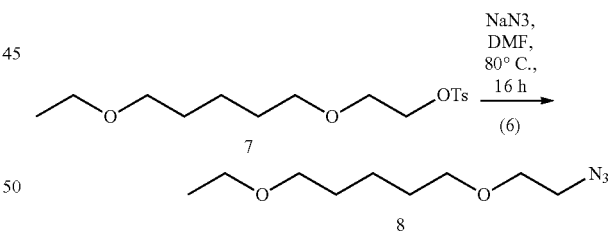

To a stirred solution of 2-((5-ethoxypentyl) oxy) ethyl 4-methylbenzenesulfonate 7 (3.5 g, 10.60 mmol) in DMF (30 mL) was added $NaN_3$ (1.1 g, 16.96 mmol) at room temperature then stirred at 60° C. for 16 h. After completion of reaction as indicated by TLC, the reaction mixture was quenched with water (200 ml) and extracted with diethyl ether (2×100 mL). Combined organic layers were washed with brine solution (100 mL), dried over $Na_2SO_4$ and concentrated under reduced pressure. Crude compound was purified through column chromatography eluting with 15% ethyl acetate in pet ether to afford 1-(2-azidoethoxy)-5-ethoxypentane 8 (1.95 g, 9.702 mmol, 92%) as a colorless oily liquid. TLC system: 20% ethyl acetate in pet ether—$R_f$: 0.50

2-((5-ethoxypentyl) oxy) ethan-1-amine (Sidechain-19)

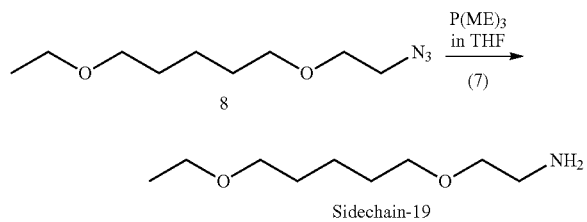

Sidechain-19

To a stirred solution of 1-azido-5-(2-ethoxyethoxy) pentane 8 (900 mg, 4.477 mmol) in THF:H$_2$O (4:1) (12.5 mL) was added 1M of P(Me)$_3$ in THF (8.9 mL, 8.955 mmol) at 0° C. then stirred at room temperature for 16 h. After completion of the reaction as indicated by TLC, organic solvents were evaporated, water (100 mL) was added to the residue and extracted with ethyl acetate (2×100 mL). Combined organic layers were washed with brine solution (100 mL), dried over sodium sulphate and concentrated under reduced pressure to afford 5-(2-ethoxyethoxy) pentan-1-amine Sidechain-19 (240 mg, 1.371 mmol, crude) as a pale yellow oily liquid. TLC system: 5% Methanol in dichloromethane—R$_f$: 0.10; Direct mass: m/z=176.31 (M+H)$^+$

Sidechain-20

2-((5-ethoxypentyl) oxy)-N-methylethan-1-amine (Sidechain-20)

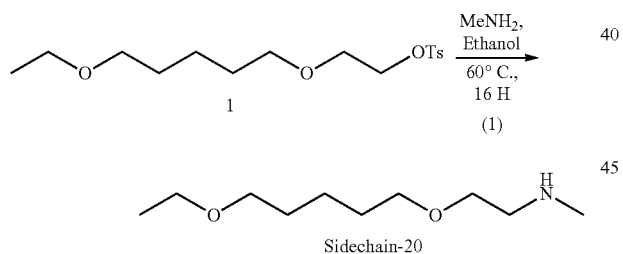

Sidechain-20

To a stirred solution of 2-((5-ethoxypentyl)oxy)ethyl 4-methylbenzenesulfonate 1 (Synthesis of Cpd-1 was reported in Sidechain-19) (1 g, 3.030 mmol) in ethanol (3 mL) in a sealed tube was added MeNH$_2$ in ethanol (1 M, 5 mL) at room temperature then stirred in a sealed tube at 60° C. for 16 h. After completion of reaction as indicated by TLC, evaporated organic solvents. To the crude was added water (10 mL), acidified with HCl solution (6N, 50 mL) and washed with dichloromethane (2×100 mL). Aqueous layer was basified with NaOH solution (100 mL) and extracted with ethyl acetate (2×100 mL). The organic layer was washed with brine solution (50 mL), dried over Na$_2$SO$_4$ and concentrated to afford 2-((5-ethoxypentyl) oxy)-N-methylethan-1-amine Sidechain-20 (240 mg, 1.269 mmol, 41%) as a colorless oily liquid. TLC system: 70% ethyl acetate in pet ether—R$_f$: 0.10; Direct mass: m/z=190.18 (M+H)$^+$

Sidechain-21

N-benzyl-2-((5-ethoxypentyl) oxy) ethan-1-amine (Sidechain-21)

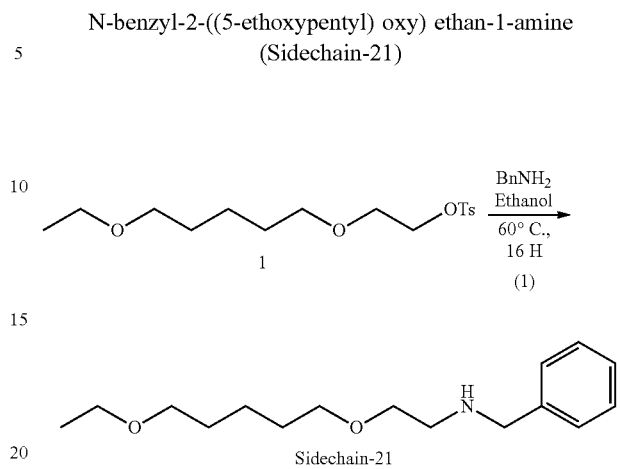

Sidechain-21

To a stirred solution of 2-((5-ethoxypentyl)oxy)ethyl 4-methylbenzenesulfonate 1 (Synthesis of Cpd-1 was reported in Sidechain-19) (65 mg, 0.196 mmol) in ethanol (4 mL) in a sealed tube was added Benzyl amine (63 mg, 0.5908 mmol) at room temperature then stirred at 60° C. for 16 h. After completion of reaction as indicated by TLC, evaporated organic solvents, to the crude added water (50 ml) and extracted with ethyl acetate (2×20 mL). Combined organic layers were washed with brine solution (30 mL), dried over Na$_2$SO$_4$ and concentrated to afford crude compound of N-benzyl-2-((5-ethoxypentyl)oxy)ethan-1-amine Sidechain-21 (95 mg, 0.358 mmol, crude) as a colorless gummy liquid. TLC system: 10% Methanol in dichloromethane—R$_f$: 0.40; LCMS: m/z=266.29 (M+H)$^+$

Sidechain-22

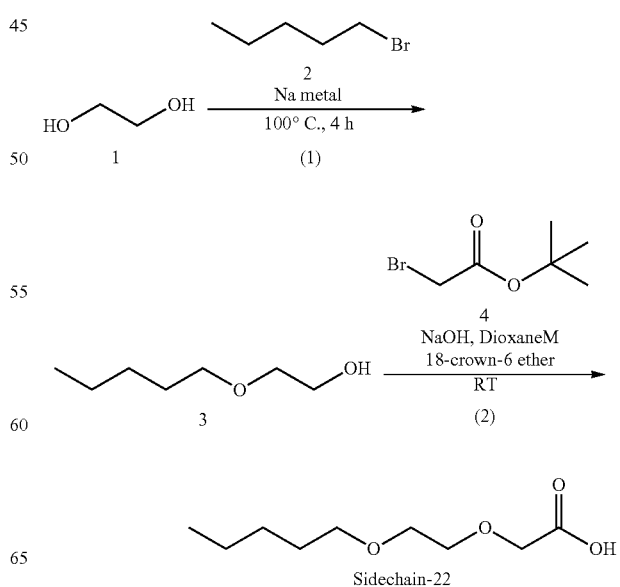

Sidechain-22

2-(Pentyl oxy) ethan-1-ol (3)

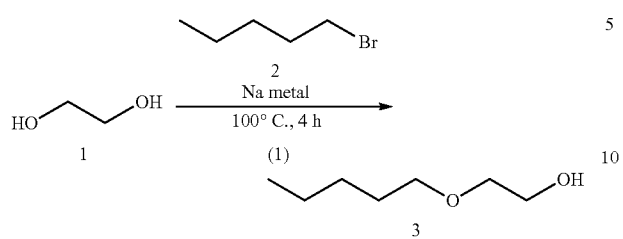

Sodium metal (0.6 g, 0.025 mmol) was added to ethylene glycol 1 (5 g, 0.083 mmol) at room temperature and heated at 80° C. Then, 1-bromopentane 2 (3.7 g, 0.025 mmol) was added to the reaction mixture at 100° C. and the reaction mixture was continued to stir for 4 h. The mixture was filtered to remove inorganic materials and diluted with ice water (200 mL), extracted with ethyl acetate (2×200 mL). Organic layer was washed with brine solution, dried ($Na_2SO_4$) and concentrated to get pure 2-(pentyl oxy) ethan-1-ol 3 (2.2 g, 0.0186 mmol, 55%) as yellow liquid. TLC system: 10% Methanol in dichloromethane—$R_f$: 0.5

2-(2-(Pentyl oxy) ethoxy) acetic acid (Sidechain-22)

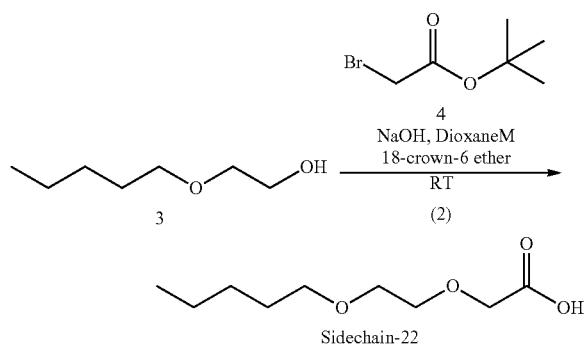

To a stirred solution of 2-(pentyl oxy) ethan-1-ol 3 (500 mg, 4.23 mmol) in 1, 4-dioxan (10 mL) was added NaOH (0.84 g, 21.12 mmol) at RT. The mixture was stirred at RT for 15 min. Then tert-butyl 2-bromoacetate 4 (1.3 mL, 8.47 mmol) and 18-crownether (25 mg) were added to the reaction mixture and stirred at room temperature for 18 h. After consumption of starting material, the mixture was diluted with ice cold water (50 mL), extracted with diethyl ether (2×50 mL). The separated aqueous layer was acidified (pH~2) with concentrated HCl and extracted with 10% methanol in dichloromethane mixture (2×100 mL). The organic layer was washed with brine solution (50 mL), dried over sodium sulfate and concentrated to get pure 2-(2-(Pentyl oxy) ethoxy) acetic acid Sidechain-22 (200 mg, 1.05 mmol, 24% yield) as a thick brown liquid. TLC system: 10% Methanol in dichloromethane—$R_f$: 0.10

Sidechain-23

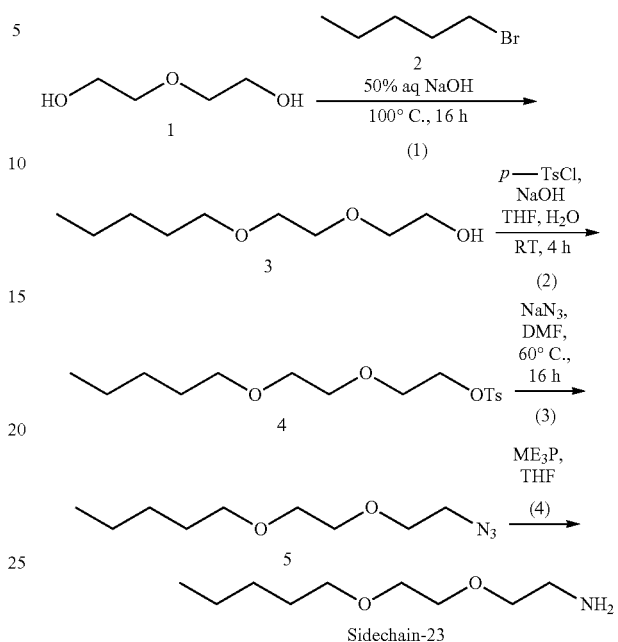

2-(2-(pentyl oxy) ethoxy) ethan-1-ol (3)

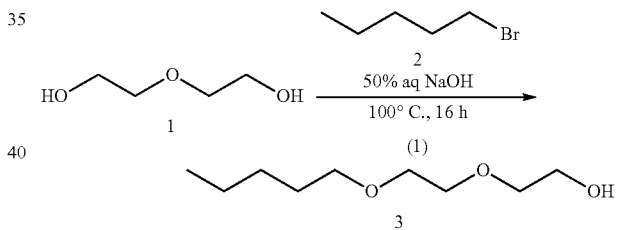

To a stirred solution of methyl 2, 2'-oxy bis(ethan-1-ol) 1 (10 g, 66.25 mmol) in 50% aqueous NaOH solution (250 ml), was added 1-bromopentane 2 and stirred at 100° C. for 16 h. After completion of reaction as indicated by TLC, Water was added to the reaction mixture (200 ml) and extracted with ethyl acetate (2×500 mL). Combined organic layers were washed with brine solution (200 mL), dried over $Na_2SO_4$ and concentrated under reduced pressure, to afford 2-(2-(pentyl oxy) ethoxy) ethan-1-ol 3 (8.4 g, 47.72 mmol, 72%) as a brown liquid. TLC system: 100% ethyl acetate—$R_f$: 0.50

2-(2-(pentyl oxy) ethoxy) ethyl 4-methylbenzenesulfonate (4)

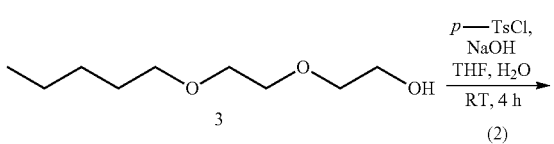

-continued

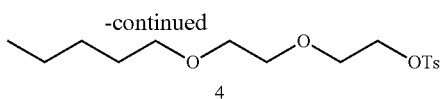

4

To a stirred solution of 2-(2-(pentyl oxy) ethan-1-ol 3 (4 g, 22.72 mmol) in THF (30 mL) was added NaOH (1.8 g, 45.45 mmol) in water (10 mL) at 0° C. The reaction mixture was stirred at room temperature for 15 min, then cooled to 0° C., p-toluene sulfonyl chloride (5.1 g, 27.27 mmol) was added to the reaction mixture and stirred at room temperature for 4 h. After consumption of starting material, the mixture was diluted with ethyl acetate (150 mL) and washed with ice cold water (2×30 mL), brine solution (30 mL), dried over sodium sulfate and concentrated under reduced pressure. Crude compound was purified by 100-200 mesh silica gel column chromatography by eluting with 30% ethyl acetate in pet ether to afford 2-(2-(pentyl oxy) ethoxy) ethyl 4-methylbenzenesulfonate 4 (5.4 g, 16.36 mmol, 72% yield) as a brown liquid. TLC system: 70% ethyl acetate in pet ether—$R_f$: 0.50; LCMS: m/z=331.09 (M+H)$^+$ 1-(2-(2-azidoethoxy) ethoxy) pentane (5)

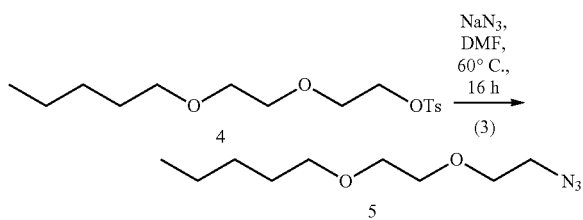

To a stirred solution of 2-(2-(pentyl oxy) ethyl 4-methylbenzenesulfonate 4 (2 g, 6.06 mmol) in DMF (20 mL) was added NaN$_3$ (630 mg, 9.696 mmol) at room temperature then stirred at 60° C. for 16 h. After completion of reaction as indicated by TLC, evaporated organic solvents, to the crude added ice water (2×50 ml) and extracted with diethyl ether (2×100 mL). Combined organic layers were washed with brine solution (50 mL), dried over Na$_2$SO$_4$ and concentrated under reduced pressure to afford 1-(2-(2-azidoethoxy) ethoxy) pentane 5 (1.1 g, 5.97 mmol, 91%) as a brown liquid. TLC system: 50% ethyl acetate in hexanes—$R_f$: 0.30; LCMS: m/z=202 (M+H)$^+$ 2-(2-(pentyl oxy) ethoxy) ethan-1-amine (Sidechain-23)

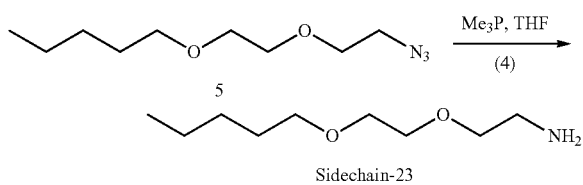

To a stirred solution of 1-(2-(2-azidoethoxy) ethoxy) pentane 5 (1.1 g, 5.47 mmol) in THF:H$_2$O (4:1) (10 mL) was added P(Me)$_3$ in THF (1M, 11 mL, 10.94 mmol) was added at 0° C. and stirred at room temperature for 16 h. After completion of reaction as indicated by TLC, evaporated organic solvents to afford 2-(2-(pentyl oxy) ethoxy) ethan-1-amine Sidechain-23 (1.1 g, 6.285 mmol, crude) as a brown liquid. TLC system: 10% Methanol in dichloromethane—$R_f$: 0.1

N-methyl-2-(2-(pentyl oxy) ethoxy) ethan-1-amine (Sidechain-24)

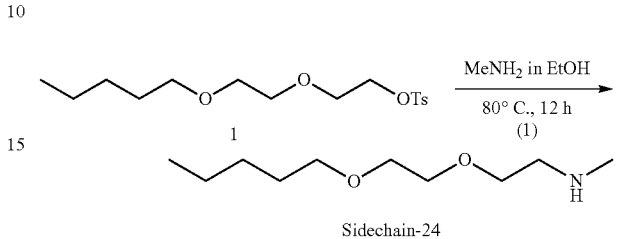

2-(2-(pentyl oxy) ethoxy) ethyl 4-methylbenzenesulfonate 1 (Synthesis of Cpd-1 was reported in Sidechain-23) (500 mg, 1.51 mmol) was added to methylamine in ethanol (1 M, 5 mL) at room temperature then stirred at 80° C. for 12 h. After completion of reaction as indicated by TLC, the reaction mixture was evaporated, diluted with water (50 mL) acidified with 1N HCl (pH~2) and washed with diethyl ether (2×50 mL). Then separated aqueous layer was basified with saturated NaHCO$_3$ solution and extracted with 10% methanol in dichloromethane (2×100 mL), washed with brine solution (50 mL), dried over Na$_2$SO$_4$ and concentrated to obtain N-methyl-2-(2-(pentyl oxy)ethoxy) ethan-1-amine Sidechain-24 (240 mg, 1.27 mmol, 84%) as a brown colored oily liquid. TLC system: 10% Methanol in dichloromethane (1 drop Et$_3$N)—$R_f$: 0.20

N-benzyl-2-(2-(pentyl oxy) ethoxy) ethan-1-amine (Sidechain 25)

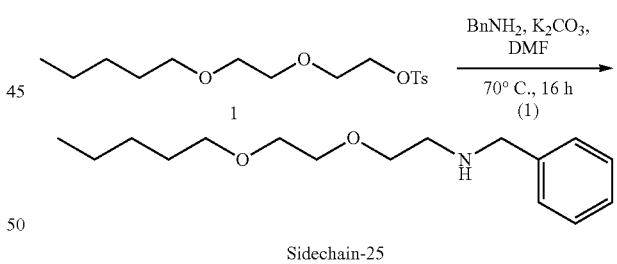

To a stirred solution of 2-(2-(pentyl oxy) ethyl 4-methylbenzenesulfonate 1 (Synthesis of Cpd-1 was reported in Sidechain-23) (500 g, 1.515 mmol) in DMF (5 ml) were added potassium carbonate (2 g, 15.15 mmol) and benzyl amine (256 mg, 2.424 mmol) at room temperature then stirred at 70° C. for 16 h. After completion of reaction as indicated by TLC, to the reaction mixture was added ice water (30 ml) and extracted with ethyl acetate (2×30 mL). Organic layer was washed with brine solution (30 mL), dried over Na$_2$SO$_4$ and concentrated under reduced pressure. Crude compound was purified by combi flash chromatography by eluting with 10% methanol in dichloromethane to afford N-benzyl-2-(2-(pentyl oxy) ethoxy) ethan-1-amine Sidechain 25 (300 mg, 1.132 mmol, 74.8% yield) as an off white solid. TLC system: 10% Methanol in dichloromethane—$R_f$: 0.20; LCMS: m/z=266.43 (M+H)$^+$ Sidechain-26

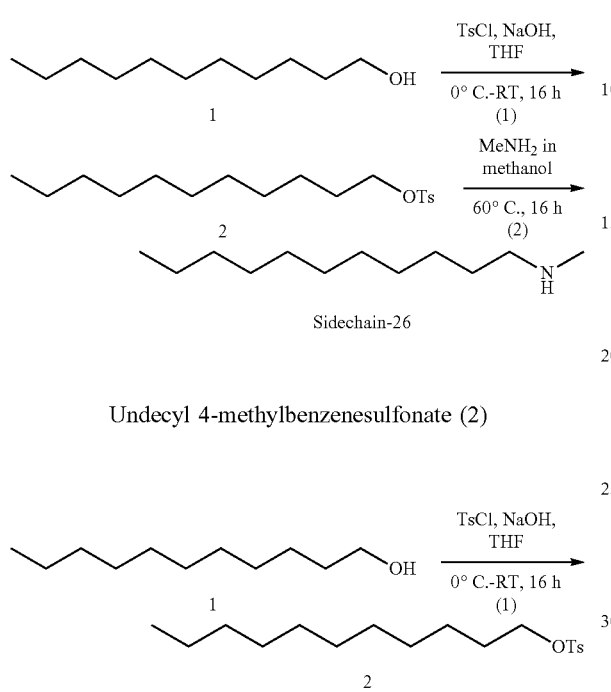

Undecyl 4-methylbenzenesulfonate (2)

To a stirred solution of undecan-1-ol 1 (2.0 g, 11.6 mmol) in THF (20 mL) was added NaOH (0.93 g, 23.2 mmol) at 0° C. The mixture was stirred at room temperature for 15 min. Then cooled to 0° C., p-toluene sulfonyl chloride (2.65 g, 13.92 mmol) was added to the reaction mixture and stirred at room temperature for 16 h. After consumption of starting material, the mixture was diluted with ethyl acetate (150 mL) and washed with ice cold water (2×20 mL), brine solution (20 mL), dried over sodium sulfate and concentrated. Crude compound was purified by 100-200 mesh silica gel column chromatography by eluting with 20% ethyl acetate in hexanes to afford Undecyl 4-methylbenzenesulfonate 2 (2.6 g, 7.97 mmol, 68% yield) as an off white solid. TLC system: 10% Methanol in dichloromethane—$R_f$: 0.70; LCMS: m/z=325.56 (M−H)

N-methylundecan-1-amine (Sidechain-26)

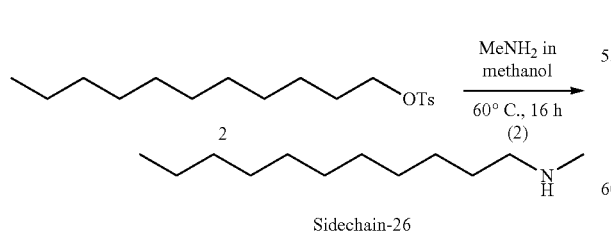

To a stirred solution of Undecyl 4-methylbenzenesulfonate 2 (600 mg, 1.84 mmol) in methanol (2 mL) in a sealed tube was added 1M of MeNH$_2$ in methanol (2.5 mL) at room temperature then stirred at 80° C. for 16 h. After completion of reaction as indicated by TLC, evaporated organic solvents. To the crude was added water (20 ml) and extracted with ethyl acetate (3×30 mL). Organic layer was washed with 1N HCL solution (20 mL) and saturated NaHCO$_3$ solution (20 mL), brine solution (100 mL), dried over Na$_2$SO$_4$ and concentrated to afford N-methylundecan-1-amine (Sidechain-26) (190 mg, 1.02 mmol, crude) as a brown colored oily liquid. TLC system: 10% Methanol in dichloromethane—$R_f$: 0.20; LCMS: m/z=186.40 (M+H)$^+$ N-benzylundecan-1-amine (Sidechain-27)

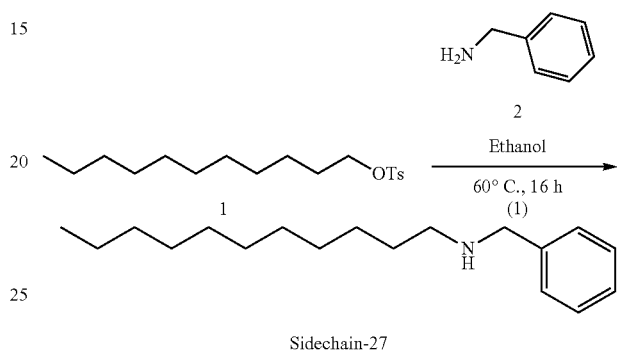

Sidechain-27

To a stirred solution of Undecyl 4-methylbenzenesulfonate 1 (Synthesis of Cpd-1 was reported in Sidechain-26) (600 mg, 1.84 mmol) in ethanol (10 mL) in a sealed tube was added Benzyl amine (0.6 mL) at room temperature then stirred at 60° C. for 16 h. After completion of reaction as indicated by TLC, evaporated organic solvents, to the crude added water (20 ml) and extracted with ethyl acetate (3×30 mL). Organic layer was washed with 1N HCL solution (20 mL) and saturated NaHCO$_3$ solution (20 mL), brine solution (50 mL), dried over Na$_2$SO$_4$ and concentrated to get crude. Crude compound was purified by 100-200 mesh silica gel column chromatography by eluting with 40% ethyl acetate in hexanes to afford N-methylundecan-1-amine Sidechain-27 (350 mg, 1.34 mmol, 72% yield) as an off white semi-solid. TLC system: 50% ethyl acetate in Pet-ether—$R_f$: 0.20; LCMS: m/z=262.47 (M+H)$^+$ Sidechain-28

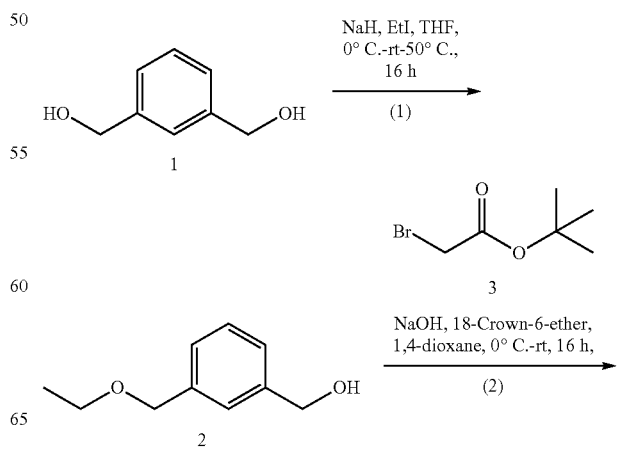

271
-continued

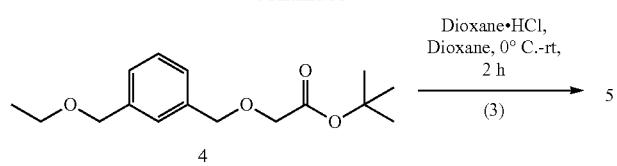

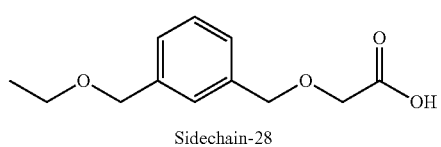

(3-(ethoxy methyl) phenyl) methanol (2)

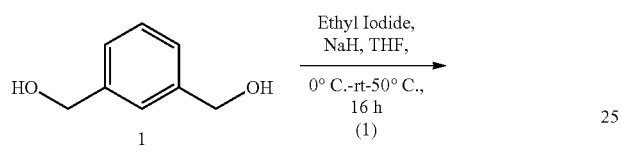

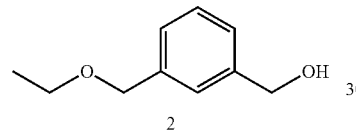

To a stirred solution of 1, 3-phenylenedimethanol (1) (5 g, 36.496 mmol) in THF (100 mL) was treated with NaH (1.17 g, 29.197 mmol) at 0° C. to RT for 30 min. Ethyl iodide (2.3 ml, 29.197 mmol) in THF (10 mL) was added to above reaction mixture at 0° C. and stirred at 50° C. for 16 h under nitrogen atmosphere. The reaction mixture was quenched with ice water and extracted with ethyl acetate (3×100 mL). Combined organic layers were washed with brine (2×100 mL) and dried over $Na_2SO_4$, evaporated under reduced pressure. Crude residue was purified by Combi-flash chromatography using 20% ethyl acetate in pet-ether to afford (3-(ethoxy methyl) phenyl) methanol 3 (2.1 g, 12.65 mmol, 34% yield) as a yellowish oily liquid. TLC system: 40% ethyl acetate in pet-ether—$R_f$: 0.50; LCMS: m/z=120.99 $(M-46)^+$ Tert-butyl 2-(3-(ethoxy methyl) benzyl oxy) acetate (4)

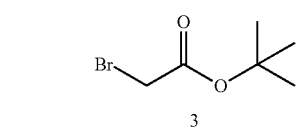

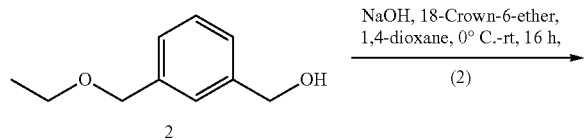

272
-continued

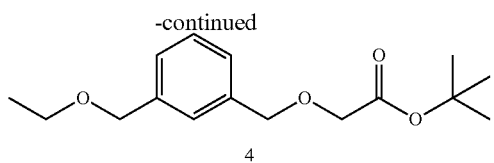

To a stirred solution of (3-(ethoxy methyl) phenyl) methanol 2 (750 mg, 4.158 mmol) in 1, 4-dioxane (10 mL) was added NaOH (542 mg, 13.55 mmol) at 0° C. The mixture was stirred at RT for 15 min, then cooled to 0° C., tert-butyl 2-bromoacetate 3 (1.76 g, 9.036 mmol) and 18-crownether (40 mg) were added and stirred at room temperature for 16 h. After consumption of starting material, the reaction mixture was diluted with ethyl acetate (50 mL) and washed with ice cold water (50 mL), brine solution (20 mL), dried over sodium sulfate and concentrated under reduced pressure. Crude compound was purified by combi-flash chromatography and eluted with 10% ethyl acetate in pet ether to afford tert-butyl 2-(3-(ethoxy methyl) benzyl oxy) acetate 4 (900 mg, 3.21 mmol, 71.1% yield) as a colorless oily liquid. TLC system: 30% ethyl acetate in pet-ether—$R_f$: 0.50

2-(3-(ethoxy methyl) benzyl oxy) acetic acid (Sidechain-28)

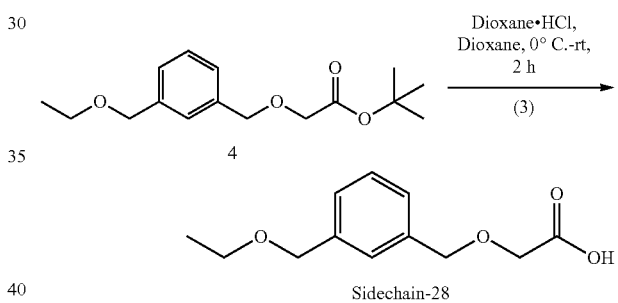

To a stirred solution of tert-butyl 2-(3-(ethoxy methyl) benzyl oxy)acetate 4 (300 mg, 1.0714 mmol) in 1,4-dioxane (2 mL) in a sealed tube was added 4M HCl in 1,4-dioxane (2.5 mL) at room temperature then stirred at rt for 2 h. After completion of reaction as indicated by TLC, organic solvents were evaporated, water was added (50 ml) to the crude and extracted with ethyl acetate (2×30 mL). Organic layer was washed with brine solution (30 mL), dried over $Na_2SO_4$ and concentrated under reduced pressure. Crude compound was purified by triturating with diethyl ether (30 mL) and obtained 2-(3-(ethoxy methyl) benzyl oxy) acetic acid Sidechain-28 (190 mg, 0.848 mmol, 79.1% yield) as a yellowish oily liquid. TLC system: 5% Methanol in dichloromethane—$R_f$: 0.20; LCMS: m/z=225.41 $(M+H)^+$ Sidechain-29

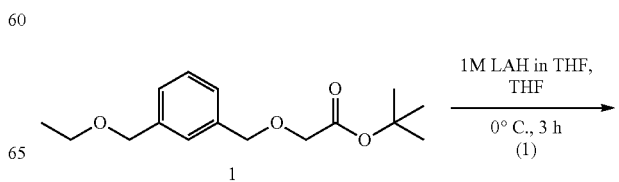

-continued

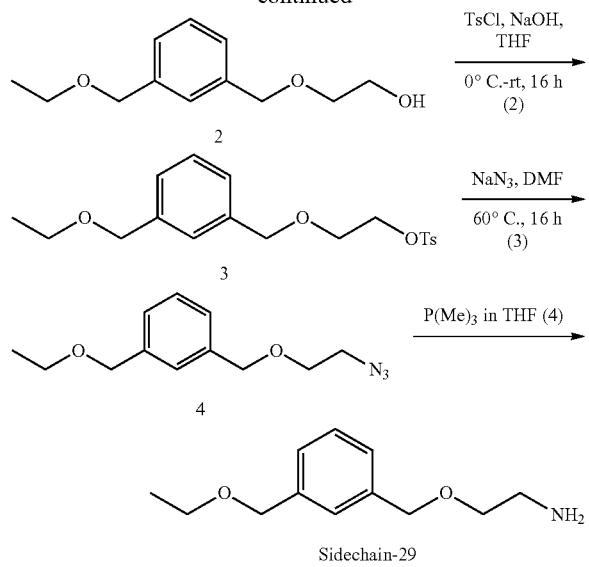

2-(3-(ethoxy methyl) benzyl oxy) ethanol (2)

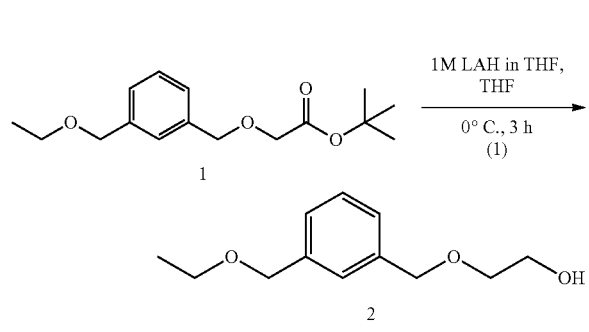

To a stirred solution of tert-butyl 2-(3-(ethoxy methyl) benzyl oxy)acetate 1 (Synthesis of Cpd-1 was reported in Sidechain-28) (500 mg, 1.7857 mmol) in THF (10 mL) was added 1M of LiAlH$_4$ in THF (5.3 mL, 5.357 mmol) at 0° C. for 3 h. After completion of reaction as indicated by TLC, reaction mixture was quenched with saturated NH$_4$Cl solution (20 mL) and brine solution (20 ml) and extracted with ethyl acetate (2×50 mL). Organic layer was washed with brine solution (50 mL), dried over Na$_2$SO$_4$ and concentrated to get 2-(3-(ethoxy methyl) benzyl oxy) ethanol 2 (350 mg, 1.666 mmol, 93%) as a color less oily liquid. TLC system: 40% ethyl acetate in hexanes—R$_f$: 0.20; LCMS: m/z=233.33 (M+Na)$^+$ 2-(3-(ethoxy methyl) benzyl oxy) ethyl 4-methylbenzenesulfonate (3)

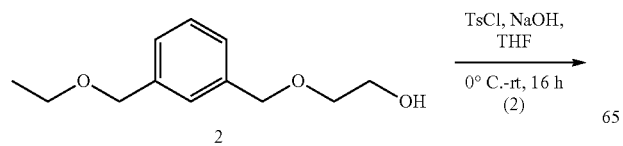

-continued

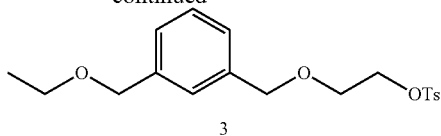

To a stirred solution of 2-(3-(ethoxy methyl) benzyl oxy) ethanol 2 (1.1 g, 5.23 mmol) in THF (30 mL) was added NaOH (0.42 g, 10.47 mmol) at 0° C. The mixture was stirred at room temperature for 15 min. Then cooled to 0° C., p-toluene sulfonyl chloride (1.2 g, 6.28 mmol) was added to the reaction mixture and stirred at room temperature for 16 h. After consumption of starting material, the mixture was diluted with ethyl acetate (100 mL) and washed with ice cold water (2×50 mL), brine solution (50 mL), dried over sodium sulfate and concentrated. Crude compound was purified by 100-200 mesh silica gel column chromatography and eluted with 10% ethyl acetate in hexanes to afford 2-(3-(ethoxy methyl) benzyl oxy)ethyl 4-methylbenzenesulfonate 3 (1.6 g, 4.39 mmol, 84% yield) as a color less oily liquid. TLC system: 30% ethyl acetate in hexanes—R$_f$: 0.70; LCMS: m/z=386.98 (M+Na)$^+$ 1-((2-azidoethoxy) methyl)-3-(ethoxy methyl) benzene (4)

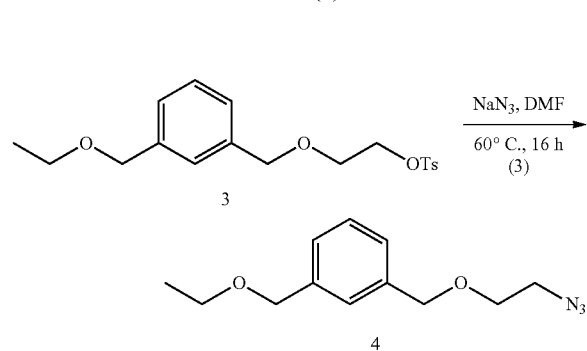

To a stirred solution of 2-(3-(ethoxy methyl) benzyl oxy) ethyl 4-methylbenzenesulfonate 3 (1.7 g, 4.39 mmol) in DMF (30 mL) was added NaN$_3$ (0.48 g, 7.47 mmol) at room temperature then stirred at 60° C. for 16 h. After completion of reaction as indicated by TLC, to the crude added water (2×100 ml) and extracted with diethyl ether (2×50 mL). Organic layer was washed with brine solution (50 mL), dried over Na$_2$SO$_4$ and concentrated. Crude compound was purified by giving washings with n-pentane (100 mL) to obtain 1-((2-azidoethoxy) methyl)-3-(ethoxy methyl) benzene 4 (1.1 g, 4.68 mmol, quantitative) as a brown colored gummy liquid. TLC system: 30% ethyl acetate in hexanes—R$_f$: 0.70

2-(3-(ethoxy methyl) benzyl oxy) ethanamine (Sidechain-29)

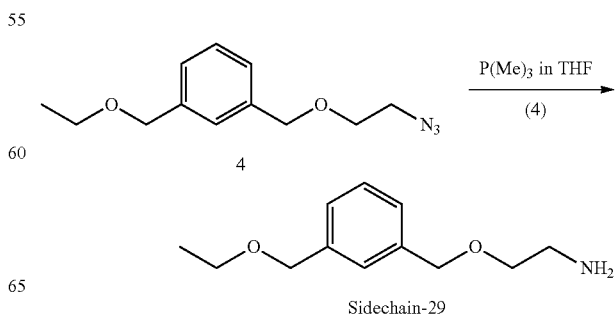

To a stirred solution of 1-((2-azidoethoxy)methyl)-3-(ethoxy methyl)benzene 4 (600 mg, 2.564 mmol) in THF:H$_2$O (20 mL) was added 1M of P(Me)$_3$ in THF (7.7 ml, 7.69 mmol) then stirred at room temperature for 16 h. After completion of reaction as indicated by TLC, organic solvents were evaporated and the crude compound was co-distilled with toluene (50 mL) to obtain 2-(3-(ethoxy methyl)benzyl oxy)ethanamine Sidechain-29 (500 mg, 2.39 mmol, 93%) as a brown colored semi-solid. TLC system: 10% Methanol in dichloromethane—R$_f$: 0.20; LCMS: m/z=210.32 (M+H)$^+$ Sidechain-30

2-((3-(ethoxy methyl) benzyl) oxy)-N-methylethan-1-amine (Sidechain-30)

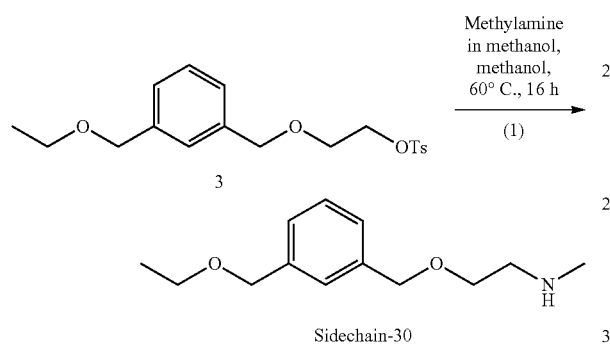

Sidechain-30

To a stirred solution of 2-(3-(ethoxy methyl) benzyl oxy) ethyl 4-methylbenzenesulfonate 3 (Synthesis of Cpd-3 was reported in Sidechain-29) (500 mg, 1.373 mmol) in methanol (3 mL) in a sealed tube was added 1M of MeNH$_2$ in methanol (5 mL) at room temperature then stirred at 60° C. for 16 h. After completion of reaction as indicated by TLC, organic solvents were evaporated and the crude residue was diluted with water (50 ml) and extracted with ethyl acetate (2×50 mL). Organic layer was washed with 1N HCL solution (20 mL) and saturated NaHCO$_3$ solution (20 mL), brine solution (50 mL), dried over Na$_2$SO$_4$ and concentrated to afford 2-(3-(ethoxy methyl)benzyl oxy)-N-methyl ethanamine Sidechain-30 (300 mg, 1.345 mmol, crude) as a yellow solid. TLC system: 10% Methanol in dichloromethane—R$_f$: 0.20; LCMS: m/z=224.38 (M+H)$^+$ Sidechain-31

2-(3-(2-ethoxyethoxy) phenyl) acetic acid (Sidechain-31)

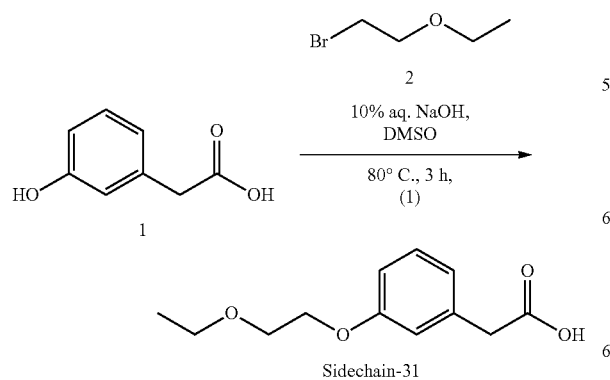

Sidechain-31

To a stirred solution of 2-(3-hydroxyphenyl) acetic acid 1 (2.0 g, 13.157 mmol) in 10% NaOH solution (10 ml) and DMSO (20 ml) at room temperature. The mixture was stirred at room temperature for 15 min. Then was added 1-bromo-2-ethoxyethane 2 (2.01 g, 13.15 mmol) to reaction mixture and stirred at 80° C. for 3 h. After consumption of starting material, the mixture was quenched with 1N HCl solution (20 mL) and extracted with ethyl acetate (3×50 mL) and washed with brine solution (50 mL), dried over sodium sulfate and concentrated. Crude compound was purified by (100-200 mesh silica gel) column chromatography and eluted with 40% ethyl acetate in hexanes to afford to obtain 2-(3-(2-ethoxyethoxy)phenyl)acetic acid Sidechain-31 (520 mg, 2.32 mmol, 18%) as an off white solid. TLC system: 100% ethyl acetate—R$_f$: 0.60; LCMS: m/z=225.08 (M+H)$^+$ Sidechain-32

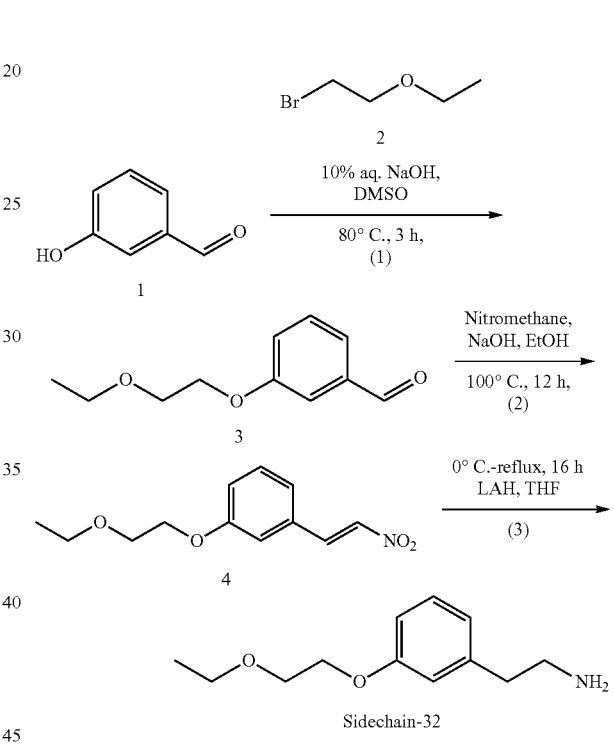

Sidechain-32

3-(2-ethoxyethoxy) benzaldehyde (3)

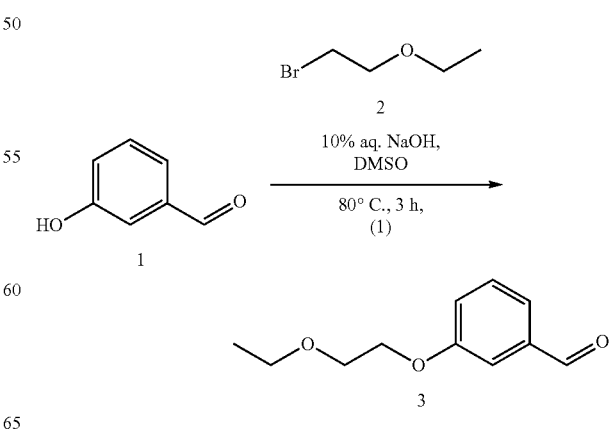

To a stirred solution of 3-hydroxybenzaldehyde 1 (15 g, 122.9 mmol) in DMSO (100 mL) and 10% aqueous NaOH solution was added 1-bromo-2-ethoxyethane 2 (34 mL, 307.3 mmol) in DMSO (50 mL) drop wise at 80° C. then stirred at same temperature for 10 h. After completion of reaction as indicated by TLC, reaction mixture was poured into 1M HCl solution (200 ml) and extracted with diethyl ether (2×500 mL). Combined organic layers were washed with brine solution (100 mL), dried over $Na_2SO_4$ and concentrated under reduced pressure to afford 3-(2-ethoxyethoxy) benzaldehyde 3 (5.4 g, 27.83 mmol, 22%) as a colorless oily liquid. TLC system: 30% ethyl acetate in pet ether—$R_f$: 0.50; LCMS: m/z=195.31 $(M+H)^+$ (E)-1-(2-ethoxyethoxy)-3-(2-nitrovinyl) benzene (4)

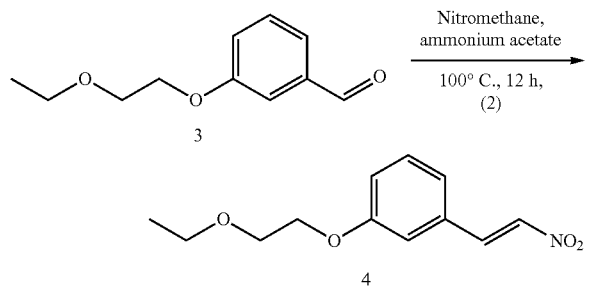

To a stirred solution of 3-(2-ethoxyethoxy) benzaldehyde (200 mg, 1.03 mmol) in nitromethane (0.55 mL, 10.3 mmol) was added ammonium acetate (88 mg, 1.133 mmol) at room temperature then stirred at 100° C. for 12 h. After completion of reaction as indicated by TLC, reaction mixture was diluted with water (50 ml) and extracted with ethyl acetate (2×30 mL). Combined organic layers were washed with brine solution (20 mL), dried over $Na_2SO_4$ and concentrated under reduced pressure. Crude compound was purified through grace column chromatography by eluting with 60% of acetonitrile in 0.1% of formic acid in water to afford (E)-1-(2-ethoxyethoxy)-3-(2-nitrovinyl) benzene 4 (120 mg, 0.506 mmol, 49%) as a colorless gummy liquid. TLC system: 100% dichloromethane—$R_f$: 0.50; LCMS: m/z=238.31 $(M+H)^+$ 2-(3-(2-ethoxyethoxy) phenyl) ethan-1-amine (Sidechain-32)

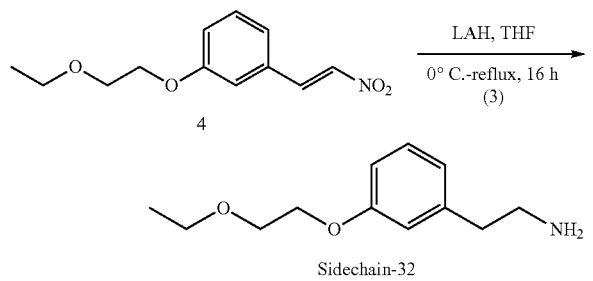

To a stirred solution of (E)-1-(2-ethoxyethoxy)-3-(2-nitrovinyl) benzene 4 (1.25 g, 5.27 mmol) in THF (15 mL) was added LAH in THF (1M, 26.3 mL, 26.37 mmol) at 0° C. then stirred at reflux for 16 h. After completion of reaction as indicated by TLC, the reaction mixture was diluted with ice water (100 mL) and extracted with ethyl acetate (2×100 mL). Combined organic layers were washed with brine solution (50 mL), dried over $Na_2SO_4$ and concentrated to afford 2-(3-(2-ethoxyethoxy) phenyl) ethan-1-amine Sidechain-32 (310 mg, 1.483 mmol, crude) as a reddish brown gummy liquid. TLC system: 10% Methanol in dichloromethane—$R_f$: 0.10; LCMS: m/z=210.32 $(M+H)^+$ Sidechain-33

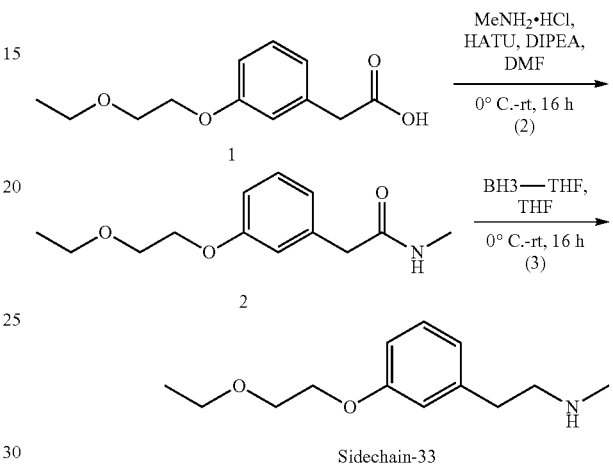

2-(3-(2-ethoxyethoxy) phenyl)-N-methyl acetamide (2)

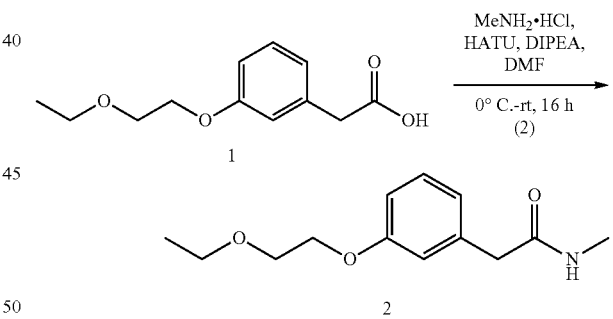

To a stirred solution of 2-(3-(2-ethoxyethoxy) phenyl) acetic acid 1 (Synthesis of Cpd-1 was reported in Sidechain-31) (400 mg, 1.785 mmol) in DMF (5 mL) was added methylamine hydrochloride (299 mg, 4.464 mmol), HATU (458 mg, 2.678 mmol) and DIPEA (1.24 mL, 7.143 mmol) at 0° C. and stirred at room temperature for 16 h. After completion of reaction as indicated by TLC, organic solvents were evaporated and to the crude residue water (50 ml) was added and extracted with ethyl acetate (2×50 mL). Combined organic layers were washed with brine solution (30 mL), dried over $Na_2SO_4$ and concentrated under reduced pressure. Crude compound was purified through 100-200 silica gel column chromatography by eluting with 2% methanol in dichloromethane to afford 2-(3-(2-ethoxyethoxy) phenyl)-N-methyl acetamide 2 (270 mg, 1.139 mmol, crude) as an off white solid. TLC system: 5% Methanol in dichloromethane—R$_f$: 0.50; LCMS: m/z=238.28 (M+H)$^+$

2-(3-(2-ethoxyethoxy) phenyl)-N-methylethan-1-amine (Sidechain-33)

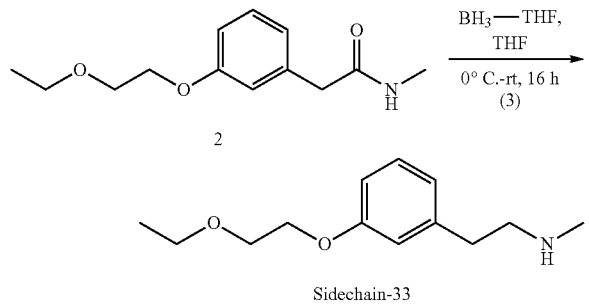

To a stirred solution of 2-(3-(2-ethoxyethoxy) phenyl)-N-methyl acetamide 2 (165 mg, 0.696 mmol) in THF (2 mL) was added 1M of BH$_3$-THF (2.08 mL, 2.088 mmol) at 0° C. then stirred at room temperature for 16 h. After completion of reaction as indicated by TLC, reaction mixture was quenched with methanol (20 mL) and organic solvents were evaporated. To the crude residue was added water (50 mL) and extracted with ethyl acetate (2×50 mL). Combined organic layers were washed with brine solution (30 mL), dried over Na$_2$SO$_4$ and concentrated under reduced pressure to afford 2-(3-(2-ethoxyethoxy)phenyl)-N-methylethan-1-amine Sidechain-33 (125 mg, 0.560 mmol, crude) as a reddish brown liquid. TLC system: 5% Methanol in dichloromethane—R$_f$: 0.70

Sidechain-34

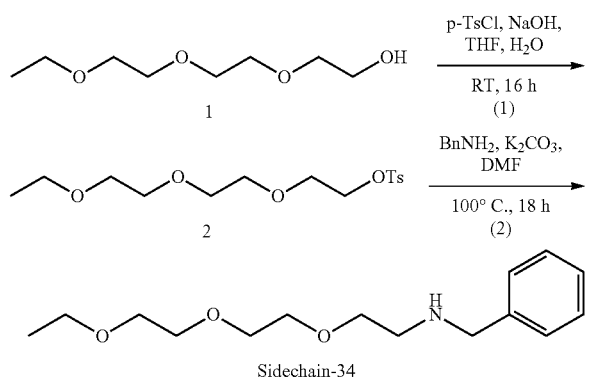

2-(2-(2-ethoxyethoxy) ethoxy) ethyl 4-methylbenzenesulfonate (2)

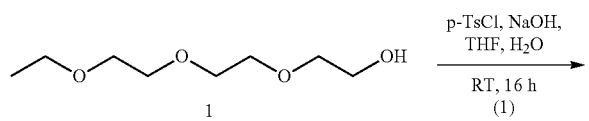

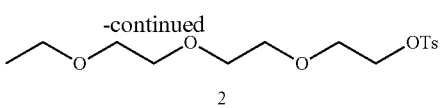

To a stirred solution of 2-(2-(2-ethoxyethoxy) ethoxy) ethan-1-ol 1 (8.5 g, 47.69 mmol) in THF (30 mL) was added NaOH (3.89 g, 97.415 mmol) in water (10 ml) at 0° C. The mixture was stirred at room temperature for 15 min. Then cooled to 0° C., p-toluene sulfonyl chloride (11.63 g, 61.04 mmol) was added to the reaction mixture and stirred at room temperature for 16 h. After consumption of starting material by TLC, the mixture was diluted with ethyl acetate (150 mL) and washed with ice cold water (2×20 mL), brine solution (20 mL), dried over sodium sulfate and concentrated. Crude compound was purified by 100-200 mesh silica gel column chromatography by eluting with 20% ethyl acetate in pet ether to afford 2-(2-(2-ethoxyethoxy) ethoxy) ethyl 4-methylbenzenesulfonate 2 (4 g, 12.048 mmol, 25% yield) as a brown liquid. TLC system: 40% ethyl acetate in pet ether—R$_f$: 0.50

N-benzyl-2-(2-(2-ethoxyethoxy) ethoxy) ethan-1-amine (Sidechain-34)

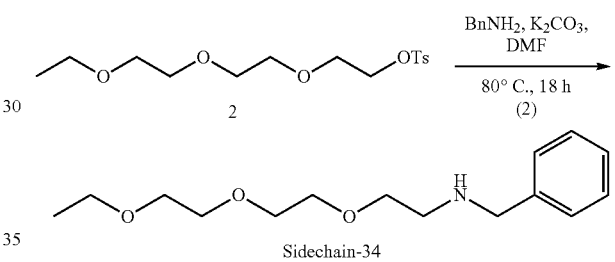

To a stirred solution of 2-(2-(2-ethoxyethoxy)ethoxy) ethyl 4-methylbenzenesulfonate 2 (500 g, 1.506 mmol) in DMF (5 ml) were added potassium carbonate (2 g, 15.06 mmol) and benzyl amine (273 mg, 2.409 mmol) at room temperature and stirred at 80° C. for 18 h. After completion of reaction (as indicated by TLC), ice water was added to the reaction mixture (100 ml) and extracted with ethyl acetate (2×100 mL). Organic layer was washed with brine solution (50 mL), dried over Na$_2$SO$_4$ and concentrated under reduced pressure. Crude compound was purified by combi flash chromatography by eluting with 10% methanol in DCM to afford N-benzyl-2-(2-(2-ethoxyethoxy) ethoxy) ethan-1-amine Sidechain 34 (500 mg, 0.93 mmol, 62% yield) as a yellow liquid. TLC system: 10% Methanol in dichloromethane—R$_f$: 0.20

Sidechain-35

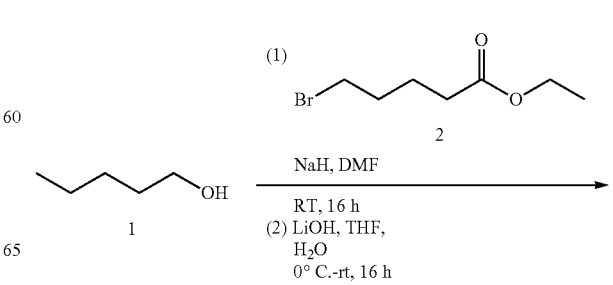

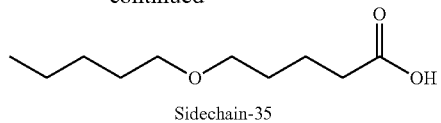

Sidechain-35 bined organic layers were washed with brine (2×15 mL) and dried over Na$_2$SO$_4$ and concentrated. The residue was washed with pentane (2×30 mL) to afford Sidechain-35 (150 mg, 0.797 mmol, 86% yield) as oily liquid. LC system: 50% ethyl acetate in hexanes—R$_f$: 0.10; LCMS: m/z=189.21 (M+H)$^+$ Ethyl 5-(pentyl oxy) pentanoate (3)

Sidechain-36

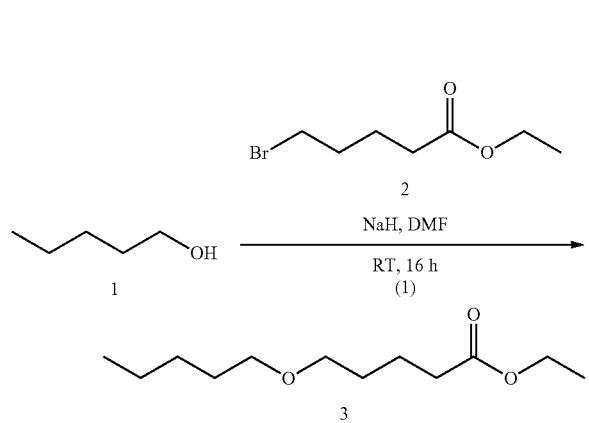

To a stirred solution of pentan-1-ol 1 (1.0 g, 11.36 mmol) in N,N-dimethyl formamide (10 mL) was added NaH (450 mg, 11.63 mmol) at 0° C. and stirred at room temperature for 30 min. Ethyl 5-bromopentanoate 2 (1.99 ml, 12.49 mmol) in N,N-dimethyl formamide (5 mL) was added to the above reaction mixture at 0° C. and stirred at room temperature for 16 h under nitrogen atmosphere. The reaction mixture was quenched with aqueous ammonium chloride solution and extracted with ethyl acetate (3×30 mL). Combined organic layers were washed with brine (2×50 mL) and dried over Na$_2$SO$_4$, evaporated under reduced pressure. Crude residue was purified by Column chromatography using 2% ethyl acetate in hexanes to afford ethyl 5-(pentyl oxy) pentanoate 3 (200 mg, 0.925 mmol, 8% yield) as a pale yellow oily liquid. LC system: 5% ethyl acetate in hexanes—R$_f$: 0.30

5-(pentyl oxy) pentanoic acid (Sidechain-35)

To a stirred solution of ethyl 5-(pentyl oxy) pentanoate (200 mg, 0.92 mmol) in a mixture of THF:H2O (4:1, 5 mL) was added lithium hydroxide (88 mg, 3.073 mmol) at 0° C. and stirred at room temperature for 16 h. Reaction mixture was evaporated under reduced pressure and the crude residue was washed with ether and acidified with aq. 1N HCl solution and extracted with ethyl acetate (3×10 ml). Com- 5-(pentyl oxy) pentan-1-ol (3)

To a stirred solution of pentane-1,5-diol 1 (10 g, 96.153 mmol) in N,N-dimethyl formamide (70 mL) was added 60% of NaH (4.2 g, 105.768 mmol) at 0° C. and stirred at room temperature for 1 h. The solution of 1-bromopentane (14.5 g, 96.153 mmol) in N,N-dimethyl formamide (30 mL) was added to above reaction mixture at 0° C. and stirred at room temperature for 16 h under nitrogen atmosphere. The reaction mixture was quenched with ice water and extracted with ethyl acetate (3×100 mL). Combined organic layers were washed with brine (2×100 mL) and dried over Na$_2$SO$_4$, evaporated under reduced pressure. Crude residue was purified by 100-200 silica gel column chromatography by using 20% ethyl acetate in hexanes to afford 5-(pentyl oxy)

pentan-1-ol 3 (7 g, 40.23 mmol, 43% yield) as a pale yellow oily liquid. LC system: 50% ethyl acetate in hexanes—$R_f$: 0.50

5-(pentyl oxy) pentyl 4-methylbenzenesulfonate (4)

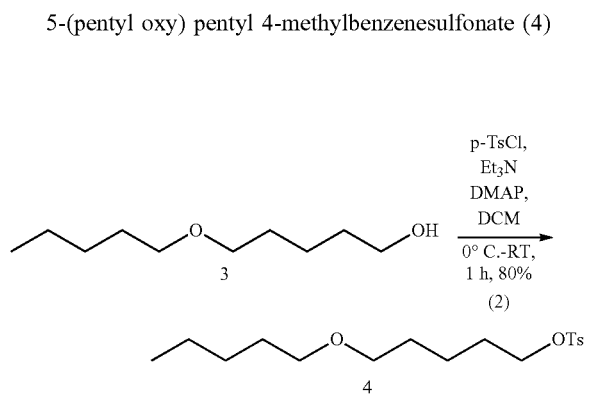

To a stirred solution of 5-(pentyl oxy) pentan-1-ol 3 (4 g, 22.98 mmol) in DCM (40 mL) was added triethylamine (7 g, 68.94 mmol) at 0° C. and DMAP (0.28 g, 2.298 mmol). The mixture was stirred at room temperature for 15 min. Then cooled to 0° C., p-toluene sulfonyl chloride (6.58 g, 34.48 mmol) was added to the reaction mixture and stirred at room temperature for 1 h. After consumption of starting material, the mixture was diluted with ethyl acetate (200 mL) and washed with ice cold water (2×200 mL), brine solution (100 mL), dried over sodium sulfate and concentrated under reduced pressure. Crude compound was purified by combi-flash chromatography by eluting with 10% ethyl acetate in hexanes to afford 5-(pentyl oxy)pentyl 4-methylbenzenesulfonate 4 (6 g, 18.29 mmol, 80% yield) as a colorless oily liquid. LC system: 20% ethyl acetate in hexanes—$R_f$: 0.50

1-azido-5-(pentyl oxy) pentane (5)

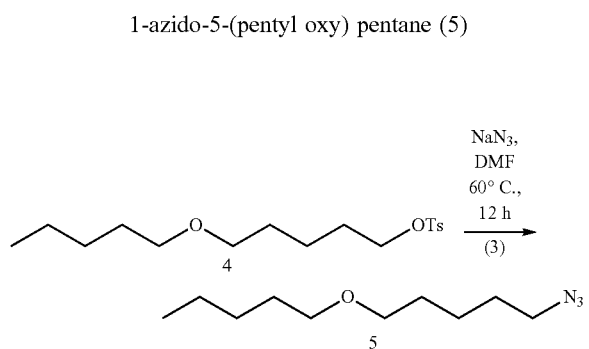

To a stirred solution of 5-(pentyl oxy) pentyl 4-methylbenzenesulfonate 4 (4.0 g, 12.195 mmol) in DMF (30 mL) was added NaN₃ (1.2 g, 18.292 mmol) at room temperature then stirred at 60° C. for 16 h. After completion of reaction as indicated by TLC, organic solvents were evaporated. To the crude residue was added water (2×200 ml) and extracted with ethyl acetate (2×100 mL). Organic layer was washed with brine solution (100 mL), dried over Na₂SO₄ and concentrated. Crude compound was purified by washed with pentane (3×25 mL) to obtain 1-azido-5-(pentyl oxy) pentane 5 (2.3 g, 11.55 mmol, 95%) as an oily liquid. TLC system: 20% ethyl acetate in hexanes $R_f$: 0.80

5-(pentyl oxy) pentan-1-amine (Sidechain-36)

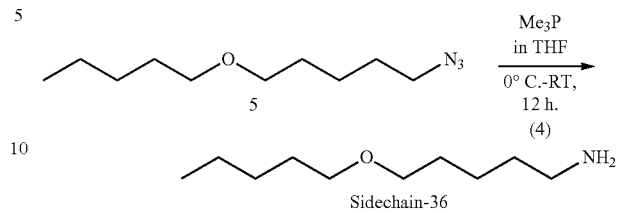

To a stirred solution 1-azido-5-(pentyl oxy) pentane (5) (2.3 g, 11.55 mmol) in THF:H₂O (30 mL) was added 1M of P(Me)₃ in THF (23 ml, 23.11 mmol) then stirred at room temperature for 12 h. After completion of reaction as indicated by TLC, evaporated organic solvents to afford 5-(pentyl oxy) pentan-1-amine Sidechain-36 (2.8 g, 16.185 mmol, crude) as an oily liquid. LC system: 50% ethyl acetate in hexanes—$R_f$: 0.10

N-methyl-5-(pentyl oxy) pentan-1-amine (Sidechain-37)

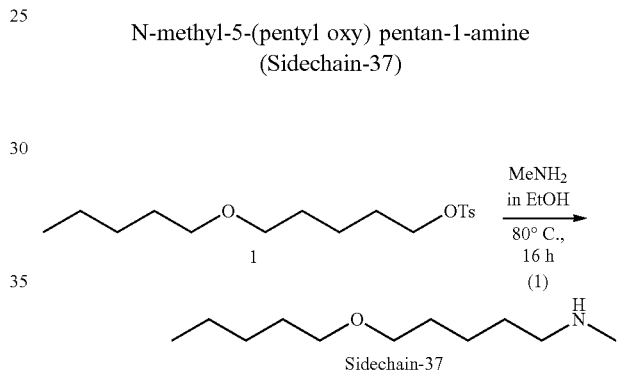

To a stirred solution of 5-(pentyl oxy) pentyl 4-methylbenzenesulfonate 1 (Synthesis of Cpd-1 was reported in Sidechain-36) (6 g, 18.29 mmol) in ethanol (20 mL) in a sealed tube was added 1M of methylamine in ethanol (91 mL, 91.45 mmol) at room temperature then stirred at 80° C. for 16 h. After completion of reaction as indicated by TLC, organic solvents were evaporated. To the crude residue water was added (2×200 ml) and extracted with ethyl acetate (2×100 mL). Organic layer was washed with 1% triethylamine solution in water (200 mL), brine solution (100 mL), dried over Na₂SO₄ and concentrated to afford N-methyl-5-(pentyl oxy)pentan-1-amine (Sidechain-37) (2.6 g, 13.90 mmol, 76%) as a pale yellow oily liquid. LC system: 10% Methanol in dichloromethane—$R_f$: 0.10

Example 2: Compound Preparation

Shown below are representative examples of the synthesis of certain of the compounds described herein, as well as intermediates used to prepare these compounds. Certain terms used in the reaction schemes shown below are defined as follows: SFC=Preparative supercritical fluid chiral separation; Borsm=Based on recovered starting material

Intermediate-013

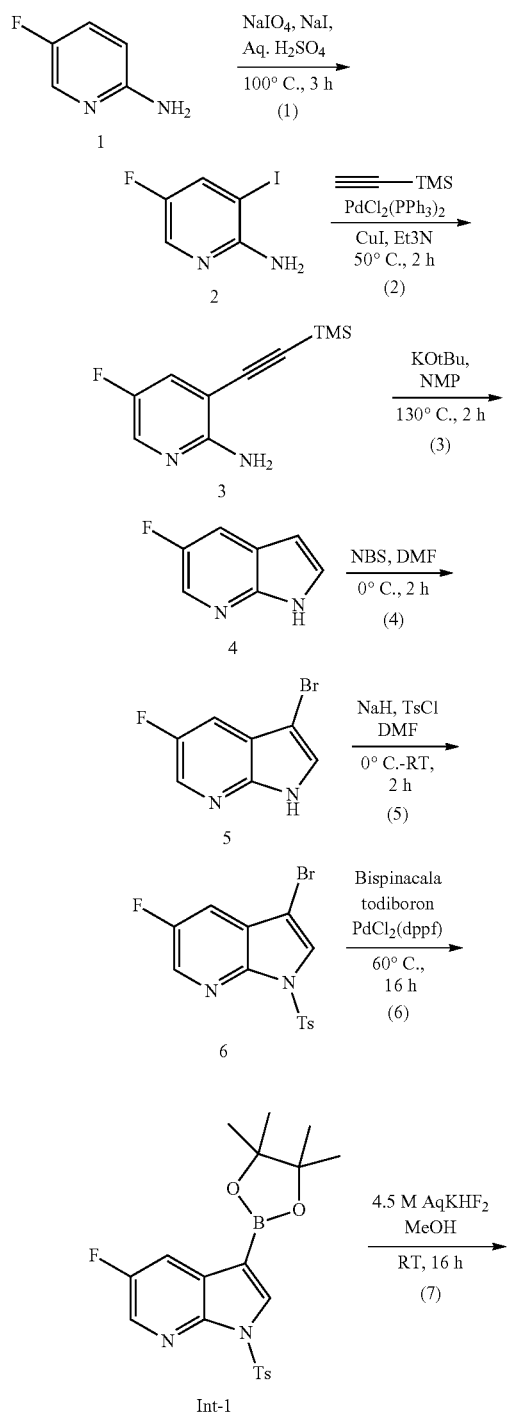

5-Fluoro-3-iodopyridin-2-amine (2)

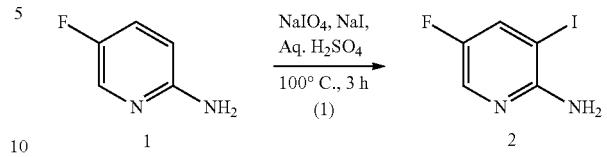

To a stirred solution of 5-fluoropyridin-2-amine (1) (10 g, 89.28 mmol) in 2 M aq.H$_2$SO$_4$ (150 mL) was added sodium meta periodate (7.5 g, 35 mmol) at 0° C. and heated at 100° C. Then, sodium iodide (13.5 g, 89.28 mmol) in water (30 mL) was added drop wise at same temp and maintained for 3 h. After consumption of starting material, the mixture was poured into ice cold water (300 mL), basified with solid NaHCO$_3$ (pH~8) and extracted with ethyl acetate (2×500 mL). The combined organic layer was washed with sodium thiosulfate solution (2×200 mL), water (200 mL) followed by brine solution (100 mL), dried over anhydrous sodium sulfate and concentrated under reduced pressure. The crude compound was purified by column chromatography using 100-200 silica and eluted with 15-20% ethyl acetate in pet ether to afford 5-fluoro-3-iodopyridin-2-amine (2) (12 g, 50 mmol, 56%) as brown solid. TLC system: 30% EtOAc in hexane R$_f$: 0.5 LCMS (ESI): m/z 239 [M+H]$^+$

5-fluoro-3-((trimethylsilyl)ethynyl)pyridin-2-amine (3)

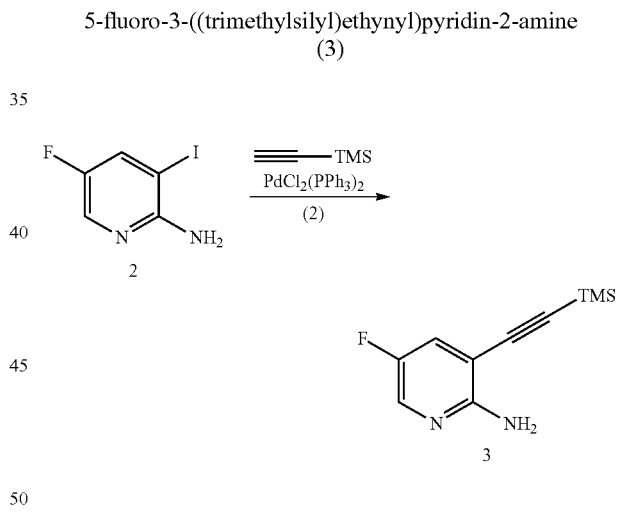

A mixture of 5-fluoro-3-iodopyridin-2-amine (Cmpd. 2) (12 g, 50 mmol), trimethylsilylethyne (10 mL, 75 mmol) and triethylamine (40 mL) in DMF (20 mL) was degassed with argon for 15 min. Then, dichlorobis(triphenylphosphine) palladium(II) (350 mg, 0.5 mmol) and CuI (280 mg, 1.5 mmol) were added, the reaction mixture was heated to 50° C. and stirred for 2 h. After consumption of starting material, the mixture was filtered through celite pad, washed the pad thoroughly with ethyl acetate. The combined filtrate was washed with water, brine solution, dried (anhydrous Na$_2$SO$_4$) and concentrated. Crude compound was purified by column chromatography using 100-200 silica and eluted compound with 5-10% ethyl acetate in pet ether to obtain 5-fluoro-3-((trimethylsilyl)ethynyl)pyridin-2-amine (3) (8 g, 38 mmol, 76%) as a yellow thick liquid. TLC system: 20% EtOAc in hexane R$_f$: 0.4 LCMS (ESI): m/z 209 [M+H]$^+$

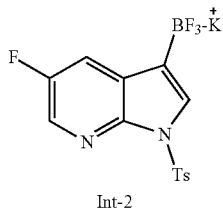

5-fluoro-1H-pyrrolo[2,3-b]pyridine (4)

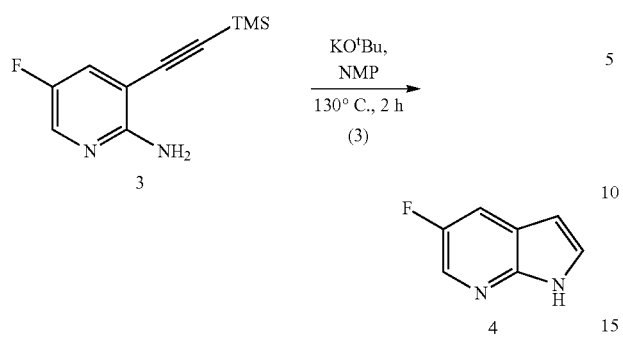

To a stirred solution of 5-fluoro-3-((trimethylsilyl)ethynyl)pyridin-2-amine (3) (500 mg, 2.4 mmol) in NMP (5 mL) was added potassium tert-butoxide (430 mg, 3.8 mmol) at rt. The reaction mixture was stirred at 130° C. for 2 h. After completion of the reaction as indicated by TLC, the mixture was poured into saturated aqueous sodium chloride solution (50 mL) and extracted with diethyl ether (3×100 mL). The combined organic layer was washed with ice cold water (2×50 mL), dried over anhydrous sodium sulphate and concentrated to obtain 5-fluoro-1H-pyrrolo[2,3-b]pyridine (4) (200 mg, 1.47 mmol, 61%) as pale brown solid. TLC system: 20% EtOAc in hexane $R_f$: 0.3 LCMS (ESI): m/z 137 [M+H]$^+$.

3-bromo-5-fluoro-1H-pyrrolo[2,3-b]pyridine (5)

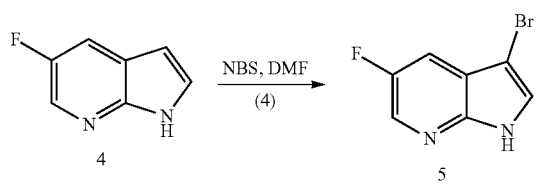 [SMILES: Fc1cnc2[nH]ccc2c1 ; Fc1cnc2[nH]cc(Br)c2c1]

To a stirred solution of 5-fluoro-1H-pyrrolo[2,3-b]pyridine (4.5 g, 33 mmol) in DMF (50 mL) was added NBS (6.4 g, 36 mmol) in portions at 0° C. and left it for 2 h. After completion of the reaction as indicated by TLC, the reaction mixture was poured into ice cold water (100 mL), filtered the precipitated solid and dried under vacuum to afford 3-bromo-5-fluoro-1H-pyrrolo[2,3-b]pyridine (5) (4.6 g, 21 mmol, 64%) as pale brown solid. TLC system: 20% EtOAc in hexanes $R_f$: 0.5 LCMS (ESI): m/z 215 [M+H]$^+$.

3-bromo-5-fluoro-1-tosyl-1H-pyrrolo[2,3-b]pyridine (6)

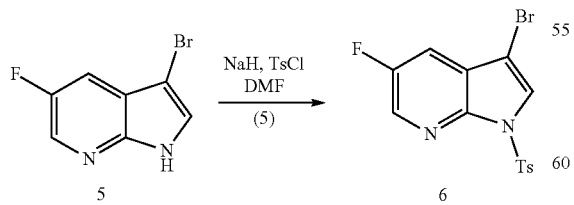

To a stirred suspension of NaH (1.3 g, 34 mmol) in DMF (30 mL) was added 3-bromo-5-fluoro 1H pyrrolo[2,3-b]pyridine 5 (4.6 g, 21 mmol) in DMF at 0° C. After 1 h, a solution of p-TsCl (5.7 g, 30 mmol) in DMF (20 mL) was added slowly at the same temperature and stirred for 2 h. After completion of the reaction as indicated by TLC, the mixture was poured into ice cold water (200 mL) and filtered the precipitated solid and dried to afford 3-bromo-5-fluoro-1-tosyl-1H-pyrrolo[2,3-b]pyridine (6) (6.2 g, 16 mmol, 76%) as an off-white solid. TLC system: 10% EtOAc in hexane $R_f$: 0.8 LCMS (ESI): m/z 369 [M+H]$^+$

5-fluoro-3-(4,4,5,5-tetramethyl-1,3,2-dioxaborolan-2-yl)-1-tosyl-1H-pyrrolo[2,3-b]pyridine (Intermediate-13-1)

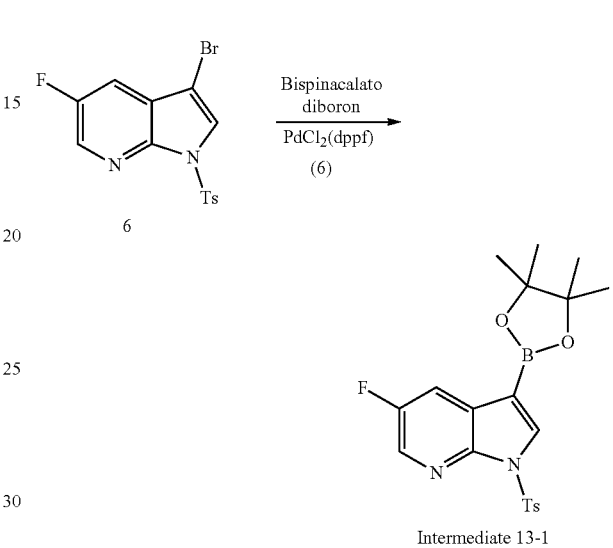

Intermediate 13-1

To a argon purged solution of 3-bromo-5-fluoro-1-tosyl-1H-pyrrolo[2,3-b]pyridine 6 (1 g, 2.7 mmol) in dioxane (10 mL) was added bispinacalatodiboron (2 g, 8.1 mmol), potassium acetate (0.8 g, 8.1 mmol) and PdCl$_2$(dppf) (0.2 g, 0.27 mmol) at RT. The reaction mixture was heated at 60° C. for 16 h in sealed tube. After consumption of the starting material, the mixture was diluted with ice cold water (50 mL) and extracted with EtOAc (3×100 mL). The combined organic layer was washed with brine solution (2×50 mL), dried over anhydrous sodium sulphate and concentrated. The crude residue was purified by combi-flash chromatography to afford 5-fluoro-3-(4,4,5,5-tetramethyl-1,3,2-dioxaborolan-2-yl)-1-tosyl-1H-pyrrolo[2,3-b]pyridine (Intermediate 13-1) (620 mg, 1.49 mmol, 55% yield) as white solid. TLC system: 20% EtOAc in hexane $R_f$: 0.3 LCMS (ESI): m/z 417 [M+H]$^+$.

Potassium trifluoro(5-fluoro-1-tosyl-1H-pyrrolo[2,3-b]pyridin-3-yl)borate (Intermediate-13-2)

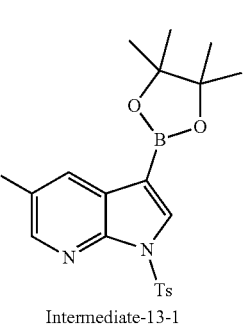

Intermediate-13-1

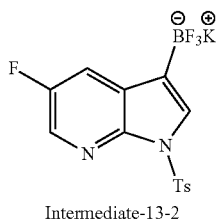

Intermediate-13-2

To a stirred solution of 5-fluoro-3-(4,4,5,5-tetramethyl-1,3,2-dioxaborolan-2-yl)-1-tosyl-1H-pyrrolo[2,3-b]pyridine (Intermediate-13-1) (36 g, 0.086 mol) in MeOH (100 mL) was added 4.5 M KHF$_2$ (29 g, 0.389 mol) at RT and the mixture was stirred for 6 h. After consumption of the starting material, the reaction mixture was concentrated under reduced pressure and co-distilled with MeOH for 3-4 times. The crude compound was dissolved in acetone (200 mL) and filtered to remove the undissolved inorganic solid. The filtrate was concentrated under reduced pressure and the resulting crude compound was triturated with diethyl ether until the less polar spot disappears on TLC to obtain potassium trifluoro(5-fluoro-1-tosyl-1H-pyrrolo[2,3-b]pyridin-3-yl)borate (Intermediate-13-2), 11 g, 27.7 mmol, 32%, as a brown solid. TLC system: 10% MeOH in DCM R$_f$: 0.1 LCMS (ESI): m/z 397 [M+H]$^+$.

Methyl 3-(2-chloro-7H-pyrrolo[2,3-d]pyrimidin-7-yl)propanoate

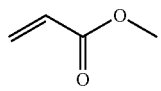

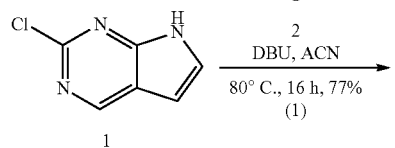

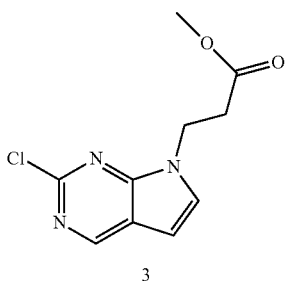

To a stirred solution of 2-chloro-7H-pyrrolo[2,3-d]pyrimidine 1 (1.0 g, 6.51 mmol) in ACN (8 mL) was added 1,8-Diazabicyclo[5.4.0]undec-7-ene (0.49 mL, 3.255 mmol) and methyl acrylate (2) (0.7 mL, 7.812 mmol) at RT and the mixture was stirred at 80° C. for 16 h. After consumption of the starting material, the mixture was quenched with water (25 mL) and extracted with EtOAc (3×50 mL). The combined organic layer was washed with brine solution (2×20 mL), dried over anhydrous sodium sulphate and concentrated. The crude residue was purified by combi-flash chromatography to afford methyl 3-(2-chloro-7H-pyrrolo[2,3-d]pyrimidin-7-yl)propanoate 3 (1.2 g, 5.02 mmol, 77% yield) as white solid. TLC system: 5% MeOH/DCM R$_f$: 0.3 LCMS (ESI): m/z 240.2 (M+H)$^+$ Intermediate-013-18

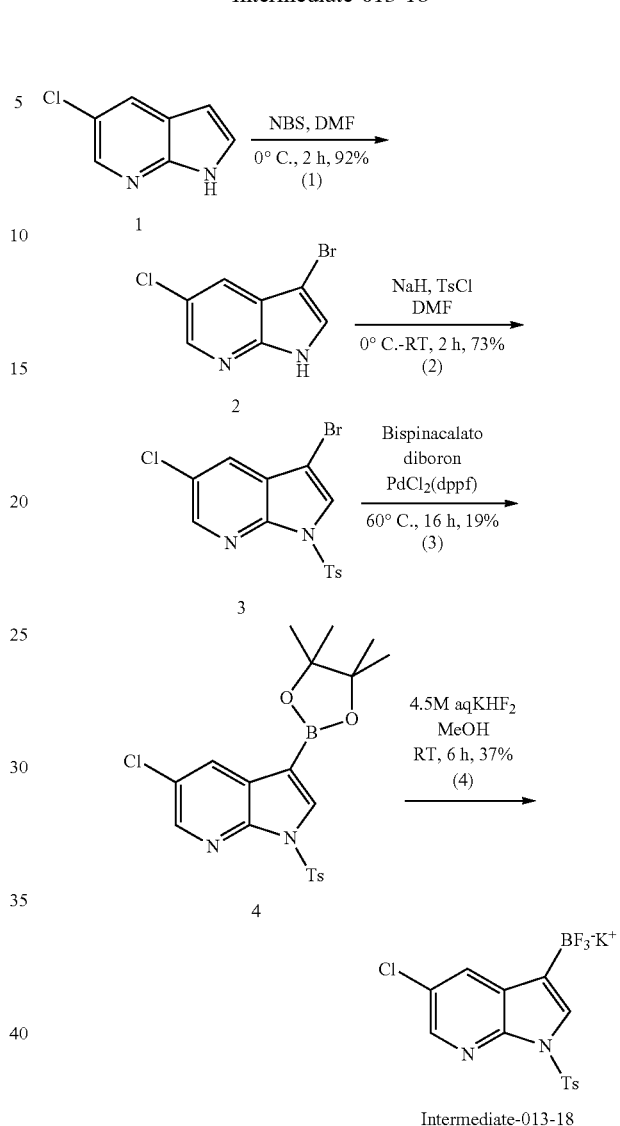

3-bromo-5-chloro-1H-pyrrolo[2,3-b]pyridine (2)

To a stirred solution of 5-chloro-1H-pyrrolo[2,3-b]pyridine 1 (5.0 g, 32.89 mmol) in acetone (50 mL) was added NBS (7.02 g, 39.46 mmol) in portions at 0° C. and stirred for 2 h. After completion of the reaction as indicated by TLC, the reaction mixture was concentrated under vacuum. Crude was diluted with water (50 mL) and extracted with EtOAc (3×100 mL). The combined organic layer was washed with brine solution (2×50 mL), dried over anhydrous sodium sulphate and concentrated to afford 3-bromo-5-chloro-1H- pyrrolo[2,3-b]pyridine 2 (7.0 g, 30.43 mmol, 92%) as pale brown solid. TLC system: 20% EtOAc in hexanes $R_f$: 0.5 LCMS (ESI): m/z 230.8 [M+H]$^+$.

3-bromo-5-chloro-1-tosyl-1H-pyrrolo[2,3-b]pyridine (3)

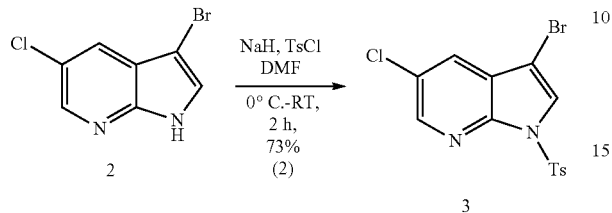

To a stirred suspension of NaH (1.4 g, 58.33 mmol) in DMF (30 mL) was added 3-bromo-5-chloro 1H pyrrolo[2,3-b]pyridine 2 (7.0 g, 30.43 mmol) in DMF at 0° C. After 1 h, a solution of p-TsCl (6.3 g, 33.47 mmol) in DMF (20 mL) was added slowly at the same temperature and stirred for 2 h. After completion of the reaction (as indicated by TLC), the mixture was poured in to ice cold water (200 mL), filtered the precipitated solid and dried to afford 3-bromo-5-chloro-1-tosyl-1H-pyrrolo[2,3-b]pyridine 3 (8.5 g, 22.14 mmol, 73%) as an off-white solid. TLC system: 10% EtOAc in hexane $R_f$: 0.8 LCMS (ESI): m/z 386.4 [M+H]$^+$ 5-chloro-3-(4,4,5,5-tetramethyl-1,3,2-dioxaborolan-2-yl)-1-tosyl-1H-pyrrolo[2,3-b]pyridine (4)

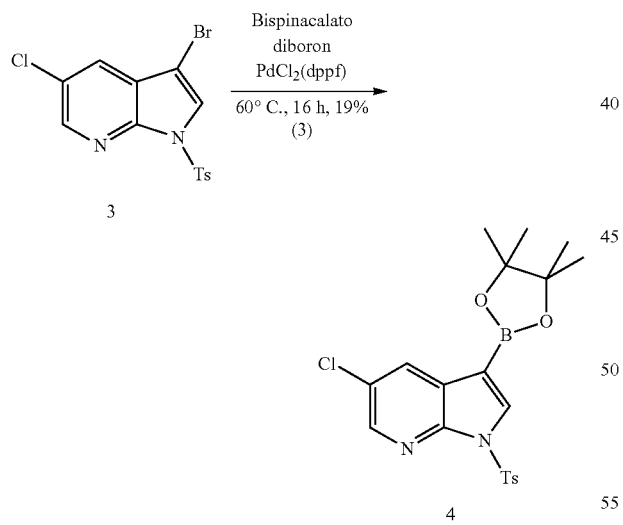

To an argon purged solution of 3-bromo-5-chloro-1-tosyl-1H-pyrrolo[2,3-b]pyridine 3 (2.8 g, 7.29 mmol) in DMF (10 mL) were added bispinacalatodiboron (3.71 g, 14.58 mmol), potassium acetate (2.14 g, 21.87 mmol) and PdCl$_2$(dppf) (678 mg, 0.729 mmol) at RT. The reaction mixture was heated at 60° C. for 16 h in sealed tube. After consumption of the starting material, the mixture was diluted with ice cold water (50 mL) and extracted with EtOAc (3×100 mL). The combined organic layer was washed with brine solution (2×50 mL), dried over anhydrous sodium sulphate and concentrated. The crude residue was purified by combi-flash chromatography to afford 5-chloro-3-(4,4,5,5-tetramethyl-1,3,2-dioxaborolan-2-yl)-1-tosyl-1H-pyrrolo[2,3-b]pyridine 4 (602 mg, 1.39 mmol, 19% yield) as white solid. TLC system: 20% EtOAc in hexane $R_f$: 0.3 LCMS (ESI): m/z 432.7 [M+H]$^+$.

Potassium (5-chloro-1-tosyl-1H-pyrrolo[2,3-b]pyridin-3-yl)trifluoroborate (13-int-18)

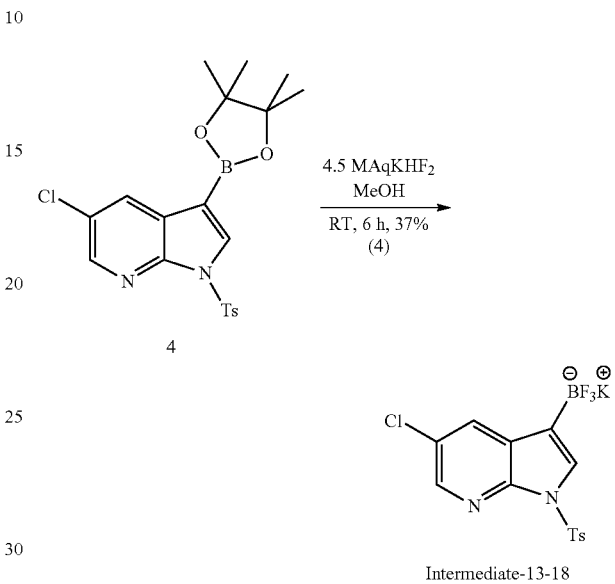

Intermediate-13-18

To a stirred solution of 5-chloro-3-(4,4,5,5-tetramethyl-1,3,2-dioxaborolan-2-yl)-1-tosyl-1H-pyrrolo[2,3-b]pyridine 4 (9.0 g, 20.83 mmol) in MeOH (50 mL) was added 4.5 M KHF$_2$ (7.32 g, 93.74 mmol) at RT for 6 h. After consumption of the starting material, the reaction mixture was concentrated under reduced pressure and co-distilled with MeOH for 3-4 times. The crude compound was dissolved in acetone (100 mL) and filtered the undissolved inorganic solid. Filtrate was concentrated under reduced pressure to get crude compound which was triturated with diethyl ether until the less polar spot disappears on TLC. Then the solid was filtered and dried to obtain potassiumtrifluoro(5-chloro-1-tosyl-1H-pyrrolo[2,3-b]pyridin-3-yl)borate Intermediate 13-18 (3.2 g, 7.766 mmol, 37%) as brown solid. TLC system: 10% MeOH in DCM $R_f$: 0.1 LCMS (ESI): m/z 351 [M-60]$^+$.

Intermediate-013-19

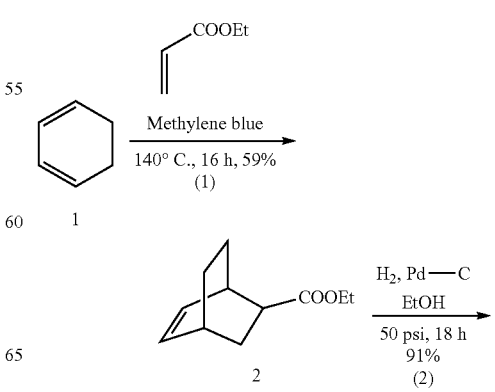

293
-continued

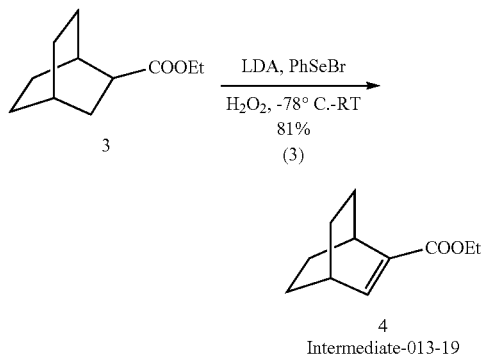

Intermediate-013-19

Ethyl (1R, 4R)-bicyclo[2.2.2]oct-5-ene-2-carboxylate (2)

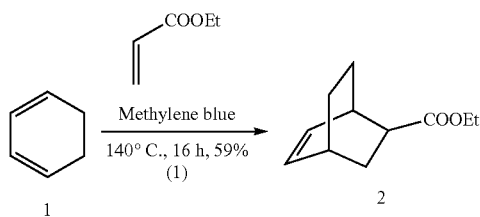

In a sealed tube cyclohexa-1,3-diene 1 (15.0 g, 187.19 mmol), Ethyl acrylate (18.74 g, 187.19 mmol) and Methylene blue (119 mg, 0.37 mmol) were placed and the mixture was heated at 140° C. for 16 h. After consumption of starting material, Ethyl (1R,4R)-bicyclo[2.2.2]oct-5-ene-2-carboxylate 2 (20.0 g, 111.11 mmol, 59% yield) was afforded by fractional distillation (at 70° C. and 0.1 mmHg) as colorless oil. 1 HNMR complies. TLC system: 5% EA in pet Ether R$_f$: 0.5

Ethyl (1S, 4S)-bicyclo[2.2.2]octane-2-carboxylate (3)

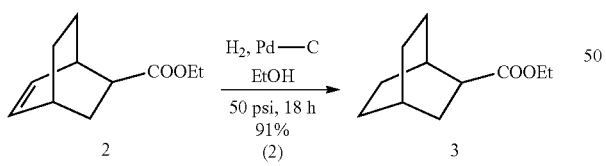

In a Parr shaker apparatus, a solution of Ethyl (1R,4R)-bicyclo[2.2.2]oct-5-ene-2-carboxylate 2 (20.0 g, 111.11 mmol) in EtOH (100 mL) was added 10% Pd/C (2.0 g, 10% w/w). The reaction mixture was stirred under H$_2$ gas at 50 Psi for 18 h. After consumption of starting material, the mixture was filtered through celite pad, washed the pad thoroughly with ethanol. The combined filtrate was concentrated under reduced pressure to afford Ethyl (1S,4S)-bicyclo[2.2.2]octane-2-carboxylate 3 (18.5 g, 101.64 mmol, 91% yield) as colorless oil. 1HNMR complies TLC system: 5% EtOAc in pet Ether R$_f$: 0.5

294

(1S, 4S)-ethyl bicyclo[2.2.2]oct-2-ene-2-carboxylate (4)

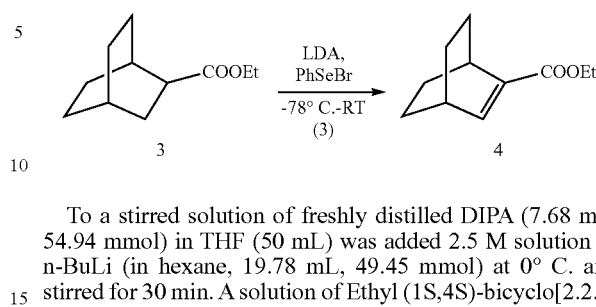

To a stirred solution of freshly distilled DIPA (7.68 mL, 54.94 mmol) in THF (50 mL) was added 2.5 M solution of n-BuLi (in hexane, 19.78 mL, 49.45 mmol) at 0° C. and stirred for 30 min. A solution of Ethyl (1S,4S)-bicyclo[2.2.2] octane-2-carboxylate 3 (5.0 g, 27.47 mmol) in THF (10 mL) was added at −78° C. and stirred at same temperature for 1 h. Then a solution of PhSeBr (9.724 g, 41.20 mmol) in THF was added at −78° C. and allowed to warm up to 0° C. and stirred for 30 min. Then added H$_2$O (35 mL), H$_2$O$_2$ (20 mL) fallowed by AcOH (7.5 mL) at 0° C. and allowed to stir at room temperature for 1 h, diluted with ethyl acetate and separated the two layers and the aqueous layer was extracted with ethyl acetate (2×50 mL). The combined organic layer was washed with water, brine solution, dried over Na$_2$SO$_4$ and concentrated. The crude compound was purified by column chromatography using 100-200 silica and eluted compound with 5-10% ethyl acetate in pet ether to afford (1S,4S)-ethyl bicyclo[2.2.2]oct-2-ene-2-carboxylate 4 (4.02 g, 22.33 mmol, 81% yield) as a yellow liquid. TLC system: 5% EtOAc in pet Ether R$_f$: 0.5 LCMS (ESI): m/z 181.1 (M+H)$^+$

Synthesis of Anti-Influenza Compounds

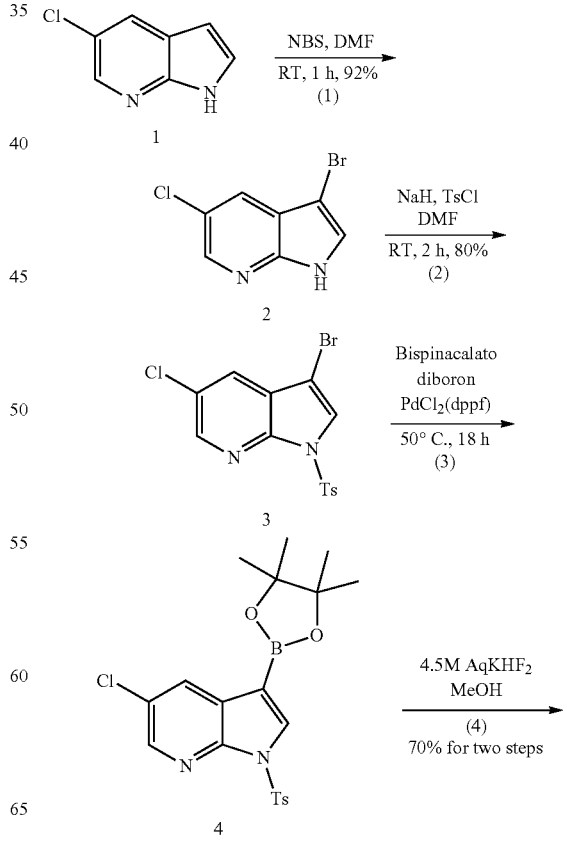

-continued
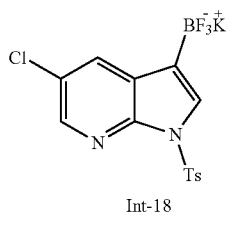
Int-18
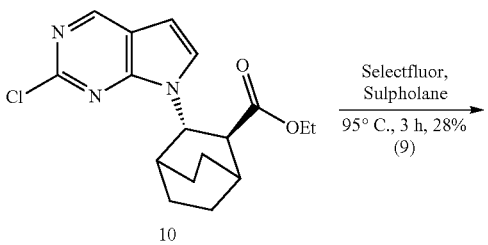
10
Synthesis of Int-19:
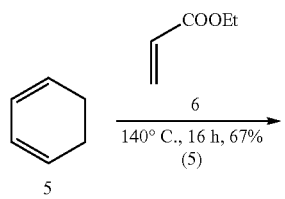
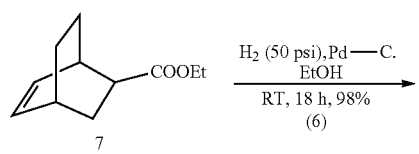
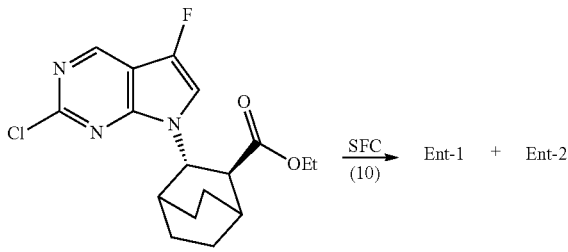
11
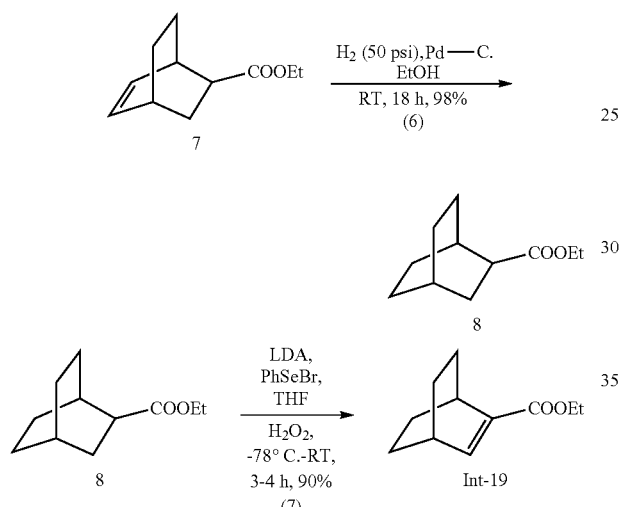
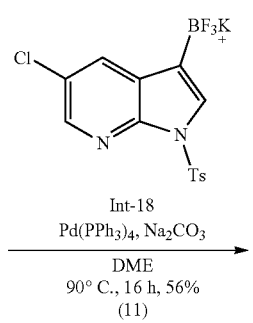
Ent-2
Int-18
Pd(PPh₃)₄, Na₂CO₃
DME
90° C., 16 h, 56%
(11)
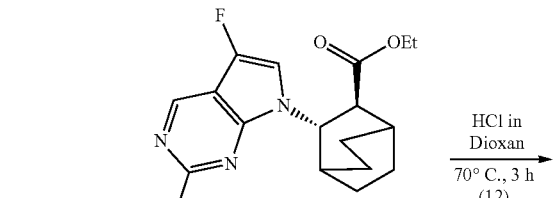
12
HCl in
Dioxan
70° C., 3 h
(12)
Compound 14A
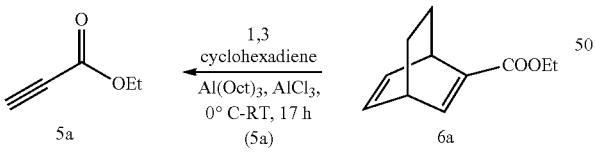
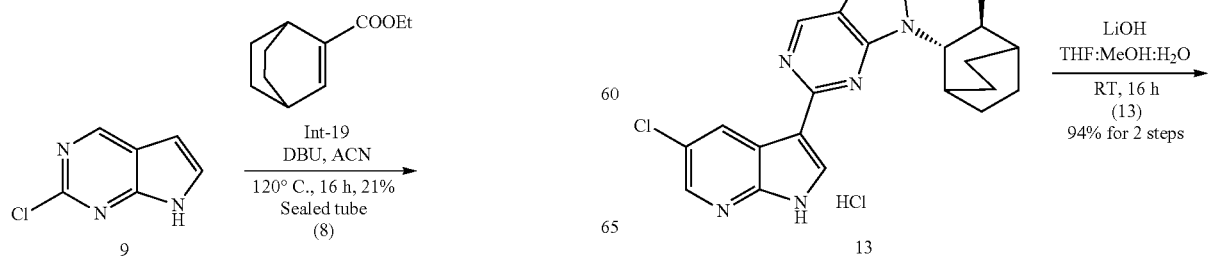
13
LiOH
THF:MeOH:H₂O
RT, 16 h
(13)
94% for 2 steps

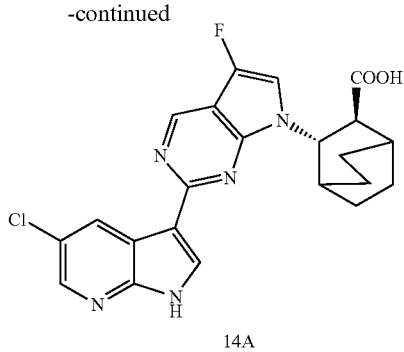

14A

Preparation of Int-18

3-Bromo-5-chloro-1H-pyrrolo[2,3-b]pyridine (2)

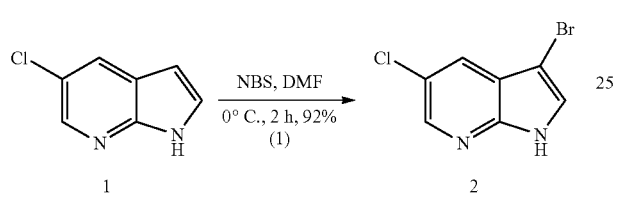

To a stirred solution of 5-chloro-1H-pyrrolo[2,3-b]pyridine (1) (50 g, 0.3289 mol) in DMF (200 mL) was added N-bromosuccinimide (70.26 g, 0.3947 mol) by portion wise at 0° C. and stirred for 2 h. After completion of the reaction as indicated by TLC, the reaction mixture was poured into ice cold water (600 mL) to form brown precipitate which was filtered and dried under air to afford 3-bromo-5-chloro-1H-pyrrolo[2,3-b]pyridine (2) (70 g, 0.3043 mol, 92% yield) as pale brown solid. TLC system: 20% EtOAc in hexane $R_f$: 0.5 LCMS (ESI): m/z 230.8 [M+H]$^+$ 3-Bromo-5-chloro-1-tosyl-1H-pyrrolo[2,3-b]pyridine (3)

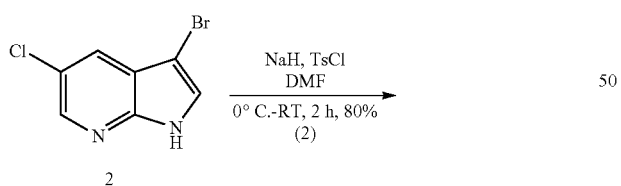

To a stirred suspension of 60% sodium hydride (5.7 g, 143 mmol) was added 3-bromo-5-chloro 1 Hpyrrolo[2,3-b]pyridine (2) (30 g, 130 mmol) in DMF (200 mL) at 0° C. After 1 h, a solution of 4-toluenesulfonyl chloride (37.17 g, 195 mmol) in DMF (100 mL) was added slowly at the same temperature and stirred for 2 h. After completion of the reaction (as indicated by TLC), the mixture was poured in to cold water (500 mL), filtered the precipitated solid and dried under reduced pressure to afford 3-bromo-5-chloro-1-tosyl-1H-pyrrolo[2,3-b]pyridine (3) (40 g, 103 mmol, 80% yield) as an off-white solid. TLC system: 10% EtOAc in hexane $R_f$: 0.8 LCMS (ESI): m/z 386.4 [M+H]$^+$ 5-Chloro-3-(4,4,5,5-tetramethyl-1,3,2-dioxaborolan-2-yl)-1-tosyl-1H-pyrrolo[2,3-b]pyridine (4)

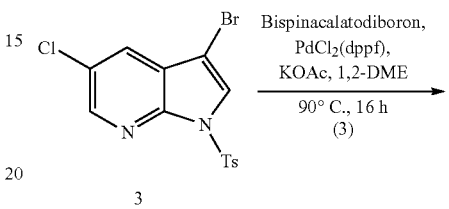

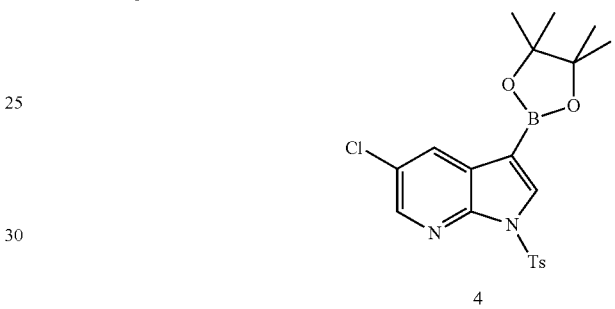

To an argon purged solution of 3-bromo-5-chloro-1-tosyl-1H-pyrrolo[2,3-b]pyridine (3) (2×50 g, 129 mmol) in 1,2-DME (2×500 mL) were added bispinacalatodiboron (2×49.6 g, 194 mmol), potassium acetate (2×38.1 g, 389 mol) and [1,1'-Bis(diphenylphosphino) ferrocene] dichloro palladium (II) (2×9.4 g, 12.9 mmol) at room temperature. The reaction mixture was stirred at 90° C. for 16 h. After consumption of the starting material, the reaction mixture was filtered through celite bed then filtrate was diluted with ice water (500 mL) and extracted with ethyl acetate (3×200 mL). The combined organic layer was washed with brine solution (100 mL), dried over anhydrous sodium sulfate, filtered and concentrated to get crude residue (130 g). The crude compound was used directly for next step without any purification. TLC system: 20% EtOAc in hexane $R_f$: 0.3

Potassium (5-chloro-1-tosyl-1H-pyrrolo[2,3-b]pyridin-3-yl)trifluoroborate (Int-18)

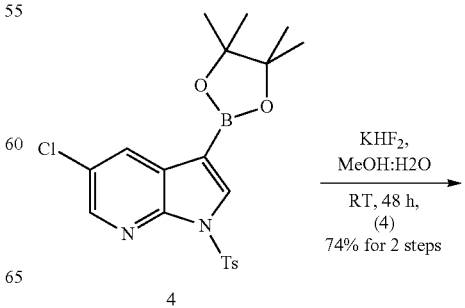

-continued

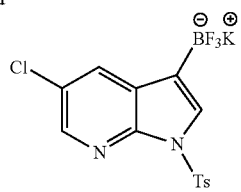

Int-18

To a stirred solution of 5-chloro-3-(4,4,5,5-tetramethyl-1,3,2-dioxaborolan-2-yl)-1-tosyl-1H-pyrrolo[2,3-b]pyridine (4) (130 g (crude)) in methanol (650 mL) was added aqueous potassium hydrogen fluoride (164 g, 2.10 mol) in water (260 mL) at room temperature for 48 h. The reaction mixture was concentrated under reduced pressure and co-distilled with methanol for 2 times. The crude compound was dissolved in acetone (350 mL) and filtered the undissolved inorganic solid. Filtrate was concentrated under reduced pressure to get crude compound which was triturated with diethyl ether and DCM (until the less polar spot disappears on TLC) to afford pure potassium (5-chloro-1-tosyl-1H-pyrrolo[2,3-b]pyridin-3-yl)trifluoroborate (Int-18) (80 g, 0.194 mol, 74% yield) as brown solid. TLC system: 10% MeOH in DCM $R_f$: 0.2 LCMS (ESI): m/z 351 (for corresponding boronic acid).

Preparation of Int-19

Ethyl (1R, 4R)-bicyclo[2.2.2]oct-5-ene-2-carboxylate (7)

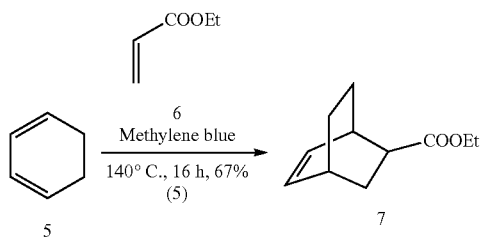

In a sealed tube cyclohexa-1,3-diene (5) (48.0 g, 600.0 mmol), ethyl acrylate 6 (50.0 g, 500.0 mmol) and methylene blue (320 mg, 1.0 mmol) were placed and the mixture was stirred at 140° C. for 16 h. After consumption of starting material, (Monitored by HNMR) the reaction mixture was distilled (fractional distillation at 70-80° C. and 0.1 mmHg) to afford ethyl (1R,4R)-bicyclo[2.2.2]oct-5-ene-2-carboxylate (7) (60.0 g, 333.0 mmol, 67% yield) as colorless liquid.

Ethyl (1S, 4S)-bicyclo[2.2.2]octane-2-carboxylate (8)

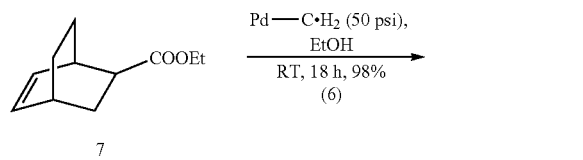

In a Parr shaker apparatus, a solution of ethyl (1R,4R)-bicyclo[2.2.2]oct-5-ene-2-carboxylate (7) (100.0 g, 555.0 mmol) in ethanol (250 mL) was added 10% Pd/C (8.0 g, 8% w/w). The reaction mixture was stirred under $H_2$ gas at 50 Psi for 16 h at room temperature. After consumption of starting material, the mixture was filtered through celite pad and the celite pad was washed with ethanol (3×). The combined filtrate was concentrated under reduced pressure to afford ethyl (1S,4S)-bicyclo[2.2.2]octane-2-carboxylate (8) (100 g, mmol, 98% yield) as a colorless liquid. TLC system: 5% EtOAc in pet Ether $R_f$: 0.5

Ethyl (1S, 4S)-bicyclo[2.2.2]oct-2-ene-2-carboxylate (Intermediate-19)

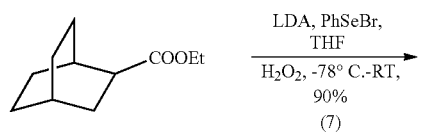

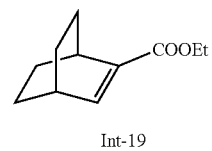

Int-19

To a stirred solution of freshly distilled diisopropylamine (69 mL, 494.5 mmol) in THF (230 mL) was added 2.5 M solution of n-butyl lithium (in hexane, 178 mL, 445.05 mmol) at −78° C. and stirred for 30 min, then allowed to 0° C. and stirred for 30 min. The reaction mixture was cooled to −78° C., added a solution of ethyl (1S,4S)-bicyclo[2.2.2]octane-2-carboxylate (8) (45.0 g, 247.25 mmol) in THF (45 mL) and stirred at same temperature for 1 h. Then a solution of phenylselenylbromide (75.85 g, 321.42 mmol) in THF (150 mL) was added at −78° C. and allowed to warm up to 0° C. and stirred for 30 min. After consumption of starting material indicated by TLC, the reaction mixture was quenched with saturated $NH_4Cl$ solution (250 mL) and diluted with ethyl acetate (250 mL). Then the organic layer was separated and taken into separate R B Flask which was fitted with condenser and cooled to 0° C. Then added water (150 mL), hydrogen peroxide (100 mL) followed by acetic acid (30 mL) at same temperature very slowly (observed exothermicity and frothing) and stirred at room temperature for 1 h. Then, the mixture was diluted with ethyl acetate (2×300 mL). The combined organic layer was washed with water (100 mL), brine solution (100 mL), dried over sodium sulfate, filtered and concentrated. The crude compound was purified by column chromatography (100-200 silica) and eluted with 5-10% ethyl acetate in pet ether to afford (1S,4S)-ethyl bicyclo[2.2.2]oct-2-ene-2-carboxylate (Int-19) (40 g, 222 mmol, 90% yield) as a yellow liquid. TLC system: 5% EtOAc in pet Ether $R_f$: 0.5 LCMS (ESI): m/z 181.1 (M+H)⁺ Note: PhenylselenylChloride (1.5 eq) was also used in place of Phenylselenylbromide (1.3 eq).

Alternative Scheme for Int-19

Ethyl (1R,4S)-bicyclo[2.2.2]octa-2,5-diene-2-carboxylate (7a)

To a stirred solution of AlCl₃ (1.98 g, 14.270 mmol) in heptane (10 mL) was added trioctyl aluminum (1.5 mL, 7.135 mmol) at 0° C. with drop wise and stirring was continued at same temperature for 1 h. Ethyl propiolate (5a) (2 g, 20.387 mmol) followed by 1,3 cyclohexadiene (2.1 g, 26.50 mmol) were added at 0° C. The reaction was left to stir at RT for 16 h. After completion of reaction; reaction mixture was cooled to 0° C. and quenched with 10% oxalic acid in water (40 mL) [exothermic observed] then extracted with diethyl ether (2×30 mL), combined the org layer washed with water (2×30 mL). Org layer was dried over sodium sulphate and concentrated under reduced pressure to afford crude product. This crude was purified by column chromatography using SiO₂ (100-200) with eluent 3-5% ethyl acetate in hexane to afford ethyl(1R,4S)-bicyclo[2.2.2] octa-2,5-diene-2-carboxylate (6a) (2.5 g, 14.04 mmol) as light green colour liquid.

Ethyl (1S, 4S)-bicyclo[2.2.2]oct-2-ene-2-carboxylate (Int-19)

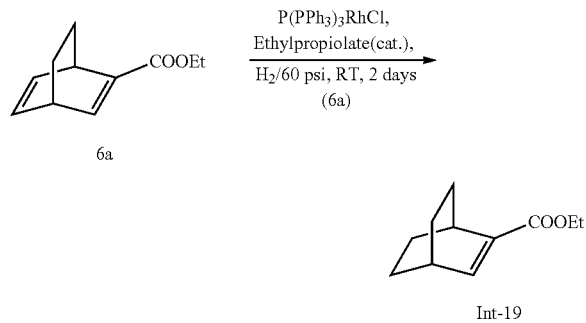

To a stirred solution of ethyl(1R,4S)-bicyclo[2.2.2]octa-2,5-diene-2-carboxylate (6a) (2.5 g, 14.04 mmol) in acetone (10 mL) was added Wilkinson's catalyst (60 mg, 0.064 mmol) followed by ethyl propiolate (50 μL, catalytic) and it was transferred into hydrogenator. Reaction was kept under 60 psi of hydrogen pressure at RT for 2 days. After completion of reaction; reaction mixture was filtered through celite bed and washed with acetone. Filtrate was evaporated under reduced pressure to afford crude product. This crude was purified by column chromatography using SiO₂ (100-200) with eluent 2-3% ethyl acetate in hexane to afford Ethyl (1S, 4S)-bicyclo[2.2.2]oct-2-ene-2-carboxylate (Intermediate-19) (1.8 g, 10.04 mmol) as colourless liquid.

Ethyl (2S, 3S)-3-(2-chloro-7H-pyrrolo[2,3-d]pyrimidin-7-yl)bicyclo[2.2.2]octane-2-carboxylate (10)

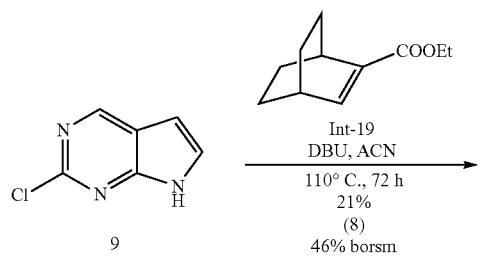

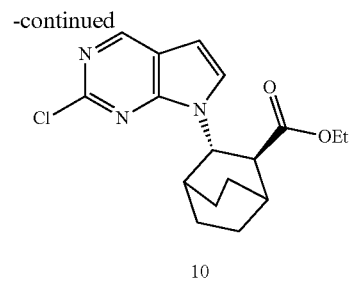

In a sealed tube, to a solution of 2-chloro-7H-pyrrolo[2,3-d]pyrimidine 9 (15.0 g, 97.7 mmol) in ACN (150 mL) was added DBU (14.85 g, 97.7 mmol) (Observed clear solution as pale yellow). Then added (1S,4S)-ethyl bicyclo[2.2.2]oct-2-ene-2-carboxylate Int-19 (19.34 g, 107.49 mmol) at same temperature and heated at 110° C. for 24 h. Then, ACN was removed under reduced pressure, the residue was diluted with water (150 mL) and extracted with ethyl acetate (2×200 mL). The combined organic layers were washed with brine solution (50 mL), dried over sodium sulfate and filtered. The filtrate was concentrated under reduced pressure. Crude compound was triturated with diethyl ether (~100 mL) and filtered to separate unreacted starting material 9 and the solid was washed with diethylether (50 mL). The combined filtrate layers were concentrated under reduced pressure and obtained crude compound was purified by column chromatography using 100-200 silica and eluted with 5% ethyl acetate in pet ether to isolate unreacted starting material Int-19 (7 g), further elusion with 15% ethyl acetate in pet ether afforded desired Ethyl-(2S,3S)-3-(2-chloro-7H-pyrrolo[2,3-d]pyrimidin-7-yl)bicyclo[2.2.2]octane-2-carboxylate 10 (7 g, 21.02 mmol, 21%) as an off-white solid. TLC system: 40% EtOAc in pet Ether R$_f$: 0.6 LCMS (ESI): m/z 334.1 (M+H)⁺

Ethyl (2S,3S)-3-(2-chloro-5-fluoro-7H-pyrrolo[2,3-d]pyrimidin-7-yl)bicyclo[2.2.2]octane-2-carboxylate (11) (racemic)

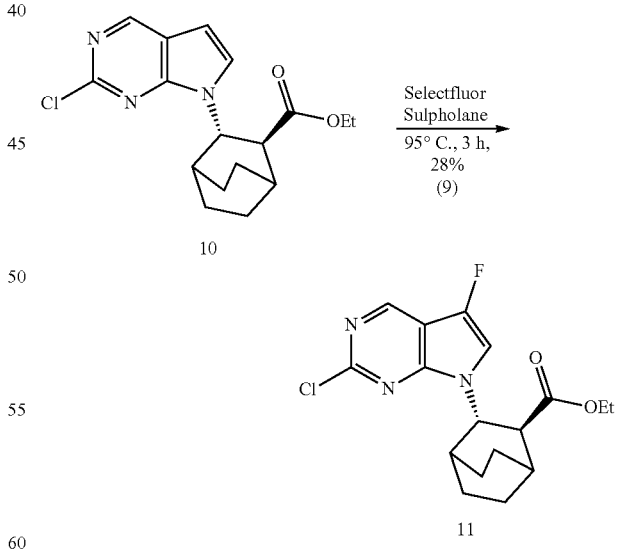

To a stirred solution of ethyl (2S,3S)-3-(2-chloro-7H-pyrrolo[2,3-d]pyrimidin-7-yl)bicyclo[2.2.2]octane-2-carboxylate (10) (4 g, 12.00 mmol) in Sulpholane (40 mL) was added selectfluor (5.1 g, 14.4 mmol) at room temperature in a 100 mL RBF. The RBF was dipped in a pre-heated oil bath at 95° C. and stirred for 3 h. After consumption of starting material as indicated by TLC, the reaction was cooled to room temperature, diluted with water (60 mL) and extracted with ethyl acetate (3×100 mL), washed the organic layer with water (50 mL), brine solution (50 mL), dried over sodium sulfate, and concentrated under reduced pressure. Crude compound was dissolved in diethyl ether and washed with cold water to remove remaining sulfolane. The ether layer was concentrated and the residue was purified by column chromatography using 230-400 silica and eluted compound with 7% ethyl acetate in pet ether to afford ethyl(2S,3S)-3-(2-chloro-7H-pyrrolo[2,3-d]pyrimidin-7-yl)bicyclo[2.2.2]octane-2-carboxylate (11) (1.2 g, 3.41 mmol, 28%) as off-white solid. TLC system: 20% EtOAc in pet Ether R$_f$: 0.5 LCMS (ESI): m/z 352.0 (M+H)$^+$ Ethyl (2S,3S)-3-(2-chloro-5-fluoro-7H-pyrrolo[2,3-d]pyrimidin-7-yl)bicyclo[2.2.2]octane-2-carboxylate (11)(Ent-2)

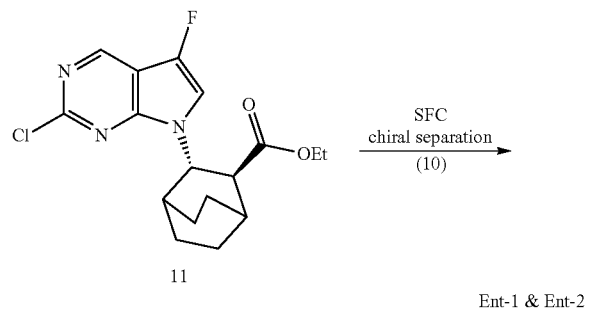

(2S,3S)-ethyl 3-(2-(5-chloro-1-tosyl-1H-pyrrolo[2,3-b]pyridin-3-yl)-5-fluoro-7H-pyrrolo[2,3-d]pyrimidin-7-yl)bicyclo[2.2.2]octane-2-carboxylate (12)

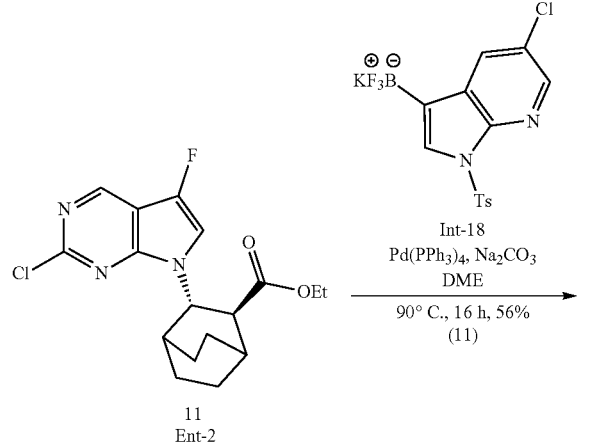

To a stirred solution of (2S,3S)-3-(2-chloro-5-fluoro-7H-pyrrolo[2,3-d]pyrimidin-7-yl)bicyclo[2.2.2]octane-2-carboxylate (11)(Ent-2) (1.5 g, 4.27 mmol), Int-18 (3.85 g, 9.39 mmol) and sodium carbonate (2.26 g, 21.35 mmol) in water (10 mL) and 1,2-DME (50 mL) was degassed with argon for 15 min. Then, added tetrakis (triphenylphosphine) palladium (1.48 g, 1.28 mmol) and again degassed with argon for 30 min. The reaction was heated at 90° C. for 16 h. After consumption of starting material, the reaction mixture was diluted with water (30 mL) and extracted with ethyl acetate (2×70 mL), combined organics ware washed with brine solution (15 mL), dried over sodium sulfate, filtered and concentrated under reduced pressure. Crude compound was purified by column chromatography using 100-200 silica and eluted compound with 20% ethyl acetate in pet ether to afford (2S,3S)-ethyl 3-(2-(5-chloro-1-tosyl-1H-pyrrolo[2,3-b]pyridin-3-yl)-5-fluoro-7H-pyrrolo[2,3-d]pyrimidin-7-yl)bicyclo[2.2.2]octane-2-carboxylate (12) (1.5 g, 2.41 mmol, 56% yield) as an off-white solid. TLC system: 40% EtOAc in pet Ether R$_f$: 0.4 LCMS (ESI): m/z 621.9 (M+H)$^+$ (2S,3S)-ethyl 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylate hydrochloride salt (13)

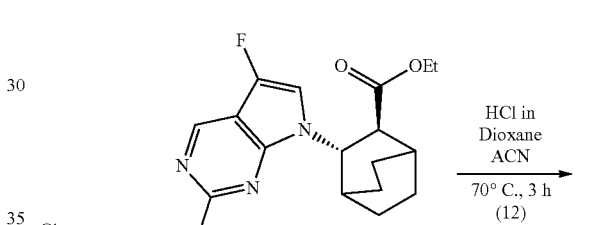

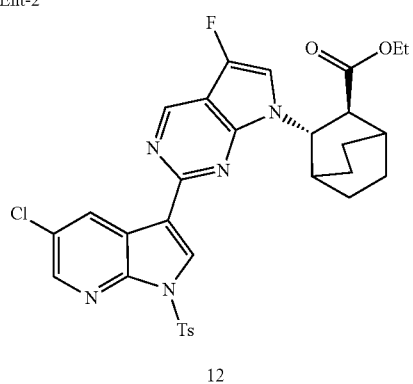

In a sealed tube a solution of ethyl (2S,3S)-3-(5-fluoro-2-(5-fluoro-1-tosyl-1H-pyrrolo[2,3-b]pyridin-3-yl)-7H-pyrrolo[2,3-d]pyrimidin-7-yl)bicyclo[2.2.2]octane-2-carboxylate (12) (3.0 g, 4.83 mmol) in Acetonitrile (30 mL) was added 4N of hydrogen chloride in dioxane (15 mL), closed the cap tightly in a sealed tube and heated at 70° C. for 3 h. After completion of reaction as indicated by TLC, the reaction was cooled to room temperature, diluted with diethyl ether (50 mL) to form yellow precipitate, filtered and dried to afford (2S,3S)-ethyl 3-(2-(5-chloro-1H-pyrrolo[2,3- b]pyridin-3-yl)-5-fluoro-7H-pyrrolo[2,3-d]pyrimidin-7-yl)bicyclo[2.2.2]octane-2-carboxylate hydrochloride salt (13) (2.5 g, HCl salt) as yellow solid. TLC system: 40% Ethyl-acetate in pet ether $R_f$: 0.2 LCMS (ESI): m/z 468.0 (M+H)$^+$ (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A)

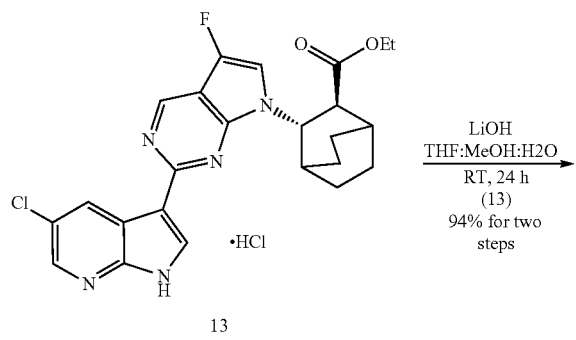

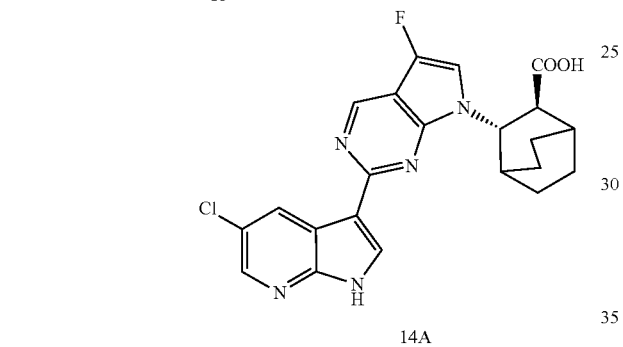

To a stirred solution of (2S,3S)-ethyl 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylate hydrochloride salt (13) (2.5 g, 4.97 mmol) in THF (30 mL) and MeOH (10 mL) was added a solution of Lithium hydroxide.H$_2$O (2.08 g, 49.7 mmol) in water (10 mL) at 0° C. then allowed to room temperature and stirred for 24 h. The volatiles were removed under reduced pressure and the crude was diluted with water (10 mL) and acidified by 6 N HCl to adjust the $_p$H~3 to form an off white solid, filtered the solid and washed with water, dried under air to afford (2S,3S)-3-(2-(5-chloro-1H-pyrrolo[2,3-b]pyridin-3-yl)-5-fluoro-7H-pyrrolo[2,3-d]pyrimidin-7-yl)bicycle [2.2.2]octane-2-carboxylic acid (2.0 g, 4.55 mmol, 94% for two steps) as off white solid. TLC system: 10% MeOH in DCM $R_f$: 0.5 LCMS (ESI): m/z 424.14 (M+H)$^+$ Ent-2

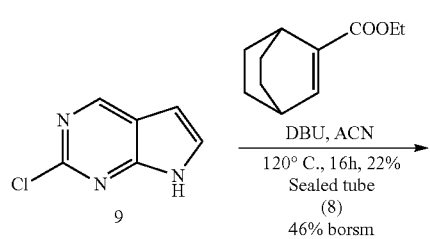

-continued

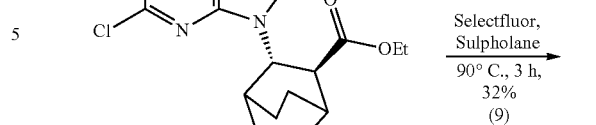

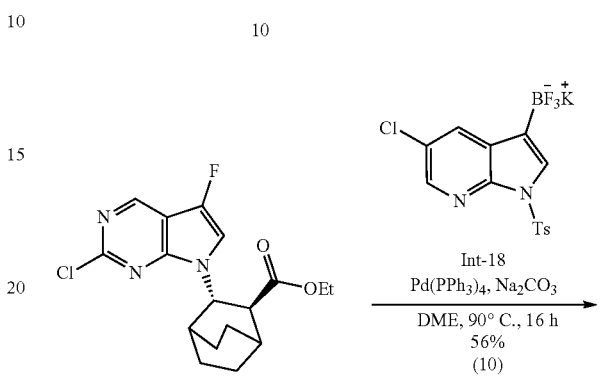

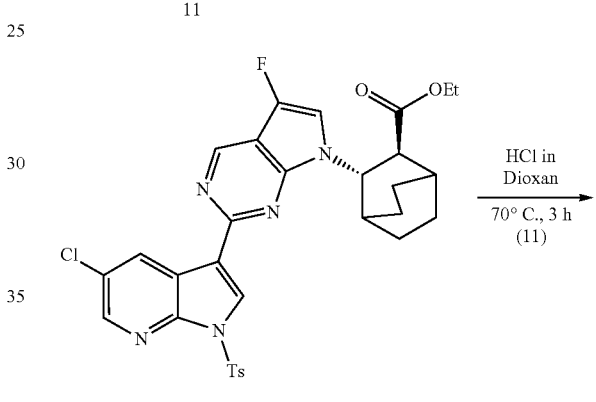

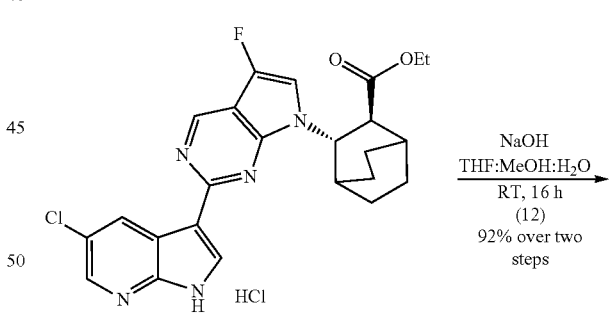

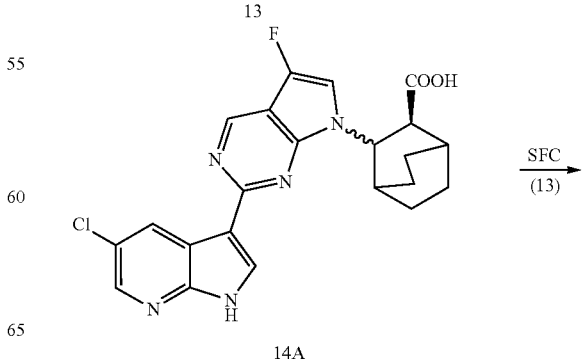

307

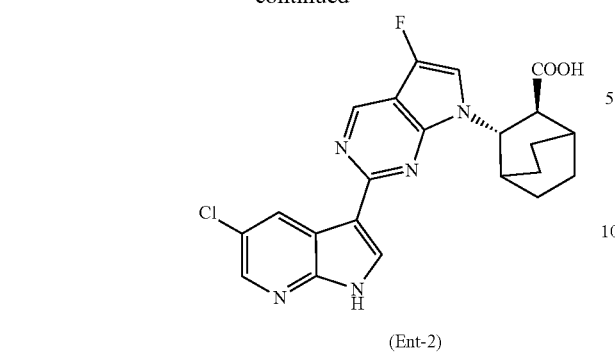

(Ent-2)

Ethyl (2S, 3S)-3-(2-chloro-7H-pyrrolo[2,3-d]pyrimidin-7-yl)bicyclo[2.2.2]octane-2-carboxylate (10)

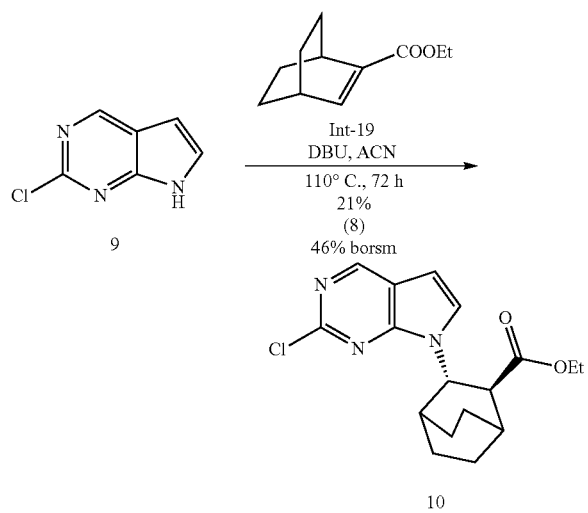

In a sealed tube, to a solution of 2-chloro-7H-pyrrolo[2,3-d]pyrimidine 9 (15.0 g, 97.7 mmol) in ACN (150 mL) was added DBU (14.85 g, 97.7 mmol) (Observed clear solution as pale yellow). Then added (1S,4S)-ethyl bicyclo[2.2.2]oct-2-ene-2-carboxylate Int-19 (19.34 g, 107.49 mmol) at same temperature and heated at 110° C. for 24 h. Then, ACN was removed under reduced pressure, the residue was diluted with water (150 mL) and extracted with ethyl acetate (2×200 mL). The combined organic layers were washed with brine solution (50 mL), dried over sodium sulfate and filtered. The filtrate was concentrated under reduced pressure. Crude compound was triturated with diethyl ether (~100 mL) and filtered to separate unreacted starting material 9 and the solid was washed with diethylether (50 mL). The combined filtrate layers were concentrated under reduced pressure and obtained crude compound was purified by column chromatography using 100-200 silica and eluted with 5% ethyl acetate in pet ether to isolate unreacted starting material Int-19 (7 g), further elusion with 15% ethyl acetate in pet ether afforded desired Ethyl-(2S,3S)-3-(2-chloro-7H-pyrrolo[2,3-d]pyrimidin-7-yl)bicyclo[2.2.2]octane-2-carboxylate 10 (7 g, 21.02 mmol, 21%) as an off-white solid. TLC system: 40% EtOAc in pet Ether R$_f$: 0.6 LCMS (ESI): m/z 334.1 (M+H)$^+$

308

Ethyl (2S,3S)-3-(2-chloro-5-fluoro-7H-pyrrolo[2,3-d]pyrimidin-7-yl)bicyclo[2.2.2]octane-2-carboxylate (11)

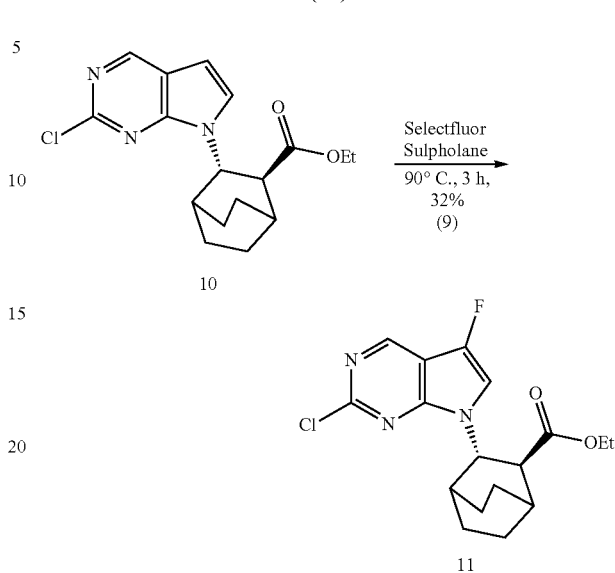

To a stirred solution of ethyl (2S,3S)-3-(2-chloro-7H-pyrrolo[2,3-d]pyrimidin-7-yl)bicyclo[2.2.2]octane-2-carboxylate (10) (3 g, 9.00 mmol) in Sulpholane (30 mL) was added Selectfluor (3.82 g, 10.8 mmol) and at room temperature. The reaction was immersed in a pre-heated oil bath and maintained at 90° C. for 3 h. The reaction was cooled to room temperature, diluted with water (50 mL) and extracted with ethyl acetate (3×75 mL), washed the organic layer with water (30 mL), brine solution (35 mL), dried over sodium sulfate and filtered. The filtrate was concentrated under reduced pressure. Crude compound was filtered through small plug of silica using 7-15% of EtOAc in pet ether and the crude after concentrated was re-purified by column chromatography using 230-400 silica and eluted compound with 7% ethyl acetate in pet ether to afford ethyl-(2S,3S)-3-(2-chloro-5-fluoro-7H-pyrrolo[2,3-d]pyrimidin-7-yl)bicyclo[2.2.2]octane-2-carboxylate (11) (1.0 g, 2.84 mmol, 31%) as off-white solid. TLC system: 20% EtOAc in pet Ether R$_f$: 0.5 LCMS (ESI): m/z 352.0 (M+H)$^+$ (2S,3S)-ethyl 3-(2-(5-chloro-1-tosyl-1H-pyrrolo[2,3-b]pyridin-3-yl)-5-fluoro-7H-pyrrolo[2,3-d]pyrimidin-7-yl)bicyclo[2.2.2]octane-2-carboxylate (12)

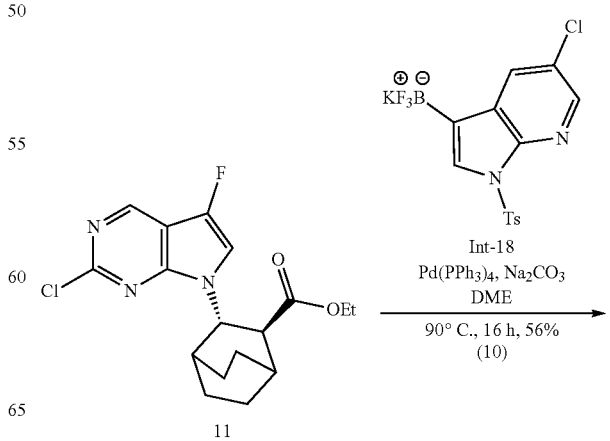

-continued

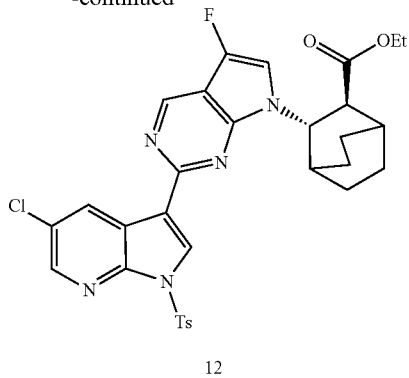

12

To a stirred solution of (2S,3S)-3-(2-chloro-5-fluoro-7H-pyrrolo[2,3-d]pyrimidin-7-yl)bicyclo[2.2.2]octane-2-carboxylate (3) (3 g, 8.54 mmol), Int-18 (7.747 g, 18.8 mmol) and sodium carbonate (4.52 g, 42.73 mmol) in water (25 mL) and 1,2-DME (100 mL) was degassed with argon for 15 min. Then, added tetrakis (triphenylphosphine) palladium (1.48 g, 1.28 mmol) and again degassed with argon for 10 min. The reaction was heated at 90° C. for 16 h. The reaction mixture was cooled to rt, diluted with water (50 mL) and extracted with ethyl acetate (2×100 mL), combined organics ware washed with brine solution (15 mL), dried over sodium sulfate, filtered and concentrated under reduced pressure. Crude compound was purified by column chromatography using 100-200 silica and eluted compound with 20% ethyl acetate in pet ether to afford (2S,3S)-ethyl 3-(2-(5-chloro-1-tosyl-1H-pyrrolo[2,3-b]pyridin-3-yl)-5-fluoro-7H-pyrrolo[2,3-d]pyrimidin-7-yl)bicyclo[2.2.2]octane-2-carboxylate (12) (3 g, 4.83 mmol, 56% yield) as an off-white solid. TLC system: 40% EtOAc in pet Ether R$_f$: 0.4 LCMS (ESI): m/z 621.9 (M+H)$^+$ (2S,3S)-ethyl 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylate hydrochloride salt (13)

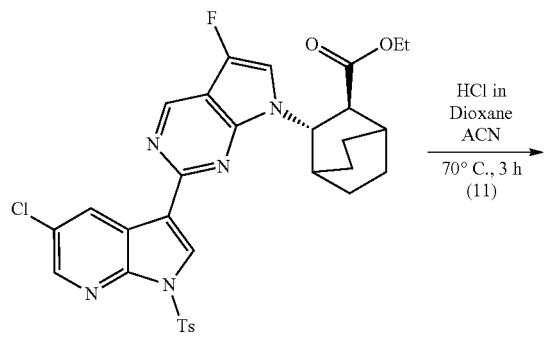

In a sealed tube, a solution of ethyl (2S,3S)-3-(5-fluoro-2-(5-fluoro-1-tosyl-1H-pyrrolo[2,3-b]pyridin-3-yl)-7H-pyrrolo[2,3-d]pyrimidin-7-yl)bicyclo[2.2.2]octane-2-carboxylate (12) (8.0 g, 12.88 mmol) in Acetonitrile (50 mL) was added 4N of hydrogen chloride in 1,4-dioxane (25 mL), closed the cap tightly and heated at 70° C. for 3 h. After completion of reaction as indicated by TLC, the reaction was cooled to room temperature, diluted with diethyl ether (50 mL) to form yellow precipitate which was filtered and dried under vacuum to afford (2S,3S)-ethyl 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylate hydrochloride salt (13) (7.5 g) as yellow solid. TLC system: 40% Ethylacetate in pet ether R$_f$: 0.2 LCMS (ESI): m/z 468.0 (M+H)$^+$ (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (racemic 14A)

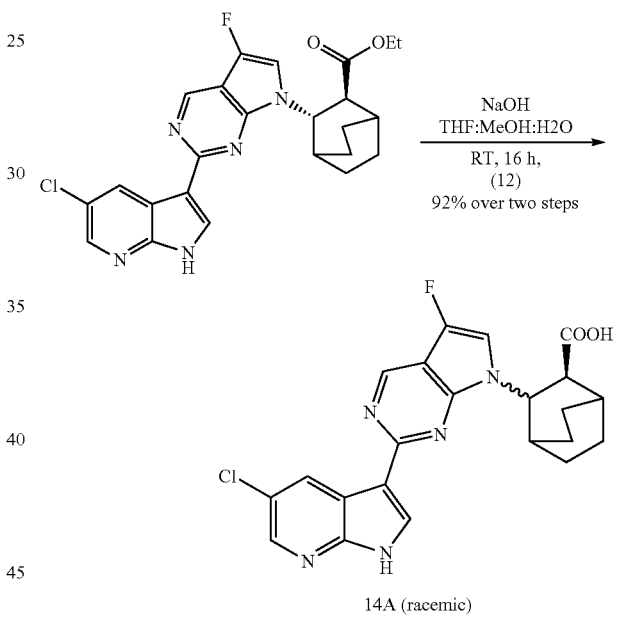

To a stirred solution of (2S,3S)-ethyl 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylate hydrochloride salt (13) (7.5 g, 14.89 mmol) in THF (75 mL) and MeOH (25 mL) was added a solution of sodium hydroxide (2.97 g, 74.47 mmol) in water (25 mL) at 0° C., then allowed to room temperature and stirred for 16 h. The volatiles were removed under vacuum and the crude was acidified by 1N HCl to adjust the PH-3 to form white precipitate, filtered washed with water and dried under air to afford racemic (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (5.2 g, 11.84 mmol, overall yield for two step 92%) as an off-white solid. Note: 4% of Transesterification was observed in LCMS, later lithium hydroxide was used in place of sodium hydroxide, where trans-esterification was not observed. TLC system: 10% MeOH in DCM R$_f$: 0.5 LCMS (ESI): m/z 440.14 (M+H)$^+$

311

(2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A Enantiomers)

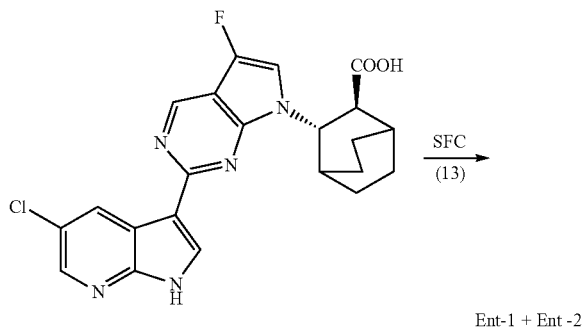

Ent-1 + Ent-2

3.6 g of racemic (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A) was separated by Chiral SFC using column as Chiralcel-OD-H (250×30) mm, 5p to afford (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A) (1 g, 95.8% ee) as an off white solid. Note: 1.0 g/95.8% ee of 14A was re-purified by SFC Chiralcel-AD-H to obtain (600 mg/99.04% ee) as an off-white solid.

Reaction Scheme Involving Fluorination Before Michael addition

14A Enantiomers 1 and 2

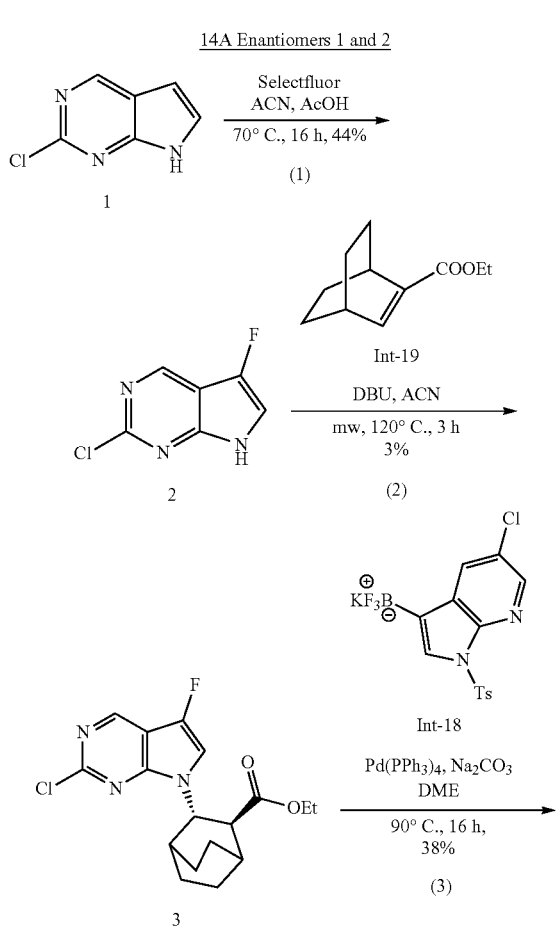

312

-continued

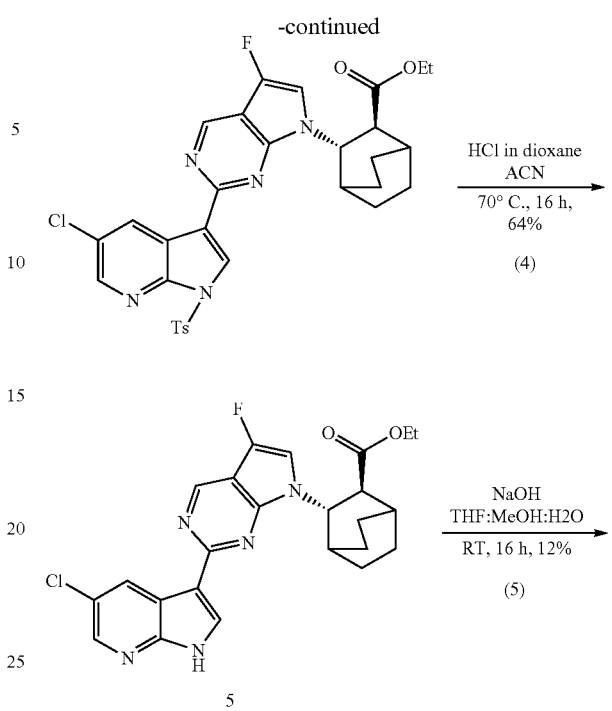

2-Chloro-5-fluoro-7H-pyrrolo[2,3-d]pyrimidine (2)

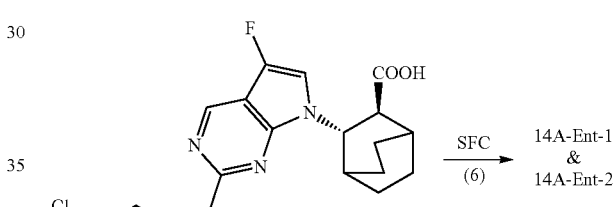

To a stirred solution of 2-chloro-7H-pyrrolo[2,3-d]pyrimidine (1) (5.0 g, 32.57 mmol) in acetonitrile (250 mL) and Acetic acid (50 mL) was added 1-Chloromethyl-4- fluoro-1,4-diazoniabicyclo[2.2.2]octanebis(tetrafluoroborate) (Selectfluor) (17.29 g, 48.85) at room temperature. The reaction mixture was heated to 70° C. and stirred for 6 h. After consumption of starting material, the mixture was concentrated under reduced pressure, crude compound was diluted with water (150 mL) and extracted with ethylaceate (2×250 mL). The combined organics were washed with sat.NaHCO$_3$ solution, brine solution (50 ml), dried over sodium sulfate, filtered and concentrated under reduced pressure to afford 2-chloro-5-fluoro-7H-pyrrolo[2,3-d]pyrimidine (2) (2.45 g, 14.32 mmol, 44% yield) as brown solid. TLC system: 50% EtOAc in pet Ether R$_f$: 0.6 LCMS (ESI): m/z 172.0 (M+H)$^+$ Ethyl (2S,3S)-3-(2-chloro-5-fluoro-7H-pyrrolo[2,3-d]pyrimidin-7-yl)bicyclo[2.2.2]octane-2-carboxylate (3)

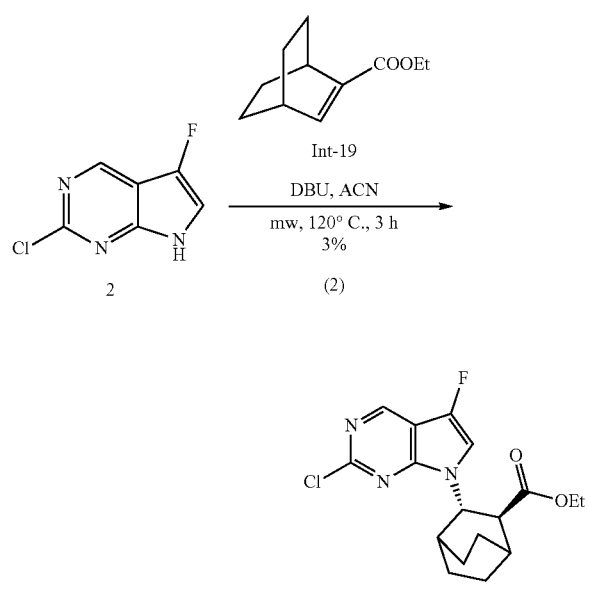

In a microwave vial a solution of (1S,4S)-ethyl bicyclo[2.2.2]oct-2-ene-2-carboxylate (Int-19) (1.157 g, 6.43 mmol) in ACN (7 mL) was added 2-chloro-5-fluoro-7H-pyrrolo[2,3-d]pyrimidine (2) (1.0 g, 5.84 mmol) and DBU (0.887 g, 5.84 mmol) at room temperature. The reaction was kept in microwave at 120° C. for 3 h. The reaction mixture was concentrated under reduced pressure. The crude compound was diluted with water (50 mL) and extracted with ethyl acetate (2×100 mL), combined organics ware washed with brine solution (15 mL), dried over sodium sulfate, filtered and concentrated under reduced pressure. Crude compound was purified by column chromatography using 100-200 silica and eluted compound with 15% ethyl acetate in pet ether to afford ethyl (2S,3S)-3-(2-chloro-5-fluoro-7H-pyrrolo[2,3-d]pyrimidin-7-yl)bicyclo[2.2.2]octane-2-carboxylate (3) (50 mg, 0.14 mmol, 3% yield) as off white solid. Note: 700 mg of the Int-19 was recovered. TLC system: 20% EtOAc in pet Ether R$_f$: 0.6 LCMS (ESI): m/z 352.1 (M+H)$^+$ Ethyl (2S,3S)-3-(2-(5-chloro-1-tosyl-1H-pyrrolo[2,3-b]pyridin-3-yl)-5-fluoro-7H-pyrrolo[2,3-d]pyrimidin-7-yl)bicyclo[2.2.2]octane-2-carboxylate (4)

A solution of ethyl (2S,3S)-3-(2-chloro-5-fluoro-7H-pyrrolo[2,3-d]pyrimidin-7-yl)bicyclo[2.2.2]octane-2-carboxylate 3 (95 mg, 0.2706 mmol), Int-18 (334.5 mg, 0.812 mmol) and aq 2 M sodium carbonate solution (4 mL) in 1,2-DME (16 mL) was degassed with argon for 15 min. Then, tetrakis (triphenylphosphine) palladium (31 mg, 1.3535 mmol) was added and heated at 90° C. for 16 h. After consumption of starting material, the reaction mixture was diluted with water (25 mL) was extracted with ethyl acetate (50 mL) and washed with water (3×15 mL), brine solution (15 mL), dried over sodium sulfate and concentrated under reduced pressure. Crude compound was purified by column chromatography using 100-200 silica and eluted compound with 20% ethyl acetate in pet ether to afford ethyl (2S,3S)-3-(2-(5-chloro-1-tosyl-1H-pyrrolo[2,3-b]pyridin-3-yl)-5-fluoro-7H-pyrrolo[2,3-d]pyrimidin-7-yl)bicycle [2.2.2] octane-2-carboxylate 4 (65 mg, 0.1046 mmol, 38.6% yield) as off white solid. TLC system: 30% EtOAc in pet Ether R$_f$: 0.3 LCMS (ESI): m/z 622.42 (M+H)$^+$

315

Ethyl (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylate) (5)

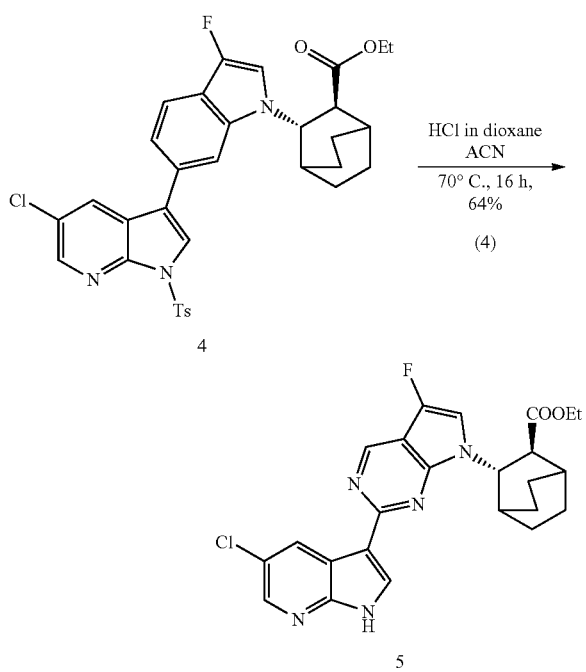

To a stirred solution of ethyl (2S,3S)-3-(2-(5-chloro-1-tosyl-1H-pyrrolo[2,3-b]pyridin-3-yl)-5-fluoro-7H-pyrrolo[2,3-d]pyrimidin-7-yl)bicycle [2.2.2] octane-2-carboxylate 4 (65 mg, 0.1046 mmol) in acetonitrile (2 mL) was added 4N of hydrogen chloride in dioxane (1 mL) at rt to 70° C. for 16 h in a seal. After completion of reaction as indicated by TLC, the volatile solvent was removed by vacuum. The crude was basified with sat.NaHCO₃ solution and extracted with 10% methanol in dichloromethane (2×50 mL) and washed the organics with brine (20 mL), dried over sodium sulfate and concentrated under reduced pressure to afford ethyl(2S,3S)-3-(2-(5-chloro-1H-pyrrolo[2,3-b]pyridin-3-yl)-5-fluoro-7H-pyrrolo[2,3-d] pyrimidin-7-yl)bicyclo[2.2.2] octane-2-carboxylate) (5) (31 mg, 0.066 mmol, 64% yield) as off white solid. TLC system: 5% MeOH in DCM R$_f$: 0.4 LCMS (ESI): m/z 468.21 (M+H)⁺

(2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A, Racemic Mixture)

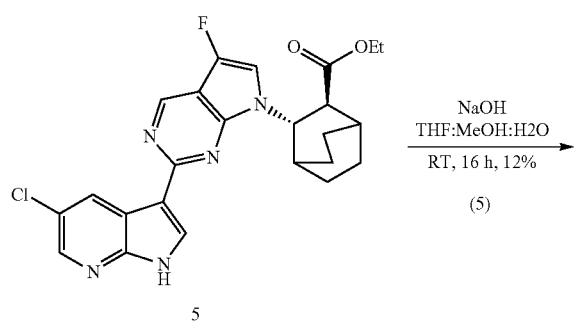

316

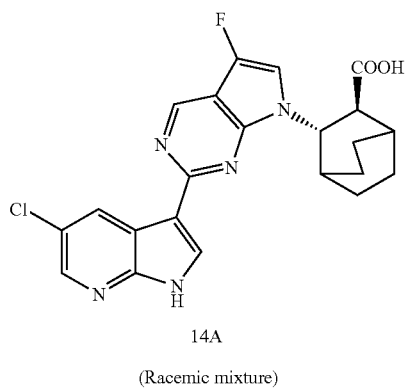

14A (Racemic mixture)

To a stirred solution of ethyl (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2] octane-2-carboxylate) (5) (25 mg, 0.0535 mmol) in THF (3 mL) and MeOH (1 mL) was added a solution of 2M Sodium hydroxide (1 ml) at 0° C. Then allowed to room temperature and stirred for 16 h. Concentrated the volatiles under vacuum. The crude was purified by prep HPLC to afford (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2] octane-2-carboxylic acid (14A) (Racemic mixture) (3.0 mg, 0.0068 mmol, 12%) as an off white solid. TLC system: 10% MeOH in DCM R$_f$: 0.3 LCMS (ESI): m/z 440.21 (M+H)⁺

(2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A Enantiomers 1 and 2)

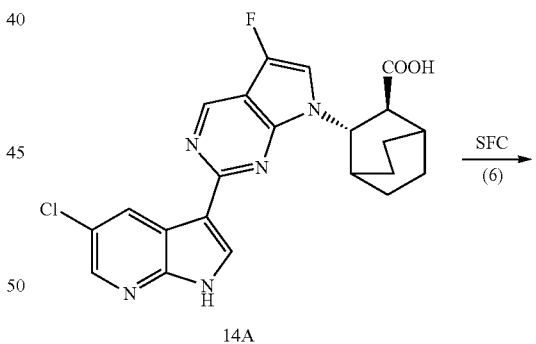

14A

14A-Ent-1
&
14A-Ent-2

100 mg of (2S,3S)-3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid (14A) (Racemic mixture) was soluble in acetonitrile, ethanol and dichloromethane separated each enantiomer by Thar SFC-200-005 and using column as Chiralcel-OD-H (250×30) mm, 5p and eluted with 100% methanol. Enantiomer fractions ware collected and concentrated under reduced pressure, dried to afford 14A ENT-1 (20 mg) & 14A ENT-2 (20 mg) as an off-white solids.

Preparative Supercritical Fluid Chiral Separation (SFC) Conditions:
Column/dimensions: Chiralcel OD-H (250×30) mm, 5μ
% CO2: 65.0%
% Co solvent: 35.0% (100% Methanol)
Total Flow: 70.0 g/min
Back Pressure: 100.0 bar
UV: 273 nm
Stack time: 3.6 min
Load/Inj: 1.7 mg
Solubility: ACN+DCM+Ethanol
Total No of injections: 60

Preparative supercritical fluid chiral separation (SFC) Conditions:
Column/dimensions: Chiralcel OD-H (250×30) mm, 5μ
% CO2: 65.0%
% Co solvent: 35.0% (100% Methanol)
Total Flow: 70.0 g/min
Back Pressure: 100.0 bar
UV: 273 nm
Stack time: 3.6 min
Load/Inj: 1.7 mg
Solubility: ACN+DCM+Ethanol
Total No of injections: 60

Preparation of Intermediate 13-4-X, and Final Compounds Derived from this Intermediate

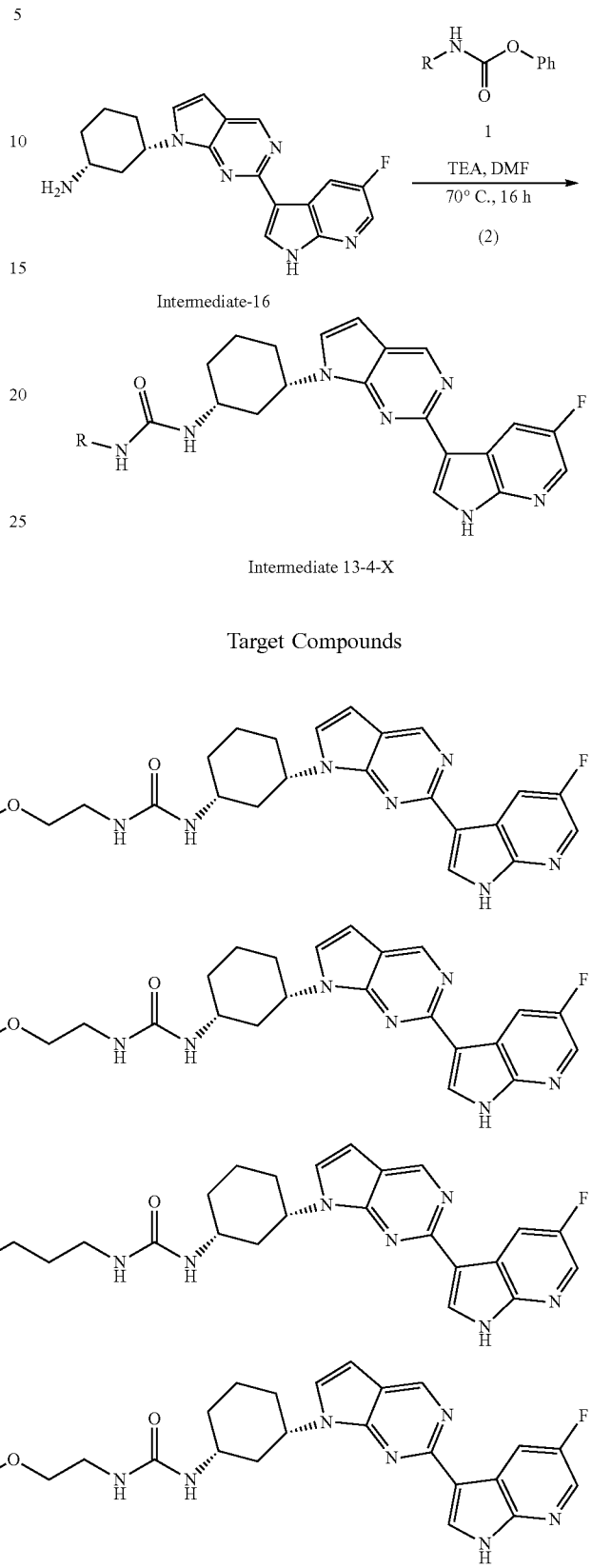

-continued

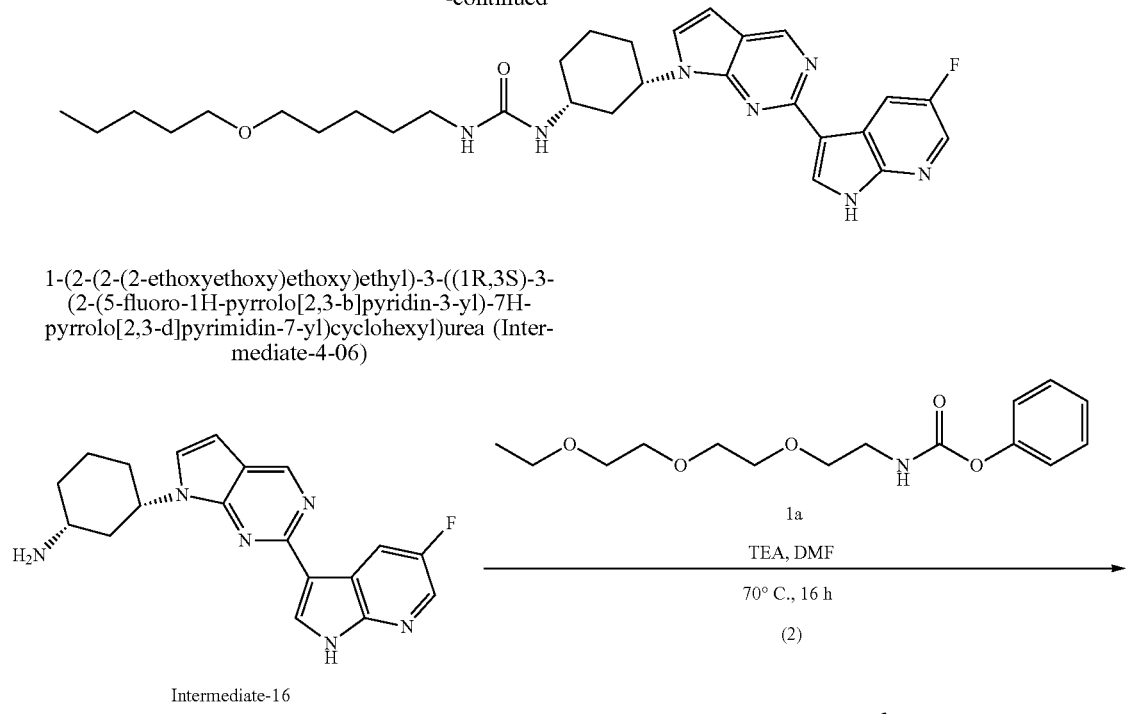

1-(2-(2-(2-ethoxyethoxy)ethoxy)ethyl)-3-((1R,3S)-3-(2-(5-fluoro-1H-pyrrolo[2,3-b]pyridin-3-yl)-7H-pyrrolo[2,3-d]pyrimidin-7-yl)cyclohexyl)urea (Intermediate-4-06)

To a stirred solution of (1R,3S)-3-(2-(5-fluoro-1H-pyrrolo[2,3-b]pyridin-3-yl)-7H-pyrrolo[2,3-d]pyrimidin-7-yl)cyclohexan-1-amine Intermediate 16 (70 mg, 0.20 mmol) in dimethylformamide (2 mL) was added triethylamine (0.3 mL, 2.0 mmol) and phenyl (2-(2-(2-ethoxyethoxy)ethoxy)ethyl)carbamate (1a) (89 mg, 0.3 mmol) at 0° C. then stirred at 80° C. for 16 h. To the reaction mixture was added water (20 mL), and the mixture was extracted with ethyl acetate (3×30 mL). The combined organic layers were washed with brine solution (20 mL), dried over sodium sulphate and concentrated under reduced pressure to afford crude compound, which was purified by prep-HPLC to obtain 1-(2-(2-(2-ethoxyethoxy)ethoxy)ethyl)-3-((1R,3S)-3-(2-(5-fluoro-1H-pyrrolo[2,3-b]pyridin-3-yl)-7H-pyrrolo[2,3-d]pyrimidin-7-yl)cyclohexyl)urea (20 mg, 0.036 mmol, 18%) as an off white solid.

This synthetic scheme was also employed, using Intermediate 16 but different carbamates (RNHCOOPh) to produce a series of final compounds (in yields of around 8-19%). A table showing these intermediates, and final compounds, is provided below.

| Int. 16 | RNHCOOPh (#1) | Final Compound |
|---|---|---|
| (70 mg, 0.20 mmol) | ![structure] prepared from Sidechain-2 (89 mg, 3.0 mmol) | ![structure] MS (ESI): m/z 554.4 (M + H)+ |

| Int. 16 | RNHCOOPh (#1) | Final Compound |
|---|---|---|
| (75 mg, 0.21 mmol) | 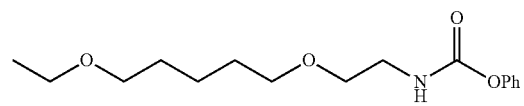
prepared from Sidechain-19
(48 mg, 0.16 mmol) | 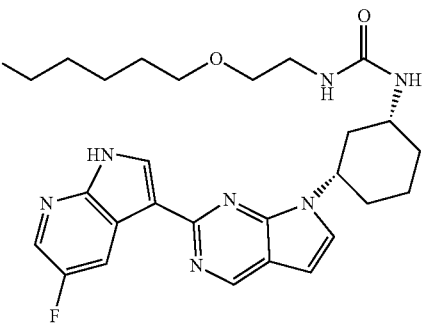
MS (ESI): m/z 552.4 (M + H)$^+$ |
| (50 mg, 0.14 mmol) | 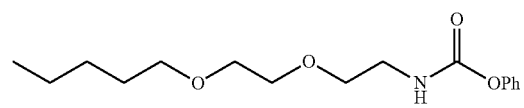
prepared from Sidechain-23
(59 mg, 0.2 mmol) | 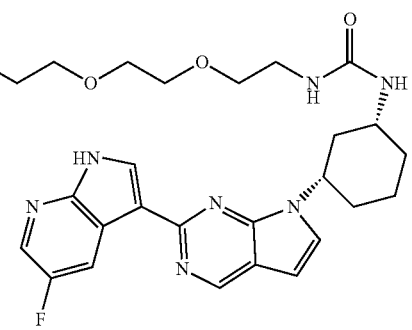
MS (ESI): m/z 552.4 (M + H)$^+$ |
| (70 mg, 0.2 mmol) | 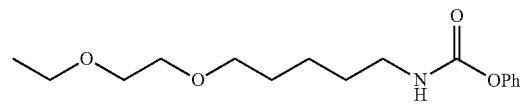
prepared from Sidechain-15
(48 mg, 0.16 mmol) | 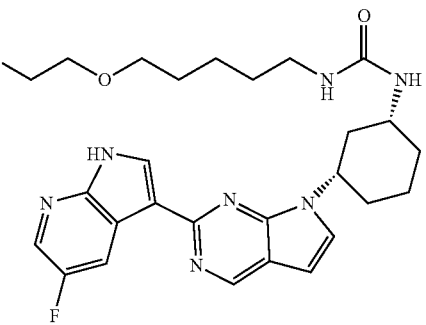
MS (ESI): m/z 552.3 (M + 1)$^+$ |
| (75 mg, 0.21 mmol) | 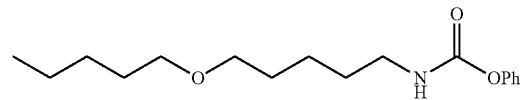
prepared from Sidechain-36
(63 mg, 0.214 mmol) | 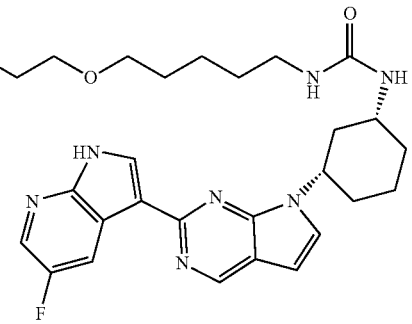
MS (ESI): m/z 550.4 (M + 1)$^+$ |

Synthesis of Intermediate 13-4-13

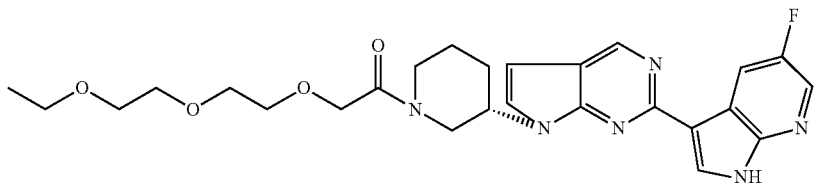 [SMILES: CCOCCOCCOCC(=O)N1CCC[C@H](n2ccc3cnc(-c4c[nH]c5ncc(F)cc45)nc32)C1]

(S)-2-(2-(2-ethoxyethoxy) ethoxy)-1-(3-(2-(5-fluoro-1H-pyrrolo [2, 3-b] pyridin-3-yl)-7H-pyrrolo [2, 3-d] pyrimidin-7-yl) piperidin-1-yl) ethan-1-one

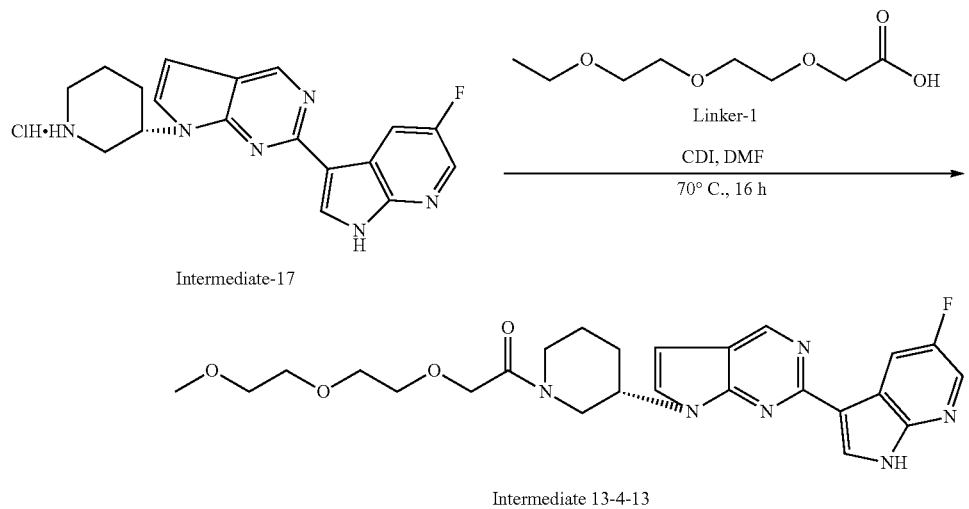

Intermediate 13-4-13

To a stirred solution of (S)-2-(5-fluoro-1H-pyrrolo[2,3-b]pyridin-3-yl)-7-(piperidin-3-yl)-7H-pyrrolo[2,3-d]pyrimidine hydrochloride Intermediate 17 (50 mg, 0.13 mmol) in DMF (2 mL) was added 2-(2-(2-ethoxyethoxy)ethoxy)acetic acid (Sidechain 1) (34 mg, 0.177 mmol), HATU (92 mg, 0.241 mmol) and diisopropylethylamine (62 mg, 0.483 mmol) at 0° C. then stirred at room temperature for 16 h. To the reaction mixture added water (50 mL) and extracted with ethyl acetate (2×50 mL). Combined organic layers were washed with brine solution (50 mL), dried over sodium sulphate and concentrated under reduced pressure. Crude compound was purified through Prep HPLC method to afford (S)-2-(2-(2-ethoxyethoxy)ethoxy)-1-(3-(2-(5-fluoro-1H-pyrrolo[2,3-b]pyridin-3-yl)-7H-pyrrolo[2,3-d]pyrimidin-7-yl)piperidin-1-yl)ethan-1-one (Intermediate 13-4-13) (23 mg, 0.045 mmol, 34% yield) as a brown gummy liquid. TLC system: 10% methanol in dichloromethane $R_f$: 0.5 LCMS (ESI): m/z 511.41 (M+H)$^+$ Synthesis of (S)—N-(2-(2-(2-ethoxyethoxy)ethoxy)ethyl)-3-(2-(5-fluoro-1H-pyrrolo[2,3-b]pyridin-3-yl)-7H-pyrrolo[2,3-d]pyrimidin-7-yl)piperidine-1-carboxamide

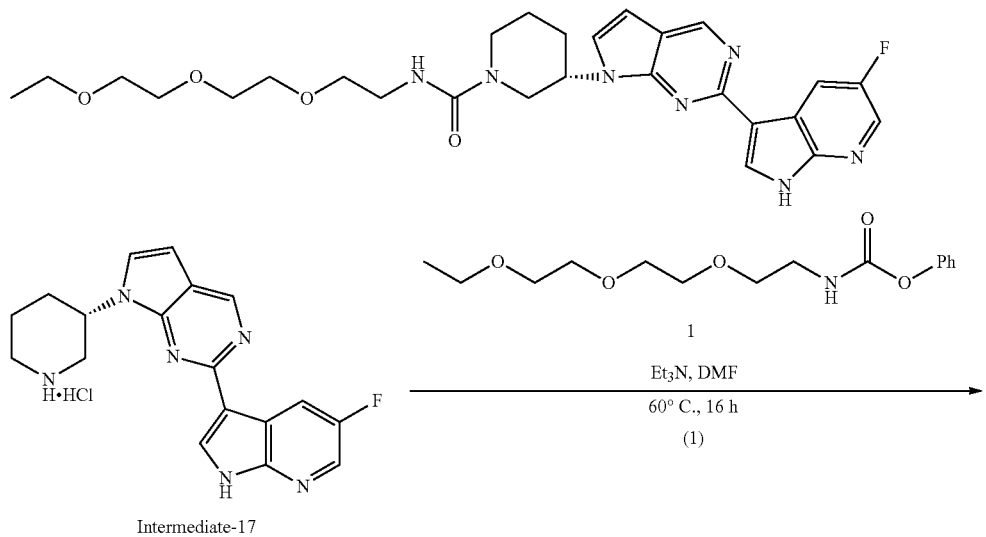

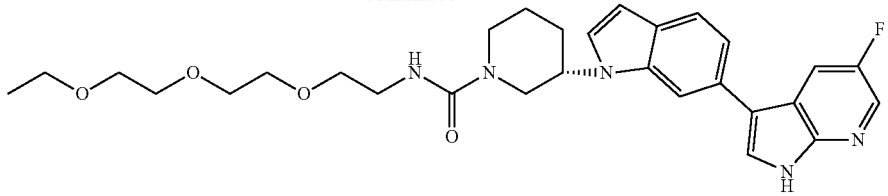

To a stirred solution of (S)-2-(5-fluoro-1H-pyrrolo[2,3-b]pyridin-3-yl)-7-(piperidin-3-yl)-7H-pyrrolo[2,3-d]pyrimidine hydrochloride Intermediate 17 (100 mg, 0.268 mmol) in DMF (2 mL) was added phenyl (2-(2-(2-ethoxyethoxy)ethoxy)ethyl)carbamate (96 mg, 0.322 mmol) and triethylamine (0.11 mL, 0.805 mmol) then stirred at 60° C. for 16 h. To the reaction mixture added water (50 mL) and extracted with ethyl acetate (50 mL) and washed with ice cold water (2×75 mL), brine solution (50 mL), dried over anhydrous sodium sulphate, filtered and concentrated under reduced pressure. Crude compound was purified through grace column purification by eluting with 54% of acetonitrile in 0.1% of formic acid in water to afford (S)—N-(2-(2-(2-ethoxyethoxy) ethoxy) ethyl)-3-(2-(5-fluoro-1H-pyrrolo [2, 3-b] pyridin-3-yl)-7H-pyrrolo [2, 3-d] pyrimidin-7-yl) piperidine-1-carboxamide (20 mg, 0.037 mmol, 14% yield) as a dark brown gummy solid. TLC system: 10% methanol in dichloromethane $R_f$: 0.5 LCMS (ESI): m/z 540.13 (M+H)$^+$ Compounds Prepared from Intermediate 013

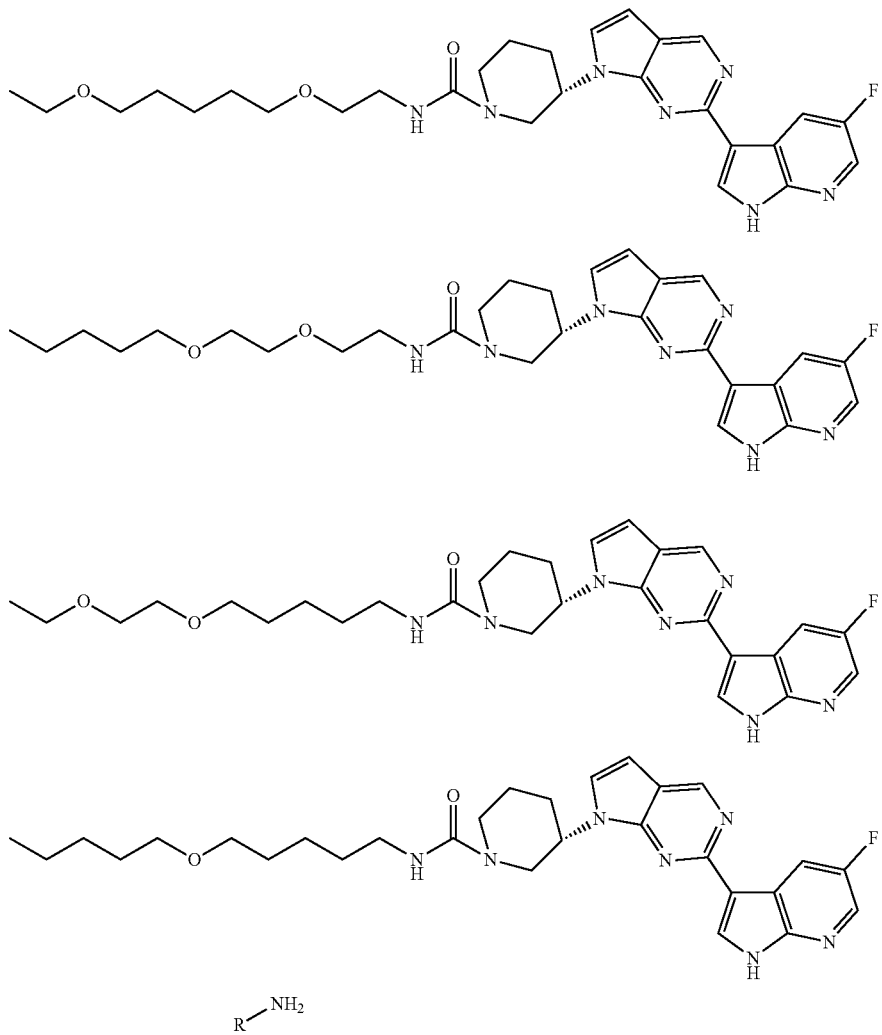

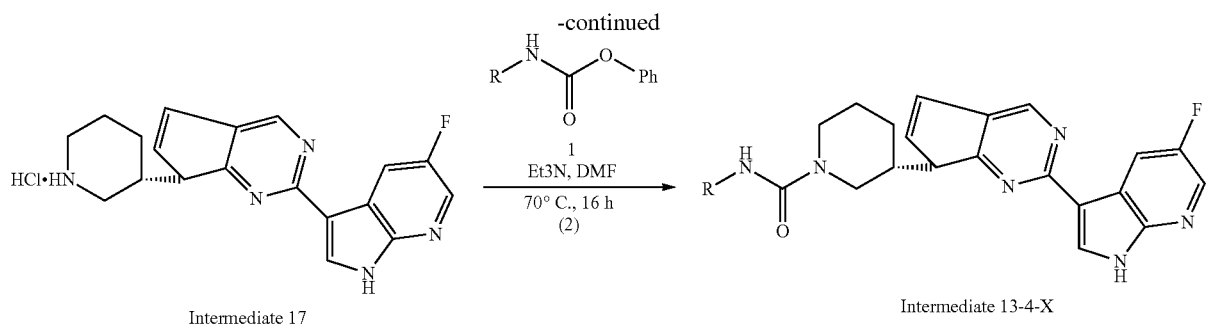

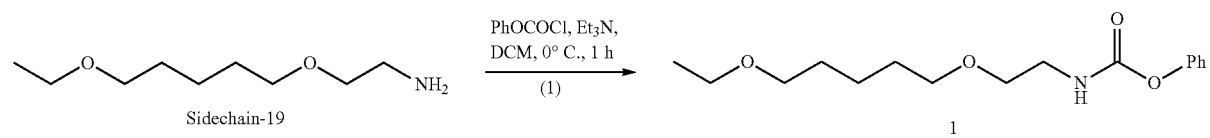 [SMILES: CCOCCCCCOCCN ; CCOCCCCCOCCNC(=O)Oc1ccccc1]

To a stirred solution of 2-((5-ethoxypentyl)oxy)ethan-1-amine (Sidechain-19) (260 mg, 1.48 mmol) in dichloromethane was added triethylamine (0.6 mL, 4.44 mmol) and phenylchloroformate (460 mg, 2.96 mmol) at 0° C. then stirred at room temperature for 1 h. To the reaction mixture added water (50 mL) and extracted with excess of dichloromethane (2×50 mL). Combined organic layers were washed with brine solution (50 mL), dried over sodium sulphate and concentrated under reduced pressure to afford crude compound-1 (330 mg, 1.11 mmol, 75%) as pale yellow liquid.

A series of additional compounds was prepared using this general reaction scheme, but with different sidechains. The yield ranged from 35-75%.

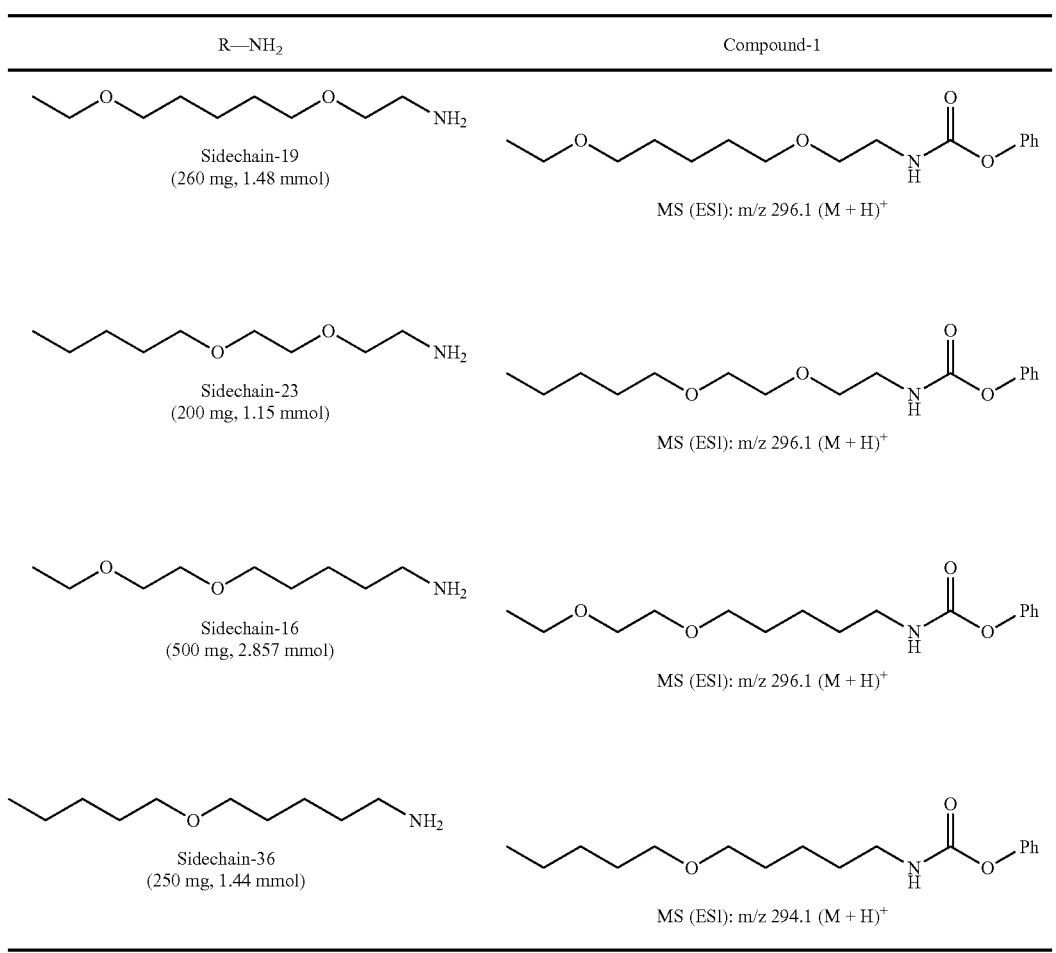

ethoxypentyl)oxy)ethyl)-3-(2-(5-fluoro-1H-pyrrolo[2,3-b]pyridin-3-yl)-7H-pyrrolo[2,3-d]pyrimidin-7-yl)piperidine-1-carboxamide (Intermediate 13-4-18)

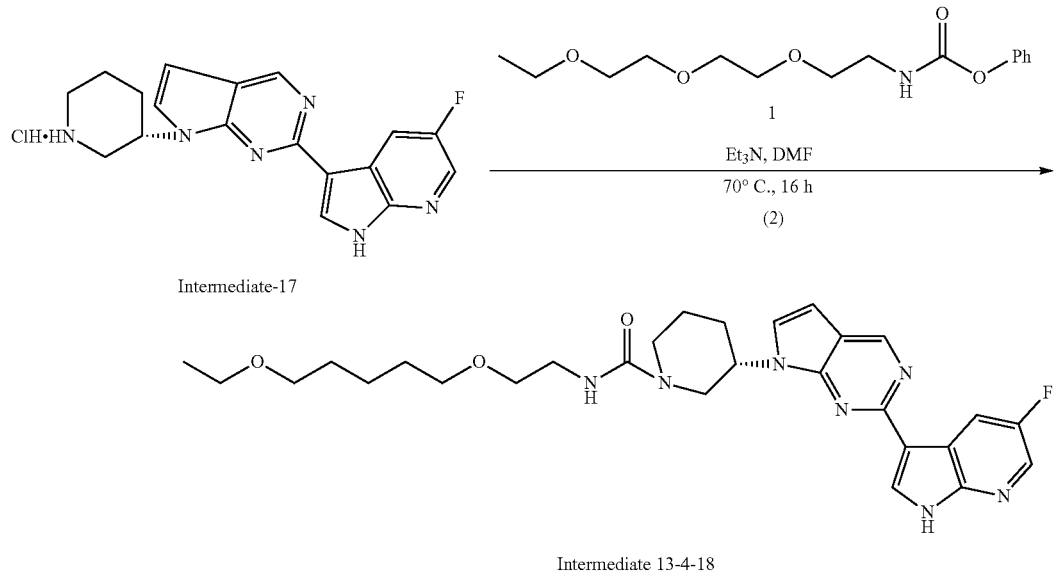

Intermediate 13-4-18

To a stirred solution of (S)-2-(5-fluoro-1H-pyrrolo[2,3-b]pyridin-3-yl)-7-(piperidin-3-yl)-7H-pyrrolo[2,3-d]pyrimidine hydrochloride Intermediate 17 (75 mg, 0.201 mmol) in dimethylformamide (2 mL) was added triethylamine (0.28 mL, 2.01 mmol) and phenyl (2-((5-ethoxypentyl)oxy)ethyl) carbamate (1) (88 mg, 0.30 mmol) at 0° C. then stirred at 80° C. for 16 h. To the reaction mixture added water (20 mL) and extracted with ethyl acetate (3×30 mL). Combined organic layers were washed with brine solution (20 mL), dried over sodium sulphate and concentrated under reduced pressure to afford crude compound which was purified by prep-HPLC to obtain (S)—N-(2-((5-ethoxypentyl)oxy)ethyl)-3-(2-(5-fluoro-1H-pyrrolo[2,3-b]pyridin-3-yl)-7H-pyrrolo[2,3-d]pyrimidin-7-yl)piperidine-1-carboxamide (Intermediate 18) (20 mg, 0.036 mmol, 18%) as off white solid.

A series of additional compounds were prepared by reacting Intermediate 17 with a different amine. The yields in this step ranged from 18-37%.

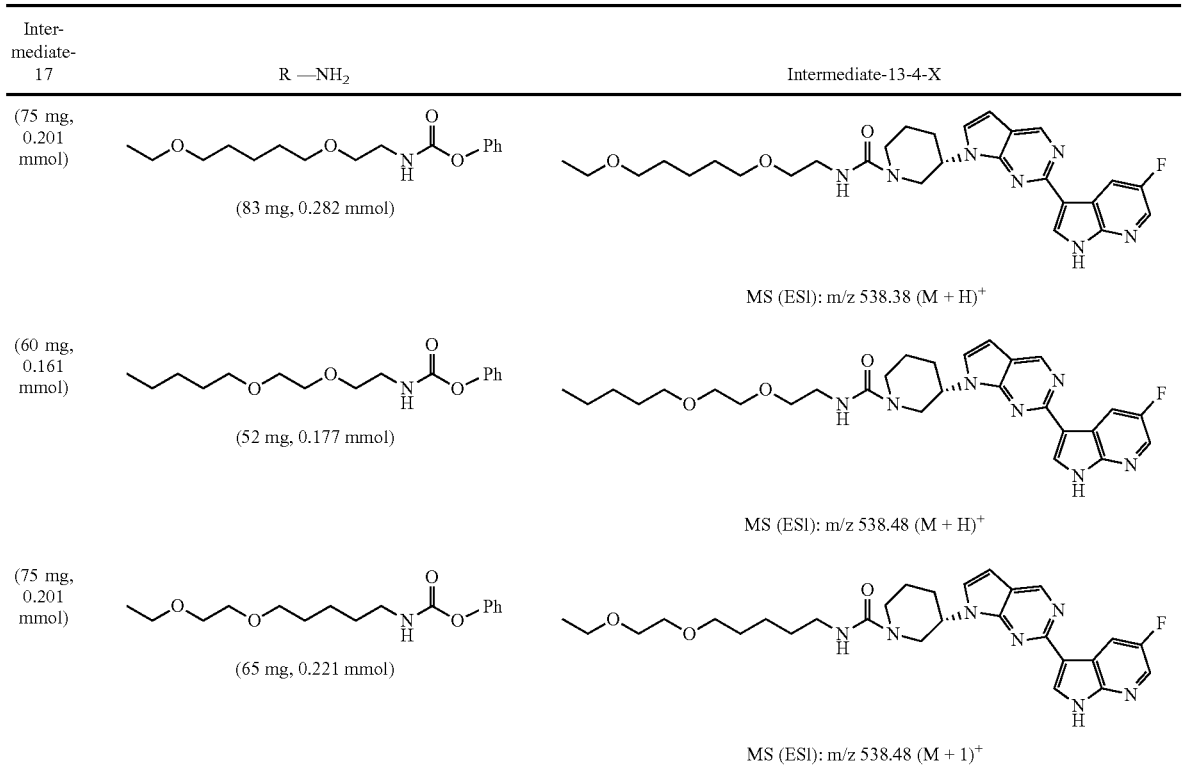

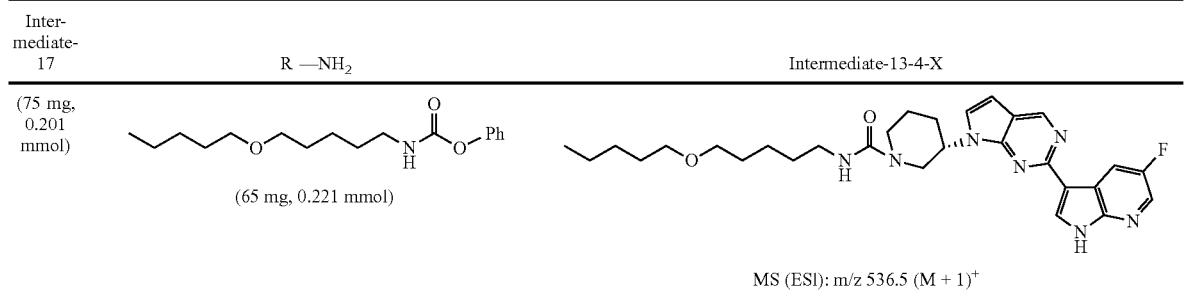
Additional Compounds Prepared Using Intermediate 13
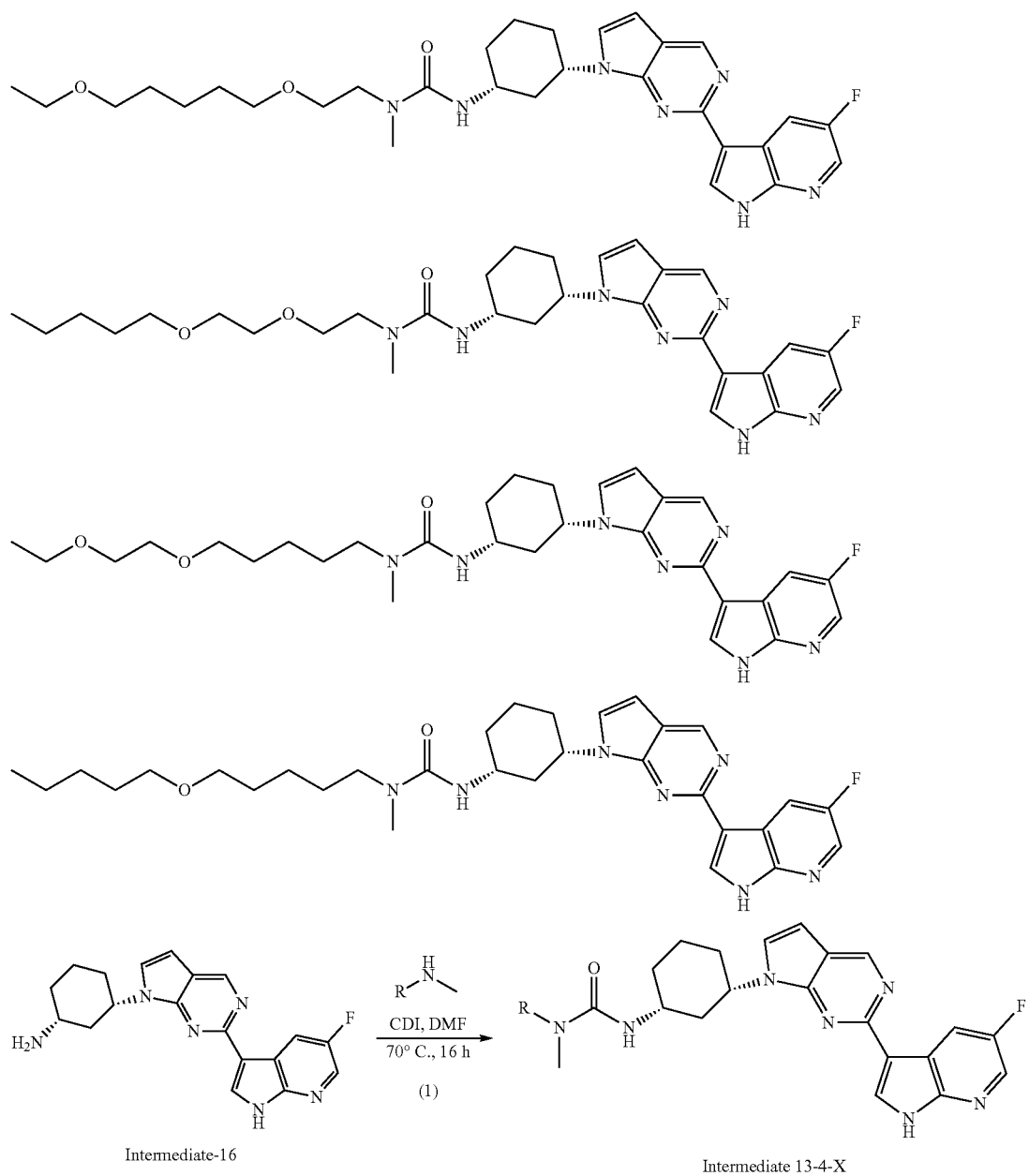

To a stirred solution of (1R,3S)-3-(2-(5-fluoro-1H-pyrrolo[2,3-b]pyridin-3-yl)-7H-pyrrolo[2,3-d]pyrimidin-7-yl)cyclohexan-1-amine (Intermediate 16) (70 mg, 0.2 mmol) in A series of compounds were prepared using the scheme shown above, and reacting Intermediate 16 with a variety of sidechains, with overall yields ranging from 4-23%.

Intermediate 16
(70 mg, 0.2 mmol)

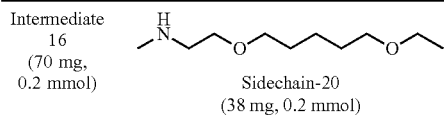

Sidechain-20
(38 mg, 0.2 mmol)

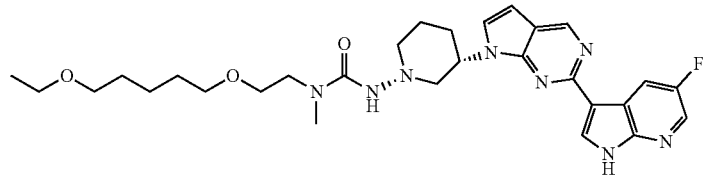

MS (ESI): m/z 566.4 (M + H)⁺

(50 mg, 0.14 mmol)

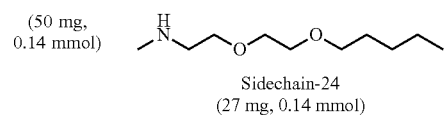

Sidechain-24
(27 mg, 0.14 mmol)

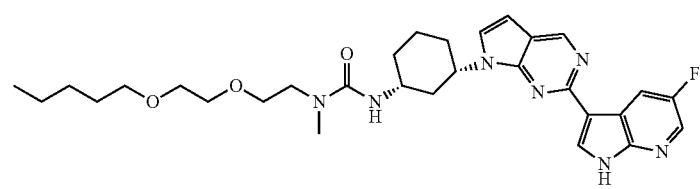

MS (ESI): m/z 566.20 (M + H)⁺

(80 mg, 0.22 mmol)

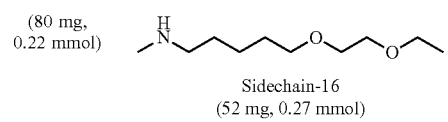

Sidechain-16
(52 mg, 0.27 mmol)

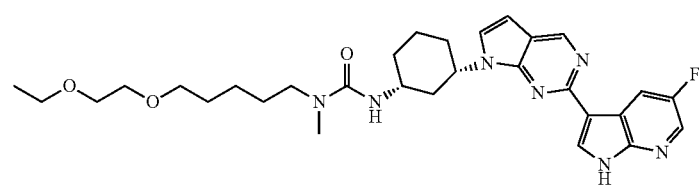

MS (ESI): m/z 566.4 (M + H)⁺

(70 mg, 0.2 mmol)

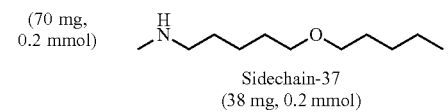

Sidechain-37
(38 mg, 0.2 mmol)

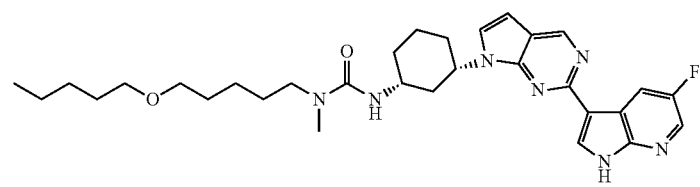

MS (ESI): m/z 564.4 (M + H)⁺

DMF (2 mL) was added 2-((5-ethoxypentyl)oxy)-N-methylethan-1-amine (Sidechain-20) (38 mg, 0.2 mmol) and carbonyldiimidazole (48 mg, 0.3 mmol) at room temperature and stirred at 70° C. for 16 h. To the reaction mixture added water (20 mL) and extracted with ethyl acetate (2×50 mL). Combined organic layers were washed with brine solution (50 mL), dried over sodium sulphate and concentrated under reduced pressure. Crude compound was purified by Prep-HPLC to afford 1-(2-((5-ethoxypentyl)oxy)ethyl)-3-((1R,3S)-3-(2-(5-fluoro-1H-pyrrolo[2,3-b]pyridin-3-yl)-7H-pyrrolo[2,3-d]pyrimidin-7-yl)cyclohexyl)-1-methylurea (Intermediate 13-4-17) (26 mg, 23%) as off white solid.

Other specific compounds disclosed herein were synthesized using the reaction schemes as described above, with use of the appropriate starting materials and sidechains. The mass spectra of compounds disclosed herein are provided below in Table E.

TABLE E

| Compound No. | MS (ESI): m/z | Compound No. | MS (ESI): m/z | Compound No. | MS (ESI): m/z |
|---|---|---|---|---|---|
| A1 | 339.39 | B5 | 326.39 | A11 | 459.45 |
| B1 | 339.39 | C2 | 353.42 | A12 | 454.8 |
| B2 | 353.38 | C3 | 340.3 | B6 | 341.4 |

TABLE E-continued

| Compound No. | MS (ESI): m/z | Compound No. | MS (ESI): m/z | Compound No. | MS (ESI): m/z |
|---|---|---|---|---|---|
| A2 | 340.35 | A6 | 369.3 | A13 | 412.98 |
| B3 | 340.38 | A7 | 383.38 | A14 | 427.37 |
| C1 | 339.42 | A8 | 473.4 | A15 | 423.41 |
| A3 | 312.3 | A9 | 409.39 | A16 | 397.41 |
| A4 | 353.45 | C4 | 312.3 | B7 | 397.47 |
| AS | 326.36 | C5 | 326.39 | B8 | 473.4 |
| B4 | 312.3 | A10 | 397.44 | B9 | 313.93 |
| A17 | 426.4 | B47 | 539.44 | B164 | 472 |
| A18 | 487.44 | B48 | 380.24 | B165 | 498 |
| A19 | 427.37 | B49 | 550.4 | C6 | 367.1 |
| B10 | 382.93 | B50 | 521.4 | C7 | 340 |
| B11 | 382.93 | B51 | 408.29 | C8 | 340.1 |
| B12 | 355.4 | B53 | 380.27 | C9 | 325.09 |
| B13 | 328.34 | B125 | 622.33 | B166 | 453 |
| A20 | 399.39 | B126 | 468.47 | B167 | 411.18 |
| B14 | 459.38 | B127 | 440.35 | B168 | 468 |
| B15 | 380.35 | B124 | 422.13 | B169 | 483.2 |
| B16 | 366.32 | B128 | 450.25 | B170 | 512.2 |
| B17 | 380.35 | B130 | 453.22 | C10 | 326 |
| B18 | 324.34 | B131 | 424.14 | C11 | 339 |
| B19 | 380.45 | B132 | 440.48 | B171 | 482 |
| B120 | 406.38 | B133 | 440.28 | B172 | 511 |
| B20 | 394.37 | B52 | 523.1 | B173 | 486.2 |
| B21 | 366.42 | B136 | 455.9 | B174 | 500.1 |
| B22 | 366.42 | B137 | 456 | B54 | 411 |
| B121 | 434.4 | B138 | 424 | B55 | 369.1 |
| B23 | 338.37 | B139 | 424 | C12 | 339.1 |
| B24 | 379.93 | B140 | 422 | C13 | 397 |
| B122 | 406.32 | B141 | 453 | C14 | 354 |
| B123 | 406.29 | B142 | 483 | C15 | 355.1 |
| B25 | 539.15 | B145 | 498 | C16 | 368.1 |
| B26 | 553.5 | B146 | 510 | C17 | 368 |
| B28 | 525.09 | B147 | 483 | B56 | 422.1 |
| B29 | 568.4 | B148 | 510.1 | B151 | 474 |
| B30 | 539.1 | B149 | 469 | B152 | 484 |
| B31 | 540.13 | B150 | 482 | B153 | 470 |
| B32 | 511.41 | B160 | 498 | B154 | 498 |
| B39 | 523.36 | B161 | 472 | C18 | 396.1 |
| B43 | 523.36 | B162 | 488 | B57 | 408.2 |
| B46 | 539.44 | B163 | 420 | B175 | 448.1 |
| B176 | 511 | B186 | 511 | B210 | 628 |
| B177 | 502 | B187 | 497 | B88 | 456 |
| B178 | 526 | B78 | 469.1 | B211 | 516.9 |
| B179 | 472 | B79 | 408.1 | B212 | 532.9 |
| B58 | 411 | B80 | 422.1 | B89 | 412 |
| B59 | 422.1 | B81 | 442 | B90 | 440 |
| B180 | 476.1 | B82 | 441 | B91 | 428 |
| B181 | 511 | B188 | 453 | B92 | 441 |
| B182 | 526 | B83 | 428 | B93 | 427 |
| B183 | 516 | B191 | 447 | B94 | 427 |
| B60 | 369.1 | B192 | 508 | B95 | 427.28 |
| B61 | 426 | B193 | 487 | B214 | 431.07 |
| B62 | 426.1 | B194 | 453 | B215 | 459.12 |
| B63 | 440 | B196 | 466.14 | B216 | 474.28 |
| B64 | 351.1 | B197 | 479 | B217 | 502.34 |
| B65 | 408.1 | B198 | 404 | B218 | 447.07 |
| B66 | 442 | B199 | 433.1 | B219 | 475.29 |
| B67 | 408 | B200 | 434 | B96 | 490.27 |
| B68 | 408 | B84 | 368 | B97 | 417.31 |
| B69 | 351.1 | B201 | 536 | B220 | 524.29 |
| B70 | 422.1 | B202 | 515 | B221 | 451.29 |
| B71 | 394.1 | B203 | 511 | B98 | 440.23 |
| B72 | 428 | B85 | 426 | B222 | 422.25 |
| B73 | 476 | B86 | 440 | B101 | 548.32 |
| B74 | 462 | B204 | 493.28 | B99 | 412.03 |
| B184 | 539 | B205 | 405 | B102 | 530.3 |
| B75 | 440.2 | B206 | 420 | B103 | 412.2 |
| B76 | 369.1 | B207 | 494 | B144 | 440.3 |
| B77 | 426 | B87 | 414 | | |
| B185 | 532 | B209 | 422 | | |

Example 3: Data on Selected Compounds

As can be seen below, many of the compounds described herein showed positive effect on the survival of the A/PR/8/34 infected cells, and inhibitory effect on the replication of A/PR/8/34 influenza virus.

In Vitro Antiviral Assays

Influenza Antiviral Assays:

Inhibition of virus-induced cytopathic effects (CPE) and cell viability following Influenza type A (strain A/PR/8/34, ATCC VR-95) or Influenza type B (cell culture adapted strain B/Lee/40, ATCC VR-1535) replication in MDCK cells (Female cocker spaniel kidney epithelial, ATCC CCL-34) were measured by XTT dye reduction (Appleyard et al. J Antimicrob Chemother. 1(4 Suppl): 49-53, 1975 and Shigeta et al. Antimicrob Agents Chemother. 41(7): 1423-1427, 1997.). MDCK cells ($1\times10^4$ cells per well) are grown to monolayers in 96-well flat-bottomed tissue culture plates using Dulbecco's Minimum Essential Medium (DMEM) supplemented with 10% heat-inactivated fetal bovine serum (FBS), 2 mM L-glutamine, 100 U/mL penicillin, 100 μg/ml streptomycin, 1 mM sodium pyruvate, and 0.1 mM NEAA in a 100 μL per well volume. On the day of assay set up, the cell monolayer was washed three times with DPBS. The viruses were obtained from ATCC and were grown in MDCK cells for the production of stock virus pools. Test compounds were diluted into assay medium (DMEM, 2 mM L-glutamine, 100 U/mL penicillin, 100 μg/mL streptomycin, 50 ng/ml TPCK-treated trypsin, 0.1 mM NEAA, and 1 mM sodium pyruvate) at 2× the desired starting concentration and serially diluted. Test compound was added at 100 μL per well volume in triplicate for efficacy, duplicate for cytotoxicity and a single well per concentration for colorimetric evaluation immediately prior to the addition of diluted virus. Ribavirin and oseltamivir carboxylate were evaluated in parallel as control compounds. A pretitered aliquot of virus was removed from the freezer (−80° C.) and was rapidly thawed in a biological safety cabinet. Virus was diluted in assay medium such that the amount of virus added to each well in a volume of 100 μL was the amount determined to yield 85 to 95% cell killing at 4 days post-infection. Cell controls containing medium alone, virus-infected controls containing medium and virus, cytotoxicity controls containing medium and each Following incubation at 37° C., 5% $CO_2$ for four days, inhibition of CPE (increased cell viability) was measured by reduction of the formazan dye XTT following a 4 hour incubation at 37° C. and measured spectrophotometrically at 450 nm, with 650 nm as the reference wavelength using Softmax Pro 4.6 software. Percent CPE reduction of the virus-infected wells and the percent cell viability of uninfected drug control wells are calculated by four parameter curve fit analysis using Microsoft Excel XLfit4.

PB2 binding assay is for a homogenous, high throughput binding/displacement assay designed for determination of IC50s of PB2 inhibitors. The principle of the assay replies on the competitive displacement of the fluorescent probe (m7GTP analogs) from its complex with the PB2 by a PB2 inhibitor. Briefly, purified PB2 was incubated with the fluorescent m7GTP analogs and test inhibitors were added to the reaction mixtures. The replacement of fluorescent m7GTP was read with Perkin Elmer Envision.

The data on a number of compounds is provided below in Table F. Influenza PB2 affinity, as IC50 is indicated as follows: ++++: $IC_{50}$, <1 uM; +++: $IC_{50}$, 1-10 uM; ++: $IC_{50}$, 10-100 uM; +: $IC_{50}$, >100 uM

TABLE F

| Compound No. | Influenza PB2 affinity, IC50 | Compound No. | Influenza PB2 affinity, IC50 |
|---|---|---|---|
| A1 | ++ | A16 | + |
| B1 | ++ | B7 | + |
| B2 | ++ | B8 | + |
| A2 | ++ | B9 | + |
| B3 | + | A17 | +++ |
| C1 | ++ | A18 | + |
| A3 | +++ | A19 | ++ |
| A4 | ++ | B10 | + |
| A5 | ++ | B11 | ++ |
| B4 | ++ | B12 | ++ |
| B5 | ++ | B13 | ++ |
| C2 | + | A20 | +++ |
| C3 | + | B14 | ++ |
| A6 | ++ | B15 | +++ |
| A7 | ++ | B16 | +++ |
| A8 | + | B17 | ++++ |
| A9 | ++ | B18 | ++ |
| C4 | + | B19 | +++ |
| C5 | + | B120 | ++++ |
| A10 | ++ | B20 | ++ |
| A11 | ++ | B21 | +++ |
| A12 | + | B22 | +++ |
| B6 | ++ | B121 | ++ |
| A13 | + | B23 | ++ |
| A14 | +++ | B24 | ++++ |
| A15 | + | B122 | +++ |
| B123 | +++ | B135 | ++++ |
| B25 | +++ | B100 | ++ |
| B26 | ++ | B52 | + |
| B27 | ++ | B136 | +++ |
| B28 | ++ | B137 | ++++ |
| B29 | ++ | B138 | ++++ |
| B30 | ++ | B139 | +++ |
| B31 | ++ | B140 | ++++ |
| B32 | ++ | B141 | +++ |
| B33 | ++ | B142 | ++++ |
| B34 | + | B143 | ++++ |
| B35 | ++ | B144 | ++++ |
| B36 | + | B145 | ++++ |
| B37 | + | B146 | +++ |
| B38 | + | B147 | +++ |
| B39 | ++ | B148 | +++ |
| B40 | + | B149 | +++ |
| B41 | ++ | B150 | +++ |
| B42 | + | B160 | +++ |
| B43 | + | B161 | ++++ |
| B44 | + | B162 | ++++ |
| B45 | ++ | B163 | ++++ |
| B46 | ++ | B164 | ++++ |
| B47 | + | B165 | +++ |
| B48 | +++ | C6 | ++ |
| B49 | + | C7 | ++ |
| B50 | + | C8 | ++ |
| B51 | + | C9 | ++ |
| B53 | +++ | B166 | ++ |
| B125 | + | B167 | +++ |
| B126 | + | B168 | +++ |
| B127 | ++++ | B169 | ++++ |
| B124 | +++ | B170 | ++ |
| B128 | ++ | C10 | + |
| B129 | ++ | C11 | + |
| B130 | +++ | B171 | +++ |
| B131 | ++++ | B172 | + |
| B132 | ++++ | B173 | +++ |
| B133 | ++++ | B174 | ++ |
| B134 | + | B54 | +++ |
| B55 | + | B76 | ++ |
| C12 | + | B77 | ++ |
| C13 | + | B185 | + |
| C14 | + | B186 | ++++ |
| C15 | + | B187 | +++ |
| C16 | + | B78 | + |
| C17 | + | B79 | + |
| B56 | ++ | B80 | + |
| B151 | ++++ | B81 | + |
| B152 | ++ | B82 | ++ |
| B153 | ++++ | B188 | +++ |
| B154 | ++ | B189 | +++ |
| B57 | ++ | B190 | +++ |
| B175 | ++++ | B83 | +++ |
| B176 | ++ | B191 | ++++ |
| B177 | ++ | B192 | ++++ |
| B178 | ++ | B193 | ++++ |
| B179 | ++++ | B194 | +++ |
| B58 | ++ | B195 | ++ |
| B59 | ++ | B196 | +++ |
| B180 | ++ | B197 | ++++ |
| B181 | +++ | B198 | ++ |
| B182 | +++ | B199 | ++ |
| B183 | ++ | B200 | ++ |
| B60 | ++ | B84 | +++ |
| B61 | +++ | B201 | + |
| B62 | + | B202 | + |
| B63 | ++ | B203 | ++ |
| B65 | +++ | B85 | +++ |
| B66 | ++ | B86 | +++ |
| B67 | ++ | B204 | ++++ |
| B68 | +++ | B205 | +++ |
| B69 | ++ | B206 | +++ |
| B70 | ++ | B207 | ++++ |
| B71 | ++++ | B208 | +++ |
| B72 | ++++ | B87 | ++++ |
| B73 | ++ | B209 | +++ |
| B74 | ++++ | B210 | +++ |
| B184 | ++ | B88 | + |
| B75 | ++ | B211 | +++ |
| B212 | +++ | B218 | + |
| B89 | ++++ | B219 | + |
| B90 | + | B96 | + |
| B91 | ++++ | B97 | + |
| B92 | ++ | B220 | ++ |
| B93 | +++ | B221 | +++ |
| B94 | ++ | B98 | + |
| B95 | ++ | B222 | ++++ |
| B213 | ++++ | B101 | + |
| B214 | +++ | B99 | ++++ |
| B215 | + | B102 | + |
| B216 | +++ | B103 | ++++ |
| B217 | + | | |

All references provided herein are incorporated herein in its entirety by reference. As used herein, all abbreviations, symbols and conventions are consistent with those used in the contemporary scientific literature. See, e.g., Janet S. Dodd, ed., The ACS Style Guide: A Manual for Authors and Editors, 2nd Ed., Washington, D.C.: American Chemical Society, 1997.

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A compound having a structure of one of the following formulae:

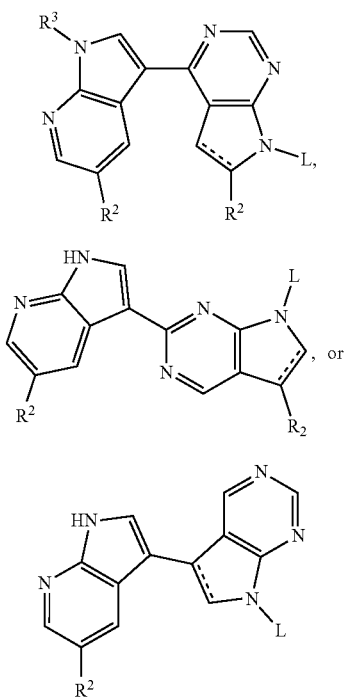

Formula I

Formula II

Formula III wherein
a dashed line represents either a single or a double bond,
L is:
i) H,
ii) —$C_{1-6}$ alkyl, —$C_{1-6}$ alkyl-OCONR$_2$, —$C_{1-6}$ alkyl-CONR$_2$, $C_{1-6}$ alkyl-CO$_2$R, $C_{1-6}$ alkyl-COR, $C_{1-6}$ alkyl-NRC(O)NR$_2$, $C_{1-6}$ alkyl-NRC(O)OR, $C_{1-6}$ alkyl-NRC(O)R, and $C_{1-6}$ alkyl-NR$_2$, wherein the $C_{2-6}$ alkyl can optionally include a double bond;
iii) $C_{5-6}$ cycloalkyl-OCONR$_2$, $C_{5-6}$ cycloalkyl-CONR$_2$, $C_{5-6}$ cycloalkyl-CO$_2$R, $C_{5-6}$ cycloalkyl-COR, $C_{5-6}$ cycloalkyl-NRC(O)NR$_2$, $C_{5-6}$ cycloalkyl-NRC(O)OR, $C_{5-6}$ cycloalkyl-NRC(O)R, and $C_{5-6}$ cycloalkyl-NR$_2$, where the cycloalkyl ring can be substituted with from one to three $C_{1-6}$ alkyl groups, and where the $C_{5-6}$ cycloalkyl ring can optionally include a double bond, an oxygen, or an NR group;
iv) —$C_{1-6}$ alkyl-O$_{5-6}$ cycloalkyl, —$C_{1-6}$ alkyl—$C_{5-6}$ cycloalkyl-OCONR$_2$, —$C_{1-6}$ alkyl—$C_{5-6}$ cycloalkyl—CONR$_2$, —$C_{1-6}$ alkyl—$C_{5-6}$ cycloalkyl—CO$_2$R, —$C_{1-6}$ alkyl—$C_{5-6}$ cycloalkyl—COR, —$C_{1-6}$ alkyl—$C_{5-6}$ cycloalkyl—NRC(O)NR$_2$, —$C_{1-6}$ alkyl—$C_{5-6}$ cycloalkyl—NRC(O)OR, —$C_{1-6}$ alkyl—$C_{5-6}$ cycloalkyl—NRC(O)R, and —$C_{1-6}$ alkyl—$C_{5-6}$ cycloalkyl—NR$_2$, where the cycloalkyl ring can be substituted with from one to three $C_{1-6}$ alkyl groups, and where the $C_{5-6}$ cycloalkyl ring can optionally include a double bond, an oxygen, or an NR group;
v) 2.2.2 bicyclooctyl-OCONR$_2$, 2.2.2 bicyclooctyl-CONR$_2$, 2.2.2 bicyclooctyl-CO$_2$R, 2.2.2 bicyclooctyl-COR, 2.2.2 bicyclooctyl-NRC(O)NR$_2$, 2.2.2 bicyclooctyl-NRC(O)OR, 2.2.2 bicyclooctyl-NRC(O)R, and 2.2.2 bicyclooctyl-NR$_2$, wherein the 2.2.2 bicyclooctyl ring can optionally include a double bond;

R is H, $C_{1-6}$alkyl, $C_{1-6}$alkyl-CO$_2$R$^1$, —CO$_2$R$^1$, CON(R$^1$)$_2$, or $C_{1-6}$ alkyl-CON(R$^1$)$_2$, and R$^1$ is H or $C_{1-6}$ alkyl;

each R$^2$ is independently H, halo, —CN, $C_{1-6}$ alkyl, $C_{1-6}$ haloalkyl, $C_{2-6}$ alkenyl, $C_{2-6}$ alkynyl, CO$_2$R, CONR$_2$, phenyl, pyridinyl, thiophenyl, furanyl, or imidazolyl, wherein the phenyl, pyridinyl, thiophenyl, furanyl, or imidazolyl is optionally substituted with one or more substituents selected from the group consisting of hydroxy, $C_{1-6}$ alkoxy, $C_{2-8}$ alkoxyalkyl, alkoxycarbonyl, $C_{1-8}$ alkyl, arylalkoxycarbonyl, $C_{2-6}$ alkenyl, $C_{2-6}$ alkynyl, carboxy, halogen, haloalkyl, N$_3$, CN, N(R')$_2$, SR', OCOR', N(COR')R', N(COR')COR', SCOR', S(O)$_2$NR'$_2$, S(O)$_2$R', and each R' is independently H or $C_{1-6}$ alkyl;

R$^3$ is H, or —SO$_2$-phenyl, wherein the phenyl is optionally substituted with one or more substituents selected from the group consisting of hydroxy, $C_{1-6}$ alkoxy, $C_{2-8}$ alkoxyalkyl, alkoxycarbonyl, $C_{1-8}$ alkyl, arylalkoxycarbonyl, $C_{2-6}$ alkenyl, $C_{2-6}$ alkynyl, carboxy, halogen, haloalkyl, N$_3$, CN, N(R')$_2$, SR', OCOR', N(COR')R', N(COR')COR', SCOR', S(O)$_2$NR'$_2$, S(O)$_2$R', and each R' is independently H or $C_{1-6}$ alkyl;

wherein a $C_{1-6}$ alkyl, $C_{2-6}$ alkenyl, or $C_{2-6}$ alkynyl moiety, wherever it occurs, can optionally be substituted with from one to three substituents which are not further substituted and which are independently selected from the group consisting of —CN, thio, aryl—$C_{1-6}$ alkyl, pyridinyl, ethoxymethyl-pyridinyl, indolinyl, $C_{1-6}$ alkyl, $C_{1-6}$ alkyl—$C_{3-6}$cycloalkyl, $C_{3-6}$cycloalkyl, —$C_{1-6}$ thioalkyl, $C_{1-6}$ haloalkyl, —$C_{1-6}$ hydroxyalkyl, —$C_{1-6}$ alkoxy, —$C_{1-6}$ alkoxy—$C_{1-6}$ alkoxy, —$C_{1-6}$ alkoxy—$C_{1-6}$ alkoxy—$C_{1-6}$ alkoxy, CO$_2$H, CO$_2$C$_{1-6}$ alkyl), CONH$_2$, CONHC$_{1-6}$ alkyl, and —CON(C$_{1-6}$alkyl)$_2$; and wherein if two alkyl groups reside on an amide moiety, they can optionally together form a 5-7 membered ring with the nitrogen of the amide moiety;

or a pharmaceutically acceptable salt thereof.

2. The compound or salt of claim 1, having a structure of Formula I, II, or III:

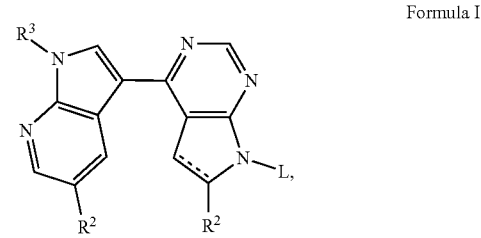

Formula I

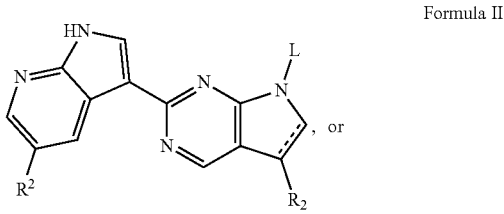

Formula II

Formula III

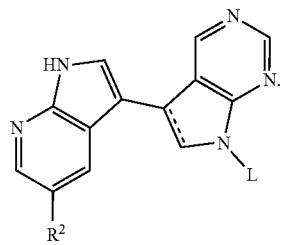

3. The compound or salt of claim 2, having a structure of Formula IA, IIA, or IIIA:

Formula IA

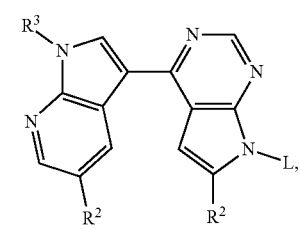

Formula IIA

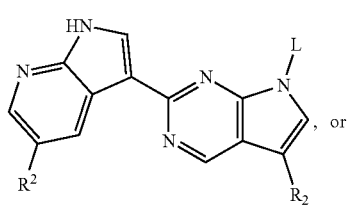

, or

Formula IIIA

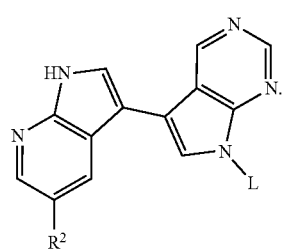

4. The compound or salt of claim 1, wherein L is
(i) $C_{1-6}$alkylCONR$_2$;
(ii) $C_{1-6}$alkyl-CO$_2$R;
(iii) $C_{1-6}$alkyl-NRC(O)R, $C_{1-6}$akllyl-NRC(O)OR, or $C_{1-6}$alkyl-NRC(O)NR;
(iv) X-A; X is a bond, CH$_2$, or CH$_2$CH$_2$; and A is

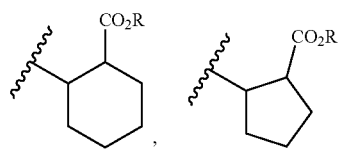 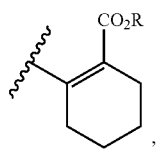

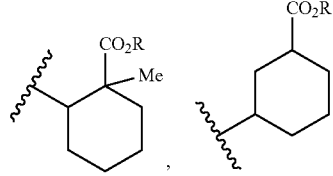 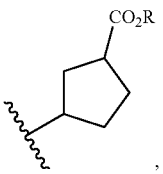

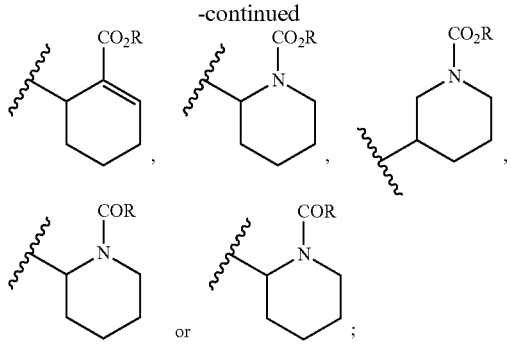

or (v) $C_{5-6}$cycloalkyl-CONR$_2$, $C_{5-6}$cycloalkyl-NRCONR$_2$, $C_{5-6}$cycloalkyl-NRCOR, $C_{5-6}$cycloalkyl-COR, or $C_{s-6}$cycloalkyl-NR$_2$; or (vi) L is X-A; X is a bond, CH$_2$, or CH$_2$CH$_2$; and A is

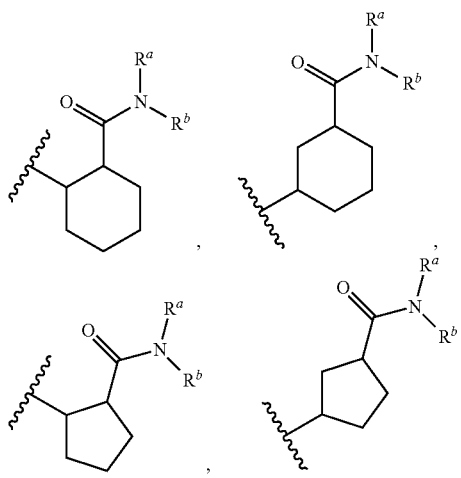

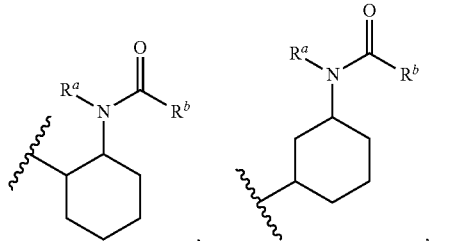

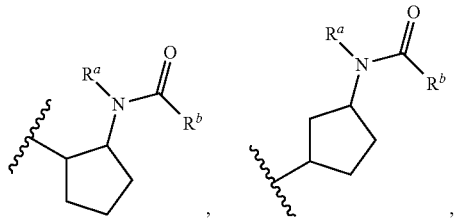

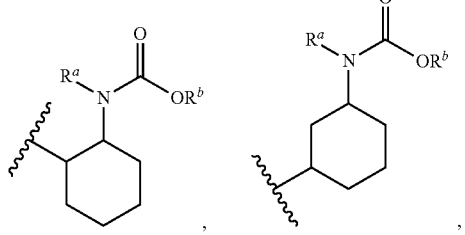

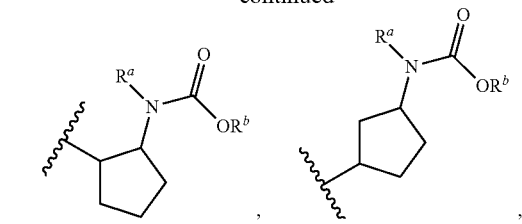

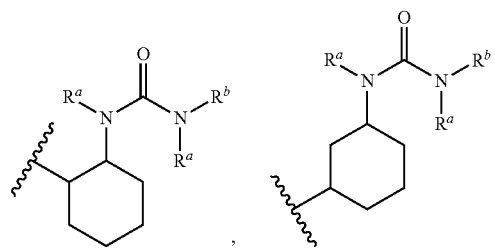

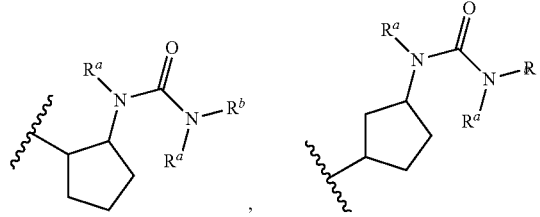

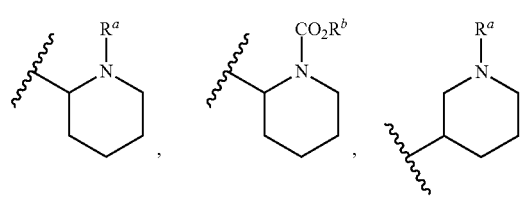

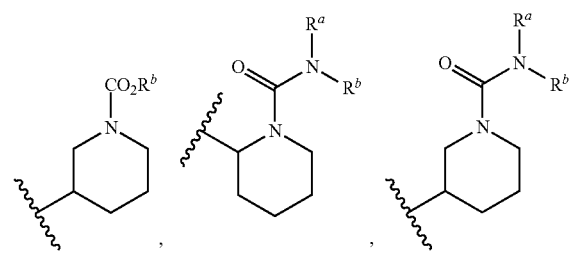

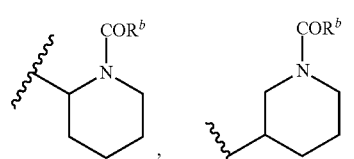

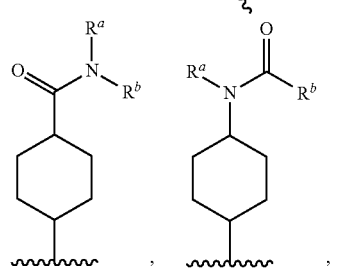

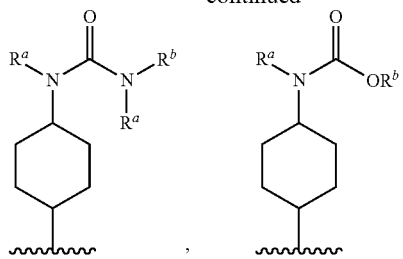

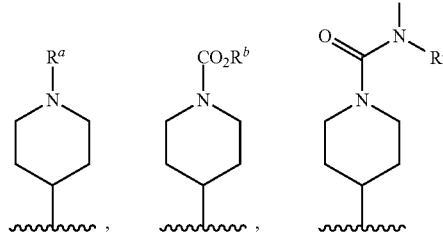

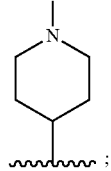

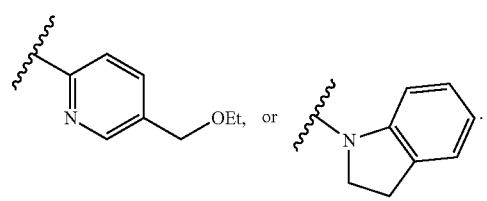 [SMILES: *c1ccc(COCC)cn1 ; "or" ; *N1CCc2ccccc21 ; "."]

each $R^a$ is independently H or Me; and each $R^b$ is independently H, Me, $CMe_3$, $(CH_2CH_2O)_3Et$, $CH_2O(CH_2CH_2O)_2Et$, $CH_2CH_2OCH_2CH_2O(CH_2)_3Me$, $(CH_2)_5O(CH_2)_4Me$, $(CH_2)_4O(CH_2)_4Me$, $CH_2CH_2O(CH_2)_5OEt$, $CH_2CH_2OCH_2CH_2O(CH_2)_4Me$, $(CH_2)_5OCH_2CH_2OEt$, $(CH_2)_4OCH_2CH_2OEt$, $CH_2OCH_2CH_2O(CH_2)_4Me$, pyrindinyl, or

5. The compound or salt of claim 4, wherein L is (i) $CH_2CONHMe$, $CH_2CONMe_2$, $CH_2CH_2CONHMe$, $CH_2CH_2CONMe_2$, $CH_2CH(Me)CONHMe$, $CH_2CH(Me)CONMe_2$, $C(Me)(Et)CONHCH_2CF_3$, $CH_2CONHCH_2CO_2H$, $CH_2CH_2CONHCH_2CO_2H$, $CH_2CONHCH(Me)CO_2H$, $CH_2CH_2CONHCH(Me)CO_2H$, $CH_2CONHCH(CH_2OH)CO_2H$, $CH_2CH_2CONHCH(CH_2OH)CO_2H$, $CH_2CONHCH(CH_2Ph)CO_2H$, $CH_2CH_2CONHCH(CH_2Ph)CO_2H$, $CH_2CONHCH(CO_2H)CH_2CO_2H$, $CH_2CH_2CONHCH(CO_2H)CH_2CO_2H$, $CH_2CONHCH(CO_2H)CH_2CONH_2$, $CH_2CH_2CONHCH(CO_2H)CH_2CONH_2$, $CH_2CONHCH(CO_2Me)CH_2CO_2H$, $CH_2CH_2CONHCH(CO_2Me)CH_2CO_2H$, $CH_2CONHCH(CO_2Me)CH_2CONH_2$, $CH_2CH_2CONHCH(CO_2Me)CH_2CONH_2$, $CH_2CONHCH_2CO_2Me$, $CH_2CH_2CONHCH_2CO_2Me$, $CH_2CONHCH(Me)CO_2Me$, $CH_2CH_2CONHCH(Me)CO_2Me$, $CH_2CONHCH(CH_2OH)CO_2Me$, $CH_2CH_2CONHCH(CH_2OH)CO_2Me$, $CH_2CONHCH(CH_2Ph)CO_2Me$,

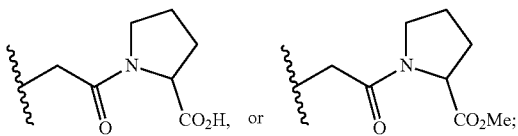 [SMILES: *CC(=O)N1CCCC1C(=O)O ; "or" ; *CC(=O)N1CCCC1C(=O)OC]

CH$_2$CONHCH(CO$_2$Me)CH$_2$CO$_2$Me, CH$_2$CONHCH(CO$_2$H)CH$_2$CO$_2$Me, (ii) CH$_2$CO$_2$H, CH$_2$CH$_2$CO$_2$H, CH=CHCO$_2$H, CH$_2$CH=CHCO$_2$H, CH(CMe$_3$)CO$_2$H, CH$_2$CH(CMe$_3$)CO$_2$H, CH$_2$CH(Me)CO$_2$H, CH(Me)CO$_2$H, CH(Me)CH$_2$CO$_2$H, CH$_2$CO$_2$Me, CH$_2$CH$_2$CO$_2$Me, CH=CHCO$_2$Me, CH$_2$CH=CHCO$_2$Me, CH(CMe$_3$)CO$_2$Me, CH$_2$CH(CMe$_3$)CO$_2$Me, CH$_2$CH(Me)CO$_2$Me, CH(Me)CO$_2$Me, CH(Me)CH$_2$CO$_2$Me, CH$_2$CO$_2$Et, CH$_2$CH$_2$CO$_2$Et, CH=CHCO$_2$Et, CH$_2$CH=CHCO$_2$Et, CH(CMe$_3$)CO$_2$Et, CH$_2$CH(CMe$_3$)CO$_2$Et, CH$_2$CH(Me)CO$_2$Et, CH(Me)CO$_2$Et, CH(Me)CH$_2$CO$_2$Et, CH$_2$CO$_2$CMe$_3$, CH$_2$CH$_2$CO$_2$CMe$_3$, CH=CHCO$_2$CMe$_3$, CH$_2$CH=CHCO$_2$CMe$_3$, CH(CMe$_3$)CO$_2$CMe$_3$, CH$_2$CH(CMe$_3$)CO$_2$CMe$_3$, CH$_2$CH(Me)CO$_2$CMe$_3$, CH(Me)CO$_2$CMe$_3$, or CH(Me)CH$_2$CO$_2$CMe$_3$; or (iii) CH$_2$CH$_2$NHCOMe, CH$_2$CH$_2$NHCO$_2$CMe$_3$, CH$_2$CH$_2$NHCONHMe, CH$_2$CH$_2$NHCO$_2$Me, or CH$_2$CH$_2$NHCONMe$_2$.

6. The compound or salt of claim 1, wherein R is H, Me, Et, or CMe$_3$.

7. The compound or salt of claim 1, wherein L is

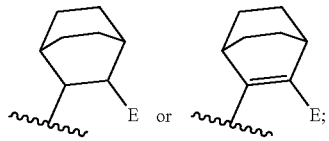

E is CO$_2$R$^a$, CONR$^a$R$^b$, NR$^a$R$^b$, NR$^a$CONR$^a$R$^b$, NR$^a$COR$^a$; or NR$^a$CO$_2$R$^a$;

each R$^a$ is independently H, Me, Et, or CMe$_3$; and each R$^b$ is independently H, Me, Et, CH$_2$CONHMe, CH$_2$CONMe$_2$, or CH$_2$CONH$_2$.

8. The compound or salt of claim 7, wherein L is

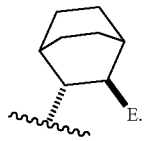

9. The compound or salt of claim 1, wherein (i) at least one R$^2$ is F;

(ii) at least one R$^2$ is Cl; or (iii) one R$^2$ is F and the other R$^2$ is Cl or F.

10. The compound or salt of claim 1, wherein (i) at least one R$^2$ is H; or (ii) each R$^2$ is H.

11. The compound or salt of claim 1, wherein at least one R$^2$ is phenyl, pyridinyl, hydroxyphenyl, CF$_3$, —C≡C—CH$_2$cyclopropyl, -C≡C-cyclopropyl, furanyl, thienyl, methyl, imidazolyl, CH(CH$_3$)$_2$, -(CH$_2$)$_2$pyridinyl, -C≡C—(CH$_2$)$_2$SCH$_3$, CN, —(CH$_2$)$_4$SCH$_3$, —(CH$_2$)$_4$CN, CO$_2$H, CONHCH$_3$, -C≡C—(CH$_2$)$_2$CN, CON(CH$_3$)$_2$, CO$_2$CH$_2$CH$_3$, —CH=CH$_2$, fluoropyridinyl, chloropyridinyl, or cyanopyridinyl.

12. The compound or salt of claim 1, wherein R$^3$ is H.

13. A compound as recited in Table A, or a pharmaceutically acceptable salt thereof:

TABLE A

A1

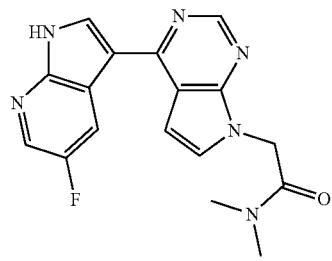 [SMILES: CN(C)C(=O)Cn1ccc2c(-c3c[nH]c4ncc(F)cc34)ncnc21]

A2

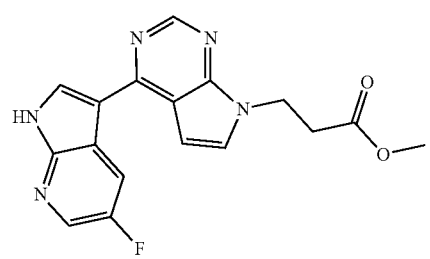 [SMILES: COC(=O)CCn1ccc2c(-c3c[nH]c4ncc(F)cc34)ncnc21]

TABLE A-continued
A3 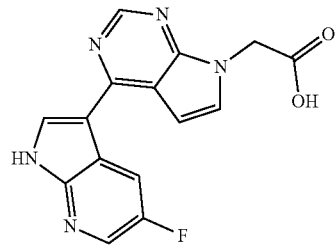
A4 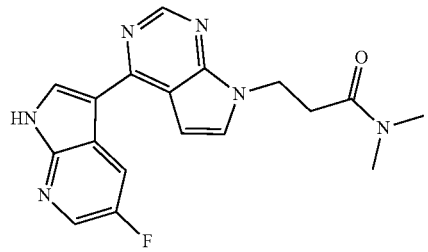 [SMILES: CN(C)C(=O)CCn1ccc2c(-c3c[nH]c4ncc(F)cc34)ncnc21]
A5 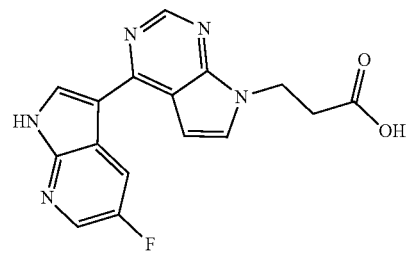 [SMILES: O=C(O)CCn1ccc2c(-c3c[nH]c4ncc(F)cc34)ncnc21]
A6 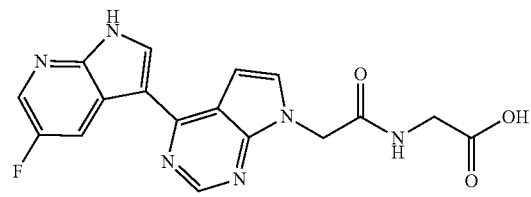 [SMILES: O=C(O)CNC(=O)Cn1ccc2c(-c3c[nH]c4ncc(F)cc34)ncnc21]
A7 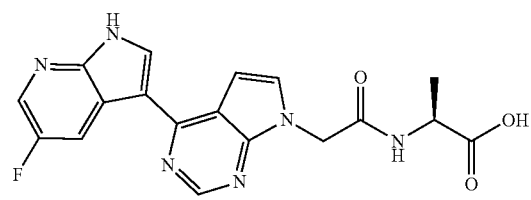 [SMILES: C[C@H](NC(=O)Cn1ccc2c(-c3c[nH]c4ncc(F)cc34)ncnc21)C(=O)O]
A8 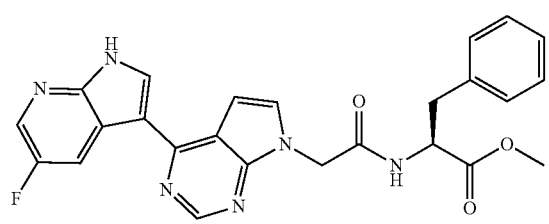 [SMILES: COC(=O)[C@H](Cc1ccccc1)NC(=O)Cn1ccc2c(-c3c[nH]c4ncc(F)cc34)ncnc21]
A9 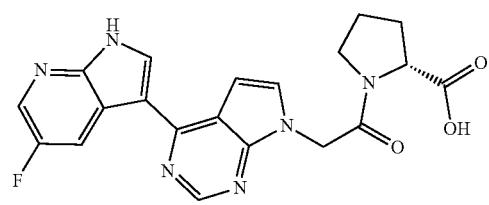 [SMILES: O=C(O)[C@H]1CCCN1C(=O)Cn1ccc2c(-c3c[nH]c4ncc(F)cc34)ncnc21]

TABLE A-continued
A10 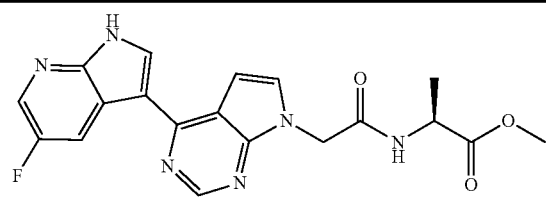
A11 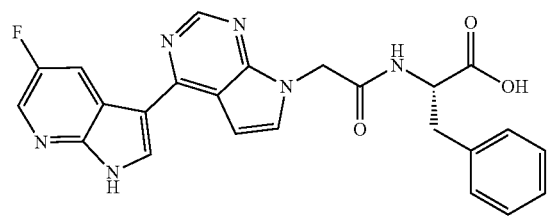 [SMILES: O=C(Cn1ccc2c(-c3c[nH]c4ncc(F)cc34)ncnc21)N[C@@H](Cc1ccccc1)C(=O)O]
A12 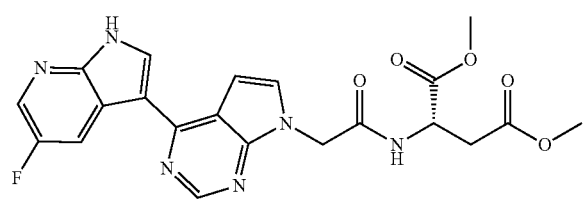 [SMILES: COC(=O)C[C@H](NC(=O)Cn1ccc2c(-c3c[nH]c4ncc(F)cc34)ncnc21)C(=O)OC]
A13 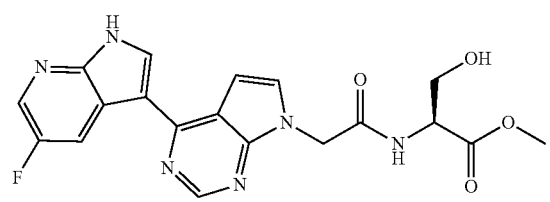 [SMILES: COC(=O)[C@H](CO)NC(=O)Cn1ccc2c(-c3c[nH]c4ncc(F)cc34)ncnc21]
A14 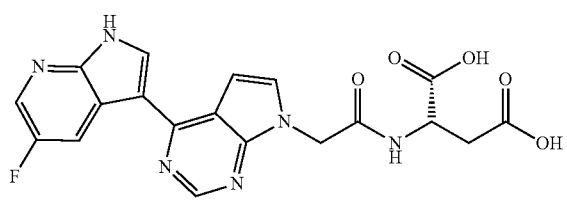
A15 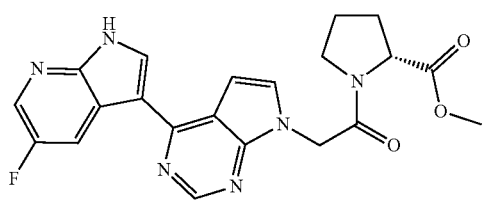 [SMILES: COC(=O)[C@H]1CCCN1C(=O)Cn1ccc2c(-c3c[nH]c4ncc(F)cc34)ncnc21]
A16 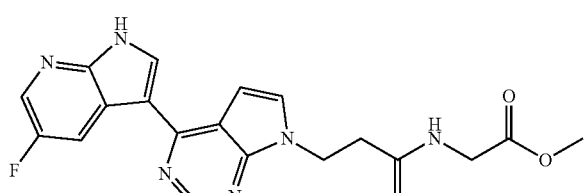
A17 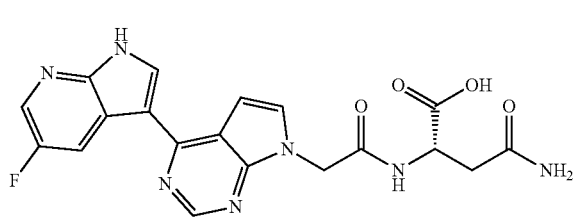 [SMILES: NC(=O)C[C@H](NC(=O)Cn1ccc2c(-c3c[nH]c4ncc(F)cc34)ncnc21)C(=O)O]

TABLE A-continued
A18 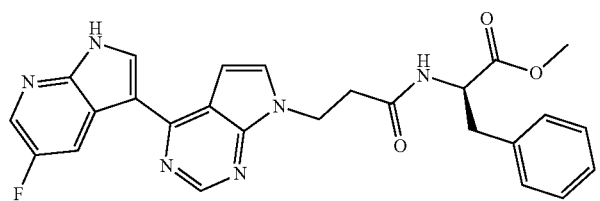 [SMILES: COC(=O)[C@@H](Cc1ccccc1)NC(=O)CCn1ccc2c(-c3c[nH]c4ncc(F)cc34)ncnc21]
A19 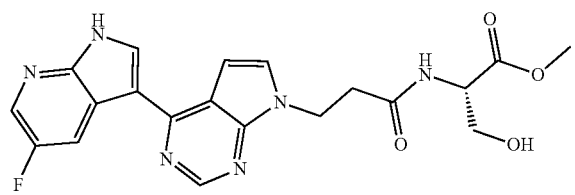 [SMILES: COC(=O)[C@H](CO)NC(=O)CCn1ccc2c(-c3c[nH]c4ncc(F)cc34)ncnc21]
A20 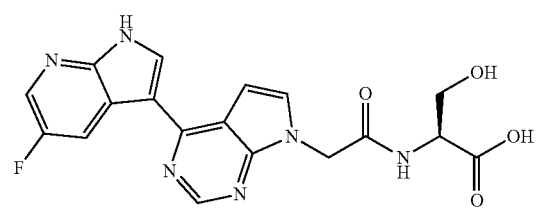 [SMILES: O=C(Cn1ccc2c(-c3c[nH]c4ncc(F)cc34)ncnc21)N[C@@H](CO)C(=O)O]
B1 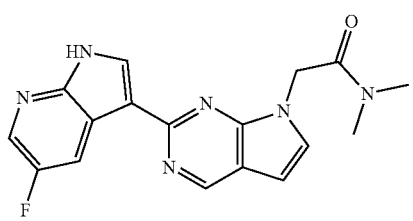 [SMILES: CN(C)C(=O)Cn1ccc2cnc(-c3c[nH]c4ncc(F)cc34)nc21]
B2 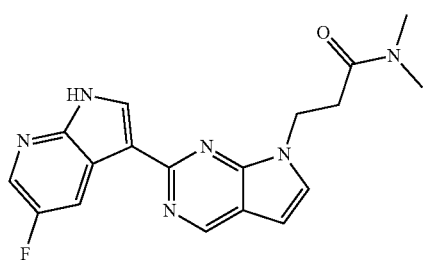 [SMILES: CN(C)C(=O)CCn1ccc2cnc(-c3c[nH]c4ncc(F)cc34)nc21]
B3 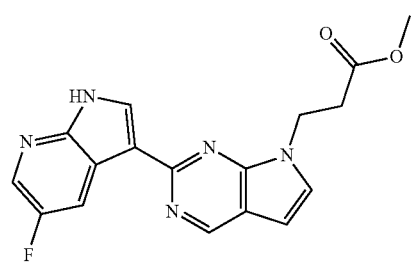 [SMILES: COC(=O)CCn1ccc2cnc(-c3c[nH]c4ncc(F)cc34)nc21]
B4 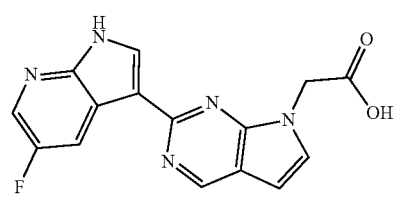 [SMILES: O=C(O)Cn1ccc2cnc(-c3c[nH]c4ncc(F)cc34)nc21]

TABLE A-continued
B5 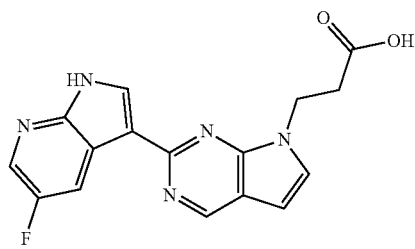 [SMILES: O=C(O)CCn1ccc2cnc(-c3c[nH]c4ncc(F)cc34)nc21]
B6 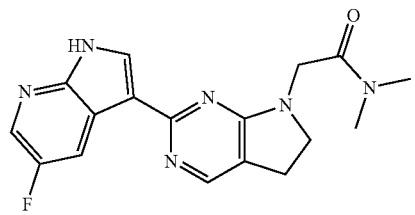 [SMILES: CN(C)C(=O)CN1CCc2cnc(-c3c[nH]c4ncc(F)cc34)nc21]
B7 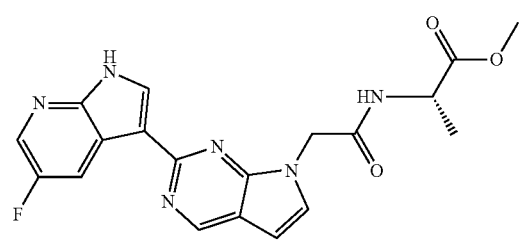 [SMILES: COC(=O)[C@H](C)NC(=O)Cn1ccc2cnc(-c3c[nH]c4ncc(F)cc34)nc21]
B8 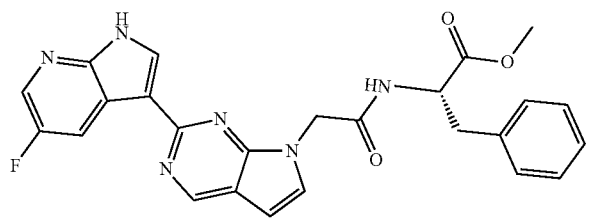 [SMILES: COC(=O)[C@H](Cc1ccccc1)NC(=O)Cn1ccc2cnc(-c3c[nH]c4ncc(F)cc34)nc21]
B9 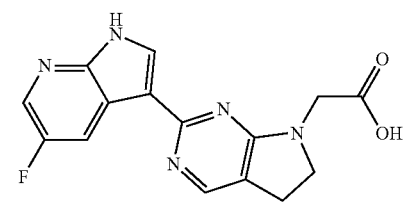 [SMILES: O=C(O)CN1CCc2cnc(-c3c[nH]c4ncc(F)cc34)nc21]
B10 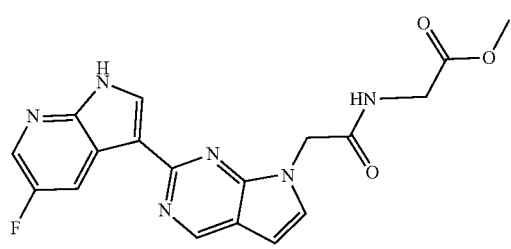 [SMILES: COC(=O)CNC(=O)Cn1ccc2cnc(-c3c[nH]c4ncc(F)cc34)nc21]
B11 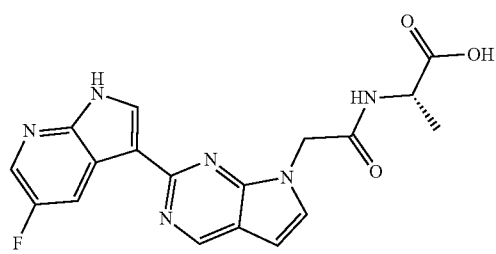 [SMILES: C[C@H](NC(=O)Cn1ccc2cnc(-c3c[nH]c4ncc(F)cc34)nc21)C(=O)O]

TABLE A-continued
B12 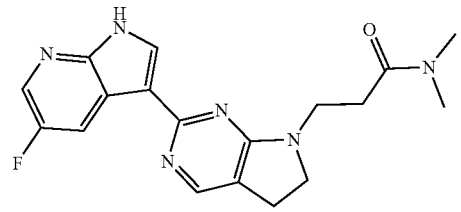 [SMILES: CN(C)C(=O)CCN1CCc2cnc(-c3c[nH]c4ncc(F)cc34)nc21]
B13 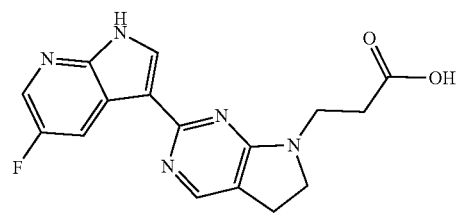 [SMILES: O=C(O)CCN1CCc2cnc(-c3c[nH]c4ncc(F)cc34)nc21]
B14 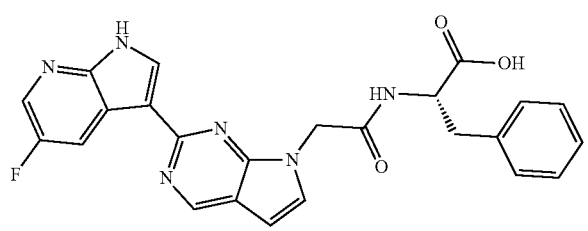 [SMILES: O=C(Cn1ccc2cnc(-c3c[nH]c4ncc(F)cc34)nc21)N[C@@H](Cc1ccccc1)C(=O)O]
B15 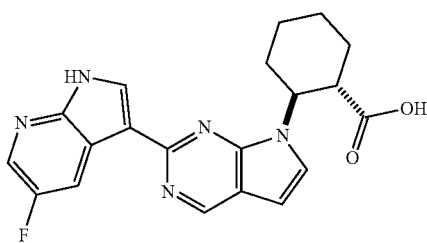
B16 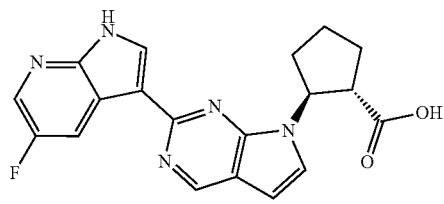 [SMILES: O=C(O)[C@H]1CCC[C@@H]1n1ccc2cnc(-c3c[nH]c4ncc(F)cc34)nc21]
B17 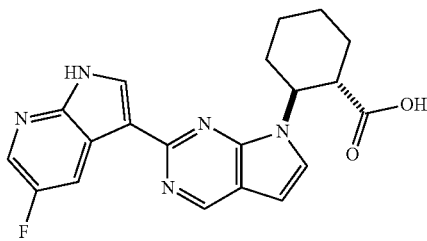
B18 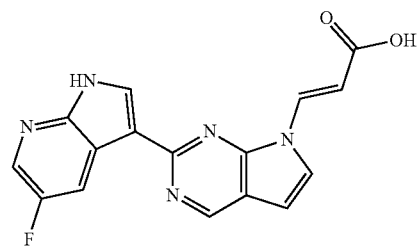 [SMILES: O=C(O)/C=C/n1ccc2cnc(-c3c[nH]c4ncc(F)cc34)nc21]

TABLE A-continued
B19 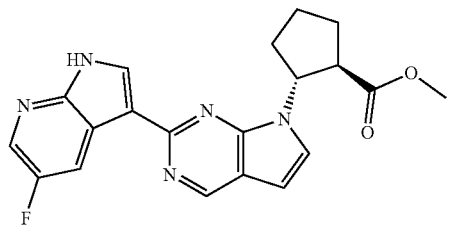 [SMILES: COC(=O)[C@@H]1CCC[C@H]1n1ccc2cnc(-c3c[nH]c4ncc(F)cc34)nc21]
B20 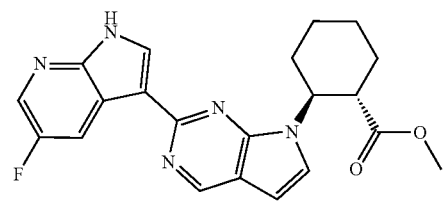 [SMILES: COC(=O)[C@H]1CCCC[C@@H]1n1ccc2cnc(-c3c[nH]c4ncc(F)cc34)nc21]
B21 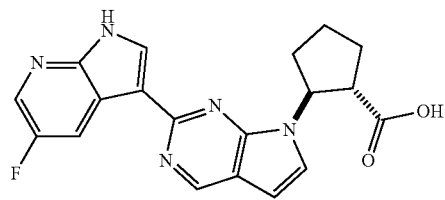
B22 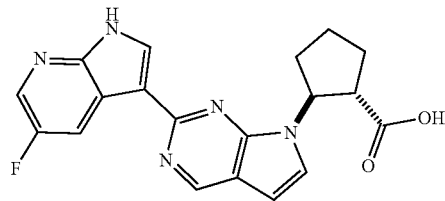
B23 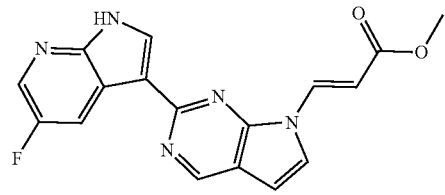 [SMILES: COC(=O)/C=C/n1ccc2cnc(-c3c[nH]c4ncc(F)cc34)nc21]
B24 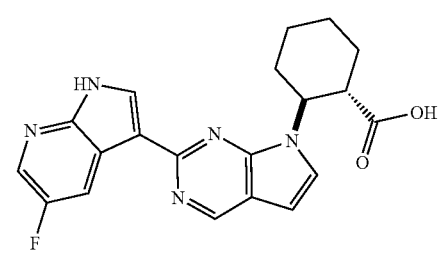

TABLE A-continued
B25 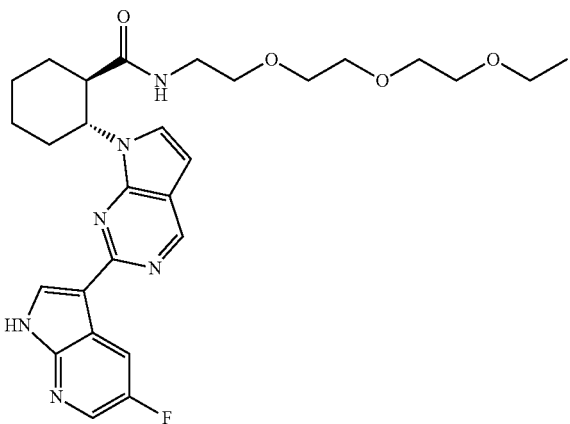 [SMILES: CCOCCOCCOCCNC(=O)[C@@H]1CCCC[C@H]1n1ccc2cnc(-c3c[nH]c4ncc(F)cc34)nc21]
B26 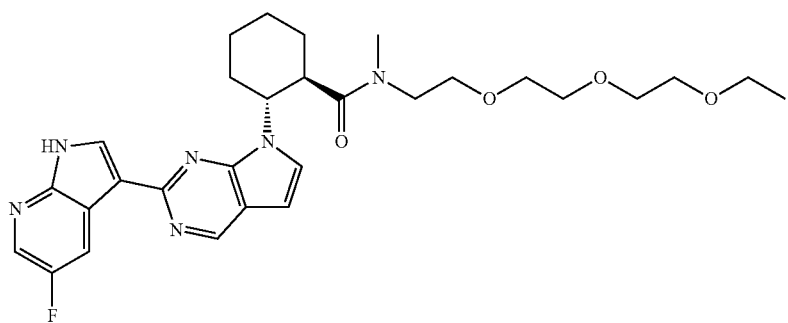 [SMILES: CCOCCOCCOCCN(C)C(=O)[C@@H]1CCCC[C@H]1n1ccc2cnc(-c3c[nH]c4ncc(F)cc34)nc21]
B27 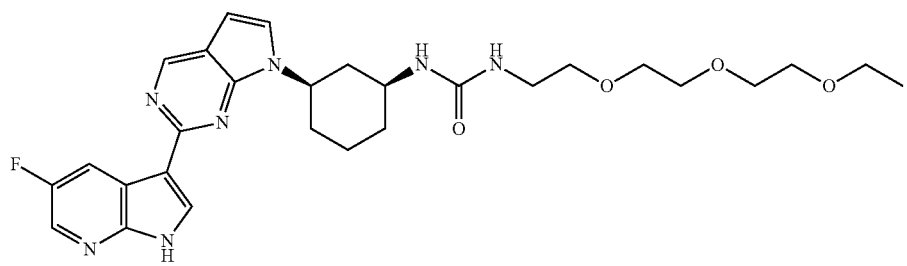 [SMILES: CCOCCOCCOCCNC(=O)N[C@H]1CCC[C@@H](n2ccc3cnc(-c4c[nH]c5ncc(F)cc45)nc32)C1]
B28 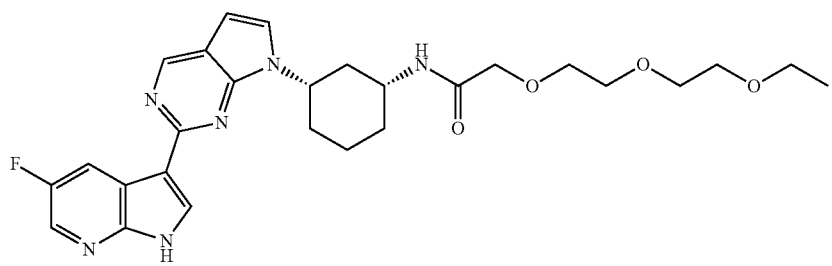 [SMILES: CCOCCOCCOCC(=O)N[C@@H]1CCC[C@H](n2ccc3cnc(-c4c[nH]c5ncc(F)cc45)nc32)C1]
B29 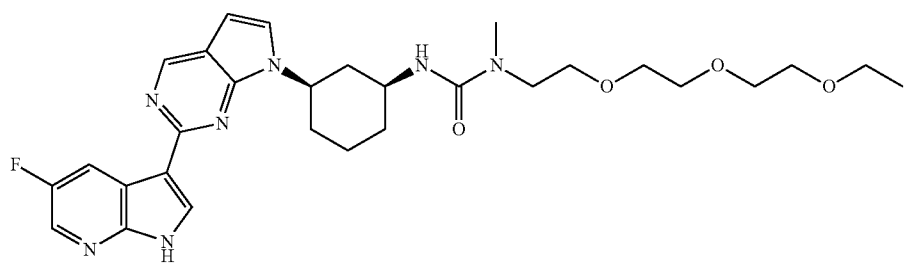 [SMILES: CCOCCOCCOCCN(C)C(=O)N[C@H]1CCC[C@@H](n2ccc3cnc(-c4c[nH]c5ncc(F)cc45)nc32)C1]

TABLE A-continued
B30
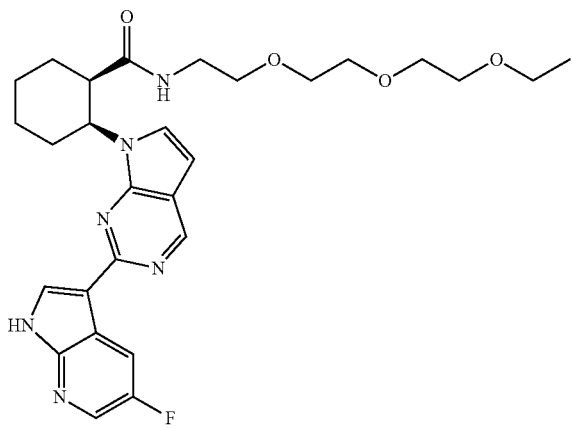 [SMILES: CCOCCOCCOCCNC(=O)[C@@H]1CCCC[C@@H]1n1ccc2cnc(-c3c[nH]c4ncc(F)cc34)nc21]
B31
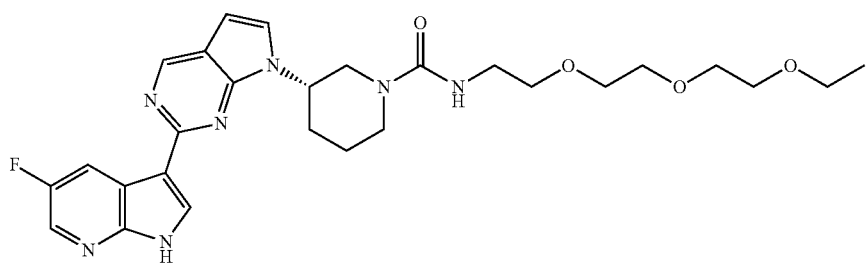 [SMILES: CCOCCOCCOCCNC(=O)N1CCC[C@H](n2ccc3cnc(-c4c[nH]c5ncc(F)cc45)nc32)C1]
B32
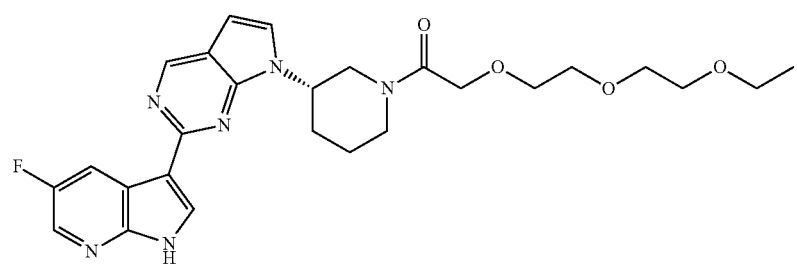 [SMILES: CCOCCOCCOCC(=O)N1CCC[C@H](n2ccc3cnc(-c4c[nH]c5ncc(F)cc45)nc32)C1]
B33
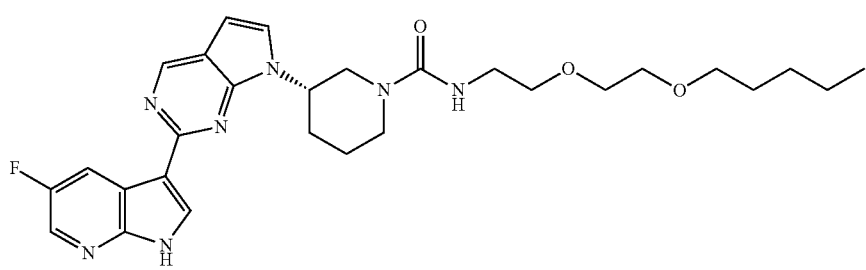
B34
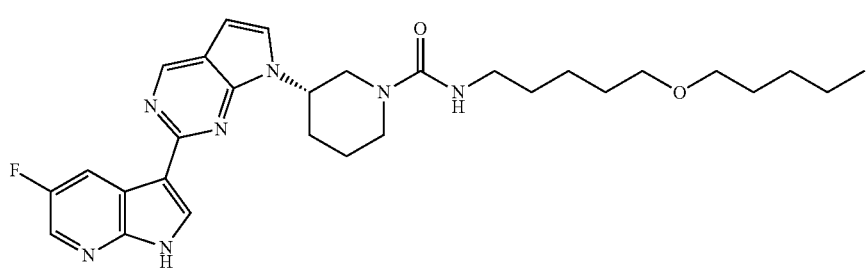

TABLE A-continued
B35 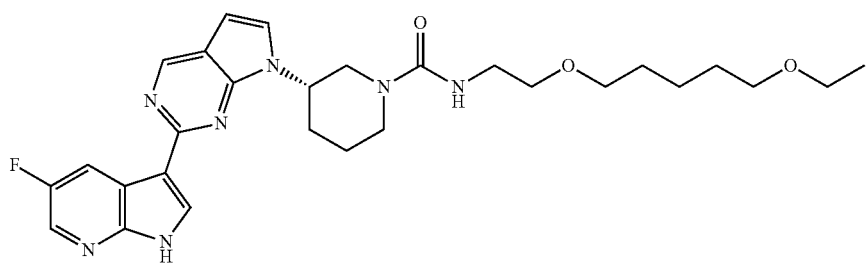 [SMILES: CCOCCCCCOCCNC(=O)N1CCC[C@H](n2ccc3cnc(-c4c[nH]c5ncc(F)cc45)nc32)C1]
B36 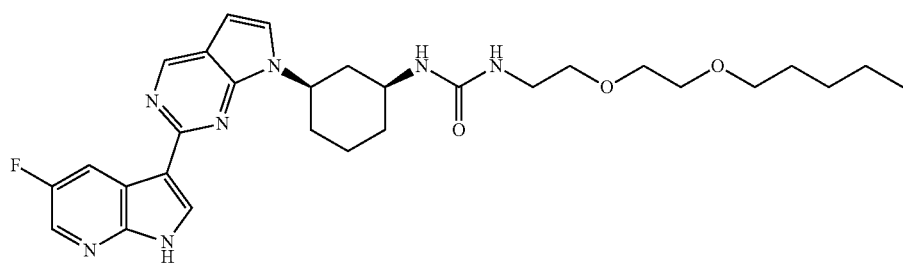
B37 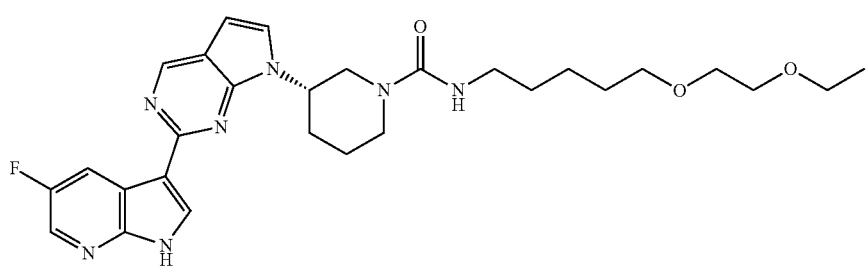
B38 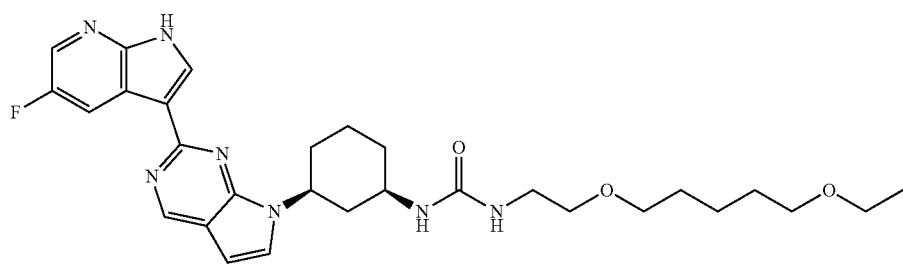 [SMILES: CCOCCCCCOCCNC(=O)N[C@@H]1CCC[C@H](n2ccc3cnc(-c4c[nH]c5ncc(F)cc45)nc32)C1]
B39 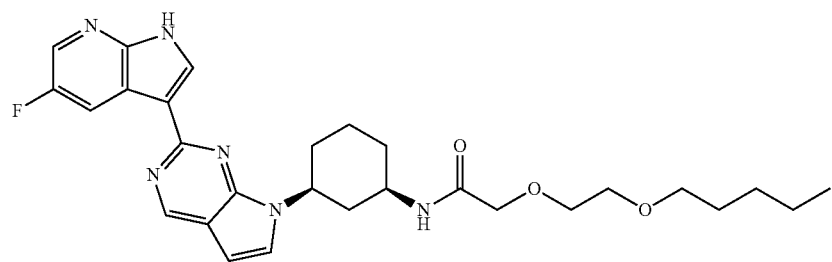 [SMILES: CCCCCOCCOCC(=O)N[C@@H]1CCC[C@H](n2ccc3cnc(-c4c[nH]c5ncc(F)cc45)nc32)C1]
B40 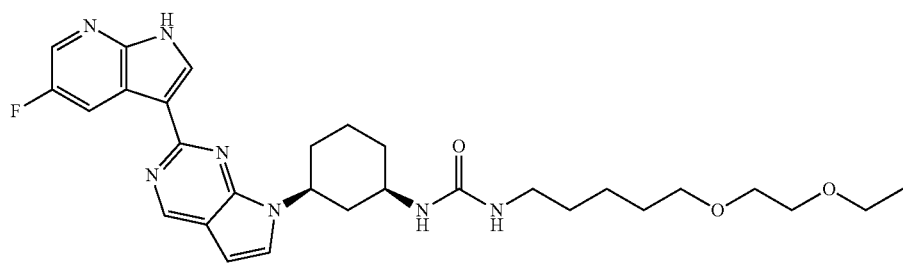 [SMILES: CCOCCOCCCCCNC(=O)N[C@@H]1CCC[C@H](n2ccc3cnc(-c4c[nH]c5ncc(F)cc45)nc32)C1]

TABLE A-continued
B41 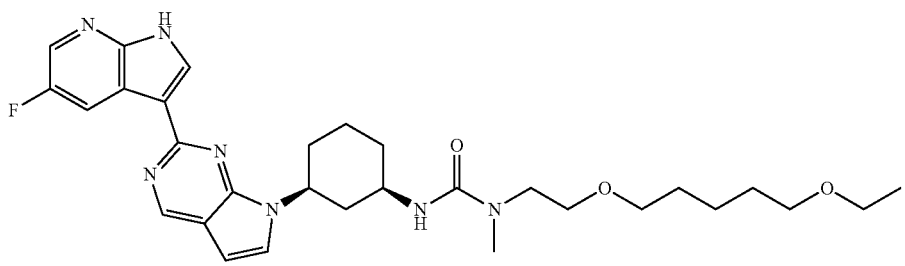 [SMILES: CCOCCCCCOCCN(C)C(=O)N[C@@H]1CCC[C@H](n2ccc3cnc(-c4c[nH]c5ncc(F)cc45)nc32)C1]
B42 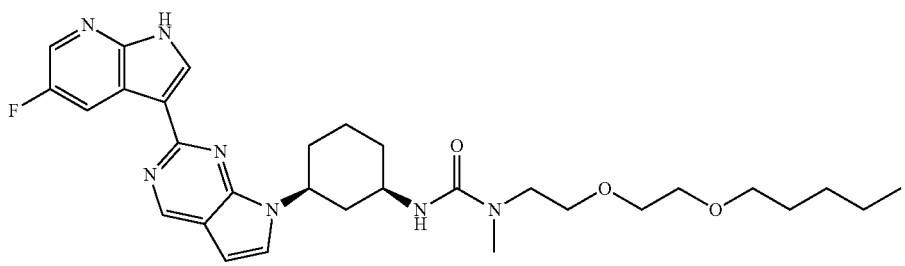 [SMILES: CCCCCOCCOCCN(C)C(=O)N[C@@H]1CCC[C@H](n2ccc3cnc(-c4c[nH]c5ncc(F)cc45)nc32)C1]
B43 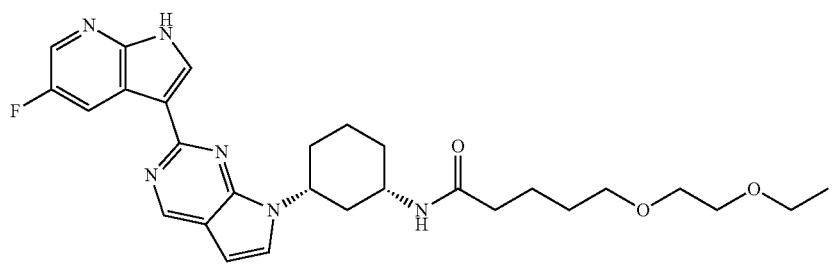 [SMILES: CCOCCOCCCCC(=O)N[C@H]1CCC[C@@H](n2ccc3cnc(-c4c[nH]c5ncc(F)cc45)nc32)C1]
B44 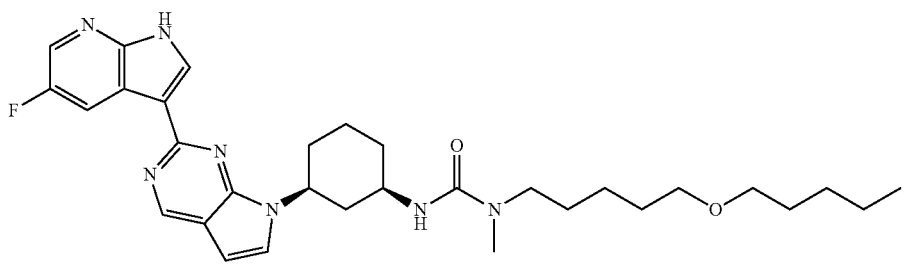 [SMILES: CCCCCOCCCCCN(C)C(=O)N[C@@H]1CCC[C@H](n2ccc3cnc(-c4c[nH]c5ncc(F)cc45)nc32)C1]
B45 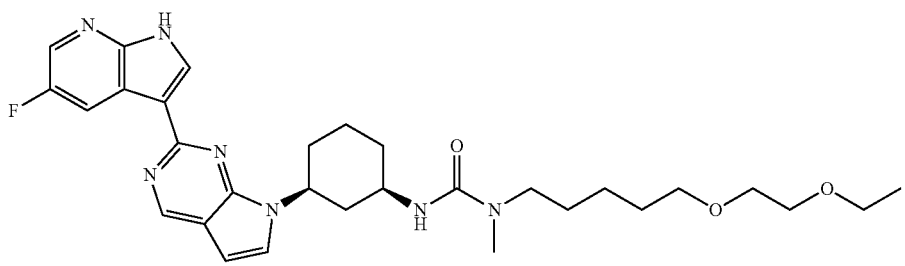 [SMILES: CCOCCOCCCCCN(C)C(=O)N[C@@H]1CCC[C@H](n2ccc3cnc(-c4c[nH]c5ncc(F)cc45)nc32)C1]
B46 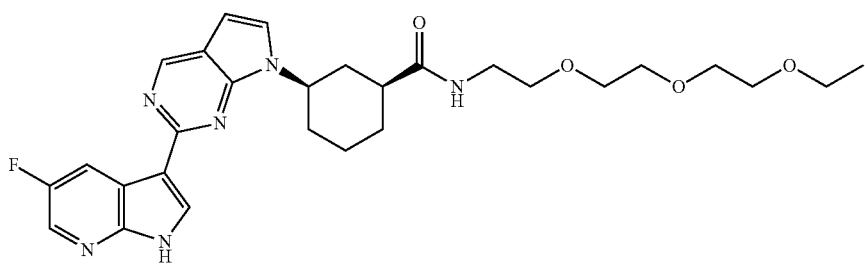 [SMILES: CCOCCOCCOCCNC(=O)[C@H]1CCC[C@@H](n2ccc3cnc(-c4c[nH]c5ncc(F)cc45)nc32)C1]

TABLE A-continued
B47
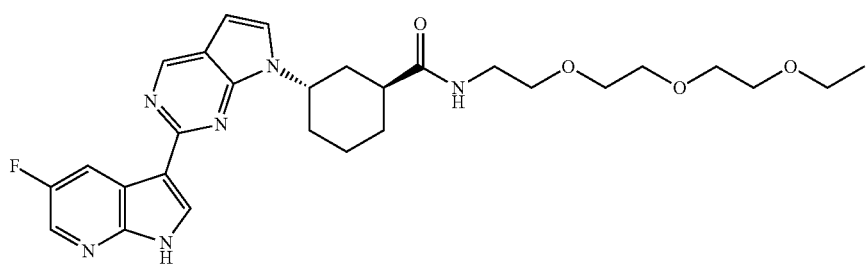 [SMILES: CCOCCOCCOCCNC(=O)[C@H]1CCC[C@H](n2ccc3cnc(-c4c[nH]c5ncc(F)cc45)nc32)C1]
B48
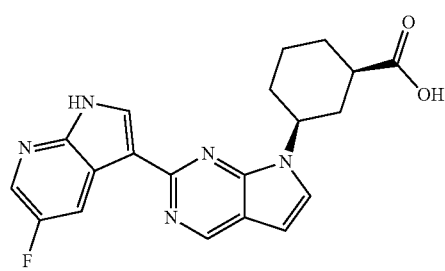 [SMILES: O=C(O)[C@@H]1CCC[C@H](n2ccc3cnc(-c4c[nH]c5ncc(F)cc45)nc32)C1]
B49
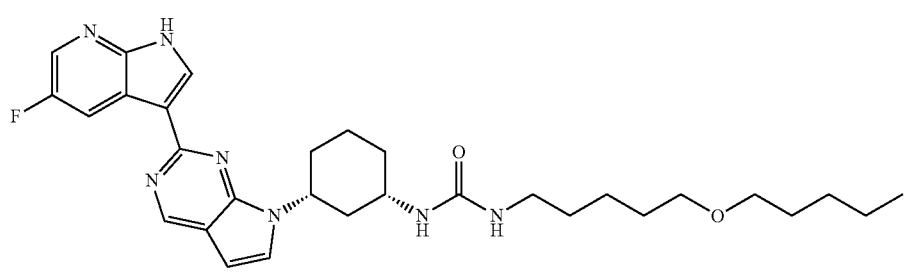 [SMILES: CCCCCOCCCCCNC(=O)N[C@H]1CCC[C@@H](n2ccc3cnc(-c4c[nH]c5ncc(F)cc45)nc32)C1]
B50
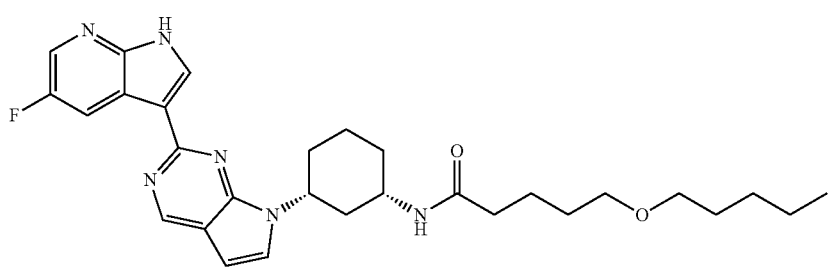
B51
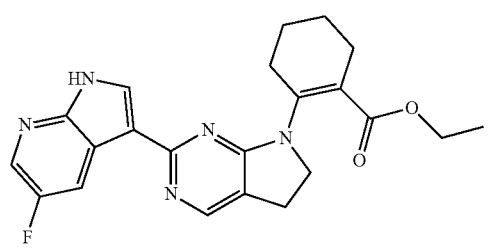 [SMILES: CCOC(=O)C1=C(N2CCc3cnc(-c4c[nH]c5ncc(F)cc45)nc32)CCCC1]
B100
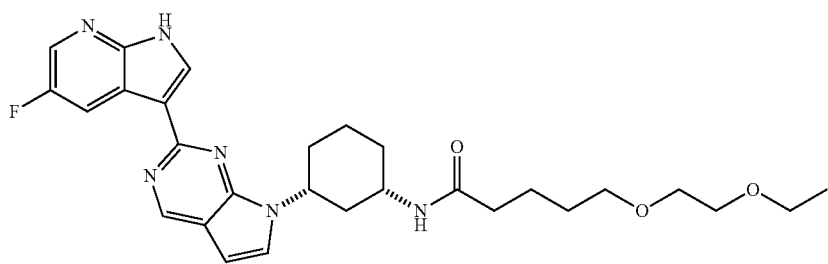

TABLE A-continued
B52 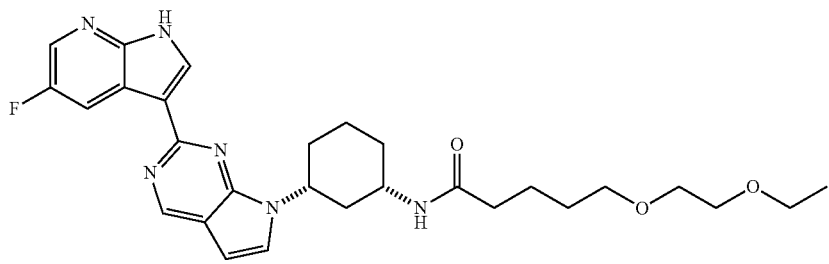
B53 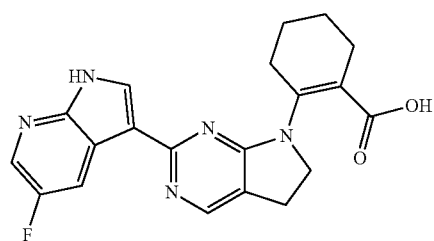 [SMILES: O=C(O)C1=C(N2CCc3cnc(-c4c[nH]c5ncc(F)cc45)nc32)CCCC1]
B54 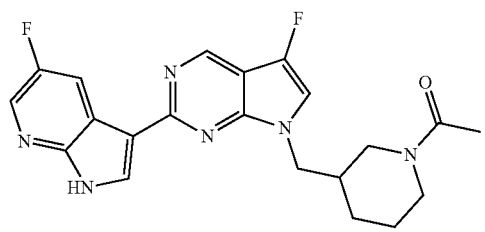 [SMILES: CC(=O)N1CCCC(Cn2cc(F)c3cnc(-c4c[nH]c5ncc(F)cc45)nc32)C1]
B55 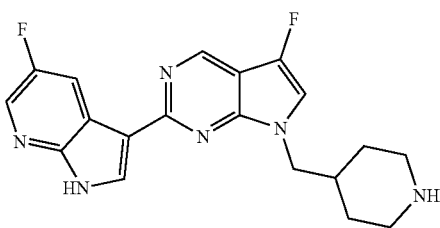 [SMILES: Fc1cnc2[nH]cc(-c3ncc4c(F)cn(CC5CCNCC5)c4n3)c2c1]
B56 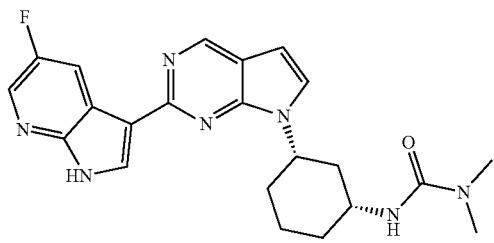 [SMILES: CN(C)C(=O)N[C@@H]1CCC[C@H](n2ccc3cnc(-c4c[nH]c5ncc(F)cc45)nc32)C1]
B57 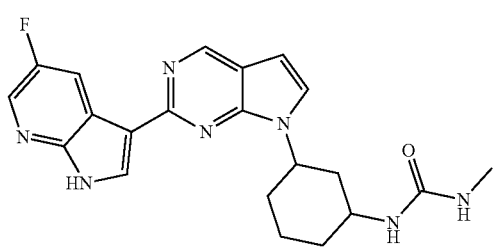 [SMILES: CNC(=O)NC1CCCC(n2ccc3cnc(-c4c[nH]c5ncc(F)cc45)nc32)C1]

TABLE A-continued
B58 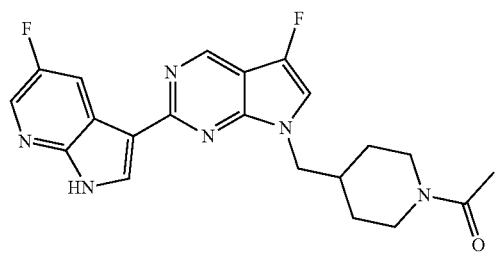 [SMILES: CC(=O)N1CCC(Cn2cc(F)c3cnc(-c4c[nH]c5ncc(F)cc45)nc32)CC1]
B59 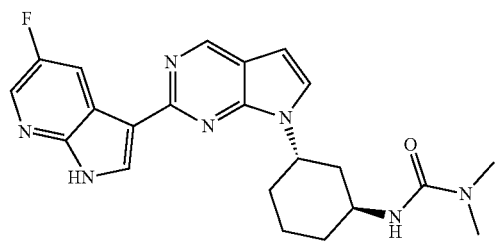 [SMILES: CN(C)C(=O)N[C@H]1CCC[C@H](n2ccc3cnc(-c4c[nH]c5ncc(F)cc45)nc32)C1]
B60 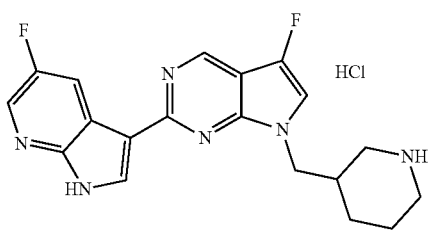 [SMILES: Fc1cnc2[nH]cc(-c3ncc4c(F)cn(CC5CCCNC5)c4n3)c2c1 ; Cl]
B61 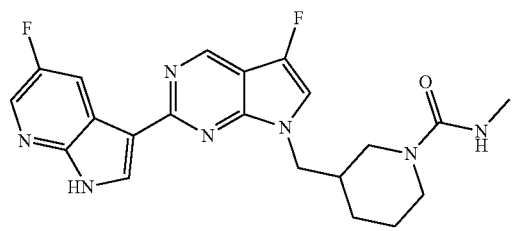 [SMILES: CNC(=O)N1CCCC(Cn2cc(F)c3cnc(-c4c[nH]c5ncc(F)cc45)nc32)C1]
B62 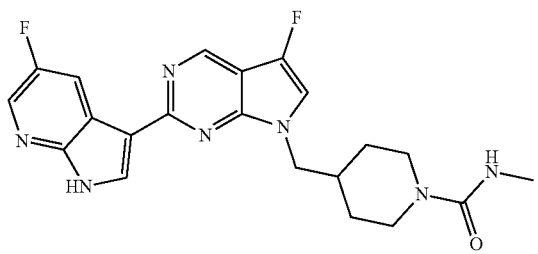 [SMILES: CNC(=O)N1CCC(Cn2cc(F)c3cnc(-c4c[nH]c5ncc(F)cc45)nc32)CC1]
B63 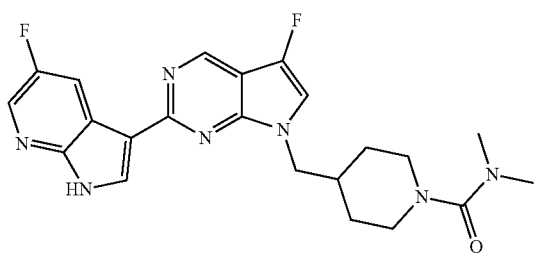 [SMILES: CN(C)C(=O)N1CCC(Cn2cc(F)c3cnc(-c4c[nH]c5ncc(F)cc45)nc32)CC1]

TABLE A-continued
B64 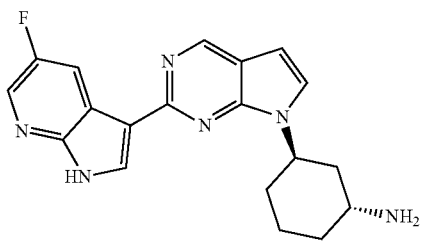 [SMILES: N[C@@H]1CCC[C@@H](n2ccc3cnc(-c4c[nH]c5ncc(F)cc45)nc32)C1]
B65 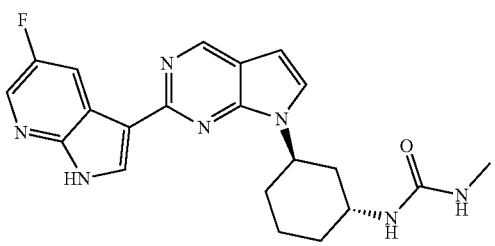 [SMILES: CNC(=O)N[C@@H]1CCC[C@@H](n2ccc3cnc(-c4c[nH]c5ncc(F)cc45)nc32)C1]
B66 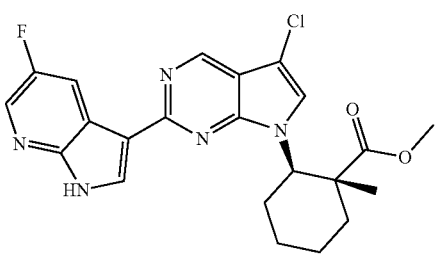 [SMILES: COC(=O)[C@]1(C)CCCC[C@H]1n1cc(Cl)c2cnc(-c3c[nH]c4ncc(F)cc34)nc21]
B67 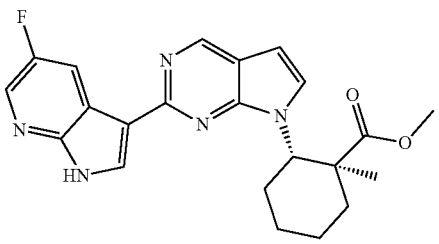 [SMILES: COC(=O)[C@@]1(C)CCCC[C@@H]1n1ccc2cnc(-c3c[nH]c4ncc(F)cc34)nc21]
B68 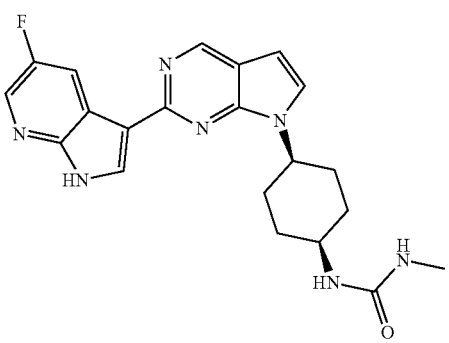 [SMILES: CNC(=O)N[C@H]1CC[C@@H](n2ccc3cnc(-c4c[nH]c5ncc(F)cc45)nc32)CC1]
B69 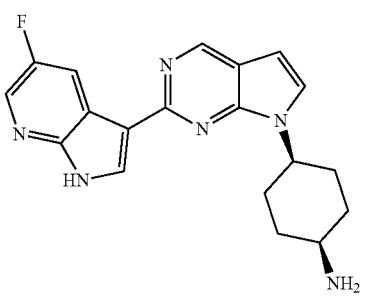 [SMILES: N[C@H]1CC[C@@H](n2ccc3cnc(-c4c[nH]c5ncc(F)cc45)nc32)CC1]

TABLE A-continued
B70 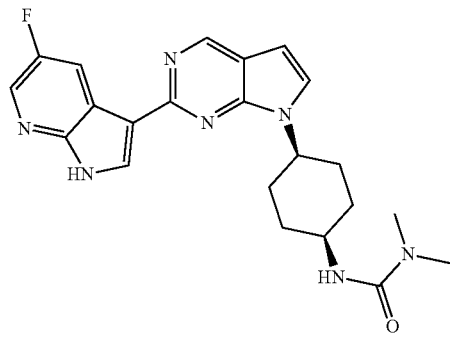 [SMILES: CN(C)C(=O)N[C@H]1CC[C@@H](n2ccc3cnc(-c4c[nH]c5ncc(F)cc45)nc32)CC1]
B71 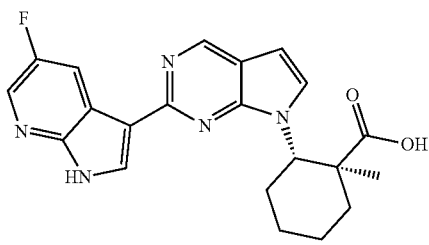 [SMILES: C[C@]1(C(=O)O)CCCC[C@@H]1n1ccc2cnc(-c3c[nH]c4ncc(F)cc34)nc21]
B72 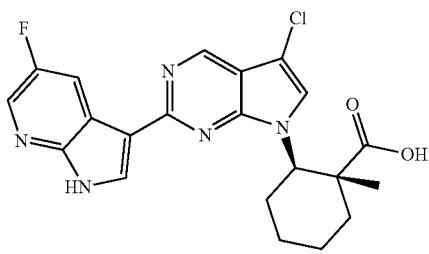 [SMILES: C[C@@]1(C(=O)O)CCCC[C@H]1n1cc(Cl)c2cnc(-c3c[nH]c4ncc(F)cc34)nc21]
B73 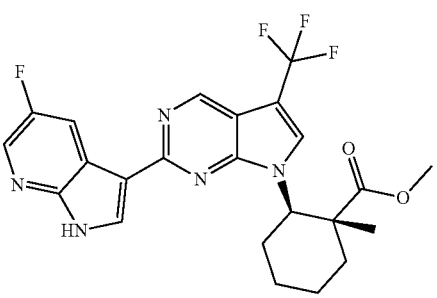 [SMILES: COC(=O)[C@]1(C)CCCC[C@H]1n1cc(C(F)(F)F)c2cnc(-c3c[nH]c4ncc(F)cc34)nc21]
B74 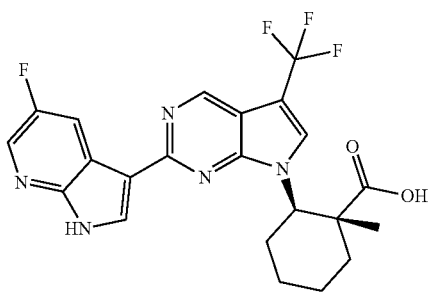 [SMILES: C[C@@]1(C(=O)O)CCCC[C@H]1n1cc(C(F)(F)F)c2cnc(-c3c[nH]c4ncc(F)cc34)nc21]

TABLE A-continued
B75 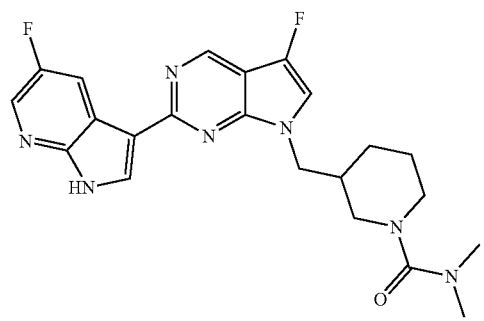 [SMILES: CN(C)C(=O)N1CCCC(Cn2cc(F)c3cnc(-c4c[nH]c5ncc(F)cc45)nc32)C1]
B76 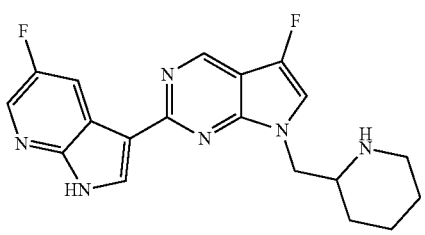 [SMILES: Fc1cnc2[nH]cc(-c3ncc4c(F)cn(CC5CCCCN5)c4n3)c2c1]
B77 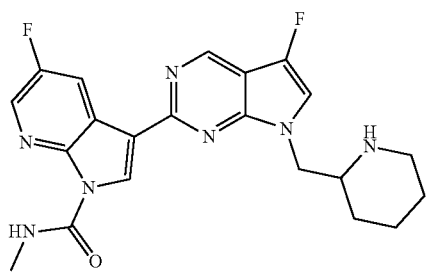 [SMILES: CNC(=O)n1cc(-c2ncc3c(F)cn(CC4CCCCN4)c3n2)c2cc(F)cnc21]
B78 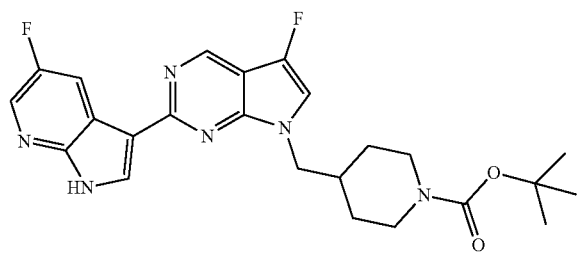 [SMILES: CC(C)(C)OC(=O)N1CCC(Cn2cc(F)c3cnc(-c4c[nH]c5ncc(F)cc45)nc32)CC1]
B79 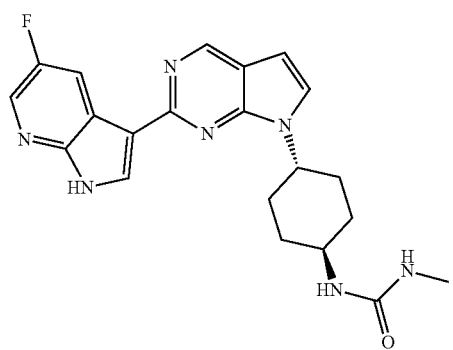 [SMILES: CNC(=O)N[C@H]1CC[C@H](n2ccc3cnc(-c4c[nH]c5ncc(F)cc45)nc32)CC1]

TABLE A-continued
B80 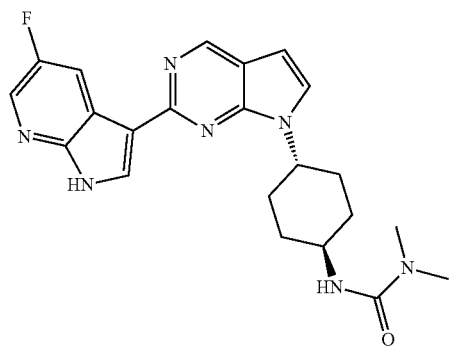 [SMILES: CN(C)C(=O)N[C@H]1CC[C@H](n2ccc3cnc(-c4c[nH]c5ncc(F)cc45)nc32)CC1]
B81 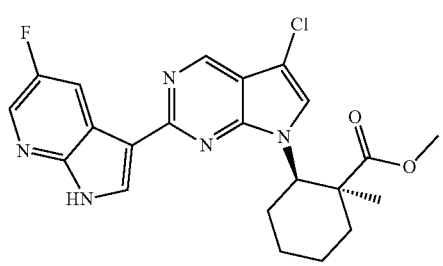 [SMILES: COC(=O)[C@@]1(C)CCCC[C@H]1n1cc(Cl)c2cnc(-c3c[nH]c4ncc(F)cc34)nc21]
B82 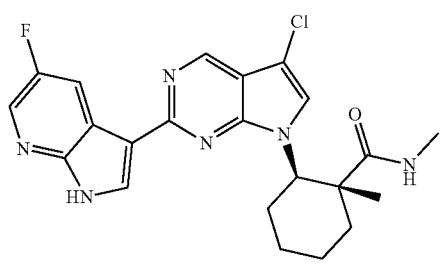 [SMILES: CNC(=O)[C@]1(C)CCCC[C@H]1n1cc(Cl)c2cnc(-c3c[nH]c4ncc(F)cc34)nc21]
B83 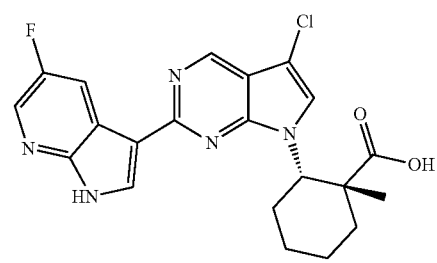 [SMILES: C[C@@]1(C(=O)O)CCCC[C@@H]1n1cc(Cl)c2cnc(-c3c[nH]c4ncc(F)cc34)nc21]
B84 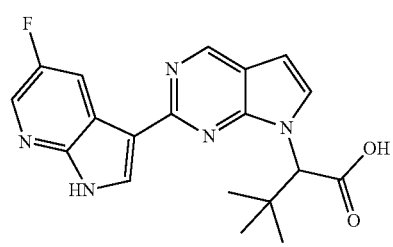 [SMILES: CC(C)(C)C(C(=O)O)n1ccc2cnc(-c3c[nH]c4ncc(F)cc34)nc21]

TABLE A-continued
B85 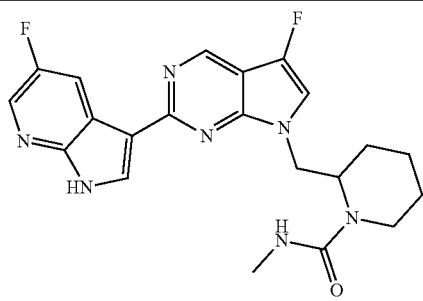
B86 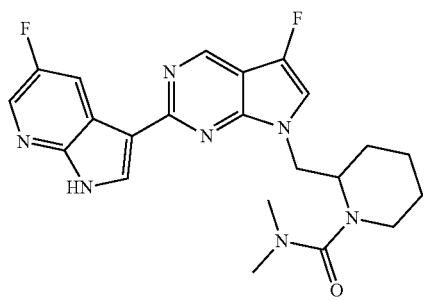 [SMILES: CN(C)C(=O)N1CCCCC1Cn1cc(F)c2cnc(-c3c[nH]c4ncc(F)cc34)nc21]
B87 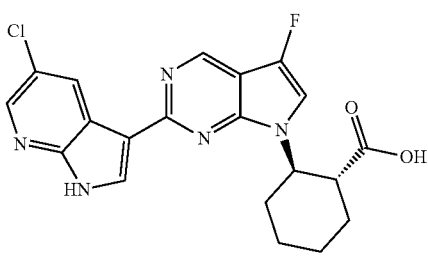 [SMILES: O=C(O)[C@@H]1CCCC[C@H]1n1cc(F)c2cnc(-c3c[nH]c4ncc(Cl)cc34)nc21]
B88 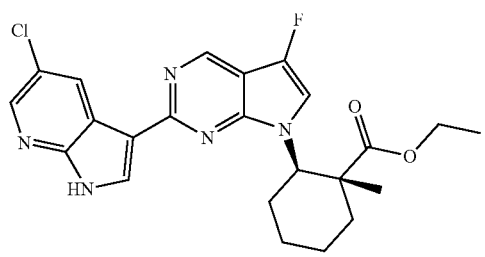
B89 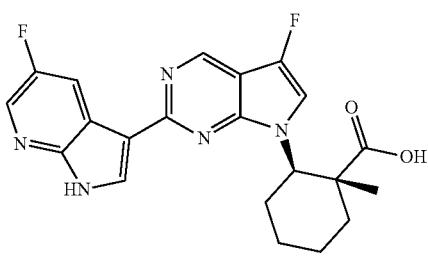 [SMILES: C[C@@]1(C(=O)O)CCCC[C@H]1n1cc(F)c2cnc(-c3c[nH]c4ncc(F)cc34)nc21]
B90 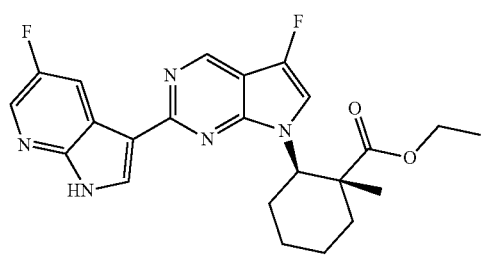 [SMILES: CCOC(=O)[C@]1(C)CCCC[C@H]1n1cc(F)c2cnc(-c3c[nH]c4ncc(F)cc34)nc21]

TABLE A-continued
B91 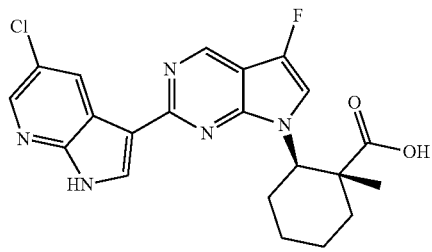
B92 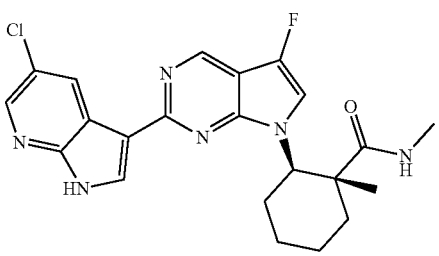 [SMILES: CNC(=O)[C@]1(C)CCCC[C@H]1n1cc(F)c2cnc(-c3c[nH]c4ncc(Cl)cc34)nc21]
B93 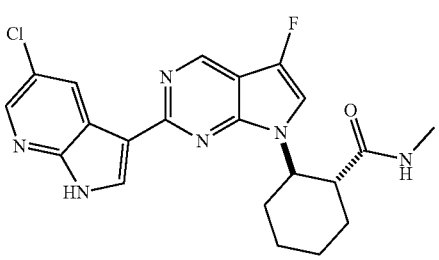
B94 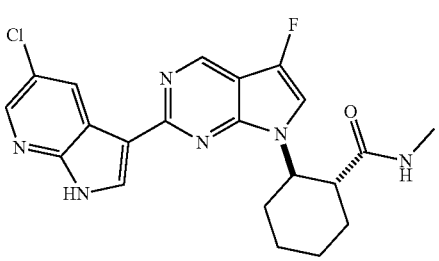
B95 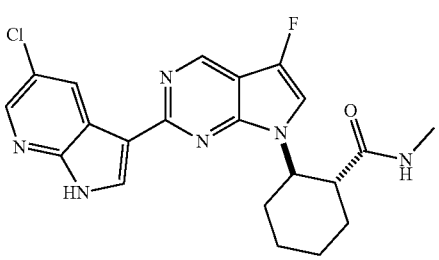
B96 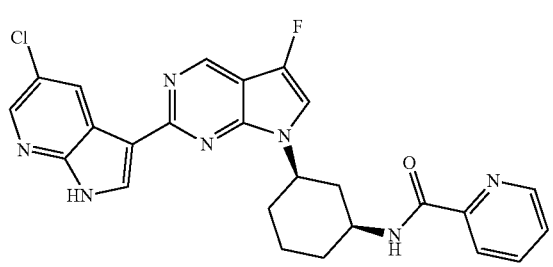 [SMILES: O=C(N[C@H]1CCC[C@@H](n2cc(F)c3cnc(-c4c[nH]c5ncc(Cl)cc45)nc32)C1)c1ccccn1]

TABLE A-continued
B97
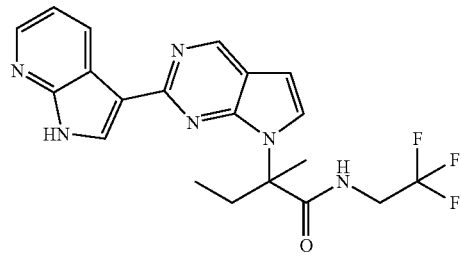 [SMILES: CCC(C)(C(=O)NCC(F)(F)F)n1ccc2cnc(-c3c[nH]c4ncccc34)nc21]
B98
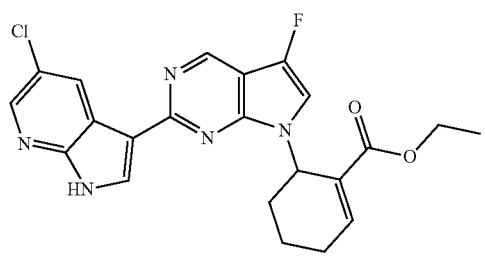 [SMILES: CCOC(=O)C1=CCCCC1n1cc(F)c2cnc(-c3c[nH]c4ncc(Cl)cc34)nc21]
B99
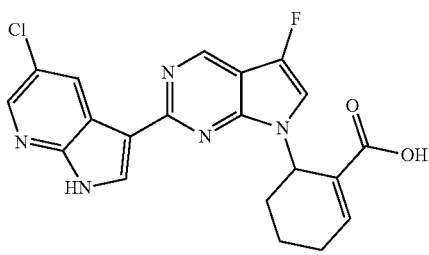 [SMILES: O=C(O)C1=CCCCC1n1cc(F)c2cnc(-c3c[nH]c4ncc(Cl)cc34)nc21]
B101
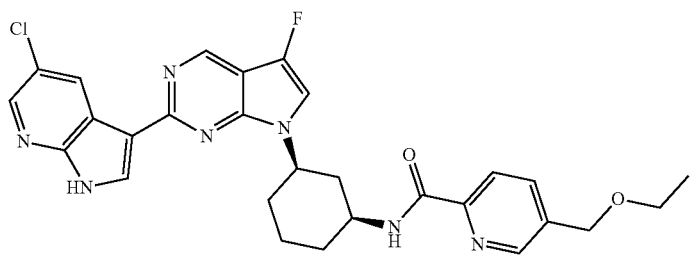 [SMILES: CCOCc1ccc(C(=O)N[C@H]2CCC[C@@H](n3cc(F)c4cnc(-c5c[nH]c6ncc(Cl)cc56)nc43)C2)nc1]
B102
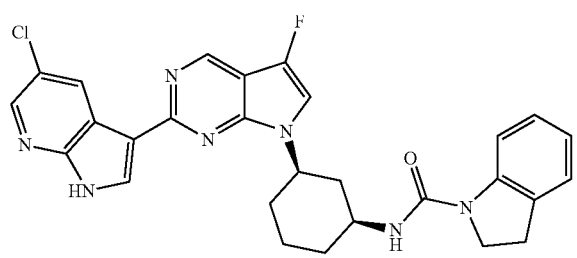 [SMILES: O=C(N[C@H]1CCC[C@@H](n2cc(F)c3cnc(-c4c[nH]c5ncc(Cl)cc45)nc32)C1)N1CCc2ccccc21]
B103
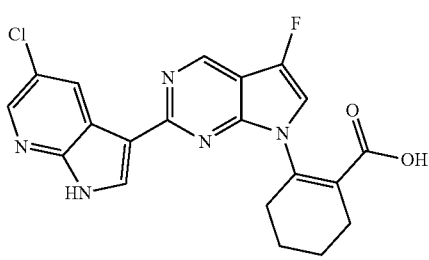 [SMILES: O=C(O)C1=C(n2cc(F)c3cnc(-c4c[nH]c5ncc(Cl)cc45)nc32)CCCC1]

TABLE A-continued
B109 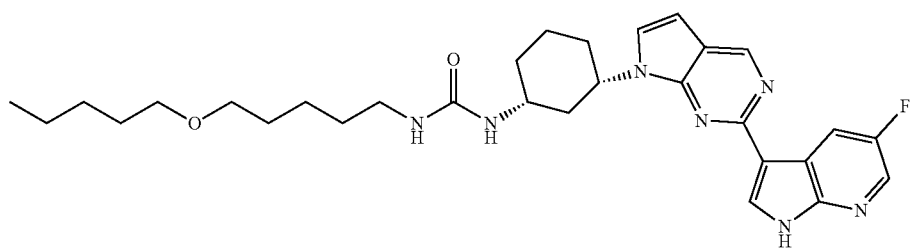 [SMILES: CCCCCOCCCCCNC(=O)N[C@@H]1CCC[C@H](n2ccc3cnc(-c4c[nH]c5ncc(F)cc45)nc32)C1]
B120 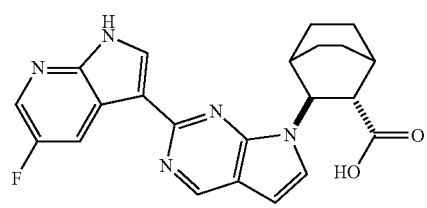
B121 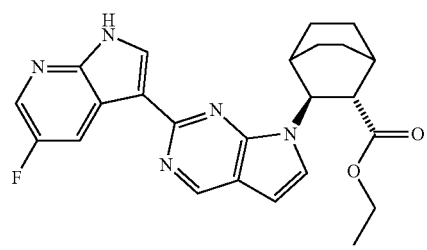 [SMILES: CCOC(=O)[C@H]1C2CCC(CC2)[C@@H]1n1ccc2cnc(-c3c[nH]c4ncc(F)cc34)nc21]
B122 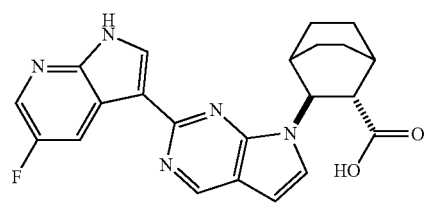
B123 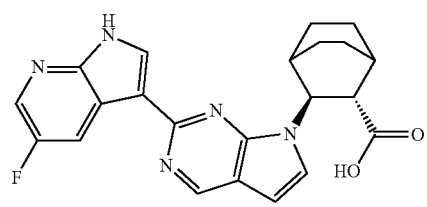 [SMILES: O=C(O)[C@H]1C2CCC(CC2)[C@@H]1n1ccc2cnc(-c3c[nH]c4ncc(F)cc34)nc21]
B124 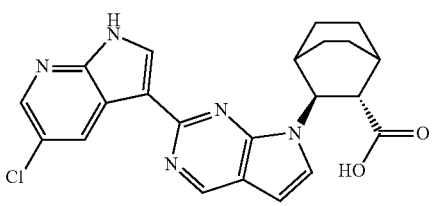 [SMILES: O=C(O)[C@H]1C2CCC(CC2)[C@@H]1n1ccc2cnc(-c3c[nH]c4ncc(Cl)cc34)nc21]

TABLE A-continued
B125 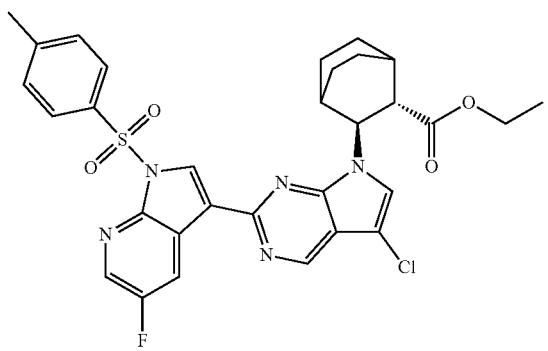 [SMILES: CCOC(=O)[C@H]1C2CCC(CC2)[C@@H]1n1cc(Cl)c2cnc(-c3cn(S(=O)(=O)c4ccc(C)cc4)c4ncc(F)cc34)nc21]
B126 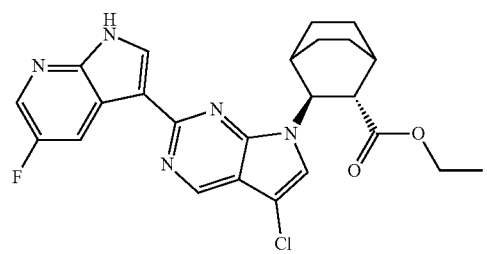 [SMILES: CCOC(=O)[C@H]1C2CCC(CC2)[C@@H]1n1cc(Cl)c2cnc(-c3c[nH]c4ncc(F)cc34)nc21]
B127 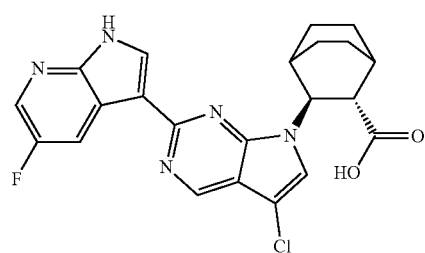 [SMILES: O=C(O)[C@H]1C2CCC(CC2)[C@@H]1n1cc(Cl)c2cnc(-c3c[nH]c4ncc(F)cc34)nc21]
B128 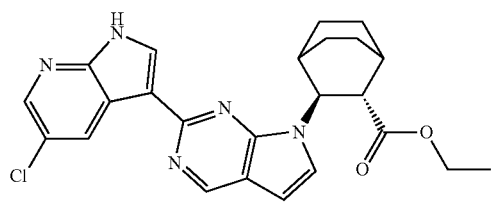 [SMILES: CCOC(=O)[C@H]1C2CCC(CC2)[C@@H]1n1ccc2cnc(-c3c[nH]c4ncc(Cl)cc34)nc21]
B129 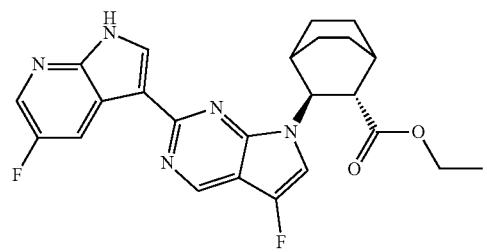 [SMILES: CCOC(=O)[C@H]1C2CCC(CC2)[C@@H]1n1cc(F)c2cnc(-c3c[nH]c4ncc(F)cc34)nc21]
B130 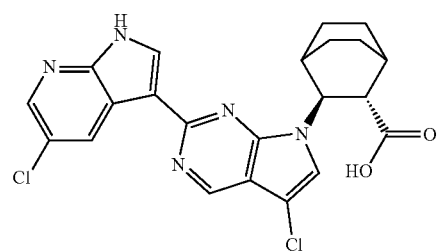 [SMILES: O=C(O)[C@H]1C2CCC(CC2)[C@@H]1n1cc(Cl)c2cnc(-c3c[nH]c4ncc(Cl)cc34)nc21]

TABLE A-continued
B131 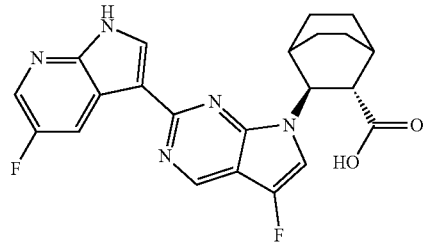 [SMILES: O=C(O)[C@H]1C2CCC(CC2)[C@@H]1n1cc(F)c2cnc(-c3c[nH]c4ncc(F)cc34)nc21]
B132 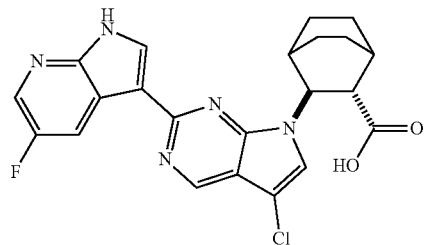
B133 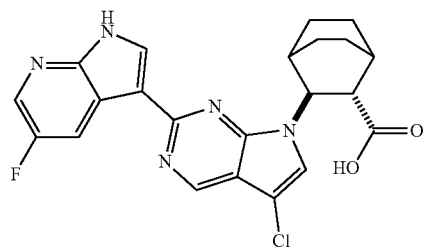
B134 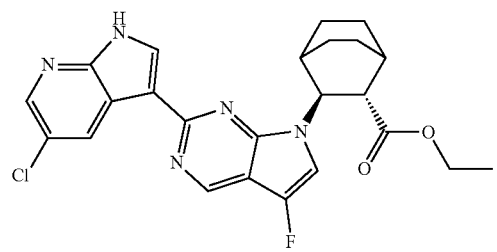 [SMILES: CCOC(=O)[C@H]1C2CCC(CC2)[C@@H]1n1cc(F)c2cnc(-c3c[nH]c4ncc(Cl)cc34)nc21]
B135 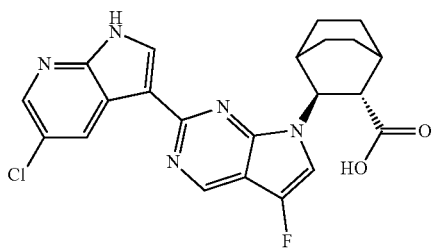 [SMILES: O=C(O)[C@H]1C2CCC(CC2)[C@@H]1n1cc(F)c2cnc(-c3c[nH]c4ncc(Cl)cc34)nc21]
B136 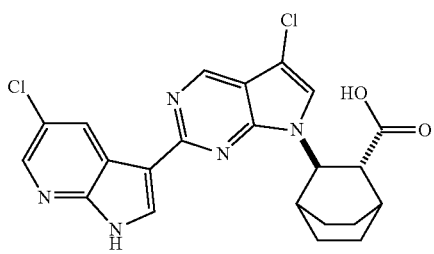

TABLE A-continued
B137
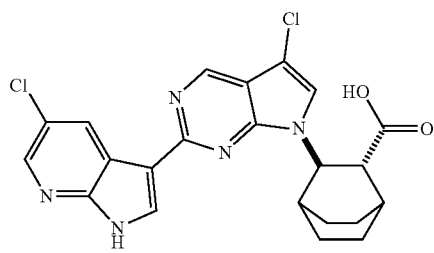
B138
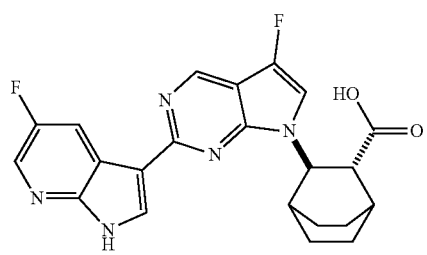
B139
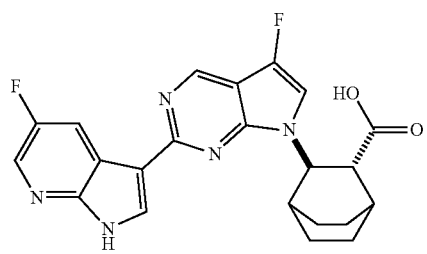
B140
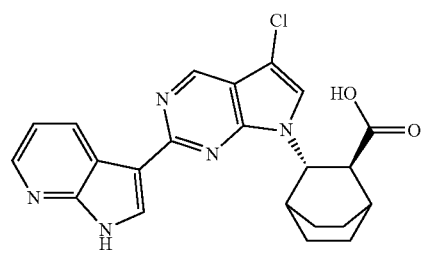 [SMILES: O=C(O)[C@H]1C2CCC(CC2)[C@@H]1n1cc(Cl)c2cnc(-c3c[nH]c4ncccc34)nc21]
B141
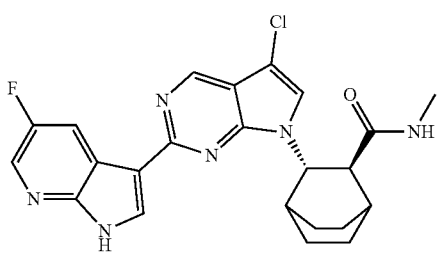 [SMILES: CNC(=O)[C@H]1C2CCC(CC2)[C@@H]1n1cc(Cl)c2cnc(-c3c[nH]c4ncc(F)cc34)nc21]
B142
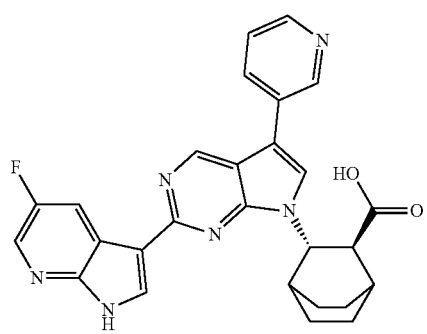 [SMILES: O=C(O)[C@H]1C2CCC(CC2)[C@@H]1n1cc(-c2cccnc2)c2cnc(-c3c[nH]c4ncc(F)cc34)nc21]

TABLE A-continued
B143
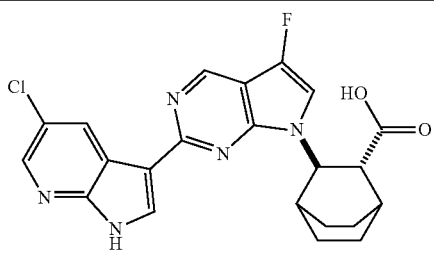
B144
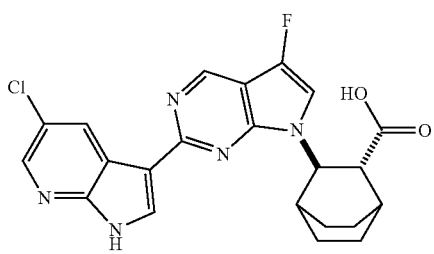
B145
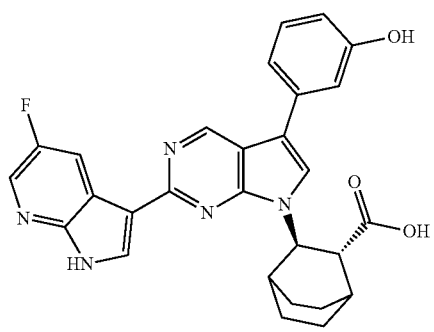 [SMILES: O=C(O)[C@@H]1C2CCC(CC2)[C@H]1n1cc(-c2cccc(O)c2)c2cnc(-c3c[nH]c4ncc(F)cc34)nc21]
B146
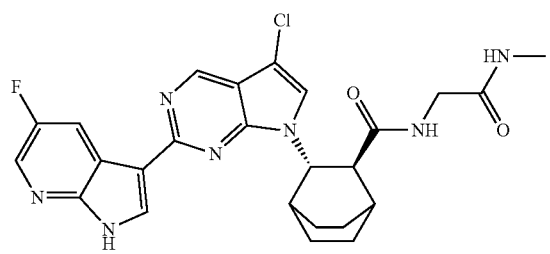 [SMILES: CNC(=O)CNC(=O)[C@H]1C2CCC(CC2)[C@@H]1n1cc(Cl)c2cnc(-c3c[nH]c4ncc(F)cc34)nc21]
B147
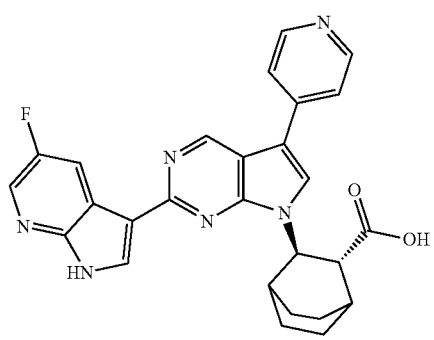 [SMILES: O=C(O)[C@@H]1C2CCC(CC2)[C@H]1n1cc(-c2ccncc2)c2cnc(-c3c[nH]c4ncc(F)cc34)nc21]

TABLE A-continued
B148
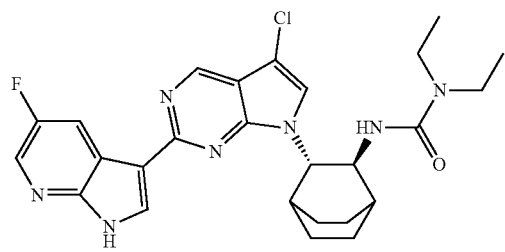 [SMILES: CCN(CC)C(=O)N[C@H]1C2CCC(CC2)[C@@H]1n1cc(Cl)c2cnc(-c3c[nH]c4ncc(F)cc34)nc21]
B149
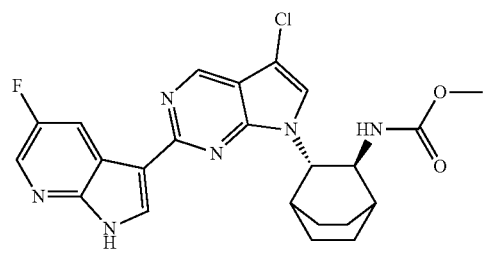 [SMILES: COC(=O)N[C@H]1C2CCC(CC2)[C@@H]1n1cc(Cl)c2cnc(-c3c[nH]c4ncc(F)cc34)nc21]
B150
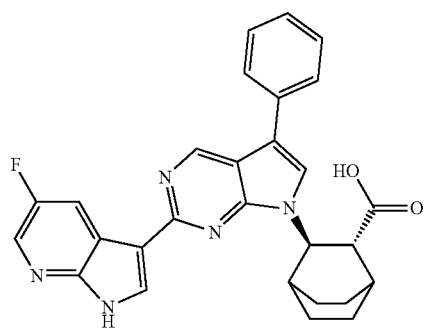 [SMILES: O=C(O)[C@@H]1C2CCC(CC2)[C@H]1n1cc(-c2ccccc2)c2cnc(-c3c[nH]c4ncc(F)cc34)nc21]
B151
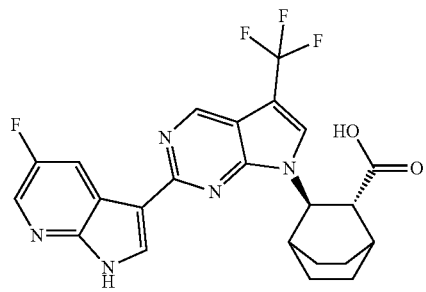 [SMILES: O=C(O)[C@@H]1C2CCC(CC2)[C@H]1n1cc(C(F)(F)F)c2cnc(-c3c[nH]c4ncc(F)cc34)nc21]
B152
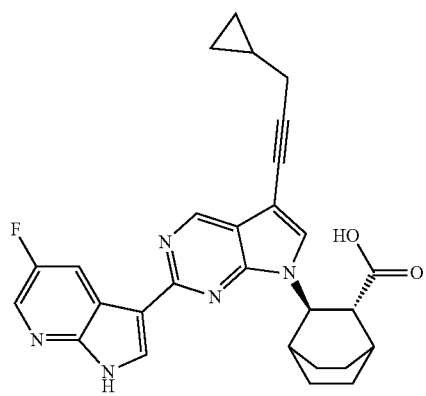 [SMILES: O=C(O)[C@@H]1C2CCC(CC2)[C@H]1n1cc(C#CCC2CC2)c2cnc(-c3c[nH]c4ncc(F)cc34)nc21]

TABLE A-continued
B153
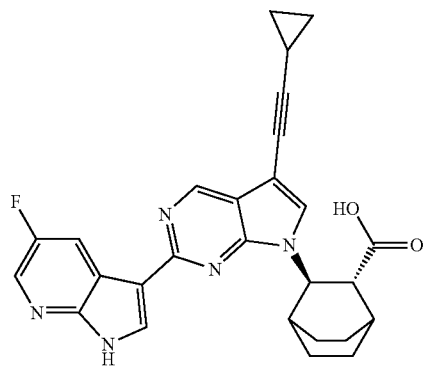 [SMILES: O=C(O)[C@@H]1C2CCC(CC2)[C@H]1n1cc(C#CC2CC2)c2cnc(-c3c[nH]c4ncc(F)cc34)nc21]
B154
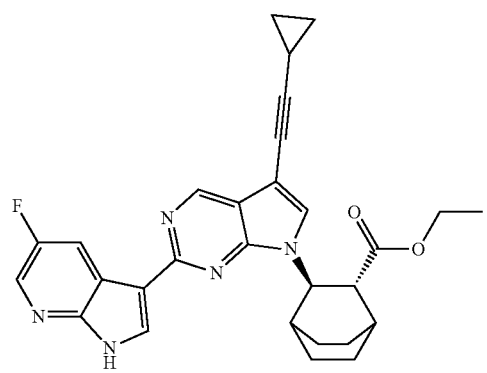 [SMILES: CCOC(=O)[C@@H]1C2CCC(CC2)[C@H]1n1cc(C#CC2CC2)c2cnc(-c3c[nH]c4ncc(F)cc34)nc21]
B160
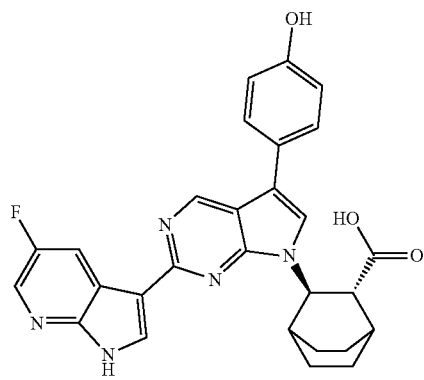 [SMILES: O=C(O)[C@@H]1C2CCC(CC2)[C@H]1n1cc(-c2ccc(O)cc2)c2cnc(-c3c[nH]c4ncc(F)cc34)nc21]
B161
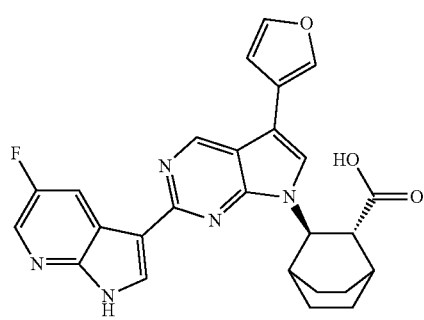

TABLE A-continued
B162
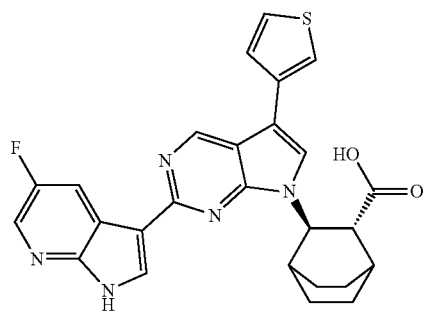 [SMILES: O=C(O)[C@@H]1C2CCC(CC2)[C@H]1n1cc(-c2ccoc2)c2cnc(-c3c[nH]c4ncc(F)cc34)nc21]
B163
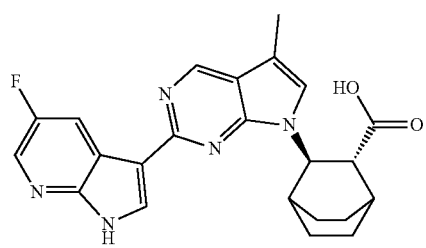 [SMILES: Cc1cn([C@@H]2C3CCC(CC3)[C@H]2C(=O)O)c2nc(-c3c[nH]c4ncc(F)cc34)ncc12]
B164
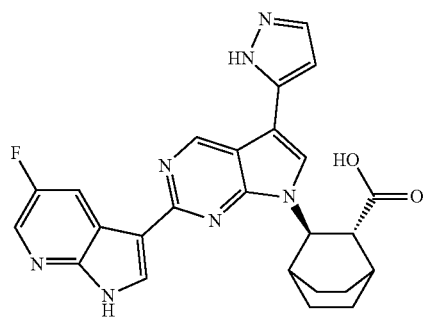 [SMILES: O=C(O)[C@@H]1C2CCC(CC2)[C@H]1n1cc(-c2ccn[nH]2)c2cnc(-c3c[nH]c4ncc(F)cc34)nc21]
B165
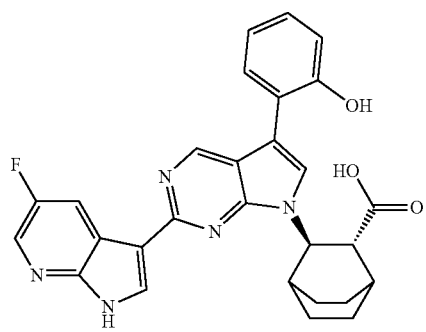 [SMILES: O=C(O)[C@@H]1C2CCC(CC2)[C@H]1n1cc(-c2ccccc2O)c2cnc(-c3c[nH]c4ncc(F)cc34)nc21]
B166
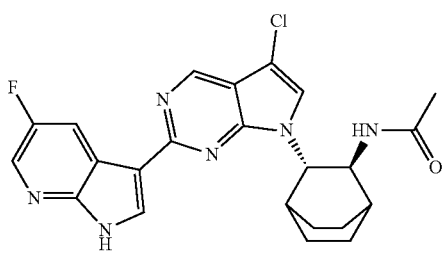 [SMILES: CC(=O)N[C@H]1C2CCC(CC2)[C@@H]1n1cc(Cl)c2cnc(-c3c[nH]c4ncc(F)cc34)nc21]

TABLE A-continued
B167
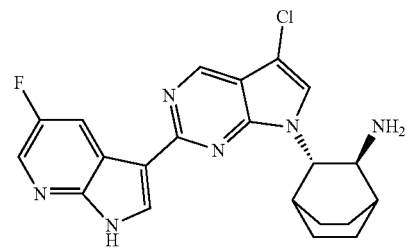 [SMILES: N[C@H]1C2CCC(CC2)[C@@H]1n1cc(Cl)c2cnc(-c3c[nH]c4ncc(F)cc34)nc21]
B168
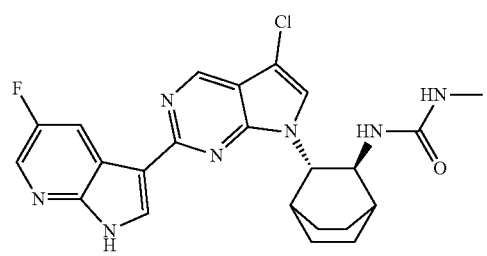 [SMILES: CNC(=O)N[C@H]1C2CCC(CC2)[C@@H]1n1cc(Cl)c2cnc(-c3c[nH]c4ncc(F)cc34)nc21]
B169
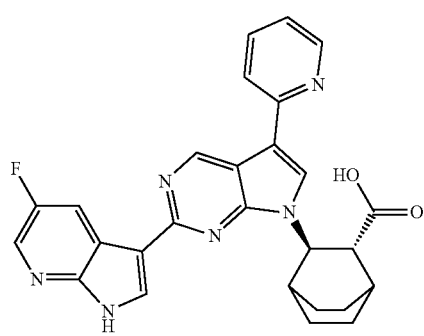 [SMILES: O=C(O)[C@@H]1C2CCC(CC2)[C@H]1n1cc(-c2ccccn2)c2cnc(-c3c[nH]c4ncc(F)cc34)nc21]
B170
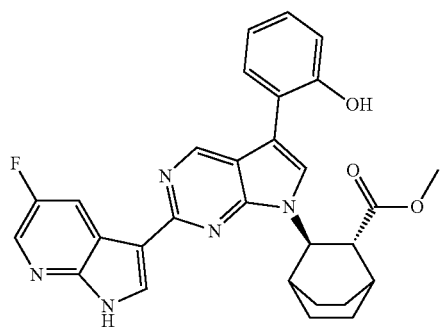 [SMILES: COC(=O)[C@@H]1C2CCC(CC2)[C@H]1n1cc(-c2ccccc2O)c2cnc(-c3c[nH]c4ncc(F)cc34)nc21]
B171
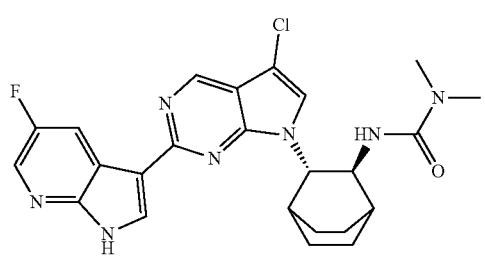 [SMILES: CN(C)C(=O)N[C@H]1C2CCC(CC2)[C@@H]1n1cc(Cl)c2cnc(-c3c[nH]c4ncc(F)cc34)nc21]

TABLE A-continued
B172
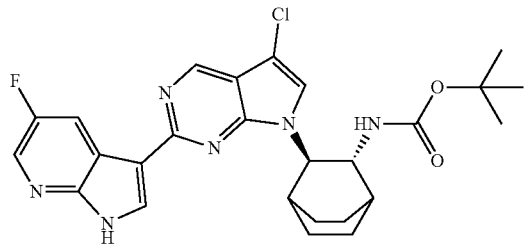 [SMILES: CC(C)(C)OC(=O)N[C@@H]1C2CCC(CC2)[C@H]1n1cc(Cl)c2cnc(-c3c[nH]c4ncc(F)cc34)nc21]
B173
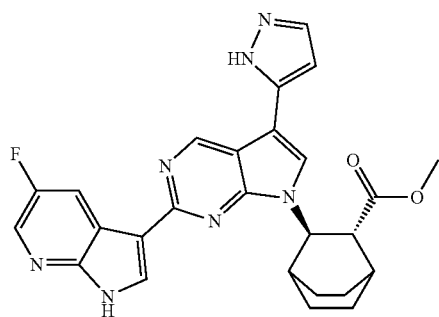 [SMILES: COC(=O)[C@@H]1C2CCC(CC2)[C@H]1n1cc(-c2ccn[nH]2)c2cnc(-c3c[nH]c4ncc(F)cc34)nc21]
B174
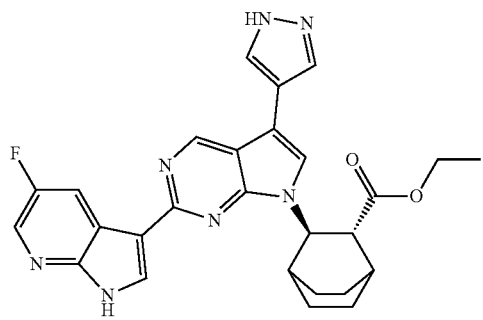 [SMILES: CCOC(=O)[C@@H]1C2CCC(CC2)[C@H]1n1cc(-c2cn[nH]c2)c2cnc(-c3c[nH]c4ncc(F)cc34)nc21]
B175
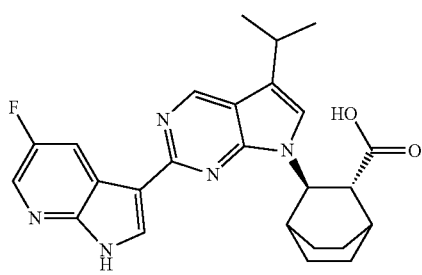 [SMILES: CC(C)c1cn([C@@H]2C3CCC(CC3)[C@H]2C(=O)O)c2nc(-c3c[nH]c4ncc(F)cc34)ncc12]
B176
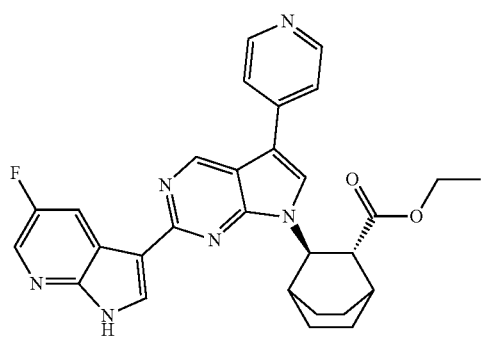 [SMILES: CCOC(=O)[C@@H]1C2CCC(CC2)[C@H]1n1cc(-c2ccncc2)c2cnc(-c3c[nH]c4ncc(F)cc34)nc21]

TABLE A-continued
B177
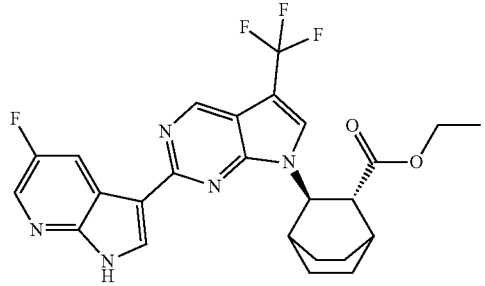 [SMILES: CCOC(=O)[C@@H]1C2CCC(CC2)[C@H]1n1cc(C(F)(F)F)c2cnc(-c3c[nH]c4ncc(F)cc34)nc21]
B178
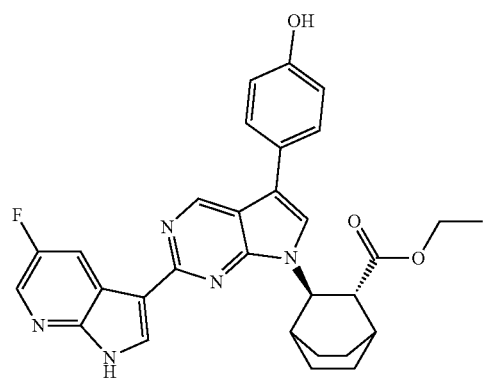 [SMILES: CCOC(=O)[C@@H]1C2CCC(CC2)[C@H]1n1cc(-c2ccc(O)cc2)c2cnc(-c3c[nH]c4ncc(F)cc34)nc21]
B179
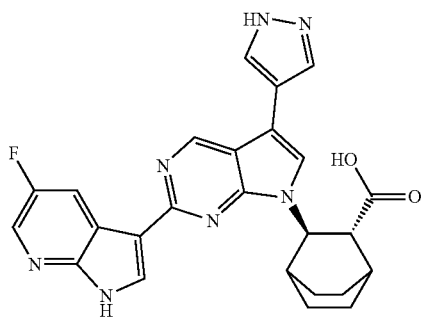 [SMILES: O=C(O)[C@@H]1C2CCC(CC2)[C@H]1n1cc(-c2cn[nH]c2)c2cnc(-c3c[nH]c4ncc(F)cc34)nc21]
B180
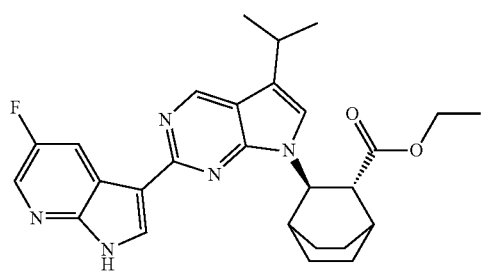 [SMILES: CCOC(=O)[C@@H]1C2CCC(CC2)[C@H]1n1cc(C(C)C)c2cnc(-c3c[nH]c4ncc(F)cc34)nc21]
B181
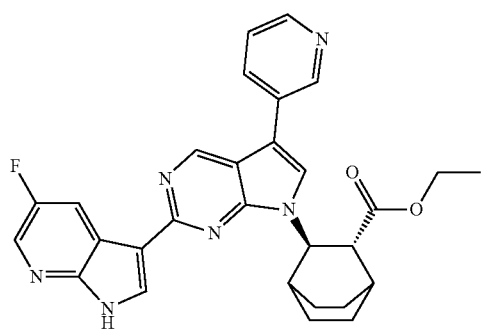 [SMILES: CCOC(=O)[C@@H]1C2CCC(CC2)[C@H]1n1cc(-c2cccnc2)c2cnc(-c3c[nH]c4ncc(F)cc34)nc21]

TABLE A-continued
B182
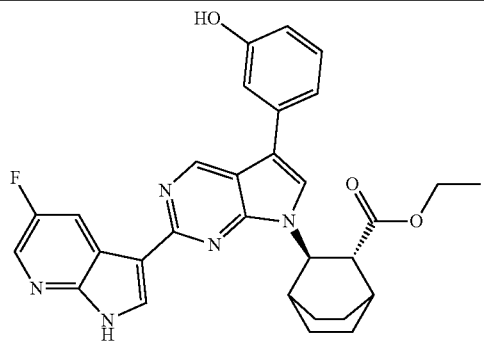
B183
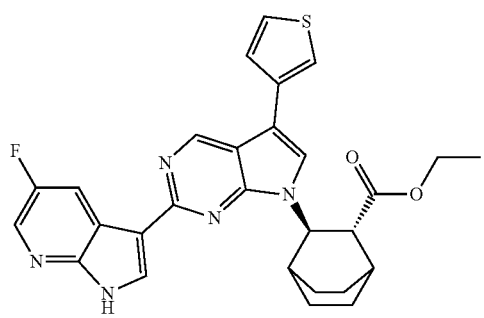 [SMILES: CCOC(=O)[C@@H]1C2CCC(CC2)[C@H]1n1cc(-c2ccsc2)c2cnc(-c3c[nH]c4ncc(F)cc34)nc21]
B184
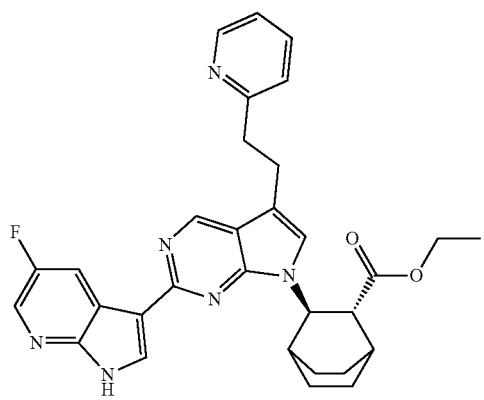 [SMILES: CCOC(=O)[C@@H]1C2CCC(CC2)[C@H]1n1cc(CCc2ccccn2)c2cnc(-c3c[nH]c4ncc(F)cc34)nc21]
B185
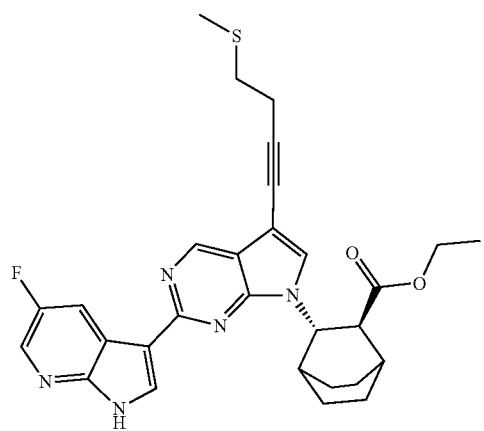 [SMILES: CCOC(=O)[C@H]1C2CCC(CC2)[C@@H]1n1cc(C#CCCSC)c2cnc(-c3c[nH]c4ncc(F)cc34)nc21]

TABLE A-continued
B186
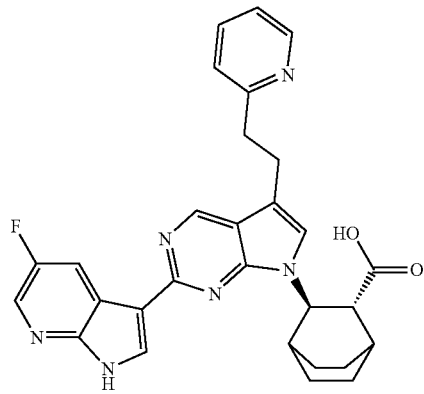 [SMILES: O=C(O)[C@@H]1C2CCC(CC2)[C@H]1n1cc(CCc2ccccn2)c2cnc(-c3c[nH]c4ncc(F)cc34)nc21]
B187
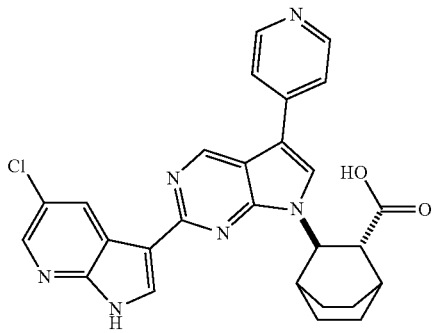
B188
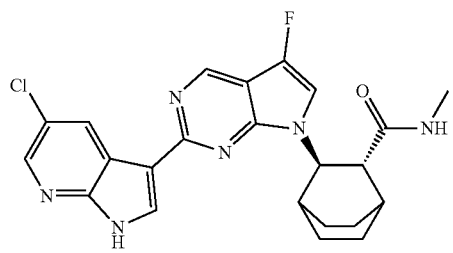 [SMILES: CNC(=O)[C@@H]1C2CCC(CC2)[C@H]1n1cc(F)c2cnc(-c3c[nH]c4ncc(Cl)cc34)nc21]
B189
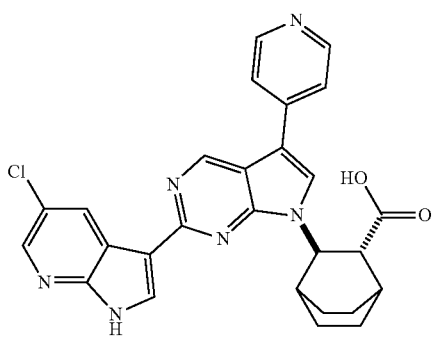
B190
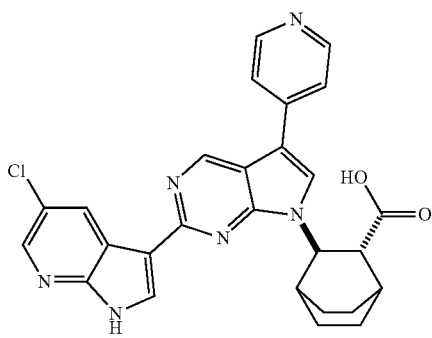

TABLE A-continued
B191 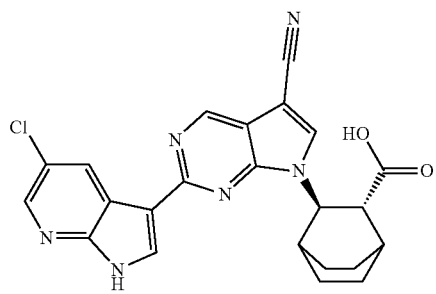 [SMILES: N#Cc1cn([C@@H]2C3CCC(CC3)[C@H]2C(=O)O)c2nc(-c3c[nH]c4ncc(Cl)cc34)ncc12]
B192 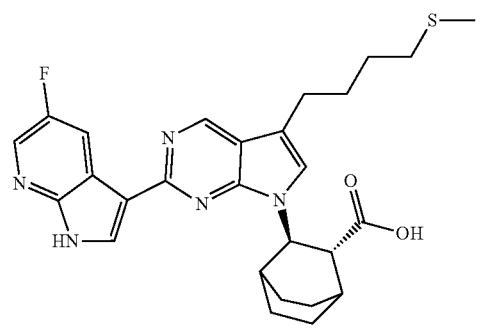 [SMILES: CSCCCCc1cn([C@@H]2C3CCC(CC3)[C@H]2C(=O)O)c2nc(-c3c[nH]c4ncc(F)cc34)ncc12]
B193 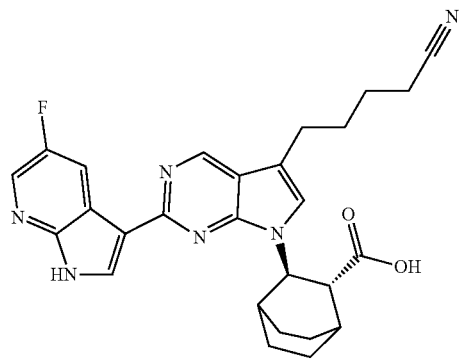 [SMILES: N#CCCCCc1cn([C@@H]2C3CCC(CC3)[C@H]2C(=O)O)c2nc(-c3c[nH]c4ncc(F)cc34)ncc12]
B194 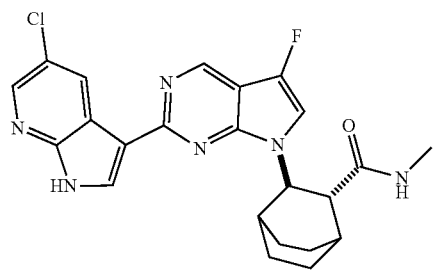 [SMILES: CNC(=O)[C@@H]1C2CCC(CC2)[C@H]1n1cc(F)c2cnc(-c3c[nH]c4ncc(Cl)cc34)nc21]
B195 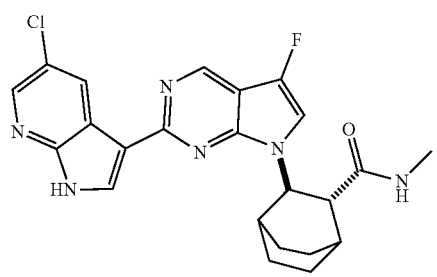 [SMILES: CNC(=O)[C@@H]1C2CCC(CC2)[C@H]1n1cc(F)c2cnc(-c3c[nH]c4ncc(Cl)cc34)nc21]

TABLE A-continued
B196
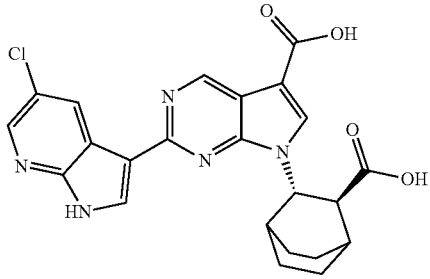 [SMILES: O=C(O)c1cn([C@H]2C3CCC(CC3)[C@@H]2C(=O)O)c2nc(-c3c[nH]c4ncc(Cl)cc34)ncc12]
B197
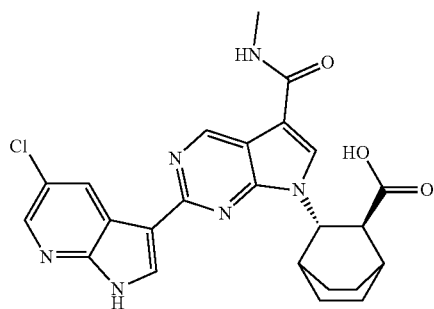 [SMILES: CNC(=O)c1cn([C@H]2C3CCC(CC3)[C@@H]2C(=O)O)c2nc(-c3c[nH]c4ncc(Cl)cc34)ncc12]
B198
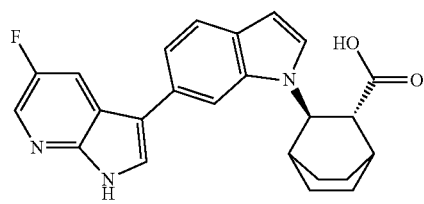 [SMILES: O=C(O)[C@@H]1C2CCC(CC2)[C@H]1n1ccc2ccc(-c3c[nH]c4ncc(F)cc34)cc21]
B199
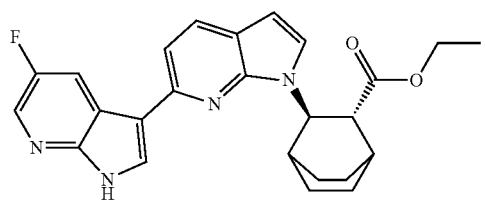 [SMILES: CCOC(=O)[C@@H]1C2CCC(CC2)[C@H]1n1ccc2ccc(-c3c[nH]c4ncc(F)cc34)nc21]
B200
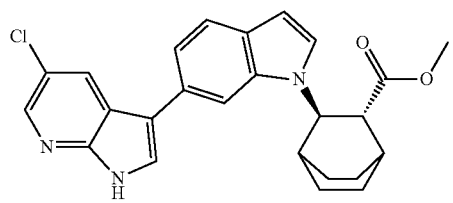 [SMILES: COC(=O)[C@@H]1C2CCC(CC2)[C@H]1n1ccc2ccc(-c3c[nH]c4ncc(Cl)cc34)cc21]
B201
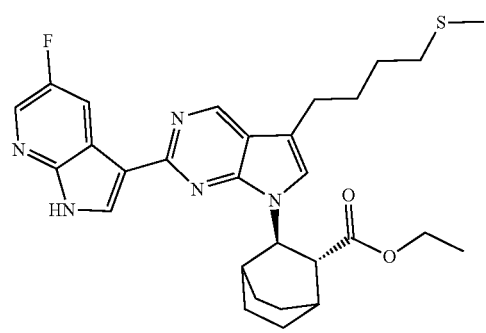 [SMILES: CCOC(=O)[C@@H]1C2CCC(CC2)[C@H]1n1cc(CCCCSC)c2cnc(-c3c[nH]c4ncc(F)cc34)nc21]

TABLE A-continued
B202
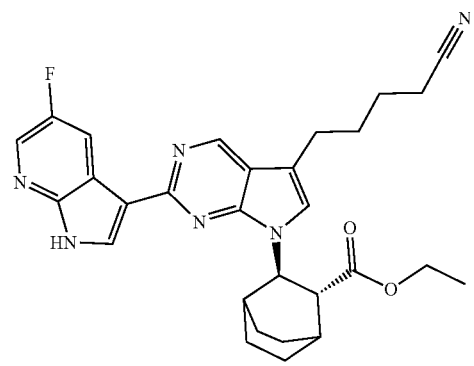 [SMILES: CCOC(=O)[C@@H]1C2CCC(CC2)[C@H]1n1cc(CCCCC#N)c2cnc(-c3c[nH]c4ncc(F)cc34)nc21]
B203
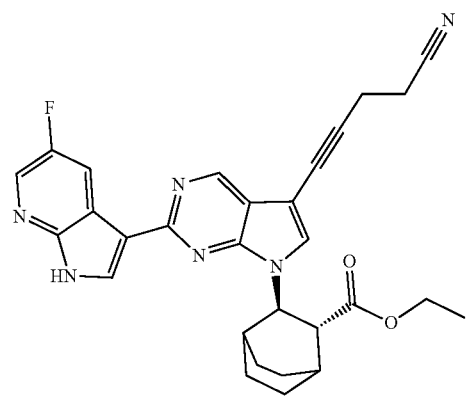 [SMILES: CCOC(=O)[C@@H]1C2CCC(CC2)[C@H]1n1cc(C#CCCC#N)c2cnc(-c3c[nH]c4ncc(F)cc34)nc21]
B204
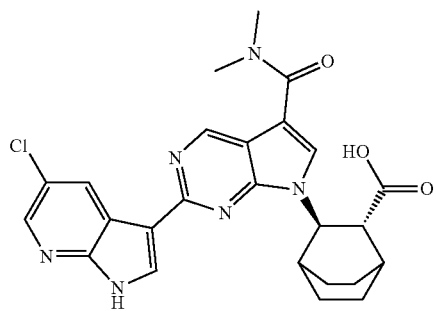 [SMILES: CN(C)C(=O)c1cn([C@@H]2C3CCC(CC3)[C@H]2C(=O)O)c2nc(-c3c[nH]c4ncc(Cl)cc34)ncc12]
B205
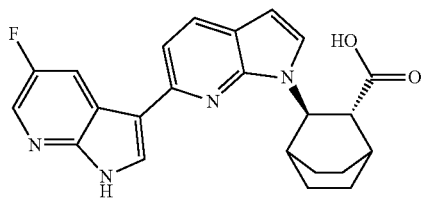 [SMILES: O=C(O)[C@@H]1C2CCC(CC2)[C@H]1n1ccc2ccc(-c3c[nH]c4ncc(F)cc34)nc21]
B206
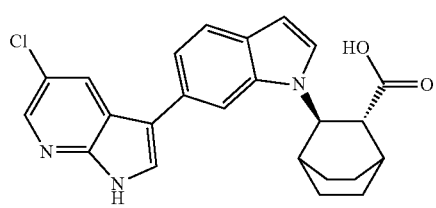 [SMILES: O=C(O)[C@@H]1C2CCC(CC2)[C@H]1n1ccc2ccc(-c3c[nH]c4ncc(Cl)cc34)cc21]

TABLE A-continued
B207
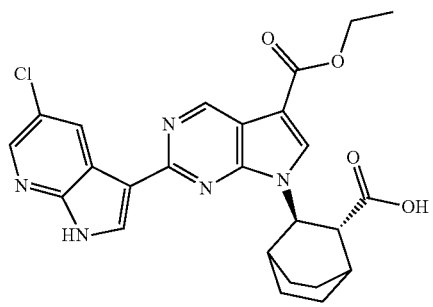 [SMILES: CCOC(=O)c1cn([C@@H]2C3CCC(CC3)[C@H]2C(=O)O)c2nc(-c3c[nH]c4ncc(Cl)cc34)ncc12]
B208
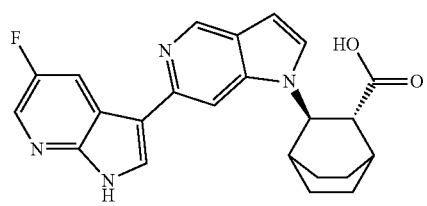 [SMILES: O=C(O)[C@@H]1C2CCC(CC2)[C@H]1n1ccc2cnc(-c3c[nH]c4ncc(F)cc34)cc21]
B209
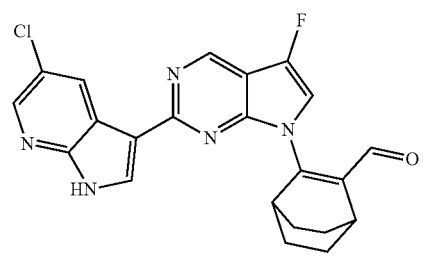 [SMILES: O=CC1=C(n2cc(F)c3cnc(-c4c[nH]c5ncc(Cl)cc45)nc32)C2CCC1CC2]
B210
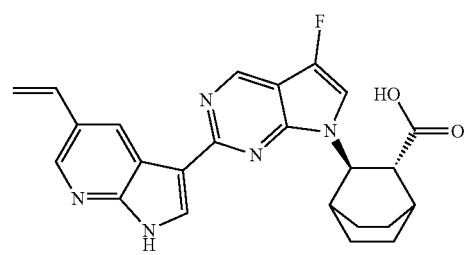 [SMILES: C=Cc1cnc2[nH]cc(-c3ncc4c(F)cn([C@@H]5C6CCC(CC6)[C@H]5C(=O)O)c4n3)c2c1]
B211
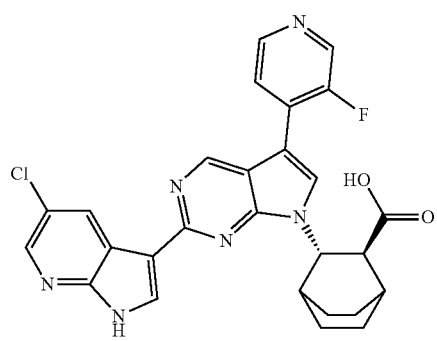 [SMILES: O=C(O)[C@H]1C2CCC(CC2)[C@@H]1n1cc(-c2ccncc2F)c2cnc(-c3c[nH]c4ncc(Cl)cc34)nc21]

TABLE A-continued
B212 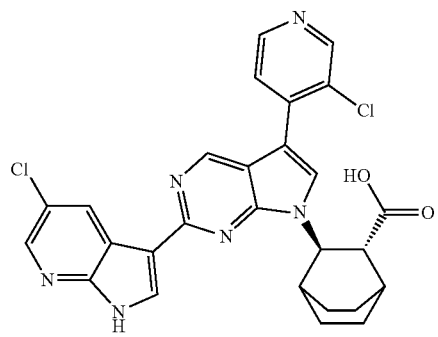 [SMILES: O=C(O)[C@@H]1C2CCC(CC2)[C@H]1n1cc(-c2ccncc2Cl)c2cnc(-c3c[nH]c4ncc(Cl)cc34)nc21]
B213 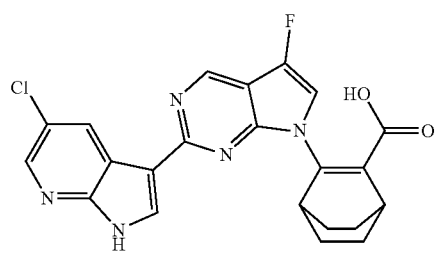 [SMILES: O=C(O)C1=C(n2cc(F)c3cnc(-c4c[nH]c5ncc(Cl)cc45)nc32)C2CCC1CC2]
B214 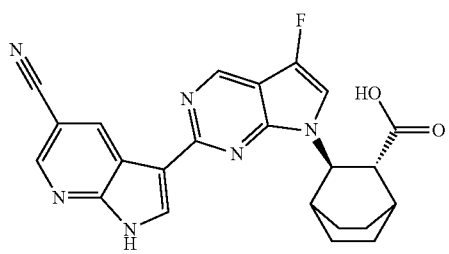 [SMILES: N#Cc1cnc2[nH]cc(-c3ncc4c(F)cn([C@@H]5C6CCC(CC6)[C@H]5C(=O)O)c4n3)c2c1]
B215 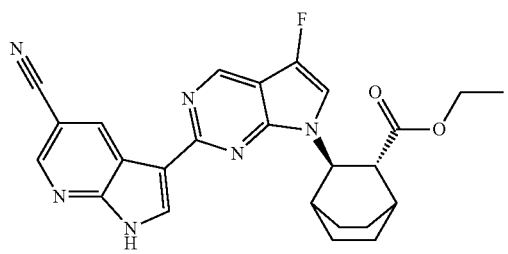 [SMILES: CCOC(=O)[C@@H]1C2CCC(CC2)[C@H]1n1cc(F)c2cnc(-c3c[nH]c4ncc(C#N)cc34)nc21]
B216 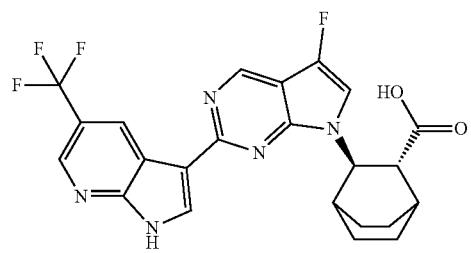 [SMILES: O=C(O)[C@@H]1C2CCC(CC2)[C@H]1n1cc(F)c2cnc(-c3c[nH]c4ncc(C(F)(F)F)cc34)nc21]
B217 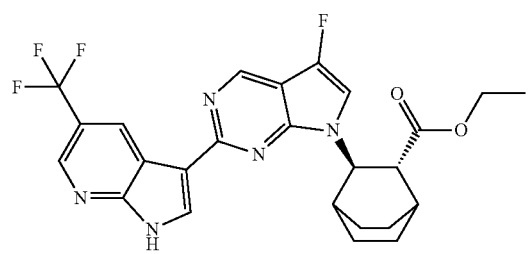 [SMILES: CCOC(=O)[C@@H]1C2CCC(CC2)[C@H]1n1cc(F)c2cnc(-c3c[nH]c4ncc(C(F)(F)F)cc34)nc21]

TABLE A-continued
B218 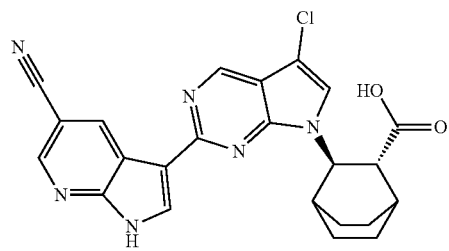
B219 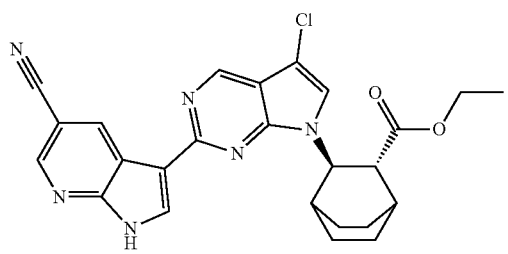 [SMILES: CCOC(=O)[C@@H]1C2CCC(CC2)[C@H]1n1cc(Cl)c2cnc(-c3c[nH]c4ncc(C#N)cc34)nc21]
B220 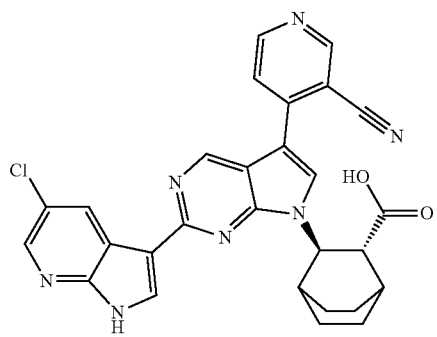 [SMILES: N#Cc1cnccc1-c1cn([C@@H]2C3CCC(CC3)[C@H]2C(=O)O)c2nc(-c3c[nH]c4ncc(Cl)cc34)ncc12]
B221 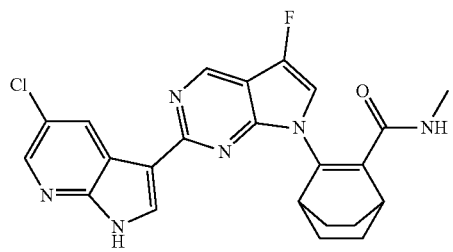 [SMILES: CNC(=O)C1=C(n2cc(F)c3cnc(-c4c[nH]c5ncc(Cl)cc45)nc32)C2CCC1CC2]
B222 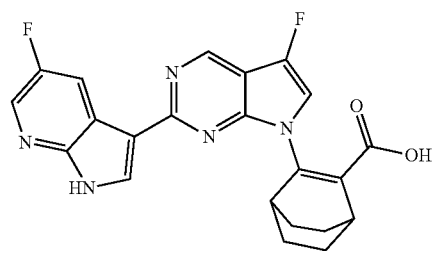 [SMILES: O=C(O)C1=C(n2cc(F)c3cnc(-c4c[nH]c5ncc(F)cc45)nc32)C2CCC1CC2]
C1 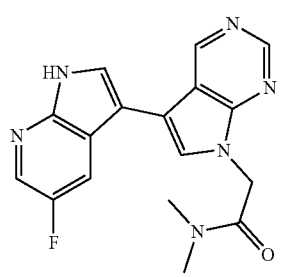 [SMILES: CN(C)C(=O)Cn1cc(-c2c[nH]c3ncc(F)cc23)c2cncnc21]

TABLE A-continued
C2
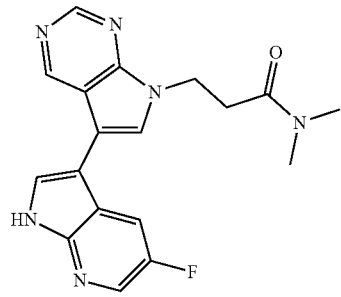 [SMILES: CN(C)C(=O)CCn1cc(-c2c[nH]c3ncc(F)cc23)c2cncnc21]
C3
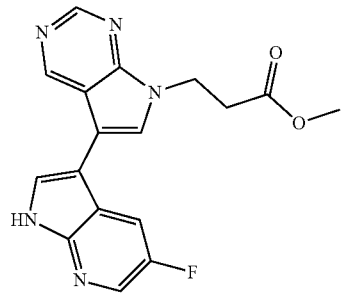 [SMILES: COC(=O)CCn1cc(-c2c[nH]c3ncc(F)cc23)c2cncnc21]
C4
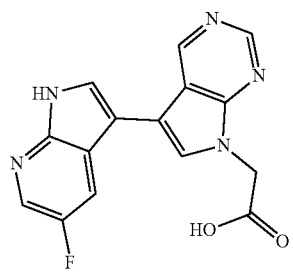 [SMILES: O=C(O)Cn1cc(-c2c[nH]c3ncc(F)cc23)c2cncnc21]
C5
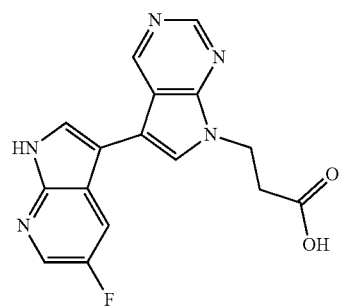 [SMILES: O=C(O)CCn1cc(-c2c[nH]c3ncc(F)cc23)c2cncnc21]
C6
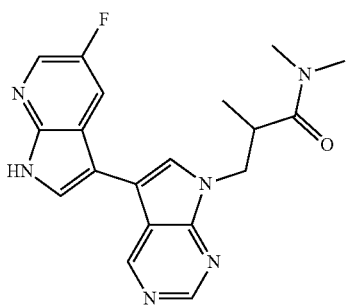 [SMILES: CC(Cn1cc(-c2c[nH]c3ncc(F)cc23)c2cncnc21)C(=O)N(C)C]

TABLE A-continued
C7
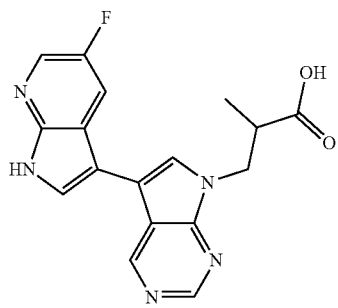
C8
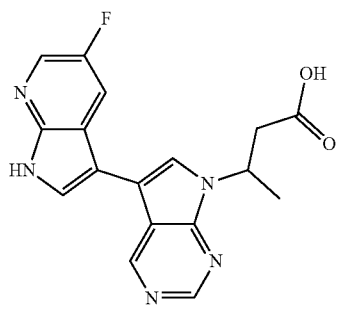 [SMILES: CC(CC(=O)O)n1cc(-c2c[nH]c3ncc(F)cc23)c2cncnc21]
C9
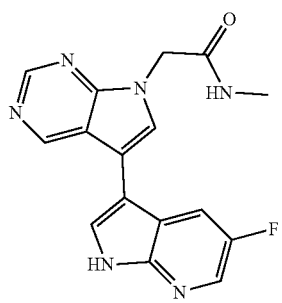 [SMILES: CNC(=O)Cn1cc(-c2c[nH]c3ncc(F)cc23)c2cncnc21]
C10
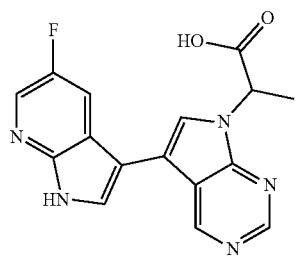 [SMILES: CC(C(=O)O)n1cc(-c2c[nH]c3ncc(F)cc23)c2cncnc21]
C11
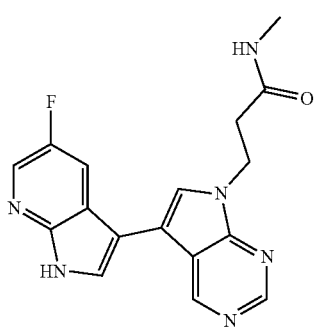 [SMILES: CNC(=O)CCn1cc(-c2c[nH]c3ncc(F)cc23)c2cncnc21]

TABLE A-continued
C12
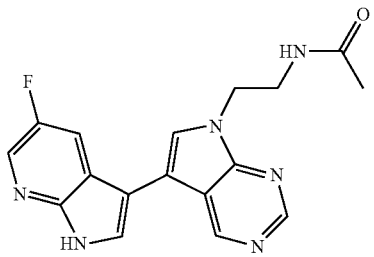 [SMILES: CC(=O)NCCn1cc(-c2c[nH]c3ncc(F)cc23)c2cncnc21]
C13
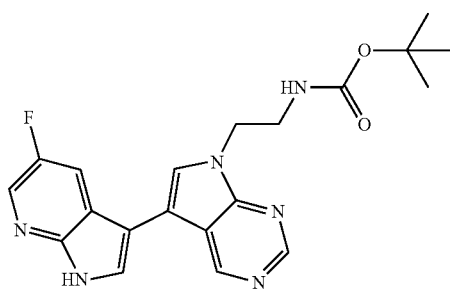 [SMILES: CC(C)(C)OC(=O)NCCn1cc(-c2c[nH]c3ncc(F)cc23)c2cncnc21]
C14
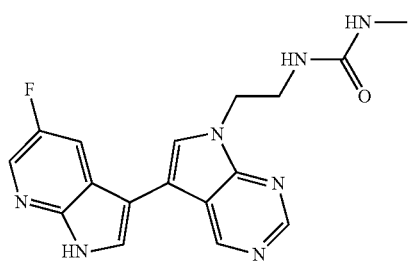 [SMILES: CNC(=O)NCCn1cc(-c2c[nH]c3ncc(F)cc23)c2cncnc21]
C15
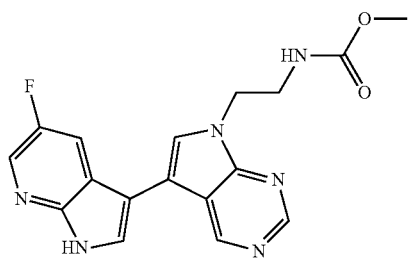 [SMILES: COC(=O)NCCn1cc(-c2c[nH]c3ncc(F)cc23)c2cncnc21]
C16
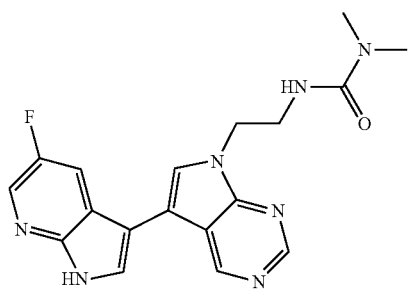 [SMILES: CN(C)C(=O)NCCn1cc(-c2c[nH]c3ncc(F)cc23)c2cncnc21]
C17
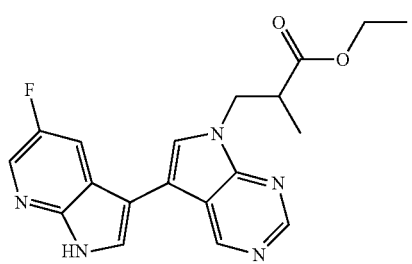 [SMILES: CCOC(=O)C(C)Cn1cc(-c2c[nH]c3ncc(F)cc23)c2cncnc21]

TABLE A-continued
C18 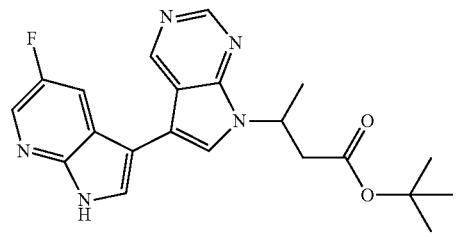 [SMILES: CC(CC(=O)OC(C)(C)C)n1cc(-c2c[nH]c3ncc(F)cc23)c2cncnc21]
TABLE B
A1 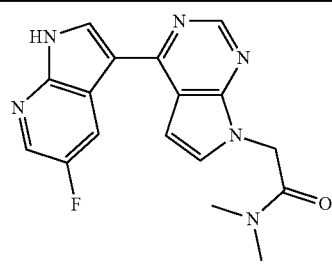
A2 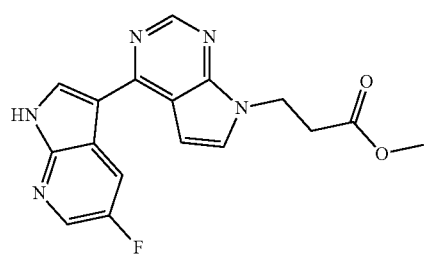 [SMILES: COC(=O)CCn1ccc2c(-c3c[nH]c4ncc(F)cc34)ncnc21]
A3 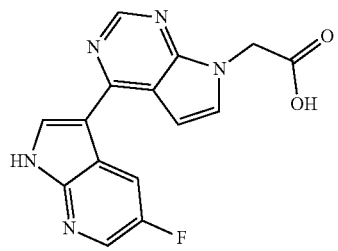 [SMILES: O=C(O)Cn1ccc2c(-c3c[nH]c4ncc(F)cc34)ncnc21]
A4 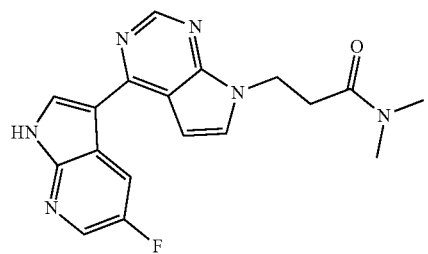 [SMILES: CN(C)C(=O)CCn1ccc2c(-c3c[nH]c4ncc(F)cc34)ncnc21]
A5 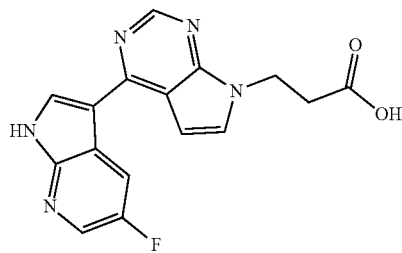 [SMILES: O=C(O)CCn1ccc2c(-c3c[nH]c4ncc(F)cc34)ncnc21]

TABLE B-continued
A6 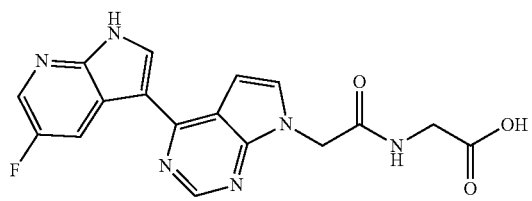 [SMILES: O=C(O)CNC(=O)Cn1ccc2c(-c3c[nH]c4ncc(F)cc34)ncnc21]
A7 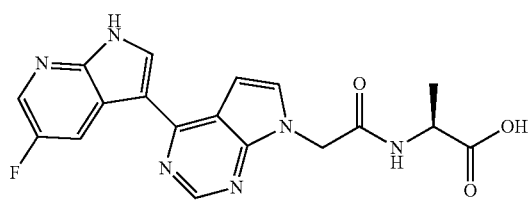 [SMILES: C[C@H](NC(=O)Cn1ccc2c(-c3c[nH]c4ncc(F)cc34)ncnc21)C(=O)O]
A8 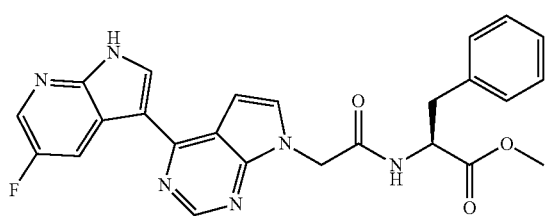 [SMILES: COC(=O)[C@H](Cc1ccccc1)NC(=O)Cn1ccc2c(-c3c[nH]c4ncc(F)cc34)ncnc21]
A9 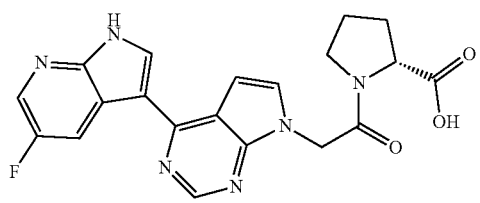 [SMILES: O=C(O)[C@H]1CCCN1C(=O)Cn1ccc2c(-c3c[nH]c4ncc(F)cc34)ncnc21]
A10 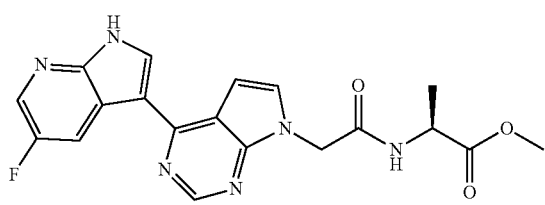 [SMILES: COC(=O)[C@H](C)NC(=O)Cn1ccc2c(-c3c[nH]c4ncc(F)cc34)ncnc21]
A11 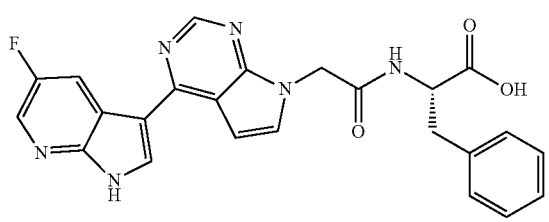 [SMILES: O=C(Cn1ccc2c(-c3c[nH]c4ncc(F)cc34)ncnc21)N[C@@H](Cc1ccccc1)C(=O)O]
A12 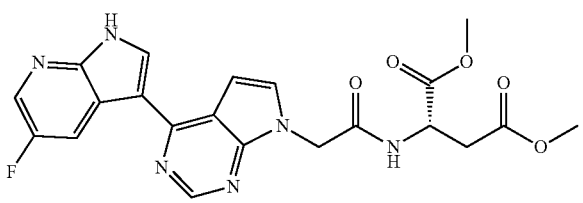 [SMILES: COC(=O)C[C@H](NC(=O)Cn1ccc2c(-c3c[nH]c4ncc(F)cc34)ncnc21)C(=O)OC]

TABLE B-continued
A13 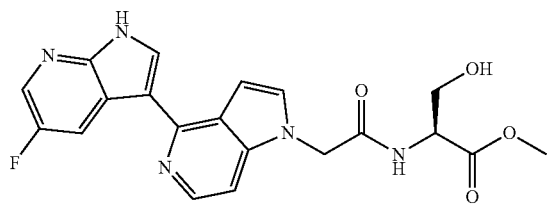 [SMILES: COC(=O)[C@H](CO)NC(=O)Cn1ccc2c(-c3c[nH]c4ncc(F)cc34)nccc21]
A14 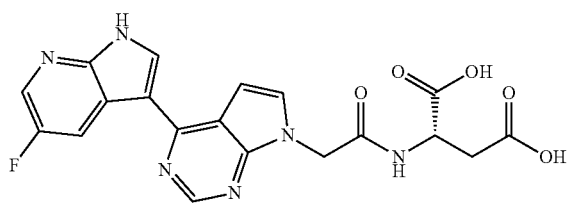 [SMILES: O=C(O)C[C@H](NC(=O)Cn1ccc2c(-c3c[nH]c4ncc(F)cc34)ncnc21)C(=O)O]
A15 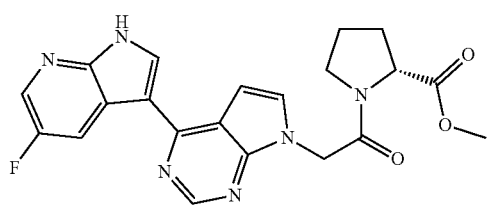 [SMILES: COC(=O)[C@H]1CCCN1C(=O)Cn1ccc2c(-c3c[nH]c4ncc(F)cc34)ncnc21]
A16 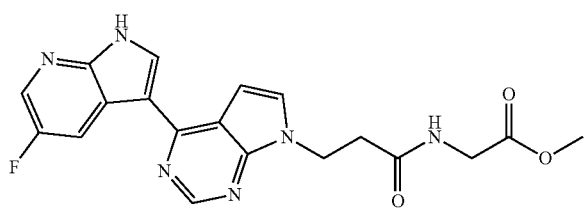 [SMILES: COC(=O)CNC(=O)CCn1ccc2c(-c3c[nH]c4ncc(F)cc34)ncnc21]
A17 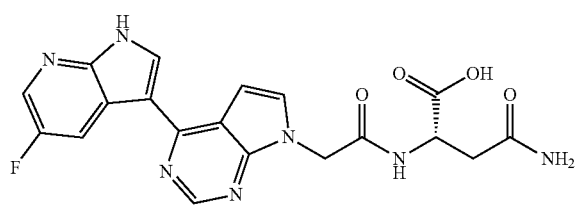 [SMILES: NC(=O)C[C@H](NC(=O)Cn1ccc2c(-c3c[nH]c4ncc(F)cc34)ncnc21)C(=O)O]
A18 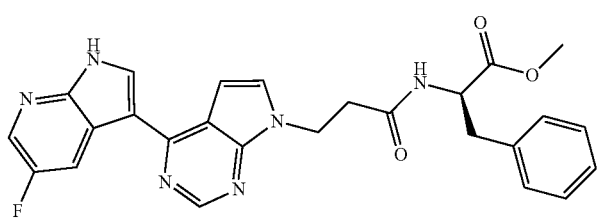 [SMILES: COC(=O)[C@@H](Cc1ccccc1)NC(=O)CCn1ccc2c(-c3c[nH]c4ncc(F)cc34)ncnc21]
A19 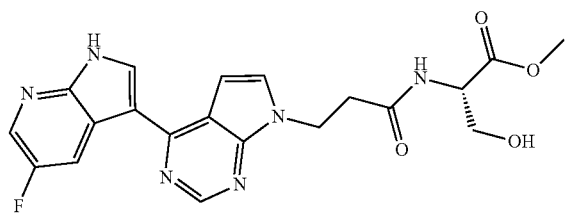 [SMILES: COC(=O)[C@H](CO)NC(=O)CCn1ccc2c(-c3c[nH]c4ncc(F)cc34)ncnc21]

TABLE B-continued
A20
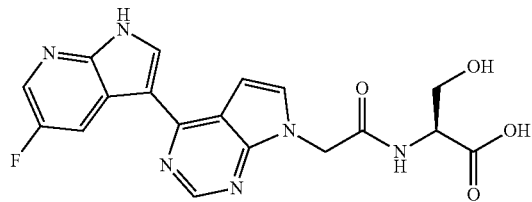 [SMILES: O=C(Cn1ccc2c(-c3c[nH]c4ncc(F)cc34)ncnc21)N[C@@H](CO)C(=O)O]
TABLE C
B1
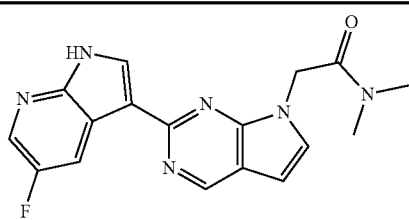
B2
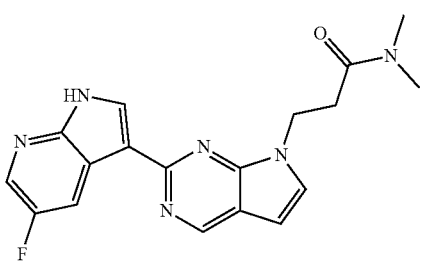 [SMILES: CN(C)C(=O)CCn1ccc2cnc(-c3c[nH]c4ncc(F)cc34)nc21]
B3
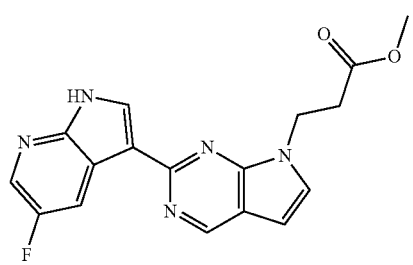 [SMILES: COC(=O)CCn1ccc2cnc(-c3c[nH]c4ncc(F)cc34)nc21]
B4
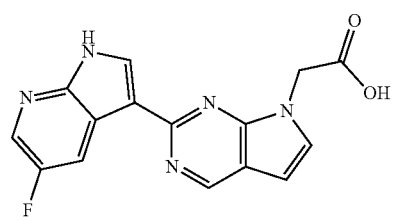 [SMILES: O=C(O)Cn1ccc2cnc(-c3c[nH]c4ncc(F)cc34)nc21]
B5
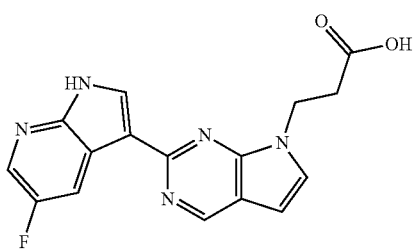 [SMILES: O=C(O)CCn1ccc2cnc(-c3c[nH]c4ncc(F)cc34)nc21]

TABLE C-continued
B6 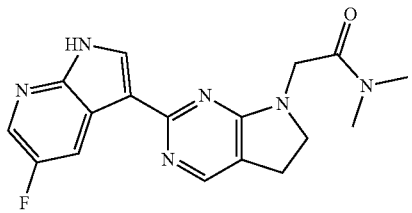 [SMILES: CN(C)C(=O)CN1CCc2cnc(-c3c[nH]c4ncc(F)cc34)nc21]
B7 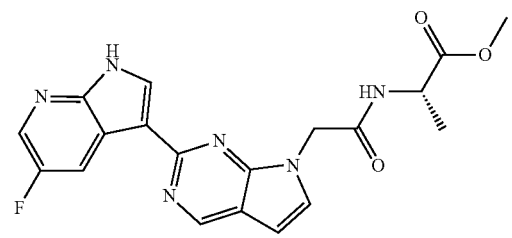 [SMILES: COC(=O)[C@H](C)NC(=O)Cn1ccc2cnc(-c3c[nH]c4ncc(F)cc34)nc21]
B8 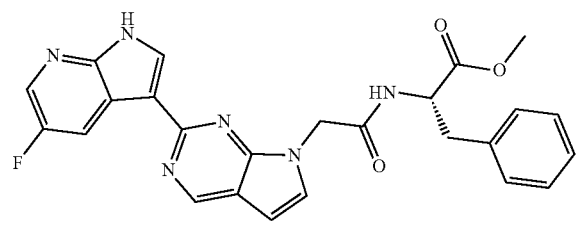 [SMILES: COC(=O)[C@H](Cc1ccccc1)NC(=O)Cn1ccc2cnc(-c3c[nH]c4ncc(F)cc34)nc21]
B9 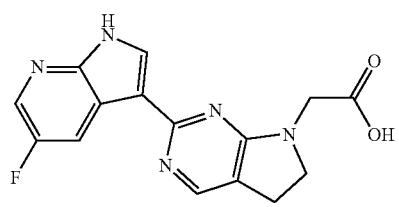 [SMILES: O=C(O)CN1CCc2cnc(-c3c[nH]c4ncc(F)cc34)nc21]
B10 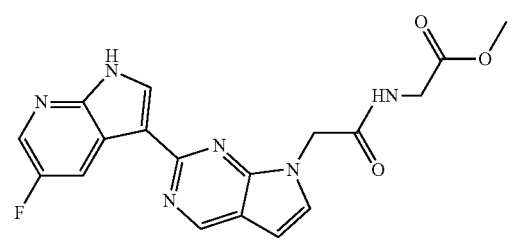 [SMILES: COC(=O)CNC(=O)Cn1ccc2cnc(-c3c[nH]c4ncc(F)cc34)nc21]
B11 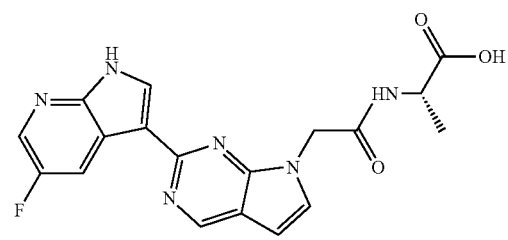 [SMILES: C[C@H](NC(=O)Cn1ccc2cnc(-c3c[nH]c4ncc(F)cc34)nc21)C(=O)O]
B12 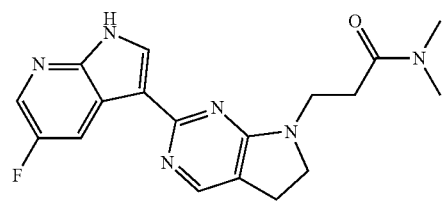 [SMILES: CN(C)C(=O)CCN1CCc2cnc(-c3c[nH]c4ncc(F)cc34)nc21]

TABLE C-continued
B13 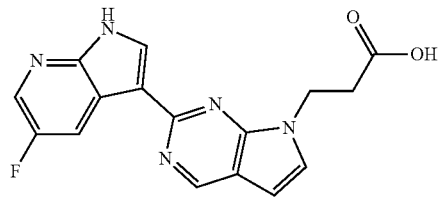 [SMILES: O=C(O)CCn1ccc2cnc(-c3c[nH]c4ncc(F)cc34)nc21]
B14 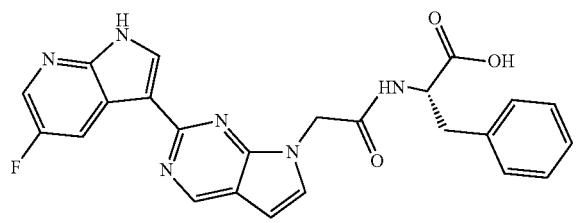 [SMILES: O=C(Cn1ccc2cnc(-c3c[nH]c4ncc(F)cc34)nc21)N[C@@H](Cc1ccccc1)C(=O)O]
B15 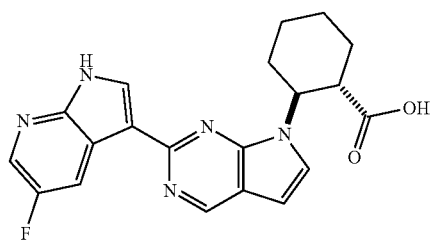
B16 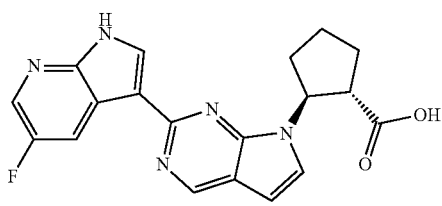
B17 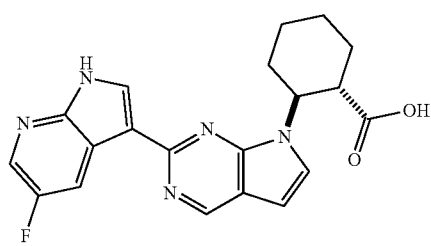
B18 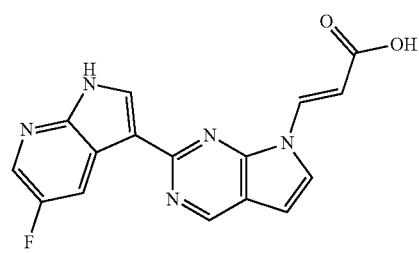 [SMILES: O=C(O)/C=C/n1ccc2cnc(-c3c[nH]c4ncc(F)cc34)nc21]
B19 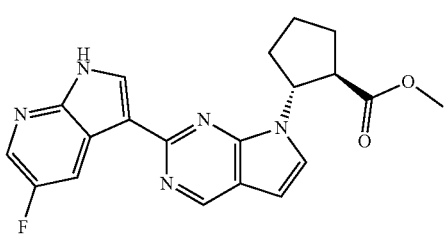 [SMILES: COC(=O)[C@@H]1CCC[C@H]1n1ccc2cnc(-c3c[nH]c4ncc(F)cc34)nc21]

TABLE C-continued
B20 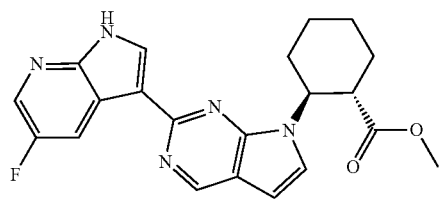 [SMILES: COC(=O)[C@H]1CCCC[C@@H]1n1ccc2cnc(-c3c[nH]c4ncc(F)cc34)nc21]
B21 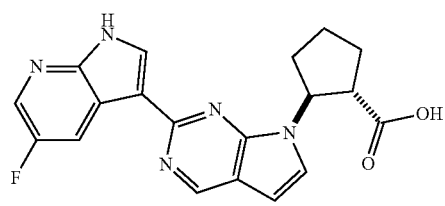
B22 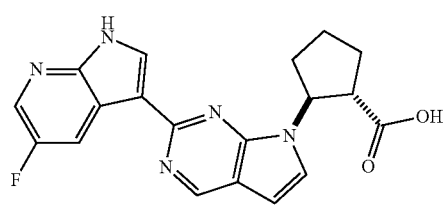
B23 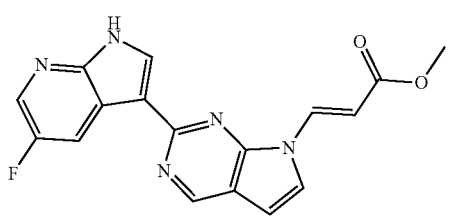 [SMILES: COC(=O)/C=C/n1ccc2cnc(-c3c[nH]c4ncc(F)cc34)nc21]
B24 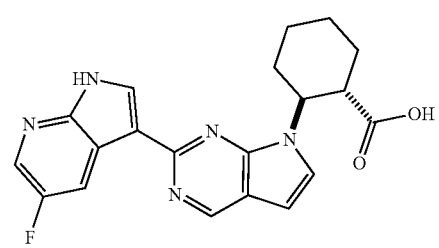
B25 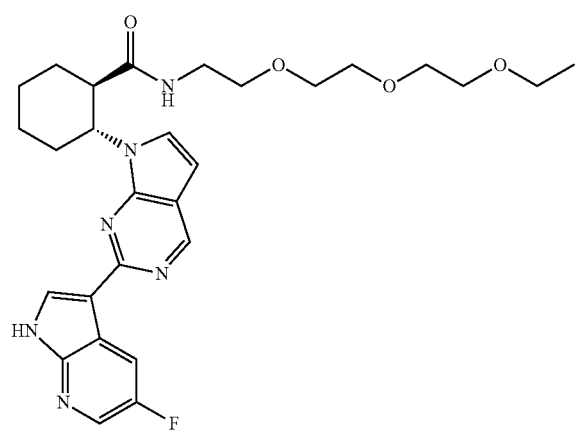 [SMILES: CCOCCOCCOCCNC(=O)[C@@H]1CCCC[C@H]1n1ccc2cnc(-c3c[nH]c4ncc(F)cc34)nc21]

TABLE C-continued
B26
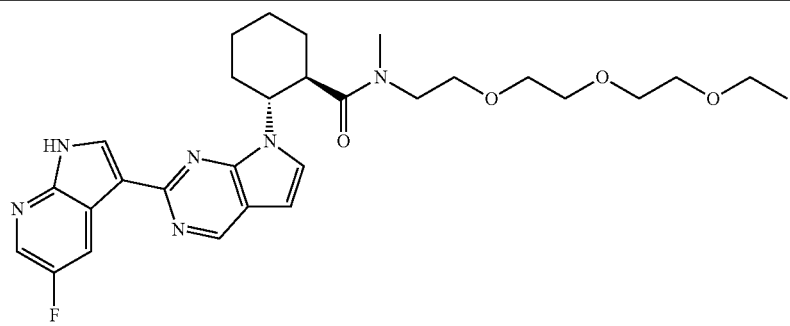
B27
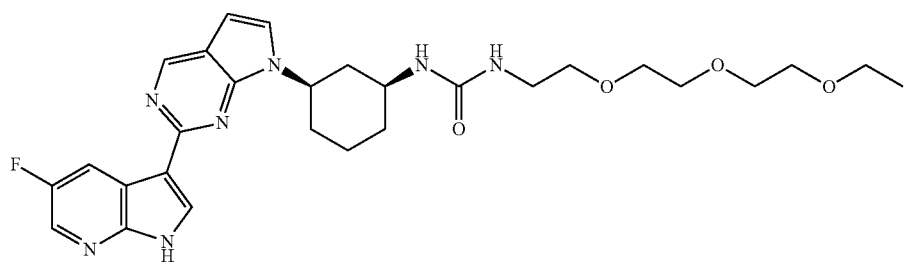 [SMILES: CCOCCOCCOCCNC(=O)N[C@H]1CCC[C@@H](n2ccc3cnc(-c4c[nH]c5ncc(F)cc45)nc32)C1]
B28
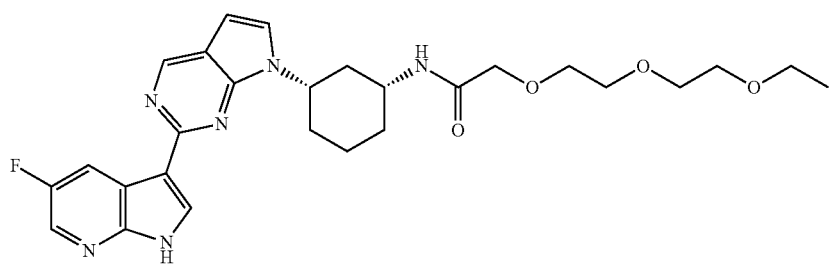 [SMILES: CCOCCOCCOCC(=O)N[C@@H]1CCC[C@H](n2ccc3cnc(-c4c[nH]c5ncc(F)cc45)nc32)C1]
B29
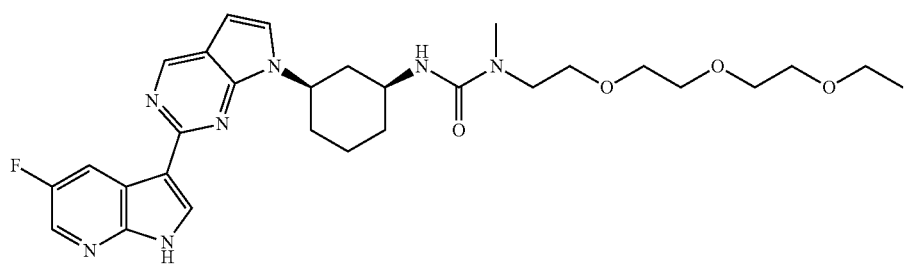 [SMILES: CCOCCOCCOCCN(C)C(=O)N[C@H]1CCC[C@@H](n2ccc3cnc(-c4c[nH]c5ncc(F)cc45)nc32)C1]
B30
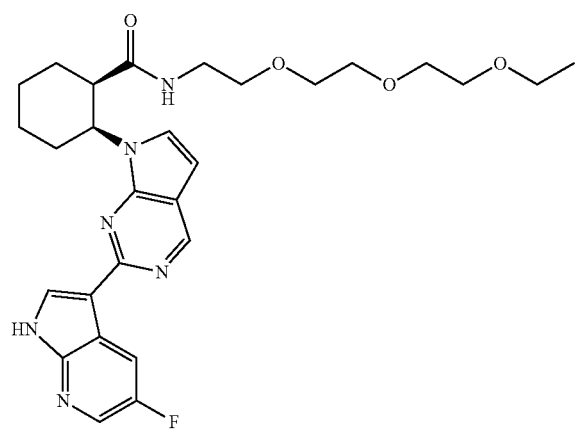 [SMILES: CCOCCOCCOCCNC(=O)[C@@H]1CCCC[C@@H]1n1ccc2cnc(-c3c[nH]c4ncc(F)cc34)nc21]

TABLE C-continued
B31
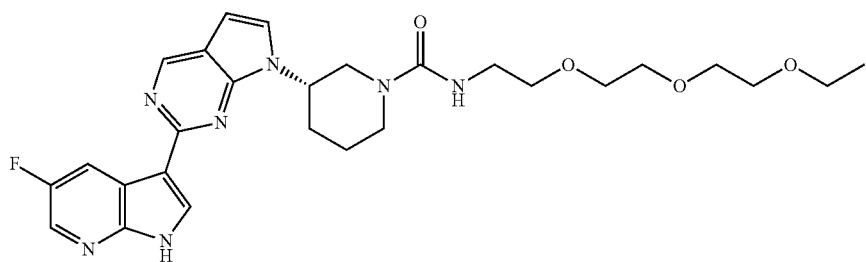 [SMILES: CCOCCOCCOCCNC(=O)N1CCC[C@H](n2ccc3cnc(-c4c[nH]c5ncc(F)cc45)nc32)C1]
B32
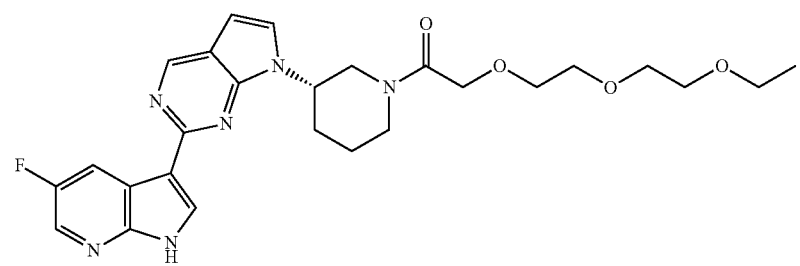 [SMILES: CCOCCOCCOCC(=O)N1CCC[C@H](n2ccc3cnc(-c4c[nH]c5ncc(F)cc45)nc32)C1]
B33
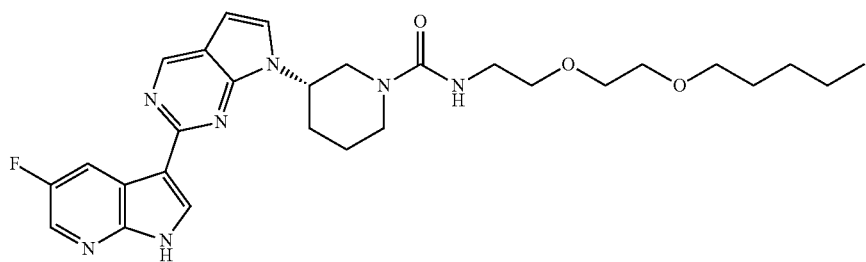
B34
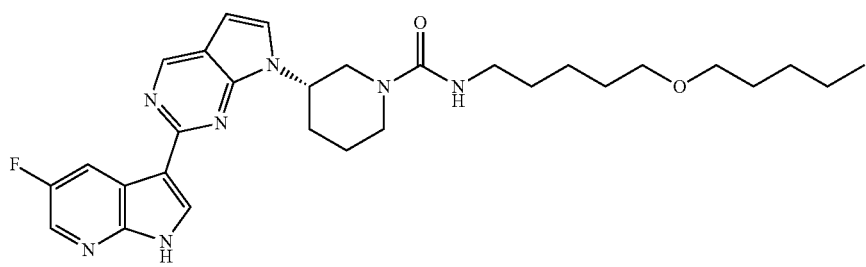
B35
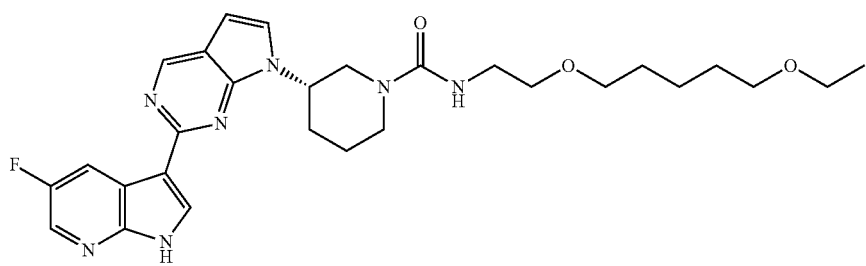 [SMILES: CCOCCCCCOCCNC(=O)N1CCC[C@H](n2ccc3cnc(-c4c[nH]c5ncc(F)cc45)nc32)C1]
B36
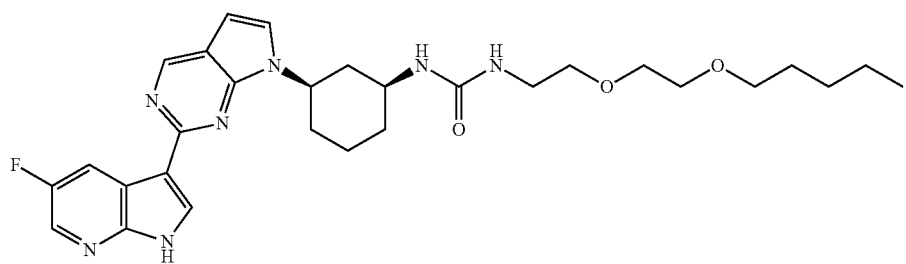

TABLE C-continued
B37
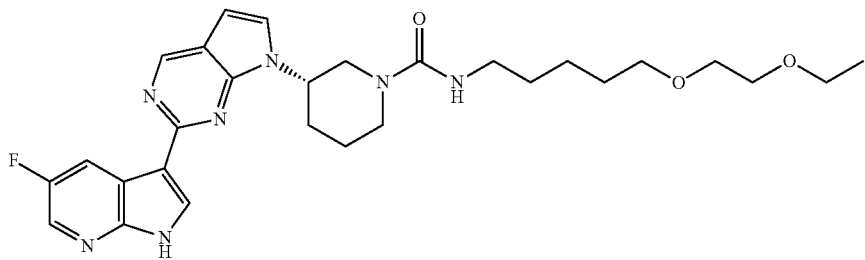
B38
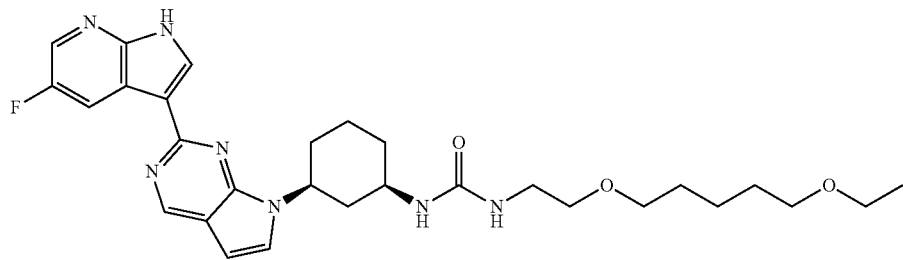 [SMILES: CCOCCCCCOCCNC(=O)N[C@@H]1CCC[C@H](n2ccc3cnc(-c4c[nH]c5ncc(F)cc45)nc32)C1]
B39
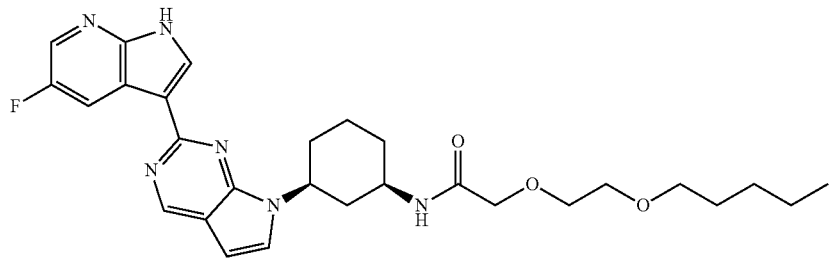 [SMILES: CCCCCOCCOCC(=O)N[C@@H]1CCC[C@H](n2ccc3cnc(-c4c[nH]c5ncc(F)cc45)nc32)C1]
B40
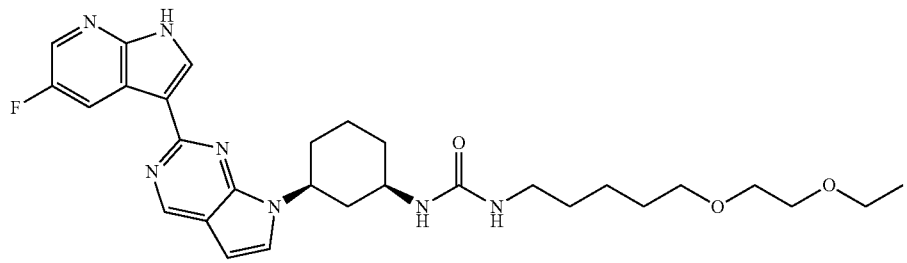 [SMILES: CCOCCOCCCCCNC(=O)N[C@@H]1CCC[C@H](n2ccc3cnc(-c4c[nH]c5ncc(F)cc45)nc32)C1]
B41
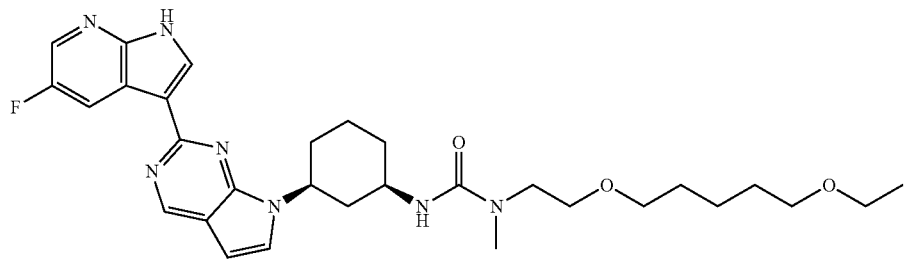 [SMILES: CCOCCCCCOCCN(C)C(=O)N[C@@H]1CCC[C@H](n2ccc3cnc(-c4c[nH]c5ncc(F)cc45)nc32)C1]
B42
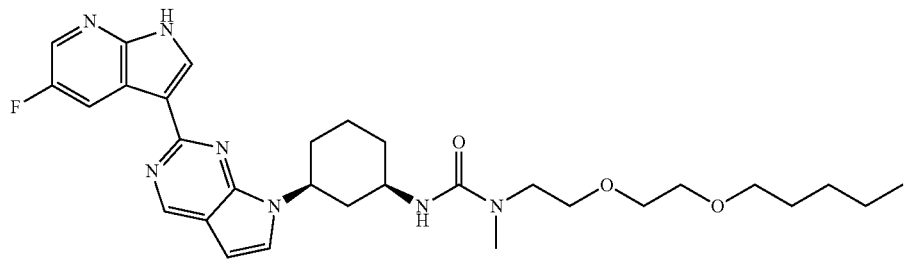

TABLE C-continued
B43 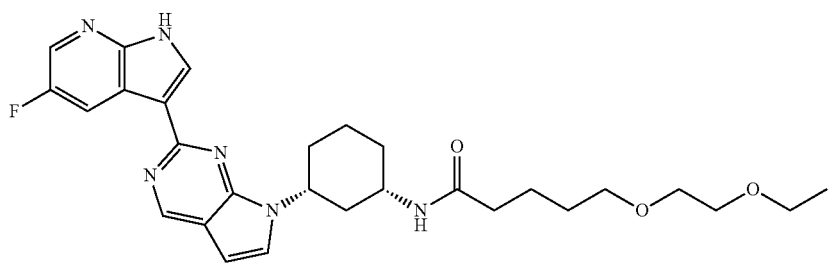 [SMILES: CCOCCOCCCCC(=O)N[C@H]1CCC[C@@H](n2ccc3cnc(-c4c[nH]c5ncc(F)cc45)nc32)C1]
B44 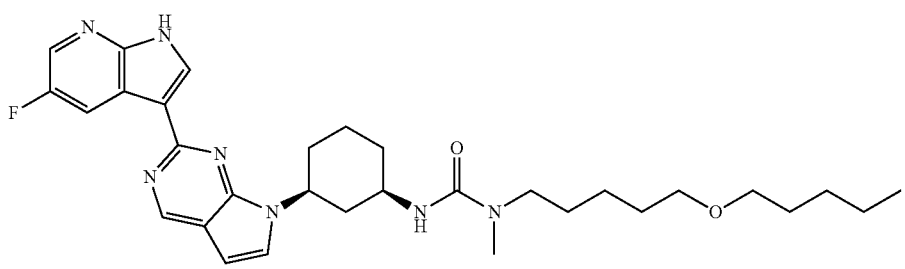 [SMILES: CCCCCOCCCCCN(C)C(=O)N[C@@H]1CCC[C@H](n2ccc3cnc(-c4c[nH]c5ncc(F)cc45)nc32)C1]
B45 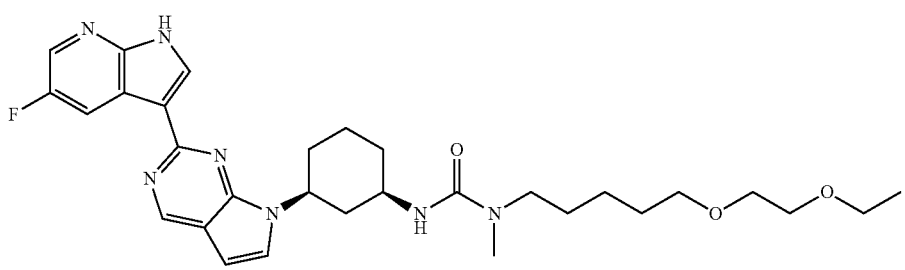
B46 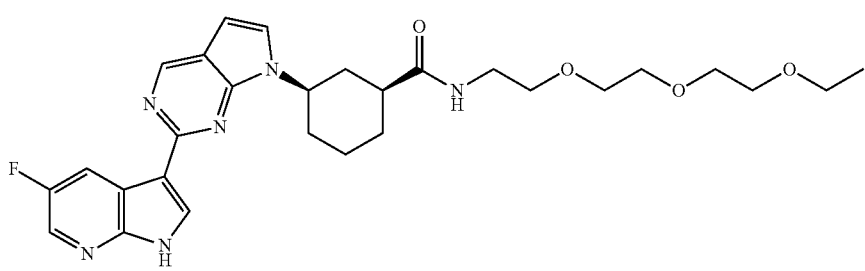 [SMILES: CCOCCOCCOCCNC(=O)[C@H]1CCC[C@@H](n2ccc3cnc(-c4c[nH]c5ncc(F)cc45)nc32)C1]
B47 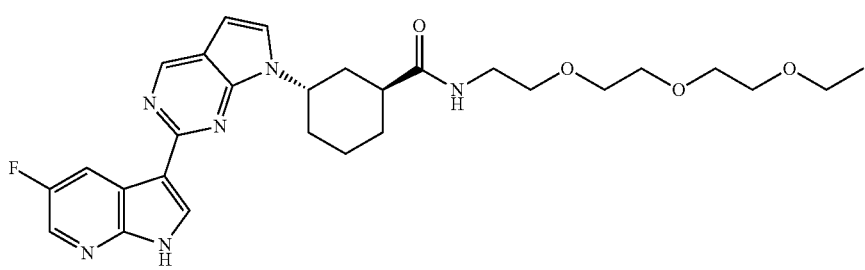 [SMILES: CCOCCOCCOCCNC(=O)[C@H]1CCC[C@H](n2ccc3cnc(-c4c[nH]c5ncc(F)cc45)nc32)C1]
B48 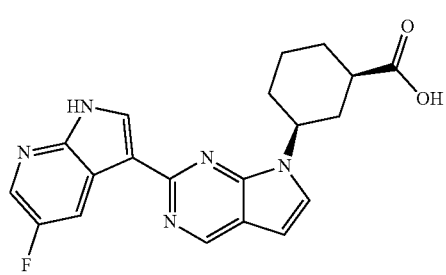 [SMILES: O=C(O)[C@@H]1CCC[C@H](n2ccc3cnc(-c4c[nH]c5ncc(F)cc45)nc32)C1]

TABLE C-continued
B49
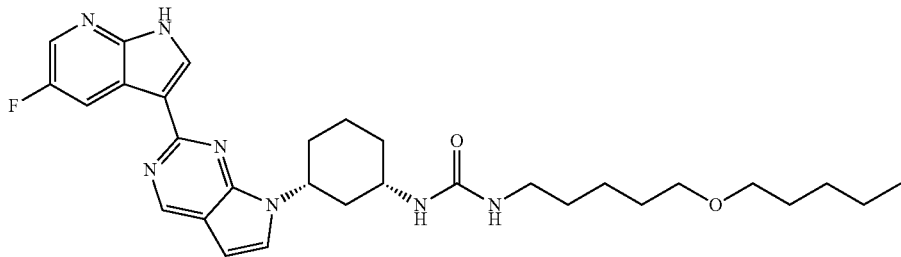 [SMILES: CCCCCOCCCCCNC(=O)N[C@H]1CCC[C@@H](n2ccc3cnc(-c4c[nH]c5ncc(F)cc45)nc32)C1]
B50
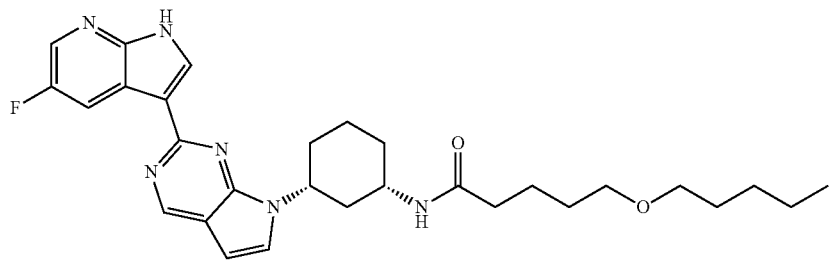
B51
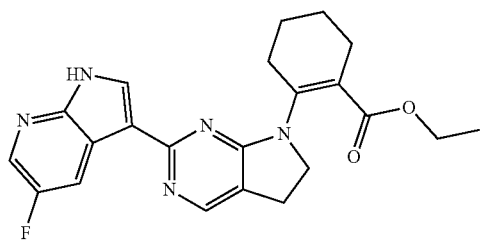 [SMILES: CCOC(=O)C1=C(N2CCc3cnc(-c4c[nH]c5ncc(F)cc45)nc32)CCCC1]
B100
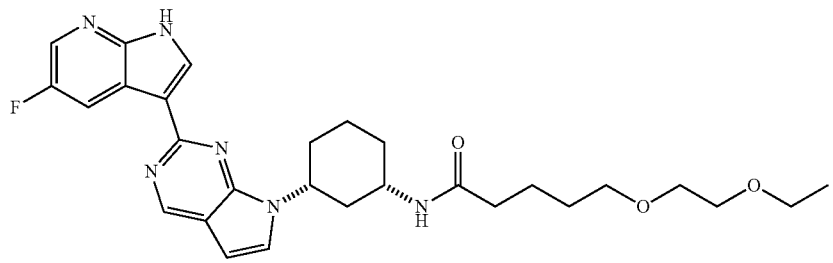
B52
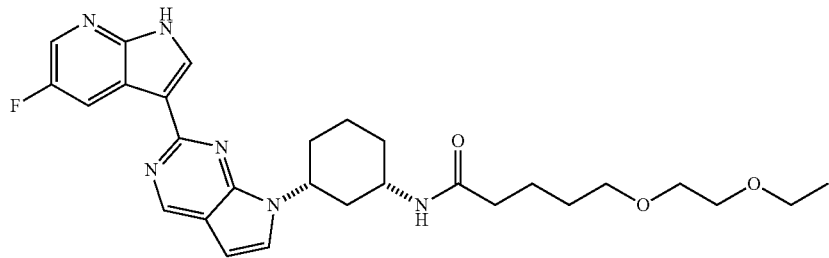
B53
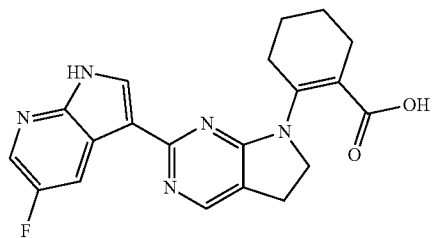 [SMILES: O=C(O)C1=C(N2CCc3cnc(-c4c[nH]c5ncc(F)cc45)nc32)CCCC1]

TABLE C-continued
B54 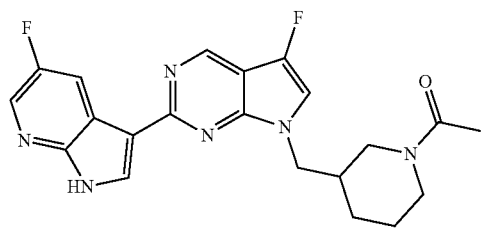 [SMILES: CC(=O)N1CCCC(Cn2cc(F)c3cnc(-c4c[nH]c5ncc(F)cc45)nc32)C1]
B55 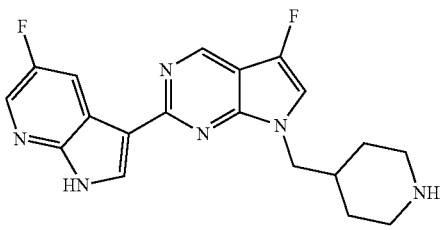 [SMILES: Fc1cnc2[nH]cc(-c3ncc4c(F)cn(CC5CCNCC5)c4n3)c2c1]
B56 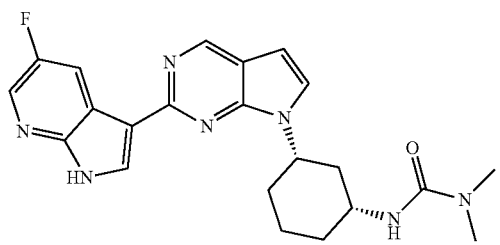 [SMILES: CN(C)C(=O)N[C@@H]1CCC[C@H](n2ccc3cnc(-c4c[nH]c5ncc(F)cc45)nc32)C1]
B57 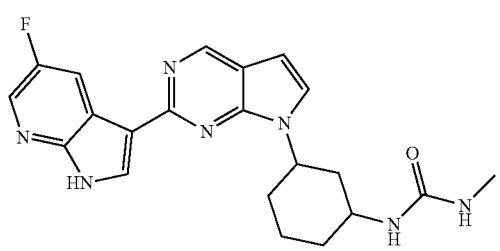 [SMILES: CNC(=O)NC1CCCC(n2ccc3cnc(-c4c[nH]c5ncc(F)cc45)nc32)C1]
B58 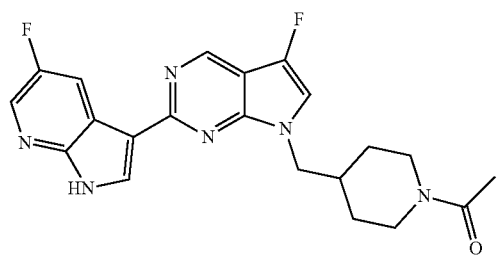 [SMILES: CC(=O)N1CCC(Cn2cc(F)c3cnc(-c4c[nH]c5ncc(F)cc45)nc32)CC1]
B59 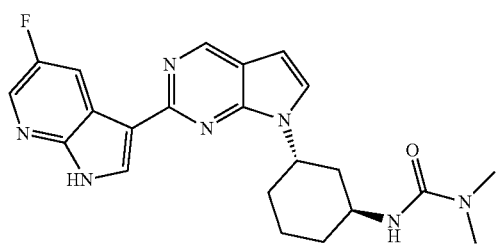 [SMILES: CN(C)C(=O)N[C@H]1CCC[C@H](n2ccc3cnc(-c4c[nH]c5ncc(F)cc45)nc32)C1]

TABLE C-continued
B60 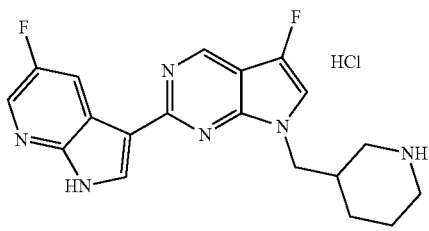 [SMILES: Fc1cnc2[nH]cc(-c3ncc4c(F)cn(CC5CCCNC5)c4n3)c2c1 ; Cl]
B61 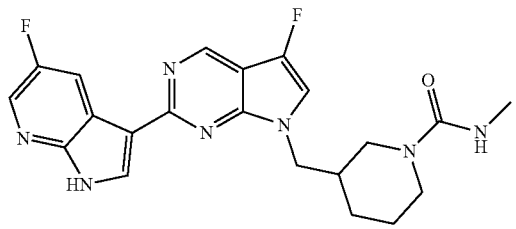 [SMILES: CNC(=O)N1CCCC(Cn2cc(F)c3cnc(-c4c[nH]c5ncc(F)cc45)nc32)C1]
B62 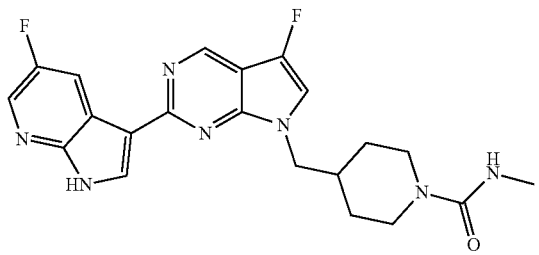 [SMILES: CNC(=O)N1CCC(Cn2cc(F)c3cnc(-c4c[nH]c5ncc(F)cc45)nc32)CC1]
B63 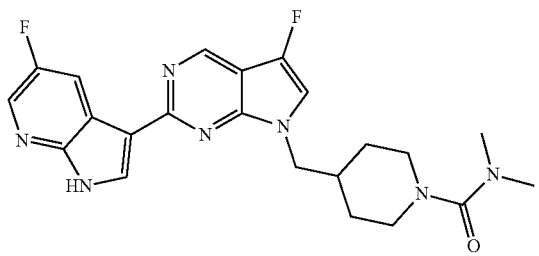 [SMILES: CN(C)C(=O)N1CCC(Cn2cc(F)c3cnc(-c4c[nH]c5ncc(F)cc45)nc32)CC1]
B64 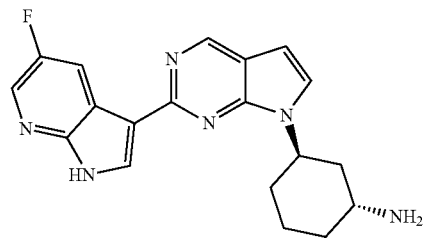 [SMILES: N[C@@H]1CCC[C@@H](n2ccc3cnc(-c4c[nH]c5ncc(F)cc45)nc32)C1]
B65 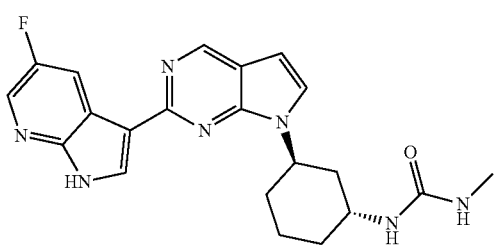 [SMILES: CNC(=O)N[C@@H]1CCC[C@@H](n2ccc3cnc(-c4c[nH]c5ncc(F)cc45)nc32)C1]

TABLE C-continued
| B66 | 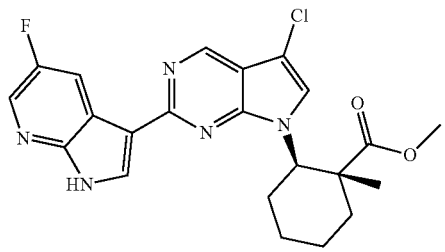 [SMILES: COC(=O)[C@]1(C)CCCC[C@H]1n1cc(Cl)c2cnc(-c3c[nH]c4ncc(F)cc34)nc21] |
|---|---|
| B67 | 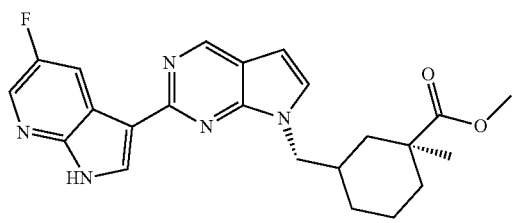 |
| B68 | 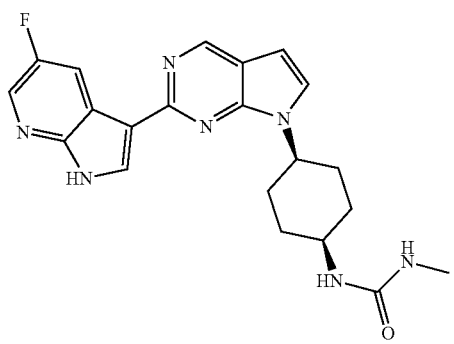 [SMILES: CNC(=O)N[C@H]1CC[C@@H](n2ccc3cnc(-c4c[nH]c5ncc(F)cc45)nc32)CC1] |
| B69 | 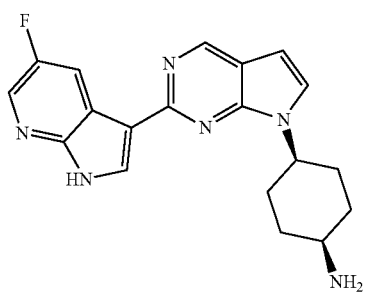 [SMILES: N[C@H]1CC[C@@H](n2ccc3cnc(-c4c[nH]c5ncc(F)cc45)nc32)CC1] |
| B70 | 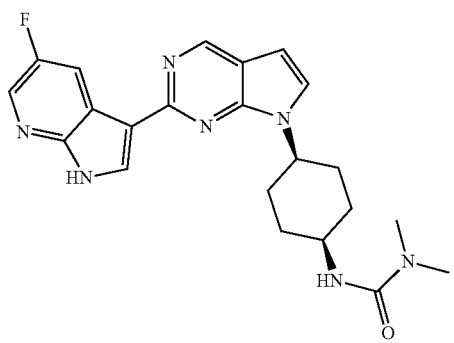 [SMILES: CN(C)C(=O)N[C@H]1CC[C@@H](n2ccc3cnc(-c4c[nH]c5ncc(F)cc45)nc32)CC1] |

TABLE C-continued
B71 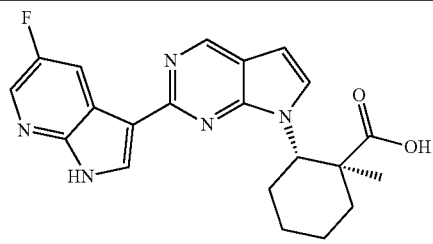
B72 
B73 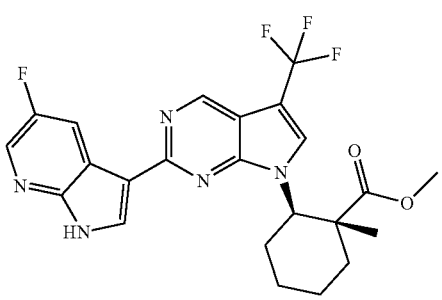 [SMILES: COC(=O)[C@]1(C)CCCC[C@H]1n1cc(C(F)(F)F)c2cnc(-c3c[nH]c4ncc(F)cc34)nc21]
B74 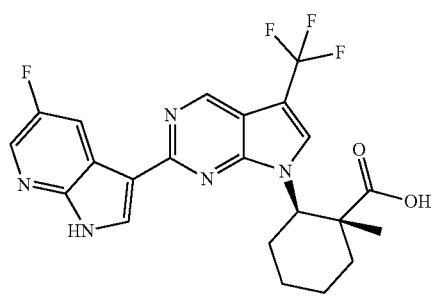 [SMILES: C[C@@]1(C(=O)O)CCCC[C@H]1n1cc(C(F)(F)F)c2cnc(-c3c[nH]c4ncc(F)cc34)nc21]
B75 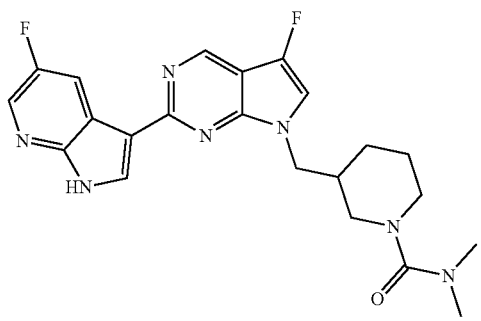 [SMILES: CN(C)C(=O)N1CCCC(Cn2cc(F)c3cnc(-c4c[nH]c5ncc(F)cc45)nc32)C1]
B76 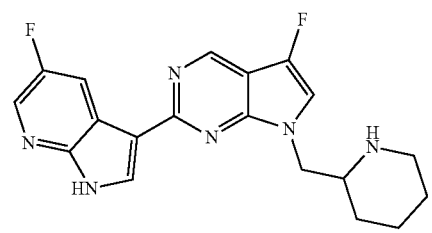 [SMILES: Fc1cnc2[nH]cc(-c3ncc4c(F)cn(CC5CCCCN5)c4n3)c2c1]

TABLE C-continued
B77 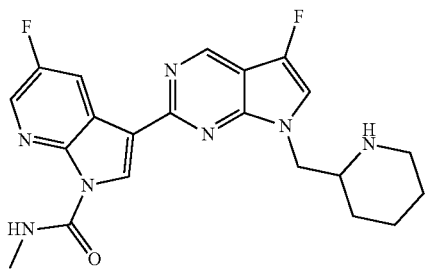 [SMILES: CNC(=O)n1cc(-c2ncc3c(F)cn(CC4CCCCN4)c3n2)c2cc(F)cnc21]
B78 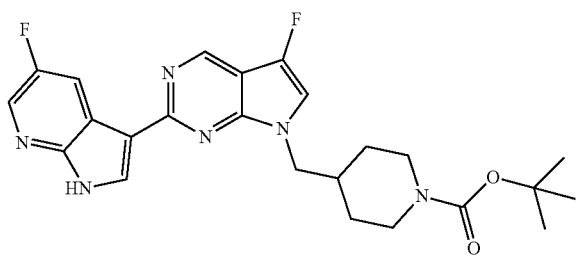 [SMILES: CC(C)(C)OC(=O)N1CCC(Cn2cc(F)c3cnc(-c4c[nH]c5ncc(F)cc45)nc32)CC1]
B79 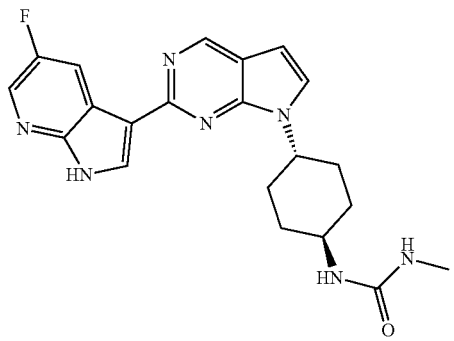 [SMILES: CNC(=O)N[C@H]1CC[C@H](n2ccc3cnc(-c4c[nH]c5ncc(F)cc45)nc32)CC1]
B80 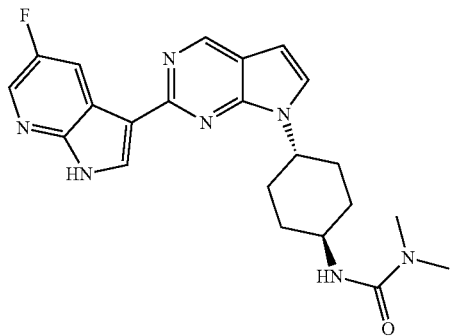 [SMILES: CN(C)C(=O)N[C@H]1CC[C@H](n2ccc3cnc(-c4c[nH]c5ncc(F)cc45)nc32)CC1]
B81 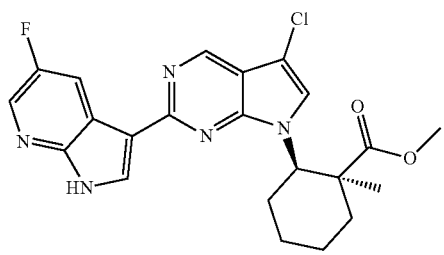 [SMILES: COC(=O)[C@@]1(C)CCCC[C@H]1n1cc(Cl)c2cnc(-c3c[nH]c4ncc(F)cc34)nc21]

TABLE C-continued
B82 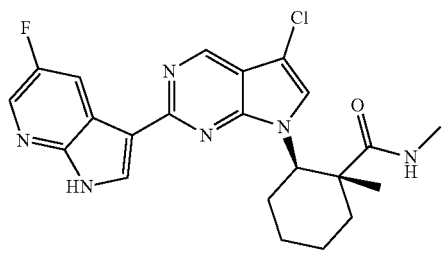 [SMILES: CNC(=O)[C@]1(C)CCCC[C@H]1n1cc(Cl)c2cnc(-c3c[nH]c4ncc(F)cc34)nc21]
B83 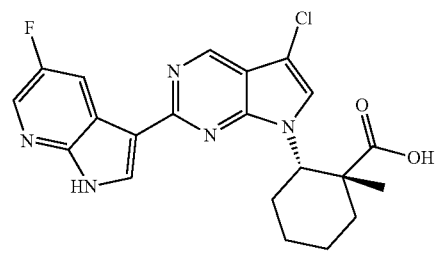 [SMILES: C[C@@]1(C(=O)O)CCCC[C@@H]1n1cc(Cl)c2cnc(-c3c[nH]c4ncc(F)cc34)nc21]
B84 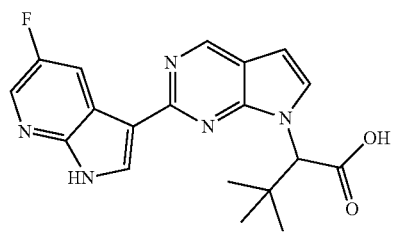 [SMILES: CC(C)(C)C(C(=O)O)n1ccc2cnc(-c3c[nH]c4ncc(F)cc34)nc21]
B85 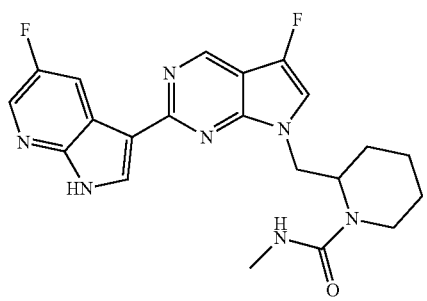 [SMILES: CNC(=O)N1CCCCC1Cn1cc(F)c2cnc(-c3c[nH]c4ncc(F)cc34)nc21]
B86 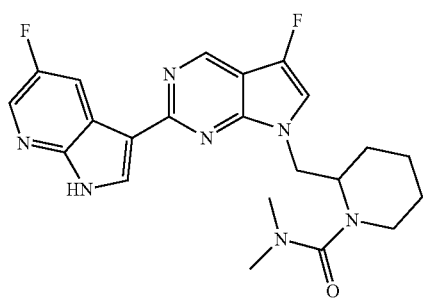 [SMILES: CN(C)C(=O)N1CCCCC1Cn1cc(F)c2cnc(-c3c[nH]c4ncc(F)cc34)nc21]
B87 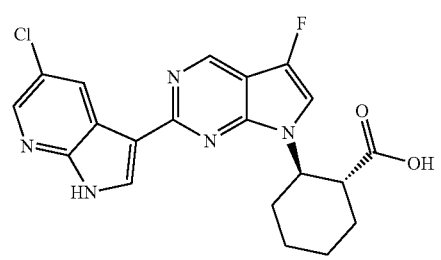 [SMILES: O=C(O)[C@@H]1CCCC[C@H]1n1cc(F)c2cnc(-c3c[nH]c4ncc(Cl)cc34)nc21]

TABLE C-continued
B88 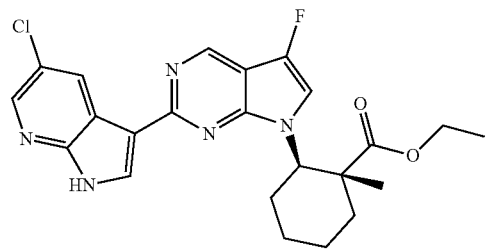 [SMILES: CCOC(=O)[C@]1(C)CCCC[C@H]1n1cc(F)c2cnc(-c3c[nH]c4ncc(Cl)cc34)nc21]
B89 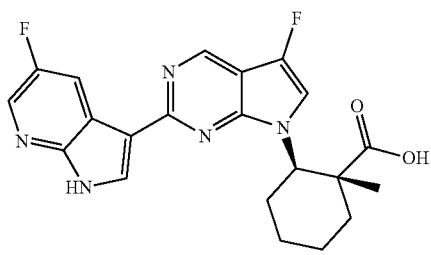 [SMILES: C[C@@]1(C(=O)O)CCCC[C@H]1n1cc(F)c2cnc(-c3c[nH]c4ncc(F)cc34)nc21]
B90 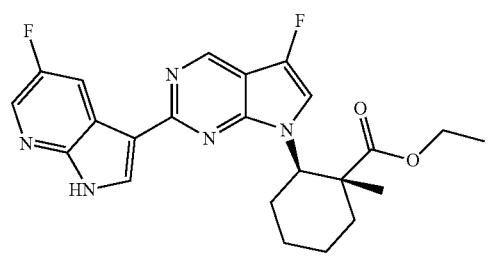 [SMILES: CCOC(=O)[C@]1(C)CCCC[C@H]1n1cc(F)c2cnc(-c3c[nH]c4ncc(F)cc34)nc21]
B91 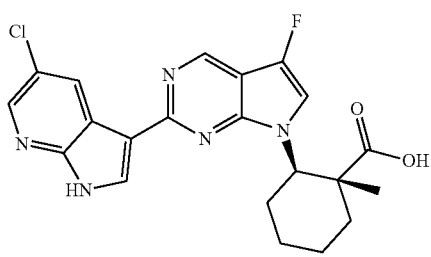 [SMILES: C[C@@]1(C(=O)O)CCCC[C@H]1n1cc(F)c2cnc(-c3c[nH]c4ncc(Cl)cc34)nc21]
B92 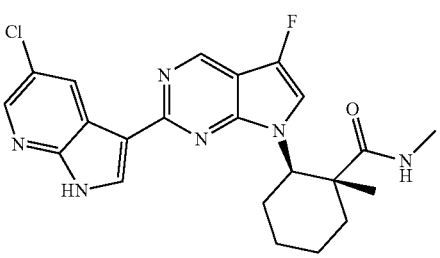 [SMILES: CNC(=O)[C@]1(C)CCCC[C@H]1n1cc(F)c2cnc(-c3c[nH]c4ncc(Cl)cc34)nc21]
B93 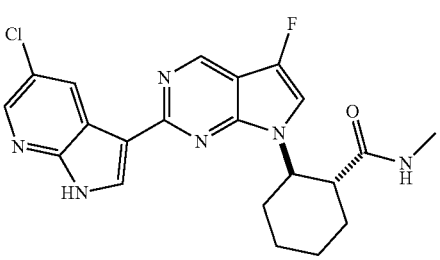

| | |
|---|---|
| B94 | 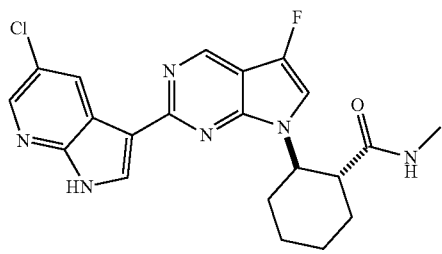 |
| B95 | 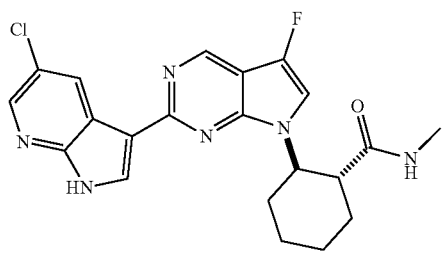 |
| B96 | 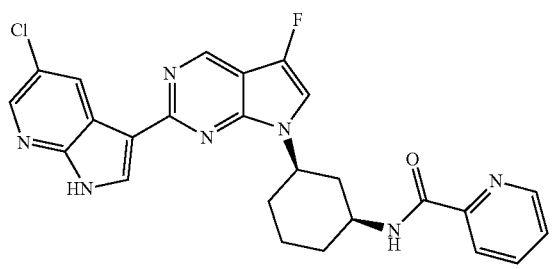 [SMILES: O=C(N[C@H]1CCC[C@@H](n2cc(F)c3cnc(-c4c[nH]c5ncc(Cl)cc45)nc32)C1)c1ccccn1] |
| B97 | 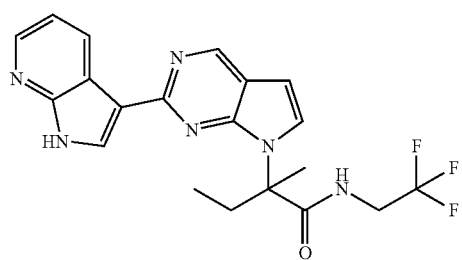 [SMILES: CCC(C)(C(=O)NCC(F)(F)F)n1ccc2cnc(-c3c[nH]c4ncccc34)nc21] |
| B98 | 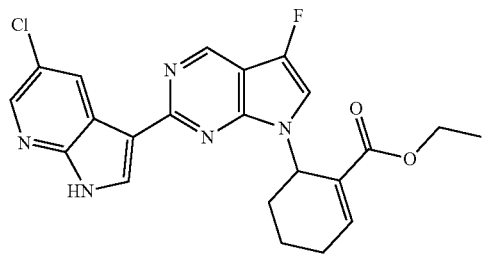 [SMILES: CCOC(=O)C1=CCCCC1n1cc(F)c2cnc(-c3c[nH]c4ncc(Cl)cc34)nc21] |
| B99 | 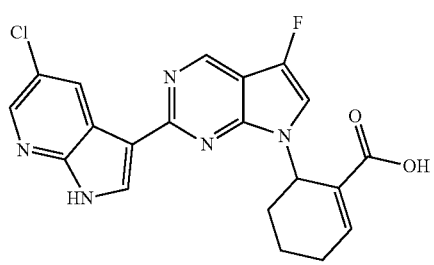 [SMILES: O=C(O)C1=CCCCC1n1cc(F)c2cnc(-c3c[nH]c4ncc(Cl)cc34)nc21] |

TABLE C-continued
B101 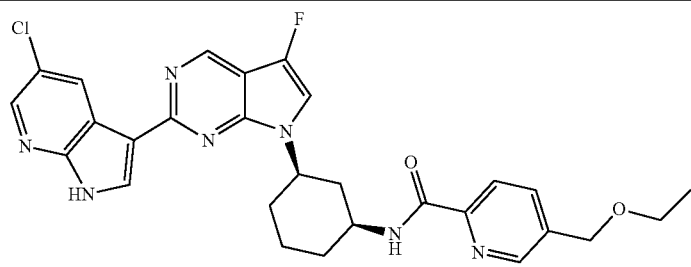
B102 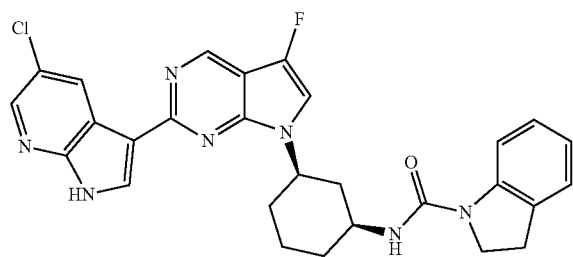 [SMILES: O=C(N[C@H]1CCC[C@@H](n2cc(F)c3cnc(-c4c[nH]c5ncc(Cl)cc45)nc32)C1)N1CCc2ccccc21]
B103 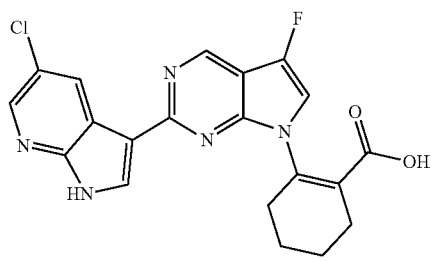 [SMILES: O=C(O)C1=C(n2cc(F)c3cnc(-c4c[nH]c5ncc(Cl)cc45)nc32)CCCC1]
B109 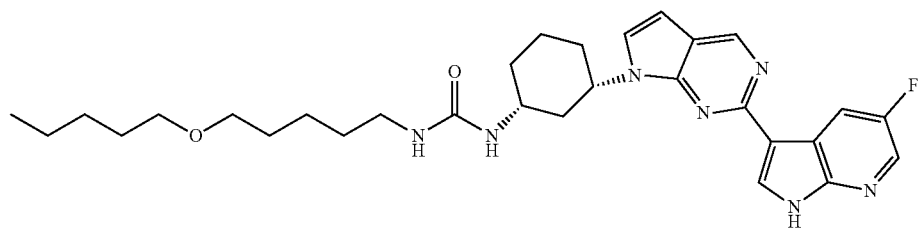 [SMILES: CCCCCOCCCCCNC(=O)N[C@@H]1CCC[C@H](n2ccc3cnc(-c4c[nH]c5ncc(F)cc45)nc32)C1]
B120 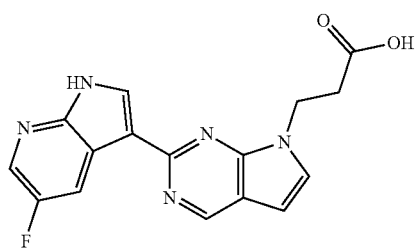 [SMILES: O=C(O)CCn1ccc2cnc(-c3c[nH]c4ncc(F)cc34)nc21]
B121 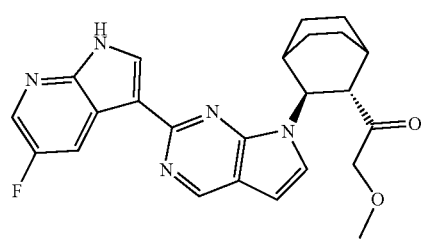 [SMILES: COCC(=O)[C@H]1C2CCC(CC2)[C@@H]1n1ccc2cnc(-c3c[nH]c4ncc(F)cc34)nc21]

TABLE C-continued
B122 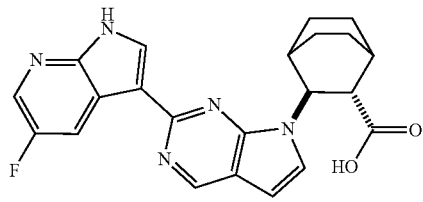
B123 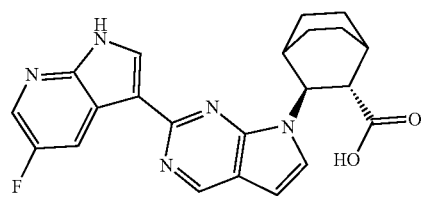 [SMILES: O=C(O)[C@H]1C2CCC(CC2)[C@@H]1n1ccc2cnc(-c3c[nH]c4ncc(F)cc34)nc21]
B124 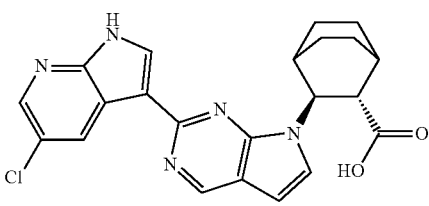 [SMILES: O=C(O)[C@H]1C2CCC(CC2)[C@@H]1n1ccc2cnc(-c3c[nH]c4ncc(Cl)cc34)nc21]
B125 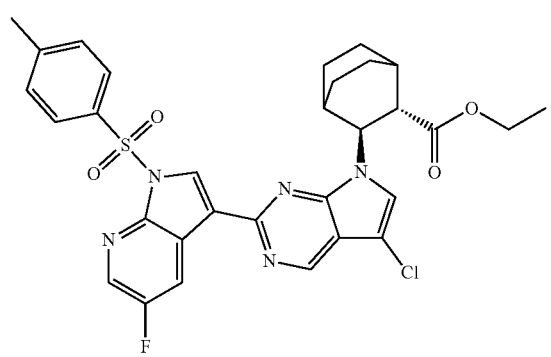 [SMILES: CCOC(=O)[C@H]1C2CCC(CC2)[C@@H]1n1cc(Cl)c2cnc(-c3cn(S(=O)(=O)c4ccc(C)cc4)c4ncc(F)cc34)nc21]
B126 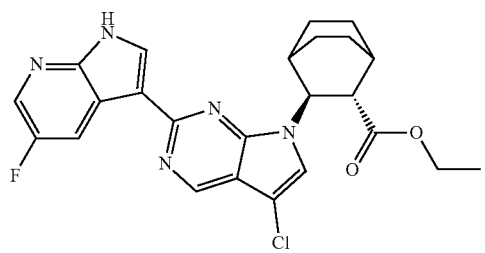 [SMILES: CCOC(=O)[C@H]1C2CCC(CC2)[C@@H]1n1cc(Cl)c2cnc(-c3c[nH]c4ncc(F)cc34)nc21]
B127 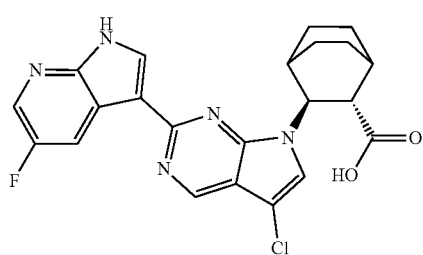

TABLE C-continued
B128 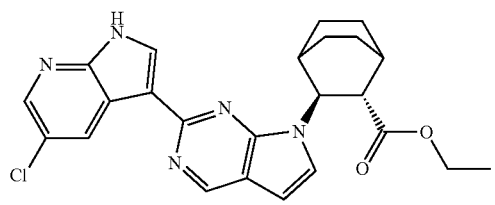 [SMILES: CCOC(=O)[C@H]1C2CCC(CC2)[C@@H]1n1ccc2cnc(-c3c[nH]c4ncc(Cl)cc34)nc21]
B129 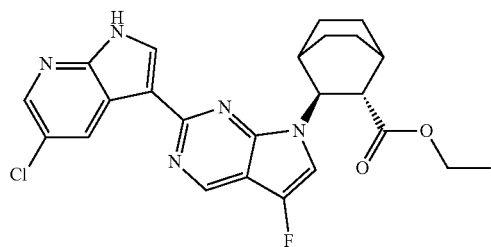 [SMILES: CCOC(=O)[C@H]1C2CCC(CC2)[C@@H]1n1cc(F)c2cnc(-c3c[nH]c4ncc(Cl)cc34)nc21]
B130 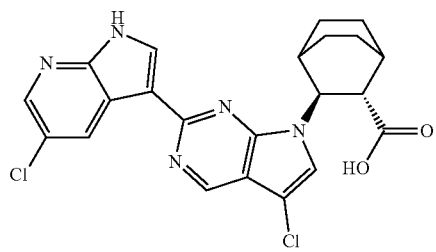 [SMILES: O=C(O)[C@H]1C2CCC(CC2)[C@@H]1n1cc(Cl)c2cnc(-c3c[nH]c4ncc(Cl)cc34)nc21]
B131 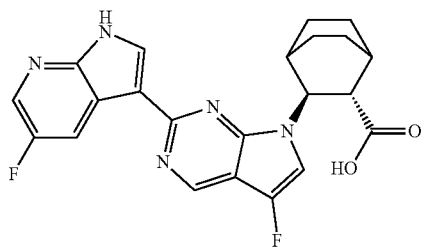 [SMILES: O=C(O)[C@H]1C2CCC(CC2)[C@@H]1n1cc(F)c2cnc(-c3c[nH]c4ncc(F)cc34)nc21]
B132 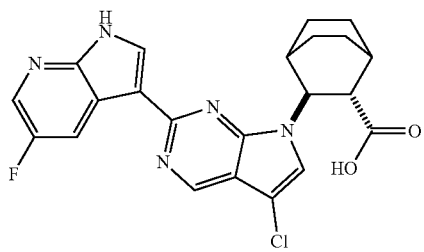 [SMILES: O=C(O)[C@H]1C2CCC(CC2)[C@@H]1n1cc(Cl)c2cnc(-c3c[nH]c4ncc(F)cc34)nc21]
B133 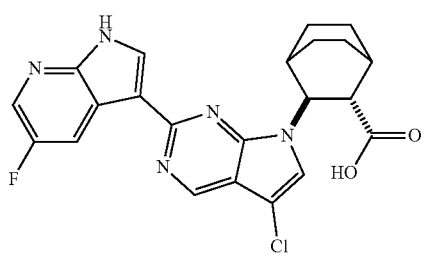 [SMILES: O=C(O)[C@H]1C2CCC(CC2)[C@@H]1n1cc(Cl)c2cnc(-c3c[nH]c4ncc(F)cc34)nc21]

TABLE C-continued
B134
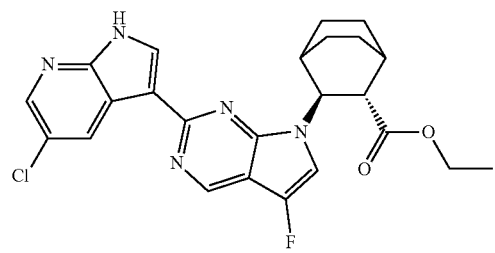 [SMILES: CCOC(=O)[C@H]1C2CCC(CC2)[C@@H]1n1cc(F)c2cnc(-c3c[nH]c4ncc(Cl)cc34)nc21]
B135
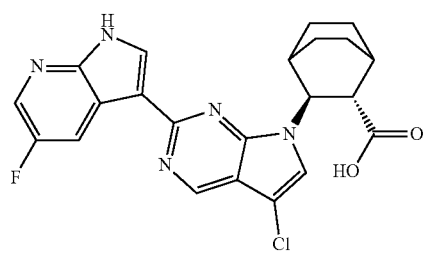
B136
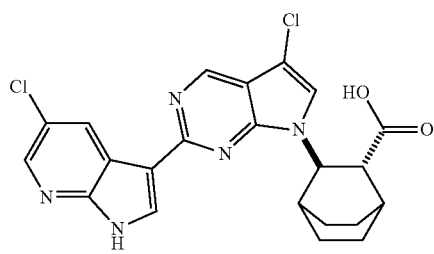
B137
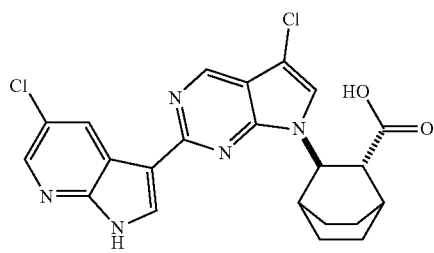
B138
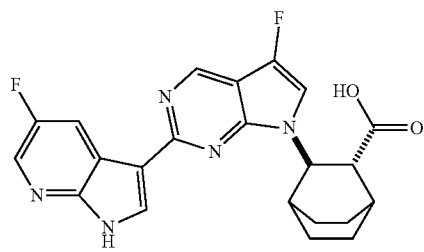
B139
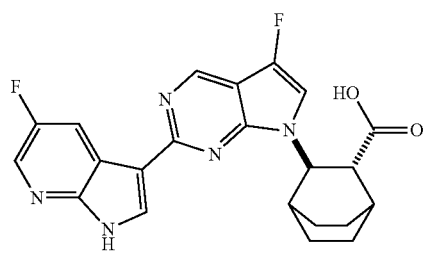 [SMILES: O=C(O)[C@@H]1C2CCC(CC2)[C@H]1n1cc(F)c2cnc(-c3c[nH]c4ncc(F)cc34)nc21]

TABLE C-continued
B140
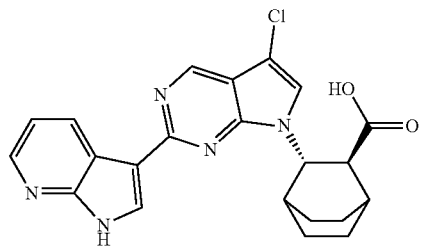 [SMILES: O=C(O)[C@H]1C2CCC(CC2)[C@@H]1n1cc(Cl)c2cnc(-c3c[nH]c4ncccc34)nc21]
B141
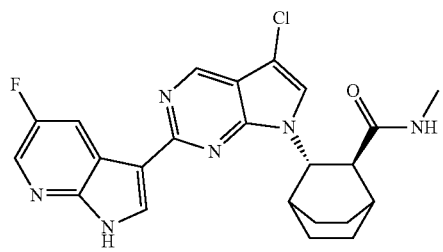 [SMILES: CNC(=O)[C@H]1C2CCC(CC2)[C@@H]1n1cc(Cl)c2cnc(-c3c[nH]c4ncc(F)cc34)nc21]
B142
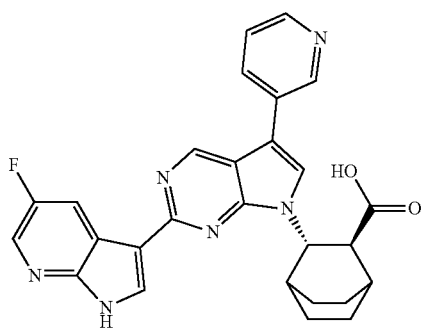 [SMILES: O=C(O)[C@H]1C2CCC(CC2)[C@@H]1n1cc(-c2cccnc2)c2cnc(-c3c[nH]c4ncc(F)cc34)nc21]
B143
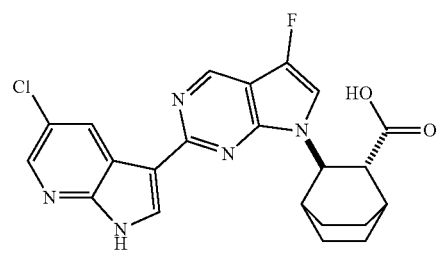
B144
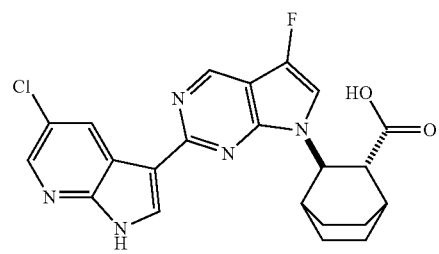

TABLE C-continued
B145
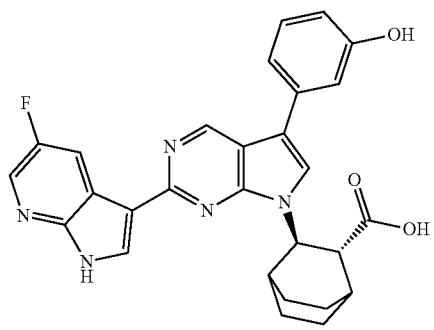 [SMILES: O=C(O)[C@@H]1C2CCC(CC2)[C@H]1n1cc(-c2cccc(O)c2)c2cnc(-c3c[nH]c4ncc(F)cc34)nc21]
B146
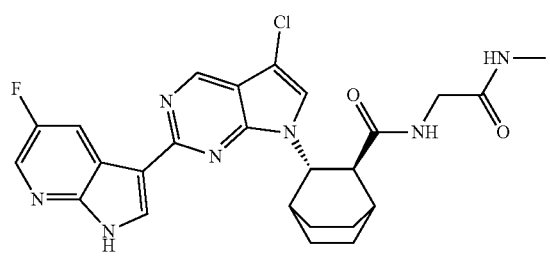 [SMILES: CNC(=O)CNC(=O)[C@H]1C2CCC(CC2)[C@@H]1n1cc(Cl)c2cnc(-c3c[nH]c4ncc(F)cc34)nc21]
B147
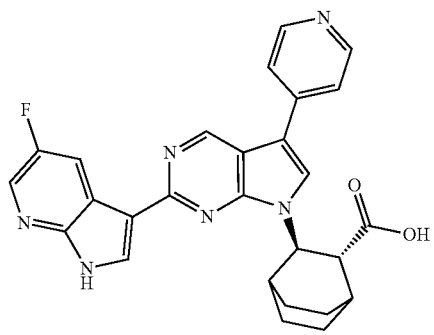 [SMILES: O=C(O)[C@@H]1C2CCC(CC2)[C@H]1n1cc(-c2ccncc2)c2cnc(-c3c[nH]c4ncc(F)cc34)nc21]
B148
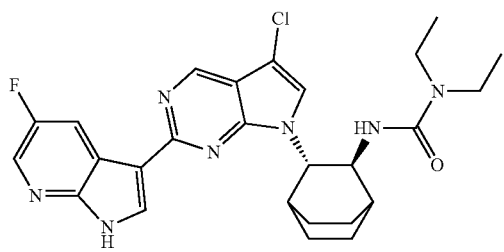 [SMILES: CCN(CC)C(=O)N[C@H]1C2CCC(CC2)[C@@H]1n1cc(Cl)c2cnc(-c3c[nH]c4ncc(F)cc34)nc21]
B149
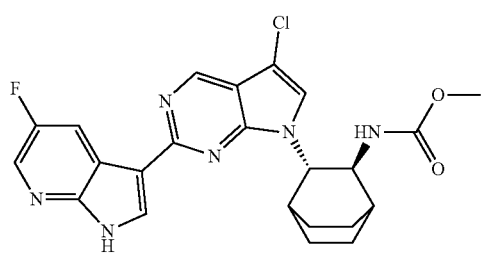 [SMILES: COC(=O)N[C@H]1C2CCC(CC2)[C@@H]1n1cc(Cl)c2cnc(-c3c[nH]c4ncc(F)cc34)nc21]

TABLE C-continued
B150
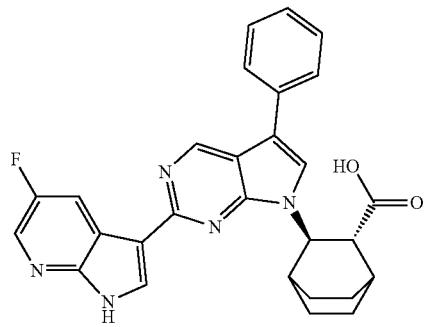 [SMILES: O=C(O)[C@@H]1C2CCC(CC2)[C@H]1n1cc(-c2ccccc2)c2cnc(-c3c[nH]c4ncc(F)cc34)nc21]
B151
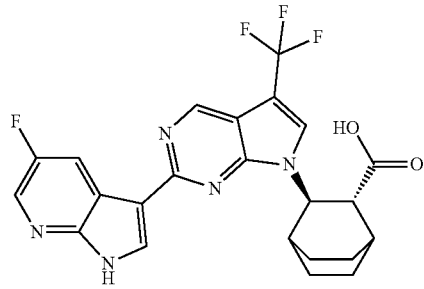 [SMILES: O=C(O)[C@@H]1C2CCC(CC2)[C@H]1n1cc(C(F)(F)F)c2cnc(-c3c[nH]c4ncc(F)cc34)nc21]
B152
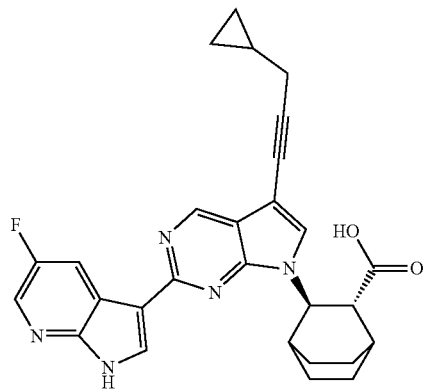 [SMILES: O=C(O)[C@@H]1C2CCC(CC2)[C@H]1n1cc(C#CCC2CC2)c2cnc(-c3c[nH]c4ncc(F)cc34)nc21]
B153
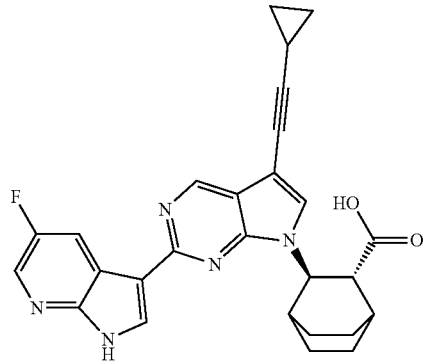 [SMILES: O=C(O)[C@@H]1C2CCC(CC2)[C@H]1n1cc(C#CC2CC2)c2cnc(-c3c[nH]c4ncc(F)cc34)nc21]

TABLE C-continued
B154
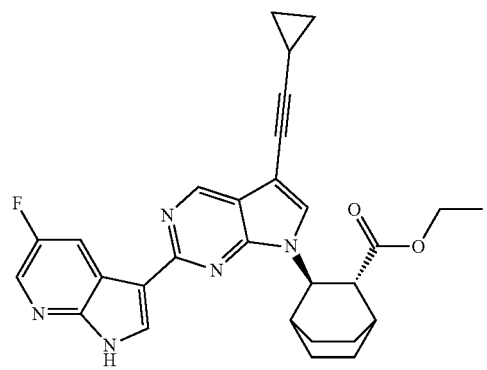 [SMILES: CCOC(=O)[C@@H]1C2CCC(CC2)[C@H]1n1cc(C#CC2CC2)c2cnc(-c3c[nH]c4ncc(F)cc34)nc21]
B160
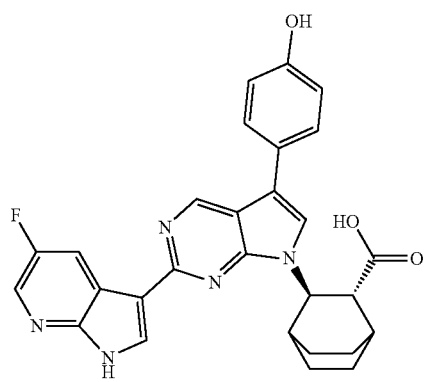 [SMILES: O=C(O)[C@@H]1C2CCC(CC2)[C@H]1n1cc(-c2ccc(O)cc2)c2cnc(-c3c[nH]c4ncc(F)cc34)nc21]
B161
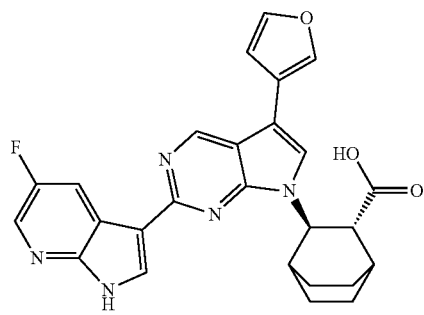 [SMILES: O=C(O)[C@@H]1C2CCC(CC2)[C@H]1n1cc(-c2ccoc2)c2cnc(-c3c[nH]c4ncc(F)cc34)nc21]
B162
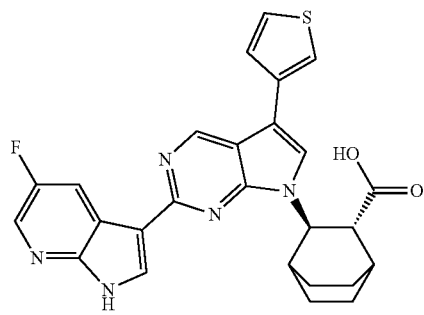
B163
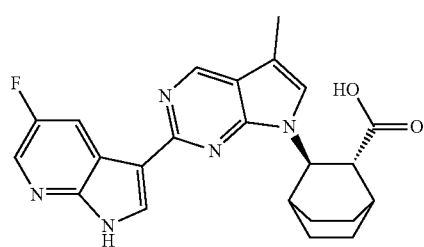 [SMILES: Cc1cn([C@@H]2C3CCC(CC3)[C@H]2C(=O)O)c2nc(-c3c[nH]c4ncc(F)cc34)ncc12]

TABLE C-continued
B164
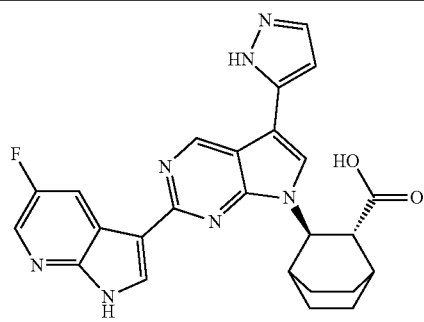
B165
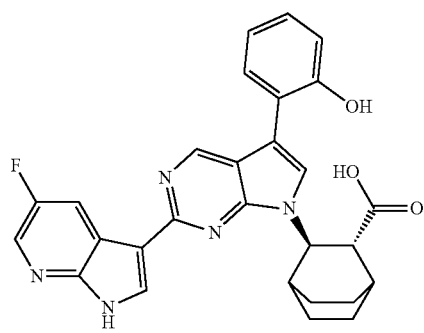 [SMILES: O=C(O)[C@@H]1C2CCC(CC2)[C@H]1n1cc(-c2ccccc2O)c2cnc(-c3c[nH]c4ncc(F)cc34)nc21]
B166
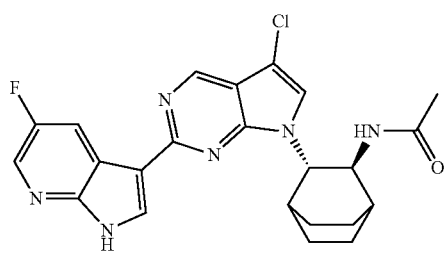 [SMILES: CC(=O)N[C@H]1C2CCC(CC2)[C@@H]1n1cc(Cl)c2cnc(-c3c[nH]c4ncc(F)cc34)nc21]
B167
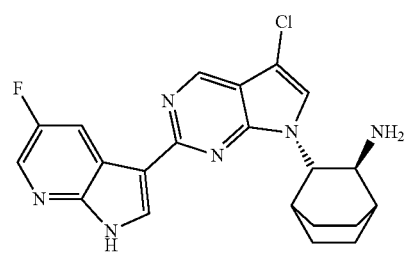
B168
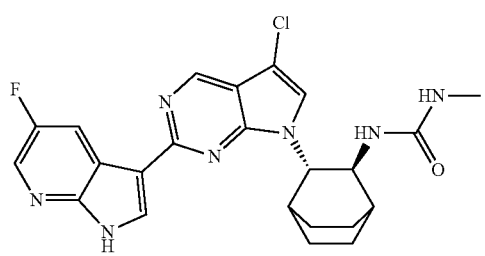 [SMILES: CNC(=O)N[C@H]1C2CCC(CC2)[C@@H]1n1cc(Cl)c2cnc(-c3c[nH]c4ncc(F)cc34)nc21]

TABLE C-continued
B169
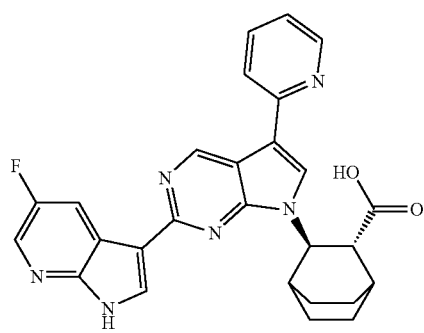 [SMILES: O=C(O)[C@@H]1C2CCC(CC2)[C@H]1n1cc(-c2ccccn2)c2cnc(-c3c[nH]c4ncc(F)cc34)nc21]
B170
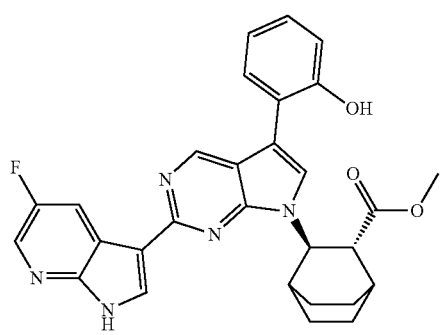 [SMILES: COC(=O)[C@@H]1C2CCC(CC2)[C@H]1n1cc(-c2ccccc2O)c2cnc(-c3c[nH]c4ncc(F)cc34)nc21]
B171
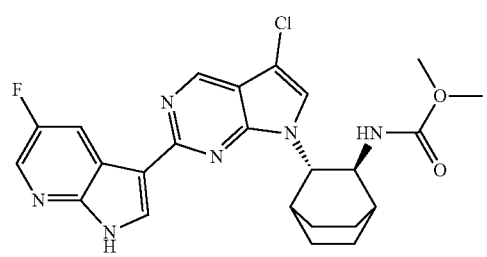
B172
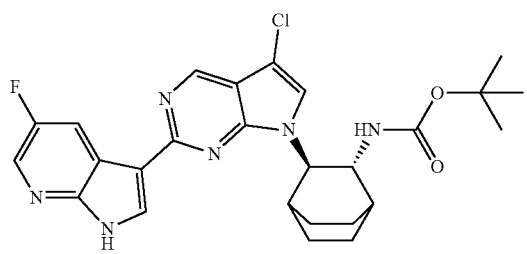 [SMILES: CC(C)(C)OC(=O)N[C@@H]1C2CCC(CC2)[C@H]1n1cc(Cl)c2cnc(-c3c[nH]c4ncc(F)cc34)nc21]
B173
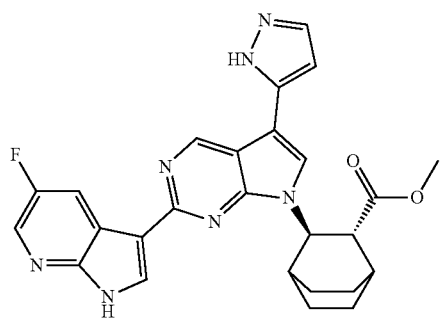 [SMILES: COC(=O)[C@@H]1C2CCC(CC2)[C@H]1n1cc(-c2ccn[nH]2)c2cnc(-c3c[nH]c4ncc(F)cc34)nc21]

TABLE C-continued
B174 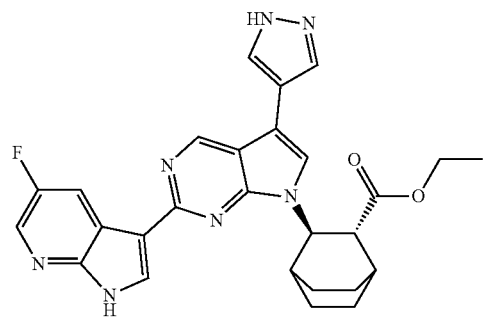 [SMILES: CCOC(=O)[C@@H]1C2CCC(CC2)[C@H]1n1cc(-c2cn[nH]c2)c2cnc(-c3c[nH]c4ncc(F)cc34)nc21]
B175 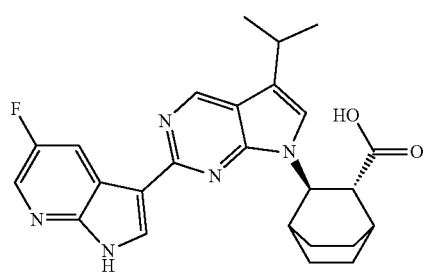 [SMILES: CC(C)c1cn([C@@H]2C3CCC(CC3)[C@H]2C(=O)O)c2nc(-c3c[nH]c4ncc(F)cc34)ncc12]
B176 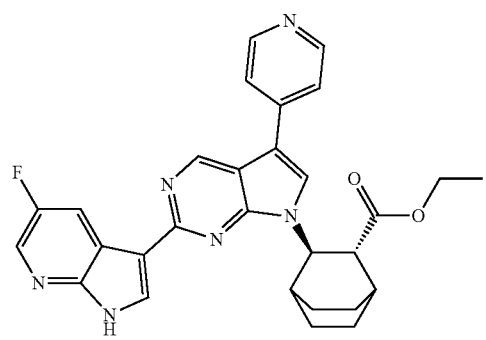 [SMILES: CCOC(=O)[C@@H]1C2CCC(CC2)[C@H]1n1cc(-c2ccncc2)c2cnc(-c3c[nH]c4ncc(F)cc34)nc21]
B177 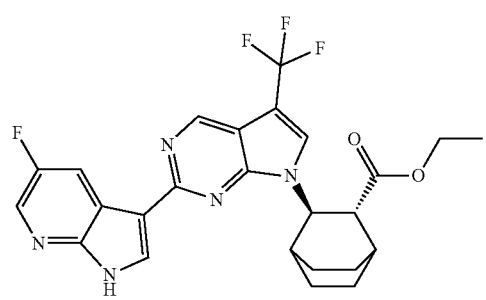 [SMILES: CCOC(=O)[C@@H]1C2CCC(CC2)[C@H]1n1cc(C(F)(F)F)c2cnc(-c3c[nH]c4ncc(F)cc34)nc21]
B178 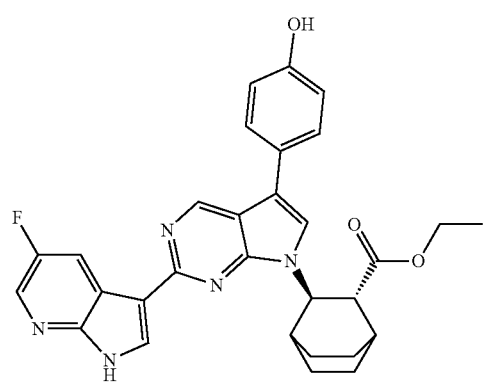 [SMILES: CCOC(=O)[C@@H]1C2CCC(CC2)[C@H]1n1cc(-c2ccc(O)cc2)c2cnc(-c3c[nH]c4ncc(F)cc34)nc21]

TABLE C-continued
B179 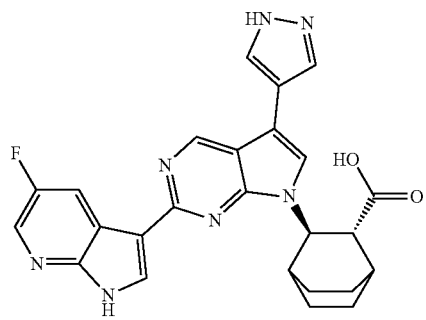 [SMILES: O=C(O)[C@@H]1C2CCC(CC2)[C@H]1n1cc(-c2cn[nH]c2)c2cnc(-c3c[nH]c4ncc(F)cc34)nc21]
B180 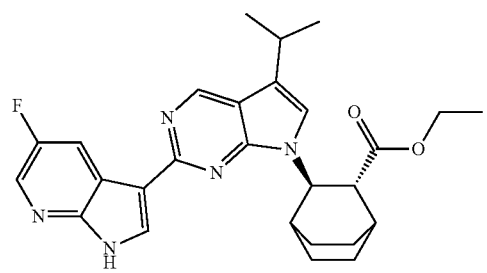 [SMILES: CCOC(=O)[C@@H]1C2CCC(CC2)[C@H]1n1cc(C(C)C)c2cnc(-c3c[nH]c4ncc(F)cc34)nc21]
B181 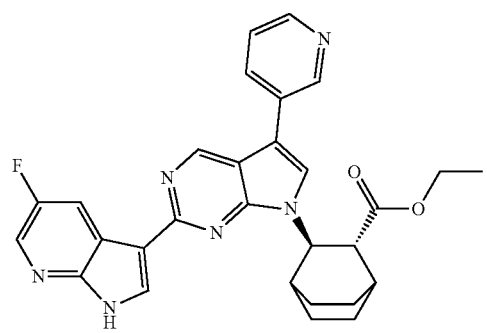 [SMILES: CCOC(=O)[C@@H]1C2CCC(CC2)[C@H]1n1cc(-c2cccnc2)c2cnc(-c3c[nH]c4ncc(F)cc34)nc21]
B182 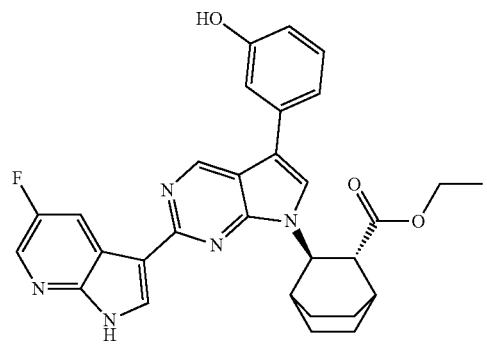 [SMILES: CCOC(=O)[C@@H]1C2CCC(CC2)[C@H]1n1cc(-c2cccc(O)c2)c2cnc(-c3c[nH]c4ncc(F)cc34)nc21]
B183 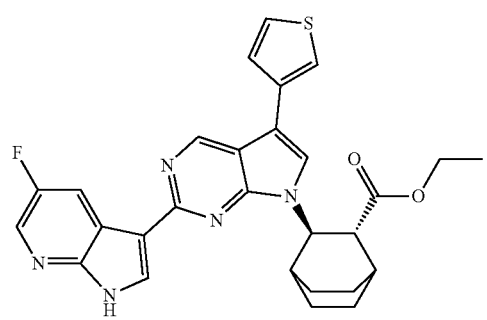 [SMILES: CCOC(=O)[C@@H]1C2CCC(CC2)[C@H]1n1cc(-c2ccsc2)c2cnc(-c3c[nH]c4ncc(F)cc34)nc21]

TABLE C-continued
B184
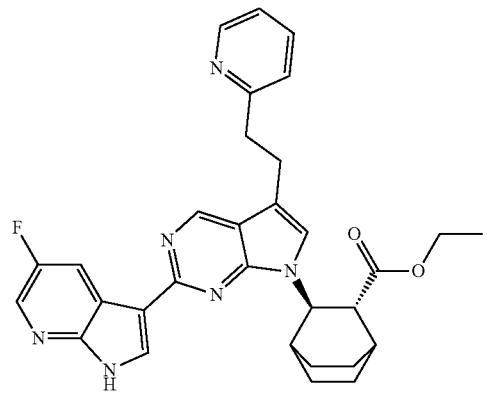 [SMILES: CCOC(=O)[C@@H]1C2CCC(CC2)[C@H]1n1cc(CCc2ccccn2)c2cnc(-c3c[nH]c4ncc(F)cc34)nc21]
B185
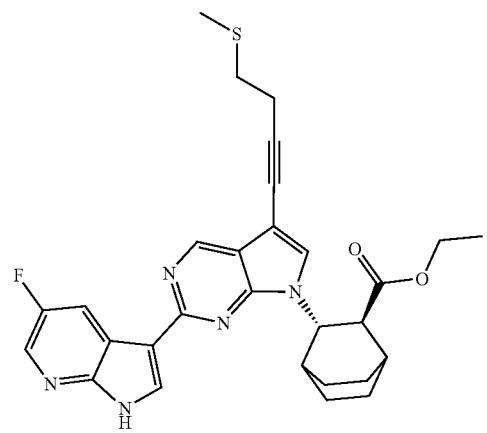 [SMILES: CCOC(=O)[C@H]1C2CCC(CC2)[C@@H]1n1cc(C#CCCSC)c2cnc(-c3c[nH]c4ncc(F)cc34)nc21]
B186
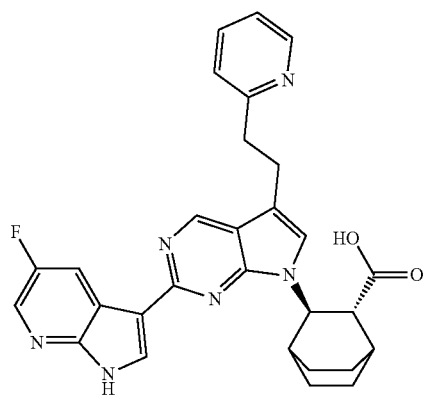 [SMILES: O=C(O)[C@@H]1C2CCC(CC2)[C@H]1n1cc(CCc2ccccn2)c2cnc(-c3c[nH]c4ncc(F)cc34)nc21]
B187
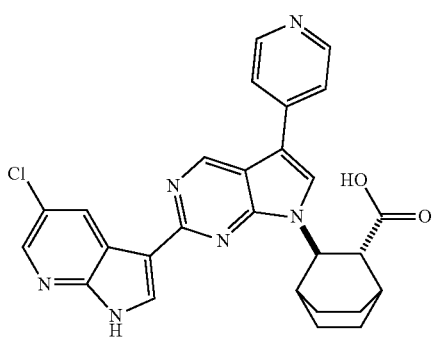

TABLE C-continued
B188 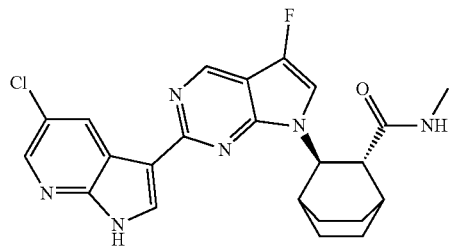 [SMILES: CNC(=O)[C@@H]1C2CCC(CC2)[C@H]1n1cc(F)c2cnc(-c3c[nH]c4ncc(Cl)cc34)nc21]
B189 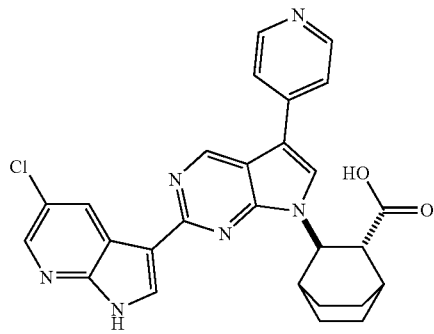
B190 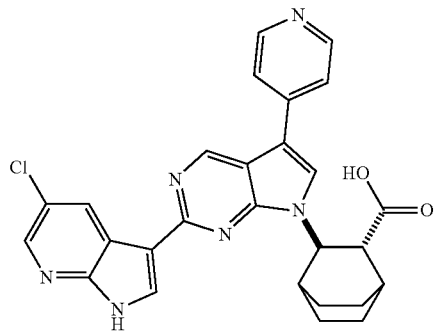
B191 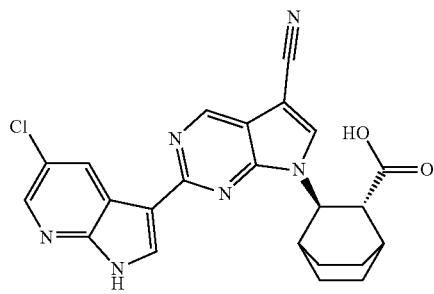 [SMILES: N#Cc1cn([C@@H]2C3CCC(CC3)[C@H]2C(=O)O)c2nc(-c3c[nH]c4ncc(Cl)cc34)ncc12]
B192 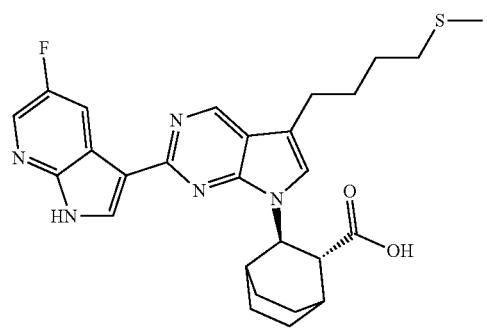 [SMILES: CSCCCCc1cn([C@@H]2C3CCC(CC3)[C@H]2C(=O)O)c2nc(-c3c[nH]c4ncc(F)cc34)ncc12]

TABLE C-continued
B193
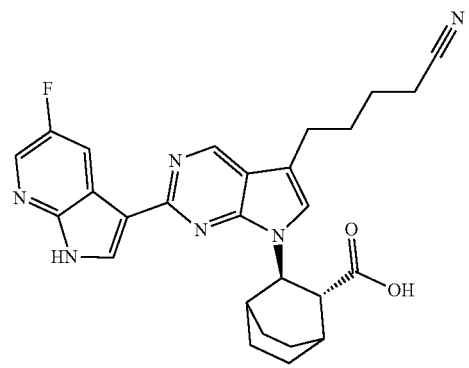 [SMILES: N#CCCCCc1cn([C@@H]2C3CCC(CC3)[C@H]2C(=O)O)c2nc(-c3c[nH]c4ncc(F)cc34)ncc12]
B194
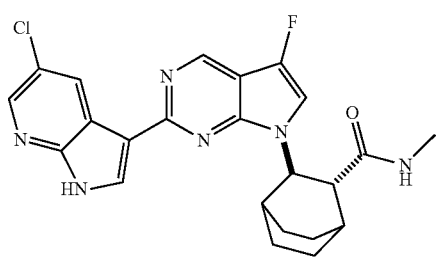
B195
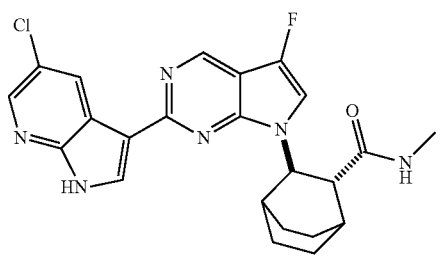
B196
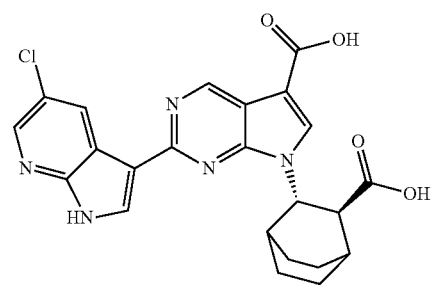 [SMILES: O=C(O)c1cn([C@H]2C3CCC(CC3)[C@@H]2C(=O)O)c2nc(-c3c[nH]c4ncc(Cl)cc34)ncc12]
B197
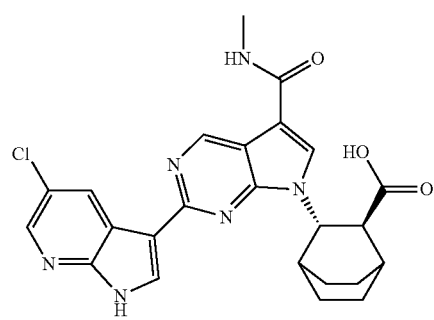 [SMILES: CNC(=O)c1cn([C@H]2C3CCC(CC3)[C@@H]2C(=O)O)c2nc(-c3c[nH]c4ncc(Cl)cc34)ncc12]

TABLE C-continued
B198
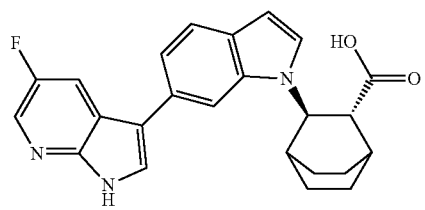 [SMILES: O=C(O)[C@@H]1C2CCC(CC2)[C@H]1n1ccc2ccc(-c3c[nH]c4ncc(F)cc34)cc21]
B199
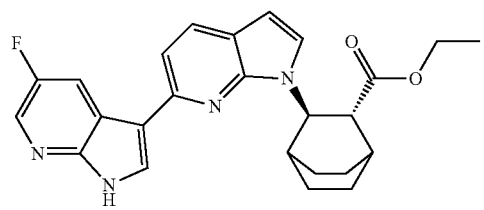 [SMILES: CCOC(=O)[C@@H]1C2CCC(CC2)[C@H]1n1ccc2ccc(-c3c[nH]c4ncc(F)cc34)nc21]
B200
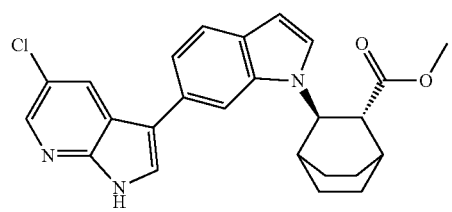 [SMILES: COC(=O)[C@@H]1C2CCC(CC2)[C@H]1n1ccc2ccc(-c3c[nH]c4ncc(Cl)cc34)cc21]
B201
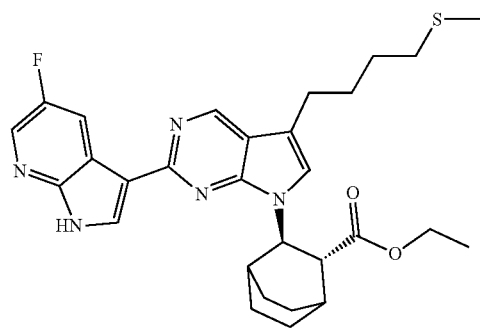 [SMILES: CCOC(=O)[C@@H]1C2CCC(CC2)[C@H]1n1cc(CCCCSC)c2cnc(-c3c[nH]c4ncc(F)cc34)nc21]
B202
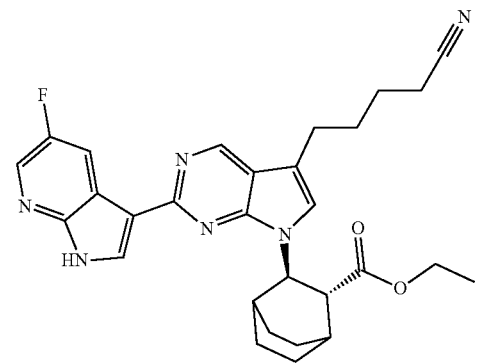 [SMILES: CCOC(=O)[C@@H]1C2CCC(CC2)[C@H]1n1cc(CCCCC#N)c2cnc(-c3c[nH]c4ncc(F)cc34)nc21]

TABLE C-continued
B203
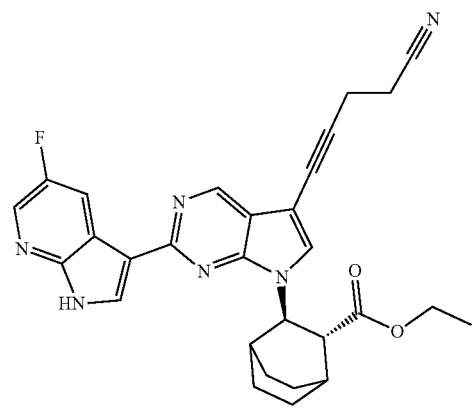 [SMILES: CCOC(=O)[C@@H]1C2CCC(CC2)[C@H]1n1cc(C#CCCC#N)c2cnc(-c3c[nH]c4ncc(F)cc34)nc21]
B204
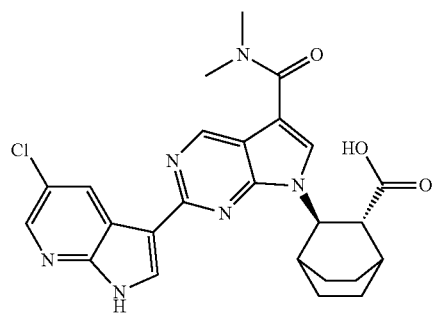 [SMILES: CN(C)C(=O)c1cn([C@@H]2C3CCC(CC3)[C@H]2C(=O)O)c2nc(-c3c[nH]c4ncc(Cl)cc34)ncc12]
B205
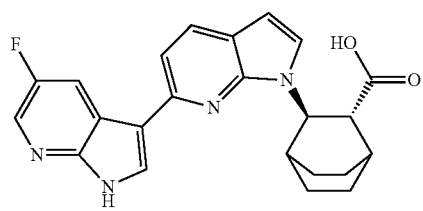 [SMILES: O=C(O)[C@@H]1C2CCC(CC2)[C@H]1n1ccc2ccc(-c3c[nH]c4ncc(F)cc34)nc21]
B206
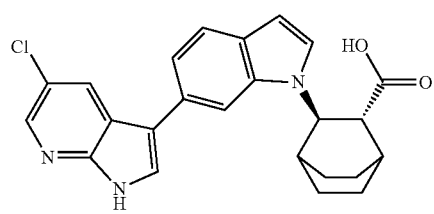 [SMILES: O=C(O)[C@@H]1C2CCC(CC2)[C@H]1n1ccc2ccc(-c3c[nH]c4ncc(Cl)cc34)cc21]
B207
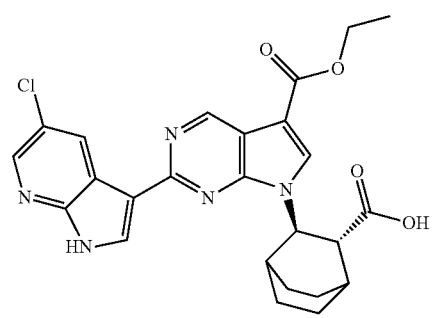 [SMILES: CCOC(=O)c1cn([C@@H]2C3CCC(CC3)[C@H]2C(=O)O)c2nc(-c3c[nH]c4ncc(Cl)cc34)ncc12]

TABLE C-continued
B208
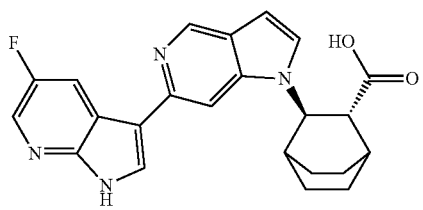 [SMILES: O=C(O)[C@@H]1C2CCC(CC2)[C@H]1n1ccc2cnc(-c3c[nH]c4ncc(F)cc34)cc21]
B209
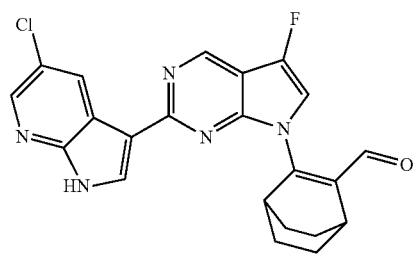 [SMILES: O=CC1=C(n2cc(F)c3cnc(-c4c[nH]c5ncc(Cl)cc45)nc32)C2CCC1CC2]
B210
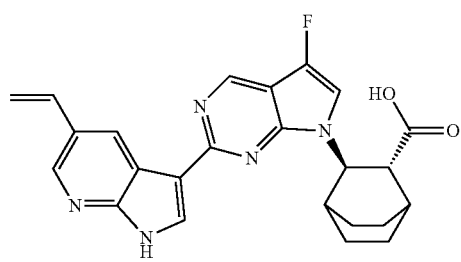 [SMILES: C=Cc1cnc2[nH]cc(-c3ncc4c(F)cn([C@@H]5C6CCC(CC6)[C@H]5C(=O)O)c4n3)c2c1]
B211
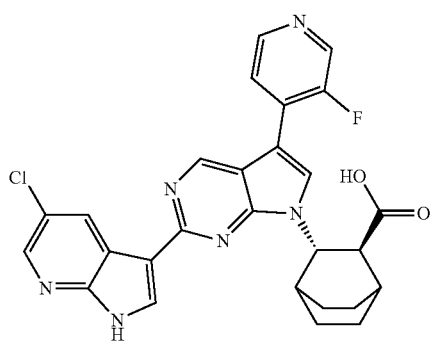 [SMILES: O=C(O)[C@H]1C2CCC(CC2)[C@@H]1n1cc(-c2ccncc2F)c2cnc(-c3c[nH]c4ncc(Cl)cc34)nc21]
B212
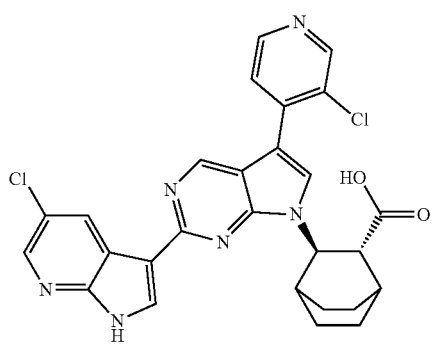 [SMILES: O=C(O)[C@@H]1C2CCC(CC2)[C@H]1n1cc(-c2ccncc2Cl)c2cnc(-c3c[nH]c4ncc(Cl)cc34)nc21]

TABLE C-continued
B213 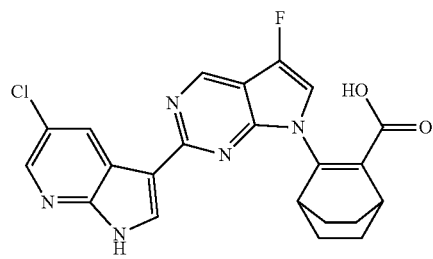 [SMILES: O=C(O)C1=C(n2cc(F)c3cnc(-c4c[nH]c5ncc(Cl)cc45)nc32)C2CCC1CC2]
B214 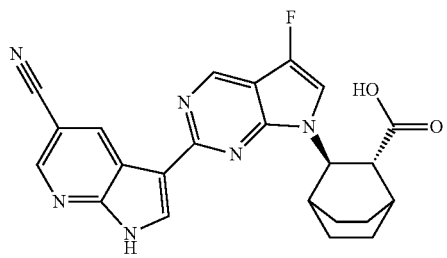 [SMILES: N#Cc1cnc2[nH]cc(-c3ncc4c(F)cn([C@@H]5C6CCC(CC6)[C@H]5C(=O)O)c4n3)c2c1]
B215 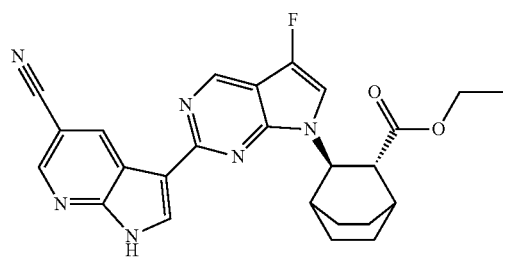 [SMILES: CCOC(=O)[C@@H]1C2CCC(CC2)[C@H]1n1cc(F)c2cnc(-c3c[nH]c4ncc(C#N)cc34)nc21]
B216 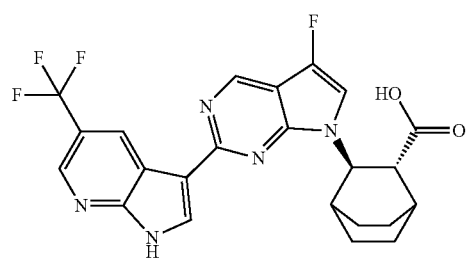 [SMILES: O=C(O)[C@@H]1C2CCC(CC2)[C@H]1n1cc(F)c2cnc(-c3c[nH]c4ncc(C(F)(F)F)cc34)nc21]
B217 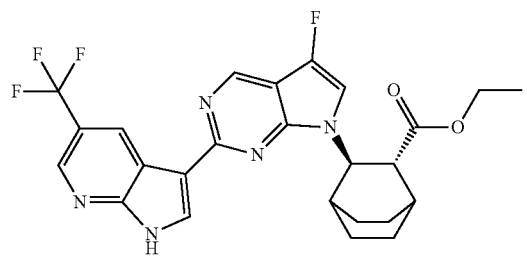 [SMILES: CCOC(=O)[C@@H]1C2CCC(CC2)[C@H]1n1cc(F)c2cnc(-c3c[nH]c4ncc(C(F)(F)F)cc34)nc21]
B218 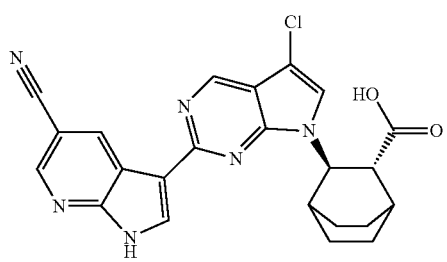 [SMILES: N#Cc1cnc2[nH]cc(-c3ncc4c(Cl)cn([C@@H]5C6CCC(CC6)[C@H]5C(=O)O)c4n3)c2c1]

TABLE C-continued
B219 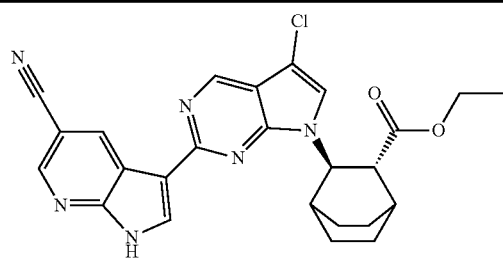
B220 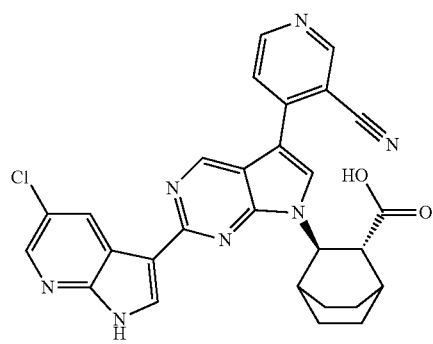 [SMILES: N#Cc1cnccc1-c1cn([C@@H]2C3CCC(CC3)[C@H]2C(=O)O)c2nc(-c3c[nH]c4ncc(Cl)cc34)ncc12]
B221 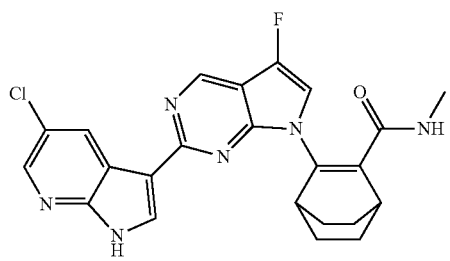 [SMILES: CNC(=O)C1=C(n2cc(F)c3cnc(-c4c[nH]c5ncc(Cl)cc45)nc32)C2CCC1CC2]
B222 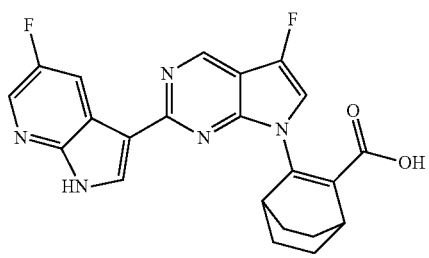 [SMILES: O=C(O)C1=C(n2cc(F)c3cnc(-c4c[nH]c5ncc(F)cc45)nc32)C2CCC1CC2]
| TABLE D | TABLE D-continued |
|---|---|
| C1 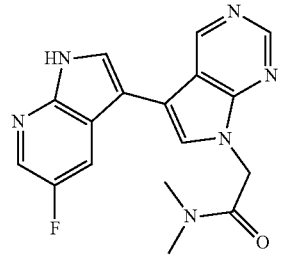 | C2 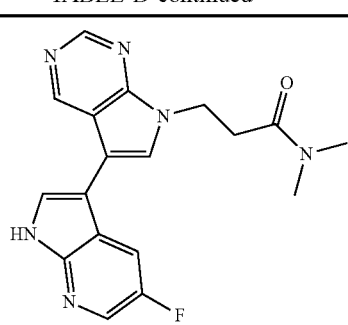 |

TABLE D-continued
C3 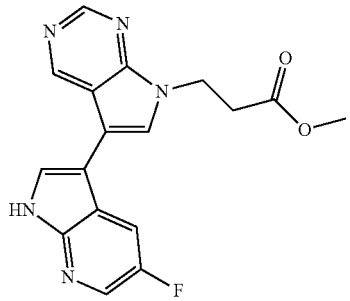 [SMILES: COC(=O)CCn1cc(-c2c[nH]c3ncc(F)cc23)c2cncnc21]
C4 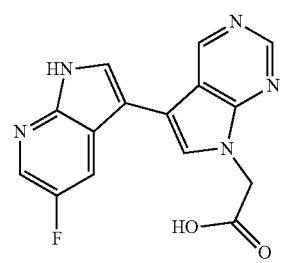 [SMILES: O=C(O)Cn1cc(-c2c[nH]c3ncc(F)cc23)c2cncnc21]
C5 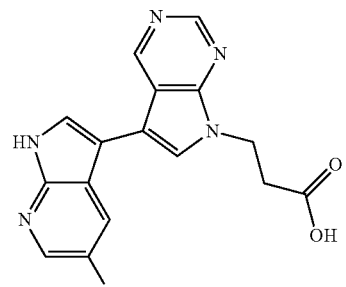
C6 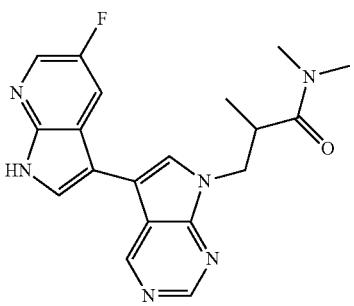 [SMILES: CC(Cn1cc(-c2c[nH]c3ncc(F)cc23)c2cncnc21)C(=O)N(C)C]
C7 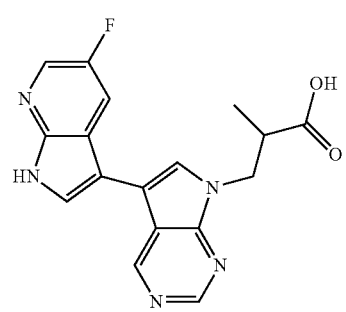 [SMILES: CC(Cn1cc(-c2c[nH]c3ncc(F)cc23)c2cncnc21)C(=O)O]
C8 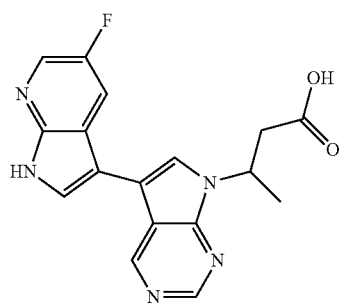 [SMILES: CC(CC(=O)O)n1cc(-c2c[nH]c3ncc(F)cc23)c2cncnc21]
C9 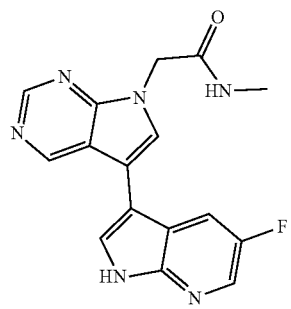 [SMILES: CNC(=O)Cn1cc(-c2c[nH]c3ncc(F)cc23)c2cncnc21]
C10 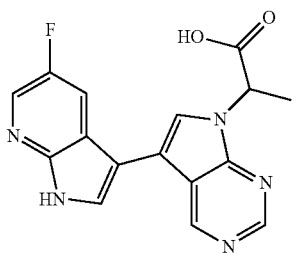 [SMILES: CC(C(=O)O)n1cc(-c2c[nH]c3ncc(F)cc23)c2cncnc21]
C11 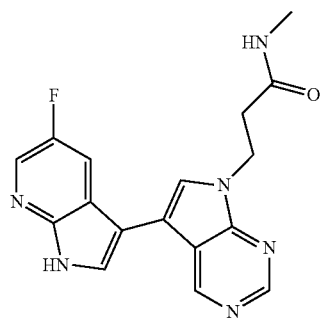 [SMILES: CNC(=O)CCn1cc(-c2c[nH]c3ncc(F)cc23)c2cncnc21]
C12 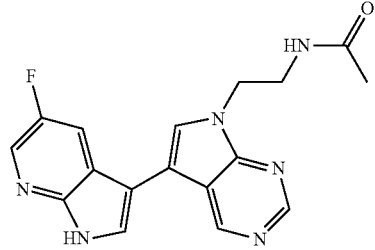 [SMILES: CC(=O)NCCn1cc(-c2c[nH]c3ncc(F)cc23)c2cncnc21]

TABLE D-continued

| | |
|---|---|
| C13 | 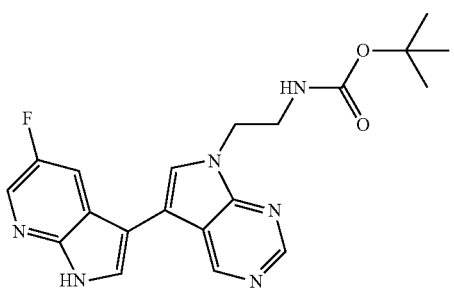 |
| C14 | 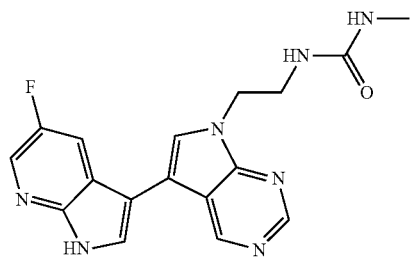 |
| C15 | 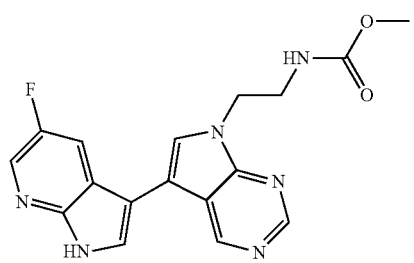 |
| C16 | 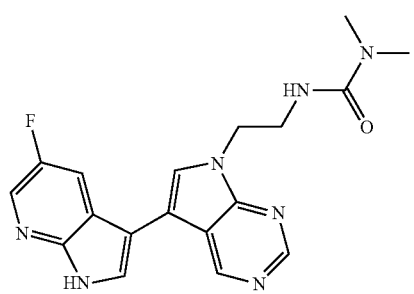 |
| C17 | 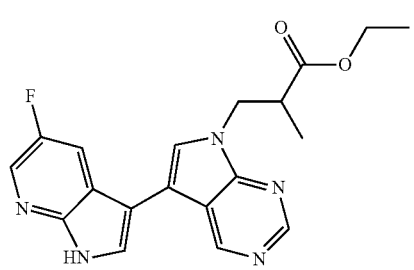 |
| C18 | 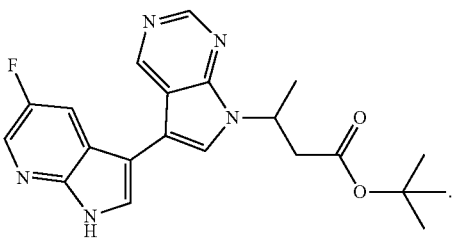 |

14. A method of treating influenza in a subject in need thereof, comprising administering to said subject a safe and effective amount of a compound or salt of claim 1.

15. A method of reducing an amount of influenza viruses in a biological sample or in a subject in need thereof, comprising administering to said biological sample or subject a safe and effective amount of a compound or salt of claim 1.

16. A pharmaceutical composition for treatment of an influenza infection in a subject, comprising a compound or salt of claim 1 and a pharmaceutically acceptable carrier, wherein the composition optionally comprises an additional agent selected from neuraminidase inhibitors, ion channel inhibitors, and polymerase inhibitors.

17. A compound having the structure of:

B143

[structure]

or a pharmaceutically acceptable salt thereof.

18. A method of treating influenza in a subject in need thereof, comprising administering to said subject a safe and effective amount of the compound or salt of claim 17.

19. A method of reducing an amount of influenza viruses in a biological sample or in a subject in need thereof, comprising administering to said biological sample or subject a safe and effective amount of the compound or salt of claim 17.

20. A pharmaceutical composition for treatment of an influenza infection in a subject, comprising the compound or salt of claim 17 and a pharmaceutically acceptable carrier, wherein the composition optionally comprises an additional agent selected from neuraminidase inhibitors, ion channel inhibitors, and polymerase inhibitors.

* * * * *